US006262333B1

(12) United States Patent
Endege et al.

(10) Patent No.: US 6,262,333 B1
(45) Date of Patent: Jul. 17, 2001

(54) HUMAN GENES AND GENE EXPRESSION PRODUCTS

(75) Inventors: Wilson O. Endege, Norwood; Kathleen E. Steinmann, Winchester; Jon H. Astle, Taunton; Christopher C. Burgess, Westwood; Steven E. Bushnell, Medfield; Eddie Carroll, III, Waltham; Theodore J. Catino, Attleboro; Adnan Derti, Boston; Donna M. Ford, Plainville; Marcia E. Lewis, Cohasset; John E. Monahan, Walpole; Robert Schlegel, Auburndale, all of MA (US)

(73) Assignee: Bayer Corporation, East Walpole, MA (US)

( * ) Notice: Subject to any disclaimer, the term of this patent is extended or adjusted under 35 U.S.C. 154(b) by 0 days.

(21) Appl. No.: 09/328,111

(22) Filed: Jun. 8, 1999

Related U.S. Application Data

(60) Provisional application No. 60/088,801, filed on Jun. 10, 1998.

(51) Int. Cl.[7] .......................... A01K 67/00; C07H 21/02; C12N 15/00; A01N 43/04

(52) U.S. Cl. ................................ 800/8; 800/13; 536/231; 536/24.1; 435/320.1; 514/44

(58) Field of Search ................................ 536/23.1, 24.1; 435/320.1; 514/44; 800/13, 8

(56) References Cited

U.S. PATENT DOCUMENTS 5,319,073 * 6/1994 Wank .................................. 530/412

FOREIGN PATENT DOCUMENTS 0 284 362 9/1988 (EP) .
WO94/01548 * 1/1994 (WO) .
WO 95 11923 5/1995 (WO) .

OTHER PUBLICATIONS

Adams, MD et al. "Initial assessment of human gene diversity and expression patterns based upon 83 million nucleotides of cDNA sequence", Nature, vol. 377, Supp, Sep. 28, 1995, pp. 3–174.*

Bouffard, GG et al, "A collection of 1814 human chromosome 7–specific STSs", Genome Research, vol. 7, No. 1, pp. 59–64, Jan. 1997.*

Bahler M, et al, "Rat myr4 defines a novel subclass of myosin I: identification, distribution, localization, and mapping of calmodulin–binding sites with differential calcium sensitivity", J of Cell Bio, vol. 126, No. 2, Jul. 1994, pp. 375–389.*

Marra et al, Sep. 17, 1997, AA592253, GenCore Version 4.5, Compugen Ltd.*

Mahairas et al., Oct. 17, 1997, B37379, GenCore Version 4.5, Compugen Ltd.*

Xp002126133: EMBL Database Hum2:SEQ. ID HS23K20, "Human DNA sequence from clone 23K20 on chromosome Xq25–26.2".

XP002126134, EMBL Database Hum2:SEQ ID HS24M15, Human DNA sequence from PAC 24M15 on chromosome, contains tenascin–R (restrictin).

Ausuble, et al., Current Protocols in Molecular Biology, vol. 1, and 2, JohnWiely & Sons, NY (1988).

Altschul, et al., Nature Genetics 6:119 (1994).

Altschul, et al., Nucleic Acids Research 25:3389 (1997).

Sambrook , et al., Molecular Cloning: A Laboratory Manual, 2nd ED., Cold Spring Harbor Press, Cold Spring Harbor, NY (1989).

Daitchenko, et al., PNAS, 93:6025–6030 (1996).

Gurskaya, et al., Analytical Biochemistry 240:90–97 (1996).

Von Stein, et al. Nucleic Acids Research 25 (13):2598–2602 (1997).

Jin, et al., Biotechniques 23:1084–1086 (1997).

Mullis, et al., Methods Enzymol 155:335–350 (1987).

Harlow & Lane, Antibodies: A Laboratory Manual, Cold Spring Harbor Press, (1988).

Summary of BLAST searching (850 sequences).

XP002119315: Hillier L. et al.: "Stratagene human cDNA clone 550176 3'end", *EMBL Sequence database*, Oct. 30, 1996, Heidelberg, Ger.

XP002119316, Marra M., et al.: "Mouse CDNA clone 779685 5'end", *EMBL Sepqunce Database*, Jun. 14, 1997, Heidelberg, Ger.

XP002089887, Schwienfest, C.W., et al.: "Subtraction hybridization cDNA libraries from colon carcinoma and hepatic cancer", *Gene Analysis Techniques*, vol, 7, Jan. 1, 1990, pp. 64–70.

XP002104685, Vider, B., et al.: "Human colorectal carcinogenesis is associated with deregulation of homeobox gene expression", *Biochemical and Biophysical Research Communications*, vol. 232, No. 3, Mar. 1997, pp. 742–748.

(List continued on next page.)

*Primary Examiner*—John S. Brusca
*Assistant Examiner*—Stephen Siu
(74) *Attorney, Agent, or Firm*—Palmer & Dodge LLP

(57) ABSTRACT

This invention relates to novel human genes, to proteins expressed by the genes, and to variants of the proteins. The invention also relates to diagnostic assays and therapeutic agents related to the genes and proteins, including probes, antisense constructs. and antibodies. The subject nucleic acids have been found to be differentially regulated in tumor cells, particularly colon cancer cell lines and/or tissue.

10 Claims, 1 Drawing Sheet

OTHER PUBLICATIONS

XP002024627, Jau Min Wong, et al.; "Ubiquitin–Ribosomal protein S27A gene overexpresses in human colorectal carinoma is an early growth response gene", *Cancer Research*, vol. 53, No. 8, Apr. 15, 1993 pp. 1916–1920.

XP002089891, Van Belzen, N., et al.; "A novel gene which is up–regulated during colon epithelial cell differentiation and down–regulated in colorectal neoplasms", *Laboratory Investigation*, vol. 77, No. 1, Jul. 1, 1997, pp. 85–92.

XP002119317, Kondoh, N., et al.; "differential expression of S19 ribosomal protein, laminin–binding protein, and human lymphocyte antigen class–I messenger RNAs associated with colon–carcinoma progression and differentiation", *Cancer Research*, vol. 42, No. 4, Feb. 15 1992, pp. 791–796.

P002119318, Kutay, U., et al.; "A human homologue of yeast Mtr10p and its role in nuclear protein import", *EMBL Sequence Database*, May 10 1999, Heidelberg, Ger.

* cited by examiner

Differential Expression Analysis
SW480 Clone Number
838 839 840 841 842
Cancer Probe
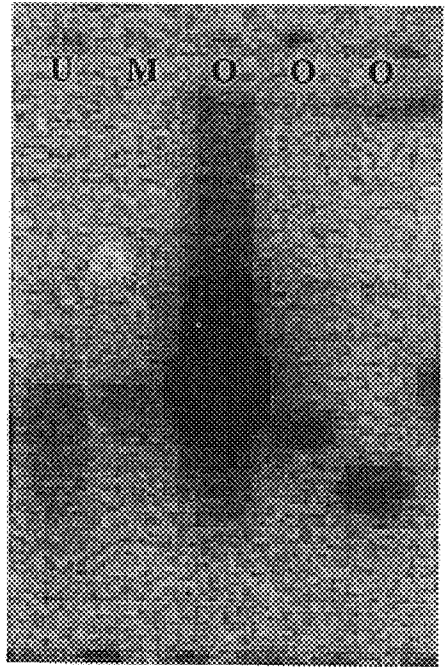
Normal Probe
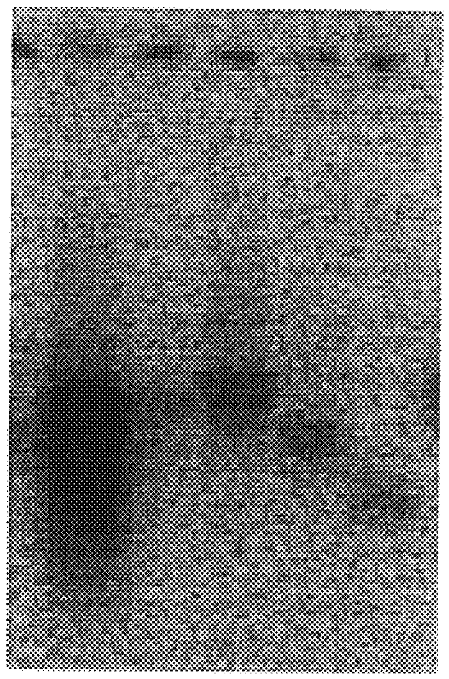

HUMAN GENES AND GENE EXPRESSION PRODUCTS

This application is based on Provisional Application No. 60/088,801, filed Jun. 10, 1998, which is hereby incorporated herein by reference.

FIELD OF THE INVENTION

The present invention provides nucleic acid sequences and proteins encoded thereby, as well as probes derived from the nucleic acid sequences, antibodies directed to the encoded proteins, and diagnostic methods for detecting cancerous cells, especially colon cancer cells.

BACKGROUND OF THE INVENTION

Colorectal carcinoma is a malignant neoplastic disease. There is a high incidence of colorectal carcinoma in the Western world, particularly in the United States. Tumors of this type often metastasize through lymphatic and vascular channels. Many patients with colorectal carcinoma eventually die from this disease. In fact, it is estimated that 62,000 persons in the United States alone die of colorectal carcinoma annually.

However, if diagnosed early, colon cancer may be treated effectively by surgical removal of the cancerous tissue. Colorectal cancers originate in the colorectal epithelium and typically are not extensively vascularized (and therefore not invasive) during the early stages of development. Colorectal cancer is thought to result from the clonal expansion of a single mutant cell in the epithelial lining of the colon or rectum. The transition to a highly vascularized, invasive and ultimately metastatic cancer which spreads throughout the body commonly takes ten years or longer. If the cancer is detected prior to invasion, surgical removal of the cancerous tissue is an effective cure. However, colorectal cancer is often detected only upon manifestation of clinical symptoms, such as pain and black tarry stool. Generally, such symptoms are present only when the disease is well established, often after metastasis has occurred, and the prognosis for the patient is poor, even after surgical resection of the cancerous tissue. Early detection of colorectal cancer therefore is important in that detection may significantly reduce its morbidity.

Invasive diagnostic methods such as endoscopic examination allow for direct visual identification, removal, and biopsy of potentially cancerous growths such as polyps. Endoscopy is expensive, uncomfortable, inherently risky, and therefore not a practical tool for screening populations to identify those with colorectal cancer. Non-invasive analysis of stool samples for characteristics indicative of the presence of colorectal cancer or precancer is a preferred alternative for early diagnosis, but no known diagnostic method is available which reliably achieves this goal. A reliable, non-invasive, and accurate technique for diagnosing colon cancer at an early stage would help save many lives.

SUMMARY OF THE INVENTION

The present invention provides nucleic acid sequences and proteins encoded thereby, as well as probes derived from the nucleic acid sequences, antibodies directed to the encoded proteins, and diagnostic methods for detecting cancerous cells, especially colon cancer cells.

In one aspect, the invention provides an isolated nucleic acid comprising a nucleotide sequence which hybridizes under stringent conditions to a sequence of SEQ ID Nos. 1–127 or a sequence complementary thereto. In a related embodiment, the nucleic acid is at least about 80% or about 100% identical to a sequence corresponding to at least about 12, at least about 15, at least about 25, or at least about 40 consecutive nucleotides up to the full length of one of SEQ ID Nos. 1–127 or a sequence complementary thereto or up to the full length of the gene of which said sequence is a fragment. In certain embodiments, a nucleic acid of the present invention includes at least about five, at least about ten, or at least about twenty nucleic acids from a region designated as novel in Table 2. In certain other embodiments, a nucleic acid of the present invention includes at least about five, at least about ten, or at least about twenty nucleotides which are not included in corresponding clones whose accession numbers are listed in Table 2.

In one embodiment, the invention provides a nucleic acid comprising a nucleotide sequence which hybridizes under stringent conditions to a sequence of SEQ ID Nos. 1–127 or a sequence complementary thereto, and a transcriptional regulatory sequence operably linked to the nucleotide sequence to render the nucleotide sequence suitable for use as an expression vector. In another embodiment, the nucleic acid may be included in an expression vector capable of replicating in a prokaryotic or eukaryotic cell. In a related embodiment, the invention provides a host cell transfected with the expression vector.

In another embodiment, the invention provides a transgenic animal having a transgenc of a nucleic acid comprising a nucleotide sequence which hybridizes tinder stringent conditions to a sequence of SEQ ID Nos. 1–127 or a sequence complementary thereto incorporated in cells thereof. The transgene modifies the level of expression of the nucleic acid, the stability of an mRNA transcript of the nucleic acid, or the activity of the encoded product of the nucleic acid.

In yet another embodiment, the invention provides substantially pure nucleic acid which hybridizes under stringent conditions to a nucleic acid probe corresponding to at least about 12, at least about 15, at least about 25, or at least about 40 consecutive nucleotides up to the full length of one of SEQ ID Nos. 1–127 or a sequence complementary thereto or up to the full length of the gene of which said sequence is a fragment. The invention also provides an antisensc oligonucleotide analog which hybridizes under stringent conditions to at least 12, at least 25, or at least 50 consecutive nucleotides of one of SEQ ID Nos. 1–850 up to the full length of one of SEQ ID Nos. 1–850 or a sequence complementary thereto or up to the full length of the gene of which said sequence is a fragment, and which is resistant to cleavage by a nuclease., preferably an endogenous endonuclease or exonuclease.

In another embodiment, the invention provides a probe/primer comprising a substantially purified oligonucleotide, said oligonucleotide containing a region of nucleotide sequence which hybridizes under stringent conditions to at least about 12, at least about 15, at least about 25, or at least about 40 consecutive nucleotides of sense or antisense sequence selected from SEQ ID Nos. 1–127 up to the full length of one of SEQ ID Nos. 1–127 or a sequence complementary thereto or up to the fill length of the gene of which said sequence is a fragment. In preferred embodiments, the probe selectively hybridizes with a target nucleic acid. In another embodiment, the probe may include a label group attached thereto and able to be detected. The label group may be selected from radioisotopes, fluorescent compounds, enzymes, and enzyme co-factors. The invention further provides arrays of at least about 10, at least about 25, at least about 50, or at least about 100 different probes as described above attached to a solid support.

In yet another embodiment, the invention pertains to a method of determining the phenotype of a cell, comprising detecting the differential expression, relative to a normal cell, of at least one nucleic acid which hybridizes under stringent conditions to one of SEQ ID Nos. 1–850. wherein the nucleic acid is differentially expressed by at least a factor of two, at least a factor of five, at least a factor of twenty, or at least a factor of fifty.

In another aspect, the invention provides polypeptides encoded by the subject nucleic acids. In one embodiment, the invention pertains to a polypeptide including an amino acid sequence encoded by a nucleic acid comprising a nucleotide sequence which hybridizes under stringent conditions to a sequence of SEQ ID Nos. 1–127 or a sequence complementary thereto, or a fragment comprising at least about 25, or at least about 40 amino acids thereof. Further provided are antibodies immunoreactive with these polypeptides.

In still another aspect, the invention provides diagnostic methods. In one embodiment, the invention pertains to a method for determining the phenotype of cells from a patient by providing a nucleic acid probe comprising a nucleotide sequence having at least 12, at least about 15, at least about 25, or at least about 40 consecutive nucleotides represented in a sequence of SEQ ID Nos. 1–850 up to the fill length of one of SEQ ID Nos. 1–850 or a sequence complementary thereto or up to the full length of the gene of which said sequence is a fragment, obtaining a sample of cells from a patient, providing a second sample of cells substantially all of which are non-cancerous, contacting the nucleic acid probe under stringent conditions with mRNA of each of said first and second cell samples, and comparing (a) the amount of hybridization of the probe with mRNA of the first cell sample, with (b) the amount of hybridization of the probe with mRNA of the second cell sample, wherein a difference of at least a factor of two, at least a factor of five, at least a factor of twenty, or at least a factor of fifty in the amount of hybridization with the mRNA of the first cell sample as compared to the amount of hybridization with the mRNA of the second cell sample is indicative of the phenotype of cells in the first cell sample. Determining the phenotype includes determining the genotype, as the term is used herein.

In another embodiment, the invention provides a test kit for identifying an transformed cells, comprising a probe/primer as described above, for measuring a level of a nucleic acid which hybridizes under stringent conditions to a nucleic acid of SEQ ID Nos. 1–850 in a sample of cells isolated from a patient. In certain embodiments, the kit may further include instructions for using the kit, solutions for suspending or fixing the cells, detectable tags or labels; solutions for rendering a nucleic acid susceptible to hybridization, solutions for lysing cells, or solutions for the purification of nucleic acids.

In another embodiment, the invention provides a method of determining the phenotype of a cell, comprising detecting the differential expression, relative to a normal cell, of at least one protein encoded by a nucleic acid which hybridizes under stringent conditions to one of SEQ ID Nos. 1–850, wherein the protein is differentially expressed by at least a factor of two, at least a factor of five, at least a factor of twenty, or at least a factor of fifty. In one embodiment, the level of the protein is detected in an immunoassay. The invention also pertains to a method for determining the presence or absence of a nucleic acid which hybridizes under stringent conditions to one of SEQ ID Nos. 1–127 in a cell, comprising contacting the cell with a probe as described above. The invention further provides a method for determining the presence of absence of a subject polypeptide encoded by a nucleic acid which hybridizes under stringent conditions to one of SEQ ID Nos. 1–127 in a cell, comprising contacting the cell with an antibody as described above. In yet another embodiment, the invention provides a method for determining the presence of an aberrant mutation (e.g., deletion, insertion, or substitution of nucleic acids) or aberrant methylation in a gene which hybridizes under stringent conditions to a sequence of SEQ ID Nos. 1–383 or a sequence complementary thereto, comprising collecting a sample of cells from a patient, isolating nucleic acid from the cells of the sample, contacting the nucleic acid sample with one or more primers which specifically hybridize to a nucleic acid sequence of SEQ ID Nos. 1–850 under conditions such that hybridization and amplification of the nucleic acid occurs, and comparing the presence, absence, or size of an amplification product to the amplification product of a normal cell.

In one embodiment, the invention provides a test kit for identifying transformed cells, comprising an antibody specific for a protein encoded by a nucleic acid which hybridizes under stringent conditions to any one of SEQ Nos. 1–850. In certain embodiments, the kit further includes instructions for using the kit. In certain embodiments, the kit may further include instructions for using the kit, solutions for suspending or fixing the cells, detectable tags or labels, solutions for rendering a polypeptide susceptible to the binding of an antibody, solutions for lysing cells, or solutions for the purification of polypeptides.

In yet another aspect, the invention provides pharmaceutical compositions including the subject nucleic acids. In one embodiment, an agent which alters the level of expression in a cell of a nucleic acid which hybridizes under stringent conditions to one of SEQ ID Nos. 1–850 or a sequence complementary thereto is identified by providing a cell, treating the cell with a test agent, determining the level of expression in the cell of a nucleic acid which hybridizes under stringent conditions to one of SEQ ID Nos. 1–850 or a sequence complementary thereto, and comparing the level of expression of the nucleic acid in the treated cell with the level of expression of the nucleic acid in an untreated cell, wherein a change in the level of expression of the nucleic acid in the treated cell relative to the level of expression of the nucleic acid in the untreated cell is indicative of an agent which alters the level of expression of the nucleic acid in a cell. The invention further provides a pharmaceutical composition comprising an agent identified by this method. In another embodiment, the invention provides a pharmaccutical composition which includes a polypeptide encoded by a nucleic acid having a nucleotide sequence that hybridizes under stringent conditions to one of SEQ ID Nos. 1–850 or a sequence complementary thereto. In one embodiment, the invention pertains to a pharmaceutical composition comprising a nucleic acid including a sequence which hybridizes under stringent conditions to one of SEQ ID Nos. 1–850 or a sequence complementary thereto.

BRIEF DESCRIPTION OF THE FIGURE

The FIGURE depicts an exemplary assay result for determining differential expression of gene products in cells.

DETAILED DESCRIPTION OF THE INVENTION

The invention relates to nucleic acids having the disclosed nucleotide sequences (SEQ ID Nos. 1–850), as well as full length cDNA, mRNA, and genes corresponding to these sequences, and to polypeptides and proteins encoded by these nucleic acids and genes and portions thereof.

Also included are nucleic acids that encode polypeptides and proteins encoded by the nucleic acids of SEQ ID Nos. 1–850. The various nucleic acids that can encode these polypeptides and proteins differ because of the degeneracy of the genetic code, in that most amino acids are encoded by more than one triplet codon. The identity of such codons is well known in this art, and this information can be used for the construction of the nucleic acids within the scope of the invention.

Nucleic acids encoding polypeptides and proteins that are variants of the polypeptides and proteins encoded by the nucleic acids and related cDNA and genes are also within the scope of the invention. The variants differ from wild-type protein in having one or more amino acid substitutions that either enhance, add, or diminish a biological activity of the wild-type protein. Once the amino acid change is selected, a nucleic acid encoding that variant is constructed according to the invention.

The following detailed description discloses how to obtain or make full-length cDNA and human genes corresponding to the nucleic acids, how to express these nucleic acids and genes, how to identify structural motifs of the genes, how to identify the function of a protein encoded by a gene corresponding to an nucleic acid, how to use nucleic acids as probes in mapping and in tissue profiling, how to use the corresponding polypeptides and proteins to raise antibodies, and how to use the nucleic acids, polypeptides, and proteins for therapeutic and diagnostic purposes.

The sequences investigated herein have been found to be differentially expressed in samples obtained from colon cancer cell lines and/or colon cancer tissue. However, it is also believed that these sequences may also have utility with other types of cancer.

Accordingly, certain aspects of the present invention relate to nucleic acids differentially expressed in tumor tissue, especially colon cancer cell lines, polypeptides encoded by such nucleic acids, and antibodies immunoreactive with these polypeptides, and preparations of such compositions. Moreover, the present invention provides diagnostic and therapeutic assays and reagents for detecting and treating disorders involving, for example, aberrant expression of the subject nucleic acids.

I. General

This invention relates in part to novel methods for identifying and/or classifying cancerous cells present in a human tumors, particularly in solid tumors, e.g., carcinomas and sarcomas, such as, for example, breast or colon cancers. The method uses genes that are differentially expressed in cancer cell lines and/or cancer tissue compared with related normal cells, such as normal colon cells, and thereby identifies or classifies tumor cells by the upregulation and/or downregulation of expression of particular genes; an event which is implicated in tumorgenesis.

Upregulation or increased expression of certain genes such as oncogenes, act to promote malignant growth. Downregulation or decreased expression of genes such as tumor suppressor genes promotes malignant growth. Thus, alteration in the expression of either type of gene is a potential diagnostic indicator for determining whether a subject is at risk of developing or has cancer, e.g., colon cancer.

Accordingly, in one aspect, the invention also provides biomarkers, such as nucleic acid markers, for human tumor cells, e.g., for colon cancer cells. The invention also provides proteins encoded by these nucleic acid markers.

The invention also features methods for identifying drugs useful for treatment of such cancer cells, and for treatment of a cancerous condition, such as colon cancer. Unlike prior methods, the invention provides a means for identifying cancer cells at an early, stage of development, so that premalignant cells can be identified prior to their spreading throughout the human body. This allows early detection of potentially cancerous conditions, and treatment of those cancerous conditions prior to spread of the cancerous cells throughout the body, or prior to development of an irreversible cancerous condition.

II. Definitions

For convenience, the meaning of certain terms and phrases used in the specification, examples, and appended claims, are provided below.

The term "an aberrant expression", as applied to a nucleic acid of the present invention, refers to level of expression of that nucleic acid which differs from the level of expression of that nucleic acid in healthy tissue, or which differs from the activity of the polypeptide present in a healthy subject. An activity of a polypeptide can be aberrant because it is stronger than the activity of its native counterpart. Alternatively, an activity can be aberrant because it is weaker or absent relative to the activity of its native counterpart An aberrant activity can also be a change in the activity; for example, an aberrant polypeptide can interact with a different target peptide. A cell can have an aberrant expression level of a gene due to overexpression or underexpression of that gene.

The term "agonist", as used herein, is meant to refer to an agent that mimics or upregulates (e.g., potentiates or supplements) the bioactivity of a protein. An agonist can be a wild-type protein or derivative thereof having at least one bioactivity of the wild-type protein. An agonist can also be a compound that upregulates expression of a gene or which increases at least one bioactivity of a protein. An agonist can also be a compound which increases the interaction of a polypeptide with another molecule, e.g., a target peptide or nucleic acid.

The term "allele", which used interchangeably herein with "allelic variant", refers to alternative forms of a gene or portions thereof. Alleles occupy the same locus or position on homologous chromosomes. When a subject has two identical alleles of a gene, the subject is said to be homozygous for that gene or allele. When a subject has two different alleles of a gene, the subject is said to be heterozygous for the gene. Alleles of a specific gene can differ from each other in a single nucleotide, or several nucleotides, and can include substitutions, deletions, and/or insertions of nucleotides. An allele of a gene can also be a form of a gene containing mutations. The term "allelic variant of a polymorphic region of a gene" refers to a region of a gene having one of several nucleotide sequences found in that region of the gene in other individuals.

"Antagonist" as used herein is meant to refer to an agent that downregulates (e.g., suppresses or inhibits) at least one bioactivity of a protein. An antagonist can be a compound which inhibits or decreases the interaction between a protein and another molecule, e.g., a target peptide or enzyme substrate. An antagonist can also be a compound that downregulates expression of a gene or which reduces the amount of expressed protein present.

The term "antibody" as used herein is intended to include whole antibodies, e.g., of any isotype (IgG, IgA, IgM, IgE, etc), and includes fragments thereof which are also specifically reactive with a vertebrate, e.g., mammalian, protein. Antibodies can be fragmented using conventional techniques and the fragments screened for utility in the same manner as described above for whole antibodies. Thus, the term includes segments of proteolytically-cleaved or recombinantly-prepared portions of an antibody molecule that are capable of selectively reacting with a certain protein. Nonlimiting examples of such proteolytic and/or recombinant fragments include Fab, F(ab')2, Fab', Fv, and single chain antibodies (scFv) containing a V[L] and/or V[H] domain joined by a peptide linker. The scFv's may be covalently or non-covalently linked to form antibodies having two or more binding sites. The subject invention includes polyclonal, monoclonal, or other purified preparations of antibodies and recombinant antibodies.

The phenomenon of "apoptosis" is well known, and can be described as a programmed death of cells. As is known, apoptosis is contrasted with "necrosis", a phenomenon when cells die as a result of being killed by a toxic material, or other external effect. Apoptosis involves chromatic condensation, membrane blebbing, and fragmentation of DNA, all of which are generally visible upon microscopic examination.

A disease, disorder, or condition "associated with" or "characterized by" an aberrant expression of a nucleic acid refers to a disease, disorder, or condition in a subject which is caused by, contributed to by, or causative of an aberrant level of expression of a nucleic acid.

As used herein the term "bioactive fragment of a polypeptide" refers to a fragment of a full-length polypeptide, wherein the fraiment specifically agonizes (mimics) or antagonizes (inhibits) the activity of a wild-type polypeptide. The bioactive fragment preferably is a fragment capable of interacting with at least one other molecule, e.g., protein, small molecule, or DNA, which a full length protein can bind.

"Biological activity" or "bioactivity" or "activity" or "biological function", which are used interchangeably, herein mean an effector or antigenic function that is directly or indirectly performed by a polypeptide (whether in its native or denatured conformation), or by any subsequence thereof. Biological activities include binding to polypeptides, binding to other proteins or molecules, activity as a DNA binding protein, as a transcription regulator, ability to bind damaged DNA, etc. A bioactivity can be modulated by directly affecting the subject polypeptide. Alternatively, a bioactivity can be altered by modulating the level of the polypeptide, such as by modulating expression of the corresponding gene.

The term "biomarker" refers a biological molecule, e.g., a nucleic acid, peptide, hormone, etc., whose presence Or concentration can be detected and correlated with a known condition, such as a disease state.

"Cells," "host cells", or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not. iii fact, be identical to the parent cell, but are still included within the scope of the term as used herein.

A "chimeric polypeptide" or "fusion polypeptide" is a fusion of a first amino acid sequence encoding one of the subject polypeptides with a second amino acid sequence defining a domain (e.g., polypeptide portion) foreign to and not substantially homologous with any domain of the subject polypeptide. A chimeric polypeptide may present a foreign domain which is found (albeit in a different polypeptide) in an organism which also expresses the first polypeptide, or it may be an "interspecics," "intergenic," etc., fusion of polypeptide structures expressed by different kinds of organisms. In general, a fusion polypeptide can be represented by the general formula $(X)_n$—$(Y)_n$—$(Z)_m$, wherein Y represents a portion of the subject polypeptide, and X and Z are each independently absent or represent amino acid sequences which are not related to the native sequence found in an organism, or which are not found as a polypeptide chain contiguous with the subject sequence, where m is an integer greater than or equal to on; and each occurrence of n is, independently, 0 or an integer greater than or equal to 1 (n and m are preferably no greater than 5 or 10).

A "delivery complex" shall mean a targeting means (e.g., a molecule that results in higher affinity binding of a nucleic acid, protein, polypeptide or peptide to a target cell surface and/or increased cellular or nuclear uptake by a target cell). Examples of targeting means include: sterols (e.g., cholesterol), lipids (e.g., a cationic lipid, virosome or liposome), viruses (e.g., adenovirus, adeno-associated virus, and retrovirus), or target cell-specific binding agents (e.g., ligands recognized by target cell specific receptors). Preferred complexes are sufficiently stable in vivo to prevent significant uncoupling prior to internalization by the target cell. However, the complex is cleavable under appropriate conditions within the cell so that the nucleic acid, protein, polypeptide or peptide is released in a functional form.

As is well known, genes or a particular polypeptide may exist in single or multiple copies within the genome of an individual. Such duplicate genes may be identical or may have certain modifications, including nucleotide substitutions, additions or deletions, which all still code far polypeptides having substantially the same activity. The term "DNA sequence encoding a polypeptide" may thus refer to one or more genes within a particular individual. Moreover, certain differences hi nucleotide sequences may exist between individual organisms, which are called alleles. Such allelic differences may or may not result in differences in amino acid sequence of the encoded polypeptide yet still encode a polypeptide with the same biological activity.

The term "equivalent" is understood to include nucleotide sequences encoding functionally equivalent polypeptides. Equivalent nucleotide sequences will include sequences that differ by one or more nucleotide substitutions, additions or deletions, such as allelic variants; and will, therefore, include sequences that differ from the nucleotide sequence of the nucleic acids shown in SEQ ID Nos. 1–850 due to the degeneracy of the genetic code.

As used herein, the terms "gene", "recombinant gene", and "gene construct" refer to a nucleic acid of the present invention associated with an open reading frame, including both exon and (optionally) intron sequences.

A "recombinant gene" refers to nucleic acid encoding a polypeptide and comprising exon sequences, though it may optionally include intron sequences which are derived from, for example, a related or unrelated chromosomal gene. The term "introit" refers to a DNA sequence present in a given gene which is not translated into protein and is generally found between exons.

The term "growth" or "growth state" of a cell refers to the proliferative state o a cell as well as to its differentiative state. Accordingly, the term refers to the phase of the cell cycle in which the cell is, e.g., G0, G1, G2, prophase, metaphase, or telophase, as well as to its state of differentiation, e.g., undifferentiated, partially differentiated, or fully differentiated. Without wanting to be limited, differentiation of a cell is usually accompanied by a decrease in the proliferative rate of a cell.

"Homology" or "identity" or "similarity" refers to sequence similarity between two peptides or between two nucleic acid molecules, with identity being a more strict comparison. Homology and identity can each be determined by comparing a position in each sequence which may be aligned for purposes of comparison. When a position in the compared sequence is occupied by the same base or amino acid, then the molecules are identical at that position. A degree of homology or similarity or identity between nucleic acid sequences is a function of the number of identical or matching nucleotides at positions shared by the nucleic acid sequences. A degree of identity of amino acid sequences is a function of the number of identical amino acids at positions shared by the amino acid sequences. A degree of homology or similarity of amino acid sequences is a function of the number of amino acids, i.e., structurally related, at positions shared by the amino acid sequences. An "unrelated" or "non-homologous" sequence shares less than 40% identity, though preferably less than 25% identity, with one of the sequences of the present invention.

The term "percent identical" refers to sequence identity between two amino acid sequences or between two nucleotide sequences. Identity can each be determined by comparing a position in each sequence which may be aligned for purposes of comparison. When an equivalent position in the compared sequences is occupied by the same base or amino acid, then the molecules are identical at that position; when the equivalent site occupied by the same or a similar amino acid residue (e.g., similar in steric and/or electronic nature), then the molecules can be referred to as homologous (similar) at that position. Expression as a percentage of homology, similarity, or identity refers to a function of the number of identical or similar amino acids at positions shared by the compared sequences. Various alignment algorithms and/or programs may be used, including FASTA, BLAST, or ENTREZ. FASTA and BLAST are available as a part of the GCG sequence analysis package (University of Wisconsin, Madison, Wis.), and can be used with, e.g., default settings. ENTREZ is available through the National Center for Biotechnology Information, National Library of Medicine, National Institutes of Health, Bethesda, Md. In one embodiment, the percent identity of two sequences can be determined by the GCG program with a gap weight of 1, e.g., each amino acid gap is weighted as if it were a single amino acid or nucleotide mismatch between the two sequences.

Other techniques for alignment are described in *Methods in Enzymology*, vol. 266: Computer Methods for Macromolecular Sequence Analysis (1996), ed. Doolittle, Academic Press, Inc., a division of Harcourt Brace & Co., San Diego, Calif., USA. Preferably, an alignment program that permits gaps in the sequence is utilized to align the sequences. The Smith-Waterman is one type of algorithm that permits gaps in sequence alignments. See *Meth. Mol. Biol.* 70: 173–187 (1997). Also, the GAP program using the Needleman and Wunsch alignment method can be utilized to align sequences. An alternative search strategy uses MPSRCH software; which runs on a MASPAR computer. MPSRCH uses a Smith-Waterman algorithm to score sequences on a massively parallel computer. This approach improves ability to pick up distantly related matches, and is especially tolerant of small gaps and nucleotide sequence errors. Nucleic acid-encoded amino acid sequences can be used to search both protein and DNA databases.

Databases with individual sequences are described in *Methods in Enzymology*, ed. Doolittle, supra. Databases include Genbank, EMBL, and DNA Database of Japan (DDBJ).

Preferred nucleic acids have a sequence at least 70%, and more preferably 80% identical and more preferably 90% and even more preferably at least 95% identical to an nucleic acid sequence of a sequence shown in one of SEQ ID NOS: 1–850. Nucleic acids at least 90%, more preferably 95%, and most preferably at least about 98–99% identical with a nucleic sequence represented in onc of SEQ ID NOS: 1–850 are of course also within the scope of the invention. In preferred embodiments, the nucleic acid is mammalian.

The term "interact" as used herein is meant to include detectable interactions (e.g., biochemical interactions) between molecules, such as interaction between protein-protein, protein-nucleic acid, nucleic acid-nucleic acid, and protein-small molecule or nucleic acid-small molecule in nature.

The term "isolated" as used herein with respect to nucleic acids, such as DNA or RNA, refers to molecules separated from other DNAs, or RNAs, respectively, that are present in the natural source of the macromolecule. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides.

The terms "modulated" and "differentially regulated" as used herein refer to both upregulation (i.e., activation or stimulation (e.g., by agonizing or potentiating)) and downregulation (i.e., inhibition or suppression (e.g., by antagonizing, decreasing or inhibiting)).

The term "mutated gene" refers to an allelic form of a gene, which is capable of altering the phenotype of a subject having the mutated gene relative to a subject which does not have the mutated gene. If a subject must be homozygous for this mutation to have an altered phenotype, the mutation is said to be recessive. If one copy of the mutated gene is sufficient to alter the genotype of the subject, the mutation is said to be dominant If a subject has one copy of the mutated gene and has a phenotype that is intermediate between that of a homozygous and that of a heterozygous subject (for that gene), the mutation is said to be co-dominant.

The designation "N", where it appears in the accompanying Sequence Listing, indicates that the identity of the corresponding nucleotide is unknown. "N" should therefore not necessarily be interpreted as permitting substitution with any nucleotide, e.g., A, T, C, or G, but rather as holding the place of a nucleotide whose identity has not been conclusively determined.

The "non-human animals" of the invention include mammalians such as rodents, non-human primates, sheep, dog, cow, chickens, amphibians, reptiles, etc. Preferred non-human animals are selected from the rodent family including rat and mouse, most preferably mouse, though transgenic amphibians, such as members of the Xenopus genus, and transgenic chickens can also provide important tools for understanding and identifying agents which can affect, for example, embryogenesis and tissue formation. The term "chimeric animal" is used herein to refer to animals in which the recombinant gene is found, or in which the recombinant gene is expressed in some but not all cells of the animal. The term "tissue-specific chimeric animal" indicates that one of the recombinant genes is present and/or expressed or disrupted in some tissues but not others.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides. ESTs, chromosomes, cDNAs, mRNAs, and rRNAs are representative examples of molecules that may be referred to as nucleic acids.

The term "nucleotide sequence complementary to the nucleotide sequence of SEQ ID NO. x" refers to the nucleotide sequence of the complementary strand of a nucleic acid strand having SEQ ID NO. x. The term "complementary strand" is used herein interchangeably with the term "complement". The complement of a nucleic acid stand can be the complement of a coding strand or the complement of a non-coding strand.

The term "polymorphism" refers to the coexistence of more than one form of a gene or portion (e.g., allelic variant) thereof A portion of a gene of which there are at least two different forms, i.e., two different nucleotide sequences, is referred to as a "polymorphic region of a gene". A polymorphic region can be a single nucleotide, the identity of which differs in different alleles. A polymorphic region can also be several nucleotides long.

A "polymorphic gene" refers to a gene having at least one polymorphic region.

As used herein, the term "promoter" means a DNA sequence that regulates expression of a selected DNA sequence operably linked to the promoter, and which effects expression of the selected DNA sequence in cells. The term encompasses "tissue specifics" promoters, i.e., promoters which effect expression of the selected DNA sequence only in specific cells (e.g., cells of a specific tissue). The term also covers so-called "leaky" promoters, which regulate expression of a selected DNA primarily in one tissue, but cause expression in other tissues as well. The term also encompasses non-tissue specific promoters and promoters that constitutively express or that are inducible (i.e., expression levels can be controlled).

The terms "protein", "polypeptide", and "peptide" are used interchangeably herein when referring to a (gene product.

The term "recombinant protein" refers to a polypeptide of the present invention which is produced by recombinant DNA techniques, wherein generally, DNA encoding a polypeptide is inserted into a suitable expression vector which is in turn used to transform a host cell to produce the heterologous protein. Moreover, the phrase "derived from", with respect to a recombinant gene. is meant to include within the meaning of "recombinant protein" those proteins having an amino acid sequence of a native polypeptide, or an amino acid sequence similar thereto which is generated by mutations including substitutions and deletions (including truncation) of a naturally occurring form of the polypeptide.

"Small molecule" as used herein, is meant to refer to a composition, which has a molecular weight of less than about 5 kD and most preferably less than about 4 kD. Small molecules can be nucleic acids, peptides, polypeptides, peptidomimetics, carbohydrates, lipids or other organic (carbon-containing) or inorganic molecules. Many pharmaceutical companies have extensive libraries Of chemical and/or biological mixtures, often fungal, bacterial, or algal extracts, which can be screened with any of the assays of the invention to identify compounds that modulate a bioactivity.

As used herein, the term "specifically hybridizes" or "specifically detects" r efers to the ability of a nucleic acid molecule of the invention to hybridize to at least a portion of, for example approximately 6, 12, 15, 20, 30, 50, 100, 150, 200, 300, 350, 400, 500, 750 or 1000 contiguous nucleotides of a nucleic acid designated in any one of SEQ ID Nos: 1–850, or a sequence complementary thereto, or naturally occurring mutants thereof; such that it has less than 15%, preferably less than 10%, and more preferably less than 5% background hybridization to a cellular nucleic acid (e.g., mRNA or genomic DNA) encoding a different protein. In preferred embodiments, the oligonucleotide probe detects only a specific nucleic acid, e.g., it does not substantially hybridize to similar or related nucleic acids, or complements thereof.

"Transcriptional regulatory sequence" is a generic term used throughout the specification to refer to DNA sequences, such as initiation signals, enhancers, and promoters, which induce or control transcription of protein coding sequences with which they are operably linked. In preferred embodiments, transcription of one of the genes is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally-occurring forms of the polypeptide.

As used herein, the term "transfection" means the introduction of a nucleic acid, e.g., via an expression vector, into a recipient cell by nucleic acid-mediated gene transfer. "Transformation", as used herein, refers to a process in which a cell's genotype is changed as a result of the cellular uptake of exogenous DNA or RNA, and, for example, the transformed cell expresses a recombinant form of a polypeptide or, in the case of anti-sense expression from the transferred gene, the expression of the target gene is disrupted.

As used herein, the term "transgene" means a nucleic acid sequence (or an antisense transcript thereto) which has been introduced into a cell. A transgene could be partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to after the genome of the cell into which it is inserted (e,g., it is inserted at a location which differs from that of the natural gene or its insertion results in a knockout). A transgene can also be present in a cell in the form of an episome. A transgene can include one or more transcriptional regulatory sequences and any other nucleic acid, such as introns, that may be necessary for optimal expression of a selected nucleic acid.

A "transgenic animal" refers to any animal, preferably a non-human mammal, bird or an amphibian, in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extra-chromosomally replicating DNA. In the typical transgenic animals described herein, the transgene causes cells to express a recombinant form of one of the subject polypeptide, e.g. either agonistic or antagonistic forms. However, transgenic animals in which the recombinant gene is silent are also contemplated, as for example, the FLP or CRE recombinase dependent constructs described below. Moreover, "transgenic animal" also includes those recombinant animals in which gene disruption of one or more genes is caused by human intervention, including both recombination and antisense techniques.

The term "treating" as used herein is intended to encompass curing as well as ameliorating at least one symptom of the condition or disease.

The term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

The term "wild-type allele" refers to an allele of a gene which, when present in two copies in a subject results in a wild-type phenotype. There can be several different wild-type alleles of a specific gene, since certain nucleotide changes in a gene may not affect the phenotype of a subject having two copies of the gene with the nucleotide changes.

III. Nucleic Acids of the Present Invention

As described below, one aspect of the invention pertains to isolated nucleic acids, variants, and/or equivalents of such nucleic acids.

Nucleic acids of the present invention have been identified as differentially expressed in tumor cells, e.g., colon cancer-derived cell lines (relative to the expression levels in normal tissue, e.g., normal colon tissue and/or normal non-colon tissue), such as SEQ ID Nos. 1–850, preferably SEQ ID Nos. 1–383, even more preferably SEQ ID Nos. 1–127, or a sequence complementary thereto. In certain embodiments, the subject nucleic acids are differentially expressed by at least a factor of two, preferably at least a factor of five, even more preferably at least a factor of twenty, still more preferably at least a factor of fifty. Preferred nucleic acids include sequences identified as differentially expressed both in colon cancer cell tissue and colon cancer cell lines. In preferred embodiments, nucleic acids of the present invention are upregulated in tumor cells, especially colon cancer tissue and/or colon cancer-derived cell lines. In another embodiment, nucleic acids of the present invention are downregulated in tumor cells, especially colon cancer tissue and/or colon cancer-derived cell lines.

Table 1 indicates those sequences which are over- or underexpressed in a colon cancer-derived cell line relative to normal tissue, and further designates those sequences which are also differentially regulated in colon cancer issue. The designation O indicates that the corresponding sequence was overexpressed, M indicates possible overexpression, N indicates no differential expression, and U indicates underexpression.

Genes which are upregulated, such as oncogenes, or downregulated, such as tumor suppressors, in aberrantly proliferating cells may be targets for diagnostic or therapeutic techniques. For example, upregulation of the cdc2 gene induces mitosis. Overexpression of the myt1 gene, a mitotic deactivator, negatively regulates the activity of cdc2. Aberrant proliferation may thus be induced either by upregulating cdc2 or by downregulating myt1. Similarly, downregulation of tumor suppressors such as p53 and Rb have been implicated in tumorigenesis.

Particularly preferred polypeptides are those that are encoded by nucleic acid sequences at least about 70%, 75%, 80%, 90%, 95%, 97%, or 98% similar to a nucleic acid sequence of SEQ ID Nos. 1–850. Preferably, the nucleic acid includes all or a portion (e.g., at least about 12, at least about 15, at least about 25, or at least about 40 nucleotides) of the nucleotide sequence corresponding to the nucleic acid of SEQ ID Nos. 1–383, preferably SEQ ID Nos. 1–127, or a sequence complementary thereto.

Still other preferred nucleic acids of the present invention encode a polypeptide comprising at least a portion of a polypeptide encoded by one of SEQ ID Nos. 1–850. For example, preferred nucleic acid molecules for use as probes/primers or antisense molecules (i.e., noncoding nucleic acid molecules) can comprise at least about 12, 20, 30, 50, 60, 70, 80, 90, or 100 base pairs in length up to the length of the complete gene. Coding nucleic acid molecules can comprise, for example, from about 50, 60, 70, 80, 90, or 100 base pairs up to the length of the complete gene.

Another aspect of the invention provides a nucleic acid which hybridizes under low, medium, or high stringency conditions to a nucleic acid sequence represented by one of SEQ ID Nos. 1–383, preferably SEQ ID Nos. 1–127, or a sequence complementary thereto. Appropriate stringency conditions which promote DNA hybridization, for example, 6.0×sodium chloride/sodium citrate (SSC) at about 45° C., followed by a wash of 2.0×SSC at 50° C., are known to those skilled in the art or can be found in Current Protocols in Molecular Biology, John Wiley & Sons, N.Y. (1989), 6.3.1–12.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In a preferred embodiment, a nucleic acid of the present invention will bind to one of SEQ ID Nos. 1–383, preferably SEQ ID Nos. 1–127, or a sequence complementary thereto, under moderately stringent conditions, for example at about 2.0×SSC and about 40° C. In a particularly preferred embodiment, a nucleic acid of the present invention will bind to one of SEQ ID Nos. 1–383, preferably SEQ ID Nos. 1–127, or a sequence complementary thereto, under high stringency conditions.

In one embodiment, the invention provides nucleic acids which hybridize under low stringency conditions of 6×SSC at room temperature followed by a wash at 2×SSC at room temperature.

In another embodiment, the invention provides nucleic acids which hybridize under high stringency conditions of 2×SSC at 65° C. followed by a wash at 0.2×SSC at 65° C.

Nucleic acids having a sequence that differs from the nucleotide sequences shown in one of SEQ ID Nos. 1–3 83, preferably SEQ ID Nos. 1–127, or a sequence complementary thereto, due to degeneracy in the genetic code, are also within the scope of the invention. Such nucleic acids encode functionally equivalent peptides (i.e., a peptide having equivalent or similar biological activity) but differ in sequence from the sequence shown in the sequence listing due to degeneracy in the genetic code. For example, a number of amino acids are designated by more than one triplet. Codons that specify the same amino acid, or synonyms (for example, CAU and CAC each encode histidine) may result in "silent" mutations which do not affect the amino acid sequence of a polypeptide. However, it is expected that DNA sequence polymorphisms that do lead to changes in the amino acid sequences of the subject polypeptides will exist among mammals. One skilled in the art will appreciate that these variations in one or more nucleotides (e.g., up to about 3–5% of the nucleotides) of the nucleic acids encoding polypeptides having an activity of a polypeptide may exist among individuals of a given species due to natural allelic variation.

Also within the scope of the invention are nucleic acids encoding splicing variants of proteins encoded by a nucleic acid of SEQ ID Nos. 1–850, preferably SEQ ID Nos. 1–383, even more preferably SEQ ID Nos. 1–127, or a sequence complementary thereto, or natural homologs of such proteins. Such homologs can be cloned by hybridization or PCR, as further described herein.

The polynucleotide sequence may also encode for a leader sequence, e.g., the natural leader sequence or a heterologous leader sequence, for a subject polypeptide. For example, the desired DNA sequence may be fused in the same reading frame to a DNA sequence which aids in expression and secretion of the polypeptide from the host cell, for example, a leader sequence which functions as a secretory sequence for controlling transport of the polypepticle from the cell. The protein having a leader sequence is a preprotein and may have the leader sequence cleaved by the host cell to form the mature form of the protein.

The polynucleotide of the present invention may also be fused in frame to a marker sequence, also referred to herein as "Tag sequence" encoding a "Tag peptide", which allows for marking and/or purification of the polypeptide of the present invention. In a preferred embodiment, the marker sequence is a hexahistidine tag, e.g., supplied by a PQE-9 vector. Numerous other Tag peptides are available commercially. Other frequently used Tags include myc-epitopes (e.g., see Ellison et al. (1991) *J Biol Chem* 266:21150–21157) which includes a 10-residue sequence from c-myc, the pFLAG system (International Biotechnologies, Inc.), the pEZZ-protein A system (Pharmacia, N.J.), and a 16 amino acid portion of the *Haemophilus influenza* hemagglutinin protein. Furthermore, any polypeptide can be used as a Tag so long as a reagent, e.g., an antibody interacting specifically with the Tag polypeptide is available or can be prepared or identified.

As indicated by the examples set out below, nucleic acids can be obtained from mRNA present in any of a number of eukaryotic cells, e.g., and are preferably obtained from metazoan cells, more preferably from vertebrate cells, and even more preferably from mammalian cells. It should also be possible to obtain nucleic acids of the present invention from genomic DNA from both adults and embryos. For example, a gene can be cloned from either a cDNA or a genomic library in accordance with protocols generally known to persons skilled in the art. cDNA can be obtained by isolating total mRNA from a cell, e.g., a vertebrate cell, a mammalian cell, or a human cell, including embryonic cells. Double stranded cDNAs can then be prepared from the total mRNA, and subsequently inserted into a suitable plasmid or bacteriophage vector using any one of a number of known techniques. The gene can also be cloned using established polymerase chain reaction techniques in accordance with the nucleotide sequence information provided by the invention.

In certain embodiments, a nucleic acid, probe, vector, or other construct of the present invention includes at least about five, at least about ten, or at least about twenty nucleic acids from a region designated as novel in Table 2. In certain other embodiments, a nucleic acid of the present invention includes at least about five, at least about ten, or at least about twenty nucleic acids which are not included in the clones whose accession numbers are listed in Table 2.

The invention includes within its scope a polynucleotide having the nucleotide sequence of nucleic acid obtained from this biological material, wherein the nucleic acid hybridizes under stringent conditions (at least about 4×SSC at 65° C., or at least about 4×SSC at 42° C.; see, for example, U.S. Pat. No. 5,707,829, incorporated herein by reference) with at least 15 contiguous nucleotides of at least one of SEQ ID Nos. 1–850. By this is intended that when at least 15 contiguous nucleotides of one of SEQ ID Nos. 1–850 is used as a probe, the probe will preferentially hybridize with a gene or mRNA (of the biological material) comprising the complementary sequence, allowing the identification and retrieval of the nucleic acids of the biological material that uniquely hybridize to the selected probe. Probes from more than one of SEQ ID Nos. 1–850 will hybridize with the same gene or mRNA if the cDNA from which they were derived corresponds to one mRNA. Probes of more than 15 nucleotides can be used, but 15 nucleotides represents enough sequence for unique identification.

Because the present nucleic acids represent partial mRNA transcripts, two or more nucleic acids of the invention may represent different regions of the same mRNA transcript and the same gene. Thus, if two or more of SEQ ID Nos. 1–850 are identified as belonging to the same clone, then either sequence can be used to obtain the full-length mRNA or gene.

Nucleic acid-related polynucleotides can also be isolated from cDNA libraries. These libraries are preferably prepared from mRNA of human colon cells, more preferably, human colon cancer cells, even more preferably, from a human colon adenocarcinoma cell line, SW480. Alignment of SEQ ID Nos. 1–850, as described above, can indicated that a cell line or tissuc source of a related protein or polynucleotide can also be used as a source of the nucleic acid-related cDNA.

Techniques for producing and probing nucleic acid sequence libraries are described, for example, in Sambrook et al., "Molecular Cloning: A Laboratory Manual" (New York, Cold Spring Harbor Laboratory, 1989). The cDNA can be prepared by using primers based on a sequence from SEQ ID Nos. 1–850. In one embodiment, the cDNA library can be made from only poly-adenylated mRNA. Thus, poly-T primers can be used to prepare cDNA from the mRNA. Alignment of SEQ ID Nos. 1–850 can result in identification of a related polypeptide or polynucleotide. Some of the polynucleotides disclosed herein contains repetitive regions that were subject to masking during the search procedures. The information about the repetitive regions is discussed below.

Constructs of polynucleotides having sequences of SEQ ID Nos. 1–850 can be generated synthetically. Alternatively, single-step assembly of a gene and entire plasmid from large numbers of oligodeoxyribonucleotides is described by Stemmer et al., *Gene* (*Amsterdam*) (1995) 164(1):49–53. In this method, assembly PCR (the synthesis of long DNA sequences from large numbers of oligodeoxyribonucleotides (oligos)) is described. The method is derived from DNA shuffling (Stemmer, *Nature* (1994) 370:389–391), and does not rely on DNA ligase, but instead relies on DNA polymerase to build increasingly longer DNA fragments during the assembly process. For example, a 1.1-kb fragment containing the TEM-1 beta-lactamasc-encoding gene (bla) can be assembled in a single reaction from a total of 56 oligos, each 40 nucleotides (nt) in length. The synthetic gene can be PCR amplified and cloned in a vector containing the tetracycline-resistance gene (Tc-R) as the sole selectable marker. Without relying on ampicillin (Ap) selection, 76% of the Tc-R colonies were Ap-R, making this approach a gencral method for the rapid and cost-effective synthesis of any gene.

IV. Identification of Functional and Structural Motifs of Novel Genes Using Art-Recognized Methods Translations of the nucleotide sequence of the nucleic acids, cDNAs, or full genes an be aligned with individual known sequences. Similarity with individual sequences can be used to determine the activity of the polypeptides encoded by the polynucleotides of the invention. For example, sequences that show similarity with a chemokine sequence may exhibit chemokine activities. Also, sequences exhibiting similarity with more than one individual sequence may exhibit activities that are characteristic of either or both individual sequences.

The full length sequences and fragments of the polynucleotide sequences of the nearest neighbors can be used as probes and primers to identify and isolate the full length sequence of the nucleic acid. The nearest neighbors can indicate a tissue or cell type to be used to construct a library for the full-length sequences of the nucleic acid.

Typically, the nucleic acids ate translated in all six frames to determine the best alignment with the individual sequences. The sequences disclosed herein in the Sequence Listing are ma 5' to 3' orientation and translation in three frames can be sufficient (with a few specific exceptions as described in the Examples). These amino acid sequences are referred to, generally, as query sequences, which will be aligned with the individual sequences.

Nucleic acid sequences can be compared with known genes by any of the methods disclosed above. Results of individual and query sequence alignments can be divided into three categories: high similarity, weak similarity, and no similarity. Individual alignment results ranging from high similarity to weak similarity provide a basis for determining polypeptide activity and/or structure.

Parameters for categorizing individual results include; percentage of the alignment region length where the strongest alignment is found; percent sequence identity, and p value.

The percentage of the alignment region length is calculated by counting the number of residues of the individual sequence found in the region of strongest alignment. This number is divided by the total residue length of the query sequence to find a percentage. An example is shown below:

```
Query sequence:          ASNPERTMIPVTRVGLIRYM

                         |    |||    ||||   |||
Individual sequence:     YMMTEYLAIPV.RVGLPRYM

                         1     5      10     15
```

The region of alignment begins at amino acid 9 and ends at amino acid 19. The total length of the query sequence is 20 amino acids. The percent of the alignment region length is 11/20 or 55%.

Percent sequence identity is calculated by counting the number of amino acid matches between the query and individual sequence and dividing total number of matches by the number of residues of the individual sequence found in the region of strongest aligment. For the example above, the percent identity would be 10 matches divided by 11 amino acids, or approximately 90.9%.

P value is the probability that the alignment was produced by chance. For a single alignment, the p value can be calculated according to Karlin et al., *Proc. Natl. Acad. Sci.* 87:2264 (1990) and Karlin et al., *Proc. Natl. Acad. Sci.* 90:(1993). The p value of multiple alignments using the same query sequence can be calculated using an heuristic approach described in Altschul et al., *Nat. Genet*. 6: 119 (1994). Alignment programs such as BLAST program can calculate the p value.

The boundaries of the region where the sequences align can be determined according to Doolittle, Methods in Enzymology, supra; BLAST or FASTA programs; or by determining the area where the sequence identity is highest.

Another factor to consider for determining identity or similarity is the location of the similarity or identity. Strong local alignment can indicate similarity even if the length of alignment is short. Sequence identity scattered throughout the length of the query sequence also can indicate a similarity between the query and profile sequences.

High Similarity

For the alignment results to be considered high similarity, the percent of the alignment region length, typically, is at least about 55% of total length query sequence; more typically, at least about 58%; even more typically; at least about 60% of the total residue length of the query sequence. Usually, percent length of the alignment region can be as much as about 62%; more usually, as much as about 64%; even more usually, as much as about 66%.

Further, for high similarity, the region of alignment, typically, exhibits at least about 75% of sequence identity; more typically, at least about 78%; even more typically; at least about 80% sequence identity. Usually, percent sequence identity can be as much as about 82%; more usually, as much as about 84%; even more usually, as much as about 86%.

The p value is used in conjunction with these methods. If high similarity is found, the query sequence is considered to have high similarity with a profile sequence when the p value is less than or equal to about $10^{-2}$; more usually; less than or equal to about $10^{-3}$; even more usually; less than or equal to about $10^{-4}$. More typically, the p value is no more than about $10^{-5}$; more typically; no more than or equal to about $10^{-10}$; even more typically; no more than or equal to about $10^{-15}$ for the query sequence to be considered high similarity.

Weak Similarity

For the alignment results to be considered weak similarity, there is no minimum percent length of the alignment region nor minimum length of alignment. A better showing of weak similarity is considered when the region of alignment is, typically, at least about 15 amino acid residues in length; more typically, at least about 20; even more typically; at least about 25 amino acid residues in length. Usually, length of the alignment region can be as much as about 30 amino acid residues; more usually, as much as about 40; even more usually, as much as about 60 amino acid residues.

Further, for weak similarity, the region of alignment, typically, exhibits at least about 35% of sequence identity; more typically, at least about 40%; even more typically; at least about 45% sequence identity. Usually, percent sequence identity can be as much as about 50%; more usually, as much as about 55%; even more usually, as much as about 60%.

If low similarity is found, the query sequence is considered to have weak similarity with a profile sequence when the p value is usually less than or equal to about $10^{-2}$; more usually; less than or equal to about $10^{-3}$, even more usually; less than or equal to about $10^{-4}$. More typically, the p value is no more than about $10^{-5}$, more usually; no more than or equal to about $10^{-10}$; even more usually; no more than or equal to about $10^{-15}$ for the query sequence to be considered weak similarity.

Simlarity Determined by Sequence Identity Alone

Sequence identity alone can be used to determine similarity of a query sequence to an individual sequence and can indicate the activity of the sequence. Such an alignment, preferably, permits gaps to align sequences. Typically, the query sequence is related to the profile sequence if the sequence identity over the entire query sequence is at least about 15%; more typically, at least about 20%; even more typically, at least about 25%; even more typically, at least about 50%. Sequence identity alone as a measure of similarity is most useful when the query sequence is usually, at least 80 residues in length; more usually, 90 residues; even more usually, at least 95 amino acid residues in length. More typically, similarity can be concluded based on sequence identity alone when the query sequence is preferably 100 residues in length; more preferably, 120 residues in length; even more preferably, 150 amino acid residues in length.

Determining Activity from Alignments with Profile and Multiple Aligned Sequences Translations of the nucleic acids can be aligned with amino acid profiles that define either protein families or common motifs. Also, translations of the nucleic acids can be aligned to multiple sequence alignments (MSA) comprising the polypeptide sequences of members of protein families or motifs. Similarity or identity with profile sequences or MSAs can be used to determine the activity of the polypeptides encoded by nucleic acids or corresponding cDNA or genes. For example, sequences that show an identity or similarity with a chemokine profile or MSA can exhibit chemokine activities.

Profiles can designed manually by (1) creating a MSA, which is an alignment of the amino acid sequence of members that belong to the family and (2) constructing a statistical representation of the alignment Such methods are described, for example, in Birney et al., *Nucl. Acid Res.* 24(14): 2730–2739 (1996).

MSAs of some protein families and motifs are publicly available. For example, these include MSAs of 547 different families and motifs. These MSAs are described also in Sonnhammer et al., *Proteins* 28: 405–420 (1997). Other sources are also available in the world wide web. A brief description of these MSAs is reported in Pascarella el al., *Prot. Eng.* 9(3):249–251 (1996).

Techniques for building profiles from MSAs are described in Sonnhammer et al., supra; Birney et al., supra; and *Methods in Enzymology*. vol. 266: "Computer Methods for Macromolecular Sequence Analysis," 1996, ed. Doolittle, Academic Press, Inc., a division of Harcourt Brace & Co., San Diego, Calif., USA.

Similarity between a query sequence and a protein family or motif can be determined by (a) comparing the query sequence against the profile and/or (b) aligning the query sequence with the members of the family or motif.

Typically, a program such as Searchwise can be used to compare the query sequence to the statistical representation of the multiple alignment, also known as a profile. The program is described in Birney et al., supra. Other techniques to compare the sequence and profile are described in Sonnhammer et al., supra and Doolittle, supra.

Next, methods described by Feng et al., *J. Mol. Evol.* 25: 351–360 (1987) and Higgins et al., *CABIOS* 5: 151–153 (1989) can be used align the query sequence with the members of a family or motif, also known as a MSA. Computer programs, such as PILEUP, can be used. See Feng et al., infra.

The following factors are used to determine if a similarity between a query sequence and a profile or MSA exists: (1) number of conserved residues found in the query sequence, (2) percentage of conserved residues found in the query sequence, (3) number of frameshifts, and (4) spacing between conserved residues.

Some alignment programs that both translate and align sequences can make any number of frameshifts when translating the nucleotide sequence to produce the best alignment. The fewer frameshifts needed to produce an alignment, the stronger the similarity or identity between the query and profile or MSAs. For example, a weak similarity resulting from no frameshifts can be a better indication of activity or structure of a query sequence, than a strong similarity resulting from two frameshifts. Preferably, three or fewer frameshifts are found in an alignment; more preferably two or fewer frameshifts; even more preferably, one or fewer frameshifts; even more preferably, no frameshifts are found in an alignment of query and profile or MSAs.

Conserved residues are those amino acids that are found at a particular position in all or some of the family or motif members. For example, most known chemokines contain four conserved cysteines. Alternatively; a position is considered conserved if only a certain class of amino acids is found in a particular position in all or some of the family members. For example, the N-terminal position may contain a positively charged amino acid, such as lysine, arginine, or histidine.

Typically, a residue of a polypeptide is conserved when a class of amino acids or a single amino acid is found at a particular position in at least about 40% of all class members; more typically, at least about 50%; even more typically, at least about 60% of the members. Usually, a residue is conserved when a class or single amino acid is found in at least about 70% of the members of a family or motif; more usually, at least about 80%; even more usually, at least about 90%; even more usually, at least about 95%.

A residue is considered conserved when three unrelated amino acids are found at a particular position in the some or all of the members; more usually, two unrelated amino acids. These residues are conserved when the unrelated amino acids are found at particular positions in at least about 40% of all class member, more typically, at least about 50%; even more typically, at least about 60% of the members. Usually, a residue is conserved when a class or single amino acid is found in at least about 70% of the members of a family or motif; more usually, at least about 80%; even more usually, at least about 90%; even more usually, at least about 95%.

A query sequence has similarity to a profile or MSA when the query sequence comprises at least about 25% of the conserved residues of the profile or MSA; more usually, at least, about 30% even more usually; at least about 40%. Typically, the query sequence has a stronger similarity to a profile sequence or MSA when the query sequence comprises at least about 45% of the conserved residues of the profile or MSA; more typically, at least about 50%; even more typically; at least about 55%.

V. Probes and Primers

The nucleotide sequences determined from the cloning of genes from tumor cells, especially colon cancer cell lines and tissues will further allow for the generation of probes and primers designed for identifying and/or cloning homologs in other cell types, e.g. from other tissues, as well as homologs from other mammalian organisms, Nucleotide sequences useful as probes/primers may include all or a portion of the sequences listed in SEQ ID Nos. 1–850 or sequences complementary thereto or sequences which hybridize under stringent conditions to all or a portion of SEQ ID Nos. 1–850. For instance, the present invention also provides a probe/primer comprising a substantially purified oligonucleotide, which oligonucleotide comprising a nucleotide sequence that hybridizes under stringent conditions to at least approximately 12, preferably 25, more preferably 40, 50, or 75 consecutive nucleotides up to the full length of the sense or anti-sense sequence selected from the group consisting of SEQ ID Nos. 1–850, preferably SEQ ID Nos. 1–383, even more preferably SEQ ID Nos. 1–127, or a sequence complementary thereto, or naturally occurring mutants thereof. For instance, primers based on a nucleic acid represented in SEQ ID Nos. 1–850, preferably SEQ ID Nos. 1–383, even more preferably SEQ ID Nos. 1–127, or a sequence complementary thereto, can be used in PCR reactions to clone homologs of that sequence.

In yet another embodiment, the invention provides probes/primers comprising a nucleotide sequence that hybridizes under moderately stringent conditions to at least approximately 12, 16, 25, 40, 50 or 75 consecutive nucleotides up to the full length of the sense or antisense sequence selected from the group consisting of SEQ ID Nos. 1–850, preferably SEQ ID Nos. 1–383, even more preferably SEQ ID Nos. 1–127, or naturally occurring mutants thereof.

In particular, these probes are useful because they provide a method for detecting mutations in wild-type genes of the present invention. Nucleic acid probes which are complementary to a wild-type gene of the present invention and can form mismatches with mutant genes are provided, allowing for detection by enzymatic or chemical cleavage or by shifts in electrophoretic mobility.

Likewise, probes based on the subject sequences can be used to detect transcripts or genomic sequences encoding the same or homologous proteins, for use, for example, in prognostic or diagnostic assays. In preferred embodiments, the probe further comprises a label group attached thereto and able to be detected, e.g., the label group is selected from radioisotopes, fluorescent compounds, chemiluminescent compounds, enzymes, and enzyme co-factors.

Full-length cDNA molecules comprising the disclosed nucleic acids are obtained as follows. A subject nucleic acid or a portion thereof comprising at least about 12, 15, 18, or 20 nucleotides up to the full length of a sequence represented in SEQ ID Nos. 1–850, preferably SEQ ID Nos. 1–383, even more preferably SEQ ID Nos. 1–127, or a sequence complementary thereto, may be used as a hybridization probe to detect hybridizing members of a cDNA library using probe design methods, cloning methods, and clone selection techniques as described in U.S. Pat. No. 5,654,173, "Secreted Proteins and Polynucleotides Encoding Them," incorporated herein by reference. Libraries of cDNA may be made from selected tissues, such as normal or tumor tissue, or from tissues of a mammal treated with, for example, a pharmaceutical agent. Preferably, the tissue is the same as that used to generate the nucleic acids, as both the nucleic acid and the cDNA represent expressed genes. Most preferably, the cDNA library is made from the biological material described herein in the Examples. Alternatively, many cDNA libraries are available commercially. (Sambrook el al., *Molecular Cloning: A Laboratory Manual*, 2nd Ed. (Cold Spring Harbor Press, Cold Spring Harbor, N.Y. 1989). The choice of cell type for library construction may be made after the identity of the protein encoded by the nucleic acid-related gene is known. This will indicate which tissue and cell types are likely to express the related gene, thereby containing the mRNA for generating the cDNA.

Members of the library that are larger than the nucleic acid, and preferably that contain the whole sequence of the native message, may be obtained. To confirm that the entire cDNA has been obtained, RNA protection experiments may be performed as follows. Hybridization of a full-length cDNA to an mRNA may protect the RNA from RNase degradation. If the cDNA is not full length, then the portions of the mRNA that are not hybridized may be subject to RNase degradation. This may be assayed, as is known in the art, by changes in electrophoretic mobility on polyacrylamide gels, or by detection of released monoribonucleotides. Sambrook et al., *Molecular Cloning: A Laboratory Manual*, 2nd Ed. (Cold Spring Harbor Press, Cold Spring Harbor, N.Y. 1989). In order to obtain additional sequences 5' to the end of a partial cDNA, 5' RACE (PCR Protocols: A Guide to Methods and Applications (Academic Press, Inc. 1990)) may be performed.

Genomic DNA may be isolated using nucleic acids in a manner similar to the isolation of full-length cDNAs. Briefly, the nucleic acids, or portions thereof, may be used as probes to libraries of genomic DNA. Preferably, the library is obtained from the cell type that was used to generate the nucleic acids. Most preferably, the genomic DNA is obtained front the biological material described herein in the Example. Such libraries may be in vectors suitable for carrying large segments of a genome, such as P1 or YAC, as described in detail in Sambrook et al., 9.4–9.30. In addition, genomic sequences can be isolated from human BAC libraries, which are commercially available from Research Genetics, Inc., Huntville, Ala., USA, for example. In order to obtain additional 5' or 3' sequences, chromosome walking may be performed, as described in Sambrook et al., such that adjacent and overlapping fragments of genomic DNA are isolated. These may be mapped and pieced together, as is known in the art, using restriction digestion enzymes and DNA ligase.

Using the nucleic acids of the invention, corresponding full Icngth genes can be isolated using both classical and PCR methods to construct and probe cDNA libraries. Using either method, Northern blots, preferably, may be performed on a number of cell types to determine which cell lines express the gene of interest at the highest rate.

Classical methods of constructing cDNA libraries are taught in Sambrook et al., supra. With these methods, cDNA can be produced from mRNA and inserted into viral or expression vectors. Typically, libraries of mRNA comprising poly(A) tails can be produced with poly(T) primers. Similarly, cDNA libraries can be produced using the instant sequences as primers.

PCR methods may be used to amplify the members of a cDNA library that comprise the desired insert. In this case, the desired insert may contain sequence from the full length cDNA that corresponds to the instant nucleic acids. Such PCR methods include gene trapping and RACE methods.

Gene trapping may entail inserting a member of a cDNA library into a vector. The vector then may be denatured to produce single stranded molecules. Next, a substrate-bound probe, such a biotinylated oligo, may be used to trap cDNA inserts of interest. Biotinylated probes can be linked to an avidin-bound solid substrate. PCR methods can be used to amplify the trapped cDNA. To trap sequences corresponding to the full length genes, the labeled probe sequence may be based on the nucleic acids of the invention, e.g., SEQ ID Nos. 1–383, preferably SEQ ID Nos. 1–127, or a sequence complementary thereto. Random primers or primers specific to the library vector an be used to amplify the trapped cDNA. Such gene trapping techniques are described in Gruber et al., PCT WO 95/04745 and Gruber et al., U.S. Pat. No. 5,500,356. Kits are commercially available to perform gene trapping experiments from, for example, Life Technologies, Gaithersburg, Md., USA.

"Rapid amplification of cDNA ends," or RACE, is a PCR method of amplifying cDNAs from a number of different RNAs. The cDNAs may be ligated to an oligonucleotide linker and amplified by PCR using two primers. One primer may be based on sequence from the instant nucleic acids, for which full length sequence is desired, and a second primer may comprise a sequence that hybridizes to the oligonucleotide linker to amplify the cDNA. A description of this method is reported in PCT Pub. No. WO 97/19110.

In preferred embodiments of RACE, a common primer may be designed to anneal to an arbitrary adaptor sequence ligated to cDNA ends (Apte and Siebert, *Biotechniques* 15:890–893, 1993; Edwards et al., *Nuc. Acids Res.* 19:5227–5232, 1991). When a single gene-specific RACE primer is paired with the common primer, preferential amplification of sequences between the single gene specific primer and the common primer occurs. Commercial cDNA pools modified for use in RACE are available.

Another PCR-based method generates full-length cDNA library with anchored ends without specific knowledge of the cDNA sequence. The method uses lock-docking primers (I–VI), where one primer, poly TV (I–III) locks over the polyA tail of eukaryotic mRNA producing first strand synthesis and a second primer, polyGH (IV–VI) locks onto the polyC tail added by terminal deoxynucleotidyl transferasc (TdT). This method is described in PCT Pub. No. WO 96/40998.

The promoter region of a gene generally is located 5' to the initiation site for RNA polymerase II. Hundreds of promoter regions contain the "TATA" box, a sequence such as TA1TA or TATAA, which is sensitive to mutations. The promoter region can be obtained by performing 5' RACE using a primer from the coding region of the gene. Alternatively, the cDNA can be used as a probe for the genomic sequence, and the region 5' to the coding region is identified by "walking up."

If the gene is highly expressed or differentially expressed, the promoter from the gene may be of use in a regulatory construct for a heterologous gene.

Once the full-length cDNA or gene is obtained, DNA encoding variants can be prepared by site-directed mutagenesis, described in detail in Sambrook et al., 15.3–15.63. The choice of codon or nucleotide to be replaced can be based on the disclosure herein on optional changes in amino acids to achieve altered protein structure and/or function.

As an alternative method to obtaining DNA or RNA from a biological material, nucleic acid comprising nucleotides having the sequence of one or more nucleic acids of the invention can be synthesized. Thus, the invention encompasses nucleic acid molecules ranging in length from 12 nucleotides (corresponding to at least 12 contiguous nucleotides which hybridize under stringent conditions to or are at least 80% identical to a nucleic acid represented by one of SEQ ID Nos. 1–850, preferably SEQ ID Nos. 1–383, even more preferably SEQ ID Nos. 1–127, or a sequence complementary thereto) up to a maximum length suitable for one or more biological manipulations, including replication and expression, of the nucleic acid molecule. The invention includes but is not limited to (a) nucleic acid having the size of a full gene, and comprising at least one of SEQ ID Nos. 1–850, preferably SEQ ID Nos. 1–383, even more preferably SEQ ID Nos. 1–127, or a sequence complementary thereto; (b) the nucleic acid of (a) also comprising at least one additional gene, operably linked to permit expression of a fusion protein; (c) an expression vector comprising (a) or (b); (d) a plasmid comprising (a) or (b); and (e) a recombinant viral particle comprising (a) or (b). Construction of (a) can be accomplished as described below in part IV.

The sequence of a nucleic acid of the present invention is not limited and can be any sequence of A, T, G, and/or C (for DNA) and A, U, G, and/or C (for RNA) or modified bases thereof, including inosine and pseudouridine. The choice of sequence will depend on the desired function and can be dictated by coding regions desired, the intron-like regions desired, and the regulatory regions desired.

VI. Vectors Carrying Nucleic Acids of the Present Invention

The invention further provides plasmids and vectors, which can be used to express a gene in a host cell. The host cell may be any prokaryotic or eukaryotic cell. Thus, a nucleotide sequence derived from any one of SEQ ID Nos. 1–850, preferably SEQ ID Nos. 1–383, even more preferably SEQ ID Nos. 1–127, or a sequence complementary thereto, encoding all or a selected portion of a protein, can be used to produce a recombinant form of an polypeptide via microbial or eukaryotic cellular processes. Ligating the polynucleotide sequence into a gene construct, such as an expression vector, and transforming or transfecting into hosts, either eukaryotic (yeast, avian, insect or mammalian) or prokaryotic (bacterial cells), are standard procedures well known in the art.

Vectors that allow expression of a nucleic acid in a cell are referred to as expression vectors. Typically, expression vectors contain a nucleic acid operably linked to at least one transcriptional regulatory sequence. Regulatory sequences are art-recognized and are selected to direct expression of the subject nucleic acids. Transcriptional regulatory sequences are described in Goeddel; Gene Expression Technology: Methods in Enzymology 185, Academic Press, San Diego, Calif. (1990). In one embodiment, the expression vector includes a recombinant gene encoding a peptide having an agonistic activity of a subject polypeptide, or alternatively, encoding a peptide which is an antagonistic form of a subject polypeptide.

The choice of plasmid will depend on the type of cell in which propagation is desired and the purpose of propagation. Certain vectors are useful for amplifying and making large amounts of the desired DNA sequence. Other vectors are suitable for expression in cells in culture. Still other vectors are suitable for transfer and expression in cells in a whole animal or person. The choice of appropriate vector is well within the skill of the art. Many such vectors are available commercially. The nucleic acid or full-length gene is inserted into a vector typically by means of DNA ligase attachment to a cleaved restriction enzyme site in the vector. Alternatively, the desired nucleotide sequence may be inserted by homologous recombination in vivo. Typically this is accomplished by attaching regions of homology to the vector on the flanks of the desired nucleotide sequence. Regions of homology are added by ligation of oligonucleotides, or by polymerase chain reaction using primers comprising both the region of homology and a portion of the desired nucleotide sequence, for example.

Nucleic acids or full-length genes are linked to regulatory sequences as appropriate to obtain the desired expression properties. These may include promoters (attached either at the 5' end of the sense strand or at the 3' end of the antisense strand), enhancers, terminators, operators, repressors, and inducers. The promoters may be regulated or constitutive. In some situations it may be desirable to use conditionally active promoters, such as tissue-specific or developmental stage-specific promoters. These are linked to the desired nucleotide sequence using the techniques described above for linkage to vectors. Any techniques known in the art may be used.

When any of the above host cells, or other appropriate host cells or organisms, are used to replicate and/or express the polynucleotides or nucleic acids of the invention, the resulting replicated nucleic acid, RNA, expressed protein or polypeptide, is within the scope of the invention as a product of the host cell or organism. The product is recovered by any appropriate means known in the art.

Once the gene corresponding to the nucleic acid is identified, its expression can be regulated in the cell to which the gene is native. For example, an endogenous gene of a cell can be regulated by an exogenous regulatory sequence as disclosed in U.S. Pat. No. 5,641,670, "Protein Production and Protein Delivery."

A number of vectors exist for the expression of recombinant proteins in yeast (see, for example, Broach et al. (1983) in Experimental Manipulation of Gene Expression, ed. M. Inouye, Academic Press, p. 83, incorporated by reference herein). In addition, drug resistance markers such as ampicillin can be used. In an illustrative embodiment, a polypeptide is produced recombinantly utilizing an expression vector generated by sub-cloning one of the nucleic acids represented in one of SEQ ID Nos. 1–850, preferably SEQ ID Nos. 1–383, even more preferably SEQ ID Nos. 1–127, or a sequence complementary thereto.

The preferred mammalian expression vectors contain both prokaryotic sequences, to facilitate the propagation of the vector in bacteria, and one or more eukaryotic transcription units that are expressed in eukaryotic cells. The various methods employed in the preparation of plasmids and transformation of host organisms are well known in the art. For other suitable expression systems for both prokaryotic and eukaryotic cells, as well as general recombinant procedures, see Molecular Cloning: A Laboratory Manual, $2^{nd}$ Ed., ed. by Sambrook, Fritsch and Maniatis (Cold Spring Harbor Laboratory Press: 1989) Chapters 16 and 17. When it is desirable to express only a portion of a gene, e.g., a truncation Mutant, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from *E. coli* (Ben-Bassat et al. (1987) J. Bacteriol. 169:751–757) and *Salmonella typhimurium* and its in vitro activity has been demonstrated on recombinant proteins (Miller et al. (1987) PNAS 84:2718–1722). Therefore, removal of an N-terminal methionine, if desired., can be achieved either in vivo by expressing polypeptides in a host which produces MAP (e.g., *E. coli* or CM89 or *S. cerevisiae*), or in vitro by use of purified MAP (e.g., procedure of Miller et al., supra).

Moreover, the nucicic acid constructs of the present invention can also be used as part of a gene therapy protocol to deliver nucleic acids such as antisense nucleic acids. Thus, another aspect of the invention features expression vectors for in vivo or in vitro transfection with an antisense oligonucleotide.

In addition to viral transfer methods, non-viral methods can also be employed to introduce a subject nucleic acid, e.g., a sequence represented by one of SEQ ID Nos. 1–850, preferably SEQ ID Nos. 1–383, even more preferably SEQ ID Nos. 1–127, or a sequence complementary thereto, into the tissue of an animal. Most nonviral methods of gene transfer rely on normal mechanisms used by mammalian cells for the uptake and intracellular transport of macromolecules. In preferred embodiments, non-viral targeting means of the present invention rely on endocytic pathways for the uptake of the subject nucleic acid by the targeted cell. Exemplary targeting means of this type include liposomal derived systems, polylysine conjugates, and artificial viral envelopes.

A nucleic acid of any of SEQ ID Nos. 1–850, preferably SEQ ID Nos. 1–383, even more preferably SEQ ID Nos. 1–127, or a sequence complementary thereto, the corresponding cDNA, or the full-length gene may be used to express the partial or complete gene product. Appropriate nucleic acid constructs are purified using standard recombinant DNA techniques as described in, for example, Sambrook et al., (1989) *Molecular Cloning: A Laboratory Manual*, 2nd ed. (Cold Spring Harbor Press, Cold Spring Harbor, N.Y.), and under current regulations described in United States Dept. of HHS, National Institute of Health (NIH) Guidelines for Recombinant DNA Research. The polypeptides encoded by the nucleic acid may be expressed in any expression system, including, for example, bacterial, yeast, insect, amphibian and mammalian systems. Suitable vectors and host cells are described in U.S. Pat. No. 5,654, 173.

Bacteria. Expression systems in bacteria include those described in Chang et al., *Nature* (1978) 275:615, Goeddel et al., *Nature* (1979) 281:544, Goeddel et al., *Nucleic Acids Res.* (1980) 8:4057; EP 0 036,776, U.S. Pat. No. 4,551,433, DeBoer et al., *Proc. Natl. Acad. Sci.* (*USA*) (1983) 80:2125, and Siebenlist et al., *Cell* (1980) 20:269.

Yeast. Expression systems in yeast include those described in Hinnen et al., *Proc. Natl. Acad. Sci.* (*USA*) (1978) 75:1929; Ito et al., *J. Bacteriol.* (1983) 153:163; Kurtz et al., *Mol. Cell. Biol.* (1986) 6:142, Kunze et al., *J. Basic Microbiol.* (1985) 25:141; Gleeson et al., *J. Gen. Microbiol.* (1986) 132:3459, Roggenkamp et al., *Mol. Gen. Genet.* (1986) 202:302) Das et al., *J. Bacteriol.* (1984) 158:1165; De Louvencourt et al., *J. Bacteriol.* (1983) 154:737, Van den Berg et al., *Bio/Technology* (1990) 8:135; Kunze et al., *J. Basic Microbiol.* (1985) 25:141; Cregg et al., *Mol. Cell. Biol.* (1985) 5:3376, U.S. Pat. Nos. 4,837,148 and 4,929,555; Beach and Nurse, *Nature* (1981) 300:706; Davidow et al., *Curr. Genet.* (1985) 10:380, Gaillardin et al., *Curr. Genet.* (1985) 10:49, Ballance et al., *Biochem. Biophys. Res. Commun.* (1983) 112:284289; Tilburn et al., *Gene* (1983) 26:205221, Yelton et al., *Proc. Natl. Acad. Sci.* (*USA*) (1984) 81:14701474, Kelly and Hynes, *EMBO J.* (1985) 4:475479; EP 0 244,234, and WO 91/00357.

Insect Cells. Expression of heterologous genes in insects is accomplished as described in U.S. Pat. No. 4,745,051, Friesen et al. (1986) "The Regulation of Baculovirus Gene Expression" in: The Molecular Biology Of Baculoviruses (W. Doerfler, ed.), EP 0 127,839, EP 0 155,476, and Vlak et al., *J. Gen. Virol.* (1988) 69:765776, Miller et al., *Ann. Rev. Microbiol.* (1988) 42:177, Carbonell et al., *Gene* (1988) 73:409, Maeda et al., *Nature* (1985) 315:592594, Lebacq Verheyden et al., *Mol. Cell Biol.* (1988) 8:3129; Smith et al., *Proc. Natl. Acad. Sci.* (*USA*) (1985) 82:8404, Miyajima et al., *Gene* (1987) 58:273; and Martin et al., *DNA* (1988) 7:99. Numerous baculoviral strains and variants and corresponding permissive insect host cells from hosts are described in Luckow et al., *Bio/Technology* (1988) 6:4755, Miller et al., Generic Engineering (Setlow, J. K. et al. eds.), Vol. 8 (Plenum Publishing, 1986), pp. 277279, and Maeda et al., *Nature*, (1985) 315:592–594.

Mammalian Cells. Mammalian expression is accomplished as described in Dijkema et al., *EMBO J.* (1985) 4:761, Gorman et al., *Proc. Natl. Acad. Sci.* (*USA*) (1982) 79:6777, Boshart et al., *Cell* (1985) 41:521 and U.S. Pat. No. 4,399,216. Other features of mammalian expression are facilitated as described in Ham and Wallace, *Meth. Enz.* (1979)58:44, Barnes and Sato, *Anal. Biochem.* (1980) 102:255, U.S. Pat. Nos. 4,767,704, 4,657,866, 4,927,762, 4,560,655, WO 90/103430, WO 87/00195, and U.S. Pat. No. RE 30,985.

II. Therapeutic Nucleic Acid Constructs

One aspect of the invention relates to the use of the isolated nucleic acid, e.g.; SEQ ID Nos. 1–850, preferably SEQ ID Nos. 1–383, even more preferably SEQ ID Nos. 1–127, or a sequence complementary thereto, in antisense therapy. As used herein, antisense therapy refers to administration or in situ generation of oligonucleotide molecules or their derivatives which specifically hybridize (e.g., bind) under cellular conditions with the cellular mRNA and/or genomic DNA, thereby inhibiting transcription and/or translation of that gene. The binding may be by conventional base pair complementarity, or, for example, in the case of binding to DNA duplexes, through specific interactions in the major groove of the double helix. In general, antisense therapy refers to the range of techniques generally employed in the art, and includes any therapy which relies on specific binding to oligonucleotide sequences.

An antisense construct of the present invention can be delivered, for example, as an expression plasmid which, when transcribed in the cell, produces RNA which is complementary to at least a unique portion of the cellular mRNA. Alternatively, the antisense construct is an oligonucleotide probe which is generated ex vivo and which, when introduced into the cell, causes inhibition of expression by hybridizing with the mRNA and/or genomic sequences of a subject nucleic acid. Such oligonucleotide probes are preferably modified oligonucleotides which are resistant to endogenous nucleases, e.g., exonucleases and/or endonucleases, and are therefore stable in vivo. Exemplary nucleic acid molecules for use as antisense oligonucleotides are phosphoramidate, phosphorothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by Van der Krol et al. (1988) BioTechniques 6:958–976; and Stein et al. (1988) Cancer Res 48:2659–2668. With respect to antisense DNA, oligodeoxyribonucleotides derived from the translation initiation site, e.g., between the −10 and +10 regions of the nucleotide sequence of interest, are preferred.

Antisense approaches involve the design of oligonucleotides (either DNA or RNA) that are complementary to mRNA. The antisense oligonucleotides will bind to the mRNA transcripts and prevent translation. Absolute complementarity, although preferred, is not required. In the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex as the case may be). One skilled in the art can ascertain a tolerable degree of mismatch by use of standard procedures to determine the melting point of the hybridized complex.

Oligonucleotides that are complementary to the 5' end of the mRNA, e.g., the 5' untranslated sequence up to and including the AUG initiation codon, should work most efficiently at inhibiting translation. However, sequences complementary to the 3' untranslated sequences of mRNAs have recently been shown to be effective at inhibiting translation of mRNAs as well. (Wagner, R. 1994. Nature 372:333). Therefore, oligonucleotides complementary to either the 5' or 3' untranslated, non-coding regions of a gene could be used in an antisense approach to inhibit translation of endogenous mRNA. Oligonucleotides complementary to the 5' untranslated region of the mRNA should include the complement of the AUG start codon; Antisense oligonucleotides complementary to mRNA coding regions are typically less efficient inhibitors of translation but could also be used in accordance with the invention. Whether designed to hybridize to the 5', 3', or coding region of subject mRNA, antisense nucleic acids should be at least six nucleotides in length, and are preferably less than about 100 and more preferably less thin about 50, 25, 17 or 10 nucleotides in length.

Regardless of the choice of target sequence, it is preferred that in vitro studies are first performed to quantitate the ability of the antisense oligonucleotide to quantitate the ability of the antisense oligonucleotide to inhibit gene expression. It is preferred that these studies utilize controls that distinguish between antisense gene inhibition and nonspecific biological effects of oligonucleotides. It is also preferred that these studies compare levels of the target RNA or protein with that of an internal control RNA or protein. Additionally, it is envisioned that results obtained using, the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors), or agents facilitating transport across the cell membrane (see, e.g., Letsinger et al., 1989, Proc. Natl. Acad. Sci. U.S.A. 86:6553–6556; Lemaitre et al., 1987, Proc. Natl. Acad. Sci. 84:648–652; PCT Publication No. WO 88/09810, published Dec. 15, 1988) or the blood-brain barrier (see, e.g., PCT Publication No. WO 89/10134, published Apr. 25, 1988), hybridization-triggered cleavage agents (See, e.g., Krol et al., 1988, BioTechniques 6:958–976), or intercalating agents (See, e.g., Zon, 1988, Pharm. Res. 5:539–549). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxytriethyl) uracil, 5-carboxymethylaminoinethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-cliaminopurine.

The antisense oligonucleotide may also comprise at least one modified sugar moiety selected from the group including but not limited to arabinose, 2-fluoroarabinose, xylulose, and hexose.

The antisense oligonucleotide can also contain a neutral peptide-like backbone. Such molecules are termed peptide nucleic acid (PNA)-oligomers and are described, e.g., in Perry-O'Keefe et al. (1996) Proc. Natl. Acad. Sci. U.S.A. 93:14670 and in Eglom et al. (1993) Nature 365:566. One advantage of PNA oligomers is their capability to bind to complementary DNA essentially independently from the ionic strength of the medium due to the neutral backbone of the DNA. In yet another embodiment, the antisense oligonucleotide comprises at least one modified phosphate backbone selected from the group consisting of a phosphorothtoate, a phosphorodithioate, a phosphoramidothioate, a phosphoramidate, a phosphordiamidate, a methylphosphonate, an alkyl phosphotriester, and a formacetal or analog thereof.

In yet a further embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641). The oligonucleotide is a 2'-O-methylribonucleotide (Inoue et al., 1987, Nucl. Acids Res. 15:6131–12148), or a chimeric RNA-DNA analogue (Inoue et al., 1987, FEBS Lett. 215:327–330).

Oligonucleotides of the invention may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate olgonucleotides can be prepared by use of controlled pore glass polymer supports (Sarin et al., 1988, Proc. Natl. Acad. Sci. U.S.A. 85:7448–7451), etc.

While antisense nucleotides complementary to a coding region sequence can be used, those complementary to the transcribed untranslated region and to the region comprising the initiating methionine are most preferred.

The antisense molecules can be delivered to cells which express the target nucleic acid in vivo. A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systemically.

However, it is often difficult to achieve intracellular concentrations of the antisense sufficient to suppress translation on endogenous mRNAs. Therefore, a preferred approach utilizes a recombinant DNA construct in which the antisense oligonucleotide is placed under the control of a strong pol III or pol II promoter. The use of such a construct to transfect target cells in the patient will result in the transcription of sufficient amounts of single stranded RNAs that will form complementary base pairs with the endogenous transcripts and thereby prevent translation of the target mRNA. For example, a vector can be introduced in vivo such that it is taken up by a cell and directs the transcription of an antisense RNA. Such a vector can remain episomal or become chrormosomally integrated, as long as it can be transcribed to produce the desired antisense RNA. Such vectors can be constructed by recombinant DNA technology methods standard in the art Vectors can be plasmid, viral, or others known in the art for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Bernoist and Chambon, 1981, Nature 290:304–310), the promoter contained in the 3' long terminal repeat of Rous sarcoma virus (Yamamoto et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42), etc. Any type of plasmid, cosmid, YAC or viral vector can be used to prepare the recombinant DNA construct which can be introduced directly into the tissue site; e.g., the choroid plexus or hypothalamus. Alternatively, viral vectors can be used which selectively infect the desired tissue (e.g., for brain, herpesvirus vectors may be used), iii which case administration may be accomplished by another route (e.g., systemically).

In another aspect of the invention, ribozyme molecules designed to catalytically cleave target mRNA transcripts can be used to prevent translation of target mRNA and expression of a target protein (See, e.g., PCT International Publication WO90/11364, published Oct. 4, 1990; Sarver et al., 1990, Science 247:1222–1225 and U.S. Pat. No. 5,093,246). While ribozymes that cleave mRNA at site specific recognition sequences can be used to destroy target mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, 1988, Nature, 334:585–591. Preferably the ribozyme is engineered so that the cleavage recognition site is located near the 5' end of the target mRNA; i.e., to increase efficiency and minimize the intracellular accumulation of non-functional mRNA transcripts.

The ribozymes of the present invention also include RNA endoribonucleases (hereinafter "Cech-type ribozymes") such as the one which occurs naturally in *Tetrahymena thermophila* (known as the IVS, or L-19 IVS RNA) and which has been extensively described by Thomas Cech and collaborators (Zaug, et al., 1984, Science, 224:574–578; Zaug and Cech, 1986, Science, 231:470–475; Zaug, et al., 1986, Nature, 34;429–433; published International patent application No. WO88/04300 by University Patents Inc., Been and Cech, 1986, Cell, 47:207–216). The Cech-type ribozymes have an eight base pair active site which hybridizes to a target RNA sequence whereafter cleavage of the target RNA takes place. The invention encompasses those Cech-type ribozymes which target eight base-pair active site sequences that are present in a target gene.

As in the antisense approach, the ribozymes can be composed of modified oligonucleotides (e.g., for improved stability, targeting, etc.) and should be delivered to cells which express the target gene in vivo. A preferred method of delivery involves using a DNA construct "encoding" the ribozyme under the control of a strong constitutive pol III or pol II promoter, so that transfected cells will produce sufficient quantities of the ribozyme to destroy endogenous messages and inhibit translation. Because ribozymes, unlike antisense molecules, are catalytic, a lower intracellular concentration is required for efficiency.

Antisense RNA, DNA, and ribozyme molecules of the invention may be prepared by any method known in the art for the synthesis of DNA and RNA molecules. These include techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Moreover, various well-known modifications to nucleic acid molecules may be introduced as a means of increasing intracellular stability and half-life. Possible modifications include but are not limited to the addition of flanking sequences of ribonucleotides or deoxyribonucleotides to the 5' and/or 3' ends of the molecule or the use of phosphorothioate or 2' O-methyl rather than phosphodiesterase linkages within the oligodeoxyribonucleotide backbone.

VIII. Polypeptides of the Present Invention

The present invention makes available isolated polypeptides which are isolated from, or otherwise substantially free of other cellular proteins, especially other signal transduction factors and/or transcription factors which may normally be associated with the polypeptide. Subject polypeptides of the present invention include polypeptides encoded by the nucleic acids of SEQ ID Nos. 1–850, preferably SEQ ID Nos. 1–383, even more preferably SEQ ID Nos. 1–127, or a sequence complementary thereto, or polypeptides encoded by genes of which a sequence in SEQ ID Nos. 1–850, preferably SEQ ID Nos. 1–383, even more preferably SEQ ID Nos. 1–127, or a sequence complementary thereto, is a fragment. Polypeptides of the present invention include those proteins which are differentially regulated in tumor cells, especially colon cancer-derived cell lines (relative to normal cells, e.g., normal colon tissue and non-colon tissue). In preferred embodiments, the polypeptides are upregulated in tumor cells, especially colon cancer cancer-derived cell lines. In other embodiments, the polypeptides are downregulated in tumor cells, especially colon cancer-derived cell lines. Proteins which are upregulated, such as oncogenes, or downregulated, such as tumor suppressors, in aberrantly proliferating cells may be targets for diagnostic or therapeutic techniques. For example, upregulation of the cdc2 gene induces mitosis. Overexpression of the myt1 gene, a mitotic deactivator, negatively regulates the activity of cdc2. Aberrant proliferation may thus be induced either by upregulating cdc2 or by downregulating myt1.

The term "substantially free of other cellular proteins" (also referred to herein as "contaminating proteins") or "substantially pure or purified preparations" are defined as encompassing preparations of polypeptides having less than about 20% (by dry weight) contaminating protein, and preferably having less than about 5% contaminating protein. Functional forms of the subject polypeptides can be prepared, for the first time, as purified preparations by using a cloned nucleic acid as described herein. Full length proteins or fragments corresponding to one or more particular motifs and/or domains or to arbitrary sizes, for example, at least about 5, 10, 25, 50, 75, or 100 amino acids in length are within the scope of the present invention.

For example, isolated polypeptides can be encoded by all or a portion of a nucleic acid sequence shown in any of SEQ ID Nos. 1–850, preferably SEQ ID Nos. 1–383, even more preferably SEQ ID Nos. 1–127, or a sequence complementary thereto. Isolated peptidyl portions of proteins can be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry. For example, a polypeptide of the present invention may be arbitrarily divided into fragments of desired length with no overlap of the fragments, or preferably divided into overlapping fragments of a desired length. The fragments can be produced (recombinantly or by chemical synthesis) and tested to identify those peptidyl fragments which can function as either agonists or antagonists of a wild-type (e.g., "authentic") protein.

Another aspect of the present invention concerns recombinant forms of the subject proteins. Recombinant polypeptides preferred by the present invention, in addition to native proteins as described above are encoded by a nucleic acid, which is at least 60%, more preferably at least 80%, and more preferably 85%, and more preferably 90%, and more preferably 95% identical to an amino acid sequence encoded by SEQ ID Nos. 1–850. Polypeptides which are encoded by a nucleic acid that is at least about 98–99% identical with the sequence of SEQ ID Nos. 1–850 are also within the scope of the invention. Also included in the present invention are peptide fragments comprising at least a portion of such a protein.

In a preferred embodiment, a polypeptide of the present invention is a mammalian polypeptide and even more preferably a human polypeptide. In particularly preferred embodiment, the polypeptide retains wild-type bioactivity. It will be understood that certain post-translational modifications, e.g., phosphorylation and the like, can increase the apparent molecular weight of the polypeptide relative to the unmodified polypeptide chain.

The present invention further pertains to recombinant forms of one of the subject polypeptides. Such recombinant polypeptides preferably are capable of functioning in one of either role of an agonist or antagonist of at least one biological activity of a wild-type ("authentic") polypeptide of the appended sequence listing. The term "evolutionarily related to", with respect to amino acid sequences of proteins, refers to both polypeptides having amino acid sequences which have arisen naturally, and also to mutational variants of human polypeptides which are derived, for example, by combinatorial mutagenesis.

In general, polypeptides referred to herein as having an activity (e.g., are "bioactive") of a protein are defined as polypeptides which include an amino acid sequence encoded by all or a portion of the nucleic acid sequences shown in one of SEQ ID Nos. 1–850, preferably SEQ ID Nos. 1–383, even more preferably SEQ ID Nos. 1–127, or a sequence complementary thereto, and which mimic or antagonize all or a portion of the biological/biochemical activities of a naturally occurring protein. According to the present invention, a polypeptide has biological activity if it is a specific agonist or antagonist of a naturally occurring form of a protein.

Assays for determining whether a compound, e.g. a protein or variant thereof, has one or more of the above biological activities are well known in the art. In certain embodiments, the polypeptides of the present invention have activities such as those outlined above.

In another embodiment, the coding sequences for the polypeptide can be incorporated as a part of a fusion gene including a nucleotide sequence encoding a different polypeptide. This type of expression system can be useful under conditions where it is desirable to produce an immunogenic fragment of a polypeptide (see, for example, EP Publication No: 0259149; and Evans et al. (1989) Nature 339:385; Huang et al. (1988) J. Virol. 62:3855; and Schlienger et al. (1992) J. Virol. 66:2). In addition to utilizing fusion proteins to enhance immunogenicity, it is widely appreciated that fusion proteins can also facilitate the expression of proteins, and, accordingly, can be used in the expression of the polypeptides of the present invention (see, for example, Current Protocols in Molecular Biology, eds. Ausubel et al. (N.Y.: John Wiley & Sons, 1991)). In another embodiment, a fusion gene coding for a purification leader sequence, such as a poly-(His)/enterokinase cleavage site sequence at the N-terminus of the desired portion of the recombinant protein, can allow purification of the expressed fusion protein by affinity chromatography using a $Ni^{2+}$ metal resin. The purification leader sequence can then be subsequently removed by treatment with enterokinase to provide the purified protein (e.g., see Hochuli et al. (1987) J. Chromatography 411:177; and Janknecht et al. PNAS 88:8972).

Techniques for making fusion genes are known to those skilled in the art. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of nucleic acid fragments can be carried out using anchor primers which give rise to complementary overhangs between two consecutive nucleic acid fragments which can subsequently be annealed to generate a chimeric nucleic acid sequence (see, for example, Current Protocols in Molecular Biology, eds. Ausubel et al. John Wiley & Sons: 1992).

The present invention further pertains to methods of producing the subject polypeptides. For example, a host cell transfected with a nucleic acid vector directing expression of a nucleotide sequence encoding the subject polypeptides can be cultured under appropriate conditions to allow expression of the peptide to occur. Suitable media for cell culture are well known in the art. The recombinant polypeptide can be isolated from cell culture medium, host cells, or both using techniques known in the art for purifying proteins including ion-exchange chromatography, gel filtration chromatography, ultrafiltration, electrophoresis, and immunoaffinity purification with antibodies specific for such peptide. In a preferred embodiment, the recombinant polypeptide is a fusion protein containing a domain which facilitates its purification, such as GST fusion protein.

Moreover, it will be generally appreciated that, under certain circumstances, it may be advantageous to provide homologs of one of the subject polypeptides which function in a limited capacity as one of either an agonist (mimetic) or an antagonist, in order to promote or inhibit only a subset of the biological activities of the naturally occurring form of the protein. Thus, specific biological effects can be elicited by treatment with a homolog of limited function, and with fewer side effects relative to treatment with agonists or antagonists which are directed to all of the biological activities of naturally occurring forms of subject proteins.

Homologs of each of the subject polypeptide can be generated by mutagenesis, such as by discrete point mutation(s), or by truncation. For instance, mutation can give rise to homologs which retain substantially the same, or merely a subset, of the biological activity of the polypeptide from which it was derived. Alternatively, antagonistic forms of the polypeptide can be generated which are able to inhibit the function of the naturally occurring form of the protein, such as by competitively binding to a receptor.

The recombinant polypeptides of the present invention also include homologs of the wild-type proteins, such as versions of those proteins which are resistant to proteolytic cleavage, for example, due to mutations which alter ubiquitination or other enzymatic targeting associated with the protein.

Polypeptides may also be chemically modified to create derivatives by forming covalent or aggregate conjugates with other chemical moieties, such as glycosyl groups, lipids, phosphate, acetyl groups and the like. Covalent derivatives of proteins can be prepared by linking the chemical moieties to functional groups on amino acid sidechains of the protein or at the N-terminus or at the C-terminus of the polypeptide.

Modification of the structure of the subject polypeptides can be for such purposes as enhancing therapeutic or prophylactic efficacy, stability (e.g., ex vivo shelf life and resistance to proteolytic degradation), or post-translational modifications (e.g., to alter phosphorylation pattern of protein). Such modified peptides, when designed to retain at least one activity of the naturally occurring form of the protein, or to produce specific antagonists thereof, are considered functional equivalents of the polypeptides described in more detail herein. Such modified peptides can be produced, for instance, by amino acid substitution, deletion, or addition. The substitution variant may be a substituted conserved amino acid or a substituted non-conserved amino acid.

For example, it is reasonable to expect that an isolated replacement of a leucine with an isoleucine or valine, an aspartate with a glutamate, a threonine with a serine, or a similar replacement of an amino acid with a structurally related amino acid (i.e., isosteric and/or isoelectric mutations) will not have a major effect on the biological activity of the resulting molecule. Conservative replacements are those that take place within a family of amino acids that are related in their side chains. Genetically encoded amino acids can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. In similar fashion, the amino acid repertoire can be grouped as (1) acidic=aspartate, glutamate; (2) basic=lysine, arginine histidine, (3) aliphatic=glycine, alanine, valine, leucine. isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur containing cysteine and methionine. (see, for example, Biochemistry, $2^{nd}$ ed., Ed. by L. Stryer, V/H Freeman and Co.: 1981). Whether a change in the amino acid sequence of a peptide results in a functional homolog (e.g., functional in the sense that the resulting polypeptide mimics or antagonizes the wild-type form) can be readily determined by assessing the ability of the variant peptide to produce a response in cells in a fashion similar to the wild-type protein, or competitively inhibit such a response. Polypeptides in which more than one replacement has taken place can readily be tested in the same manner. The variant may be designed so as to retain biological activity of a particular region of the protein. In a non-limiting example, Osawa et al., 1994*, Biochemistry and Molecular International* 34:1003–1009, discusses the actin binding region of a protein from several different species. The actin binding regions of the these species are considered homologous based on the fact that they have amino acids that fall within "homologous residue groups." Homologous residues are judged according to the following groups (using single letter amino acid designations): STAG; ILVMF; HRK DEQN; and FYW. For example, an S, a T, an A or a G can be in a position and the function (in this case actin binding) is retained.

Additional guidance on amino acid substitution is available from studies of protein evolution. Go et al., 1980*, Int. J. Peptide Protein Res*. 15:211–224, classified amino acid residue sites as interior or exterior depending on their accessibility. More frequent substitution on exterior sites was confirmed to be general in eight sets of homologous protein families regardless of their biological functions and the presence or absence of a prosthetic group. Virtually all types of amino acid residues had higher mutabilities on the exterior than in the interior. No correlation between mutability and polarity was observed of amino acid residues in the interior and exterior, respectively. Amino acid residues were classified into one of three groups depending on their polarity: polar (Arg, Lys, His, Gin, Asn, Asp, and Glu); weak polar (Ala, Pro, Gly, Thr, and Ser), and nonpolar (Cys, Val, Met, Ile, Leu, Phe, Tyr, and Trp). Amino acid replacements during protein evolution were very conservative: 88% and 76% of them in the interior or exterior, respectively, were within the same group of the three. Inter-group replacements are such that weak polar residues are replaced more often by nonpolar residues in the interior and more often by polar residues on the exterior.

Querol et al., 1996*, Prot. Eng*. 9:265–271, provides general rules for amino acid substitutions to enhance protein thermostability. New glycosylation sites can be introduced as discussed in Olsen and Thomsen, 1991, 1. *J. Gen. Microbiol*. 137:579–585. An additional disulfide bridge can be introduced, as discussed by Perry and Wetzel, 1984*, Science* 226:555–557; Pantoliano et al., 1987*, Biochemistry* 26:2077–2082; Matsumura et al., 1989*, Nature* 342:291–293; Nishikawa et al., 1990*, Protein Eng*. 3:443–448; Takagi et al., 1990*, J. Chem*. 265:6874–6878; Clarke et al., 1993*, Biochemistry* 32:4322–4329; and Wakarchuk et al., 1994*, Protein Eng*. 7:1379–1386.

An additional metal binding site can be introduced, according to Toma et al., 1991*, Biochemistry* 30:97–106, and Haezerbrouck et al., 1993*, Protein Eng*. 6:643–649. Substitutions with prolines in loops can be made according to Masul et al., 1994*, Appl. Env. Microbiol*. 60:3579-9–3584; and Hardy et al., *FEBS Lett*. 317:89–92.

Cysteine-depleted muteins are considered variants within the scope of the invention. These variants can be constructed according to methods disclosed in U.S. Pat. No. 4,959,314, which discloses how to substitute other amino acids for cysteines, and how to determine biological activity and effect of the substitution. Such methods are suitable for proteins according to this invention that have cysteine residues suitable for such substitutions, for example to eliminate disulfide bond formation.

To learn the identity and function of the gene that correlates with an nucleic acid, the nucleic acids or corresponding amino acid sequences can be screened against profiles of protein families. Such profiles focus on common structural motifs among proteins of each family. Publicly available profiles are described above. Additional or alternative profiles are described below.

In comparing a new nucleic acid with known sequences, several alignment tools are available. Examples include PileUp, which creates a multiple sequence alignment, and is described in Feng et al., *J. Mol. Evol*. (1987) 25:351–360. Another method, GAP, uses the alignment method of Needleman et al. *J. Mol. Biol*. (1970) 48:443–453. GAP is best suited for global alignment of sequences. A third method, BestFit, functions by inserting gaps to maximize the number of matches using the local homology algorithm of Smith and Waterman, *Adv. Appl Math*. (1981) 2:482–489.

Examples of such profiles are described below.

Chemokines

Chemokines are a family of proteins that have been implicated in lymphocyte trafficking, inflammatory diseases, angiogenesis, hematopoiesis, and viral infection. See, for example, Rollins, *Blood* (1997) 90(3):909–928, and Wells et al., *J. Leuk Biol.* (1997)61:545–550. U.S. Pat. No. 5,605,817 discloses DNA encoding a chemokine expressed in fetal spleen. U.S. Pat. No. 5,656,724 discloses chemokine-like proteins and methods of use. U.S. Pat. No. 5,602,008 discloses DNA encoding a chemokine expressed by liver.

Mutants of the encoded chemokines are polypeptides having an amino acid sequence that possesses at least one amino acid substitution, addition, or deletion as compared to native chemokines. Fragments possess the same amino acid sequence of the native chemokines; mutants may lack the amino and/or carboxyl terminal sequences. Fusions are mutants, fragments, or the native chemokines that also include amino and/or carboxyl terminal amino acid extensions.

The number or type of the amino acid changes is not critical, nor is the length or number of the amino acid deletions, or amino acid extensions that are incorporated in the chemokines as compared to the native chemokine amino acid sequences. A polynucleotide encoding one of these variant polypeptides will retain at least about 80% amino acid identity with at least one known chemokine. Preferably, these polypeptides will retain at least about 85% amino acid sequence identity, more preferably, at least about 90%; even more preferably, at least about 95%. In addition, the variants will exhibit at least 80%; preferably about 90%; more preferably about 95% of at least one activity exhibited by a native chemokine. Chemokine activity includes immunological, biological, receptor binding, and signal transduction functions of the native chemokine.

Chemotaxis. Assays for chemotaxis relating to neutrophils are described in Walz et al, *Biochem. Biophys. Res. Commun.* (1987)149:755, Yoshimura et al, *Proc. Natl. Acad. Sci.* (USA) (1987) 84:9233, and Schroder et al., *J. Immunol.* (1987) 139:3474; to lymphocytes, Larsen et al, *Science* (1989) 243:1464, Carr et al, *Proc. Natl. Acad Sci.* (USA) (1994) 91:3652; to tumor-infiltrating lymphocytes, Liao et al., *J. Exp. Med.* (1995). 182:1301; to hemopoietic progenitors, Aiuti et al., *J Exp. Med.* (1997) 185:111; to monocytes, Valente et al., *Biochem.* (1988) 27:4162; and to natural killer cells, Loetscher et al, *J. Immunol.* (1996) 156:322, and Allavena et al., Eur. J. Immunol (1994) 24:3233.

Assays for determining the biological activity of attracting eosinophils are described in Dahinden et al., *J. Exp. Med.* (1994) 179:751, Weber et al, *J. Immunol.* (1995) 154:4166, and Noso et al., *Biochem. Biophys. Res. Commun.* (1994) 200:1470; for attracting dendritic cells, Sozzani et al., *J. Immunol.* (1995) 155:3292; for attracting basophils, in Dahinden et al., *J. Exp. Med.* (1994) 179:751, Alam et al., *J. Immunol.* (1994) 152:1298, Alam et al., *J. Exp. Med.* (1992) 176:781; and for activating neutrophils, Maghazaci et al, *Eur. J. Immunol.* (1996) 26:315, and Taub et al., *J. Immunol.* (1995) 155:3877. Native chemokines can act as mitogens for fibroblasts, assayed as described in Mullenbach et al., *J. Biol. Chem.* (1986) 261:719.

Receptor Binding. Native chemokines exhibit binding activity with a number of receptors. Description of such receptors and assays to detect binding are described in, for example, Murphy et al., *Science.* (1991) 253:1280; Combadiere et al, *J. Biol. Chem.* (1995) 270:29671; Daugherty et al., *J. Exp. Med.* (1996) 183:2349; Samson et al., *Biochem.* (1996) 35:3362; Raport et al., *J. Biol. Chem.* (1996) 271:17161; Combadiere et al., *J. Leukoc. Biol.* (1996) 60:147; Baba et al., *J. Biol. Chem.* (1997) 23:14893; Yosida et al., *J. Biol. Chem.* (1997) 272:13803; Arvannitakis et al., *Nature.* (1997) 385:347, and many other assays are known in the art.

Kinase Activation. Assays for kinase activation are described by Yen et al, *J. Leukoc. Biol.* (1997) 61:529; Dubois et al., *J. Immunol.* (1996) 156:1356; Turner et al, *J. Immunol.* (1995)155:2437. Assays for inhibition of angiogenesis or cell proliferation are described in Malone et al., *Science.* (1990) 247:77. Glycosaminoglycan production can be induced by native chemokines, assayed as described in Castor et al., *Proc. Natl. Acad Sci.* (USA) (1983) 80:765. Chemokine mediated histamine release from basophils is assayed as described in Dahinden et al., *J. Exp. Med.* (1939) 170:1787; and White et al., *Immunol. Let.* (1989) 22:151. Heparin binding is described in Luster et al., *J. Exp. Med.* (1995) 182:219

Dimerization Activiy. Chemokines can possess dimerization activity, which can be assayed according to Burrows et al., *Biochem.* (1994) 33:1274 1; and Zhang et al., *Mol. Cell. Biol.* (1995) 15:485 1. Native chemokines can play a role in the inflammatory response of viruses. This activity can be assayed as described in Bleul et al, *Nature* (1996) 382:829; and Oberlin et al, *Nature* (1996) 382:833. Exocytosis of monocytes can be promoted by native chemokines. The assay for such activity is described in Uguccioni et al., *Eur. J. Immunol.* (1995) 25:64. Native chemokines also can inhibit hemapoietic stem cell proliferation. The method for testing for such activity is reported in Graham et al., *Nature* (1990) 344:442.

Death Domain Proteins

Several protein families contain death domain motifs (Feinstein and Kimchi, *TIBS Letters* (1995) 20:242–244). Some death domain-containing proteins are implicated in cylotoxic intracellular signaling (Cleveland and Ihle, *Cell* (1995) 81:479–482, Pan et al, *Science* (1997) 276:111–113, Duan and Dixit, *Nature* (1997) 385:86–89, and Chinnaiyan et al, *Science* (1996) 274:990–992). U.S. Pat. No. 5,563,039 describes a protein homologous to TRADD (Tumor Necrosis Factor Receptor-1 Associated Death Domain containing protein), and modifications of the active domain of TRADD that retain the functional characteristics of the protein, as well as apoptosis assays for testing the function of such death domain containing proteins. U.S. Pat. No. 5,658,883 discloses biologically active TGF-B1 peptides. U.S. Pat. No. 5,674,734 discloses protein RIP which contains a C-terminal death domain and an N-terminal kinase domain.

Leukemia Inhibitory Factor (LIF)

An LIF profile is constructed from sequences of leukemia inhibitor factor, CT-1 (cardiotrophin-1), CNTF (ciliary neurotrophic factor), OSM (oncostatin M), and IL-6 (interleukin-6). This profile encompasses a family of secreted cytokines that have pleiotropic effects on many cell types including hepatocytes, osteoclasts, neuronal cells and cardiac myocytes, and can be used to detect additional genes encoding such proteins. These molecules are all structurally related and share a common co-receptor gp130 which mediates intracellular signal transduction by cytoplasmic tyrosine kinases such as src.

Novel proteins related to this family are also likely to be secreted, to activate gp130 and to function in the development of a variety of cell types. Thus new members of this family would be candidates to be developed as growth or survival factors for the cell types that they stimulate. For more details on this family of cytokines, see Pennica et al., *Cytokine and Growth Factor Reviews* (1996) 7:81–91. U.S. Pat. No. 5,420,247 discloses LIF receptor and fusion proteins. U.S. Pat. No. 5,443,825 discloses human LIF.

Angiopoietin

Angiopoietin-1 is a secreted and of the TIE-2 tyrosine kinase; it functions as an angiogenic factor critical for normal vascular development. Angiopoietin-2 is a natural antagonist of angiopoietin-1 and thus functions as an anti-angiogenic factor. These two proteins are structurally similar and activate the same receptor. (Folkman and D'Amore, Cell (1996) 87:1153–1155, and Davis et al, Cell (1996) 87:1161–1169.)

The angiopoietin molecules are composed of two domains, a coiled-coil region and a region related to fibrinogen. The fibrinogen domain is found in many molecules including ficolin and tesascin, and is well defined structurally with many members.

Receptor Protein-Tyrosine Kinases

Receptor Protein-Tyrosine Kinases or RPTKs are described in Lindberg, *Annu. Rev. Cell Biol* (1994) 10:251–337.

Growth Factors: Epidermal Growth Factor (EGF) and Fibroblast Growth Factor (FGF)

For a discussion of growth factor superfamilies, see *Growth Factors: A Practical Approach*, Appendix A1 (Ed. McKay and Leigh, Oxford University Press, N.Y., 1993) pp. 237–243.

The alignments (pretty box) for EGF and FGF are shown in FIGS. 1 and 2, respectively. U.S. Pat. No. 4,444,760 discloses acidic brain fibroblast growth factor, which is active in the promotion of cell division and wound healing. U.S. Pat. No. 5,439,818 discloses DNA encoding human recombinant basic fibroblast growth factor, which is active in wound healing. U.S. Pat. No. 5,604,293 discloses recombinant human basic fibroblast growth factor, which is useful for wound healing. U.S. Pat. No. 5,410,832 discloses brain-derived and recombinant acidic fibroblast growth factor, which act as mitogens for mesoderm and neuroectoderm-derived cells in culture, and promote wound healing in soft tissue, cartilaginous tissue and musculo-skeletal tissue. U.S. Pat. No. 5,387,673 discloses biologically active fragments of FGF that retain activity.

Proteins of the TNF Family

A profile derived from the TNF family is created by aligning sequences of the following TNF family members: nerve growth factor (NGF), lymphotoxin, Fas ligand, tumor necrosis factor (TNF), CD40 ligand, TRAIL, ox40 ligand, 4-1BB ligand, CD27 ligand, and CD30 ligand. The profile is designed to identify sequences of proteins that constitute new members or homologues of this family of proteins.

U.S. Pat. No. 5,606,023 discloses mutant TNF proteins; U.S. Pat. No. 5,597,899 and U.S. Pat. No. 5,486,463 disclose TNF muteins; and U.S. Pat. No. 5,652,353 discloses DNA encoding TNFα muteins.

Members of the TNF family of proteins have been show in vitro to multimerize, as described in Burrows et al, *Biochem.* (1994) 33:12741 and Zhang et al, *Mol Cell Biol.* (1995) 154851 and bind receptors as described in Browning et al., *J. Immunol.* (1994) 147:1230, Androlewicz et al, *J. Biol. Chem.* (1992) 267:2542, and Crowe et al., *Science* (1994) 264:707.

In vivo, TNFs proteolytically cleave a target protein as described in Kriegel et al, Cell (1988) 53:45 and Mohler et al., *Nature* (1994) 370:218 and demonstrate cell proliferation and differentiation activity. T-cell or thymocyte proliferation is assayed as described in Armitage et al., *Eur. J Immunol.* (1992) 22:447; Current Protocols in Immunology, ed. J. E. Coligan et al., 3.1–3.19; Takai et al, *J. Inmmunol.* (1986) 137:3494–3500, Bertagnoli et al., *J. Immunol.* (1990) 145:1706–1712, Bertagnoli et al., *J. Immunol.* (1991) 133:327–340, Bertagnoli et al, *J. Immunol.* (1992) 149:3778–3783, and Bowman et al., *J. Immunol.* (1994) 152:1756–1761. B cell proliferation and Ig secretion are assayed as described in Maliszewski, *J. Immunol.* (1990) 144:3028–3033, and Assays for B Cell Function: In vitro antibody production, Mond and Brunswick, Current Protocols in Immunol., Coligan Ed vol. 1 pp 3.8.1–3.8.16, John Wiley and Sons, Toronto 1994, Kehrl et al, *Science* (1987) 238:1144 and Boussiotis et al., *PNAS USA* (1994) 91:7007.

Other in vivo activities include upregulation of cell surface antigens, upregulation of costimulatory molecules, and cellular aggregation/adhesion as described in Barrett et al., *J. Immunol.* (1991) 146:1722; Bjorck et al., *Eur. J. Immunol.* (1993) 23:1771; Clark et al., *Annu. Rev. Immunol.* (1991) 9:97; Ranheim et al., *J. Exp. Med.* (1994) 177:925; Yellin, *J. Immunol.* (1994) 153:666; and Gruss et al., *Blood* (1994) 84:2305.

Proliferation and differentiation of hematopoictic and lymphopoietic cells has also been shown in vivo for TNFs, using assays for embryonic differentiation and hematopoiesis as described in Johansson et al, *Cellular Biology* (1995) 15:141–151, Keller et al, *Mol. Cell. Biol.* (1993) 13:473–486, McClanahan et al, *Blood* (1993) 81:2903–2915 and using assays to detect stem cell survival and differentiation as described in Culture of Hematopoictic Cells, Freshney et al., eds, pp 1–21, 23–29, 139–162, 163–179, and 265–268, Wiley-Liss, Inc., New York, N.Y., 1994, and Hirajama et al., *PNAS USA* (1992) 89:5907–5911.

In vivo activities of TNFs also include lymphocyte survival and apoptosis, assayed as described in Darzynkewicz et al, *Cytometry* (1992) 13:795–808; Gorczca et al, *Leukemia* (1993) 7:659–670; Itoh et al., *Cell* (1991) 66:233–243; Zacharduk, *J. Immunol.* (1990) 145:4037–4045; Zamai et al, *Cytometry* (1993) 14:891–897; and Gorezyca et al., *Int'l. J. Oncol.* (1992) 1:639–648.

Some members of the TNF family are cleaved from the cell surface; others remain membrane bound. The three-dimensional structure of TNF is discussed in Sprang and Eck, Tumor Necrosis Factors; supra.

TNF proteins include a transmembrane domain. The protein is cleaved into a shorter soluble version, as described in Kriegler et al, *Cell* (1988) 53:45–53, Perez et al., *Cell* (1990) 63:251–258, and Shaw et al., *Cell* (1986) 46:659–667. The transmembrane domain is between amino acid 46 and 77 and the cytoplasmic domain is between position 1 and 45 on the human form of TNFα. The 3-dimensional motifs of TNF include a sandwich of two pleated β sheets. Each sheet is composed of anti-parallel α strands, α Strands facing each other on opposite sites of the sandwich are connected by short polypeptide loops, as described in Van Ostade et al, *Protein Engineering* (1994) 7(1):5–22, and Sprang et al., Tumor Necrosis Factors; supra.

Residues of the TNF family proteins that are involved in the β sheet secondary structure have been identified as described in Van Ostade et al., *Protein Engineering* (1994) 7(1):5–22, and Sprang et al., Tumor Necrosis Factors; supra.

TNF receptors are disclosed in U.S. Pat. No. 5,395,760. A profile derived from the TNF receptor family is created by aligning sequences of the TNF receptor family, including Apol/Fas, TNFR I and II, death receptor3 (DR3), CD40, ox40, CD27, and CD30. Thus, the profile is designed to identify, from the nucleic acids of the invention, sequences of proteins that constitute new members or-homologs of this family of proteins.

Tumor necrosis factor receptors exist in two forms in humans: p55 TNFR and p75 TNFR, both of which provide intracellular signals upon binding with a ligand. The extracellular domains of these receptor proteins are cysteine rich. The receptors can remain membrane bound, although some forms of the receptors are cleaved forming soluble receptors. The regulation, diagnostic, prognostic, and therapeutic value of soluble TNF receptors is discussed in Aderka, *Cytokine and Growth Factor Reviews*, (1996) 7(3):231–240.

PDGF Family

U.S. Pat. No. 5,326,695 discloses platelet derived growth factor agonists; bioactive portions of PDGF-B are used as agonists. U.S. Pat. No. 4,845,075 discloses biologically active B-chain homodimers, and also includes variants and derivatives of the PDGF-B chain. U.S. Pat. No. 5,128,3-21 discloses PDGF-analogs and methods of use. Proteins having the same bioactivity as PDGF are disclosed, including A and B chain proteins.

Kinase (Including MKK) Family

U.S. Pat. No. 5,650,501 discloses serine/threonine kinase, associated with mitotic and meiotic cell division; the protein has a kinase domain in its N-terminal and 3 PEST regions in the C-terminus. U.S. Pat. No. 5,605,825 discloses human PAK65, a serine protein kinase.

The foregoing discussion provides a few examples of the protein profiles that can be compared with the nucleic acids of the invention. One skilled in the art can use these and other protein profiles to identify the genes that correlate with the nucleic acids.

IX. Determining the Function of the Encoded Expression Products

Ribozymes, antisense constructs, dominant negative mutants, and triplex formation can be used to determine function of the expression product of an nucleic acid-related gene.

A. Ribozymes

Trans-cleaving catalytic RNAs (ribozymes) are RNA molecules possessing endoribonuclease activity. Ribozymes are specifically designed for a particular target, and the target message must contain a specific nucleotide sequence. They are engineered to cleave any RNA species site-specifically in the background of cellular RNA. The cleavage event renders the mRNA unstable and prevents protein expression. Importantly, ribozymes can be used to inhibit expression of a gene of unknown function for the purpose of determining its function in an in vitro or in vivo context, by detecting the phenotypic effect.

One commonly used ribozyme motif is the hammerhead, for which the substrate sequence requirements are minimal. Design of the hammerhead ribozyme is disclosed in Usman et al., *Current Opin. Struct. Biol.* (1996) 6:527–533. Usman also discusses the therapeutic uses of ribozymes. Ribozymes can also be prepared and used as described in Long et al, *FASEB J.* (1993) 7:25; Symons, *Ann. Rev. Biochem.* (1992) 61:641; Perrotta et al., *Biochem.* (1992) 31:16–17; Ojwang et al, *Proc. Natl. Acad. Sci.* (USA) (1992) 89:10802–10806; and U.S. Pat. No. 5,254,678. Ribozyme cleavage of HIV-I RNA is described in U.S. Pat. No. 5,144,019; methods of cleaving RJN using ribozymes is described in U.S. Pat. No. 5,116,742; and methods for increasing the specificity of ribozymes are described in U.S. Pat. No. 5,225,337 and Koizumi et al., *Nucleic Acid Res.* (1989) 17:7059–7071. Preparation and use of ribozyme fragments in a hammerhead structure are also described by Koizumi et al, *Nucleic Acids Res.* (1989) 17:7059–7071. Preparation and use of ribozyme fragments in a hairpin structure are described by Chowrira and Burke, *Nucleic Acids Res.* (1992) 20:2835. Ribozymes can also be made by rolling transcription as described in. Daubendiek and Kool, *Nat. Biotechnol.* (1997) 15(3) :273–277.

The hybridizing region of the ribozyme may be modified or may be prepared as a branched structure as described in Horn and Urdea, *Nucleic Acids Res.* (1989) 17:6959–67. The basic structure of the ribozymes may also be chemically altered in ways familiar to those skilled in the art, and chemically synthesized ribozyrmes can be administered as synthetic oligonucleotide derivatives modified by monomeric units. In a therapeutic context, liposome mediated delivery of ribozymes improves cellular uptake, as described in Birikh et al., *Eur. J. Biochem.* (1997) 245:1–16.

Using the nucleic acid sequences of the invention and methods known in the art, ribozymes are designed to specifically bind and cut the corresponding mRNA species. Ribozymes thus provide a means to inhibit the expression of any of the proteins encoded by the disclosed nucleic acids or their full-length genes. The full-length gene need not be known in order to design and use specific inhibitory ribozymes. In the-case of an nucleic acid or cDNA of unknown function, ribozymes corresponding to that nucleotide sequence can be tested in vitro for efficacy in cleaving the target transcript. Those ribozymes that effect cleavage in vitro are further tested in vivo. The ribozyme can also be used to generate an animal model for a disease, as described in Birikh et al., *Eur. J. Biochem.* (1997) 245:1-1–6. An effective ribozyme is used to determine the function of the gene of interest by blocking its transcription and detecting a change in the cell. Where the gene is found to be a mediator in a disease, an effective ribozyme is designed and delivered in a gene therapy for blocking transcription and expression of the gene.

Therapeutic and functional genomic applications of ribozymes proceed beginning with knowledge of a portion of the coding sequence of the gene to be inhibited. Thus, for many genes, a partial nucleic acid sequence provides adequate sequence for constructing an effective ribozyme. A target cleavage site is selected in the target sequence, and a ribozyme is constructed based on the 5' and 3' nucleotide sequences that flank the cleavage site. Retroviral vectors are engineered to express monomeric and multimeric hammerhead ribozymes targeting the mRNA of the target coding sequence. These monomeric and multimeric ribozymes are tested in vitro for an ability to cleave the target mRNA. A cell line is stably transduced with the retroviral vectors expressing the ribozymes, and the transduction is confirmed by Northern blot analysis and reverse-transcription polywerase chain reaction (RT-PCR). The cells are screened for inactivation of the target mRNA by such indicators as reduction of expression of disease markers or reduction of the gene product of the target mRNA.

B. Antisense

Antisense nucleic acids are designed to specifically bind to RNA, resulting in the formation of RNA-DNA or RNA-RNA hybrids, with an arrest of DNA replication, reverse transcription or messenger RNA translation. Antisense polynucleotides based on a selected nucleic acid sequence can interfere with expression of the corresponding gene Antisense polynucleotides are typically generated within the cell by expression from antisense constructs that contain the antisense nucleic acid strand as the transcribed strand. Antisense nucleic acids will bind and/or interfere with the translation of nucleic acid-related mRNA. The expression products of control cells and cells treated with the antisense construct are compared to detect the protein product of the gene corresponding to the nucleic acid. The protein is isolated and identified using routine biochemical methods.

One rationale for using antisense methods to determine the function of the gene corresponding to an nucleic acid is the biological activity of antisense therapeutics. Antisense therapy for a variety of cancers is in clinical phase and has been discussed extensively in the literature. Reed reviewed antisense therapy directed at the Bcl-2 gene in tumors; gene transfer-mediated overexpression of Bcl-2 in tumor cell lines conferred resistance to many types of cancer drugs. (Reed. J. C., *N.C.I.* (1997) 89:988–990). The potential for clinical development of antisense inhibitors of as is discussed by Cowsert., L. M., *Anti-Cancer Drug Design* (1997) 12:359–371. Additional important antisense targets include leukemia (Geurtz, A. M., *Anti-Cancer Drug Design* (1997) 12:341–358); human C-ref kinase (Moths, B. P., *Anti-Cancer Drug Design* (1997) 12:327–339); and protein kinase C (McGraw et al., *Anti-Cancer Drug Design* (1997) 12:315–326.

Given the extensive background literature and clinical experience in antisense therapy, one skilled in the art can use selected nucleic acids of the invention as additional potential therapeutics. The choice of nucleic acid can be narrowed by first testing them for binding to "hot spot" regions of the genome of cancerous cells. If an nucleic acid is identified as binding to a "hot spot", testing the nucleic acid as an antisense compound in the corresponding cancer cells clearly is warranted.

Ogunbiyi et al., *Gastroenterology* (1997) 113(3): 761–766 describe prognostic use of allelic loss in colon cancer; Barks et al., *Genes, Chromosomes, and Cancer* (1997) 19(4):278–285 describe increased chromosome copy number detected by FISH in malignant melanoma; Nishizake et al., *Genes, Chromosomes, and Cancer* (1997) 19(4) :267–272 describe genetic alterations in primary breast cancer and their metastases and direct comparison using modified comparative (genome hybridization; and Elo et al., *Cancer Research* (1997) 57(16):3356–3359 disclose that loss of heterozygosity at 16z24.1-q24.2 is significantly associated with metastatic and aggressive behavior of prostate cancer.

C. Dominant Negative Mutations

As an alternative method for identifying function of the nucleic acid-related gene, dominant negative mutations are readily generated for corresponding proteins that are active as homomultimers. A mutant polypeptide will interact with wild-type polypeptides (made from the other allele) and form a non-functional multimer. Thus, a mutation is in a substrate-binding domain, a catalytic domain, or a cellular localization domain. Preferably, the mutant polypeptide will be overproduced. Point mutations are made that have such an effect. In addition, fusion of different polypeptides of various lengths to the terminus of a protein can yield dominant negative mutants. General strategies are available for making dominant negative mutants. See Herskowitz, *Nature* (1987) 329:219–222. Such a technique can be used for creating a loss-of-function mutation, which is useful for determining the function of a protein.

D. Triplex Formation

Endogenous gene expression can also be reduced by inactivating or "knocking out" the gene or its promoter using targeted homologous recombination. (e.g., see Smithies et al., 1985, Nature 317:230–234; Thomas & Capecchi, 1987, Cell 51:503–512; Thompson et al, 1989 Cell 5:313–321; each of which is incorporated by reference herein in its entirety). For example, a mutant, non-functional gene (or a completely unrelated DNA sequence) flanked by DNA homologous to the endogenous gene (either the coding regions or regulatory regions of the gene) can be used, with or without a selectable marker and/or a negative selectable marker, to transfect cells that express that gene in vivo. Insertion of the DNA construct, via targeted homologous recombination, results in inactivation of the gene.

Alternatively, endogenous gene expression can be reduced by targeting deoxyribonucleotide sequences complementary to the regulatory region of the target gene (i.e., the gene promoter and/or enhancers) to form triple helical structures that prevent transcription of the gene in target cells in the body. (See generally, Helene, C. 1991, Anticancer Drug Des., 6(6):569–84; Helene, C., et al., 1992, Ann, N.Y. Accad. Sci., 660:27–36; and Maher, L. J., 1992, Bioassays 14(12):807–15).

Nucleic acid molecules to be used in triple helix formation for the inhibition of transcription are preferably single stranded and composed of deoxyribonucleotides. The base composition of these oligonucleotides should promote triple helix formation via Hoogsteen base-pairing rules, which generally require sizable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC pairs, in which the majority of the purine residues are located on a single strand of the targeted duplex, resulting in CGC triplets across the three strands in the triplex.

Alternatively, the potential sequences that can be targeted for triple helix formation may be increased by creating a so called "switchback" nucleic acid molecule. Switchback molecules are synthesized in an alternating 5'-3', 3'-5' manner, such that they base pair with first one strand of a duplex and then the other, eliminating the necessity for a sizable stretch of either purines or pyrimidines to be present on one strand of a duplex.

Antisense RNA and DNA, ribozyme, and triple helix molecules of the invention may be prepared by any method known in the art for the synthesis of DNA and RNA molecules. These include techniques for chemically synthesizing oligodeoxyribonucleotides and oligoribonucleotides well known in the art such as for example solid phase phosphoramidite chemical synthesis. Alternatively, RNA molecules may be generated by in vitro and in viva transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Moreover, various well known modifications to nucleic acid molecules may be introduced as a means of increasing intracellular stability and half-life. Possible modifications include but are not limited to the addition of flanking sequences of ribonucleotides or deoxyribonucleotides to the 5' and/or 3' ends of the molecule or the use of phosphorothioate or 2' O-methyl rather than phosphodiesterase linkages within the oligodeoxyribonucleotide backbone.

X. Diagnostic & Prognostic Assays and Drug Screening Methods

The present invention provides method for determining whether a subject is at risk for developing a disease or condition characterized by unwanted cell proliferation by detecting the disclosed biomarkers, i.e., the disclosed nucleic acid markers (SEQ ID Nos. 1–850) and/or polypeptide markers for colon cancer encoded thereby.

In clinical applications, human tissue samples can be screened for the presence and/or absence of the biomarkers identified herein. Such samples could consist of needle biopsy cores, surgical resection samples, lymph node tissue, or serum. For example, these methods include obtaining a biopsy, which is optionally fractionated by cryostat sectioning to enrich tumor cells to about 80% of the total cell population. In certain embodiments, nucleic acids extracted from these samples may be amplified using techniques well known in the art. The levels of selected markers detected would be compared with statistically valid groups of metastatic, non-metastatic malignant, benign, or normal colon tissue samples.

In one embodiment, the diagnostic method comprises determining whether a subject has an abnormal mRNA and/or protein level of the disclosed markers, such as by Northern blot analysis, reverse transcription-polymerase chain reaction (RT-PCR), in situ hybridization, immunoprecipitation, Western blot hybridization. or immunohistochemistry. According to the method, cells are obtained from a subject and the levels of the disclosed biomarkers, protein or mRNA level, is determined and compared to the level of these markers in a healthy subject. An abnormal level of the biomarker polypeptide or mRNA levels is likely to be indicative of cancer such as colon cancer.

Accordingly, in one aspect, the invention provides probes and primers that are specific to the unique nucleic acid markers disclosed herein. Accordingly, the nucleic acid probes comprise a nucleotide sequence at least 12 nucleotides in length, preferably at least 15 nucleotides, more preferably, 25 nucleotides, and most preferably at least 40 nucleotides, and up to all or nearly all of the coding sequence which is complementary to a portion of the coding sequence of a marker nucleic acid sequence, which nucleic acid sequence is represented by SEQ ID Nos. 1–850 or a sequence complementary thereto.

In one embodiment, the method comprises using a nucleic acid probe to determine the presence of cancerous cells in a tissue from a patient. Specifically, the method comprises:

1. providing a nucleic acid probe comprising a nucleotide sequence at least 12 nucleotides in length, preferably at least 15 nucleotides, more preferably, 25 nucleotides, and most preferably at least 40 nucleotides, and up to all or nearly all of the coding sequence which is complementary to a portion of the coding sequence of a nucleic acid sequence represented by SEQ ID Nos. 1–850 or a sequence complementary thereto and is differentially expressed in tumors cells, such as colon cancer cells;
2. obtaining a tissue sample from a patient potentially comprising cancerous cells;
3. providing a second tissue sample containing cells substantially all of which are non-cancerous;
4. contacting the nucleic acid probe under stringent conditions with RNA of each of said first and second tissue samples (e.g., in a Northern blot or in situ hybridization assay); and
5. comparing (a) the amount of hybridization of the probe with RNA of the first tissue sample, with (b) the amount of hybridization of the probe with RNA of the second tissue sample;

wherein a statistically significant difference in the amount of hybridization with the RNA of the first tissue sample as compared to the amount of hybridization with the RNA of the second tissue sample is indicative of the presence of cancerous cells in the first tissue sample.

In one aspect, the method comprises in situ hybridization with a probe derived from a given marker nucleic acid sequence, which nucleic acid sequence is represented by SEQ ID Nos. 1–850 or a sequence complementary thereto. The method comprises contacting the labeled hybridization probe with a sample of a given reduced cellular amount of the marker polypeptide relative to a normal cell of similar tissue origin. For example, a cell may have less than about 50%, 25%, 10%, or 5% of the marker polypeptide that a normal control cell. In particular, the assay evaluates the level of marker polypeptide in the test cells, and, preferably, compares the measured level with marker polypeptide detected in at least one control cell, e.g., a normal cell and/or a transformed cell of known phenotype.

Of particular importance to the subject invention is the ability to quantitate the level of marker polypeptide as determined by the number of cells associated with a normal or abnormal marker polypeptide level. The number of cells with a particular marker polypeptide phenotype may then be correlated with patient prognosis. In one embodiment of the invention, the marker polypeptide phenotype of the lesion is determined as a percentage of cells in a biopsy which are found to have abnormally high/low levels of the marker polypeptide. Such expression may be detected by immunohistochemical assays, dot-blot assays, ELISA and the like.

Where tissue samples are employed, immunohistochemical staining may be used to determine the number of cells having the marker polypeptide phenotype. For such staining, a multiblock of tissue is taken from the biopsy or other tissue sample and subjected to proteolytic hydrolysis, employing such agents as protease K or pepsin. In certain embodiments, it may be desirable to isolate a nuclear fraction from the sample cells and detect the level of the marker polypeptide in the nuclear fraction.

The tissue samples are fixed by treatment with a reagent such as formalin, glutaraldehyde, methanol, or the like. The samples are then incubated with an antibody, preferably a monoclonal antibody, with binding specificity for the marker polypeptides. This antibody may be conjugated to a label for subsequent detection of binding. Samples are incubated for a time sufficient for formation of the immunocomplexes. Binding of the antibody is then detected-by virtue of a label conjugated to this antibody. Where the antibody is unlabeled, a second labeled antibody may be employed, e.g., which is specific for the isotype of the anti-marker polypeptide antibody. Examples of labels which may be employed include radionuclides, fluorescers, chemiluminescers, enzymes and the like.

Where enzymes are employed, the substrate for the enzyme may be added to the samples to provide a colored or fluorescent product. Examples of suitable type of tissue potentially containing cancerous or precancerous cells as well as normal cells, and determining whether the probe labels some cells of the given tissue type to a degree significantly different (e.g., by at least a factor of two, or at least a factor of five, or at least a factor of twenty; or at least a factor of fifty) than the degree to which it labels other cells of the same tissue type.

Also within the invention is a method of determining the phenotype of a test cell from a given human tissue, e.g., whether the cell is (a) normal, or (b) cancerous or precancerous, by contacting the mRNA of a test cell with a nucleic acid probe at least 12 nucleotides in length, preferably at least 15 nucleotides, more preferably it least 25 nucleotides, and most preferably at-least 40 nucleotides, and up to all or nearly all of a sequence which is complementary to a portion of the coding sequence of a nucleic acid sequence represented by SEQ ID Nos. 1–850 or a sequence complementary thereto, and which is differentially expressed in tumor cells as compared to normal cells of the given tissue type; and determining the approximate amount of hybridization of the probe to the mRNA, an amount of hybridization either more or less than that seen with the mRNA of a normal cell of that tissue type being indicative that the test cell is cancerous or precancerous.

Alternatively, the above diagnostic assays may be carried out using antibodies to detect the protein product encoded by the marker nucleic acid sequence, which nucleic acid sequence is represented by SEQ ID Nos. 1–850 or a sequence complementary thereto. Accordingly, in one embodiment the assay would include contacting the proteins of the test cell with an antibody specific for the gene product of a nucleic acid represented by SEQ ID Nos. 1–850 or a sequence complementary thereto, the marker nucleic acid being one which is expressed at a given control level in normal cells of the same tissue type as the test cell, and determining the approximate amount of immunocomplex formation by the antibody and the proteins of the test cell, wherein a statistically significant difference in the amount of the immunocomplex formed with the proteins of a test cell as compared to a normal cell of the same tissue type is an indication that the test cell is cancerous or precancerous.

Another such method includes the steps of: providing an antibody specific for the gene product of a marker nucleic acid sequence represented by SEQ ID Nos. 1–850, the gene product being present in cancerous tissue of a given tissue type (e.g., colon tissue) at a level more or less than the level of the gene product in noncancerous tissue of the same tissue type; obtaining from a patient a first sample of tissue of the given tissue type, which sample potentially includes cancerous cells; providing a second sample of tissue of the same tissue type (which may be from the same patient or from a normal control, e.g. another individual or cultured cells), this second sample containing normal cells and essentially no cancerous cells; contacting the antibody with protein (which may be partially purified, in lysed but unfractionated cells, or in situ) of the first and second samples under conditions permitting immunocomplex formation between the antibody and the marker nucleic acid sequence product present in the samples; and comparing (a) the amount of immunocomplex formation in the first sample, with (b) the amount of immunocomplex formation in the second sample, wherein a statistically significant difference in the amount of immunocomplex formation in the first sample less as compared to the amount of immunocomplex formation in the second sample is indicative of the presence of cancerous cells in the first sample of tissue.

The subject invention further provides a method of determining whether a cell sample obtained from a subject possesses an abnormal amount of marker polypeptide which comprises (a) obtaining a cell sample from the subject, (b) quantitatively determining the amount of the marker polypeptide in the sample so obtained, and (c) comparing the amount of the marker polypeptide so determined' with a known standard, so as to thereby determine whether the cell sample obtained from the subject possesses an abnormal amount of the marker polypeptide. Such marker polypeptides may be detected by immunohistochemical assays, dot-blot assays, ELISA and the like.

Immunoassays are commonly used to quantitate the levels of proteins in cell samples, and many other immunoassay techniques are known in the art. The invention is not limited to a particular assay procedure, and therefore is intended to include both homogeneous and heterogeneous procedures. Exemplary immunoassays which can be conducted according to the invention include fluorescence polarization immnunoassay (FPIA), fluorescence immunoassay (FIA), enzyme immunoassay (EIA), nephelometric inhibition immunoassay (NIA), enzyme linked immunosorbent assay (ELISA), and radioimnmunoassay (RIA). An indicator moiety, or label group, can be attached to the subject antibodies and is selected so as to meet the needs of various uses of the method which are often dictated by the availability of assay equipment and compatible immunoassay procedures. General techniques to be used in performing the various immunoassays noted above are known to those of ordinary skill in the art.

In another embodiment, the level of the encoded product, i.e., the product encoded by SEQ ID Nos 1–850 or a sequence complementary thereto, in a biological fluid (e.g., blood or urine) of a patient may be determined as a way of monitoring the level of expression of the marker nucleic acid sequence in cells of that patient Such a method would include the steps of obtaining a sample of a biological fluid from the patient, contacting the sample (or proteins from the sample) with an antibody specific for a encoded marker polypeptide, and determining the amount of immune complex formation by the antibody, with the amount of immune complex formation being indicative of the level of the marker encoded product in the sample. This determination is particularly instructive when compared to the amount of immune complex formation by the same antibody in a control sample taken from a normal individual or in one or more samples previously or subsequently obtained from the same person.

In another embodiment, the method can be used to determine the amount of marker polypeptide present in a cell, which in turn can be correlated with progression of a hyperproliferative disorder, e.g., colon cancer. The level of the marker polypeptide can be used predictively to evaluate whether a sample of cells contains cells which are, or are predisposed towards becoming, transformed cells. Moreover, the subject method can be used to assess the phenotype of cells which are known to be transformed, the phenotyping results being useful in planning a particular therapeutic regimen. For instance, very high levels of the marker polypeptide in sample cells is a powerful diagnostic and prognostic marker for a cancer, such as colon cancer. The observation of marker polypeptide level can be utilized in decisions regarding, e.g., the use of more aggressive therapies.

As set out above, one aspect of the present invention relates to diagnostic assays for determining, in the context of cells isolated from a patient, if the level of a marker polypeptide is significantly reduced in the sample cells. The term "significantly reduced" refers to a cell phenotype wherein the cell possesses a enzymes for use in conjugates include horseradish peroxidase, alkaline phosphatase, malate dehydrogenase and the like. Where not commercially available, such antibody-enzyme conjugates are readily produced by techniques known to those skilled in the art.

In one embodiment, the assay is performed as a dot blot assay. The dot blot assay finds particular application where tissue samples are employed as it allows determination of the average amount of the marker polypeptide associated with a single cell by correlating the amount of marker polypeptide in a cell-free extract produced from a predetermined number of cells.

It is well established in the cancer literature that tumor cells of the same type (e.g., breast and/or colon tumor cells) may not show uniformly increased expression of individual oncogenes or uniformly decreased expression of individual tumor suppressor genes. There may also be varying levels of expression of a given marker gene even between cells of a given type of cancer, further emphasizing the need for reliance on a battery of tests rather than a single test. Accordingly, in one aspect, the invention provides for a battery of tests utilizing a number of probes of the invention, in order to improve the reliability and/or accuracy of the diagnostic test.

In one embodiment, the present invention also provides a method wherein nucleic acid probes are immobilized on a DNA chip in an organized array. Oligonucleotides can be bound to a solid support by a variety of processes, including lithography. For example a chip can hold up to 250,000 oligonucleotides (GeneChip, Affymetrix). These nucleic acid probes comprise a nucleotide sequence at least about 12 nucleotides in length, preferably at least about 15 nucleotides, more preferably at least about 25 nucleotides, and most preferably at least about 40 nucleotides, and up to all or nearly all of a sequence which is complementary to a portion of the coding sequence of a marker nucleic acid sequence represented by SEQ ID Nos. 1–850 and is differentially expressed in tumor cells, such as colon cancer cells. The present invention provides significant advantages over the available tests for various cancers, such as colon cancer, because it increases the reliability of the test by providing an array of nucleic acid markers on a single chip.

The method includes obtaining a biopsy, which is optionally fractionated by cryostat sectioning to enrich tumor cells to about 80% of the total cell population. The DNA or RNA is then extracted, amplified, arid analyzed with a DNA chip to determine the presence of absence of the marker nucleic acid sequences.

In one embodiment, the nucleic acid probes are spotted onto a substrate in a two-dimensional matrix or array. Samples of nucleic acids can be labeled and then hybridized to the probes. Double-stranded nucleic acids, comprising the labeled sample nucleic acids bound to probe nucleic acids, can be detected once the unbound portion of the sample is washed away.

The probe nucleic acids can be spotted on substrates including glass, nitrocellulose, etc. The probes can be bound to the substrate by either covalent bonds or by non-specific interactions, such as hydrophobic interactions. The sample nucleic acids can be labeled using radioactive labels, fluorophores, chromophores, etc.

Techniques for constructing arrays and methods of using these arrays are described in EP No. 0 799 397; PCT No. WO 97/29212; PCT No. WO 97/27317; EP No. 0 785 280; PCT No. WO 97/02357; U.S. Pat. No. 5,593,839; U.S. Pat. No. 5,578,832; EP No. 0728 520; U.S. Pat. No. 5,599,695; EP No. 0 721 016; U.S. Pat. No. 5,556,752; PCT No. WO 95/22058; and U.S. Pat. No. 5,631,734.

Further, arrays can be used to examine differential expression of genes and can be used to determine gene function. For example, arrays of the instant nucleic acid sequences can be used to determine if any of the nucleic acid sequences are differentially expressed between normal cells and cancer cells; for example. High expression of a particular message in a cancer cell, which is not observed in a corresponding normal cell, can indicate a cancer specific protein.

In yet another embodiment, the invention contemplates using a panel of antibodies which are generated against the marker polypeptides-of this invention, which polypeptides are encoded by SEQ ID Nos 1–850. Such a panel of antibodies may be used as a reliable diagnostic probe for colon cancer. The assay of the present invention comprises contacting a biopsy sample containing cells, e.g., colon cells, with a panel of antibodies to one or more of the encoded products to determine the presence or absence of the marker polypeptides.

The diagnostic methods of the subject invention may also be employed as follow-up to treatment, e.g., quantitation of the level of marker polypeptides may be indicative of the effectiveness of current or previously employed cancer therapies as well as the effect of these therapies upon patient prognosis.

Accordingly, the present invention makes available diagnostic assays and reagents for detecting gain and/or loss of marker polypeptides from a cell in order to aid in the diagnosis and phenotyping of proliferative disorders arising from, for example, tumorigenic transformation of cells.

The diagnostic assays described above can be adapted to be used as prognostic assays, as well. Such an application takes advantage of the sensitivity of the assays of the invention to events which take place at characteristic stages in the progression of a tumor. For example, a given marker gene may be up- or downregulated at a very early stage, perhaps before the cell is irreversibly committed to developing into a malignancy, while another marker gene may be characteristically up or down regulated only at a much later stage. Such a method could involve the steps of contacting the mRNA of a test cell with a nucleic acid probe derived from a given marker nucleic acid which is expressed at different characteristic levels in cancerous or precancerous cells at different stages of tumor progression, and determining the approximate amount of hybridization of the probe to the mRNA of the cell, such amount being an indication of the level of expression of the gene in the cell, and thus an indication of the stage of tumor progression of the cell; alternatively, the assay can be carried out with an antibody specific for the gene product of tie given marker nucleic acid, contacted with the proteins of the test cell. A battery of such tests will disclose not only the existence and location of a tumor, but also will allow the clinician to select the mode of treatment most appropriate for the tumor, and to predict the likelihood of success of that treatment.

The methods of the invention can also be used to follow the clinical course of a tumor. For example, the assay of the invention can be applied to a tissue sample from a patient; following treatment of the patient for the cancer, another tissue sample is taken and the test repeated. Successful treatment will result in either removal of all cells which demonstrate differential expression characteristic of the cancerous or precancerous cells, or a substantial increase in expression of the gene in those cells, perhaps approaching or even surpassing normal levels.

In yet another embodiment, the invention provides methods for determining whether a subject is at risk for developing a disease, such as a predisposition to develop cancer, for example colon cancer, associated with an aberrant activity of any one of the polypeptides encoded by nucleic acids of SEQ ID Nos. 1–850, wherein the aberrant activity of the polypeptide is characterized by detecting the presence or absence of a genetic lesion characterized by at least one of (i) an alteration affecting the integrity of a gene encoding a marker polypeptides. or (ii) the mis-expression of the encoding nucleic acid. To illustrate, such genetic lesions can be detected by ascertaining the existence of at least one of (i) a deletion of one or more nucleotides from the nucleic acid sequence, (ii) an addition of one or more nucleotides to the nucleic acid sequence, (iii) a substitution of one or more nucleotides of the nucleic acid sequence, (iv) a gross chromosomal rearrangement of the nucleic acid sequence, (v) a gross alteration in the level of a messenger RNA transcript of the nucleic acid sequence, (vii) aberrant modification of the nucleic acid sequence, such as of the methylation pattern of the genomic DNA, (vii) the presence of a non-wild type splicing pattern of a messenger RNA transcript of the gene, (viii) a non-wild type level of the marker polypeptide, (ix) allelic loss of the gene, and/or (x) inappropriate post-translational modification of the marker polypeptide.

The present invention provides assay techniques for detecting lesions in the encoding nucleic acid sequence. These methods include, but are not limited to, methods involving sequence analysis, Southern blot hybridization, restriction enzyme site mapping, and methods involving detection of absence of nucleotide pairing between the nucleic acid to be analyzed and a probe.

Specific diseases or disorders, e.g., genetic diseases or disorders, are associated with specific allelic variants of polymorphic regions certain genes, which do not necessarily encode a mutated protein. Thus, the presence of a specific allelic variant of a polymorphic region of a gene in a subject can render the subject susceptible to developing a specific disease or disorder. Polymorphic regions in genes, can be identified, by determining the nucleotide sequence of genes in populations of individuals. If a polymorphic region is identified then the link with a specific disease can be determined by studying specific populations of individuals, e.g., individuals which developed a specific disease, such as colon cancer. A polymorphic region can be located in any region of a gene, e.g., exons, in coding or non coding regions of exons, introns, and promoter region.

In an exemplary embodiment, there is provided a nucleic acid composition comprising a nucleic acid probe including a region of nucleotisesequence which is capable of hybridizing to a sense or antisense sequence of a gene or naturally occurring mutants thereof, or 5' or 3' flanking sequences or intronic sequences naturally associated with the subject genes or naturally occurring mutants thereof. The nucleic acid of a cell is rendered accessible for hybridization, the probe is contacted with the nucleic acid of the sample, and the hybridization of the probe to the sample nucleic acid is detected. Such techniques can be used to detect lesions or allelic variants at either the genomic or mRNA level, including deletions, substitutions, etc., as well as to determine mRNA transcript levels.

A preferred detection method is allele specific hybridization using probes overlapping the mutation or polymorphic site and having about 5, 10, 20, 25, or 30 nucleotides around the mutation or polymorphic region. In a preferred embodiment of the invention, several probes capable of hybridizing specifically to allelic variants are attached to a solid phase support, e.g., a "chip." Mutation detection analysis using these chips comprising oligonucleotides, also termed "DNA probe arrays" is described e.g., in Cronin et al. (1996) Human Mutation 7:244. In one-embodiment, a chip comprises all the allelic variants of at least one polymorphic region of a gene. The solid phase support is then contacted with a test nucleic acid and hybridization to the specific probes is detected. Accordingly, the identity of numerous allelic variants of one or more genes can be identified in a simple hybridization experiment.

In certain embodiments, detection of the lesion comprises utilizing the probe/primer in a polymerase chain reaction (PCR) (see, e.g. U.S. Pat. Nos. 4,683,195 and 4,683,202), such as anchor PCR or RACE PCR, or, alternatively, in a ligase chain reaction (LCR) (see, e.g., Landegran et al. (1988) *Science* 241:1077–1080; and Nakazawa et al (1994) *PNAS* 91:360–364), the latter of which can be particularly useful for detecting point mutations in the gene (see Abravaya et al. (1995) *Nuc Acid Res* 23:675–682). In a merely illustrative embodiment, the method includes the steps of (i) collecting a sample of cells from a patient, (ii) isolating nucleic acid (e.g., genomic, mRNA or both) from the cells of the sample, (iii) contacting the nucleic acid sample with one or more primers which specifically hybridize to a nucleic acid sequence under conditions such that hybridization and amplification of the nucleic acid (if present) occurs, and (iv) detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., 1990, Proc. Natl. Acad. Sci. USA 87:1874–1878), transcriptional amplification system (Kwoh, D. Y. et al., 1989, Proc. Natl. Acad. Sci. USA 86:1173–1177), Q-Beta Replicase (Lizardi, P. M. et al., 1988, Bio/Technology 6:1197), or any other nucleic acid amplification method, followed by the detection-of the amplified molecules using techniques well known to those of skill in the art. These detection schemes are especially useful for the detection of nucleic acid molecules if such molecules are present in very low numbers.

In a preferred embodiment of the subject assay, mutations, or allelic variants, of a gene from a sample cell are identified by alterations in restriction enzyme cleavage patterns. For example, sample and control DNA is isolated, amplified (optionally), digested with one or more restriction endonucleases, and fragment length sizes are determined by gel electrophoresis. Moreover, the use of sequence specific ribozymes (see, for example, U.S. Pat. No. 5,498,531) can be used to score for the presence of specific mutations by development or loss of a ribozyme cleavage site.

Another aspect of the invention is directed to the identification of agents capable of modulating the differentiation and proliferation of cells characterized by aberrant proliferation. In this regard, the invention provides assays for determining compounds that modulate the expression of the matter nucleic acids (SEQ ID Nos. 1–850) and/or alter for example, inhibit the bioactivity of the encoded polypeptide.

Several in vivo methods can be used to identify compounds that modulate expression of the marker nucleic acids (SEQ ID Nos. 1–850) and/or alter for example, inhibit the bioactivity of the encoded polypeptide.

Drug screening is performed by adding a test compound-to a sample of cells, and monitoring the effect. A parallel sample which does not receive the test compound is also monitored as a control. The treated and untreated cells are then compared by any suitable phenotypic criteria, including but not limited to microscopic analysis, viability testing, ability to replicate, histological examination, the level of a particular RNA or polypeptide associated with the cells, the level of enzymatic activity expressed by the cells or cell lysates, and the ability of the cells to interact with other cells or compounds. Differences between treated and untreated cells indicates effects attributable to the test compound.

Desirable effects of a test compound include an effect on any phenotype that was conferred by the cancer-associated marker nucleic acid sequence. Examples include a test compound that limits the overabundance of mRNA, limits production of the encoded protein, or limits the functional effect of the protein. The effect of the test compound would be apparent when comparing results between treated and untreated cells.

The invention thus also encompasses methods of screening for agents which inhibit expression of the nucleic acid markers (SEQ ID Nos. 1–850) in vitro, comprising exposing a cell or tissue in which the marker nucleic acid mRNA is detectable in cultured cells to an agent in order to determine whether the agent is capable of inhibiting production of the mRNA; and determining the level of mRNA in the exposed cells or tissue, wherein a decrease in the level of the mRNA after exposure of the cell line to the agent is indicative of inhibition of the market nucleic acid mRNA production.

Alternatively, the screening method may include in vitro screening of a cell or tissue in which marker protein is detectable in cultured cells to an agent suspected of inhibiting production of the marker protein; and determining the level of the marker protein in the cells or tissue, wherein a decrease in the level of marker protein after exposure of the cells or tissue to the agent is indicative of inhibition of marker protein production.

The invention also encompasses in vivo methods of screening for agents which inhibit expression of the marker nucleic acids, comprising exposing a mammal having tumor cells in which marker mRNA or protein is detectable to an agent suspected of inhibiting production of marker mRNA or protein; and determining the level of marker mRNA or protein in tumor cells of the exposed mammal. A decrease in the level of marker mRNA or protein after exposure of the mammal to the agent is indicative of inhibition of marker nucleic acid expression.

Accordingly, the invention provides a method comprising incubating a cell expressing the marker nucleic acids (SEQ ID Nos. 1–850) with a test compound and measuring the mRNA or protein level. The invention further provides a method for quantitatively determining the level of expression of the marker nucleic acids in a cell population, and a method for determining whether an agent is capable of increasing or decreasing the level of expression of the marker nucleic acids in a cell population. The method for determining whether an agent is capable of increasing or decreasing the level of expression of the marker nucleic acids in a cell population comprises the steps of (a) preparing cell extracts from control and agent-treated cell populations, (b) isolating the marker polypeptides from the cell extracts, (c) quantifying (e.g., in parallel) the amount of an immunocomplex formed between the marker polypeptide and an antibody specific to said polypeptide. The marker polypeptides of this invention may also be quantified by assaying for-its bioactivity. Agents that induce increased the marker nucleic acid expression may be identified by their ability to increase the amount of immunocomplex formed in the treated cell as compared with the amount of the immunocomplex fonred in the control tell. In a similar manner, agents that decrease expression of the marker nucleic acid may be identified by their ability to decrease the amount of the immunocomplex formed in the treated cell extract as compared to the control cell.

mRNA levels can be determined by Northern blot hybridization. mRNA levels can also be determined by methods involving PCR. Other sensitive methods for measuring mRNA, which can be used in high throughput assays, e.g., a method using a DELFIA endpoint detection and quantification method, are described, e.g., in Webb and Hurskainen (1996) *Journal of Biomolecular Screening* 1:119. Marker protein levels can be determined by immunoprecipitations or immunohistochemistry using an antibody that specifically recognizes the protein product encoded by SEQ ID Nos. 1.850.

Agents that are identified as active in the drug screening assay are candidates to be tested for their capacity to block cell proliferation activity. These agents would be useful for treating a disorder involving aberrant growth of cells, especially colon cells.

A variety of assay formats will suffice and, in light of the present disclosure, those not expressly described herein will nevertheless be comprehended by one of ordinary skill in the art. For instance, the assay can be generated in many different formats, and include assays based on cell-free systems, e.g., purified proteins or cell lysates, as well as cell-based assays which utilize intact cells.

In many drug screening programs which test libraries of compounds and natural extracts, high throughput assays are desirable in order to maximize the number of compounds surveyed in a given period of time. Assays of the present invention which are performed in cell-free systems, such as may be derived with purified or semi-purified proteins or with lysates, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with other proteins or changes in enzymatic properties of the molecular target.

A. Use of Nucleic Acids as Probes in Mapping and in Tissue Profiling Probes

Polynucleotide probes as described above, e.g., comprising at least 12 contiguous nucleotides selected from the nucleotide sequence of an nucleic acid as shown in SEQ ID Nos. 1–850, preferably SEQ ID Nos. 1–383, even more preferably SEQ ED Nos. 1–127, or sequence complementary thereto, are used for a variety of purposes, including identification of human chromosomes and determining transcription levels. Additional disclosure about preferred regions of the nucleic acid sequences is found in the accompanying tables.

The nucleotide probes are labeled, for example, with a radioactive, fluorescent, biotinylated, or chemiluminescent label, and detected by well known methods appropriate for the particular label selected. Protocols for hybridizing nucleotide probes to preparations of metaphase chromosomes are also well known in the art. A nucleotide probe will hybridize specifically to nucleotide sequences in the chromosome preparations which are complementary to the nucleotide sequence of the probe. A probe that hybridizes specifically to an nucleic acid should provide a detection signal at least 5-, 10-, or 20-fold higher than the background hybridization provided with other unrelated sequences.

In a non-limiting example, commercial programs are available for identifying regions of chromosomes commonly associated with disease, such as cancer. Nucleic acids of the invention can be used to probe these regions. For example, if, through profile searching, a nucleic acid is identified as corresponding to a gene encoding a kinase, its ability to bind to a cancer-related chromosomal region will suggest its role as a kinase in one or more stages of tumor cell development/growth. Although some experimentation would be required to elucidate the role, the nucleic acid constitutes a new material for isolating a specific protein that has potential for developing a cancer diagnostic or therapeutic.

Nucleotide probes are used to detect expression of a gene corresponding to the nucleic acid. For example, in Northern blots, mRNA is separated electrophoretically and contacted with a probe; A probe is detected as hybridizing to an mRNA species of a particular size. The amount of hybridization is quantitated to determine relative amounts of expression, for example under a particular condition. Probes are also used to detect products of amplification by polymerase chain reaction. The products of the reaction are hybridized to the probe and hybrids are detected. Probes are used for in situ hybridization to cells to detect expression. Probes can also be used in vivo for diagnostic detection of hybridizing sequences. Probes are typically labeled with a radioactive isotope. Other types of detectable labels may be used such as chromophores, fluorophores, and enzymes.

Expression of specific mRNA can vary in different cell types and can be tissue specific. This variation of mRNA levels in different cell types can be exploited with nucleic acid probe assays to determine tissue types. For example, PCR, branched DNA probe assays, or blotting techniques utilizing nucleic acid probes substantially identical or complementary to nucleic acids of SEQ ID Nos. 1–850, preferably SEQ ID Nos. 1–383, even more preferably SEQ ID-Nos. 1–127, or a sequence complementary thereto, can determine the presence or absence of target cDNA or mRNA.

Examples of a nucleotide hybridization assay are described in Urdea et al., PCI WO92/02526 and Urdea et al., U.S. Pat. No. 5,124,246, both incorporated herein by reference. The references describe an example of a sandwich nucleotide hybridization assay.

Alternatively, the Polymerase Chain Reaction (PCR) is another means for detecting small amounts of target nucleic acids, as described in Mullis et al., *Meth. Enzymol.* (1987) 155:335–350; U.S. Pat. No. 4,683,195; and U.S. Pat. No. 4,683,202, all incorporated herein by reference. Two primer polynucleotides nucleotides hybridize with the target nucleic acids and are used to prime the reaction. The primers may be composed of sequence within or 3' and 5' to the polynucleotides of the Sequence Listing. Alternatively, if the primers are 3' and 5' to these polynucleotides, they need not hybridize to them or the complements. A thermostable polymerase creates copies of target nucleic acids from the primers using the original target nucleic acids as a template. After a large amount of target nucleic acids is generated by the polymerase, it is detected by methods such as Southern blots. When using the Southern blot method, the labeled probe will hybridize to a polynucleotide of the Sequence Listing or complement.

Furthermore, mRNA or cDNA can be detected by traditional blotting techniques described in Sambrook et al., "Molecular Cloning: A Laboratory Manual" (New York, Cold Spring Harbor Laboratory, 1989). mRNA or cDNA generated from mRNA using a polymerase enzyme can be purified and separated using gel electrophoresis. The nucleic acids on the gel are then blotted onto a solid support, such as nitrocellulose. The solid support is exposed to a labeled probe and then washed to remove any unhybridized probe; Next, the duplexes containing the labeled probe are detected. Typically, the probe is labeled with radioactivity.

Mapping

Nucleic acids of the present invention are used to identify a chromosome on which the corresponding gene resides. Using fluorescence in situ hybridization (FISH) on normal metaphase spreads, comparative genomie hybridization allows total genome assessment of changes in relative copy number of DNA sequences. See Schwartz and Samad., *Current Opinions in Biotechnology* (1994) 8:70–74; Kallioniemi et al., *Seminars in Cancer Biology* (1993) 4:41–46; Valdes and Tagle, *Methods in Molecular Biology* (1997) 68:1, Boultwood, ed., Human Press, Totowa, N.J.

Preparations of human metaphase chromosomes are prepared using standard cytogenetic techniques from human primary tissues or cell lines. Nucleotide probes comprising at least 12 contiguous nucleotides selected from the nucleotide sequence of SEQ ED Nos. 1–850, preferably SEQ ID Nos. 1–383, even more preferably SEQ ID Nos. 1–127, or a sequence complementary thereto, are used to identify the corresponding chromosome. The nucleotide probes are labeled, for example, with a radioactive, fluorescent, biotinylated, or-chemiluminescent label, and detected by well known methods appropriate for the particular label selected. Protocols fbr hybridizing nucleotide probes to preparations of metaphase chromosomes are also well known in the art. A nucleotide probe will hybridize specifically to nucleotide sequences in the chromosome preparations that are complementary to the nucleotide sequence of the probe. A probe that hybridizes specifically to a target gene provides a detection signal at least 5-, 10-, or 20-fold higher than the background, hybridization provided with unrelated coding sequences.

Nucleic acids are mapped to particular chromosomes using, for example, radiation hybrids or chromosome-specific hybrid panels. See Leach et al., *Advances in Genetics*, (1995) 33:63–99; Walter et al., *Nature Genetics* (1994) 7:22–28; Walter and Goodfellow, *Trends in Genetics* (1992) 9:352. Panels for radiation hybrid mapping are available from Research Genentics, Inc., Huntsville, Ala., USA. Databases for markers using various panels are available via the world wide web at http:/F/shgc-www.stanford.edu; and other locations. The statistical program RHMAP can be used to construct a map based on the data from radiation hybridization with a measure of the relative likelihood of one order versus another. RHMAP is available via the world wide web at http://www.sph.umich.edu/group/statgenfsoftware.

Such mapping can be useful in identifying the function of the target gene by its proximity to other genes with known function. Function can also be assigned to the target gene when particular syndromes or diseases map to the same chromosome.

Tissue Profiling

The nucleic acids of the present invention can be used to determine the tissue type from which a given sample is derived. For example, a metastatic lesion is identified by its developmental organ or tissue source by identifying the expression of a particular marker of that organ or tissue. If a nucleic acid is expressed only in a specific tissue type, and a metastatic lesion is found to express that nucleic acid, then the developmental source of the lesion has been identified. Expression of a particular nucleic acid is assayed by detection of either the corresponding mRNA or the protein product. Immunological methods, such as antibody staining, are used to detect a particular protein product. Hybridization methods may be used to detect particular mRNA species, including but not limited to in situ hybridizAtion and Northern blotting.

Use of Polymorphisms

A nucleic acid will be useful in forensics, genetic analysis, mapping, and diagnostic applications if the corresponding region of a gene is polymorphic in the human population. A particular polymorphic form of the nucleic acid may be used to either identify a sample as deriving from a suspect or rule out the possibility that the sample derives from the suspect.

Any means for detecting a polymorphism in a gene are used, including but not limited to electrophoresis.of protein polymorphic variants, differential sensitivity to restriction enzyme cleavage, and hybridization to an allele-specific probe.

B. Use of Nucleic Acids and Encoded Polypeptides to Raise Antibodies

Expression products of a nucleic acid, the corresponding mRNA or cDNA, or the corresponding complete gene are prepared and used for raising antibodies for experimental, diagnostic, and therapeutic purposes. For nucleic acids to which a corresponding gene has not been assigned, this provides an additional method of identifying the corresponding gene. The nucleic acid or related cDNA is expressed as described above, and antibodies are prepared. These antibodies are specific to an epitope on the encoded polypeptide, and can precipitate or bind to the corresponding native protein in a cell or tissue preparation or in a cell-free extract of an in vitro expression system.

Immunogens for raising antibodies are prepared by mixing the polypeptides encoded by the nucleic acids of the present invention with adjuvants. Alternatively, polypeptides are made as fusion proteins to larger immunogenic proteins. Polypeptides are also covalently linked to other larger immunogenic proteins, such as keyhole limpet hemocyanin. Immunogens are typically administered intradermally, subcutaneously, or intramuscularly. Immunogens are administered to experimental animals such as rabbits, sheep, and mice, to generate antibodies. Optionally, the animal spleen cells are isolated and fused with mycloma cells to form hybridomas which secrete monoclonal antibodies. Such methods are well known in the art. According to another method known in the art, the nucleic acid is administered directly, such as by intramuscular injection, and expressed in vivo. The expressed protein generates a variety of protein-specific immune responses, including production of antibodies, comparable to administration of the protein.

Preparations of polyclonal and monoclonal antibodies specific for nucleic acid-encoded proteins and polypeptides are made using standard methods known in the art. The antibodies specifically bind to epitopes present in the polypeptides encoded by a nucleic acid of SEQ ID Nos. 1–850, preferably SEQ ID Nos. 1–383, even more preferably SEQ ID Nos. 1–127, or a sequence complementary thereto. In another embodiment, the antibodies specifically bind to epitopes present in a polypeptide encoded by SEQ ID Nos. 1–850. Typically, at least about 6, 8, –10, or 12 contiguous amino acids are required to form an epitope. However, epitopes which involve non-contiguous amino acids may require more, for example, at least about 15, 25, or 50 amino acids. A short sequence of a nucleic acid may then be unsuitable for use as an epitope to raise antibodies for identifying the corresponding novel protein, because of the potential for cross-reactivity with a known protein. However, the antibodies may be useful for other purposes, particularly if they identify common structural features of a known protein and a novel polypeptide encoded by a nucleic acid of the invention.

Antibodies that specifically bind to human nucleic acid-encoded polypeptides should provide a detection signal at least about 5-, 10-, or 20-fold higher than a detection signal provided with other proteins when used in Western blots or other immunochemical assays. Preferably, antibodies that specifically bind nucleic acid T-encoded polypeptides do not detect other proteins in immunochemical assays and can immunoprecipitate nucleic acid-encoded proteins from solution.

To test for the presence of serum antibodies to the nucleic acid-encoded polypeptide in a human population, human antibodies are purified by methods well known in the art. Preferably, the antibodies are affinity purified by passing antiserum over a column to which an nucleic acid-encoded protein, polypeptide, or fusion protein is bound. The bound antibodies can then be eluted from the column, for example using a buffer with a high salt concentration.

In addition to the antibodies discussed above, genetically engineered antibody derivatives are made, such as single chain antibodies.

Antibodies may be made by using, standard protocols known in the art (See, for example, Antibodies: A Laboratory Manual ed. by Harlow and Lane (Cold Spring Harbor Press: 1988)). A mammal, such as a mouse, hamster, or rabbit can be immunized with an immunogenic forming of the peptide (e.g., a mammalian polypeptide or an antigenic fragment which is capable of eliciting an antibody response, or a fusion protein as described above).

In one aspect, this invention includes monoclonal antibodies that show a subject polypeptide is highly expressed in colorectal tissue or tumor tissue especially colon cancer tissue or colon cancer-derived cell lines. Therefore, in one embodiment, this invention provides a diagnostic tool for the analysis of expression of a subject polypeptide in general, and in particular, as a diagnostic for colon cancer.

Techniques for conferring immunogenicity on a protein or peptide include conjugation to carriers or other techniques well known in the art. An immunogenic portion of a protein can be administered in the presence of adjuvant. The progress of immunization can be monitored by detection of antibody titers in plasma or serum. Standard ELISA or other immunoassays can be used with the immunogen as antigen to assess the levels of antibodies. In a preferred embodiment, the subject antibodies are immunospecific for antigenic determinants of a protein of a mammal, e.g., antigenic determinants of a protein encoded by one of SEQ ID Nos. 1–850 or closely related homologs (e.g., at least 90% identical, and more preferably at least 95% identical).

Following immunization of an animal with an antigenic preparation of a polypeptide, antisera can be obtained and, if desired, polyclonal antibodies isolated from the serum. To produce monoclonal antibodies, antibody-producing cells (lymphecytes) can be harvested from an immunized animal and fused by standard somatic cell fusion procedures with immortalizing cells such as myeloma cells to yield hybridoma cells. Such techniques are well known in the art, and include, for example, the hybridoma technique (originally developed by Kohler and Milstein, (1975) Nature, 256: 495–497), the human B cell hybridoma technique (Kozbar et al., (1983) Immunology Today, 4: 72), and the EBV-hybridoma technique to produce human monoclonal antibodies (Cole et al., (1985) Monoclonal Antibodies and Cancer Therapy, Alan R. Liss, Inc. pp. 77–96). Hybridoma cells can be screened immunochemically for production of antibodies specifically reactive with a polypeptide of the present invention and monoclonal antibodies isolated from a culture comprising such hybridoma cells.

The term antibody as used herein is intended to include fragments thereof which are also specifically reactive with one of the subject polypeptides. Antibodies can be fragmented using conventional techniques and the fragments screened for utility in the same manner as described above for whole antibodies. For example, $F^{(ab)}2$ fragments can be generated by treating antibody with pepsin The resulting $F^{(ab)}2$ fragment can be treated to reduce disulfide bridges to produce Fab fragments. The antibody of the present invention is further intended to include bispecific, single-chain, and chimeric and humanized molecules having affinity for a polypeptide conferred by at least one CDR region of the antibody. In preferred embodiments, the antibodies, the antibody further comprises a label attached thereto and able to be detected, (e.g., the label can be a radioisotope, fluorescent compound, chemilurninescent compound, enzyme, or enzyme co-factor).

Antibodies can be used, e.g., to monitor protein levels in an individual for determining, e.g., whether a subject has a disease or condition, such as colon cancer, associated with an aberrant protein level, or allowing determination of the efficacy of a given treatment regimen for an individual afflicted with such a disorder. The level of polypeptides may be measured from cells in bodily fluid, such as in blood samples.

Another application of antibodies of the present invention is in the immunological screening of cDNA libraries constructed in expression vectors such as gt11, gt18–23, ZAP, and ORF8. Messenger libraries of this type, having coding sequences inserted in the correct reading frame and orientation, can produce fusion proteins. For instance, gt11 will produce fusion proteins whose amino termini consist of β-galactosidase amino acid sequences and whose carboxyl termini consist of a foreign polypeptide. Antigenic epitopes of a protein, e.g., other orthologs of a particular protein or other paralogs from the same species, can then be detected with antibodies, as, for example, reacting nitrocellulose filters lifted from infected plates with antibodies. Positive phage detected by this assay can then be isolated from the infected plate. Thus, the presence of homologs can be detected and cloned from other animals, as can alternate isoforms (including splicing variants) from humans.

In another embodiment, a panel of monoclonal antibodies may be used, wherein each of the epitope's involved functions are represented by a monoclonal antibody. Loss or perturbation of binding of a monoclonal antibody in the panel would be indicative of a mutational attention of the protein and thus of the corresponding gene.

C. Differential Expression

The present invention also provides a method to identify abnormal or diseased tissue in a human. For nucleic acids corresponding to profiles of protein families as described above, the choice of tissue may be dictated by the putative biological function. The expression of a gene corresponding to a specific nucleic acid is compared between a first tissue that is suspected of being diseased and a second, normal tissue of the human. The normal tissue is any tissue of the human, especially those that express the target gene including, but not limited to, brain, thymus, testis, heart, prostate, placenta, spleen, small intestine, skeletal muscle, pancreas, and the mucosal lining of the colon.

The tissue suspected of being abnormal or diseased can be derived from a different tissue type of the human, but preferably it is derived from the same tissue type; for example an intestinal polyp or other abnormal growth should be compared with normal intestinal tissue. A difference between the target gene, mRNA, or protein in the two tissues which are compared, for example in molecular weight, amino acid or nucteotide sequence, or relative abundance, indicates a change in the gene, or a gene which regulates it, in the tissue of the human that was suspected of being diseased.

The target genes in the two tissues are compared by any means known in the art. For example, the two genes are sequenced, and the sequence of the gene in the tissue suspected of being diseased is compared with the gene sequence in the normal tissue. The target genes, or portions thereof, in the two tissues are amplified, for example using nucteotide primers based on the nucleotide sequence shown in the Sequence Listing, using the polymerase chain reaction. The amplified genes or portions of genes are hybridized to nucleotide probes selected from a corresponding nucleotide sequence shown SEQ ID No. 1–850. A difference in the nucleotide sequence of the target gene in the tissue suspected of being diseased compared with the normal nucleotide sequence suggests a role of the nucleic acid-encoded proteins in the disease, and provides a lead for preparing a therapeutic agent The nucleotide probes are labeled by a variety of methods, such as radiolabeling, biotinylation, or labeling with fluorescent or chemiluminescent tags, and detected by standard methods known in the art.

Alternatively, target mRNA in the two tissues is compared. PolyA$^{+}$RNA is isolated from the two tissues as is known in the art. For example, one of skill in the art can readily determine differences in the size or amount of target mRNA transcripts between the two tissues using Northern blots and nucleotide probes selected froth the nucleotide sequence shown in the Sequence Listing. Increased or decreased expression of a target mRNA in a tissue sample suspected of being diseased, compared with the expression of the same target mRNA in a normal tissue, suggests that the expressed protein has a role in the disease, and also provides a lead for preparing a therapeutic agent.

Any method for analyzing proteins is used to compare two nucleic acid-encoded proteins from matched samples. The sizes of the proteins in the two tissues are compared, for example, using antibodies of the present invention to detect nucleic acid-encoded proteins in Western blots of protein extracts from the two tissues. Other changes, such as expression levels and subcellular localization, can also be detected immunologically, using antibodies to the corresponding protein. A higher or lower level of nucleic acid-encoded protein expression in a tissue suspected of being diseased, compared with the same nucleic acid-encoded protein expression level in a normal tissue, is indicative that the expressed protein has a tote in the disease, and provides another lead for preparing a therapeutic agent.

Similarly, comparison of gene sequences or of gene expression products, e.g., mRNA and protein, between a human tissue that is suspected of being diseased and a normal tissue of a human, are used to follow disease progression or remission in the human. Such comparisons of genes, mRNA, or protein are made as described above.

For example, increased or decreased expression of the target gene in the tissue suspected of being neoplastic can indicate the presence of neoplastic cells in the tissue. The degree of increased expression of the target gene in the neoplastic tissue relative to expression of the gene in normal tissue, or differences in the amount of increased expression of the target gene in the neoplastic tissue over time, is used to assess the progression of the neoplasia in that tissue or to monitor the response of the neoplastic tissue to a therapeutic protocol over time.

The expression pattern of any two cell types can be compared, such as low and high metastatic tumor cell lines, or cells from tissue which have and have not been exposed to a therapeutic agent A genetic predisposition to disease in a human is detected by comparing an target gene, mRNA, or protein in a fetal tissue with a normal target gene, mRNA, or protein. Fetal tissues that are used for this purpose include, but are not limited to, amniotic fluid, chorionic villi, blood, and the blastomere of an in vitro-fertilized embryo.

The comparable normal target gene is obtained front any tissue. The mRNA or protein is obtained from a normal tissue of a human in which the target gene is expressed. Differences such as alterations in the nucleotide sequence or size of the fetal target gene or mRNA, or alterations in the molecular weight, amino acid sequence, or relative abundance of fetal target protein, can indicate a germline mutation in the target gene of the fetus, which indicates a genetic predisposition to disease.

D. Use of Nucleic Acids, and Encoded Polyentides to Screen for Petide Analogs and Antagonists Polypeptides encoded by the instant nucleic acids, e.g., SEQ ID Nos. 1–850, preferably SEQ ID Nos. 1–383, even more preferably SEQ ID Nos. 1–127, or a sequence complementary thereto, and corresponding full length genes can be used to screen peptide libraries to identify binding partners, such as receptors, from among the encoded polypeptides.

A library of peptides may be synthesized following the methods disclosed in U.S. Pat. No. 5,010,175, and in a WO 91/17823. As described below in brief, one prepares a mixture of peptides, which is then screened to identify the peptides exhibiting the desired signal transduction and receptor binding activity. In the '175 method, a suitable peptide synthesis support (e.g., a resin) is coupled to a mixture of appropriately protected, activated amino acids. The concentration of each amino acid in the reaction mixture is balanced or adjusted in inverse proportion to its coupling reaction rate so that the product is an equimolar mixture of amino acids coupled to the starting resin. The bound amino acids are then deprotected, and reacted with another balanced amino acid mixture to form an equimolar mixture of all possible dipeptides. This process is repeated until a mixture of peptides of the desired length (e.g., hexamers) is formed. Note that one need not include all amino acids in each step: one may include only one or two amino acids in some steps (e.g., where it is known that a particular amino acid is essential in a given position), thus reducing the complexity of the mixture. After the synthesis of the peptide library is completed, the mixture of peptides is screened for binding to the selected polypeptide. The peptides are then tested for their ability to inhibit or enhance activity. Peptides exhibiting the desired activity are then isolated and sequenced.

The method described in WO 91/17823 is similar. However, instead of reacting the synthesis resin with a mixture of activated amino acids, the resin is divided into twenty equal portions (or into a number of portions corresponding to the number of different amino acids to be added in that step), and each amino acid is coupled individually to its portion of resin. The resin portions are then combined, mixed, and again divided into a number of equal portions for reaction with the second amino acid. In this manner, each reaction may be easily driven to completion. Additionally, one may maintain separate "subpools" by treating portions in parallel, rather than combining all resins at each step. This simplifies the process of determining which peptides are responsible for any observed receptor binding or signal transduction activity.

In such cases, the subpools containing, e.g., 1–2,000 candidates each are exposed to one or more polypeptides of the invention. Each subpool that produces a positive result is then resynthesized as a group of smaller subpools (sub-subpools) containing, e.g., 20–100 candidates, and reassayed. Positive sub-subpools may be resynthesizth as individual compounds, and assayed finally to determine the peptides that exhibit a high binding constant. These peptides can be tested for their ability to inhibit or enhance the native activity. The methods described in WO 91/7823 and U.S. Pat. No. 5,194,392 (herein incorporated by reference) enable the preparation of such pools and subpools by automated techniques in parallel, such that all synthesis and resynthesis may be performed in a matter of days.

Peptide agonists or antagonists are screened using any available method, such as signal transduction, antibody binding, receptor binding, mitogenic assays, chemotaxis assays, etc. The methods described herein are presently preferred. The assay conditions ideally should resemble the conditions under which the native activity is exhibited in vivo, that is, under physiologic pH, temperature, and ionic strength. Suitable agonists or antagonists will exhibit strong inhibition or enhancement of the native activity at concentrations that do not cause toxic side effects in the subject. Agonists or antagonists that compete for binding to the native polypeptide may require concentrations equal to or greater than the native concentration, while inhibitors capable of binding irreversibly to the polypeptide may be added in concentrations on the order of the native concentration.

The end results of such screening and experimentation will be at least one novel polypeptide binding partner, such as a receptor, encoded by a nucleic acid of the invention, and at least one peptide agonist or antagonist of the novel binding partner. Such agonists and antagonists can be used to modulate, enhance, or inhibit receptor function in cells to which the receptor is native, or in cells that possess the receptor as a result of genetic engineering. Further, if the novel receptor shares biologically important characteristics with a known receptor, information about agonist/antagonist binding may help in developing improved agonists/antagonists of the known receptor.

E. Pharmaceutical Compositions and Therapeutic Uses

Pharmaceutical compositions can comprise polypeptides, antibodies, or polynucleotides of the claimed invention. The pharmaceutical compositions will comprise a therapeutically effective amount of either polypeptides, antibodies, or polynucleotides of the claimed invention.

The term "therapeutically effective amount" as used herein refers to an amount of a therapeutic agent to treat, ameliorate, or prevent a desired disease or condition, or to exhibit a detectable therapeutic or preventative effect The effect can be detected by, for example, chemical markers or antigen levels. Therapeutic effects also include reduction in physical symptoms, such as decreased body temperature. The precise effective amount for a subject will depend upon the subjects size and health, the nature and extent of the condition, and the therapeutics or combination of therapeutics selected for administration. Thus, it is not useful to specify an exact effective amount in advance. However, the effective amount for a given situation can be determined by routine experimentation and is within the judgment of the clinician.

For purposes of the present invention, an effective dose will be from about 0.01 mg/kg to 50 mg/kg or 0.05 mg/kg to about 10 mg/kg of the DNA constructs in the individual to which it is administered.

A pharmaceutical composition can also contain a pharmaceutically acceptable carrier. The term "pharmaceutically acceptable carrier" refers to a carrier for administration of a therapeutic agent, such as antibodies or a polypeptide, genes, and other therapeutic agents. The term refers to any pharmaceutical carrier that does not itself induce the production of antibodies harmful to the individual receiving the composition, and which may be administered without undue toxicity. Suitable carriers may be large, slowly metabolized macromolecules such as proteins, cells polysaccharides, polylactic acids, polyglycolic acids, polymeric amino acids, amino acid copolymers, and inactive virus particles. Such carriers are well known to those of ordinary skill in the art.

Pharmaccutically acceptable salts can be used therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in *Remington's Pharmaceutical Sciences* (Mack Pub. Co., N.J. 1991).

Pharmaceutically acceptable carriers in therapeutic compositions may contain liquids such as water, saline, glycerol and ethanol. Additionally, auxiliary substances, such as wetting or emulsifying agents, pH buffering substances, and the like, may be present in such vehicles. Typically, the therapeutic compositions are prepared as injectables, either as liquid solutions or suspensions; solid forms suitable for solution in, or suspension in, liquid vehicles prior to injection may also be prepared. Liposomes are included within the definition of a pharmaceutically acceptable carrier.

Delivery Methods

Once formulated, the nucleic acid compositions of the invention can be (1) administered directly to the subject; (2) delivered ex vivo, to cells derived from the subject; or (3) delivered in vitro for expression of recombinant proteins.

Direct delivery of the compositions will generally be accomplished by injection, either subcutaneously, intraperitoneally, intravenously or intramuscularly, or delivered to the interstitial space of a tissue. The compositions can also be administered into a tumor or lesion. Other modes of administration include oral and pulmonary administration, suppositories, and transdermal applications, needles, and gene guns or hyposprays. Dosage treatment may be a single dose schedule or a multiple dose schedule.

Methods for the ex vivo delivery and reimplantation of transformed cells into a subject are known in the art and described in e.g., International Publication No. WO 93/14778. Examples of cells useful in ex vivo applications include, for example, stem cells, particularly hematopoetic, lymph cells, macrophages dendritic cells, or tumor cells.

Generally, delivery of nucleic acids for both ex vivo and in vitro applications can be accomplished by, for example, dextran-mediated transfection, calcium phosphate precipitation, polybrene mediated transfection, protoplast fusion, electroporation, encapsulation of the polynucleotide (s) in liposomes, and direct microinjection of the DNA into nuclei, all well known in the art.

Once a subject gene has been found to correlate with a proliferative disorder, such as neoplasia, dysplasia, and hyperplasia, the disorder may be amenable to treatment by administration of a therapeutic agent based on the nucleic acid or corresponding polypeptide.

Preparation of antisense polypeptides is discussed above. Neoplasias that are treated with the antisense composition include, but are not limited to, cervical cancers, melanornas, colorectal adenocarcinomas, Wilms' tumor, retinoblastoma, sarcomas, myosarcomas, lung carcinomas, leukemias, such as chronic myclogenous leukemia, promyelocytic leukemia, monocytic leukemia, and myeloid leukemia, and lymphomas, such as histiocytic lymphoma. Proliferative disorders that are treated with the therapeutic composition include disorders such as anhydric hereditary ectodeimal dysplasia, congenital alveolar dysplasia, epithelial dysplasia ofthe cervix, fibrous dysplasia of bone, and mammary dysplasia. Hyperplasias, for example, endometrial, adrenal, breast, prostate, or thyroid hyperplasias or pseudoepitheliomatous hyperplasia of the skin, are treated with antisense therapeutic compositions. Even in disorders in which mutations in the corresponding gene are not implicated, downregulation or inhibition of nucleic acid-related gene expression can have therapeutic application. For example, decreasing-nucleic acid-related gene expression can help to suppress tumors in which enhanced expression of the gene is implicated.

Both the dose of the antisense composition and the means of administration are determined based on-the specific qualities of the therapeutic composition, the condition, age, and weight of the patient, the progression of the disease, and other relevant factors. Administration of the therapeutic antisense agents of the invention includes local or systemic administration, including injection, oral administration, particle gun or catheterized administration, and topical administration. Preferably, the therapeutic antisense composition contains an expression construct comprising a promoter and a polynucleotide segment of at least about 12, 22, 25, 30, or 35 contiguous nucleotides of the antisense strand of a nucleic acid. Within the expression construct, the polynucleotide segment is located downstream from the promoter, and transcription of the polynucleotide segment initiates at the promoter.

Various methods are used to administer the therapeutic composition directly to a specific site in the body. For example, a small metastatic lesion is located and the therapeutic composition injected several times in several different locations within the body of tumor. Alternatively, arteries which serve a tumor are identified, and the therapeutic composition injected into such an artery, in order to deliver the composition directly into the tumor. A tumor that has a necrotic center is aspirated and the composition injected directly into the now empty center of the tumor. The antisense composition is directly administered to the surface of the tumor, for example, by topical application of the composition. X-ray imaging is used to assist in ertain of the above delivery methods.

Receptor-mediated targeted delivery of therapeutic compositions containing an antisense olynucleotide, subgenomic polynucleotides, or antibodies to specific tissues is also used. Receptor-mediated DNA delivery techniques are described in, for example, Findeis et al, *Trends in Biotechnol.* (1993) 11:202–205; Chiou et al., (1994) Gene Therapeutics: Methods And Applications Of Direct Gene Transfer (J. A. Wolff, ed.); Wu & Wu, *J Biol. Chem.* (1988) 263:621–24; Wu et al., *J. Biol. Chem.* (1994) 269:54246; Zenke et al., *Proc. Natl. Acad. Sci.* (USA) (1990) 87:3655–59; Wu et al., *J. Biol Chem.* (1991) 266:338–42. Preferably, receptor-mediated targeted delivery of therapeutic compositions containing antibodies of the invention is used to deliver the antibodies to specific tissue.

Therapeutic compositions containing antisense subgenomic polynucleotides are administered in a range of about 100 ng to about 200 mg of DNA for local administration in a gene therapy protocol. Concentration ranges of about 500 ng to about 50 mg, about 1 mg to about 2 mg, about 5 mg to about 500 mg, and about 20 mg to about 100 mg of DNA can also be used during a gene therapy protocol. Factors such as method of action and efficacy of transformation and expression are considerations which will affect the dosage required for ultimate efficacy of the antisense subgenomic nucleic acids. Where greater expression is desired over a larger area of tissue, larger amounts olantisense subgenomic nucleic acids or the same amounts readministered in a successive protocol of administrations, or several administrations to different adjacent or close tissue portions of, for example, a tumor site, may be required to effect a positive therapeutic outcome. In all cases, routine experimentation in clinical trials will determine specific ranges for optimal therapeutic effect A more complete description of gene therapy vectors, especially retroviral vectors, is contained in U.S. Ser. No. 08/869,309, which is expressly incorporated herein, and in section F below.

For genes encoding polypeptides or proteins with anti-inflammatory activity, suitable use, doses, and administration are described in U.S. Pat. No. 5,654,173, incorporated herein by reference. Therapeutic agents also include antibodies to proteins and polypeptides encoded by the subject nucleic acids, as described in U.S. Pat. No. 5,654,173.

F. Gene Therapy

The therapeutic nucleic acids of the present invention may be utilized in gene delivery vehicles. The gene delivery vehicle may be of viral or non-viral origin (see generally, Jolly, *Cancer Gene Therapy* (1994) 1:51–64; Kimura, *Human Gene Therapy* (1994) 5:845–852; Connelly, *Human Gene Therapy* (1995) 1:185–193; and Kaplitt, *Nature Genetics* (1994) 6:148–153). Gene therapy vehicles for delivery of constructs including a coding sequence of a therapeutic of the invention can-be administered either locally or systemically. These constructs can utilize viral or non-viral vector approaches. Expression of such coding sequences can be induced using endogenous mammalian or heterologous promoters. Expression of the coding sequence can be either constitutive or regulated.

The present invention can employ-recombinant retroviruses which-are constructed to cany or express a selected nucleic acid molecule of interest. Retrovirus vectors that can be employed include those described in EP 0 415 731; WO 90/07936; WO 94/03622; WO 93/25698; WO 93/25234; U.S. Pat. No. 5,219,740; WO 93/11230; WO 93/10218; Vile and Hart, *Cancer Res.* (1993) 53:3860–3864; Vile and Hart, *Cancer Res.* (1993) 53:962–967; Ram et al., *Cancer Res.* (1993) 53:83–88; Takamiya et al., *J. Neurosci. Res.* (1992) 33:493–503; Baba et al. I Neurosurg. (1993) 79:729–735; U.S. Pat. No. 4,777,127; GB Patent No. 2,200,651; and EP 0 345 242. Preferred recombinant retroviruses include those described in WO 91/02805.

Packaging cell lines suitable for use with the above-described retroviral vector constructs may be readily prepared (see PCT publications WO 95/30763 and WO 92/05266), and used to create producer cell lines (also termed vector cell lines) for the production of recombinant vector particles. Within particularly preferred embodiments of the invention, packaging cell lines are made from human (such as HT1080 cells) or mink parent cell lines, thereby allowing production of recombinant retroviruses that can survive inactivation in human serum.

The present invention also employs alphavirus-based vectors that can Junction as gene delivery vehicles. Such vectors can be constructed from a wide variety of alphaviruses, including, for example, Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532). Representative examples of such vector systems include those described in U.S. Pat. Nos. 5,091,309; 5,217,879; and 5,185,440; and PCT Publication Nos. WO 92/10578; WO 94/21792; WO 95/27069; WO 95/27044; and WO 95/07994.

Gene delivery vehicles of the present invention can also employ parvovinis such as adeno-associated virus (AAV) vectors. Representative examples include the AAV vectors disclosed by Srivastava in WO 93/09239, Samulski et. al., *J. Vir.* (1989) 63:3822–3828; Mendelson et al., *Virol.* (1988) 166:154–165; and Flotte et al., *PNAS* (1993) 90:10613–10617.

Representative examples of adenoviral vectors include those described by Berkner, *Biotechniques* (1988) 6:616–627; Rosenfeld et al., *Science* (1991) 252:431–434; WO 93/19191; Kolls et al., *PNAS* (1994) 91:215–219; Kass-Eisler et al, *PNAS* (1993) 90:11498–11 502; Guzman; et al., *Circulation* (1993) 88:2838–2848; Guzman et al., *Cir. Res.* (1993) 73:1202–1207; Zabner et al., *Cell* (1993) 75:207–216; Li et al., *Hum. Gene Ther.* (1993) 4:403409; Cailaud et al, *Eur. J. Neurosci.* (1993) 5:1287–1291; Vincent et al., *Nat. Genet.* (1993) 5:130–134; Jaffe et al., *Nat Genet.* (1992) 1:372–378; and Levrero et al., *Gene* (1991) 101:195–202. Exemplary adenoviral gene therapy vectors employable in this invention also include those described in WO 94/12649, WO 93/03769; WO 93/19191; WO 94/28938; WO 95/11984 and WO 95/00655. Administration of DNA linked to killed adenovirus as described in Curiel, *Hum. Gene Ther.* (1992) 3:147–154 may be employed.

Other gene delivery vehicles and methods may be employed, including polycationic condensed DNA linked or unlinked to killed adenovirus hone, for example Curiel, *Hum. Gene Ther.* (1992) 3:147–154; ligand linked DNA, for example see Wu, *J. Biol Chem.* (1989) 264:16985–16987; eukaryotic cell delivery vehicles cells, for example see U.S. Ser. No. 08/240,030, filed May 9, 1994, and U.S. Ser. No. 08/404,796; deposition of photopolymerized hydrogel materials; hand-held gene transfer particle gun, as described in U.S. Pat. No. 5,149,655; ionizing radiation as described in U.S. Pat. No. 5,206,152 and in WO 92/11033; nucleic charge neutralization or fusion with cell membranes. Additional approaches are described in Philip, *Mol. Cell Blot* (1994) 14:2411–2418, and in Woffendin, *Proc. Natl. Acad. Sci.* (1994) 91:1581–1585.

Naked DNA may also be employed. Exemplary naked DNA introductions methods are described in WO 90/11092 and U.S. Pat. No. 5,580,859. Uptake efficiency may be improved using biodegradable latex beads. DNA coated latex beads are efficiently transported into cells after endocytosis initiation by the beads. The method may be improved further by treatment of the beads to increase hydrophobicity and thereby facilitate disruption of the endosome and release of the DNA into the cytoplasm. Liposomes that can act as gene delivery vehicles are described in U.S. Pat. No. 5,422, 120, PCT Nos. WO 95/13796, WO 94/23697, and WO 91/14445, and EP No. 0 524 968.

Further non-viral delivery suitable for use includes mechanical delivery systems such as the approach described in Woffendin et al.; *Proc. Natl Acad. Sci.* USA (1994) 91(24):11581–11585. Moreover, the coding sequence and the product of expression of such can be delivered through deposition of photopolymerized hydrogel materials. Other conventional methods for gene delivery that can be used for delivery of the coding sequence include, for example, use of hand-held gene transfer particle gun, as described in U.S. Pat. No. 5,149,655; use of ionizing radiation for activating transferred gene, as described in U.S. Pat. No. 5,206,152 and PCT No. WO92/11033.

G. Transgenic Animals

One aspect of the present invention relates to transgenic non-human animals having germline and/or somatic cells in which the biological activity of one or more genes are altered by a chromosornally-incorporated transgene.

In a preferred embodiments, the transgene encodes a mutant protein, such as dominant negative protein which antagonizes at least a portion of the biological function of a wild-type protein.

Yet another preferred transgenic animal includes a transgene encoding an antisense transcript which, when transcribed from the transgene, hybridizes with a gene or a mRNA transcript thereof, and inhibits expression of the gene.

In one embodiment, the present invention provides a desired non-human animal or an animal (including human) cell which contains a predefined, specific and desired alteration rendering the non-human animal or animal cell predisposed to cancer. Specifically, the invention pertains to a genetically altered non-human animal (most preferably, a mouse), or a cell (either non-human animal or human) in culture, that is defective in at least one of two alleles of a tumor-suppressor gene. The inactivation of at least one these tumor suppressor alleles results in an animal with a higher susceptibility to tumor induction or other proliferative or differentiative disorders, or disorders marked by aberrant signal transduction, e.g., from a cytokine or growth factor. A genetically altered mouse of this type is able to serve as a useful model for hereditary cancers and as a test animal for carcinogen studies. The invention additionally pertains to the use of such non-human animals or animal cells, and their progeny in research and medicine.

Furthermore, it is contemplated that cells of the transgenic animals of the present invention can include other transgenes, e.g., which alter the biological activity of a second tumor suppressor gene or an oncogene. For instance, the second transgene can functionally disrupt the biological activity of a second tumor suppressor gene, such as p53, p73, DCC, $p21^{cip1}$, $p\ 27^{kip1}$, Rb, Mad or E2F. Alternatively, the second transgene can cause overexpression or loss of regulation of an oricogene, such as ras, myc, a cdc25 phosphatase, Bcl-2, BcF4, a transforming growth factor, neu, int-3, polyoma virus middle T antigen, SV4O large T antigen, a papillomaviral a protein, a papillomaviral E7 protein, CDK4, or cyclin D1.

A preferred transgenic non-human animal of the present invention has germline and/or somatic cells in which one or more alleles of a gene are disrupted by a chromosomally incorporated transgene, wherein the transgenc includes a marker sequence providing a detectable signal for identifying the presence of the transgene in cells of the transgenic animal, and replaces at least a portion of the gene or is inserted into the gene or disrupts expression of a wild-type protein.

Still another aspect of the present invention relates to methods for generating non-human animals and stem cells having a functionally disrupted endogenous gene. In a preferred embodiment, the method comprises the steps of:

(i) constructing a transgene construct including (a) a recombination region having at least a portion of the gene, which recombination region directs recombination of the transgene with the gene, and (b) a marker sequence which provides a detectable signal for identifying-the presence of the transgene in a cell;

(ii) transferring the transgene into stem cells of a non-human animal;

(iii) selecting stem cells having a correctly targeted homologous recombination between the transgene and the gene;

(iv) transferring cells identified in step (iii) into a non-human blastocyst and implanting the resulting chimeric blastocyst into a non-human female; and (v) collecting offspring harboring an endogenous gene allele having the correctly targeted recombination.

Yet another aspect of the invention provides a method for evaluating the carcinogenic potential of an agent by (i) contacting a transgenic animal of the present invention with a test agent, and (ii) comparing the number of transformed cells in a sample from the treated animal with the number of transformed cells in a sample from an untreated transgenic animal or transgenic animal treated with a control agent. The difference in the number of transformed cells in the treated animal, relative to the number of transformed cells in the absence of treatment with a control agent, indicates the carcinogenic potential of the test compound.

Another aspect of the invention provides a method of evaluating an anti-proliferative activity of a test compound. In preferred embodiments, the method includes contacting a transgenic animal of the present invention, or a sample of cells from such animal, with a test agent, and determining the number of transformed cells in a specimen from the transgenic animal or in the sample of cells. A statistically significant decrease in the number of transformed cells, relative to the number of transformed cells in the absence of the test agent, indicates the test compound is a potential anti-proliferative agent.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, *Molecular Cloning A Laboratory Manual* 2nd Ed., ed. by Sambrook, Fritsch and Maniatis (Cold Spring Harbor Laboratory Press:1989); *DNA Cloning*, Volumes I and II (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IIRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Cabs eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I–IV (D. M. Weir and C. C. Blackwell, eds., 1986); *Manipulating the Mouse Embryo*, (Cold Spring Harbor Laboratory Press, Cold Spring Harbor, N.Y., 1986).

As mentioned above, the sequences described herein are believed to have particular utility in regards to colon cancer. However, they may also be useful with other types of cancers and other disease states.

The present invention will now be illustrated by reference to the following examples which set forth particularly advantageous embodiments. However, it should be noted that these embodiments are illustrative and are not to be construed as restricting the invention in any way.

XI. Exanmies

A. Identification of Differentially Expressed Sequences in the SW480 Library

Description of the SW480 Library

SEQ ID NO 1–850 were derived from the SW480 library. The SW480 library is a normalized, subtracted cDNA library that was generated from the RNA derived from colon cancer cell line SW480 and normal human colon tissue. Human colorectal adenocarcinoma (cancer) cell line SW480; ATCC #CCL228. (Leibovitz et al., Cancer Research 36:4562–4569, 1976) was used to generate double-stranded cDNA that was subsequently used as the tester sample for the subtraction experiment. Poly $A^{+}$RNA from normal human colon tissue (purchased from OriGene Technologies, Inc. Rockville, Md.) was used was used to generate double-stranded cDNA that was used as the driver sample for the subtraction experiment The growth conditions of the driver and tester sources in this library were different as SW480 is a rapidly growing cell line and may have higher cellular metabolism. Therefore some of the differential expression in this library might be due to non-relevant growth effects of the two sources of tissue.

Construction of the SW480 Library

Double-stranded cDNA was generated using the Clontech SMART PCR cDNA Synthesis Kit (purchased from Clontech Laboratories Inc., Palo Alto, Calif.) following the manufacturer's instructions. Subtraction hybridization steps were performed in accordance with the manufacturer's instructions for the Clontech PCR-Select kit (purchased from Clontech Laboratories Inc, Palo Alto, Calif.). The subtracted cDNAs were then directly inserted into a T/A cloning vector (TOPO TA Cloning Kit, Invitrogen Corporation, Carlsbad, Calif.) according to manufacturer's instructions, transformed into *E. Coli*, and plated onto LB-amp plates, containing X-gal and IPTG. 1248 bacterial colonies were picked, transferred to LB-amp broth and propagated. Plasmids were isolated using column chromatography (QIAprep 96 Turbo Miniprep Kits, Qiagen Corporation, Valencia, Calif.) on the QIAGEN Biorobot 9600.

Initial Validation of Differential Expression

The inserts from subtracted clones were amplified by PCR and 10 ul of the PCR reaction product was run on a 2.0% agarose gel for 2 hr at 100 volts. The gel was blotted onto a nylon membrane according to standard methods and hybridized as follows: 50 ng aliquots of the RSA1 cut SW480 and normal colon cDNA libraries were labeled with [a-$^{32}$P] dCTP by Prime-It RmT Random Primer labeling kit (Stratagene, La Jolla, Calif.). Nylon membranes containing the PCR amplified DNA from the SW480 library clones were hybridized to the labeled probes at $4\times10^{6}$ cpm/ml in Express hybridization buffer (Cloneteeh) at 68° C. for approximately 16 hours. The membranes were subjected to stringent washes (0.1×SSC; 0.1% SDS) done at 68° C. and were then exposed to phosphorimager screens. The screens were analyzed using Molecular Dynamics ImageQuant soitware. Clones that exhibited a stronger hybridization signal with the SW480 probe relative to the normal colon probe were deemed to be differentially expressed.

Validation of Differential Expression in Colon Cancer

To validate that the differentially expressed sequences found in this library were specific colon cancer, the clones were screened with cDNAs prepared from a colon cancer specific library, Delaware (DE), and a normal, tissue specific library Maryland (MD).

The DE library is specific for sequences expressed in colon cancer [proximal and distal Dukes' B, microsatellite instibility negative (MSI−)] but not expressed in normal tissues, including colon. This colon cancer tissue specific cDNA library, was made using pooled colon cancer cDNA as tester (tumor tissue cDNA pooled from eight patients with either proximal stage B MSI or distal stage B MSI cancers). The driver cDNA consisted a combination of cDNAs made from 50% normal colon tissue and a pool of peripheral blood leukocytes (PBL), and normal liver, spleen, lung, kidney, heart, small intestine, skeletal muscle, and prostate tissue cDNAs as the remaining 50% of the driver.

The MD library is specific for sequences expressed in normal tissue, but oat expressed in proximal and distal Dukes' B, MSI− colon cancers. The tester cDNA in this case was made up of 50% normal colon tissue cDNA while the other 50% was made up of PBL, liver spleen, lung, kidney, heart, small intestine, skeletal muscle, and prostate tissue cDNAs. The driver for this library was generated from pools of proximal stage B, MSI and distal stage B, MSI tumor tissue cDNAs obtained from eight cancer patients.

SW 480 clones that hybridized with the DE probe, but hybridized to a lesser degree (or not at all) to the MD probe were determined to be differentially expressed. This confirmation of differential expression is additional evidence that the up regulation of the individual clones is related to colon cancer.

Sequencing and Analysis of Differentially Expressed Clones

The nucleotide sequence of the inserts from clones shown to be differentially expressed was determined by single-pass sequencing from either the T7 or M13 promoter sites using fluorescently labeled dideoxynucleotides via the Sanger sequencing method. Sequences were analyzed according to methods described in the text (XI., Examples; B. Results of Public Database Search).

Each nucleic acid represents sequence from at least a partial mRNA transcript. The nucleic acids of the invention were assigned a sequence identification number (see attachments). The DNA sequences are provided in the attachments containing the sequences.

Of the 1248 colonies examined, 826 individual clones were found to be differentially expressed using the SW480 and normal colon probes. Of these, 681 were found to be differentially expressed using the DE and MD tissue probes. 145 clones that previously showed differential expression with the SW480 and normal colon probes did not show differential expression with the DE and MD probes. 363 of these clones contained known sequences, 213 contained ESTs, and 105 contained novel sequences. An examination of the known sequences revealed that many of the genes are involved in cellular metabolism.

An example of an experiment to identify differentially expressed clones is shown in the FIGURE, "Differential Expression Analysis". The inserts from subtracted clones were amplified, electrophoresed, and blotted on to membranes as described above. The gel was hybridized with RSA1 cut DE and MD cDNA probes as described above.

In the FIGURE, individual clones are designated by a number at the top of each lane; the blots are aligned so that the same clone is represented in the same vertical lane in both the upper ("Cancer Probe") and lower ("Normal Probe") blot. Lanes labeled "O" indicate clones that are overexpressed, i.e., show a darker, more prominent band in the upper blot ("Cancer Probe") relative to that observed, in the same lane, in the lower blot ("Normal Probe"). The Lane labeled "U" indicates a clone that is underexpressed, i.e., shows a darker, more prominent band in the lower blot ("Normal Probe") relative to that observed, in the same lane, in the upper blot ("Cancer Probe"). The lane labeled "M", indicates a clone that is marginally overexpressed in cancer and normal cells.

B. Results of Public Database Searches

The nucleotide sequence of SEQ ID Nos. 1–850 were aligned with individual sequences that were publicly available. Genbank and divisions of GenBank, such as dbEST, CGAP, and Unigene were the primary databases used to perform the sequence similarity searches. The patent database, GENESEQ, was also utilized.

A total of 850 sequences were analyzed; most sequences were between 200 and 700 nucleotides in length. The sequences were first masked to identify vector-derived sequences, which were subsequently removed. The remaining sequence information was used to create the sequences listed in the Sequence Listing (SEQ ID Nos. 1–850). Each of these sequences was used as the query sequence to perform a Blast 2 search against the databases listed above. The Blast 2 search differs from the traditional Blast search in-that it allows for the introduction of gaps in order to produce an optimal alignment of two sequences.

A proprietary algorithm was developed to utilize the output from the Blast 2 searches and categorize the sequences based upon high similarity (e value<1e-40) or identity to entries contained in the GenBank and dbEST databases. Three categories were created as follows: 1) matches to known human genes, 2) matches to human EST sequences, and 3) no significant match to either-i or 2, and therefore a potentially novel human sequence.

Those skilled in the art will recognize, or be able to ascertain, using not more than routine experimentation, many equivalents to the specific embodiments of the invention described herein. Such specific embodiments and equivalents are intended to be encompassed by the following claims.

All patents, published patent applications, and publications cited herein are incorporated by reference as if set forth fully herein.

TABLE 1

| SEQ ID NO | Clone Name | Cell line probe | Cancer Tissue Probes |
|---|---|---|---|
| 1 | SW006 | O | O |
| 2 | SW0019M13 | O | O |
| 3 | SW0025T7 | O | O |
| 4 | SW0026T7 | O | O |
| 5 | SW0044 | O | O |
| 6 | SW0071 | O | O |
| 7 | SW0081T7 | O | O |
| 8 | SW0106 | O | O |
| 9 | SW0116 | O | O |
| 10 | SW0124 | O | O |
| 11 | SW0142M13 | O | O |
| 12 | SW0142T7 | O | O |
| 13 | SW0162T7 | M | N |
| 14 | SW0181T7 | O | O |
| 15 | SW0184 | M | O |
| 16 | SW0208T7 | O | O |
| 17 | SW0212M13 | O | O |
| 18 | SW0212T7 | O | O |
| 19 | SW0249 | M | O |
| 20 | SW0277 | O | O |
| 21 | SW0292 | O | O |
| 22 | SW0305T7 | M | O |
| 23 | SW0306 | O | O |
| 24 | SW0328 | M | O |
| 25 | SW0337 | O | O |
| 26 | SW0345 | O | O |
| 27 | SW0348 | M | O |
| 28 | SW0353 | O | O |
| 29 | SW0389T7 | O | O |
| 30 | SW0392T7 | M | O |
| 31 | SW0402T7 | O | O |
| 32 | SW0410T7 | M | O |
| 33 | SW0411T7 | M | M |
| 34 | SW0433 | O | O |
| 35 | SW0445T7 | O | O |
| 36 | SW0450T7 | O | M |
| 37 | SW0464 | O | O |

TABLE 1-continued

| SEQ ID NO | Clone Name | Cell line probe | Cancer Tissue Probes |
|---|---|---|---|
| 38 | SW0466 | M | O |
| 39 | SW0469T7 | M | O |
| 40 | SW0489T7 | O | O |
| 41 | SW0498 | O | O |
| 42 | SW0511M13 | O | O |
| 43 | SW0511T7 | O | O |
| 44 | SW0519T7 | O | M |
| 45 | SW0522 | O | O |
| 46 | SW0539 | O | O |
| 47 | SW0558 | O | O |
| 48 | SW0585T7 | O | O |
| 49 | SW0602T7 | O | O |
| 50 | SW0605T7 | O | O |
| 51 | SW0638M13 | O | O |
| 52 | SW0638T7 | O | O |
| 53 | SW0652T7 | O | O |
| 54 | SW0659 | O | O |
| 55 | SW0663T7 | O | O |
| 56 | SW0678T7 | O | O |
| 57 | SW0682T7 | O | O |
| 58 | SW0684 | O | O |
| 59 | SW0693T7 | M | O |
| 60 | SW0704M13 | O | O |
| 61 | SW0704T7 | O | O |
| 62 | SW0709M13 | O | O |
| 63 | SW0709T7 | O | O |
| 64 | SW0730T7 | O | O |
| 65 | SW0749T7 | O | O |
| 66 | SW0758T7 | M | O |
| 67 | SW0766 | O | O |
| 68 | SW0796M13 | M | O |
| 69 | SW0797T7 | O | O |
| 70 | SW0799T7 | O | O |
| 71 | SW0800T7 | M | O |
| 72 | SW0815T7 | M | O |
| 73 | SW0824M13 | N | O |
| 74 | SW0824T7 | N | O |
| 75 | SW0837 | O | O |
| 76 | SW0843T7 | N | O |
| 77 | SW0852 | M | O |
| 78 | SW0906T7 | O | O |
| 79 | SW0925 | N | O |
| 80 | SW0926T7 | O | O |
| 81 | SW0931T7 | M | O |
| 82 | SW0932 | M | O |
| 83 | SW0961T7 | O | N |
| 84 | SW0962 | O | O |
| 85 | SW0971 | O | O |
| 86 | SW0973T7 | M | M |
| 87 | SW0985 | O | O |
| 88 | SW1000M13 | O | O |
| 89 | SW1000T7 | O | O |
| 90 | SW1015T7 | O | O |
| 91 | SW1032T7 | O | O |
| 92 | SW1051 | O | O |
| 93 | SW1052 | O | O |
| 94 | SW1053 | O | O |
| 95 | SW1059T7 | O | O |
| 96 | SW1067 | M | O |
| 97 | SW1068M13 | O | O |
| 98 | SW1068T7 | O | O |
| 99 | SW1085T7 | M | O |
| 100 | SW1086M13 | M | O |
| 101 | SW1086T7 | M | O |
| 102 | SW1088M13 | O | O |
| 103 | SW1088T7 | O | O |
| 104 | SW1089M13 | O | O |
| 105 | SW1089T7 | O | O |
| 106 | SW1093T7 | O | O |
| 107 | SW1098 | O | O |
| 108 | SW1115 | O | O |
| 109 | SW1116M13 | O | O |
| 110 | SW1116T7 | O | O |
| 111 | SW1122 | O | O |
| 112 | SW1138M13 | O | O |

TABLE 1-continued

| SEQ ID NO | Clone Name | Cell line probe | Cancer Tissue Probes |
|---|---|---|---|
| 113 | SW1138T7 | O | O |
| 114 | SW1139M13 | O | O |
| 115 | SW1139T7 | O | O |
| 116 | SW1144M13 | O | O |
| 117 | SW1144T7 | O | O |
| 118 | SW1145M13 | M | O |
| 119 | SW1187T7 | O | O |
| 120 | SW1195M13 | M | O |
| 121 | SW1195T7 | M | O |
| 122 | SW1209T7 | M | N |
| 123 | SW1225M13 | O | O |
| 124 | SW1225T7 | O | O |
| 125 | SW1227M13 | M | O |
| 126 | SW1227T7 | M | O |
| 127 | SW1242 | M | O |
| 128 | SW004M13 | O | O |
| 129 | SW0004T7 | O | O |
| 130 | SW0011M13 | O | O |
| 131 | SW0011T7 | O | O |
| 132 | SW0015T7 | O | O |
| 133 | SW0024T7 | M | O |
| 134 | SW0026M13 | O | O |
| 135 | SW0026T7 | O | O |
| 136 | SW0033T7 | O | O |
| 137 | SW0038T7 | M | O |
| 138 | SW0069T7 | O | O |
| 139 | SW0073T7 | O | O |
| 140 | SW0076T7 | O | O |
| 141 | SW0078T7 | O | O |
| 142 | SW0082T7 | O | O |
| 143 | SW0091T7 | O | O |
| 144 | SW0093T7 | O | O |
| 145 | SW0101M13 | O | O |
| 146 | SW0101T7 | O | O |
| 147 | SW0102T7 | O | O |
| 148 | SW0105T7 | O | O |
| 149 | SW0108T7 | O | M |
| 150 | SW0111T7 | O | O |
| 151 | SW0112T7 | O | O |
| 152 | SW0117T7 | O | O |
| 153 | SW0119T7 | O | O |
| 154 | SW0122T7 | M | O |
| 155 | SW0131T7 | O | O |
| 156 | SW0132T7 | O | O |
| 157 | SW0144T7 | M | O |
| 158 | SW0146T7 | M | O |
| 159 | SW0156T7 | O | O |
| 160 | SW0160T7 | O | O |
| 161 | SW0163T7 | O | O |
| 162 | SW0166T7 | O | O |
| 163 | SW1075T7 | M | O |
| 164 | SW0177M13 | O | O |
| 165 | SW0182T7 | O | O |
| 166 | SW0185T7 | O | O |
| 167 | SW0189T7 | O | O |
| 168 | SW0191T7 | O | O |
| 169 | SW0195T7 | O | O |
| 170 | SW0202T7 | O | O |
| 171 | SW0203T7 | O | O |
| 172 | SW0213T7 | O | N |
| 173 | SW0224T7 | O | O |
| 174 | SW0229T7 | O | O |
| 175 | SW0231M13 | O | O |
| 176 | SW0241T7 | O | O |
| 177 | SW0242T7 | O | O |
| 178 | SW0246T7 | O | O |
| 179 | SW0248T7 | O | O |
| 180 | SW0254T7 | O | O |
| 181 | SW0260T7 | M | M |
| 182 | SW0264T7 | O | O |
| 183 | SW0267T7 | M | O |
| 184 | SW0269T7 | O | O |
| 185 | SW0271T7 | O | O |
| 186 | SW0273T7 | O | O |
| 187 | SW0280T7 | O | O |

TABLE 1-continued

| SEQ ID NO | Clone Name | Cell line probe | Cancer Tissue Probes |
|---|---|---|---|
| 188 | SW0281T7 | O | O |
| 189 | SW0291T7 | O | O |
| 190 | SW0294T7 | O | O |
| 191 | SW0295T7 | O | O |
| 192 | SW0296T7 | O | O |
| 193 | SW0297T7 | O | O |
| 194 | SW0301T7 | O | O |
| 195 | SW0310T7 | O | O |
| 196 | SW0311M13 | O | O |
| 197 | SW0325T7 | O | O |
| 198 | SW0326T7 | O | O |
| 199 | SW0330T7 | M | O |
| 200 | SW0334T7 | O | N |
| 201 | SW0339T7 | O | O |
| 202 | SW0341T7 | O | O |
| 203 | SW0358T7 | O | O |
| 204 | SW0359T7 | M | O |
| 205 | SW0360T7 | O | O |
| 206 | SW0361M13 | O | O |
| 207 | SW0367T7 | O | O |
| 208 | SW0369T7 | O | O |
| 209 | SW0394T7 | O | O |
| 210 | SW0399T7 | O | O |
| 211 | SW0401T7 | O | O |
| 212 | SW0403T7 | O | O |
| 213 | SW0412T7 | M | O |
| 214 | SW0419T7 | O | O |
| 215 | SW0429T7 | M | M |
| 216 | SW0434T7 | O | O |
| 217 | SW0441T7 | O | O |
| 218 | SW0446T7 | O | O |
| 219 | SW0454T7 | O | O |
| 220 | SW0461T7 | O | O |
| 221 | SW0468T7 | O | O |
| 222 | SW0484T7 | O | U |
| 223 | SW0489M13 | O | U |
| 224 | SW0496T7 | O | U |
| 225 | SW0499T7 | O | O |
| 226 | SW0507T7 | O | M |
| 227 | SW0514T7 | O | M |
| 228 | SW0520T7 | O | M |
| 229 | SW0531T7 | M | N |
| 230 | SW0537T7 | M | N |
| 231 | SW0548T7 | O | U |
| 232 | SW0555T7 | O | N |
| 233 | SW0557T7 | O | N |
| 234 | SW0560T7 | O | N |
| 235 | SW0563T7 | O | U |
| 236 | SW0570T7 | O | O |
| 237 | SW0572T7 | O | M |
| 238 | SW0573T7 | M | U |
| 239 | SW0574T7 | O | O |
| 240 | SW0575T7 | O | O |
| 241 | SW0577T7 | O | O |
| 242 | SW0583T7 | O | O |
| 243 | SW0604T7 | O | O |
| 244 | SW0605M13 | O | O |
| 245 | SW0609T7 | M | O |
| 246 | SW0610M13 | M | O |
| 247 | SW0610T7 | M | O |
| 248 | SW0613T7 | O | M |
| 249 | SW0621T7 | O | O |
| 250 | SW0633T7 | O | O |
| 251 | SW0647T7 | O | O |
| 252 | SW0654M13 | M | O |
| 253 | SW0658T7 | M | O |
| 254 | SW0662T7 | O | O |
| 255 | SW0663M13 | M | O |
| 256 | SW0668T7 | O | O |
| 257 | SW0672T7 | O | O |
| 258 | SW0674T7 | O | N |
| 259 | SW0676T7 | O | M |
| 260 | SW0677T7 | O | O |
| 261 | SW0678M13 | O | O |
| 262 | SW0681T7 | O | M |

TABLE 1-continued

| SEQ ID NO | Clone Name | Cell line probe | Cancer Tissue Probes |
|---|---|---|---|
| 263 | SW0683T7 | O | M |
| 264 | SW0687T7 | O | M |
| 265 | SW0688T7 | O | O |
| 266 | SW0692T7 | O | N |
| 267 | SW0694T7 | O | O |
| 268 | SW0697T7 | O | O |
| 269 | SW0710T7 | O | O |
| 270 | SW0711T7 | O | O |
| 271 | SW0713T7 | N | M |
| 272 | SW0724T7 | M | U |
| 273 | SW0734T7 | M | O |
| 274 | SW0736T7 | N | M |
| 275 | SW0744T7 | O | O |
| 276 | SW0751T7 | O | O |
| 277 | SW0753T7 | O | O |
| 278 | SW0763T7 | O | O |
| 279 | SW0768T7 | M | M |
| 280 | SW0770T7 | O | M |
| 281 | SW0772T7 | O | N |
| 282 | SW0774T7 | M | O |
| 283 | SW0778T7 | M | M |
| 284 | SW0779T7 | M | M |
| 285 | SW0783T7 | O | O |
| 286 | SW0784T7 | O | M |
| 287 | SW0786T7 | N | O |
| 288 | SW0787T7 | O | N |
| 289 | SW0797M13 | O | O |
| 290 | SW0803T7 | O | O |
| 291 | SW0809T7 | O | N |
| 292 | SW0811T7 | M | N |
| 293 | SW0815M13 | M | O |
| 294 | SW0821T7 | O | O |
| 295 | SW0825T7 | M | M |
| 296 | SW0826T7 | M | M |
| 297 | SW0827M13 | O | O |
| 298 | SW0828T7 | O | M |
| 299 | SW0836T7 | M | O |
| 300 | SW0839T7 | O | M |
| 301 | SW0843M13 | N | O |
| 302 | SW0846M13 | O | M |
| 303 | SW0847T7 | O | M |
| 304 | SW0849T7 | M | M |
| 305 | SW0850T7 | O | O |
| 306 | SW0855T7 | O | O |
| 307 | SW0863T7 | M | M |
| 308 | SW0866T7 | O | O |
| 309 | SW086T7 | N | O |
| 310 | SW0896M13 | N | O |
| 311 | SW0912T7 | O | O |
| 312 | SW0914T7 | O | O |
| 313 | SW0916T7 | O | O |
| 314 | SW0918T7 | O | O |
| 315 | SW092T7 | N | O |
| 316 | SW0923T7 | O | O |
| 317 | SW0926M13 | O | O |
| 318 | SW0928T7 | N | M |
| 319 | SW0947T7 | O | O |
| 320 | SW0949T7 | O | O |
| 321 | SW0954T7 | M | O |
| 322 | SW0964T7 | M | N |
| 323 | SW0969T7 | M | N |
| 324 | SW0972T7 | M | N |
| 325 | SW00982T7 | O | M |
| 326 | SW0994T7 | O | N |
| 327 | SW0998T7 | O | N |
| 328 | SW1001T7 | O | O |
| 329 | SW1002T7 | O | N |
| 330 | SW1012T7 | O | O |
| 331 | SW1018T7 | O | M |
| 332 | SW1045T7 | O | M |
| 333 | SW1046T7 | M | O |
| 334 | SW1058T7 | O | O |
| 335 | SW1059M13 | O | O |
| 336 | SW1061T7 | O | O |
| 337 | SW1064T7 | O | O |

TABLE 1-continued

| SEQ ID NO | Clone Name | Cell line probe | Cancer Tissue Probes |
|---|---|---|---|
| 338 | SW1065T7 | O | O |
| 339 | SW1080T7 | M | M |
| 340 | SW1085M13 | M | O |
| 341 | SW1087T7 | O | O |
| 342 | SW1091T7 | O | O |
| 343 | SW1093M13 | O | O |
| 344 | SW1097T7 | O | O |
| 345 | SW1104T7 | O | O |
| 346 | SW1105T7 | O | O |
| 347 | SW1106T7 | O | O |
| 348 | SW1107T7 | O | O |
| 349 | SW1108T7 | O | O |
| 350 | SW1109T7 | O | O |
| 351 | SW1114T7 | O | O |
| 352 | SW1123T7 | O | O |
| 353 | SW1124T7 | O | O |
| 354 | SW1130T7 | M | O |
| 355 | SW1131T7 | M | O |
| 356 | SW1132T7 | M | O |
| 357 | SW1133M13 | M | O |
| 358 | SW1134T7 | O | O |
| 359 | SW1136T7 | O | N |
| 360 | SW1141T7 | M | O |
| 361 | SW1146T7 | M | O |
| 362 | SW1147T7 | O | O |
| 363 | SW1155T7 | O | N |
| 364 | SW1156T7 | O | N |
| 365 | SW1160T7 | O | N |
| 366 | SW1161T7 | O | N |
| 367 | SW1169T7 | O | N |
| 368 | SW1176T7 | O | O |
| 369 | SW1182T7 | O | O |
| 370 | SW1193T7 | O | O |
| 371 | SW1201T7 | O | O |
| 372 | SW1203T7 | O | O |
| 373 | SW1212T7 | O | M |
| 374 | SW1213M13 | O | M |
| 375 | SW1214T7 | O | N |
| 376 | SW1218T7 | O | N |
| 377 | SW1220T7 | O | N |
| 378 | SW1232T7 | O | N |
| 379 | SW1236M13 | O | N |
| 380 | SW1238T7 | O | O |
| 381 | SW1239T7 | O | O |
| 382 | SW1245M13 | M | N |
| 383 | SW1247T7 | O | O |
| 384 | SW0003T7 | O | O |
| 385 | SW0009T7 | O | O |
| 386 | SW0012T7 | O | O |
| 387 | SW0013T7 | O | O |
| 388 | SW0015T7 | O | O |
| 389 | SW0016T7 | U | N |
| 390 | SW0018T7 | O | O |
| 391 | SW0019T7 | O | O |
| 392 | SW0023T7 | O | O |
| 393 | SW0025T7 | O | O |
| 394 | SW0027T7 | O | O |
| 395 | SW0029M13 | O | O |
| 396 | SW0030T7 | O | O |
| 397 | SW0039T7 | O | O |
| 398 | SW0043T7 | O | O |
| 399 | SW0046T7 | O | O |
| 400 | SW0048T7 | O | O |
| 401 | SW0050T7 | O | O |
| 402 | SW0052T7 | O | O |
| 403 | SW0063T7 | O | O |
| 404 | SW0064T7 | O | O |
| 405 | SW0068T7 | O | N |
| 406 | SW0072T7 | O | O |
| 407 | SW0074T7 | O | N |
| 408 | SW0075T7 | O | O |
| 409 | SW0077T7 | O | O |
| 410 | SW0080T7 | O | O |
| 411 | SW0081T7 | O | O |
| 412 | SW0085T7 | O | O |

TABLE 1-continued

| SEQ ID NO | Clone Name | Cell line probe | Cancer Tissue Probes |
|---|---|---|---|
| 413 | SW0088T7 | O | O |
| 414 | SW0090T7 | O | O |
| 415 | SW0095T7 | O | O |
| 416 | SW0103T7 | M | O |
| 417 | SW0104T7 | M | O |
| 418 | SW0121T7 | O | N |
| 419 | SW0123T7 | O | O |
| 420 | SW0125T7 | O | O |
| 421 | SW0127T7 | O | O |
| 422 | SW0128T7 | O | O |
| 423 | SW0129T7 | O | O |
| 424 | SW0130T7 | O | N |
| 425 | SW0133T7 | M | M |
| 426 | SW0134T7 | O | O |
| 427 | SW0135T7 | M | O |
| 428 | SW0140T7 | O | O |
| 429 | SW0141T7 | M | O |
| 430 | SW0143T7 | O | O |
| 431 | SW0145T7 | O | O |
| 432 | SW0147T7 | O | O |
| 433 | SW0152T7 | O | O |
| 434 | SW0155T7 | O | N |
| 435 | SW0157T7 | O | O |
| 436 | SW0158T7 | O | O |
| 437 | SW0159T7 | O | O |
| 438 | SW0169T7 | O | O |
| 439 | SW0170T7 | O | O |
| 440 | SW0171T7 | O | O |
| 441 | SW0173T7 | O | O |
| 442 | SW1078T7 | O | O |
| 443 | SW0179T7 | O | O |
| 444 | SW0180T7 | O | O |
| 445 | SW0183T7 | O | N |
| 446 | SW0186T7 | M | M |
| 447 | SW0187T7 | M | U |
| 448 | SW0188T7 | O | O |
| 449 | SW0190T7 | O | O |
| 450 | SW0192T7 | O | O |
| 451 | SW0196T7 | O | O |
| 452 | SW0199T7 | O | O |
| 453 | SW0201T7 | O | M |
| 454 | SW0204T7 | O | M |
| 455 | SW0205T7 | O | N |
| 456 | SW0206T7 | O | O |
| 457 | SW0207T7 | O | M |
| 458 | SW0210T7 | O | O |
| 459 | SW0211T7 | O | O |
| 460 | SW0214T7 | O | O |
| 461 | SW0217T7 | O | O |
| 462 | SW0218T7 | O | O |
| 463 | SW0220T7 | O | O |
| 464 | SW0223T7 | O | O |
| 465 | SW0229T7 | O | O |
| 466 | SW0237T7 | O | O |
| 467 | SW0244T7 | O | O |
| 468 | SW0247T7 | O | O |
| 469 | SW0250T7 | O | O |
| 470 | SW0251T7 | O | O |
| 471 | SW0252T7 | O | O |
| 472 | SW0253T7 | O | O |
| 473 | SW0255T7 | O | O |
| 474 | SW0256T7 | O | O |
| 475 | SW0257T7 | O | O |
| 476 | SW0258T7 | O | O |
| 477 | SW0262T7 | O | O |
| 478 | SW0275T7 | O | O |
| 479 | SW0278T7 | M | O |
| 480 | SW0285T7 | O | O |
| 481 | SW0289T7 | O | M |
| 482 | SW0290T7 | O | O |
| 483 | SW0293T7 | O | O |
| 484 | SW0300T7 | O | O |
| 485 | SW0302T7 | O | O |
| 486 | SW0303T7 | O | O |
| 487 | SW0307T7 | O | O |

TABLE 1-continued

| SEQ ID NO | Clone Name | Cell line probe | Cancer Tissue Probes |
|---|---|---|---|
| 488 | SW0308T7 | O | O |
| 489 | SW0311T7 | O | O |
| 490 | SW0312T7 | O | O |
| 491 | SW0313T7 | O | O |
| 492 | SW0314T7 | O | O |
| 493 | SW0319T7 | O | O |
| 494 | SW0322T7 | O | N |
| 495 | SW0333T7 | O | O |
| 496 | SW0338T7 | M | O |
| 497 | SW0340T7 | O | O |
| 498 | SW0342T7 | O | O |
| 499 | SW0344T7 | O | O |
| 500 | SW0346T7 | O | O |
| 501 | SW0347T7 | O | O |
| 502 | SW0349T7 | M | O |
| 503 | SW0350T7 | O | O |
| 504 | SW0351T7 | O | O |
| 505 | SW0352T7 | O | O |
| 506 | SW0354T7 | O | O |
| 507 | SW0355T7 | O | O |
| 508 | SW0356T7 | O | M |
| 509 | SW0357T7 | O | O |
| 510 | SW0361T7 | O | O |
| 511 | SW0362T7 | O | O |
| 512 | SW0365T7 | O | O |
| 513 | SW0366T7 | O | O |
| 514 | SW0381T7 | O | O |
| 515 | SW0391M13 | O | O |
| 516 | SW0393T7 | O | O |
| 517 | SW0395T7 | O | M |
| 518 | SW0396T7 | M | O |
| 519 | SW0398T7 | O | O |
| 520 | SW0400T7 | O | O |
| 521 | SW0404T7 | O | O |
| 522 | SW0405T7 | O | O |
| 523 | SW0406T7 | M | O |
| 524 | SW0407T7 | O | O |
| 525 | SW0408T7 | M | O |
| 526 | SW0413T7 | M | O |
| 527 | SW0414T7 | O | U |
| 528 | SW0415T7 | O | O |
| 529 | SW0417T7 | N | O |
| 530 | SW0418T7 | O | O |
| 531 | SW0426T7 | O | O |
| 532 | SW0427T7 | O | O |
| 533 | SW0428T7 | M | U |
| 534 | SW0430T7 | M | O |
| 535 | SW0435T7 | O | O |
| 536 | SW0436T7 | O | O |
| 537 | SW0438T7 | O | O |
| 538 | SW0439M13 | O | O |
| 539 | SW0440T7 | O | O |
| 540 | SW0442M13 | O | N |
| 541 | SW0443T7 | O | O |
| 542 | SW0444T7 | O | O |
| 543 | SW0448T7 | O | M |
| 544 | SW0452M13 | O | O |
| 545 | SW0455T7 | O | O |
| 546 | SW0456T7 | O | O |
| 547 | SW0457T7 | O | O |
| 548 | SW0458T7 | O | O |
| 549 | SW0459T7 | O | O |
| 550 | SW0460T7 | M | M |
| 551 | SW0463T7 | O | O |
| 552 | SW0467M13 | O | O |
| 553 | SW0469M13 | M | O |
| 554 | SW0473M13 | O | M |
| 555 | SW0474T7 | O | O |
| 556 | SW0476T7 | O | O |
| 557 | SW0481T7 | O | U |
| 558 | SW0485T7 | O | U |
| 559 | SW0486T7 | O | U |
| 560 | SW0487T7 | O | U |
| 561 | SW0488T7 | O | O |
| 562 | SW0490T7 | U | U |

TABLE 1-continued

| SEQ ID NO | Clone Name | Cell line probe | Cancer Tissue Probes |
|---|---|---|---|
| 563 | SW0491T7 | O | U |
| 564 | SW0492T7 | O | U |
| 565 | SW0494T7 | O | U |
| 566 | SW0495T7 | O | O |
| 567 | SW0497T7 | O | N |
| 568 | SW0500T7 | O | U |
| 569 | SW0501T7 | N OR U | U |
| 570 | SW0502T7 | M | N |
| 571 | SW0503T7 | O | U |
| 572 | SW0504T7 | O | N |
| 573 | SW0505T7 | N | N |
| 574 | SW0506T7 | O | U |
| 575 | SW0509T7 | O | M |
| 576 | SW0512T7 | O | U |
| 577 | SW0513T7 | O | U |
| 578 | SW0515T7 | O | O |
| 579 | SW0516T7 | O | M |
| 580 | SW0517T7 | O | M |
| 581 | SW0518T7 | O | N |
| 582 | SW0525T7 | M | N |
| 583 | SW0529T7 | O | N |
| 584 | SW0532T7 | O | N |
| 585 | SW0533T7 | O | N |
| 586 | SW0534T7 | O | M |
| 587 | SW0535T7 | O | O |
| 588 | SW0536T7 | M | U |
| 589 | SW0538T7 | O | N |
| 590 | SW0540T7 | O | O |
| 591 | SW0541T7 | O | O |
| 592 | SW0542T7 | O | O |
| 593 | SW0543T7 | O | O |
| 594 | SW0544M13 | O | M |
| 595 | SW0545T7 | O | O |
| 596 | SW0546T7 | O | O |
| 597 | SW0547T7 | O | U |
| 598 | SW0550T7 | O | M |
| 599 | SW0551T7 | O | M |
| 600 | SW0552T7 | O | U |
| 601 | SW0554T7 | O | U |
| 602 | SW0559T7 | O | M |
| 603 | SW0561T7 | O | N |
| 604 | SW0562T7 | O | U |
| 605 | SW0566T7 | O | O |
| 606 | SW0567T7 | O | N |
| 607 | SW0568T7 | O | N |
| 608 | SW0569T7 | O | O |
| 609 | SW0571T7 | O | O |
| 610 | SW0578T7 | O | N |
| 611 | SW0580T7 | O | O |
| 612 | SW0582T7 | O | O |
| 613 | SW0584T7 | O | O |
| 614 | SW0591T7 | N | O |
| 615 | SW0606T7 | O | O |
| 616 | SW0607T7 | O | O |
| 617 | SW0608T7 | O | O |
| 618 | SW0611T7 | O | O |
| 619 | SW0612T7 | N | O |
| 620 | SW0616T7 | O | M |
| 621 | SW0623T7 | O | O |
| 622 | SW0629T7 | O | O |
| 623 | SW0635T7 | O | O |
| 624 | SW0636T7 | O | O |
| 625 | SW0637T7 | O | M |
| 626 | SW0640T7 | N | O |
| 627 | SW0641T7 | O | M |
| 628 | SW0642T7 | O | O |
| 629 | SW0644T7 | O | O |
| 630 | SW0645T7 | O | O |
| 631 | SW0646T7 | O | O |
| 632 | SW0651T7 | O | N |
| 633 | SW0653T7 | M | O |
| 634 | SW0655T7 | O | O |
| 635 | SW0656T7 | O | O |
| 636 | SW0664T7 | M | O |
| 637 | SW0666T7 | O | O |

TABLE 1-continued

| SEQ ID NO | Clone Name | Cell line probe | Cancer Tissue Probes |
|---|---|---|---|
| 638 | SW0667T7 | O | U |
| 639 | SW0671T7 | O | O |
| 640 | SW0673T7 | O | M |
| 641 | SW0675T7 | O | O |
| 642 | SW0686T7 | O | O |
| 643 | SW0689T7 | O | O |
| 644 | SW0693M13 | M | O |
| 645 | SW0695T7 | O | M |
| 646 | SW0698T7 | M | M |
| 647 | SW0710T7 | O | O |
| 648 | SW0708T7 | O | M |
| 649 | SW0714T7 | O | O |
| 650 | SW0715T7 | O | N |
| 651 | SW0716T7 | O | M |
| 652 | SW0720T7 | O | O |
| 653 | SW0722T7 | O | N |
| 654 | SW0723T7 | O | O |
| 655 | SW0725T7 | O | M |
| 656 | SW0726T7 | O | O |
| 657 | SW0727T7 | M | U |
| 658 | SW0728T7 | O | U |
| 659 | SW0729T7 | O | O |
| 660 | SW0730M13 | O | M |
| 661 | SW0731T7 | O | O |
| 662 | SW0732T7 | O | N |
| 663 | SW0733T7 | O | O |
| 664 | SW0735T7 | O | O |
| 665 | SW0738T7 | O | O |
| 666 | SW0740T7 | O | N |
| 667 | SW0750T7 | O | O |
| 668 | SW0752T7 | O | O |
| 669 | SW0755T7 | O | O |
| 670 | SW0756T7 | O | N |
| 671 | SW0757T7 | O | O |
| 672 | SW0761T7 | O | N |
| 673 | SW0762T7 | O | O |
| 674 | SW0764T7 | M | O |
| 675 | SW0765T7 | O | O |
| 676 | SW0767T7 | M | O |
| 677 | SW0769T7 | M | M |
| 678 | SW0771T7 | O | M |
| 679 | SW0775T7 | M | M |
| 680 | SW0776T7 | O | O |
| 681 | SW0780T7 | O | O |
| 682 | SW0782T7 | M | M |
| 683 | SW0785T7 | O | O |
| 684 | SW0789T7 | O | O |
| 685 | SW0790T7 | O | N |
| 686 | SW0795T7 | O | O |
| 687 | SW0796T7 | M | M |
| 688 | SW0798T7 | M | M |
| 689 | SW0799M13 | O | O |
| 690 | SW0801T7 | O | O |
| 691 | SW0802T7 | M | M |
| 692 | SW0804T7 | O | O |
| 693 | SW0806T7 | O | M |
| 694 | SW0807T7 | N | N |
| 695 | SW0810T7 | M | O |
| 696 | SW0814T7 | O | O |
| 697 | SW0816T7 | N | N |
| 698 | SW0819T7 | O | O |
| 699 | SW0822T7 | O | M |
| 700 | SW0827T7 | O | O |
| 701 | SW0829T7 | O | M |
| 702 | SW0830T7 | O | M |
| 703 | SW0831T7 | O | O |
| 704 | SW0834T7 | O | O |
| 705 | SW0835T7 | O | N |
| 706 | SW0838T7 | O | U |
| 707 | SW0840T7 | O | O |
| 708 | SW0842T7 | O | O |
| 709 | SW0845T7 | O | O |
| 710 | SW0846T7 | O | M |
| 711 | SW0848T7 | O | M |
| 712 | SW0851T7 | M | M |

TABLE 1-continued

| SEQ ID NO | Clone Name | Cell line probe | Cancer Tissue Probes |
|---|---|---|---|
| 713 | SW0853T7 | O | O |
| 714 | SW0854T7 | N | O |
| 715 | SW0857T7 | O | O |
| 716 | SW0858T7 | M | N |
| 717 | SW0859T7 | M | M |
| 718 | SW0860T7 | O | M |
| 719 | SW0862T7 | M | M |
| 720 | SW0865T7 | N | O |
| 721 | SW0868T7 | O | O |
| 722 | SW0891T7 | O | O |
| 723 | SW0897T7 | O | O |
| 724 | SW0898T7 | O | O |
| 725 | SW0901T7 | O | O |
| 726 | SW0904T7 | O | O |
| 727 | SW0905T7 | N | O |
| 728 | SW0917T7 | O | O |
| 729 | SW0919T7 | O | O |
| 730 | SW0920T7 | O | O |
| 731 | SW0922T7 | O | O |
| 732 | SW0929T7 | O | O |
| 733 | SW0930T7 | O | O |
| 734 | SW0933T7 | M | O |
| 735 | SW0936T7 | M | O |
| 736 | SW0937T7 | O | O |
| 737 | SW0938T7 | N | O |
| 738 | SW0940T7 | O | O |
| 739 | SW0943T7 | O | O |
| 740 | SW0945T7 | O | O |
| 741 | SW0946T7 | N | O |
| 742 | SW0951T7 | O | O |
| 743 | SW0952T7 | O | O |
| 744 | SW0953T7 | O | O |
| 745 | SW0955T7 | N | O |
| 746 | SW0957T7 | O | O |
| 747 | SW0967T7 | O | M |
| 748 | SW0968T7 | O | O |
| 749 | SW0970T7 | O | N |
| 750 | SW0974T7 | O | O |
| 751 | SW0975T7 | O | O |
| 752 | SW0976T7 | O | O |
| 753 | SW0977T7 | M | N |
| 754 | SW0978T7 | O | N |
| 755 | SW0983T7 | O | M |
| 756 | SW0988T7 | O | N |
| 757 | SW0989T7 | M | O |
| 758 | SW0990T7 | M | N |
| 759 | SW0991T7 | O | N |
| 760 | SW0992T7 | O | O |
| 761 | SW0997T7 | M | N |
| 762 | SW1004T7 | O | O |
| 763 | SW1007T7 | M | N |
| 764 | SW1008T7 | O | O |
| 765 | SW1024T7 | O | M |
| 766 | SW1027T7 | O | O |
| 767 | SW1028T7 | O | O |
| 768 | SW1029T7 | O | M |
| 769 | SW1030T7 | M | O |
| 770 | SW1032M13 | O | O |
| 771 | SW1036T7 | O | N |
| 772 | SW1037T7 | O | N |
| 773 | SW1039T7 | O | N |
| 774 | SW1047T7 | M | N |
| 775 | SW1048T7 | O | O |
| 776 | SW1050T7 | O | O |
| 777 | SW1055T7 | O | N |
| 778 | SW0162T7 | O | O |
| 779 | SW1063T7 | O | O |
| 780 | SW1066T7 | O | O |
| 781 | SW1069T7 | O | O |
| 782 | SW1070T7 | M | O |
| 783 | SW1074T7 | O | O |
| 784 | SW1075T7 | O | O |
| 785 | SW1076T7 | O | O |
| 786 | SW1077T7 | O | O |
| 787 | SW1078T7 | O | O |

TABLE 1-continued

| SEQ ID NO | Clone Name | Cell line probe | Cancer Tissue Probes |
|---|---|---|---|
| 788 | SW1081T7 | O | O |
| 789 | SW1082T7 | O | O |
| 790 | SW1094T7 | O | O |
| 791 | SW1095T7 | O | N |
| 792 | SW1096T7 | O | O |
| 793 | SW1099T7 | O | O |
| 794 | SW1101T7 | O | O |
| 795 | SW1103T7 | O | O |
| 796 | SW1111T7 | O | O |
| 797 | SW1112T7 | O | O |
| 798 | SW1113T7 | O | O |
| 799 | SW1117T7 | O | O |
| 800 | SW1118T7 | O | O |
| 801 | SW1119T7 | O | O |
| 802 | SW1121T7 | O | N |
| 803 | SW1125T7 | O | O |
| 804 | SW1128T7 | M | N |
| 805 | SW1129T7 | O | O |
| 806 | SW1140T7 | M | N |
| 807 | SW1143T7 | O | O |
| 808 | SW1145T7 | M | O |
| 809 | SW1149T7 | M | O |
| 810 | SW1153T7 | O | N |
| 811 | SW1157T7 | O | O |
| 812 | SW1158T7 | O | N |
| 813 | SW1164T7 | O | M |
| 814 | SW1165T7 | O | N |
| 815 | SW1166T7 | O | O |
| 816 | SW1167T7 | O | N |
| 817 | SW1179T7 | M | N |
| 818 | SW1171T7 | O | N |
| 819 | SW1172T7 | O | N |
| 820 | SW1173T7 | O | N |
| 821 | SW1175T7 | O | N |
| 822 | SW1178T7 | O | O |
| 823 | SW1197T7 | O | O |
| 824 | SW1180T7 | M | N |
| 825 | SW1183T7 | O | M |
| 826 | SW1187M13 | O | N |
| 827 | SW1189T7 | O | N |
| 828 | SW1192T7 | O | N |
| 829 | SW1196T7 | M | N |
| 830 | SW1199T7 | M | O |
| 831 | SW1200T7 | O | M |
| 832 | SW1202T7 | O | N |
| 833 | SW1204T7 | O | N |
| 834 | SW1205T7 | O | N |
| 835 | SW1207T7 | O | N |
| 836 | SW1210T7 | M | N |
| 837 | SW1213T7 | O | M |
| 838 | SW1221T7 | O | N |
| 839 | SW1223T7 | O | O |
| 840 | SW1224T7 | O | N |
| 841 | SW1228T7 | O | O |
| 842 | SW1230T7 | O | N |
| 843 | SW1231T7 | O | O |
| 844 | SW1234T7 | O | O |
| 845 | SW1235T7 | O | N |
| 846 | SW1237T7 | O | N |
| 847 | SW1240T7 | O | O |
| 948 | SW1241T7 | O | O |
| 949 | SW1243T7 | O | O |
| 850 | SW1246T7 | O | N |

TABLE 2

| SEQ ID NO. | Clone Name | "Novel" Region 1 Start/Stop | "Novel" Region 2 Start/Stop | GenBank Identifier for top 5 matching EST sequences | | | | |
|---|---|---|---|---|---|---|---|---|
| 128 | SW0004M13 | 742–865 | | g1947473 | g1969195 | g2216795 | g1246508 | g1952906 |
| 129 | SW0004T7 | 752–910 | | g1947473 | g1969195 | g2216795 | g1236508 | g2209605 |
| 130 | SW0011M13 | 1–218 | 553–932 | g2241970 | g214706 | g1720731 | | |
| 131 | SW0011T7 | 1–264 | 599–890 | g2241970 | g2140706 | g1720731 | | |
| 132 | SW0015T7 | 483–606 | | g675241 | g900355 | g705376 | g1774265 | g2337538 |
| 133 | SW0024T7 | 1–148 | 268–606 | g4033911 | g1960000 | g679294 | g2180239 | g942639 |
| 134 | SW0026M13 | 400–598 | | g767139 | g880785 | g696474 | g2558187 | g2038504 |
| 135 | SW0026T7 | 1–199 | 285–336 | g767139 | g880785 | g696474 | g2558187 | g1494014 |
| 136 | SW0033T7 | 427–610 | | g2873486 | g1960450 | g4440193 | g2268964 | g1721900 |
| 137 | SW0038T7 | 321–645 | | g4222862 | g2583432 | g3052863 | g2768420 | g3229743 |
| 138 | SW0069T7 | 366–612 | | g770924 | g1308307 | g4741105 | g1844710 | |
| 139 | SW0073T7 | 521–592 | | g1152099 | g2191626 | g1750705 | g2025963 | g1296011 |
| 140 | SW0076T7 | 456–618 | | g2567157 | g2236340 | g2620190 | g3754642 | g2031668 |
| 142 | SW0082T7 | 511–601 | | g1718668 | g1274002 | g2265780 | g3214360 | g1137129 |
| 146 | SW0101T7 | 420–624 | | g1376510 | g708780 | g792817 | g901666 | g390100 |
| 147 | SW0102T7 | 512–599 | | g422023 | g3430515 | g3900153 | g4125195 | g2931421 |
| 148 | SW0105T7 | 1–219 | 570–609 | g2835475 | g1482129 | g1624179 | g1817372 | g2007732 |
| 149 | SW0108T7 | 220–296 | 552–589 | g2154028 | g1303058 | g1645371 | g1792312 | g2882934 |
| 150 | SW0111T7 | 1–68 | | g1308307 | g4332333 | | | |
| 153 | SW0119T7 | 510–596 | | g4265953 | g2836717 | g4487239 | g3228921 | g2876545 |
| 154 | SW0122T7 | 1–51 | | g1760809 | g3804685 | g2457104 | g661521 | |
| 158 | SW0146T7 | 1–76 | 333–617 | g2009649 | g985491 | g1011403 | g956142 | g961346 |
| 159 | SW0156T7 | 1–71 | 782–1002 | g2902747 | g3887935 | g4223262 | g4684438 | g1162310 |
| 162 | SW0166T7 | 1–48 | 444–638 | g2264624 | g3755582 | g1891049 | g4440147 | g2357138 |
| 163 | SW0175T7 | 1–303 | 839–1002 | g724430 | g2154572 | g1958041 | | |
| 166 | SW0185T7 | 113–208 | | g1647210 | g1647264 | g3886862 | g2444221 | |
| 168 | SW0191T7 | 388–683 | | g829950 | g771211 | g766442 | g2785582 | g1441052 |
| 172 | SW0213T7 | 449–617 | | g3886373 | g1940943 | g961389 | g955941 | |
| 174 | SW0229T7 | 293–987 | | g2033455 | | | | |
| 176 | SW0241T7 | 494–570 | | g2010030 | g202190 | g918739 | g893890 | g1976699 |
| 177 | SW0242T7 | 1–41 | 440–621 | g3645529 | g4565156 | g2335995 | g1978587 | g2019409 |
| 178 | SW0246T7 | 1–202 | | g1162850 | g1140707 | g1990341 | g1191239 | g2538237 |
| 179 | SW0248T7 | 497–650 | | g4079044 | g2158663 | g2788869 | g1195625 | g3750745 |
| 182 | SW0264T7 | 1–94 | 479–609 | g1976294 | g3446793 | g2459258 | g1153656 | g2577184 |
| 186 | SW0273T7 | 1–89 | 546–638 | g3677131 | g3805522 | g3244458 | g4525163 | g4598742 |
| 187 | SW0280T7 | 412–628 | | g1815110 | g1933167 | g2817266 | | |
| 188 | SW0281T7 | 109–160 | 572–654 | g2436919 | g2185995 | g3758001 | g654599 | g4523959 |
| 189 | SW0291T7 | 461–650 | | g1992596 | g1138351 | g1146820 | g395782 | g1837320 |
| 190 | SW0294T7 | 431–699 | | g2839339 | g3838466 | g1307860 | g2617794 | g1479221 |
| 196 | SW0311M13 | 1–46 | 456–658 | g4195712 | g464841 | g2750125 | g796654 | g683242 |
| 197 | SW0325T7 | 511–615 | | g1270394 | g3896108 | g2009344 | g1238973 | g2184702 |
| 198 | SW0326T7 | 499–557 | | g1967113 | g1967684 | g1966134 | g1966828 | g2904744 |
| 200 | SW0334T7 | 525–615 | | g1624696 | g2356793 | g1784223 | g1774696 | g1764577 |
| 202 | SW0341T7 | 414–584 | | g774421 | g570881 | g1623681 | g3040994 | g1481791 |
| 203 | SW0358T7 | 112–188 | 513–608 | g1984379 | g3789679 | g3741829 | g4531886 | g1524800 |
| 204 | SW0359T7 | 57–159 | 561–621 | g1802072 | g1663807 | g1894318 | g1775584 | g1678033 |
| 206 | SW0361M13 | 1–65 | 183–572 | g2030884 | g645753 | g1988795 | g1577434 | g1578203 |
| 207 | SW0367T7 | 559–616 | | g644105 | g716356 | g901097 | g1188705 | g712897 |
| 210 | SW0399T7 | 486–589 | | g1856563 | g1690249 | g1966703 | g1952828 | g1639845 |
| 211 | SW0401T7 | 470–590 | | g1165586 | g1690123 | g1967659 | g1491055 | g918845 |
| 212 | SW0403T7 | 369–614 | | g3214476 | g1648508 | g1802846 | g2703245 | g1686573 |
| 213 | SW0412T7 | 1–304 | 509–624 | g681577 | g712993 | g4305548 | g3428224 | g318414 |
| 214 | SW0419T7 | 134–612 | | g1388511 | g4533033 | g2552190 | g3240798 | g3366974 |
| 215 | SW0429T7 | 516–618 | | g1349681 | g1269881 | g4522374 | g1272714 | g3933264 |
| 216 | SW434T7 | 349–595 | | g4261346 | g3596444 | g3755357 | g3329909 | g4684571 |
| 217 | SW0441T7 | 428–610 | | g4762076 | g2158733 | g2158750 | g2809783 | g2113084 |
| 218 | SW0446T7 | 458–585 | | g4111486 | g1484542 | g3415988 | g1959348 | g2874960 |
| 219 | SW0454T7 | 116–599 | | g1319069 | g1319055 | g2669407 | g2355953 | g3181853 |
| 220 | SW0461T7 | 1–189 | 411–602 | g1295370 | g2008512 | g1783876 | g1571056 | |
| 221 | SW0468T7 | 1–55 | 477–573 | g2163292 | g2162568 | g4534378 | g1225564 | g1696820 |
| 223 | SW0489M13 | 449–564 | | g1779025 | g2027299 | g1960180 | g2016248 | g2879596 |
| 224 | SW0496T7 | 160–277 | | g1040448 | g1012154 | g1023347 | g713991 | g2102784 |
| 225 | SW0499T7 | 451–589 | | g1745433 | g4535376 | g3933969 | g1202500 | g2036548 |
| 226 | SW0507T7 | 539–636 | | g1694289 | g1959749 | g3075884 | g2819611 | g1959689 |
| 227 | SW0514T7 | 348–451 | | g815990 | g4824527 | g4281629 | g2110723 | g2445651 |
| 228 | SW0520T7 | 1–200 | | g1999728 | g1959807 | g3897416 | g3178305 | g1305759 |
| 231 | SW0548T7 | 511–639 | | g2036727 | g1692039 | g1951783 | g2715495 | g1467798 |
| 234 | SW0560T7 | 237–408 | | g1180638 | g2110980 | g664974 | g1061663 | |
| 237 | SW0572T7 | 1–47 | 530–607 | g2825571 | g4395571 | g896553 | g4686751 | g2209790 |
| 239 | SW0574T7 | 1–53 | g1721900 | g1962046 | g2268964 | g1516296 | g1317142 | |
| 242 | SW0583T7 | 156–284 | 500–565 | g1983062 | g1779675 | g3924063 | g1689139 | |
| 243 | SW0604T7 | 272–647 | | g1151602 | g1799297 | g1406230 | g1799313 | g1522519 |
| 244 | SW0605M13 | 436–603 | | g3255034 | g4523614 | g2322572 | g820653 | g2195650 |
| 245 | SW0609T7 | 553–640 | | g870149 | 870280 | g2064580 | g793188 | g2069435 |
| 246 | SW0610M13 | 263–312 | 545–608 | g1689308 | g1289557 | g1042368 | g1617963 | g758860 |
| 247 | SW0610T7 | 1–81 | 496–632 | g27910 | g873209 | g812805 | g1183490 | g1183486 |

TABLE 2-continued

| SEQ ID NO. | Clone Name | "Novel" Region 1 Start/Stop | "Novel" Region 2 Start/Stop | GenBank Identifier for top 5 matching EST sequences | | | | |
|---|---|---|---|---|---|---|---|---|
| 248 | SW0613T7 | 274–264 | | g3118093 | g877748 | g781949 | g565336 | g2714808 |
| 249 | SW0621T7 | 295–363 | | g4070350 | g4087920 | g1898671 | g3897398 | g3869687 |
| 250 | SW0633T7 | 478–669 | | g4300499 | g3307939 | g2840238 | g1386618 | g1986484 |
| 251 | SW0647T7 | 530–670 | | g1959511 | g1689297 | g1306866 | g813671 | g1379450 |
| 252 | SW0654M13 | 398–461 | | g1894108 | g838679 | g788785 | g815632 | g1639675 |
| 253 | SW0658T7 | 133–433 | | g2878157 | g3091572 | g3923528 | g3917060 | g4687687 |
| 254 | SW0662T7 | 505–652 | | g4083719 | g2539985 | g3649260 | g3735769 | g2526564 |
| 255 | SW0663M13 | 315–605 | | g2786351 | g645679 | g961061 | g1178347 | g1880239 |
| 256 | SW0668T7 | 371–654 | | g1273871 | g1978052 | g2001412 | g3094537 | g3959666 |
| 257 | SW0672T7 | 477–594 | | g1376487 | g1815330 | g691414 | g3399778 | g3648989 |
| 258 | SW0674T7 | 505–648 | | g1280912 | g774134 | g3849587 | g1516408 | g774915 |
| 260 | SW0677T7 | 1–148 | 432–584 | g1999506 | g1967695 | g2358776 | g1886210 | g1923470 |
| 261 | SW0768M13 | 146–219 | 309–526 | g1502150 | g2027232 | g2013528 | g597973 | g2219539 |
| 262 | SW0681T7 | 1–105 | 422–703 | g2329443 | g3897476 | g4534909 | g2786614 | |
| 263 | SW0683T7 | 301–344 | 410–475 | g1645468 | g1507025 | g3280794 | g865342 | g866161 |
| 264 | SW0687T7 | 276–601 | | g2986269 | g4665361 | g2988563 | g3755365 | g1264045 |
| 265 | SW0688T7 | 404–643 | | g1188074 | g1188536 | g1693906 | g1199366 | g689454 |
| 266 | SW0692T7 | 1–54 | 490–582 | g1969153 | g4534166 | g3990730 | g2215531 | g1927555 |
| 267 | SW0694T7 | 503–565 | | g2184535 | g812780 | g3117755 | g4688064 | g4267188 |
| 268 | SW0697T7 | 279–661 | | g2986269 | g4665361 | g2988563 | g3755365 | g2821651 |
| 269 | SW0710T7 | 476–643 | | g1307580 | g2053081 | g1299364 | g2021058 | g1515716 |
| 270 | SW0711T7 | 540–650 | | g1967859 | g1970279 | g1967270 | g1966441 | g1958872 |
| 271 | SW0713T7 | 478–620 | | g1308937 | g1484655 | g1967497 | g685648 | g1990513 |
| 272 | SW0724T7 | 431–490 | 575–670 | g3030963 | g389972 | g1060573 | g3679607 | g1391607 |
| 273 | SW0734T7 | 320–688 | | g3037561 | g1068430 | g4851814 | g2198924 | g2240396 |
| 274 | SW0736T7 | 499–674 | | g4735776 | g2458732 | g4451965 | | |
| 275 | SW0744T7 | 488–638 | | g835606 | g4291133 | g1367232 | g879361 | g835655 |
| 276 | SW0751T7 | 1–67 | 348–638 | g2033666 | g4525902 | g4094551 | | |
| 277 | SW0753T7 | 457–734 | | g1281367 | g2013326 | g1423548 | g711455 | g1254955 |
| 279 | SW0768T7 | 1–457 | | g816902 | g2028907 | g1977384 | g4126279 | |
| 281 | SW0772T7 | 1–116 | 524–677 | g1389446 | g989175 | g4685207 | g4736243 | g1629372 |
| 282 | SW0774T7 | 515–691 | | g1280912 | g1516408 | g774134 | g3849587 | g774915 |
| 283 | SW0778T7 | 166–688 | | g709101 | g692097 | g1843758 | g1849532 | |
| 284 | SW0779T7 | 247–777 | | g572918 | g672436 | g2873870 | g2903123 | g4307250 |
| 285 | SW0783T7 | 433–692 | | g2884478 | g2882317 | g3918382 | g2810893 | g1760738 |
| 286 | SW0784T7 | 557–709 | | g1147127 | g2269337 | g3674707 | g1670065 | g3934061 |
| 288 | SW0787T7 | 476–681 | | g1624696 | g2356793 | g1784223 | g1764577 | g1959061 |
| 289 | SW0797M13 | 1–48 | 527–565 | g647094 | g4329924 | g1296124 | g3648342 | g3277126 |
| 290 | SW0803T7 | 464–699 | | g869902 | g698828 | g1496517 | g1521347 | g1512645 |
| 291 | SW0809T7 | 1–120 | 495–699 | g815129 | g814313 | g791801 | g711356 | g565905 |
| 292 | SW0811T7 | 337–688 | | g775252 | g1064596 | g2106148 | g2009858 | g2012888 |
| 293 | SW0815M13 | 411–572 | | g2369395 | g1495178 | g715203 | g1978754 | g893190 |
| 294 | SW0821T7 | 192–692 | | g1847887 | g899896 | g3055436 | | |
| 296 | SW0826T7 | 451–677 | | g4850460 | g864989 | g793071 | g2524536 | g2993137 |
| 297 | SW0827M13 | 476–536 | | g1779025 | g2027299 | g1960180 | g2210077 | g1712368 |
| 299 | SW0836T7 | 485–644 | | g2912733 | g3330967 | g1166303 | g2562807 | g2563437 |
| 301 | SW0843M13 | 114–589 | | g1211744 | g1320893 | g825200 | g817462g | |
| 303 | SW0847T7 | 1–346 | 555–673 | g1547479 | g2410830 | g1012926 | g1505518 | |
| 304 | SW0849T7 | 115–426 | | g2079660 | g3099047 | g2341367 | g2198300 | g2197847 |
| 305 | SW0850T7 | 521–655 | | g1036156 | g1923678 | g2874241 | g2805210 | 4630217g |
| 306 | SW0855T7 | 511–684 | | g2402087 | g1781722 | g1303037 | g2005846 | g2218908 |
| 308 | SW0866T7 | 487–660 | | g1894503 | g2191248 | g3898116 | g1785384 | g1114295 |
| 312 | SW0914T7 | 123–168 | 592–654 | g783104 | g1496681 | g1687044 | g2006571 | g1440899 |
| 313 | SW0916T7 | 541–656 | | g1255268 | g1809627 | g1815279 | g1049496 | g1388310 |
| 316 | SW0923T7 | 461–637 | | g389604 | g1983913 | g573354 | g772210 | g3429552 |
| 317 | SW0926M13 | 315–505 | | g2110746 | g1958300 | g850595 | g1040607 | g848805 |
| 318 | SW0928T7 | 546–645 | | g2835368 | g2159357 | g1320607 | g961005 | g1692986 |
| 321 | SW0954T7 | 351–588 | | g1713128 | g4296983 | g3152028 | g3597337 | g3134671 |
| 322 | SW0964T7 | 275–368 | 455–589 | g2617590 | g1983739 | g2321557 | g661505 | |
| 327 | SW0998T7 | 1–430 | | g1665148 | g873211 | g1734568 | g1722041 | g1137689 |
| 331 | SW1018T7 | 369–421 | | g815990 | g4824527 | g3213763 | g4281629 | g2445651 |
| 332 | SW1045T7 | 171–616 | | g1960129 | g2797281 | g3678504 | g2907669 | g1299288 |
| 333 | SW1046T7 | 1–58 | 227–650 | g1689803 | g747999 | g3094753 | g1969991 | g4599383 |
| 334 | SW1058T7 | 256–734 | | g3076981 | g4764472 | g4244708 | g3675166 | g3057227 |
| 335 | SW1059M13 | 164–451 | | g314363 | g2842317 | g2291325 | g2035592 | g4076865 |
| 336 | SW1061T7 | 435–732 | | g1720353 | g4083719 | g2188948 | g3649260 | g1966864 |
| 337 | SW1064T7 | 465–642 | | g1898567 | g1984998 | g1577078 | g1969872 | g1577114 |
| 338 | SW1065T7 | 466–723 | | g4737452 | g1721911 | g2567423 | g3595294 | g4564556 |
| 340 | SW1085M13 | 195–502 | | g2994840 | g652041 | g728040 | g1741474 | g3739875 |
| 342 | SW1091T7 | 1–177 | 457–669 | g1139868 | g4740134 | g1123719 | g4690317 | g4690888 |
| 343 | SW1093M13 | 179–372 | | g2876843 | g1212266 | g1277704 | g3842193 | g650405 |
| 344 | SW1097T7 | 345–483 | | g1966405 | g2000446 | g1984682 | g1162830 | g |
| 345 | SW1104T7 | 348–667 | | g1987181 | g1975635 | g2575165 | g2901280 | g |
| 346 | SW1105T7 | 450–754 | | g3849721 | g4606643 | g1696922 | g2725769 | g3147355 |
| 348 | SW1107T7 | 507–693 | | g4223536 | g2539603 | g4763850 | g3921215 | g4190351 |
| 350 | SW1109T7 | 372–622 | | g1969153 | g4534166 | g3990730 | g3052018 | g |

TABLE 2-continued

| SEQ ID NO. | Clone Name | "Novel" Region 1 Start/Stop | "Novel" Region 2 Start/Stop | GenBank Identifier for top 5 matching EST sequences | | | | |
|---|---|---|---|---|---|---|---|---|
| 351 | SW1114T7 | 436–574 | | g2094727 | g3034248 | g2445722 | g2318514 | g2884719 |
| 353 | SW1124T7 | 424–727 | | g1801953 | g834048 | g867043 | g4599665 | g1491375 |
| 354 | SW1130T7 | 1–151 | 311–411 | g834106 | g857314 | g2880334 | g1166307 | g697528 |
| 356 | SW1132T7 | 428–678 | | g2167403 | g2080455 | g1996679 | g565319 | g659447 |
| 358 | SW1134T7 | 144–267 | 504–633 | g3190963 | g1921067 | g1210922 | g711478 | g874773 |
| 359 | SW1136T7 | 420–635 | | g1740775 | g657385 | g983198 | g831166 | g1959091 |
| 361 | SW1146T7 | 425–631 | | g4524079 | g2154010 | g4703413 | g3648263 | g3752988 |
| 362 | SW1147T7 | 480–660 | | g4739574 | g4301551 | g1312127 | g1721536 | g658245 |
| 364 | SW1156T7 | 1–176 | 409–686 | g1729323 | g1729322 | g1989919 | g1314949 | g1988870 |
| 365 | SW1160T7 | 408–638 | | g2834800 | g3429486 | g3049810 | g1140898 | g3665193 |
| 366 | SW1161T7 | 400–585 | | g2807169 | g4681663 | g4393979 | g1155820 | g1153641 |
| 367 | SW1169T7 | 422–628 | | g2526582 | g2525859 | g3595746 | g4190711 | g4190042 |
| 368 | SW1176T7 | 425–618 | | g1781738 | g2674401 | g1501716 | g656431 | g1522532 |
| 370 | SW1193T7 | 447–636 | | g4391165 | g4295071 | g3146054 | g2357775 | g3238462 |
| 372 | SW1203T7 | 487–612 | | g1012013 | g1288510 | g1716758 | g1264038 | g3330122 |
| 373 | SW1212T7 | 500–640 | | g1384656 | g1696886 | g1891098 | g2825672 | g4084026 |
| 374 | SW1213M13 | 218–503 | | g3076981 | g4764472 | g4244708 | g3675166 | g3057227 |
| 375 | SW1214T7 | 426–611 | | g1386338 | g2162796 | g1616215 | g1965789 | g29070 |
| 376 | SW1218T7 | 424–601 | | g1191932 | g1952078 | g1328929 | g2329319 | g2618462 |
| 377 | SW1220T7 | 1–67 | 487–621 | g1690249 | g1856563 | g1966703 | g1952828 | g1965610 |
| 379 | SW1236M13 | 390–516 | | g875363 | g2100509 | g4187897 | g1623528 | g1157854 |
| 381 | SW1239T7 | 420–480 | 501–620 | g1017274 | g1999568 | g1987290 | g3754140 | g1182700 |

We claim:

1. An isolated nucleic acid molecule consisting of a nucleotide sequence selected from the group consisting of SEQ ID Nos. 34, 40, 55, 57, 60, 72, 128, 408, 790, and 815.

2. An isolated nucleic acid molecule consisting of a nucleotide sequence at least 85% identical to a sequence selected from the group consisting of SEQ ID Nos. 34, 40, 55, 57, 60, 72, 128, 408, 790, and 815.

3. An expression vector, capable of replicating in at least one of a prokaryotic cell and eukaryotic cell, consisting of vector sequences and the nucleic acid of claim 1.

4. The expression vector of claim 3, wherein the vector sequences include a transcriptional regulatory sequence operably linked to said nucleotide sequence so as to render said expression vector capable of replicating in said at least one of a prokaryotic cell and eukaryotic cell.

5. A host cell transfected with the expression vector of claim 3.

6. A pharmaceutical composition comprising a nucleic acid molecule consisting of a sequence selected from the group consisting of SEQ ID Nos. 34, 40, 55, 57, 60, 72, 128, 408, 790, and 815.

7. The isolated nucleic acid molecule of claim 1, wherein said nucleic acid molecule is resistant to cleavage by a nuclease.

8. An isolated nucleic acid molecule consisting of a nucleotide sequence complementary to a nucleotide sequence selected from the group consisting of SEQ ID Nos. 34, 40, 55, 57, 60, 72, 128, 408, 790, and 815.

9. An isolated nucleic acid molecule consisting of a nucleotide sequence complementary to a nucleotide sequence at least 85% identical to a sequence selected from the group consisting of SEQ ID Nos. 34, 40, 55, 57, 60, 72, 128, 408, 790, and 815.

10. A pharmaceutical composition comprising a nucleic acid molecule consisting of a nucleotide sequence complementary to a nucleic acid molecule selected from the group consisting of SEQ ID Nos. 34, 40, 55, 57, 60, 72, 128, 408, 790, and 815.

* * * * *

SEQUENCE LISTING

```
<160> NUMBER OF SEQ ID NOS: 850

<210> SEQ ID NO 1
<211> LENGTH: 359
<212> TYPE: DNA
<213> ORGANISM: Homo sapiens

<400> SEQUENCE: 1

tacaaaacta acgatgaagt tattcatggc atcttcaaag cttacattca gaggctgctt      60

cacgccttgg ctcgacactg ccagctggaa ccagaccatg agggggttcc tgaggagact     120

gatgactttg gggagtttcg catgagggta tcagacctgg taaaggactt gattttcttg     180

atagggtcta tggagtgttt tgctcagtta tattctactc tgaaagaagg caacccaccc     240

tgggaggtga cagaagcggt tctctttatc atgactgcta tagcaaagag tgttgatccg     300

gaaaacaatc caacacttgt ggaagtccta gaaggagttg tccgcctccc ggagaccgt      359


<210> SEQ ID NO 2
<211> LENGTH: 901
<212> TYPE: DNA
<213> ORGANISM: Homo sapiens
<220> FEATURE:
<221> NAME/KEY: misc_feature
<222> LOCATION: (1)...(901)
<223> OTHER INFORMATION: n = A,T,C or G

<400> SEQUENCE: 2

tacactacct tttaaaaaaa attggtatat attactttta ctgtaaagaa atgctttaaa      60

tcaggggtcc ccaaccccca ngtcacanac ctgaangggt ccatgntatg nnatgaacca     120

ngccacacag nnggangtaa gcanctgaga gcgagggaag cctagnntgn atttacagaa     180

aagggaagct ncatctgtat ttacagccac tccccactgc tcacattatg gcctgagctc     240

tgcctcccgt nagatcagga gacattatat tctcatagga gcatgaacac tattgngaac     300

tgcacatnca anggatctgg gttgtctggg ttgtgcgctc cttataaaaa tctaatggtg     360
```

-continued

```
gatgatttgt cactgtctgc catcatccct agatggaaaa caagctcacc caaagtctcn    420
cttntgccna ggngtncctg atgccaagat tcncattttt gacctggggc ggaaaaaggc    480
naaagnggat gagttccgct ttgnggccac atgntgtnag atgaatntga gcagctgcct    540
ctgaagccct ggaggctgcc cgaatttgng ccaatannta ccccgaagcg ctggtacgat    600
tcccaagggg agcgcctttt acactgngcc ctganacttc nnttccagat cggtcnggcc    660
ttttaacttt tggtttcccg tttgtcaaan gacattgctt cctttanttt tncagctggt    720
gngncttgga aaggattggg ccctggcttc tcnaggatgg ctaaggatga anngatatca    780
aggnctggca tgaaanaant cnccggtccn nctttnggct nggttncctt gggacctggc    840
cgggccggtc cgtttcgaaa gggcnaaatt ctggcagaat ttccttgana cctgggcggg    900
g                                                                    901
```

<210> SEQ ID NO 3
<211> LENGTH: 553
<212> TYPE: DNA
<213> ORGANISM: Homo sapiens
<220> FEATURE:
<221> NAME/KEY: misc_feature
<222> LOCATION: (1)...(553)
<223> OTHER INFORMATION: n = A,T,C or G

<400> SEQUENCE: 3

```
actgctttct gctgccgctc aggatagcac tggctttcac agggattanc cttctggtgg     60
tgggcacaac tgtggtggga tacttgccaa atgggaggtt taaggagttc atgagtaaac    120
atgttcactt aatgtgttac cggatctgcg tgcgagcgct gacagccatc atcacctacc    180
atgacaggga aaacagacca agaaatggtg gcatctgtgt ggccaatcat acctcaccga    240
tcgatgngat catcttggcc agcgatggct attatgccat ggtgggtcaa gtgcacgggg    300
gactcatggn tgtgattcac agagccatgg tgaaggcctg cccacacgtc tggtttgagc    360
gctcggaagt gaaggatcgc cacctggtgg ctaagagact gactgaacat gtgcaagatn    420
aaagcaagct gcctatcctc atcttcccag aaggaacctg catcaataat acatcggnga    480
tgatgttcaa aaagggaagn tttgaaattg nagccacagt ttaccctggn gctatnaagt    540
atgaccctca att                                                       553
```

<210> SEQ ID NO 4
<211> LENGTH: 565
<212> TYPE: DNA
<213> ORGANISM: Homo sapiens
<220> FEATURE:
<221> NAME/KEY: misc_feature
<222> LOCATION: (1)...(565)
<223> OTHER INFORMATION: n = A,T,C or G

<400> SEQUENCE: 4

```
actgctttct gctgccgctc aggatagcac tggctttcac agggattagc cttctggtgg     60
tgggcacaac tgtggtggga tacttgccaa atgggaggtt taaggagttc atgagtaaac    120
atgttcactt aatgtgttac cggatctgcg tgcgagcgct gacagccatc atcacctacc    180
atgacaggga aaacagacca agaaatggtg gcatctgtgt ggccaatcat acctcaccga    240
tcgatgtgat catcttggcc agcgatggct attatgccat ggtgggtcaa gtgcacgggg    300
gactcatggg tgtgattcag agagccatgg tgaaggcctg cccacacgtc tggtttgagc    360
gctcggaagt gaaggatcgc cacctggtgg ctaagagact gactgaacat gtgcaagata    420
aaagcaagct gcctatctca tctttccaga aggaacctgc atcataatac attggtgata    480
```

```
tgtcaaaaan gggaagtttt gaaatgganc cccagtttaa cctgnngntt tnagtttnac    540

ccttaatttg gcaagccttt tggan                                          565


<210> SEQ ID NO 5
<211> LENGTH: 500
<212> TYPE: DNA
<213> ORGANISM: Homo sapiens

<400> SEQUENCE: 5

caggtacaca ttcaggggtc actgactctt cagataatgc cctaaacaac tggagtgtgg     60

gcttgtttgc tccaagagca gctgccctgt cagtggaact ccggcgcact tccactcaat    120

actggactgg gggggatgaa agagggattt ttaaatggca gaaaagtgtt cttctgggct    180

gtctggcccg ggcagggcgg gttgtgactt ggaaaagaag gggaaggtag ggaggccttg    240

aacttaggga cagccagcaa atgatccttg cagcttttgg aacacaaggc agggctaagg    300

ttacctttca gcttccttgc ttaagtagca gtggctaagt gggttaaact ttgctcggcc    360

tgcaggctcc ccctgttggt cagatacttg cattgacatc ctcagtgttc aatgctcctg    420

gaagagccca ggagagggcg gcactggccc agggattgca ggtcagggaa ctctagcaaa    480

ttcccacacc ctagggtacc                                                500


<210> SEQ ID NO 6
<211> LENGTH: 622
<212> TYPE: DNA
<213> ORGANISM: Homo sapiens

<400> SEQUENCE: 6

acaaggaaat gtcagtcagg ggtgttgcat attacataca tgtggttacc gaacttggtt     60

tacattattg attaaattca ttttctcttt ctctttttta gacctttgga tatctcctcc    120

tccttcccct tatctataaa tatgtaagaa agaaaacatg tttaaaatac aatattttat    180

ttcttttgat cacagattag acttaaagaa cagagatgcc ctataatgtg atctttaaga    240

gatattacaa agcttccaat ctcactgtga ggatcgttaa agtataataa taaaaaaaaa    300

tgtatattat aaaagaatgt aagaatgtgc atatttattt ccttgcatat taatggcata    360

agaaactgtt aacagggact tggggtaagg cttgtgggaa ggaaggtagt tttcactgta    420

ttccttttgt attgttttaa gtttttactt gtttttttaag caagcatgta tcactttata    480

tgatatttaa aagttgctct tctcaagaca gaaaatcatt ttgattcatt tctaattcaa    540

ataagcacta attgaggata ttttaatata tcctcacatt gtgaaaggat taaggcacaa    600

tttctagctt caaaactgta cc                                             622


<210> SEQ ID NO 7
<211> LENGTH: 621
<212> TYPE: DNA
<213> ORGANISM: Homo sapiens
<220> FEATURE:
<221> NAME/KEY: misc_feature
<222> LOCATION: (1)...(621)
<223> OTHER INFORMATION: n = A,T,C or G

<400> SEQUENCE: 7

ggtacccttg tctttaaaag gattccccct tataaggact cttcaagtaa atccacacat     60

atatagtcaa ctaatttttg acaaagacac caagaataca caatggggaa aggatagtgt    120

cttcaataaa cagtattgga aatactggat atccacatgc aaaagaatga aattggatga    180
```

-continued

```
aatatggtga aattatttta caccgtaccg gctccccaac gtgcacggca ggagctacgg    240

cccagcgccg ggcgctggcc acgtgcagaa atggagtttc atcatgttgt cctctcgaac    300

tcctgacctc aagtgatcca cccgnctcgc ccttccaaag tgctgagatt acaggaagag    360

tctaacctgc tctgcaagct cttgagtccc gccaagatga tatttaaaac gtctgtatga    420

agttgaaagc tgcagntgat ggcctnttca agatgattca aaccncngat gcnnacttgg    480

atgtaancca ccntaattca agccggtnan nccncnnant taacccnaag ggcctggatt    540

tgaattcagg cnttggnaag gttnccgggc ccttaaaana nattggggtt aacgcaaacc    600

ggcttccntt ccttttcttg n                                              621
```

<210> SEQ ID NO 8
<211> LENGTH: 649
<212> TYPE: DNA
<213> ORGANISM: Homo sapiens

<400> SEQUENCE: 8

```
actgatctcc tgttggcctg cttcatttgt cctgcagttg tcaatccaga acaatatgga     60

ataatttccg atgctcctat taatgaagta gcacgattta atctgatgca ggtaggccgc    120

cttttgcagc agttagcaat gactggctct gaagagggag atccccgaac aaagagcagc    180

cttggaaagt ttgacaaaag ctgtgttgcc gctttccttg atgttgtgat tgggggccgt    240

gcagtggaga cccctccatt gtcttccgtc aatcttctgg aaggattgag cagaactgtg    300

gtttatataa cctacagtca ggcttattac tctggtgaat tttatgaaag agtgtgatgt    360

ctggagatca actgagagaa gatagaatgg ctcttgacaa tttattggca aacctacccc    420

cggccaagcc aggaaaaagt agcagtttag aaatgactcc ctacaataca cctcagctat    480

ctccagcaac cactccagca aataaaaaga atcgattacc tatagcaact cggagcagaa    540

gccgcaccaa tatgctaatg gacctacata tggaccatga aggatcatct caagaaacca    600

tccaggaggt gcaaccagaa gaggtgttgg tcatttcctt aggtacctc                649
```

<210> SEQ ID NO 9
<211> LENGTH: 645
<212> TYPE: DNA
<213> ORGANISM: Homo sapiens

<400> SEQUENCE: 9

```
acttagtgca acatattgaa cttaaattcc agttttcctg gaattacttg tgtcttgagc     60

taaaggctgt atttgatata acagggaagg aaagaaatta tttttcctat aaaattagtt    120

tagtttaaaa acacatataa ttaaacaaaa taaaaatatt attccatctt ttaaagaaca    180

tttactaatt cacagatatt acccgaagtt tagaaagtca cctaagaaca attgtttaaa    240

aattatttag ggaaaatgaa gcaaaattgt tttcaatctg agattttaac agccagtgca    300

ctcctgttcc tcagctgaaa gtccccttca ttctgaatgt ctgcagtagt attgaattgg    360

ggagcagtta ggttccaggg acatattcac tcctgttttg ttctcccatc aatctcagcc    420

ctttcggtga ctgtttgggc aaagcctccc ttgtggtaga agatgcctca cttctgggga    480

gaagaggctc ctcatcttgc agacaagaag cagcacccac tgtttcttgc tccaaaagcc    540

attaacatta taaactggcc agttgcagtg gctcaaactt gtaatcccag caccttttgg    600

gaggttgagg cacaaggatt gcttgagccc aggagtttga gtacc                    645
```

<210> SEQ ID NO 10
<211> LENGTH: 564

```
<212> TYPE: DNA
<213> ORGANISM: Homo sapiens

<400> SEQUENCE: 10

cgcggccgag gtacctgggc ttaacagtaa tagagaacct catttatacc atacagacac     60

agcaacttag gaagacagca ctgatagcat ttagctagtt gtaaccaaat ccaaatatgt    120

aaaattgaga attatgatta acatatgcaa ctttagtaat aggaatagat gataattttc    180

ctgtattgtt tcaaataagt gactgttcag ctgggatcca ttggattata atttacaatg    240

tcacataata ttatgctttt caatattgat gagtgatgta aacaatataa agttggcagt    300

ttgtagtagt tcagtatcct agaaatacat tgaacttcat aagtatcagt tcatttttaa    360

gcatacagaa ttgaactgat acttactgaa atcataaact cagaggaaac aagcccatct    420

ttatcactaa ttacttagct tgaatacttt tctattttaa aataatccta attattgcct    480

tttcaattat agtctactgt atttatttat atgggatcaa caggtattta tcaaacatct    540

actgtgtgcc cagcactacc tagt                                           564


<210> SEQ ID NO 11
<211> LENGTH: 593
<212> TYPE: DNA
<213> ORGANISM: Homo sapiens
<220> FEATURE:
<221> NAME/KEY: misc_feature
<222> LOCATION: (1)...(593)
<223> OTHER INFORMATION: n = A,T,C or G

<400> SEQUENCE: 11

cgaggtgcct cgcctcgggc attttcttgc agcaagaagg gacgcatgcc tctggcataa     60

atccaaccag agagtcaccc ctctcaagct gattttttaa aaatctagat attatttaga    120

tcatttcagc aaattcttaa tgctttggcc tttcacagta agatgttgct taatcggctg    180

gatctccccc ctccttgcca aggagactca attttgcagt tgcccatatc tgcctagtta    240

aatcgttgct atactaaagg ttctgggagg gtggggacag aatttccccg gtgctaatgc    300

ggcactgaat cgcaggaggc tgccatgcat ttcttcagtc atctacaacc aagaattctc    360

agagcagtcc ctcggcagcc ttttgaagct gtgctagagc agaaagctgc tattgntctc    420

atctctcaac aaggaaagga tcaaactttg cctctttcaa tttgaaagat ttttttttat    480

ggtggtgggg ggaagggatt gcaatcttga tnctcaagtt aactttgagg atttggagtg    540

gtctnccagt ttaaactgca gatcaaatca cagaagccct aacgcctgca tnt           593


<210> SEQ ID NO 12
<211> LENGTH: 602
<212> TYPE: DNA
<213> ORGANISM: Homo sapiens
<220> FEATURE:
<221> NAME/KEY: misc_feature
<222> LOCATION: (1)...(602)
<223> OTHER INFORMATION: n = A,T,C or G

<400> SEQUENCE: 12

acacacaatt ccactctacc acccaacatc aatgagcatt tattgagcat ctactgaagc     60

tcacagcatt gtgcaggcag gatacatatc atacaaatgc tgtttcctcc tcccaccaaa    120

tgagggagaa ttagatgaga tttttaaaaa ttcctcctag ttctacaacc agtattgtat    180

actgatccaa tttggaagtt taagtttaaa attaattcaa ggattccagt tgaggaaatg    240

gtcccacttc cttggaaagt aaactagctc ggtcaccagg ctaggttacc cacgttgtaa    300
```

-continued

```
ttgcttgtga ttgactactc caccgtatta atgatgaagt gcccccgact tgagatgcag    360

gcgttagggc atctgtgatt tgatctgcag tttaaactgg gagaccactc caaatcctca    420

aagttaactt tgagtatcag attgcaatcc ttcccccacc accataaaaa aaaatctttc    480

aaattgaaga ggcaaaagtt ggatcctttc cttgttgaga gatgagacca ttgccgcttt    540

ttgntntagc caggtttcaa anggttgcca nggactgntn tganaatctn ggtgganaaa    600

an                                                                   602
```

<210> SEQ ID NO 13
<211> LENGTH: 487
<212> TYPE: DNA
<213> ORGANISM: Homo sapiens

<400> SEQUENCE: 13

```
gcgtggcgcg gccgaggtac tggaggccat ccagcccata ccctggcggg gggcaaacct     60

cagatgcctc cttcttgggt ttcattgggc accaggatcc atcttccatg aattggatct    120

catcacaatc tgaacaggaa ctaagaatct ccataaataa accatcaatg ataagagatt    180

catagggagc cttcttgtca cacacaggac atgtccatgt aggcttcttc tcattcatct    240

gtagataaag ggcagcatcg aagctctgca ggtgggcgca ggtgagggca cgacaaggga    300

cagtcaggcg catcttccct agcgggcaca tgagtgacac ccggagactt gtagtggcca    360

cctcactgtc agggtcagca gtcaatttct ccttgatcag tgcccgcgag tggtctgggt    420

tccggatacc ctttgctctg agtttttgta gaagggttcc tgcagtcaac tgcctcacca    480

ggtacct                                                              487
```

<210> SEQ ID NO 14
<211> LENGTH: 300
<212> TYPE: DNA
<213> ORGANISM: Homo sapiens

<400> SEQUENCE: 14

```
acagaaattc ttaactgctt atgaaatgct gattgttaaa cagcatccac agctattttg     60

tgttgtttcc ctgaccccac cctgaagaaa agaaaaatta tggcatattg aaaacagcag    120

tatgatgtaa gagaaaagat cacaaattcc ttgagggtgg gtcttttcca tactcataag    180

cctatttata atattcagag taatttattg acacatatta atattccctc ctatcccatt    240

aattgccaaa tcatcaaaca tttattgagc acctactctg tgtagggtgt aagcagtacc    300
```

<210> SEQ ID NO 15
<211> LENGTH: 882
<212> TYPE: DNA
<213> ORGANISM: Homo sapiens

<400> SEQUENCE: 15

```
acctcataac aaatgcctgc catgtgttcc agattcacct tctttctttc tgccccagcc     60

ctggaatcag ctgcttctcc aagcactcag gactcctctt aacagagaat gataaatact    120

tagaaacccc tgaggcccgg tgtgctcagt gttctaggct gtcctccttc taagcccttc    180

tcgtggccag aaccacacaa agtatcatca cgacagcttt atagtaagtg ctggtgtttg    240

cagggcaaat ggccctcttc ttcacaagtg ttttaattaa tcctggactt gcactcttct    300

cagtgaattc tagtcacctt gtcaggaaag agaagtggct ggatgtcgat gggaacgtca    360

ttgaatgtta agagcaactt tgggagacct gacacctggc atcttccttt ctctgaacat    420

agaggagaat taagcaaatc ttccttaaat gtccttcaat aaagtttata tattttctgc    480
```

```
atgcagatct tatctgtctt aaaatttacc ccagatacct ttttgctact gtaagcatta    540

tgttttaaat tacattttgt aaccaattaa attgttggtt taacaaaatg aattgatttt    600

atattttgat cttaaatttg ctcaactctc taatctgttc tgagatccct atttaggaaa    660

ttacatcaca tcacatgcca gtaacagcag ttttatttct gcctttttca ccctctgccc    720

tgctgaaaac agtgttgtga ggctgaggat gatgtgggtt acacaaaact tggctgcact    780

gcagggggga atggaaatct acataaccac cttggaaaaa tcgatatgta tcaatatgca    840

gacgtctgcg ttatcctgca gaactggaca tttgcacgta cc                        882
```

<210> SEQ ID NO 16
<211> LENGTH: 568
<212> TYPE: DNA
<213> ORGANISM: Homo sapiens
<220> FEATURE:
<221> NAME/KEY: misc_feature
<222> LOCATION: (1)...(568)
<223> OTHER INFORMATION: n = A,T,C or G

<400> SEQUENCE: 16

```
ggtactcccg gctttacagt taaaaccagt tttctgggaa catttgtcaa acacagggaa     60

aggctgtcct tttaagttag tgtttactgc atttcaccta agactaaatg gacaaatgaa    120

ttataaattc attttttagg aggcataata aactttggaa atattttttc ttaattagag    180

ggaagaaatg agcaaaagag aacccgaggc tctagctaga agcccgtgtt tctctgccct    240

aattgcatca aacaatgcct taataatctg tgtcttcatg tgggaggcat ctactctgtc    300

ctctactttt tcacttttat gcaaactcag gggaaactca ggggaaaaaa tgattctatg    360

aaattataat tagagccata tttctagatt ttaattttca acattggcat ttattaattt    420

cctgcagctg ctgtaacaag ttaccacaaa ctggtaaaaa tggcttaaaa gaacngaaat    480

ttattttnct acaggtcaag gccggaaatn ccaaatctaa gcatcanggg ggtggggtcc    540

ctttggangn tcccanggna ntttttcc                                        568
```

<210> SEQ ID NO 17
<211> LENGTH: 584
<212> TYPE: DNA
<213> ORGANISM: Homo sapiens
<220> FEATURE:
<221> NAME/KEY: misc_feature
<222> LOCATION: (1)...(584)
<223> OTHER INFORMATION: n = A,T,C or G

<400> SEQUENCE: 17

```
acaactgaag accctagaaa taagggtttc aaccctggtt gcccattaga atcatgaaag     60

agcccccgag atttgggttg aattggtctg cagagactcc aggccccttc ttttgaagct    120

ccacagatga ttcttttctg cctgagggga ggtgctgagt tcccatcacc caccagcttc    180

atcctacaca ngtgcaatna gaggcctagt gagagtggca ctggggggtg gccccccagc    240

gagtgccaag tagatcccac caggcccttn ctttaggcca gaggttctag aaactttgat    300

gaatgtngca ataaccaggg ggtgctctga aaaggnccta nggctgggct gcacctgnta    360

aaatnaagcc cagtctttct ggttgggacc agaagattcc naagggcagc ncgctcttta    420

aaaaccaagt gcctttctgn taaacnaatc cttaggnccn ttatgtctgc agttnttaag    480

ntaangggtt ggtaagntan taacntccat taantttnag tntacactta agcttttggg    540

ggtatcngnt tnnagtgnna ttangnagtc tttcacaggt ngtt                      584
```

<210> SEQ ID NO 18
<211> LENGTH: 560
<212> TYPE: DNA
<213> ORGANISM: Homo sapiens
<220> FEATURE:
<221> NAME/KEY: misc_feature
<222> LOCATION: (1)...(560)
<223> OTHER INFORMATION: n = A,T,C or G

<400> SEQUENCE: 18

```
ggtactcaaa gcttggactc catccctgaa ggtcttcctg attgatagcc tggccttaat     60
accctacaga aagcctgtcc attggctgtt tcttcctcag tcagttcctg gaagacctta    120
ccccatgacc ccagcttcag atgtggtctt tggaaacaga ggtcgaagga aagtaaggag    180
ctgagagctc acattcatag gtgccgccag ccttcgtgca tcttcttgca tcatctctaa    240
ggagctcctc taattacacc atgcccgtca ccccatgagg gatcagagaa gggatgagtc    300
ttctaaactc tatattcgct gtgagtccag gttgtaaggg ggagcactgt ggatgcatcc    360
tattgcactc cagctgatga caccaaagct taggtgtttg ctgaaagttc ttgatgntgn    420
gacttaccac ccctgcctna caactgcaga cataaggga ctatggattg cttaacagga    480
aaggcactng ntctcaangg cggntgcccn ttgggaaact tntgggccca ccccaaagaa    540
tgtggntttn agtttttcnn                                                560
```

<210> SEQ ID NO 19
<211> LENGTH: 425
<212> TYPE: DNA
<213> ORGANISM: Homo sapiens

<400> SEQUENCE: 19

```
ggtacaaaga gaaaaggtca agacattttt caaatgaggg aaaactaaca ggatttatca     60
ctagtaaacc tgctctaaaa gaattcaagg gaagcttttt aaaaagaagg gaagttatag    120
cagaaggaaa cttagaatgg caggaataaa gaaggcataa tgtatagggt aaatataata    180
gacttctctt gaggttttaa aaattacatt tgttatttga aagaaaaaaa ttaacgttgt    240
tgtatgtgat tctctgtaga ggatatacag tttttttgt tgttcttgtt tctgtttttt    300
taaggtgaag tctctgtcac ccaagctgga gtgcagttct gtgatcatgg ctcactgcag    360
cttcaccctg ggttcaggtg atcctcccac ttcagcctct tcagtaactg ggactacagg    420
catgt                                                                425
```

<210> SEQ ID NO 20
<211> LENGTH: 655
<212> TYPE: DNA
<213> ORGANISM: Homo sapiens

<400> SEQUENCE: 20

```
tgttacttcc caagcactgt agggcgtaag gaaaatctgg tccttatcaa atcccaggag     60
cttctgctta gttggggaag aaattacatg aagcaaccag aggttataag gccacacttg    120
tatatcgtgc accctgtgtg gacaagatta gggactgttg agagaggagg aaaccagtag    180
agagcaaagc tctacccagg ctccttgtaa gcctctgggc tcccccgaga gggcctcgct    240
actctacgct tccctagcaa cgttgatgtc cccacaaccc cacatcagtg cagctgtggc    300
ttgtgtggag gggctctgag gcctctgagg ccagatgtgt aaacagtgct gaggttcagt    360
aataggatga agtcttcagg tgtggagcag cccaccttgg ctcttcccat gtctctgtgt    420
tacttctcat attctgctgt cctttcaaac ttcaaggaca gtattaattt atactagtat    480
```

-continued ttcttcctca gttttgtgac ttgaatgcag tgagtgcctt agaggatcca aggatgaagg 540
aatgcgggtt ggtggttctc tctttcagaa tgggaacttc ccaaaaatgg ggctgcgtct 600
cgcctctcag taggttccct acctctgggt cttccaccct tcaaaatctg gtacc 655

<210> SEQ ID NO 21
<211> LENGTH: 566
<212> TYPE: DNA
<213> ORGANISM: Homo sapiens

<400> SEQUENCE: 21
ggtacagccc tttctttgaa tggggatctg ggatgcaga ggagcataat gagcctttta 60
taattacaaa catgctcttc tctagctctt aaggttatgc ctaacgctca tttgctcttg 120
gctaaaataa ctgagaaaaa aagtgagtag taaaaaaatg ctggaagtct gaaaatggtt 180
tagacagaac ttcattcctg aagttttagt ctgtagccag attttaattc tggcctgttt 240
tggtttttag atgatagatc ttttagtgtg tcaacaggaa tgtaaagttt gtattaacat 300
ctagggtgat cacctgccat gctattaagt cagcatggta taattaaaag ttacatatgt 360
aggttcagag cctcttagca cagtgttaca ttgtaagctc ttggagggca ggaatgagat 420
tctagtcctt acggaaatgg agtttgggct tctatcccta gcattcattc tagtgccatg 480
cacgtggtag gaattctgta aatatttgtg aaagaaatga atttctgcct gtagggttca 540
gcagtgtata cttaaatgtg atgtgt 566

<210> SEQ ID NO 22
<211> LENGTH: 269
<212> TYPE: DNA
<213> ORGANISM: Homo sapiens

<400> SEQUENCE: 22
ggtactaata gcaaggaata atcctaaaca ttttcccaat aaactgacta agcctcaaaa 60
ggacagctta ggaaaatgat taacatgcag tttttctttt ttcctagcca attcagttct 120
acttagataa atctggttgc caatcaatac atatataaat taattttttt ctgctcaatt 180
actaccattt tttctttttc accttttccc caattttctc tagcaacact tttcctttgg 240
tttgatcagt tgaactcaaa aggtttggt 269

<210> SEQ ID NO 23
<211> LENGTH: 815
<212> TYPE: DNA
<213> ORGANISM: Homo sapiens

<400> SEQUENCE: 23
gaggtaccct tcatccatca ggactgcacc tcctttccca tgagccttct ggggtcacat 60
tctcctaact gcagctactg ttgctgtttt acttatcgag ggcctattac gtgccaggct 120
ctgcgctgaa cgcttcacgc ccactggatc atttactcat aatagctcag taaggtagtt 180
accccaatta gccccatgtt agagaaaaac accaaggcac agaggtgagt cacttgtccc 240
aggtcacaca tctaggaagt agtagaacca ggactcagct caggtccaaa gtctcaacca 300
tgggccagtc tgctcatctt agtcaaaccc ccaggctgca ttctgtggtc cagctactgg 360
atcctgcaac cttctcagac tctatccatg aagccaagtg cacaggatct aggacatcag 420
gtccagaaaa attggggcca cattcttctg gacctgcaga tgggcaagga ccagactcta 480
gcctgaacag tgagatgcag cccagagaag tgggaatcca cagacagagc ctggcctgag 540

-continued

```
actcctactg agactgccca tgtggccact cggggagttc ccgtcccctg cctgatcagc    600

agtctttttg cttccccctc caagagagct ggggggcatt cctccaggaa gcctgatatg    660

taacaaactc ctttcccatt tcttgctttg cttaaatctc caaagtccct ggagctgaag    720

ccaagcgggc ctcattaggt ccactttaca gaaaagcaaa ctgagtctca aagaggggaa    780

gtcactgagc cgggtacctg ccgcgggccg ctcga                                815


<210> SEQ ID NO 24
<211> LENGTH: 555
<212> TYPE: DNA
<213> ORGANISM: Homo sapiens

<400> SEQUENCE: 24

ggtacctggg cttaacagta atagagaacc tcatttatac catacagaca cagcaactta     60

ggaagacagc actgatagca tttagctagt tgtaaccaaa tacaaatatg taaaattgag    120

aattatgatt aacatatgca actttagtaa taggaataga tgataatttt cctgtattgt    180

ttcaaataag tgactgttca gctgggatcc attggattat aatttacaat gtcacataat    240

attatgcttt tcaatattga tgagtgatgt aaacaatata aagttggcag tttgtagtag    300

ttcagtatcc tagaaataca ttgaacttca taagtatcag ttcattttta agcatacaga    360

attgaactga tacttactga aatcataaac tcagaggaaa caagcccatc tttatcacta    420

attacttagc ttgaatactt ttctattttt aaataatcct aattattgcc ttttcaatta    480

tagtctactg gatttattta tatgggatca acaggtattt atcaaacatc tactgtgtgc    540

ccagcactac ctagt                                                      555


<210> SEQ ID NO 25
<211> LENGTH: 413
<212> TYPE: DNA
<213> ORGANISM: Homo sapiens

<400> SEQUENCE: 25

ggtacaagct tttttttttt tttttttttt ttttcctttc attgtccagt ccccatgaat     60

tatttatttg ttattaaatt caactgaatg agatttcaaa gcaacgaaaa ttgaagttca    120

aatgaaacca aattaccact ctgagctcca ggtggccctg acagcccagt tttgtgaagg    180

gcccctgagg ctgttcactg aatctgagat gtcaccaggc atggagggtc tctgatcagc    240

atccagagct ccagagtagg gagcaacccc tcaccaccac ttctgggccc caggcaaggc    300

agagaccaaa agaaccctgg taaggttccc caacctccat gttcatttaa aaaaaatgtt    360

taaaactgac aaataataat tgcatatatt catggggtcc atcatgatgt ttt            413


<210> SEQ ID NO 26
<211> LENGTH: 638
<212> TYPE: DNA
<213> ORGANISM: Homo sapiens

<400> SEQUENCE: 26

acttagaatc gtgtgtccat ctgaagccag tgcagaggcc aaagtcagtc aatttaatat     60

gaccatcacg atcaatcaaa atattatcag gtttaatatc tctatgaata aaacccattt    120

taaggaacac ctttcaaact gcacaggtaa gttctgctat gtagaatcgt gccagacttt    180

ctggaaagat gcccattcta attaataggc tcatcatatc acccccagga atgtagtcca    240

ttacaaagta taaattgtcc ttatcttgga atgaataata tagacgaact acccattcat    300

tgtcagcttc agccaggata tctctctcag ccttaacatg agcgacttga tttcgaagaa    360
```

gaacatcttt atttcgaaga gtttttgttg catacaaagc cttagtatct acttttcttg 420
ctagacagac ttcaccaaat gctcctattc ctagtgtctt tatcttcaca aacatagact 480
tgtccatttt agccctttta agacggatgt aattagattc tttttggcaa agcatctttc 540
tcatttgatc ctgggcatct tgagataatc caacccgcat catttcattc tctaattgtt 600
ttttacgatg tagacgctgc tgatgagatt tgagtacc 638

<210> SEQ ID NO 27
<211> LENGTH: 236
<212> TYPE: DNA
<213> ORGANISM: Homo sapiens

<400> SEQUENCE: 27
ggtacacgtc gttctcttca agatctcata gacaatcgtg ctccgggttt tgctgtcgaa 60
aaaggaatcc ttatcagaca agtcaaatag atgctgcttc tcccgggaga agggatagga 120
gagtctcttc atggtctggg gcctgtgctc agccactttg ggctggatgg gatctgtgat 180
tttctggagc acagagttga tttttttcag gaggccacgg gtctcattaa tgtggt 236

<210> SEQ ID NO 28
<211> LENGTH: 607
<212> TYPE: DNA
<213> ORGANISM: Homo sapiens

<400> SEQUENCE: 28
ggtaccacgg gaaagatcag gactttggct gcaccctttt ccagctcctc catgttacag 60
atcatatggg cacaagtggt aaaaatctcc acggctcggg aacgggttcg aataccatac 120
acctcagcca tggtgaagat cttatacatc tctgggagaa tgacaggagc aacaaagtgg 180
catctgtgtg tctgttactt tcacgagtga attctgtcag cacacgcatg gctccatgga 240
cggcatttaa gtctccgctc accaacatct ccatgagcag gttgaagagt tggggccaag 300
cttcaggcca gtcccagtgg gcaatggctg acactgcata ggccacactg gagcgcactt 360
tgcttatcga ttctctcaac ccattaggca atagctcccg gataacaatt tttgcccttt 420
ctgtagtttc aggaggccta aatttctctg attgggcaca ccagtgagtc tccacatatt 480
gtttcaagat gactgatgcc agctgacgga ttgccagtgc cccctgggga tctacagtca 540
gttctgccaa gtgaacacca aattcctccg tcacctccag caccttaatc tgttcttcag 600
cagccgc 607

<210> SEQ ID NO 29
<211> LENGTH: 612
<212> TYPE: DNA
<213> ORGANISM: Homo sapiens
<220> FEATURE:
<221> NAME/KEY: misc_feature
<222> LOCATION: (1)...(612)
<223> OTHER INFORMATION: n = A,T,C or G

<400> SEQUENCE: 29
ggtactaact cgctttacct ttctgatatt cgtcctaaga ttttacttcc tattatatag 60
tgtttgcagt ataccagggt gaaggacctg tcacttctta atgaatggcc ttggtcaagg 120
gtttttaaag tttcaggtca gaaatgtgga tgtgaaaaaa tgttttttaa gaccttcaca 180
ggcttactag tatcacagca ataaatgatt ctaccaggat attcttcgta gacttagttg 240
gcctggaggt agacttttaa ggatatatct gtgcttctga ataaaattag ctaagaattc 300

-continued

```
aacattatgg aattcaataa attccagggg gaaatcagtg aattaggata cactgcctct    360

taaattctaa accctatata tcccacctgt tgcatgtang gggcatgtgt gcatgtggca    420

tcaaaactag ctgnggaccc tttttttcc ataaaatttg gncntactca tccttgggng    480

aaaaancctt gaaggnaaaa tctggggtna aaaaaaagct ttgggctgtg gaccaacctt    540

ccangttccc ngggaaggga ttnggaccta gnaaaaannc cntggaantg gcttgggcct    600

tggattactg cn                                                        612
```

<210> SEQ ID NO 30
<211> LENGTH: 286
<212> TYPE: DNA
<213> ORGANISM: Homo sapiens

<400> SEQUENCE: 30

```
ggtactgtta tcatagcagc actatccaac atgaaagtaa tcttataatt tgcatttgtg     60

cccactccca gctctttcat tttagcttca atccacttca tatttgttgc agaccaaata    120

acaatgtcat aatcttcata ggcagatgtt agaaattcat gaagatatgg ccgcattaat    180

tctaccccag tctctgcaca agacctgtgg tcaaataatg tataatcaac atctagcacc    240

aaaagctttt tcccttccct gggaggattc aaaatttcca ctttgc                   286
```

<210> SEQ ID NO 31
<211> LENGTH: 606
<212> TYPE: DNA
<213> ORGANISM: Homo sapiens
<220> FEATURE:
<221> NAME/KEY: misc_feature
<222> LOCATION: (1)...(606)
<223> OTHER INFORMATION: n = A,T,C or G

<400> SEQUENCE: 31

```
accttatttt gctgagctta ttatataata ccagagcaga atagaaggta gacccacggg     60

aattcaaatc ttggctgtgc cacccacttc ctgggcaagt cacttcctct ctctgtgtcc    120

atttccaaat ctttgaaatt cagttagaaa catcacttta aaaacagggt tgttgtgaag    180

attttatgag ataatgtata aaataagttc ttaccaagta tcagctatga tatttatgat    240

attttagagt tattaattat actgtgagga ttaaggaact tggcagagga atacagtagg    300

tgcttaaatg gtatcctaaa atattattta aaaataaatg acagtaatgg gaataccgca    360

attacttttg caccaacgta ataatagtag gatatttaaa gttgagatca caggaatcag    420

tgcagatatg tctcatttta cccacaggtg gcgctcatgg ccgggttaaa ttctgaaaaa    480

ccttaaaaag tcccttgggc gngaaccnnc ttanggcgaa ttcccgnnca ctngngggcc    540

gtctaangga nnccnatttg ggccaacntt ggggaaccng ggcanaccgn tcccggggna    600

aatggn                                                               606
```

<210> SEQ ID NO 32
<211> LENGTH: 615
<212> TYPE: DNA
<213> ORGANISM: Homo sapiens
<220> FEATURE:
<221> NAME/KEY: misc_feature
<222> LOCATION: (1)...(615)
<223> OTHER INFORMATION: n = A,T,C or G

<400> SEQUENCE: 32

```
ggtactcatg catcttcatg agcagctctc ttatcttctc agtaacatag tcacctcctc     60

actggaaagg tctgtatttt atactctttt gggttaagtc actggcagac agaaacatca    120
```

```
atatcctaat tcaggatgga tgccacagtc tgcccagtta gctcattaat tagataattc    180

tttaaaaata ttgacaaacc attaattaag agctgattat tcacacatca aacaattctt    240

cacttaaact agaggatttc tttaaatagc agctcccct ggctgcattt atctctttgt    300

gtaagtttat tagctatttg gcagagaaat ttcagaatgc cagctacaag tcagtgcagt    360

tgaagaacag aatgtaatgg agggaaagta tttctggaag catggcattt attccaagaa    420

attatctaag aatgnaattc ctttggaaag tgcttaatat aattatatat gnaatcncaa    480

ttaatttctt aaataantct ngggaatggn ccagattttc tggtttggaa aagcccgggt    540

ntttngaatc caaataantt gnccaggctt tttnnntnng nccnnggtng accngggttn    600

gattcaangt ttcnn                                                     615
```

<210> SEQ ID NO 33
<211> LENGTH: 297
<212> TYPE: DNA
<213> ORGANISM: Homo sapiens

<400> SEQUENCE: 33

```
acagacttcc atctccccaa catcttgaag atgtatcaat ttttttaaat taagaattac     60

tttaaacagc actcatttca gaagataggc agaggttatc aaacttctgc tccaatcttc    120

tcattattcc aaggttcata aaaaccactt aggaagacct tggttactgt gacacatcac    180

agctataagt gtaggtggcc tagactctcc ctatctctta gctgccctga gtcatgtgaa    240

ataagatagt gaccttctcc atcatcccta gaggctctct ccccgagaga gagtacc       297
```

<210> SEQ ID NO 34
<211> LENGTH: 468
<212> TYPE: DNA
<213> ORGANISM: Homo sapiens

<400> SEQUENCE: 34

```
actgtttagt gggatccatt ttatacaggt gacggtcagt gacaaaaatt gctctgtctt     60

ccaccttact aaatcgattt accttacgga cgtgacagga aaagaggaca ttcatgtatt    120

tgtccttccg tttcaattca ttagcaacag ggacaaaagt gcctgaggtc tgaggtgtat    180

ctggctttga agcaagatag ttgccctccc aggccctctg gagcccgagg tcagcccttt    240

gacccttcaa catttccacg gctgcaacct ttgccctgac ctggggcagg tctgaggccg    300

gaatgctctt gatgagctgg gatgctctcc atctattgaa aatcgtctgc agggcctcct    360

caaaacggcg aagaacttta ggagggcttg gccacttcac gtgcttcccg tagtctcgca    420

tggtcttgac gccatggaaa cgtctggcca cctcgtggat gtacctcg                 468
```

<210> SEQ ID NO 35
<211> LENGTH: 314
<212> TYPE: DNA
<213> ORGANISM: Homo sapiens

<400> SEQUENCE: 35

```
ggtacttatg gctccagata aaatctctgg tggccacatt attcaagact ttttaaagtg     60

ctttatctga aatatcttca tagacatgaa tatgaaagtt ctgaaaattg tgttcaatgg    120

cccgtgtgtc ccagaagatc ctaatgtaaa gatgcatatt tataaagtaa tttatagaat    180

aggattaaac atatgtagaa ctttattaag aaaatataat gactttggga ccaattacag    240

gcccttgaac agccacaata ggctcaggag ggctgtgctt ctgtgtaaag tcccctccca    300
```

```
gacaccacca gggt                                                    314


<210> SEQ ID NO 36
<211> LENGTH: 600
<212> TYPE: DNA
<213> ORGANISM: Homo sapiens
<220> FEATURE:
<221> NAME/KEY: misc_feature
<222> LOCATION: (1)...(600)
<223> OTHER INFORMATION: n = A,T,C or G

<400> SEQUENCE: 36

acccaatgtc atgggaatga tgtgcctgtc accccccattg gacaagctgg ggaacagcca    60

tagggggacc agcttctgcc agaagttggt gtctctcttc aatttccaca actatgacaa   120

cctgaggcac tgtgctcgga agttagaccc acggcgtgaa ggggcagaaa ttcggaacaa   180

gactgtggtc aacctgttat ttgctgccta tagtggcgat gtctcagctc ttcgaaggtt   240

tgccttgtca gccatggata tggaacagaa agactatgac tcgcgcacag ctctgcatgt   300

tgctgcagct gaaggacaca tcgaagttgt taaattcctg atcgaggctt gcaaagtgaa   360

tccttttgcc aaggacaggt ggggcaacat tcccctggat gatgctgtgc agttcaacca   420

tctggaggtg gtcaaactgc tttcaggatt accaggaatt tctacacaac cttttgaaac   480

tcaggcttga gggcacaann tgaaggccct nttcnaaang aaacttttaa aaagccttng   540

gttttaaccc ncgggtcant gnnnaatccc tggtttaana aaaaancctn gacttggccg   600


<210> SEQ ID NO 37
<211> LENGTH: 516
<212> TYPE: DNA
<213> ORGANISM: Homo sapiens

<400> SEQUENCE: 37

ggtactgctg taggaaagaa attaaggaca gttagtatgg gcctgtgaat tctggcatac    60

atgtttaaat caattacaat tatgcaagta aaaaaaggat atcccctact aattcatgca   120

ggctgaaaag tctagtatgt aaacctgcag cagaatctaa ttttaagaaa caggcaccta   180

attttgattg tgaaactcac tcacctgagg aaagcttcca tcaggctcac tatgcccctt   240

gtgctgactt gcacactaaa attagcaaaa cagactccaa ctattaaaaa tatcaaactc   300

ttcgtataca tacttttgtt ttaactttaa gtatgcttag agcaaagtag gtgcctttac   360

taagctatat ttagagcact atgggggggag ctctagtgtg agaaacagtt tctcaagggt   420

aacaatccta aaaatctagg atttggaatg aaaactttca ataatttgaa agtattttga   480

gcagaaaaat acatttgatc caagtataga aagcgt                            516


<210> SEQ ID NO 38
<211> LENGTH: 319
<212> TYPE: DNA
<213> ORGANISM: Homo sapiens

<400> SEQUENCE: 38

actgaaagga tgaaaaggtg gtgtcatgtt ttggggagaa tcttacttct caaatggaaa    60

ttgcactttt tgctgaatcc tttgcatttt tttggtagta agcagttcat tgagtatcag   120

gtcctcaaag gaatgagttg gcccggctag ggtgggccct cttgacctaa cttcagaggg   180

ggccttggct cagtaggtgt gaatcaggga agccacattg tcctcagggt gctgtatgaa   240

gctgggtgtg ggcggattcc tcccacacct tcacactggc ctgcctccaa ctcatacaga   300

tctcggagcg gtcggtacc                                               319
```

<210> SEQ ID NO 39
<211> LENGTH: 592
<212> TYPE: DNA
<213> ORGANISM: Homo sapiens
<220> FEATURE:
<221> NAME/KEY: misc_feature
<222> LOCATION: (1)...(592)
<223> OTHER INFORMATION: n = A,T,C or G

<400> SEQUENCE: 39

```
acctacactt ggaataagac actgttctga atttgtgtca tagttttttt ttcatattga     60

cattaataga ggcttctatt ggggttaggc taaaaatctt ttgtaaaaaa ttttaaatga    120

cactgctgat ttttctccgt taattatcag tttataagct aataaaaact ttggcttgat    180

attacattct agtggttaaa tttgtcatag aaggaatatg tgctgagtta cttatgtatt    240

gtaatcttga gattacgatt ttttatttga aaattagaca aagtttgttt ttaattttta    300

tttcatttta ataattgagt tcagattaaa tgggaaggct aaatttgaat tccgtttttc    360

tctcaaaata ctgnttttct attattttaa ggcattcctt ggaggtctaa aattgggcat    420

ttataggtgt tgatgaaagc acacccgatt taaagaatgg atgacccccc ttctgnatna    480

aacctttaat ngaattttaa annccaaact ttgggtcctt taaacctngg acctcctttc    540

ccnnaatccc cttaaaaaaa ncntnggcnt tngcanaatt cnntttgccc aa            592
```

<210> SEQ ID NO 40
<211> LENGTH: 577
<212> TYPE: DNA
<213> ORGANISM: Homo sapiens
<220> FEATURE:
<221> NAME/KEY: misc_feature
<222> LOCATION: (1)...(577)
<223> OTHER INFORMATION: n = A,T,C or G

<400> SEQUENCE: 40

```
ggtacagaac ctaaaggttt cactgaatgc gaaatgacga aatctagccc tttgaaaata     60

acattgtttt tagaagagga caaatcctta aaagtaacat cagacccaaa ggttgagcag    120

aaaattgaag tgatacgtga aattgagatg agtgtggatg atgatatcaa tagttcgaaa    180

gtaattaatg acctcttcag tgatgtccta gaggaaggtg aactagatat ggagaagagc    240

caagaggaga tggatcaagc attagcagaa agcagcgaag aacaggaaga tgcactgaat    300

atctcctcaa tgtctttact tgcaccattg gcacaaacag ttggtgtggt aagtccagag    360

agtttagtgn ccacacctag actggaattg aaagacccag cagaagtgat gaaagtccaa    420

accnggaaaa ttccaagaac tcgngtcctn gactggatct tggggganaac ccttggttnt    480

taaaannggg acntttttnc cggcttgggg cccntttaga tttcaaagtt tcangaaccc    540

aaacggtcct tnattaaanc cggngattgt tcgaagg                             577
```

<210> SEQ ID NO 41
<211> LENGTH: 490
<212> TYPE: DNA
<213> ORGANISM: Homo sapiens

<400> SEQUENCE: 41

```
ggtacacaag agtataggta tataaaacta aatgaagtca atcatattga ttatcccccc     60

aaaaaaaata taatctaaag aataatcagt tcctaaataa ttgaaagctg cccttacaaa    120

ataaaacaaa agaacacaca tttcgttgtg ttgcccaggc tggtctcgaa ctcctgggct    180
```

-continued

```
caagcagtcc tcccacctcg acctcccaag atgctgggat ttcgggacat gagccaccac    240

gcccgggcca aagctgcctt tttttaacat ggattttttt tcccccattc gttgtgctca    300

gaagtcattt cctcttattt ttctctgcta atgtgtgctt taacaaacct gtttaaaacg    360

acaagccttt aatcaactgg ggtgttttgt tttgtttttt tcttattttc ttaggagtca    420

gtggatcggt ggggaaaatg ctgcttaccc tgggccctgg gctgtagaaa gaagacacca    480

aaggcaaagt                                                           490
```

<210> SEQ ID NO 42
<211> LENGTH: 571
<212> TYPE: DNA
<213> ORGANISM: Homo sapiens
<220> FEATURE:
<221> NAME/KEY: misc_feature
<222> LOCATION: (1)...(571)
<223> OTHER INFORMATION: n = A,T,C or G

<400> SEQUENCE: 42

```
ggtacttgcc ttttaacttt cccccacatt actgttgagt catggaataa tgtttaagtt     60

gttatttgca tggaaattaa gtaggctgtt tatttatcta aaggaatcaa gtccactctt    120

ctgcctgcaa catttgttca aaaactaacc aaggtaaaat atttatttga aagcccaact    180

ttgatgttaa atattcttga ataaatctgt tattttaaga atatcacatt attcaatgca    240

tataaaacta tcagaagtta gtaaatcata ccagcactaa aaataagaca attggaatat    300

attttagcat cagtttacaa acaactttat tatcaacaga aattttagct cttttctttg    360

caagatatat cacagctgct ttgggcagta gctgaagccg aagtatgaac agtccatttt    420

gtttcttaaa atttgaagtc gtgtctgtcg tagcattttt actaccagca gtatgttact    480

taaaaaacta catggctttc cttgaattta tttgaccgna ttatgtaata gacttgaaac    540

aattgccatc tttgtagnta tgcctgggtt c                                   571
```

<210> SEQ ID NO 43
<211> LENGTH: 708
<212> TYPE: DNA
<213> ORGANISM: Homo sapiens
<220> FEATURE:
<221> NAME/KEY: misc_feature
<222> LOCATION: (1)...(708)
<223> OTHER INFORMATION: n = A,T,C or G

<400> SEQUENCE: 43

```
aggtactgca aaaatgaagt attattctct aagtattcat tttatccctt tcatttcagc     60

aaaatcacac atttgaataa acaggatcga aatacgacac ttgtctttcc tcttaattta    120

aggaatatat tgtttagatt attgttcata ttagacaact gcctcaaaaa tgttttaatg    180

ccatccaata aataaacttt tgatagatta tgactttttt taattttaag ttgttaagaa    240

tattaacttt gagtctccta ttaatattct aaaagctagg attcaattca gcagtttcct    300

ataacatttt agaacccaag gcataactac aaagatggca attgtttcaa gtctattaca    360

taatacccgt caaataaatt caaggaaaag cccatgtagt ttttaagtaa ccatacctgc    420

tggtaagtaa aaaatgctta cgaccggacc acgactttca aaatttttaa ggaaaaccaa    480

aaatnggacc tnggtnccat taccttttgg gnntttcaag cntaccttgg gccccaaaag    540

ccaagcttgg nggaatataa tccttggcca aaggnaaaaa ggaagcctta aaaantttcc    600

ngggngggaa naantnaaaa gttnggtttg gnaaaaaccn ggangcctaa aaaattttta    660

tttncccaaa ttggggccct naaatttttn aaagggcnng ggganang                 708
```

<210> SEQ ID NO 44
<211> LENGTH: 632
<212> TYPE: DNA
<213> ORGANISM: Homo sapiens
<220> FEATURE:
<221> NAME/KEY: misc_feature
<222> LOCATION: (1)...(632)
<223> OTHER INFORMATION: n = A,T,C or G

<400> SEQUENCE: 44

```
ggtactaggt ctattaaatc tacctgctta aaaaggtttt gaactgaaga ttccaggagc     60

tgagcagctg cctcttcaaa ggttttgaga gtaacaaatt ggacctggta gtttttgcta    120

acagggtgga ggccgttgat catgccctca gtggtgatga tggccaggta tgcaccgcag    180

gggctcactg ctatcccgtg agtccttact gagccaaaca catctgagag tttaatcaac    240

tggtgttcaa acttcaatgc aacatctgtg aaaatgggaa tcagctgcct cacctttccg    300

tcactggagc aagtatagac tgttccattc tgtttgtctg cagtcatgga gacaattggc    360

agtgagttga aggcctgtga catgggaatt gtgaaccatt nagccctgct ttggagatca    420

gaagangaca ccaaaattca taaganccte ttgcagccca cttactaaag ctgcnactac    480

actttttggt aagggatgaa taaangtggc ccacatttng atactgngca cnagntaact    540

tgggnccatt tcttttccnc aagannacca gggttgnctt aaagnggaaa tannctttna    600

cngntttnaa aattncccng gaaaaatttt tt                                  632
```

<210> SEQ ID NO 45
<211> LENGTH: 664
<212> TYPE: DNA
<213> ORGANISM: Homo sapiens

<400> SEQUENCE: 45

```
ggtacccggt ctacagtaga gaggttttat gaaaataaaa tacaagacca aattcaaaga     60

gctttaaaaa ccacagagcc agacaaatgt gagaggttat tatgagcaaa caatgacatt    120

acagaagtga aagtgctcaa gtgccatcaa gaacaagggc tctatttcac tcccatgtgt    180

caccataata aagacagagt ccctgatctt aaaggcatca attttgcccc actggaagcc    240

ttaattgtaa ttcattaata cagcagcatc ctaaaagtta ctgccgtttc taggaatcca    300

aacaactggt tttaggtcct aaagaatttg aatcattaag aaatttaaag tacccactct    360

gggccagttg atggctgcga agagagcaga aggggtgctg ctgtaggaaa tcaatggctc    420

ggaagaccac actgaggaag gtgtgagttg atactggaag atctccaggt ttgaggcatc    480

ttcagaggta tatggtggtt ttgtgtgtgt tgagggtgtg gtagcgcagc agctccctag    540

ggaattagaa ggttttattg aacatttacc ctgtgacagg cactgcaggc attcagcgcg    600

cagtgtcatc ttcattttac aggtgaggaa aagactcagg ttcaagtaga tggtcaaggc    660

cagt                                                                 664
```

<210> SEQ ID NO 46
<211> LENGTH: 633
<212> TYPE: DNA
<213> ORGANISM: Homo sapiens
<220> FEATURE:
<221> NAME/KEY: misc_feature
<222> LOCATION: (1)...(633)
<223> OTHER INFORMATION: n = A,T,C or G

<400> SEQUENCE: 46

-continued

```
ggtacgtgtt tatgggatgg gcacactaga tgagatggaa gaagatgtgc cagtgatgtg     60

gagacaggga gtgtgggaga ggagcaggta gagctcagag acggtgcact taggcctgtg    120

gtcattgggg gtgacccaag tagccagcag ctgcccagcg ttttgtgttt ctctcctggg    180

tccctaggag tggaatttgt gtaagaacaa tgtgtgaggt tgtggcctgc ggggcagtta    240

gcagttgtca gaccggtgcc tggaagtgtt tcttggatca ggaaatcagg actgaaaggg    300

gcattaagtt tgtctggacc accctgtcat tgtgcaatgg ggagatcgag gccttttggg    360

aggaaaggcc ctgcttaagg gccgtataat tgaagtcagt ggctgtgttg gggcctttga    420

acctgccaaa agctggtgcc tttctccact cctcagtgct tatgccccaa gtgagggtct    480

agnccagcct ctcccacttt cctcccactt tcactaagca cctgctctgg taggcccagt    540

gctgtatgct gtgaactcag gctggttagg tgctaattta ttcacccagc cagacattct    600

agtgtctcct gcatggcagg cactgttcga agt                                 633
```

<210> SEQ ID NO 47
<211> LENGTH: 433
<212> TYPE: DNA
<213> ORGANISM: Homo sapiens

<400> SEQUENCE: 47

```
accagttgct cctccatgat ggtctgggat cacagaggct ccaagtgggg acttcactac     60

ctagaccagt cccccacatg gtccctccct gggctgcatc tttgcctgtc ttagtctcct    120

gtgttccttg agaaagtgga gtcaataaca cctttctctt caggttgtgg gagaacggct    180

cccagccacc ttctgttttc ccttctcttt gagctctaga ttcagggagg ggttaaggca    240

agaccaggtc ccagaagctt ggctgagacc agaagccagt gcttactgtg ctactgccac    300

cttcagcagc aagggcccca ccaatcaggt ccctagattc aggccccagg tggagctgcc    360

ctcccgattc tagggagcct ctctacctga aaggtgcaca gaaaaacact gcagaaaact    420

cacccagcaa ggg                                                       433
```

<210> SEQ ID NO 48
<211> LENGTH: 633
<212> TYPE: DNA
<213> ORGANISM: Homo sapiens
<220> FEATURE:
<221> NAME/KEY: misc_feature
<222> LOCATION: (1)...(633)
<223> OTHER INFORMATION: n = A,T,C or G

<400> SEQUENCE: 48

```
acttcttcag gtaacactgt aaggatctcc agcaaaaaag gcaaagaagt cacatcattg     60

ctgtattttt ccaccagtgt ttgcacacat cccttccagg aaggcatctg tagggcaaga    120

tctgctattg ctaaagccag ctgcgttaca ataacaggtg acaagtcttt caagttctgg    180

atatgggtta gcaatgagtc ccgtaaagag gcatgagagt ctgtggggag ctcataaaat    240

gaggtctgaa tcttcatttt catggtctgt gcagcaaaat agcatgactc cacatcctgc    300

cggatctgta acaactggtc tgagatctcc catgcatgaa ccgaacgctg cagcttccca    360

agcnaaaaag aggngccgct cctttcccgc tgggatctgg ggtccgtggt aaanccgcct    420

gcactggctt ggtaccacca ataaaggnca atttncgaaa aaaaaanaaa aaaaaaaacc    480

ttggccggga ccacncttan ggcgaaatca acacactgcg gccgtctang gatccactng    540

naccaacttg gcgtancatg gcnnactggt tcctggggna attgtanccg ttcaaattcc    600

ccaattacaa cccganncta aannaaactn ggg                                 633
```

<210> SEQ ID NO 49
<211> LENGTH: 624
<212> TYPE: DNA
<213> ORGANISM: Homo sapiens
<220> FEATURE:
<221> NAME/KEY: misc_feature
<222> LOCATION: (1)...(624)
<223> OTHER INFORMATION: n = A,T,C or G

<400> SEQUENCE: 49

```
ggtacccctc tctcacacat gtcaaatatg aagaggcaga aggagccaat ggcaatgggt     60

ccgacttgct tccaataccc tgcgatgtgg ttccgctcgt gctgatccat catgtgctcg    120

ccacagaaga tgatccagaa ggacagaagc atcgcataga agatgccctg tcggatgtca    180

ccaaacagca gcatccaggt ccagtcaaac ccgatggaaa accattccac tgggatattg    240

ataaaggtca tggaaatccc aagggcaaag atgacttttt tcagaagcac cgggggtcgg    300

gacatcatgg tgatcctcct ccaataccac accataatga tgaagatgct gggccgtaag    360

gaaggtcttc atggcaaacc acaccttggt gaagcctcca ttttggtgga tccccaccaa    420

cccggatatc ctttatctcc caattcccac attgatttct tcttcttatt cacaggcagn    480

cggatgttna aangnaaaac ttatggccac agacccattt natgaaagga agacttacat    540

catagtacgg ccttatgctt ggatcttgga anntgagggc attgagntcc nggactgccg    600

gcgggcntta aagngaatcc acnn                                           624
```

<210> SEQ ID NO 50
<211> LENGTH: 733
<212> TYPE: DNA
<213> ORGANISM: Homo sapiens
<220> FEATURE:
<221> NAME/KEY: misc_feature
<222> LOCATION: (1)...(733)
<223> OTHER INFORMATION: n = A,T,C or G

<400> SEQUENCE: 50

```
ggtaccacaa agacagaagc ttcacaggaa gagcggtcta attcaagcgg cctcacatct     60

ctcaagaaat caccaaaggt ctcatccaag gacactcggg aaatcaaaac tgatttctca    120

ctttctatta gtaattcgtc agatgtgagt gctaaagata agcatgctga agacaatgag    180

aagcgtttgg cagccttgga agcgaggcaa aaagcaaaag aagtgcagaa gaagctggtg    240

cataatgctc tggcaaattt ggatggtcat ccagaggata agccaacgca catcatcttc    300

ggttctgaca gtgaatgtga aacagaggag acatcgactc aggagcagag ccnntccagg    360

agaggaatgg gtgaaagaag tctatggggt aaaacatcag gggaaagctg gttggatagc    420

agtngatgat gaccnaaatc tggantcttg naagaatgac cggtnattan ggntccaaaa    480

atttaaaccc ttangttttg aaggggccna aacttnggac cnnaaanctt cattgggatt    540

taaccaggtn ggnacntttt gggcacccca ttgacccgna tttcccccat tgggaccttt    600

tcgaatttct tanaaaactt ggnccnngga aaaaagggaa cccgggaaaa agggtaaaat    660

ggaaaaggaa aaacctggnt tngggaaaaa aaaaacnttt gcccaaanaa aaaaaangaa    720

aagccccttt ttt                                                       733
```

<210> SEQ ID NO 51
<211> LENGTH: 565
<212> TYPE: DNA
<213> ORGANISM: Homo sapiens
<220> FEATURE:

<221> NAME/KEY: misc_feature
<222> LOCATION: (1)...(565)
<223> OTHER INFORMATION: n = A,T,C or G

<400> SEQUENCE: 51

```
acattaagtc aagattgagc tttgatttaa aaggaacata aatcctttac attataaagg     60

gaagacataa atctctccaa tctaaatttt ctcatcttgg atgatgtcat taaactgcag    120

ctcaaactga gattagttta gaattttatg taaattacat ctttgaacaa atgagaacaa    180

ataactcatc tgcagaatat ataaagaacc ttcattaatc aaaaggaatt agacaagcac    240

ctagttttaa aaaataaatg gtgaataatt taaacagaaa cctcaaaaaa gaaaatatca    300

gagtggccaa taagcacata gaaagataca caacatcatt agtttttaag agaactacaa    360

attaaagcaa ccataaagat acctccccaa cactacnaga atgactaaat ttttaaagtc    420

cgacagcgtt gtgcccggtg tcccaatacc actcaggtta agtgatttct ggaanggctc    480

cagaactcag aaaagctata cttgctatcc tanngtatg ggttggtacn gtggaaaaat    540

cccggttaaa tcaggtaaag acccn                                          565
```

<210> SEQ ID NO 52
<211> LENGTH: 637
<212> TYPE: DNA
<213> ORGANISM: Homo sapiens
<220> FEATURE:
<221> NAME/KEY: misc_feature
<222> LOCATION: (1)...(637)
<223> OTHER INFORMATION: n = A,T,C or G

<400> SEQUENCE: 52

```
ggtacgttcc aaagaaccaa ctggttcttg atctgctcct gagagataac cttcaaatcc     60

ttgaaatatc ctgcatgata agagtgagtt tgtaaatgtg gggccttcga tcatgccaaa    120

tagtttatgc taaccatgtg atttatggtg gggaacttga ccatgctgtc agtttgacat    180

ccggaggggc cgagtgttaa gtaactaagg ttggccacat gggcaatcca tgcttctgta    240

actgaagcct aatagaatct ctagacaacg aacagcttgg gtgagcttcc ctgcttgata    300

atattccaca ttgntttctg gaagaattga acattcttta cacagcttca ctaggagcag    360

acaactggaa atttgcctgn ggnctctctt tgggagaact ctgggncttt tacctggatt    420

taaccnggat ctcttnactg naaccaaccn ttaccnttag tatngccaag gataactttt    480

ttgaagtctg ggagtccttc cgaaaatnct taacctgatg gnnttgggan ccccggcaan    540

cttgnggcct ttaaaattan ncntnttgna nggtgggggg gntttaaggg ggtttaattn    600

gagtncttaa aactaagngg ggggggnttt ttttggn                             637
```

<210> SEQ ID NO 53
<211> LENGTH: 632
<212> TYPE: DNA
<213> ORGANISM: Homo sapiens
<220> FEATURE:
<221> NAME/KEY: misc_feature
<222> LOCATION: (1)...(632)
<223> OTHER INFORMATION: n = A,T,C or G

<400> SEQUENCE: 53

```
ggtacatcca agatttgaag aactgaaata aatcagcttt aaacctgctt tttaaaaata     60

tctgggttgg aatttgcccc tgacaaataa taaaatgatg agtgatgcaa gtgacatgtt    120

ggctgcagcg ttggagcaga tggatggtat catagcaggt tctaaggctc tggaatattc    180

caatgggatt tttgattgcc aatctcccac ctctccattc atgggaagtt tgcgagctct    240
```

```
gcaccttgtg gaagacctgc gtggattgtt agagatgatg gaaacagatg agaaagaagg    300

cttgagatgc cagatcccag attcaacagc agaaacgctt gttgaatggc ttcagagtca    360

aatgacaaat gggacaccta ccagggaacc ggagatgtgt atcaagaaag gctggcacgt    420

ttagaaaatg ataaagaatc cctcggtctt canggtaagt gtgntaacag accagtggan    480

gctnanggag agaaaatcna gaattggagt ttggcttgaa aacccngaga gaattgaatg    540

ccccgaagaa tgctgcacag gagctntaat tggacttctt aaactcnaan ttggactgan    600

gctgaaantt acctgagttg actgnnntgg tn                                  632
```

```
<210> SEQ ID NO 54
<211> LENGTH: 661
<212> TYPE: DNA
<213> ORGANISM: Homo sapiens

<400> SEQUENCE: 54

acaatagaac tttcagaaaa ttctttactt ccagcttctt ctatgttgac tggcacacaa     60

agtaaggctg ttgctttcaa tgcatgcaat attaactttg agtgtttact aactctgtgt    120

tttgcttacc tggcttttct tccttgaagt tgcttaattt tttttcctcc aagaggaatt    180

atttaaaaag acttttgtct gtgacataac caagatttat tctgtttacc taaggaactt    240

attttctttt ttgcaatttc atttattctg agtcacttta tttgtaataa gtgaagaatt    300

ttaatactta gaaataagtt gtaaagaaaa taatgagaat cttaccatgc tttagaggaa    360

cggtaatttc tagaaatagt taaaagatga aatactaaga tattatttta ccttctttat    420

atagctgtat atactggtag tatgaaagca actagtgtca ttgatgattt tttggggggg    480

tatttttgta ttctaggctt gctgcaacct catttagaga gggttgccat cgatgctcta    540

caggttatgg tggttggtac ttcccccacc aaatcgtaga aagcttcaac ttttaatgcg    600

tatgatttcc cgaatgagtc aaaatgttga tatgcccaaa cttcatgatg caatgggtac    660

c                                                                    661
```

```
<210> SEQ ID NO 55
<211> LENGTH: 628
<212> TYPE: DNA
<213> ORGANISM: Homo sapiens
<220> FEATURE:
<221> NAME/KEY: misc_feature
<222> LOCATION: (1)...(628)
<223> OTHER INFORMATION: n = A,T,C or G

<400> SEQUENCE: 55

acaactgcct acattctttc tgtttatcac ttcagttaga agtgttacat tcccaaactc     60

taatgttaat ccgagaacgg tggggagacc ttgtgcaggt ggaaaggtat catgctggaa    120

agtgcctctc cctttcagtt tggaatcaac aggttcttgg gagaaaaact ggaacagcat    180

ctgttcacaa agttacaatt aaaattgatg agaatgatgt ctccaagcct ttacagattt    240

ttcacgatcc tcctttgcca gcttctgatt ccaaattagt agaaagagcc atgaagatcg    300

accacttatc aatagaaaaa ctcctgattg acagtgccat gcaagagctc atcagaagct    360

tcaagaactg aaggccattc ttagaggctt caatgccnat gaaaactctt tcatagagac    420

tggctccagc tcttggtggt nccatcttgg agccctgngg naattcanan tggctgccat    480

tttgnagaat tacattcttg gaaggntcaa tggagcttta tngacttgnc aggccctntg    540

ggtgaatggg aanctnggat gagatttgaa ccaatntacc cggattanca cttaagtttg    600
```

nttggcaaaa ngttcaggcg nntnaaaa 628

<210> SEQ ID NO 56
<211> LENGTH: 635
<212> TYPE: DNA
<213> ORGANISM: Homo sapiens
<220> FEATURE:
<221> NAME/KEY: misc_feature
<222> LOCATION: (1)...(635)
<223> OTHER INFORMATION: n = A,T,C or G

<400> SEQUENCE: 56
acctcagctg gggaaccgtc ctagaaagag atggccacta tgctgtagct gccaaatgct 60
atttaggggc cacttgtgct tatgatgcag ccaaagtttt ggccaaaaag ggggatgcgg 120
catcacttag aacggctgca gagttggctg ccatcgtagg agaggatgag ttgtctgctt 180
ccctggctct cagatgtgcc caagagctgc ttctggccaa caactgggtg ggagcccagg 240
aagccctgca gctgcatgaa agtctacagg gtcagagatt ggtgttttgc cttctggagc 300
tactgtccag gcatctggag gaaaagcagc tttcagaggg caaaagctcc tcctcttacc 360
acacttggaa cacgggcacc gaagggtcnt tcgtggaaag ggtgactgca atgtggaaag 420
aacatcttca gcccttgaca cccctgaccg tattanggaa nccttnanaa acttgagaac 480
attnagtacc ttgggccgga acacccttan ggcgaattcc acncactggg ggccgtacta 540
nggggntcca acttgggccc ancttggggg aanatnggcn aacnggttcc ttgggaaatg 600
ttacccttcc aatcccncaa nttnaaccgg aggnn 635

<210> SEQ ID NO 57
<211> LENGTH: 345
<212> TYPE: DNA
<213> ORGANISM: Homo sapiens

<400> SEQUENCE: 57
actgcttgga tcctgctctc tccaagctgt gcacacacat aaggcagatg atgaccattt 60
gaaagatgag aaggtccggg aggaaagcat atccactctc atactcctcc tcatcctcac 120
tggccaggct gaggttgggt gaggagggca ggtagaagag gcagaggttg aagtcctcca 180
ggactgactg gcaaagtgag gtcagctctg agtccacgga gctgcttttg ggctgtagga 240
ggctttgcag atacataaag ttcactagca accttttaat gtctttacat cgctttttgc 300
caggagacag tttccgagtc tcacacttct tcagttggtg gtacc 345

<210> SEQ ID NO 58
<211> LENGTH: 638
<212> TYPE: DNA
<213> ORGANISM: Homo sapiens

<400> SEQUENCE: 58
ggtacttcct cttcctcctc atcctcacta gaggcttctt ctgcggcatg attagacctt 60
gggggaggag cagtggcagt gccatctgcc ttctggatcg atggcttctg acagatgtat 120
ttggggtccc ttccaagatt acagatttct tcaagtaact tgatgatggc agtcgttgca 180
tctgttttaa gggtgggctg atgtctcatg agctcatcga cagcactccc caggttggat 240
gcagtatccc caaggggatc agaacttctc ctcctccgca tggctgggag gtaatctgga 300
gacagaagaa ctttgaagag gcgttcaaaa ggctgacact gaacaaaaga ctgaagacct 360
cgggcattca aacagagtgc actgaataca tttgggaggg agccaaggac ttcacgggta 420
gcaggaacat ctttgataaa gcagtgcatg cagcatgaca tctggcaatc cattgtcctg 480
gagtgaggag agcagtgatg gttcttgaaa tacaaacaca gtcaccactt cagtagctag 540
gaggaagagt gatgggccac agtattctgc attgctgatg atgtgtttca gggaggtagg 600
cagagaacca tccatcacat gtcgtatgcc atctgaga 638

<210> SEQ ID NO 59
<211> LENGTH: 728
<212> TYPE: DNA
<213> ORGANISM: Homo sapiens
<220> FEATURE:
<221> NAME/KEY: misc_feature
<222> LOCATION: (1)...(728)
<223> OTHER INFORMATION: n = A,T,C or G

<400> SEQUENCE: 59
gcgtggtcgg cggccgaggt accatgccca gctaattttt ttacttttag tagtgacggg 60
tctcactgta ttgcctaggc ttctcaaact tctggactca agcaatatgc ctgcctccgc 120
ctcccaaagt cctgggatta caggcatgag ctaccgagct cagttttgaa aggtagaagt 180
gtatgctaca agggatgtag gacttgagag tcaaggccta tggtcttgtc ctggctctac 240
cagtaagtgt gaccttcgat gttttttttct caagtaaggc tggtaataat taccacagtt 300
gtgagaattg agaatttgga aatgcagtga aagagactat actcaagtct tgttctggac 360
taacagtgat cttaaaatct ctcatttcaa agaaataaag tattttgatg atctcttgca 420
tgggngtatt aataaacctt ggnataatgg cagaaactgt acctacaaca gggttaccgt 480
taactctttt tggaaggtgg tttggaaaaa naaggaatgg acccttgaat cttggaagaa 540
cgttcaancc tcatgacnta aggaaaaant tggaaaaggg ccattggnga ncccaaggac 600
ccaatgcccn tgctcttnaa aagggaaaag ggggaccang ggntcaaaat tggaaaaacc 660
gtttttccng gaaatccttt gggccccntt nnaaaggtcc ccaccttngg ggaattttga 720
aaaaaaaa 728

<210> SEQ ID NO 60
<211> LENGTH: 581
<212> TYPE: DNA
<213> ORGANISM: Homo sapiens
<220> FEATURE:
<221> NAME/KEY: misc_feature
<222> LOCATION: (1)...(581)
<223> OTHER INFORMATION: n = A,T,C or G

<400> SEQUENCE: 60
ggtactggcc caaggcaaag atggagaata tgaagagctg ctcaattcca gttccatctc 60
ctctttgctg gatgcacagg gtttcagtga tctggagaaa agtccatcac ccactccagt 120
aatgggatct cccagttgtg acccatttaa cacaagtgtt cccgaagagt tccatactac 180
catcttgcaa gtttccatcc cttcattatt gccagcaact gtaaacatgg aaacttctga 240
aaaatcaaag ttgactccta agccagagac ttcatttgaa gaaaatgatg gaaacataat 300
ccttggtgcc actgttgata cccaactgtg tgataaactt ttaacttcaa gtctgcagaa 360
gtccagcagc ctgggcaatc tgaagaaaga gacgtctgat ggggaaaagg aaactattca 420
gaagacttca gaggacagag ctccggcaga aagcaggcca tttggggacc cttccttcca 480
ggcccccaag gcaggacacc tcatggatga caaccccttc gnactcgaaa agtcagactt 540
tcttttggcc cgggcttttt taaaatccaa agttacnaga g 581

<210> SEQ ID NO 61

<211> LENGTH: 681
<212> TYPE: DNA
<213> ORGANISM: Homo sapiens
<220> FEATURE:
<221> NAME/KEY: misc_feature
<222> LOCATION: (1)...(681)
<223> OTHER INFORMATION: n = A,T,C or G

<400> SEQUENCE: 61

```
acgagcccaa gccctgttcc atcagccaat tgcaaacctg ctccttggtc cacttggcaa     60

atggcatatc caagtcactg ttagactgtc ccaagtctcg agaccaacct aatcggggcc    120

ccgcggttgc ccttgtccct cctcttttga attcaggctc agacatgtca tctgggttga    180

atgtagttga ttgacttctc ctaagttttc caaagagttt catgatacct ctggatttct    240

ttttggaatc tggagatgga ggcggtatct ggaagggact gttcctctgt gaatcttttg    300

gccgagaaag aagcaccagc cagatctagg tgctctgctg nctctttttc tgnttcaact    360

aaatttggtg cacttgctgg tctcttggta cttttgattt taaaaaagcc ccngccaaag    420

ggaanactga cttttcgagt gccnaaaggg ttgcatccat ngangtgtcc tgcccttggg    480

gcctgggaag naaggtccaa atgggctggt ttctggccga ncttttggcc tttgganncc    540

ttctggaaaa gttnccnttt tcccattaaa cgntntttct tnaaaatggc ccagctggtt    600

ggacntttgg naacttgaag ttnaaagntt ttcccccant tgggnnttaa caggggggncc    660

cagggatatg ttnccttant t                                              681
```

<210> SEQ ID NO 62
<211> LENGTH: 569
<212> TYPE: DNA
<213> ORGANISM: Homo sapiens
<220> FEATURE:
<221> NAME/KEY: misc_feature
<222> LOCATION: (1)...(569)
<223> OTHER INFORMATION: n = A,T,C or G

<400> SEQUENCE: 62

```
actgggatta caggcgtgac ccaccacacc cggcccctaa ccactcttga aagtcccttc     60

acatctgtta gttctttaag gatgaaggct gagaattaac cttgttccct attccccgaa    120

gtgtctgacc cagtgctgaa tgtgtggtcg gagcttggtg aattctttcc aaataaagga    180

attcccacaa cagccccacg aaggacttga ggcaaggatt aggatcccca cttacagaag    240

aggaggacaa ggcccagaga agatccccca gactcagcca gggcacgagg ggtcgggtga    300

gttttgagat cgatagagcc ttctttcact ctcctgtgac gacatgacag tagataaaaa    360

gcatatacct tcatgcactc tcatgggctc tggcaccatg tttagagtcg ggctagggtt    420

ctttgcaatc tggtaaccta tggcttaaac ttatacccaa acctctcttc ctgcttcttg    480

nctgtgcaca tctctttcca tcagaccatc catagctcaa gctcaacagc tttnccagct    540

agtgntcctn ctccttttnc atggagtgc                                      569
```

<210> SEQ ID NO 63
<211> LENGTH: 650
<212> TYPE: DNA
<213> ORGANISM: Homo sapiens
<220> FEATURE:
<221> NAME/KEY: misc_feature
<222> LOCATION: (1)...(650)
<223> OTHER INFORMATION: n = A,T,C or G

<400> SEQUENCE: 63

```
gaggtacaat ggaggtatct gtgggaagga aaatgcaggt aaagatgaag aggaaaatct     60
```

-continued

```
gccttgttaa agcccagctc cccaaagtat tagacacatg aatttgcttc tgtgctgagg    120

ccatctgtgg ccgtcaggct agctgttttc tggctgatac tttttgggaa tgttattgtt    180

gctgagaaag atagttccat gtcagagcta tcaacagaat gtggccatct ggacaaccat    240

gtataaacca acttattgct tcttgaatgc cacctacaaa catgactacc tgtcctttct    300

tgtttgaagg ggcactaaca atacttggga agatggaaag tgaactggac attaaggcag    360

agatgaagaa ttctgccttg cttcctgcac tccatggaaa aaggaggagg acactanctg    420

ggaaaagctg ttgaaccttg aactatggat ggnctgatgg aaaaaggatg tcncngacca    480

naacnngaaa aaaaggtttg gtttaagtta ancctnaggt acccgaatgc aagaacctac    540

cccactttaa catgggccca anccttaaaa gcctnaagnt atgnctttat tcnggattnt    600

ncccgaaang naaaagnttt ttgantnaaa attncccncc ccnggccggg               650
```

<210> SEQ ID NO 64
<211> LENGTH: 676
<212> TYPE: DNA
<213> ORGANISM: Homo sapiens
<220> FEATURE:
<221> NAME/KEY: misc_feature
<222> LOCATION: (1)...(676)
<223> OTHER INFORMATION: n = A,T,C or G

<400> SEQUENCE: 64

```
cgaggtgcca attgggagga accttctttg gatgagggtg ctcggtttag caatatcaag     60

gtgtggctcc agataattca atcatctaat taagattcca gttatgctaa tctgttttaa    120

aattccgttt gtgtaaattc ttttacaaag cctcaacccc aatttccagg gagggttcag    180

agcctcaggt tgagttgatg accaacagcc tatagtttaa cccatcatgc ctctagagtg    240

aggtctccaa aaaaatccaa aaggaatagc tgtagagagc ttctggataa cactaactgg    300

aaggtagagc gccactccaa acaagacggg accaaaaatt tttctgaatt tttcgcaata    360

tctgcaacaa taaaatggga aatgtaatgg ccctcctacg tgttgggagc tctttcagcc    420

aatggatgcn actattacna ggantggtgg aaacctggat tataaccagc tgctgaaaaa    480

gccagtaaac aacgtaaggc tttcattggt aatantattg gaaggacagt cntgtgggac    540

ttcggccctt tgnaactaat ggtatgcccc gnanataacc gtncccttgg atttcaagac    600

ccccttttggt tggnanaatt tttgggcatt tgcttgctgg cttaattacc attggaatca    660

aatcttttcc ggccnn                                                    676
```

<210> SEQ ID NO 65
<211> LENGTH: 660
<212> TYPE: DNA
<213> ORGANISM: Homo sapiens
<220> FEATURE:
<221> NAME/KEY: misc_feature
<222> LOCATION: (1)...(660)
<223> OTHER INFORMATION: n = A,T,C or G

<400> SEQUENCE: 65

```
acgtggcctg aagagatgtt attctttaaa atggtctcgg ctgtgggcga ggtgccccca     60

tacaacaact ctcgggctat catggcagtt accgtggcct tggcaggatt cggagctgcc    120

ctggtaaaat ctttggtgtg atgtccttga ctaactccta cagcctgggc gacctcgggc    180

accatgggaa gaattccagc aggcagctgc tgatgactta gataaggcat cctgaactca    240

tcctctttat tactagtccc attttcatcc ccagagccag gttcaaaaaa ggttactttt    300
```

-continued

```
cttccatccc ctggtttctt tatgggtgtc ttctcctctg acttgagtgc cggtttggtg    360

gctgcgcctg cgggactttg aaacccagga tcttcaacat gntctcgctg cattgccttg    420

gccaccttct tgtggtgccc gtccttntgc aatgggggtt ctaaccttna cctgnatnac    480

aaacttcctt ncgcnccgga aggctngctt cntgaagaac gtgtaccttg ggcgngaaca    540

cgcttanggc gaantccacn cactgggngg ccgtactann ggaatccaac ttcggaccaa    600

cntggggnaa catggcaaac tggttcctng ggnaaatgta tccgttacaa ttcccncana    660
```

```
<210> SEQ ID NO 66
<211> LENGTH: 678
<212> TYPE: DNA
<213> ORGANISM: Homo sapiens
<220> FEATURE:
<221> NAME/KEY: misc_feature
<222> LOCATION: (1)...(678)
<223> OTHER INFORMATION: n = A,T,C or G

<400> SEQUENCE: 66

actcaaatct catcagcagc gtctacatcg taaaaaacaa ttagagaatg aaatgatgcg     60

ggttggatta tctcaagatg cccaggatca aatgagaaag atgctttgcc aaaaagaatc    120

taattacatc cgtcttaaaa gggctaaaat ggacaagtct atgtttgtga agataaagac    180

actaggaata ggagcatttg gtgaagtctg tctagcaaga aaagtagata ctaaggcttt    240

gtatgcaaca aaaactcttc gaaagaaaga tgttcttctt cgaaatcaag tcgctcatgt    300

taaggctgag agagatatcc tggctgaagc tgacaatgaa tgggtagttc gtctatatta    360

ttcattccaa gataagggcc atttatcctt gtaatggcta cattcctngg ggtgatatga    420

agagcccatt aattanaatg ggcatctttt ccagaaaggc tngcaccaat ctaccttagc    480

cagaacttac ctgngccngt tgaaagtggt ccttaaaatg gggtttaatt cttagagatt    540

tttaacctgg ataatatttg antggaccgn gaagggcctt attaaaatgg cttgctttgg    600

ccttngactg cttnanatgg ccccccaatc taagtncctg ggccggaacc ccttangggc    660

naattcagcn cactgggg                                                  678
```

```
<210> SEQ ID NO 67
<211> LENGTH: 695
<212> TYPE: DNA
<213> ORGANISM: Homo sapiens

<400> SEQUENCE: 67

ggtactatgt gtgaagaaat ggagaaaagg aaaaatcagt gtagaaaaat aaaaaaagca     60

agagtgaggt tggtgcctac agttcacagc atgtgataag gactgagcat ttattctatt    120

atttggtcat aaaaatgcag gctgtaaggg cctacacaca ccagcttatc gcagacttgg    180

ctctgagctt tcctgcagcc aatacaaaca gggagacaca acagagaatt gccaatgctg    240

gaagctagat gtctaatgct gatcctgctt gtgactaaag tctgaatctg ggctaagtca    300

cacatgtcct gacactctgg aagctctgtc tggtgggtct gggaacgggg gagaagtgaa    360

agaggaagta gcaaggaaag atgcagaggc ggagcctggg agctagggca gtgccaggtg    420

ggactgacat ggcaccagga gtccctcctg cagggatctg tcctgattca ggtcagctgc    480

atcctgcatc tctagggaat gagaccacat ctgcaactca ccaggactgt tcactgtttt    540

ttccaccccc caatctcact cccactcaat cccttggatg tgggaaggag aaatacttaa    600

gctgaatgtt gctgtggccc atttgatgac aggttaccag tgtgggggat gacccccaat    660

gactgcaaga agtggtccag atgtcagaag tgggt                               695
```

<210> SEQ ID NO 68
<211> LENGTH: 579
<212> TYPE: DNA
<213> ORGANISM: Homo sapiens
<220> FEATURE:
<221> NAME/KEY: misc_feature
<222> LOCATION: (1)...(579)
<223> OTHER INFORMATION: n = A,T,C or G

<400> SEQUENCE: 68

```
ggtaccaagg aagacattca gagtgtgatg actgagatcc gcaggtccct tggagaggta     60

tgttttactt tagtaaatgt tagtttatat ggtaattttt cctttaggaa aatctgactt    120

tttatagtga tttgcttaca ttatttacac ttctgagtta gattttgttt gaacaaaatg    180

ttctgtgttt attaaaaaaa aaaaaaaaaa aagaagcagt agcttgtaaa attctgcttt    240

agcctgtatt ctgaaggaag aatgccttag agtaagtctg acttcagaat atttatgcag    300

taaaactgac agtattcttc atcctaacaa ccttatggta gaatagaaag aacagtggac    360

taattatcag gagacctgac aattagttct agtcattgtt gtgtcgacag ttagctggag    420

gaccttgaat ataagttcct caacctaact tgacatcagt gnttttcacc tataaaataa    480

attaaaatag gtaatgatta aatactctta aggctcttat attangnaat ggactgggat    540

tgagtaataa atacctaata gcccttcagt taattnaaa                           579
```

<210> SEQ ID NO 69
<211> LENGTH: 661
<212> TYPE: DNA
<213> ORGANISM: Homo sapiens
<220> FEATURE:
<221> NAME/KEY: misc_feature
<222> LOCATION: (1)...(661)
<223> OTHER INFORMATION: n = A,T,C or G

<400> SEQUENCE: 69

```
cgaggtacaa gctttttttt tttttttttt tttttttcag aatgctaaat tctatttttg     60

tagagcagag actccattaa aaactcccaa atgacaaact agaaaaaaaa tttacaacac    120

tgtgtgaaaa tcanagtgtg attttcctta atatacaaag agctcttgca aaccaacaag    180

aaaaacacaa atacccaaat ggaaaaatca acaaaggaca ggaatagtta gttttcagaa    240

aaagaaatat gaattaccaa taagtgtgaa aatggtgctc aatgccatca tgattaaaga    300

aatgtaacca aaacagtggt gagcccattt ttcatgtggc agattactca attttagtaa    360

tttattctga aaacaatctc ccacaagtgt atacttccac ttgnatgcnc aaggaagtac    420

aagctttttt ttttttttnt tttttttttt ccttggctgn agtcatgagc cttttgaaaa    480

aggcctccaa agtaaatntt tcagggggaa tagggaaagt ntttttttaa anaaggcngt    540

gattntaant tccccgggac tatggtgaaa tactntggaa aaattnaant ggtccatggt    600

ggccnaaatg gngctnttta aaanggnggg gaaaaaantt tttgngggaa aatncccaag    660

g                                                                    661
```

<210> SEQ ID NO 70
<211> LENGTH: 697
<212> TYPE: DNA
<213> ORGANISM: Homo sapiens
<220> FEATURE:
<221> NAME/KEY: misc_feature
<222> LOCATION: (1)...(697)
<223> OTHER INFORMATION: n = A,T,C or G -continued

<400> SEQUENCE: 70

```
actgagtttc cagaaagcgc agtgcacttt tagtgcgcca aactggtaat ttgccattta     60
gagaattctt cctaaagtag attatttctg ttaaagcaaa tcactattcc taactgattt    120
ataattttgg taaatctaaa ttttcatgaa ataggcttat aaagcgtgcc acatttctgt    180
tttctcctat ggacaggaag aaaaagttgg atggggacag aaggacagaa cagggtgcgg    240
aaaccatagg ataaaagctg tgggttttcc cccaaaagtt gctcaaaaga ataatatgac    300
ttctgctttt cttctcctct gggtggcaat tggggaatcc agcagcctgt tgagaggaca    360
gaattggtta agttgtggag aggtgcagtc taattggtaa atctttaaaa gtcttggttg    420
tctaacctgc tggttttctt gctcacagcc cctgcagata tcttctcacc taccttaacg    480
ctggcatgca aggntttctt ctttgctgag tggcatttng gttaatttcc atgttnaatt    540
ctaaccttgg ccatgattac naagccccta ctatgggctt gctttgagtt angccctggg    600
gctttaagna atncctanaa ttcncccntt cttnattctt aagggcttgg anatnccaaa    660
atgatnganc ttgacnttgg tttgggaggg naactna                              697
```

<210> SEQ ID NO 71
<211> LENGTH: 705
<212> TYPE: DNA
<213> ORGANISM: Homo sapiens
<220> FEATURE:
<221> NAME/KEY: misc_feature
<222> LOCATION: (1)...(705)
<223> OTHER INFORMATION: n = A,T,C or G

<400> SEQUENCE: 71

```
accacacagt caatgatgtc agccactccg agctttaggg tcctgggagt ggcagtaggt     60
gatagctctg tctctccaaa aagcaaaagg atcctgcttg gggacacccc aaggtgggtg    120
gccatgtggt ccaccacact ctgcaggggc tccgacatcc tgaggggcaa tctgaccagg    180
tcagcccggc aacggatttt gagtgggaag aggcttccta gatgacgggt gatgaagccc    240
aatcttccag gtggagagga cagcatgacc aaaggaagga cgtggaggtg acatggcatg    300
tgcagggaac tacactgaac actgcagaga gccactggca ggacccaggc cagggagcac    360
ctacttggtc atactgggga gcttggcctt tctcttggtg gtctggagat cccaaaagaa    420
tttatgccaa aaagttagag gtggatagat tttaaatact ggggttttta aatacccgan    480
ggattttaaa tactcttgat gggttaatct aaatttangg ggaaccaaaa ctggaggcnn    540
ntnaaaaggn cccttataag tggaaaaant gaaaagagnt tgnattangg cnncnnaaat    600
ttntggtggc nttttaagtn ccnttngatt tcccannaaa attnaatcng ggggatttta    660
atcccggaat tgggggaana aannnnggaa gggttnccaa ttttg                     705
```

<210> SEQ ID NO 72
<211> LENGTH: 683
<212> TYPE: DNA
<213> ORGANISM: Homo sapiens
<220> FEATURE:
<221> NAME/KEY: misc_feature
<222> LOCATION: (1)...(683)
<223> OTHER INFORMATION: n = A,T,C or G

<400> SEQUENCE: 72

```
actgaatgaa gtaaccgaag acaacttaat agacctgggg ccagggtctc cagcccgtgg     60
tgagcccaat ggtggggaac acagcgcccc catcttccct ctcctcccag cttgcaggct    120
tagacttggg gacagagagc gtcagtggca ccctcagttc actccagcaa tgtaatcccc    180
```

```
gtgacggctt tgacatgttt gcccagacga gaggaaactc cttggctgag cagcgcaaga    240

cggtaaccta tgaggatcct caggctgtcg gaggacttgc ttctgcacta gacaatcgaa    300

aacagagttc agaaggggta ggtctttaac cctgtttttc tgcctggagt cttctggagg    360

gaaagtcagg tggtttggca aaactggctg ggtaattcag cagaaactgg cttgcacagg    420

gggcanggac accctggggg gaaaaaccna cgggggacac cccgtggaac ccaagtantg    480

ccttatttga gtcttnacct naccccgtga gataaggccc ccatgagctt tccaatccac    540

ccaagagaaa cnagtncagc nggtgggana cagcttgnac ncccanaagc nnacngaagc    600

cgggttccaa tctnggataa gggcntttcc aaancctggt ggtcttacca aagggcccaa    660

ttttcaggcc aanttttntg gnn                                            683
```

```
<210> SEQ ID NO 73
<211> LENGTH: 566
<212> TYPE: DNA
<213> ORGANISM: Homo sapiens
<220> FEATURE:
<221> NAME/KEY: misc_feature
<222> LOCATION: (1)...(566)
<223> OTHER INFORMATION: n = A,T,C or G

<400> SEQUENCE: 73

acagtgtgga aatttcaaca tgtatataca tccgtgaaac cattatccca atcaacatca     60

tgaatttaac catcacccca aaaagtcttc tcatgatctt ttgtaatacc ttcctctttc    120

ctgtcccgtc ccccacaacc gtctgttttt tgttctatta gtttgcattt tctagagttt    180

tatataaatg aaatcaatac attatacctt ttttgtctag cttctttcac tcagcataat    240

taatgtgaga gctgtccatg ttgtctaatg tattagtagt ccatttctat ttttgtgggg    300

ttgggcaggg gctgggtagt attccattaa gaggatacac tacagtttgt ttattcattt    360

tcctattcat ggatgttttg gttgtttctg gtttgaggcc tataatgtca cttgaagata    420

gattgtgatg ttaaaggtgc atactgtaaa ccctaaaata gtcactaaaa taacnaaaac    480

gaaaaggtat tggtaataag ccaacaaagg aaataaatca aatcataaaa tacnaaagaa    540

agcngaaaaa gaccaagggc acctgg                                         566
```

```
<210> SEQ ID NO 74
<211> LENGTH: 690
<212> TYPE: DNA
<213> ORGANISM: Homo sapiens
<220> FEATURE:
<221> NAME/KEY: misc_feature
<222> LOCATION: (1)...(690)
<223> OTHER INFORMATION: n = A,T,C or G

<400> SEQUENCE: 74

cgaggtgtac aagctttttt tttttttttt tttttttttt ggctccctgt agcctcgact     60

tcccagcaat cctcctgctt cgcctcacag caggcacacg ccaccatgcc cagctaattt    120

ttgtattttt tgtagagaca gggttttgcc atgttgccta ggctggtctc aaactcctgg    180

gctcaagcaa cccatctgcc ttggccaacc aaagtgctgg gattctaggt gtgaaccact    240

gtgcccagcc aatctctgtc ttttaaatga gggtgtctgc atcgtttgtt tcacatggnt    300

atttaggact aactctatca ttctgctgct cagtaatttt gtttgccagg ctgcctttgg    360

tctttttctg ctttcttttg nattttatga tttgatttta tttcctttgn tggcttatta    420

acaataactt ttcgttttgg taatttaagn gactatttta ggggttacag tatgcaccnt    480
```

```
taacatcaca atctatcttc aagtgacatt atangnctna aaccngaaac cacccaaaca    540

tcntgaatng gaaaatgaat aaccaactnn annggaancn cttaaaggaa actaccaacc    600

ctggccaanc cccaaaatng aaaggcctct aatccnttna cacntgggcc ggtttncata    660

atntcntggn gaaaaacttt cccaaaaggn                                     690


<210> SEQ ID NO 75
<211> LENGTH: 447
<212> TYPE: DNA
<213> ORGANISM: Homo sapiens

<400> SEQUENCE: 75

ggtacaaact gtgttattca catctggccc ccaaggtatg taagggaaaa ctttaaataa     60

atctttaagc tcatcaggtg acaaagcaca gtctctatcc aaatcatgct tgtcaaaggt    120

gctttggaga aataaatatg catgatgatt taattcagta gtgcaatcag gaggtatttt    180

cagcaggggg aacaaatatt caggtgtcaa atccaggtca tcatcataac caaatcgtcg    240

aagcacagtc caagtagttt cgtgtctccc tctctggata aaaagtgtgt gtaaaaagag    300

aaaacctttc agggtcaacc cactgtcagc cacaccatca cttatatgtt ttctgactac    360

attcttgaca tcctccagag cttgaggagc taatggagtg ttgaaacaaa tcctctgaaa    420

gaagttgagt tcagcatcat tgagagt                                        447


<210> SEQ ID NO 76
<211> LENGTH: 674
<212> TYPE: DNA
<213> ORGANISM: Homo sapiens
<220> FEATURE:
<221> NAME/KEY: misc_feature
<222> LOCATION: (1)...(674)
<223> OTHER INFORMATION: n = A,T,C or G

<400> SEQUENCE: 76

actgttaggt aattttgata ttttacttag ttggtttctt ttgtttttgg agacagggtc     60

ttgctctgta gcccaggctg gactgcactg gaactcctgg gctcaagcaa tcctcctgcc    120

tcggcctcca agtagctggg actactacag gcactcacca ccattcctgg ctaattttta    180

gtttagtttt gtagaaagta agactaaata cactggatca ttcagaatgt cagaaagtaa    240

tgttttcctc agtttatttt ttcttaatag cacacaccat gttattggtt tgtgttttgt    300

tagtgcttgt aactagagtg caacttaatt aacaatttgc tcctcctcat gaggttcatg    360

gcagtataga cttaaattct agtcccatgt ttgncattta ttagctgtgt gctaagactt    420

ggttttccta tcagcagaat tgctatgtat atctaagggt atgttaaggg ttcaaaccag    480

gaaccctctt tgtaagtgaa aggtgggggg gagctattgg taaatttttt ggtcagaaat    540

tggcatacct aatttaatta ctaccttact aaangnatca attaccctca tctatttcan    600

nggtttaatg ggnccaagtg gaatattcct ttacttaaaa gccagtttta ctgggaaatc    660

ncttancaag gntt                                                      674


<210> SEQ ID NO 77
<211> LENGTH: 441
<212> TYPE: DNA
<213> ORGANISM: Homo sapiens

<400> SEQUENCE: 77

acatggtctt ttgttcccta aaagactgca tcacacctct gattgggagg ccaactgtca     60

tttaactgag tgtttgagtg tctaaaacca agttcagcat ttgtctatct agcaagcttc    120
```

```
cctttccaac ttgcttactc ctctcaattt catctgcaga tctcctggtt caataaggct    180

caaaaactgg ctgttccctt gcattcctct ctcttctccc aggcactctt catccttttt    240

tctctcaggc tcacccttac aatccaacac cttccaatgg cctctcctag tccagtccat    300

cctgacacca agtaactggc ccgctttgga agtcctgaca ctttcagtcc ctctttcctg    360

ttctttccac tttcctcggc ccccaggagg atcctggatg gtcgtcacag ctgacaaatg    420

atgagcagaa tgccctgtac c                                              441


<210> SEQ ID NO 78
<211> LENGTH: 623
<212> TYPE: DNA
<213> ORGANISM: Homo sapiens
<220> FEATURE:
<221> NAME/KEY: misc_feature
<222> LOCATION: (1)...(623)
<223> OTHER INFORMATION: n = A,T,C or G

<400> SEQUENCE: 78

ggtacacgat taacttaaca caaaaacccg aacttcaaaa tgaaggtgtg tggaggaaag     60

gtgctgctgg gtctccctac aactgttcat ttctttgtgg ggcagggggt agttcctgaa    120

tggctgtggt ccaatgacta atgtaaaaca aaaacagaaa caaaaaaaac aaggaactgt    180

catttccacg aaagcacagc ggcagtgatt ctagcaggcc tcagggccct gggcctggag    240

aggctacatg agggggagcc tcagtcacag gatcaacctg gggcccgaag gagcagggtt    300

ccctgcctct ccctctgcaa cagatcatcc catccaacac aacccccaaa atgttgatga    360

tgacgcacat ggtcaaccct caagaccttt aagacaaaac agagcacata ggaaaaaaaa    420

aacnaaacgc ccaatttctg ctgtgtcaat ggtagggcac cattttaaaa agtctgctaa    480

acagtctgct ttacttggan ggacgtatgc aaacataatn cttgttagtg aagaaccatg    540

acgcctctac ttactctaag ttagtngaca ntaaacttct gctcccttca agttaaagnc    600

nttcnaactg ggtggggaat act                                            623


<210> SEQ ID NO 79
<211> LENGTH: 462
<212> TYPE: DNA
<213> ORGANISM: Homo sapiens

<400> SEQUENCE: 79

accagttaaa aatgtattta ccaataagtg ataacagcaa caatagctaa ctgacaattg     60

attaaagaca gtatacaggg atccttttgt ggttcataag catgatgatt agattttcat    120

gctattgggt gagatatgcc ttcctcagac tttgttacag cataggcaca ttacaacctg    180

tctgatagga gaaagaaagt aaagatggta tacaggccag gtgcggtggc tcacgcctgt    240

aatcccagca ctgtgggagg ctgaggtggg tggattgctt taggcctgga gttcaagacc    300

agcctggccc acatggcaaa accccatctc tactaaaata caaaaaaatg gttgtggtgg    360

cacacacctg tatttcccgt tgcttgggag gctaaggcac aagaatctct tgaaccagga    420

ggtggaggtt gcagtgagcc aatatcgcac cactgtacct cg                       462


<210> SEQ ID NO 80
<211> LENGTH: 640
<212> TYPE: DNA
<213> ORGANISM: Homo sapiens
<220> FEATURE:
<221> NAME/KEY: misc_feature
<222> LOCATION: (1)...(640)
```

<223> OTHER INFORMATION: n = A,T,C or G

<400> SEQUENCE: 80

```
acccgttgct gctgccatgt gtgtgcttaa aacagggttc ctttttgtag catcagaatt     60
tggaaaccat tacttatatc aaattgcaca tcttggagat gatgatgaag aacctgagtt    120
ttcatcagcc atgcctctgg aagaaggaga cacattcttt tttcagccaa gaccacttaa    180
aaaccttgtg ctggttgatg agttggacag cctctctccc attctgtttt gccagatagc    240
tgatctggcc aatgaagata ctccacagtt gtatgtggcc tgtggtaggg gaccccgatc    300
atctctgaga gtcctaagac atggacttga ggtgtcagaa aatggctggt tctgagctac    360
ctggtaaccc caacgctgtc tggacagtgc gtnacacatt gaaaaatgaa tttgatgcct    420
acatcattgn gtctttcgtg aatgccacct aatggtggnc cattggagaa actgtnaaaa    480
aagtgactga ctctggggtn ctngggganca cccngaactt ngcctgntnc ttattaggag    540
atgatncntg gngcaaggct ttccaanngn attnggacaa tccaacctac caganaagtc    600
atggntggaa naaccctgga aagaaacaat ggtgaagggg                          640
```

<210> SEQ ID NO 81
<211> LENGTH: 643
<212> TYPE: DNA
<213> ORGANISM: Homo sapiens
<220> FEATURE:
<221> NAME/KEY: misc_feature
<222> LOCATION: (1)...(643)
<223> OTHER INFORMATION: n = A,T,C or G

<400> SEQUENCE: 81

```
actgccattc cttaaattca tttagattac agtgtgtaat cataactttt gatccatcag     60
ctccctttgt caaacactgg tcatactgca tgagttgatt tgcttcattg attctgaaaa    120
gctgattccc tcccatcctg tggcagggtc ctagttcaac aaagcctcca tttgtttttc    180
ccatgctatc aatgcagtaa gcagtttcga agcctctgat ttctccccag tcaacatttt    240
tgggtggcaa agggtagtgt gaggtgatat cataagctat ttcttccatg aaccacttaa    300
aacttttgca gttgtgatct tctcgaaatt ttttcaagct ccgatatatc cccatatggt    360
aatgcctgcg attcaggacg actagcatag aagtagtctt tatattcatc caccaaacct    420
tcacaactct aacataattc ttcagagttg gagaagaccc aacataaatg ggcngaggat    480
tncttggcag ccctcaagac ggtagatatg tccacacgag aaccanggac caaataataa    540
tttgncacca cacttggcat atcttggatg agatctcaaa gtttcaccac cccaaatttg    600
gaaacctgga tcttgagacc caattcaaag aaaacttttg ttn                      643
```

<210> SEQ ID NO 82
<211> LENGTH: 642
<212> TYPE: DNA
<213> ORGANISM: Homo sapiens

<400> SEQUENCE: 82

```
accaagtcat tatttctgac agcattgtgt attagaagga acactggatt tagtcaaaag     60
ataggagttt gaatcccgat gccacctctt accaactggg taaccttgga taggaattgc    120
ataacttctc tgagcctgtt ctcaaattgc ctacctcata aggttgctgt gaagaataaa    180
tgcatgatgg tttctgaagc acttatcccc tgccgttaga tctcctgagc tgcatttctg    240
tttaacacgg gcccccagtt tgtcagccaa gcagctcaaa tatatgaagt ctaaaatgaa    300
agtaatgacc ctttatgatc tctttctatt gttctcaatc agttcctttt tttttagtta    360
```

```
cctaattctg ctcacggtgt gtccctgttg ttcagattcc agatgtcagt gattgtggac    420

tcctcctttt tcttaacaga ttacataata cctgcagctg ccaagtcttt gtctgtgttt    480

tcattatttc atcatttaca tcagatcttt cttttctctt cccgttgaca caccctagtt    540

caggcctcat tcaagtcata cccagagtat tgtatcagcc tcctaattga tctttactcc    600

ttcactttgc aacctattct gtatgccttg tgaagtacct cg                       642


<210> SEQ ID NO 83
<211> LENGTH: 584
<212> TYPE: DNA
<213> ORGANISM: Homo sapiens
<220> FEATURE:
<221> NAME/KEY: misc_feature
<222> LOCATION: (1)...(584)
<223> OTHER INFORMATION: n = A,T,C or G

<400> SEQUENCE: 83

ggtacagtag agtctgagaa ctgggtcaac actgaagcat tcacaccttc aggatatgaa     60

gcagagcttc ctgtcacatc tgcagatgtt gtgctgttgg tcaagagcca gtgtgcagtg    120

atctctccac ctctcatggg tgcgactgac ctagacacag tctcagtctg agacatggga    180

cttccatttt gcacctcaga gctgctggca agctgatgtt ctccaaaggt tggggaatca    240

ttttgccaac gcaaagacgt aagtccaaat tcattttctg tggatggttc aatgaattcc    300

tcatcccctg gattcccagt tactctactg nttcttctcg attccactgc agagggtgaa    360

agaaggactg aggatgaagt ccgtagcaat tctggagtcc ttggggaagc cttctgtctt    420

gctcacaggt tccagactga cccgtcaaag atccgcagcg ttctcgggcc accttcagtg    480

aacacggggg caacatgcat tggctttgtt gactgactna ggagctttgg aggcccagtn    540

gganttgtta agcttctctg nacctgcccc gggcggccnc ccgg                     584


<210> SEQ ID NO 84
<211> LENGTH: 558
<212> TYPE: DNA
<213> ORGANISM: Homo sapiens

<400> SEQUENCE: 84

ggtaaagaaa gaaaaaaaaa aaaggcctgg atactgcttt tgctgtctct gttatgagat     60

ggaagactta catggtttgt gataaaaggg gaccatgaga atgaattggc ttggcttact    120

ttccccctga aatcctctct cctgcagact gtcttgaaga cctggtgact ggtaaataaa    180

gccctgcatg gaggctgcac agcaggggca agaggcccat cccccagcat ctcactgagg    240

acagcttcag gctgccttcc tctgaacgtg gtccacacct tcctctcctc cacagagagg    300

gtgccgccag aatcccctgt cgctttctgt gtctgcaatg gggggcagca cagggatcaa    360

agccatctaa agagtttcca gagaaagtat taattcagaa caagccaaag accctgagcc    420

tcaccacaaa caggcctttt ggagtgtgaa tttgagttga agatacaaga tcggagaatg    480

attttctggt cttaactaat cctcgtcttc atgtttgatc tttaagaagt catcacccat    540

tgatttcagt tttgctgt                                                  558


<210> SEQ ID NO 85
<211> LENGTH: 499
<212> TYPE: DNA
<213> ORGANISM: Homo sapiens

<400> SEQUENCE: 85
```

```
acaaaaccat cgccatcaaa aaaacgctgt tctgacaaca ctgaagtaga agtttctaac     60

ttggaaaata aacaaccagt tgagtcgaca tctgcaaaat cttgttctcc aagtcctgtg    120

tctcctcagg tgcagccaca agcagcagat accaccagtg attctgttgc tgtcccggca    180

tcactgctgg gcatgaggag agggctgaac tcaagattgg aagcaactgc agcctcctca    240

gttaaaacac gtatgcaaaa acttgcagag caacggcgcc gttgggataa tgatgatatg    300

acagatgaca ttcctgaaag ctcactcttc tcaccaatgc catcagagga aaaggctgct    360

tcccctccca aacctctgct ttcaaatgcc ttggcaactt cagttggcag aaggggccgt    420

ctggcccaat cttggctgca actatttgct cctgggaaaa tgatgtaaat cactcatttg    480

caaaacaaaa cagtgtacc                                                 499


<210> SEQ ID NO 86
<211> LENGTH: 146
<212> TYPE: DNA
<213> ORGANISM: Homo sapiens

<400> SEQUENCE: 86

acaggatact taaaatggaa taactttttg gttgcaaaac agagacatgg ttctataatg     60

cttcatgtcc ctccaagatt tgagatcaat ttagggattg tgaaattttt tttttcaaat    120

ttcatacaat catatttccc agtacc                                         146


<210> SEQ ID NO 87
<211> LENGTH: 572
<212> TYPE: DNA
<213> ORGANISM: Homo sapiens

<400> SEQUENCE: 87

atccctagca ttttaaaatt cagttgttac agggatccca cataatattt tgtcatttat     60

atgagggtgg atgagggctg aaatttcatc ttgggtcttg gaacagattc atgggcacac    120

attttaaagc tattggtcct cagttctgca gattaagaaa ctccaattta ttgattcccc    180

agggtaatga gaaaatgcat tgagtgatat ataacatcca ctacattcac aggaaatgct    240

gtcctggatc aaaaactgac ctggtcattg aattatgttg gagaactcat aaaaattcca    300

tggagaaagt gatattcaag ttggctcatg aattctgagt aaaagtttaa aagcaaagga    360

gaggatagcc ttacagagat aacaatagga acaaagtcac agacttgtgg aaatggaaga    420

ccgggctaga aattaggaca gttcatattc aagcaagcag ggttgggttt gtgaacaaat    480

accttgaagc tttggatgcc ttggagccct tgacagtttt tgagaatgta tcaaaacaat    540

taaatagtct atttggaagt gagagccctg gt                                  572


<210> SEQ ID NO 88
<211> LENGTH: 512
<212> TYPE: DNA
<213> ORGANISM: Homo sapiens
<220> FEATURE:
<221> NAME/KEY: misc_feature
<222> LOCATION: (1)...(512)
<223> OTHER INFORMATION: n = A,T,C or G

<400> SEQUENCE: 88

ggtaccttat ctccagaagc agactgtttg gggacaggcg cagtgcctgt ggagcggcac     60

ttgacatcag cgtctcttcc cacatggagt gaggagcctg gccttgacaa ccctgccttt    120

gaggagagcg ctggagctga caccacacaa cagccactta gtttaccaga aggagaaatc    180

accacgattg aaattcatcg gtccaatcct tacattcagt taggaatcag cattgtgggt    240
```

```
ggcaacgaaa cacctttgat taacattgtc atccaggagg tctatcggga tggggtcatt    300

gccagagacg ggagacttct tgctggagac cagattcttc aggtcaacaa ctacaatatc    360

agcaatgtgt cccataacta tgcccgagct gncctttccc agccctgcaa cacactgnat    420

cttactgggc tttcgagaga agcgcctttt ggcaacccga ngcacacaan cattctgaaa    480

ggnaactctc cccnagaaaa aaattttncn ng                                  512
```

<210> SEQ ID NO 89
<211> LENGTH: 573
<212> TYPE: DNA
<213> ORGANISM: Homo sapiens
<220> FEATURE:
<221> NAME/KEY: misc_feature
<222> LOCATION: (1)...(573)
<223> OTHER INFORMATION: n = A,T,C or G

<400> SEQUENCE: 89

```
actcggctgc tcctccgcgt tctgagtcgc ctcctcaaca atctggacct caagtgcttt     60

aagggcaaca gcaggggacg cggcactggc tttcagcatt gcaactgcct cactgtgact    120

taaattggtc aaatcaatgc cgttgatatt tagcaacaca tcacctctct ttattctgcc    180

atctcgtgca aggcagccat ggggtggcac actggtcaca aagatgggca gctcaccact    240

cttacttccc ctgcccccag caacggtcat gccaagggat tcatgtggtt ccttctttac    300

agtaatgtgt ttttcttggc atgtaacaca ctgagtaaga tccttatgtg agcttggtct    360

gctataatac ggtggtggtg tgtggtgctg gctgctgctg ctatgatttc ctgcttctct    420

aatggtgtta ccaggctggg gtttccctgg tctagcaatt ggtaaattca ctctntctcc    480

actggcctga ataatctggg cagcaagctc cggaagttcc atacttcagg tcgtgcccat    540

tgatggccac actcggcatt gctgcttanc ctg                                 573
```

<210> SEQ ID NO 90
<211> LENGTH: 658
<212> TYPE: DNA
<213> ORGANISM: Homo sapiens
<220> FEATURE:
<221> NAME/KEY: misc_feature
<222> LOCATION: (1)...(658)
<223> OTHER INFORMATION: n = A,T,C or G

<400> SEQUENCE: 90

```
ggtacctttt aacccaccct cctccaatca tgggaggagt tgttcgggat ctcagcatgt     60

ctgaagagga ccagatgatg agagcaattg ctatgtctct gggacaggat attccaatgg    120

atcaaagggc agagtcacct gaggaagttg cttgccggaa ggaggaagag gaacggaaag    180

ctcgggaaaa gcaggaggag gaagaggcta aatgtctaga gaagttccag gatgctgacc    240

cgttggaaca agatgagctc cacactttca cagatactat gttgccaggc tgcttccacc    300

ttcttgatga gctgccagac acagtatacc cgtgtgtgtg acctgatcat gacagcaatc    360

aaacgtaatg gagcagatta tcgtgacatg attctgaagc cagtagtcaa tcaggtgtgg    420

gaagcttgct tgatgtattg gatcaaaagc ttnttctttc cctggacaac cangtggaca    480

caaaaaaccg tggtcanaaa tgggttaaag tcanatnggg ccccacttgg ccccaaggcc    540

ttccaatttn ggctanctta aaaatccttg gcttttaacc nctacttttt tgnagggaat    600

ttgaagctta cctttgggcc ttgggtgggg ttgnaatcna agngggattc ctttnngg      658
```

<210> SEQ ID NO 91

-continued

<211> LENGTH: 570
<212> TYPE: DNA
<213> ORGANISM: Homo sapiens
<220> FEATURE:
<221> NAME/KEY: misc_feature
<222> LOCATION: (1)...(570)
<223> OTHER INFORMATION: n = A,T,C or G

<400> SEQUENCE: 91

```
acctctgact acaccttcat gttgggccct gaccaacaga ccctcaggtt gtgagttttg     60
gcttcgggga gaaaattctt cctgcttgat gtagggcaaa gtagctgatt tggcagattc    120
ctgttgccgt ggcagtccaa gagagataga tcccactgac ggcttgggtg tttcttgagt    180
gtaggaagcc tgattatgag aagtcaaata agtgcctggt gttccctgtg agatggagcc    240
tcccattata aaagatggtt tttctgaagc cactgtggtt ttggatgacg ggatgagagg    300
gggccggtgg cctggttggt cgagttgtcg gaagcccgaa cgccttcagg gagattagtt    360
atcacttgat gtggagcagg ctgaaggact tcccactctc tgtttggact cttggatgtg    420
ccacatggac ttgtagaact tctacattcc aaatctatct ggncttggct ctggccnttg    480
ttcctncagg agtgctgact catgcnttgn tttaatgngt cgctggtaga naacatancc    540
gttactgggg tccaatggga tgtacatngg                                     570
```

<210> SEQ ID NO 92
<211> LENGTH: 603
<212> TYPE: DNA
<213> ORGANISM: Homo sapiens

<400> SEQUENCE: 92

```
ggtacacatg tttttattag attcagtcct cacaacgaat ccattcaaag atacaactca     60
cagtggtgaa atgactggcc agaggttagc caggtagcac gtggcagagg cagggatacc    120
aagagtcctt tccatcatat cacactgact aagttttcct gggttctgtc gaaaatatta    180
atggttcatt gggcataatg gtttctagtt cttttctatt atttcatcca aatgaatttt    240
ccttctcatt tactatgaaa gattttgtta gccttcacat cttgccctac tgcttataaa    300
ctaaggaaag gcaggttcct ccacacagaa cagctctctc ctctatcact ttctatatga    360
aactttcaat aagacatatc gtgtttatct caagcccacc atagctgagg aggaatcgct    420
tgctttcccc tataattccc agtgcccagc attctcacaa ctaggaggtt cttgagaatc    480
tcctcattta tacaatatga agtaaaagcc aatttaaact tttaaatggt aacttaattc    540
aatgctgaat atcaaaataa tcaactgtta aaaatttaaa tgattgtttt gatatattct    600
tgt                                                                  603
```

<210> SEQ ID NO 93
<211> LENGTH: 627
<212> TYPE: DNA
<213> ORGANISM: Homo sapiens

<400> SEQUENCE: 93

```
ggtacacatg tgtgcccagc attaaaaaaa gatgacacag atgctgctca caaatgtcgt     60
tttgaaagga agaaaatata tataatcata aaacaaacaa caaaataaga taaaatatgg    120
ggaaatgccc aaaccaactc catgccaagg aaagagcaat tggctaattc ctaaattcac    180
caataggttc ctagaagctg gtctttgata aaatttttat tggttttcag taaaggtgga    240
aaaacaagga gaatttattg agcttcttta aaaaaaaact aaattttttt caactcaaaa    300
agattatccc ttttttaaga ttagcctttc ttatttgaga agccatcaac aaaccctttc    360
```

```
tctgactgat agtgacatac ataactggtt tgtttatgca attttaatgt catttttttgg   420

atgtggatag aggcagaaga aaagagaaga catcctgggc ccagattgca acacaaacac   480

agaactgacg tgacagctgt gggggatatg ggacagagat acaggaagga ggagcctggc   540

cagggttgca gagtgcagta aaatcagact ggggagctga gagagccctc ttggagaggc   600

tttgaaatgc aggccgggga gtctgga                                       627
```

<210> SEQ ID NO 94
<211> LENGTH: 331
<212> TYPE: DNA
<213> ORGANISM: Homo sapiens

<400> SEQUENCE: 94

```
ggtacctatg ataatcagat ggagatctgg ggaggggaga acgtggaaat gtccttccgg    60

gtgtggcagt gtgggggcca gctggagatc atcccctgct ctgtcgtagg ccatgtgttc   120

cggaccaaga gcccccacac cttccccaag ggcactagtg tcattgctcg caatcaagtg   180

cgcctggcag aggtctggat ggacagctac aagaagattt tctataggag aaatctgcag   240

gcagcaaaga tggcccaaga gaaatccttc ggtgacattt cggaacgact gcagctgagg   300

gaacaactgc actgtcacaa cttttcctgg t                                  331
```

<210> SEQ ID NO 95
<211> LENGTH: 752
<212> TYPE: DNA
<213> ORGANISM: Homo sapiens
<220> FEATURE:
<221> NAME/KEY: misc_feature
<222> LOCATION: (1)...(752)
<223> OTHER INFORMATION: n = A,T,C or G

<400> SEQUENCE: 95

```
ggtcctgtcc cgcccctctc cccaagcgcg ggcccggcca gcggaagccc ctgcgcccgc    60

gccatgtcaa agaaaaaagg actgagtgca gaagaaaaga gaactcgcat gatggaaata   120

ttttctgaaa caaaagatgt atttcaatta aaagacttgg agaagattgc tcccaaagag   180

aaaggcatta ctgctatgtc agtaaaagaa gtccttcaaa gcttagttga tgatggtatg   240

gttgactgtg agaggatcgg aacttctaat tattattggg cttttccaag taaagctctt   300

catgcaagga aacataagtt ggaggttctg gaatctcagt tgtctgaggg aagtcaaaag   360

catgcaagcc tacagaaaaa gcatttgaga aagctnaaaa ttggcccgat gtgaaaccgg   420

aaagaacnga acncaggctt accaaaaaga agctttcttc acnttcgaag aaccaaaggg   480

gaaccagctt taanggccna aagttgnaaa aatttccaaa ggactggnga atccncnaag   540

tttgtgggaa aaaaattccc ttanccttan ttccccaatt aaaaatnttt ggggncccaa   600

aagnaaaaat ttngggggttt tgaaanaaaa tttaaaantg ggntngaaac ntttttggga   660

aattccccaa aanaactttt gccttccctt tgnccttaaa aantttncca tgggggggna   720

aaanggattt nnccttgncc cnggggnggg nc                                 752
```

<210> SEQ ID NO 96
<211> LENGTH: 405
<212> TYPE: DNA
<213> ORGANISM: Homo sapiens

<400> SEQUENCE: 96

```
tacaacaaac accgaaaaca aagtaaaaaa tgaaacacaa ctagagaaaa tgtttaggac    60
```

-continued

```
acatgtcagg aggttaatat ccctaatact gaaaaatttc ttgctagtaa gccaaacaac    120

ccaataaaac tctaaatgat acttcgtgag ttgataaaat gatttccaac ttgagttgtc    180

agacaaaaca tttgagatag actaacaaaa ttattgttta tctaaaactc taattgggca    240

tgttgtattt ttatttgtgg aaggtggcaa cactatttca gacacttgtt ctcatttggc    300

cctgcagtaa ctcaatgaga tggggaaaga ggttaattaa cctctccaac agcagtttcc    360

tcatctgtca aatacagtgt gagaattaaa ttggataata taggt                    405
```

```
<210> SEQ ID NO 97
<211> LENGTH: 499
<212> TYPE: DNA
<213> ORGANISM: Homo sapiens
<220> FEATURE:
<221> NAME/KEY: misc_feature
<222> LOCATION: (1)...(499)
<223> OTHER INFORMATION: n = A,T,C or G

<400> SEQUENCE: 97

acagaaactt ggtgggaaaa ggggactgtg gccagagttg ggaccctgga gcagcatcct     60

ctgcagagaa ggattttgtc tggccagagc ctggagaaac ctgaaaaaga accagtcagc    120

tagccagggt ctcagagaaa agcagattac acactcaaat tgggtaattt gagcagagct    180

taataaaggc agtatttaca aagtgtgggc taagcctccc atgagagtgc agaaccctgg    240

ggctagcagt gtggggcgct attcccagcc ccctcaatcc attggctgag gccgctggaa    300

gccaccgggc caagggagct tgttgatgtg ggtcacacgg gcatgttccc aggtcaagag    360

aggagagtgg agagtgaatc tanggagact caagagggaa gaagtgactt ccactacctt    420

tcctttctgg ccgttttgct tccanctggc ttctcttttt ccganncent agttttgggt    480

ttaanggnan ntangtnaa                                                 499
```

```
<210> SEQ ID NO 98
<211> LENGTH: 688
<212> TYPE: DNA
<213> ORGANISM: Homo sapiens
<220> FEATURE:
<221> NAME/KEY: misc_feature
<222> LOCATION: (1)...(688)
<223> OTHER INFORMATION: n = A,T,C or G

<400> SEQUENCE: 98

naggtacaag ttatcaatcc gagggacaag agggagggac aagaaccagg tctcagctgc     60

attcacatcc tggaccctgt catctcaaag ccagttccct ccctgccttc caacttggtt    120

tcattcactt tggattgagt tgcgttctca ctgaacagaa acccacaacc caaaacaagg    180

gcagcccatg gccgtgatta agctctgcac cagtggcgaa gggatcgagt gggagaccag    240

aattcagctc cgcctctgtg cggcctcaag ggagttatga acttctgagc cttagacatg    300

cttctgagct gccaccaagc tgcctnatgg ggctgcctaa ggattaatgn attaatccaa    360

tcccaggcac atnagtcatt aataaaatta agaatacngn gaccactaaa cccactactt    420

tngaagtact tcctactaac tacnttaaac cccaacttga aggttttgga aaaganaatg    480

nccacttgga aaccaaaccg gcnnaaangg aaaggtacct tggaggcact ttttcccttt    540

tggggcttnc ctanaatccn tttccatttt ctttttgacc tnggnaaatt ncccngggga    600

ccccatttac aaagtttcct tgggcccggg ggntttnaag ggctttancc aagggnttan    660

ggggcttggg aaaaagnccc ccacttgn                                       688
```

<210> SEQ ID NO 99
<211> LENGTH: 657
<212> TYPE: DNA
<213> ORGANISM: Homo sapiens
<220> FEATURE:
<221> NAME/KEY: misc_feature
<222> LOCATION: (1)...(657)
<223> OTHER INFORMATION: n = A,T,C or G

<400> SEQUENCE: 99

```
ggtacttttc ttagtatctt aacatcacat gcattttgta gtttatggtc tccagtctcc     60

agctgttttt ggagcacctt ctaactttga gagggtgagc tctagcctgt aaaatggact    120

gtgggtggct cgtggagaag gtgccctggt gtgcttttct gtgtcctctc tggattctcc    180

ctgagctgtc cacctctgaa gcctgcttca ccttcagact gccagggcaa gacatgcagc    240

ttctgcagaa ctcatggcag ccgttttcca cttggccgag ctgggtctgt gaagcagaga    300

ggaatcagta ataggaaaga aatgtaagtt gntttttttcc cccttagaat acctaccata    360

ctggatttca gcttggagtg cgcagcatga agcatttgtg gtcaaaaaag aggncttcct    420

ttttccttct nctggtttct tttcttnctt cttcccaact tccccaangc ttactggctt    480

tctttntnaag ncacgtgtgt aaaatancct tgagggaaaa aanggttccg gcttgggana    540

tttggatnta cctaaagggn cagaataacc cttctttgcc tggttcnttt ttggcctaat    600

cnagggaatt tttcgactgg ggncattaat ggncctccgg cggccgttaa anggcaa       657
```

<210> SEQ ID NO 100
<211> LENGTH: 504
<212> TYPE: DNA
<213> ORGANISM: Homo sapiens
<220> FEATURE:
<221> NAME/KEY: misc_feature
<222> LOCATION: (1)...(504)
<223> OTHER INFORMATION: n = A,T,C or G

<400> SEQUENCE: 100

```
atttcttctt tgcatgcagg aagaaaattc actcgccgtt tgataatttg ttatggtctt     60

atttgacctg ttatccctgc ctcccatgtt ctctttaccc tacaacccat cagctgttag    120

agtttccttt tccaagactc tccatgtcca tcccctctgc attccccccct ttcactccat    180

cttctgtaac ccagcccctc gggagctgag gaggtggagg cggatataga cacggagagt    240

gctggatgca aaggtgttac ttgtggcaaa ggcgccgtgt gtgctgagga tagatggcag    300

gtatgagaga gggcaggatg aagcacaggg gtggaggga gcagagagac ctacaacaaa    360

acccactcaa ggggtatgtg agatagactt ttttttctgg ncttttttgtg tgtctgtaat    420

gggggttgga aagtggggtg gtctcancag ntaattctct ggagntctct ggacttgagc    480

ctngtcnnaa nagcccagaa nttt                                           504
```

<210> SEQ ID NO 101
<211> LENGTH: 685
<212> TYPE: DNA
<213> ORGANISM: Homo sapiens
<220> FEATURE:
<221> NAME/KEY: misc_feature
<222> LOCATION: (1)...(685)
<223> OTHER INFORMATION: n = A,T,C or G

<400> SEQUENCE: 101

```
ggtgcctgtt ttgccactta ggaagctgga aagaattttc gagtcaagtt aacccaaccc     60

cctcttcttt tcacatgtaa gcacactggc tcagccagaa ctcaggtctt tcaacctcac    120
```

-continued

```
agttggtgaa gactcttaca tgttggttcc aagttgctca actctcaggg ctcagcctac    180

aaaagactcg gcatttcgac cagctcagtc cagaggactc cagagaatga ctgctgagac    240

caccccactt tccaaccccc actacagaca cacaaaaaga acagaaaaaa aagtctatct    300

cacatacccc ttgagtgggt tttggtgnag gtctctctgn tccccttcac ccctgngctt    360

catcctgcct ctctcatacc tgccatctat cctnagcaca cacngngcct ttggcacaag    420

tacacctttg cattcaagca ctnttcgggn ctatatncgg cttcaacttc ttagcttccg    480

aaggggcttg ggtacngaaa aaggatgaaa ggggggaatg ncaangggat nggcctggga    540

aagttttgga aaaggaacct ttaccnctga agggttgtag gggnaaaaaa aacctgggag    600

ggccgggtta ccnggtcaaa taggaccttn ccaantttta acnggggagg gaatttnttc    660

cngctgccaa naaaaannnc ttccn                                          685
```

<210> SEQ ID NO 102
<211> LENGTH: 498
<212> TYPE: DNA
<213> ORGANISM: Homo sapiens
<220> FEATURE:
<221> NAME/KEY: misc_feature
<222> LOCATION: (1)...(498)
<223> OTHER INFORMATION: n = A,T,C or G

<400> SEQUENCE: 102

```
ggtaccatat acttaaggct atagtttatt tcataacttt ttttctagcc ttcatatctt     60

gtgttttcag gttgtcacaa tattctttta aaaattaagc attcttacgg cttcactcat    120

gtgcaacatt tataattatt tgcatttgcc ccctcaatga tctcaataga ataaatcagg    180

ctccactata ctcatttcac aaagacacat tcattacaaa ggataaagga ctgaaatatt    240

tgttttgcaa tctgttgacc taagtaggaa taggaagcac agtttcagtg cttccaagtt    300

tttaacccct gactgagacg ttttggttga gtattactat tcttattcta ccaatgataa    360

agggaaactg aatgcccaac catgtgctgg ctgtttacac atatgcaaca ttgactggtt    420

ctcacaacca ccttgaggaa taggcattgn cttcaattta caaatgagga aaacaaccat    480

tttcaangng cattttnc                                                  498
```

<210> SEQ ID NO 103
<211> LENGTH: 697
<212> TYPE: DNA
<213> ORGANISM: Homo sapiens
<220> FEATURE:
<221> NAME/KEY: misc_feature
<222> LOCATION: (1)...(697)
<223> OTHER INFORMATION: n = A,T,C or G

<400> SEQUENCE: 103

```
gnnatctgaa attcgccttt cnagcggcgc cgggcaggac taaaaatgta agtttatttt     60

gccatacccc taacaacatt ttatttaaat tatattgtga cttgattaca aatcttttaa    120

atgacattat tggcatattt ttcttaaact ttgtaagaaa aagataacat ttcacatttt    180

agtagcaaaa tcattgttaa gagatagtca attttgtgaa aatatttgag tgctaatcaa    240

tttttccagg atgatcttct atcctttaat atttagatct tccttttgaa gcacttacat    300

catcatcaaa tttttggtca tttgntgngn catctaattt ctggttcatt ttctaatggc    360

ttcgtatgtg aatgaatttt agttattcct aacgtcattg gtagccactc ttttgaaatt    420

tttttttaaa ccaggctttc aattttaatt tatanggaat ttgcattggg atatagatga    480

ccgctcaaaa ttcccatgng agactgntga aatgncctaa acnattcgcc tggacnctgg    540
```

```
attaanccgn ggcctcttaa ggtaatctng anggggtggc ttattgggaa aatttggatt    600

nnggcccggt tactntgcca ggttngactt nnaagggccc anaaggacct nggaaatnaa    660

gatnccctna acccttcctt ggnaaanaaa naagttn                             697
```

<210> SEQ ID NO 104
<211> LENGTH: 504
<212> TYPE: DNA
<213> ORGANISM: Homo sapiens
<220> FEATURE:
<221> NAME/KEY: misc_feature
<222> LOCATION: (1)...(504)
<223> OTHER INFORMATION: n = A,T,C or G

<400> SEQUENCE: 104

```
accatcattc agaataactc ttccaatttc tgctttcaga catgctgcag gtcctcatct     60

gaactgttgg gttcgttttt tgtttttttt cctgctccaa gaaagtgact tcaaaaataa    120

ctgatcagga tagattattt tattttactt tttaacactc cttctcccct tttcccactg    180

aaccaaaaag aaatcccatc cctaaaacct gccttctcct tttatgcaaa actgaaaatg    240

gcaatacatt attatagcca taatggtata gatagtgatt gcgtttggct atgtgttgtt    300

ttcttttttt ttaaattatg aatatgtgta aaatctgagg taacttgcta accgtgaatg    360

gtcatataac tttaaagata tatttataat tatttaatga catttggacc cttgaaacat    420

ttcttagtgn attgatatgt tgactttcgg tctctaaaag tgctctttat taaaataaca    480

aatttcttta aagggnctaa aanc                                           504
```

<210> SEQ ID NO 105
<211> LENGTH: 746
<212> TYPE: DNA
<213> ORGANISM: Homo sapiens
<220> FEATURE:
<221> NAME/KEY: misc_feature
<222> LOCATION: (1)...(746)
<223> OTHER INFORMATION: n = A,T,C or G

<400> SEQUENCE: 105

```
ggtactaggt gtctcataat tgaaccctct atccacatgt gcggctttta gctgactatg     60

tctttgctat gaagcctggc gatttagagt tttgcttaac tatgaaacca cagaacattt    120

ttctgtagtt caatgattta cttgtgcttg tctttttaat atgacaagag tcataattac    180

cccaaagaaa ttagaaaacc acatcactcc agcatttcat gctgataaag ggctaaaggt    240

tgtttttaa atccctaatt accgctttag aaggcaaagc tgtgttagag gcattcaaag    300

atctgaaaga actaaacata acatttcctt catacatcac aaaaacaatc tatatctaaa    360

atatttggag aagggaagta ttttttaaaa tcacattgng ccctggatga acctggaaat    420

ggcttancca tatttcaaga atatggntct aggacccact ggaaggaaaa tttgggtaat    480

ttaaataaaa ganccccttt ttaggaggan ccgaaagtcc aaccttattc aattcccctt    540

angaaaatng tttcaagggg gtcccnaaag ggccatttaa antaattttt taaaatatta    600

tcctttaaag ggttttttg gancccnttn nccggttgnc caaggtttnc ccttcgnaat    660

ttttncccct ttttccctaa antttaaaaa aaannggnaa acccccccct ttgnccaaag    720

cccatncctn tttttttacc ccttng                                         746
```

<210> SEQ ID NO 106
<211> LENGTH: 645
<212> TYPE: DNA

<213> ORGANISM: Homo sapiens
<220> FEATURE:
<221> NAME/KEY: misc_feature
<222> LOCATION: (1)...(645)
<223> OTHER INFORMATION: n = A,T,C or G

<400> SEQUENCE: 106

```
acaagctttt tttttttttt ttttttttga gatggagtct cacattgttg cctgggctgg     60

agtgcagtgg cacgatctcg gctcccgggt tcacgtggtt ctcctgcctc agcctcccag    120

gtagccggga ttacaggtgc ccaccaccat gcccagataa ttttttatat ttttagtaga    180

gacggggttt taccatgttg gccagactgg tctcaaactc ctgacctcat gatccgcctg    240

cctcaacctn ccaaactgct gggattacag gcgtgagcca ccacacccgg ctgagttgtt    300

gattttttag tttgntcagc tttttacttg gtagaatgaa gtgatgactg ncgacctcct    360

taagggccag actagaaact gggagtctcc tatttangnc gccttaaaaa ttgnaagctn    420

gacattggtg gtgaagcatt ggaacaattc ttaattctgg tacctganan gggtgaattt    480

tggtttcact ngcngcttat cagtantcaa ttccttgaac ttttaaaacn ttagttaccc    540

ttngtaggga cagnnttcaa attttccttg acttagggaa cccttantct ngggacaagt    600

tttattctaa ctgactgttg caaacttang gcttcntacc tggcc                    645
```

<210> SEQ ID NO 107
<211> LENGTH: 684
<212> TYPE: DNA
<213> ORGANISM: Homo sapiens

<400> SEQUENCE: 107

```
acagccagat cttaagatga gtctgtgtca aaatgacctg aacgcaagtc tgtattcttg     60

cagagtaaca gagtgttcgt ctgtttctgt ctaaaagtca taactataca gatatctggg    120

aatgcttgca tgaagctttt actcccgaga gcatactact acttacggtt ataacttgtt    180

gatgtctata ttggcttaat tcaaatgaaa agttcactcc aggagcagct ctttgtaatc    240

cacaccaccc cccagactgt tctgaataaa cccagaacaa ctcatacacc agcctaagca    300

tggtctattt ttctgggatg ggacagaaca taattgtatt aaaatataaa atcagtttta    360

aaaggtctgg aaggacatat cttaaggcca tgatagtaag tacagctggg gtgctgggga    420

ggggacctca actagggttg gtggcaaaaa tgggactttt aactttggct ttaacatcct    480

ggtcctaaaa agaagactag atttacctat tatatatgca atctaaaatt aattcaaaaa    540

gtcatcagcg aggacccccc taagattctg ggtggtaagt ccaccaaagg ccaagagcta    600

aaacaaaagc cttttccaca tgttctgaga agttggccca aaactgctga atctataggt    660

cttagcatgc tctatctatg tacc                                           684
```

<210> SEQ ID NO 108
<211> LENGTH: 236
<212> TYPE: DNA
<213> ORGANISM: Homo sapiens

<400> SEQUENCE: 108

```
ggtacacgtc gttctcttca agatctcata gacaatcgtg ctccgggttt tgctgtcgaa     60

aaaggaatcc ttatcagaca agtcaaatag atgctgcttc tcccgggaga agggatagga    120

gagtctcttc atggtctggg gcctgtgctc agccactttg ggctggatgg gatctgtgat    180

tttctggagc acagagttga ttttttttcag gaggccacgg gtctcattaa tgtggt       236
```

-continued

<210> SEQ ID NO 109
<211> LENGTH: 497
<212> TYPE: DNA
<213> ORGANISM: Homo sapiens
<220> FEATURE:
<221> NAME/KEY: misc_feature
<222> LOCATION: (1)...(497)
<223> OTHER INFORMATION: n = A,T,C or G

<400> SEQUENCE: 109

```
acgagaagtg tggtgctgga atatctttcc ggtgaggcct caagaagttt acagtcacgg     60

tggaaggcaa tgaggagcca gcatatcaca tggtgacagc aacagccaga gcaaaagagg    120

gagggagagg tgccactcac acttaaacaa ccagatctgg tgtgaactga ctcatcacca    180

aggggatggc actaacccat tcatgaggga tctgccccca tcatccagac acctcccacc    240

aggcctcatc tccaacactg ggattacat ttcatcatga gatttggagc ggacaaacat     300

ccaaaccata tcagtaggat gtctgacatt catcatacga tgtctgagtg aagggaggtt    360

taagggctta ttttgtctcc ctggatagta atggaaaatg tatatctgaa agagatgtct    420

gaaaaagaaa gtttaagtgg gtggcttgca cacttttggt ttgctagngg gctttttgag    480

ctcanattct catttgn                                                   497
```

<210> SEQ ID NO 110
<211> LENGTH: 722
<212> TYPE: DNA
<213> ORGANISM: Homo sapiens
<220> FEATURE:
<221> NAME/KEY: misc_feature
<222> LOCATION: (1)...(722)
<223> OTHER INFORMATION: n = A,T,C or G

<400> SEQUENCE: 110

```
ggtacagccg gtcctcttct tccaggaatt ggctactgtc cctctgcaat cccattcatg     60

ataaaagcat tcttatacaa cacaaaagat gctgcatcaa tgattctcaa acctccaaga    120

catccaaatc aactagcatg cttaagatgc agattcctgt gctcgactca ccaacttcca    180

gaattttcca ttccctaggt ctgaggtgaa cctgggaatc tgccttgcta acaaatgatg    240

ctgacactgt tgatttgggg accccacttg gagaacctgg gctctagatc tctaccctct    300

tactgaagtc ttcttccact tcctgcttta actggaatcc aacccgccac ccctgnagcc    360

cttgcaaagt gaattgccct tttcccttac tctggttttt tctcctctgg ttctagccta    420

gattccangg aacatnaact ttgggcntgg cattttcccc tngatntggg atccttttgg    480

nccagntttt ccccaaagna agccntnaat tcaaaatctt tccccnttng gttcctattn    540

acccggacct tcngggggna aaaaatnccc aaaagccccc ttacnaaatc ccttttttccc   600

aaacttcaat tgggaaactn gggctttaaa aaagnccccn tttnccaaan ccnaaaantg    660

ggcctaaccc ccccccnttn aaactttntt ttttnnanaa attntttttn anaaattncc    720

tt                                                                   722
```

<210> SEQ ID NO 111
<211> LENGTH: 614
<212> TYPE: DNA
<213> ORGANISM: Homo sapiens

<400> SEQUENCE: 111

```
accagggctc tcacttccaa atagactatt taattgtttt gatacattct caaaaactgt     60

caagggctcc aaggcatcca aagcttcaag gtatttgttc acaaacccaa ccctgtttgc    120
```

-continued

```
ttgaatatga actgtcctaa tttctagccc ggtcttccat ttccacaagt ctgtgacttt    180

gttcctattg ttatctctgt aaggctatcc tctcctttgc ttttaaactt ttactcagaa    240

ttcatgagcc aacttgaata tcactttctc catggaattt ttatgagttc tccaacataa    300

ttcaatgacc aggtcagttt ttgatccagg acagcatttc ctgtgaatgt ggtggatgtt    360

atatatcact caatgcattt tctcattacc ctggggaatc aataaattgg agtttcttaa    420

tctgcagaac tgaggaccaa tagctttaaa atgtgtgccc atgaatctgt tccaagaccc    480

aagatgaaat ttcagccctc atccaccctc atataaatga caaaatatta tgtgggatcc    540

ctgtaacaac tgaattttaa aatgctagga ttatcccttc cctagcacta tgtcattttt    600

aaaggtgtac ctcg                                                      614
```

```
<210> SEQ ID NO 112
<211> LENGTH: 499
<212> TYPE: DNA
<213> ORGANISM: Homo sapiens
<220> FEATURE:
<221> NAME/KEY: misc_feature
<222> LOCATION: (1)...(499)
<223> OTHER INFORMATION: n = A,T,C or G

<400> SEQUENCE: 112

acttttctgg aaattggctt taagagctca tcctgcattt ttaaaatctc tccaactgga     60

tcaaattttt tatatactcg tttgataggt ttttttaaaa cacatgactc ttcaggacta    120

caagcagtat tagtctggtt tcctacagaa gcctgtcctg aggaagaatt tggactagct    180

ggtctggaac ttaagttaga acccacaaca gctgtctttc catcactatt atttttacat    240

tctgtatcaa tgattaaaca ctcctcatct gtatcactgc tgcagagaac tgtaccttca    300

gtttttgctg cttctgatcc aacagtcttt tcctttgagt tgtctaggtt ttctagaaca    360

ttaggtcttt caccatcagc atgtaatata tctatagtca tatcattttt attagaagtt    420

tcaatttcct gagaatttct aactggaagg catcagatgt tttcaaggca ctatcttgga    480

tcaaangctt ggcaaaaaa                                                 499
```

```
<210> SEQ ID NO 113
<211> LENGTH: 697
<212> TYPE: DNA
<213> ORGANISM: Homo sapiens
<220> FEATURE:
<221> NAME/KEY: misc_feature
<222> LOCATION: (1)...(697)
<223> OTHER INFORMATION: n = A,T,C or G

<400> SEQUENCE: 113

gcgtggcgcg gcccgaggta cctaacatga cagatgctcc tacagccccc aaagcaggaa     60

ctacaactgt ggcaccaagt gcaccagaca tttctgctaa ttctagaagt ttatctcaga    120

ttctgatgga acaattgcaa aaggagaaac agctggtcac tggtatggat ggtggccctg    180

aggaatgcaa aaataaagat gatcagggat ttgaatcatg tgaaaaggta tcaaattctg    240

acaagccttt gatacaagat agtgacttga aaacatctga tgccttacag ttagaaaatt    300

ctcaggaaat tgaaacttct aataaaaatg atatgactat agatatatta catgctgatg    360

gtgaaagacc taatgttcta gaaaacctag acaactcaaa gggaaaagac tgttggatna    420

gaagcagcaa aaacctggaa ggtccagttc tctgcacant ggatncccan tgaanggaag    480

tggtttaaat caattggttc ccggaatggt aaaaaattaa ttagtggatg ggaaaagacc    540

agcttgttgg nggggttctn aacttaaagt ttcnanacca nnntangtcc naattttttc    600
```

```
cttnagggaa agggcttttn tnggnaaacc gncttaaaac gggttngnan cccctaanaa    660

ntcttggngt ttaaaaaaaa ccttttttanc cgngttt                            697
```

<210> SEQ ID NO 114
<211> LENGTH: 497
<212> TYPE: DNA
<213> ORGANISM: Homo sapiens
<220> FEATURE:
<221> NAME/KEY: misc_feature
<222> LOCATION: (1)...(497)
<223> OTHER INFORMATION: n = A,T,C or G

<400> SEQUENCE: 114

```
acccacttct gacatctgga ccacttcttg cagtcattgg gggtcatccc ccacactggt     60

aacctgtcat caaatgggcc acagcaacat tcagcttaag tatttctcct tcccacatcc    120

aagggattga gtgggagtga gattgggggg tggaaaaaac agtgaacagt cctggtgagt    180

tgcagatgtg gtctcattcc ctagagatgc aggatgcagc tgacctgaat caggacagat    240

ccctgcagga gggactcctg gtgccatgtc agtcccacct ggcactgccc tagctcccag    300

gctccgcctc tgcatctttc cttgctactt cctctttcac ttctccccg ttcccagacc     360

caccagacag agcttccaga gtgtcaggac atgtgtgact tagcccagat tcagacttta    420

gtcacaagca ggatcaagca tanacatcta acttccagca tgggcaattc tctggtgggg    480

ctccctgnnt ggantgg                                                   497
```

<210> SEQ ID NO 115
<211> LENGTH: 687
<212> TYPE: DNA
<213> ORGANISM: Homo sapiens
<220> FEATURE:
<221> NAME/KEY: misc_feature
<222> LOCATION: (1)...(687)
<223> OTHER INFORMATION: n = A,T,C or G

<400> SEQUENCE: 115

```
ggtactatgt gtgaagaaat ggagaaaagg aaaaatcang tgtagaaaaa taagaaaaag     60

caagagtgag gttggtgcct acagttcaca gcatgtgata aggactgagc atttattcta    120

ttatttggtc ataaaaatgc aggctgtaag ggcctacaca caccagctta tcgnagactt    180

ggctctgagc tttcctgcag ccaatacaaa cagggagaca cancagagaa ttgccatgct    240

gggagctaga tgtctatgct gatcctgctt gtgactaaag tctgaatctg ggctaagtca    300

cacatgtnct gacactctgg aangctctng ctggtgggtc tgggaacggg ggagaagtga    360

aagatgaagt agctagggaa nagatgcaga ggctgnncct tgggaactta ggcaagtgcc    420

aggtggggac tgaccatggt anccaggaat tccnttcctg gtangggatt ctggtcctng    480

aattcagggt taagcttgcc attcctgcat ttcttntagg ggganttgan aacccccttt    540

ttggaaactt cancaaggan ttggtctccc nggntttttc cccccccta aattnaattc     600

cccnttaatn cctttgaatt cnggnaaggg nnaattcttt ancctaantg ttcttggggc    660

nctatttggt ngacagggtt ncnangg                                        687
```

<210> SEQ ID NO 116
<211> LENGTH: 508
<212> TYPE: DNA
<213> ORGANISM: Homo sapiens
<220> FEATURE:
<221> NAME/KEY: misc_feature
<222> LOCATION: (1)...(508)

<223> OTHER INFORMATION: n = A,T,C or G

<400> SEQUENCE: 116

```
ggtacccatt ttctatttca agtagattaa ccccttatat tctgctaaaa tcatacttgt     60
tgcctaacac ccagttaaca aagcaaaaaa aaatcagtta atttataaaa acaaaatgct    120
aattcttatt ctatgtgaat gtatttcata gattttaagg ggttaatcac caattagaag    180
acatgctgtg tccacactat tttaagatta aacgttaatg ggaatatatt aattcaaatt    240
aacatggtca tgtaaaatat ataacccact caaccattta aaaactagtg tgaacactgc    300
tcaattctag aagagacaaa gacaaaacaa acaaaacagc cacacaaagg acaataaatg    360
ccaggctctg catccaaaat ccctccttta tcaaatggca gatgtgacac tgagcttttg    420
aaaaccttgg ncaaaaatcc ttccgatgtc ttggcagcaa cccctggcag gatcaatccc    480
ctctgntata aagntttggg cccngccc                                        508
```

<210> SEQ ID NO 117
<211> LENGTH: 644
<212> TYPE: DNA
<213> ORGANISM: Homo sapiens
<220> FEATURE:
<221> NAME/KEY: misc_feature
<222> LOCATION: (1)...(644)
<223> OTHER INFORMATION: n = A,T,C or G

<400> SEQUENCE: 117

```
acaggggtta aggaaggctt tgccggaaga acaattgtaa atcatgagag ttactacttg     60
cgcattgtgt ggtagtctct ttaatgcata atggtccttt ttaataccaa aaattaatta    120
ataaaggaaa tgattacatt gtccaaataa ctgttaaaca catgacagat ctgttttatg    180
atactgtgtt tgacagttaa acattaagta aacatttaat tgactttaag cttgaaatgt    240
tcagaatgct ctaacccttg ctacagaatc ttttctgcag caagttaagt attttgtgtg    300
tttttccca cctgtagctt atcaggcccg gtccaaagcc ttctagcaga ggggattgat     360
cctgtcaggg gttgctgcca agacatcgga aggatttttg accaaggntt tcaaaagctc    420
aatgncacat ctggcatttt gataaaagga gggattttgg atccaaagcn tggcnttatt    480
ggccttttgg gtggctggtt agggtggntt tggctttngc cttttcttaa aaattaacca    540
nggttnccac ttantttttt aaaagggtga atggggtaaa atttttccnt ggaccnngta    600
aattgnaata aaaattcccc tttaccgtta aacttaaaan angg                      644
```

<210> SEQ ID NO 118
<211> LENGTH: 500
<212> TYPE: DNA
<213> ORGANISM: Homo sapiens
<220> FEATURE:
<221> NAME/KEY: misc_feature
<222> LOCATION: (1)...(500)
<223> OTHER INFORMATION: n = A,T,C or G

<400> SEQUENCE: 118

```
ggtacaaacc catgcagcct ggccctcacg tggtcaagat cttctttgct ggggacacta     60
ttcctaagag tcccttcgtt gtgcaggttg gggaagcctg caatccaaat gcctgccggg    120
ccagtggccg aggcctacaa cccaaaggcg tccgtatccg ggagaccaca gatttcaagg    180
ttgacaccaa agctgcagga agtggggagc tcggtgtaac catgaagggt cctaagggtc    240
tggaggagct ggtgaagcag aaagactttc tggatggggt ctacgcattc gagtattacc    300
ccagcacccc ggggagatac agcattgcca tcacatgggg gggacaccac attccaaaga    360
```

gcccctttga agttcaagtt ggccctgaag cgggtatgca gaaagtccgt gcttggggcc 420
ctgggctcca tggtgggatt gtcnggcggt caacngactt cgtggnanaa tccattggct 480
ctgaaatnng gnctctgggg 500

<210> SEQ ID NO 119
<211> LENGTH: 624
<212> TYPE: DNA
<213> ORGANISM: Homo sapiens
<220> FEATURE:
<221> NAME/KEY: misc_feature
<222> LOCATION: (1)...(624)
<223> OTHER INFORMATION: n = A,T,C or G

<400> SEQUENCE: 119
actcaatctt tgcctgagag gggccttcaa tggcaaaccc cagagacccc acttcagagc 60
caatggattc taccacgaag tctgctgacc gcccgacaat cccaccatgg agcccagggc 120
cccaagcacg gactttctgc atacccgctt cagggccaac ttgaacttca aaggggctct 180
ttggaatgtg gtgtcccccc catgtgatgg caatgctgta tctccccggg gtgctggggt 240
aatactcgaa tgcgtagacc ccatccagaa agtctttctg cttcaccagc tcctccagac 300
ccttaggacc cttcatggtt acaccgagct ccccacttcc tgcagctttg gtgtcaacct 360
tgaaatctgt ggtctcccgg ataccgaccg cctttgggtt gtaggcctcg gccactggcc 420
cggcaggcat ttggatgcan gctttcccaa cctgcacaac gaanggactt ttangaatag 480
tggncccagc aaagaaaatc ttgaccacnt tganggggcca gctngatggg tttggacctt 540
tggccggaac acccttangg ccaantccng canttggggg ccgtacttag ggaccaactt 600
ggnnccaact ttggngaata tggn 624

<210> SEQ ID NO 120
<211> LENGTH: 504
<212> TYPE: DNA
<213> ORGANISM: Homo sapiens
<220> FEATURE:
<221> NAME/KEY: misc_feature
<222> LOCATION: (1)...(504)
<223> OTHER INFORMATION: n = A,T,C or G

<400> SEQUENCE: 120
acaggcatgg caccgacatc tgcttggctt ctgctgtagc ctcaggaagc ttatagtcgt 60
ggcagaaggc aaagagggac ggcaagagag gaagcaagag agagagcgag gaggtctcag 120
actctcttta ataatcagat ctcctgataa ctcatttcca tggggagggc accattcatg 180
agggatccgc tcccatgacc caaacagccc ccaccgggcc ccactgtcaa cactgaggat 240
cacatttcaa catgaaatgt ggaggggaca gacatccaaa ctatatcacc tccatactgt 300
tttccacagc attcccacca acagtgcaca ggggtttcag tgtctccaca tcctcatcac 360
acttgttatc ttctgttttt gtttgtttgt ttgtttgttt tttatagtag ccattctcat 420
gantgtgaag tattaacagt gtcttttgaa gatcagaaat ttctaatttg atgaaagtcc 480
ngnttancan nttttttcnt tttn 504

<210> SEQ ID NO 121
<211> LENGTH: 630
<212> TYPE: DNA
<213> ORGANISM: Homo sapiens
<220> FEATURE:
<221> NAME/KEY: misc_feature
<222> LOCATION: (1)...(630)

<223> OTHER INFORMATION: n = A,T,C or G

<400> SEQUENCE: 121

```
ggtactatcc taagtttaac actgcttcac agtaaggaaa gccgatcaaa atttaaggag     60

agattagaat ccagaaatag gcccacacat atatatagtc attgattttt aataaaggtt    120

caaaggcaaa acaatgaaga aaggatggtc ttttcaataa atgatgcaga aacaactgga    180

catccacgta tgcaaataaa ctttaatcca tgccttttac tttatccaaa agctaatcca    240

aaatagaaac ctccctttcc tccctcaaaa aagcttctag agaaaacaca ggagaaaatc    300

tttgtaacct tgggttcaca aagatttctc aggtatgaca ccataagtat gatccagaaa    360

agaaaaaaaa tgataaactg gacttcatca aattagaaat ttctggatct tcaaaagaca    420

ctgntaatac ctcacactca tgagaatggc tactataaaa acnaannanc caaccaacca    480

ataacngaag attncaggtt gatgangntt ggagacnctg aanccctgng cactgttggt    540

gggaatnntt ntggaaaaca gttggangng aattagntng gngnntngcc cttccanttc    600

atgggnaagg gacctnagnn tgancgnggg                                     630
```

<210> SEQ ID NO 122
<211> LENGTH: 431
<212> TYPE: DNA
<213> ORGANISM: Homo sapiens
<220> FEATURE:
<221> NAME/KEY: misc_feature
<222> LOCATION: (1)...(431)
<223> OTHER INFORMATION: n = A,T,C or G

<400> SEQUENCE: 122

```
actgaaaagc ttggtcataa tcttcctgaa catggaatga tctagctagc tgatagcagc     60

tctctgcttg catagcttcc acttctgtat tatggaatgc atggagggcc agatgctgga    120

ctttactata atcctttttg aagaaaaagt gatttgccaa atggttcaat accatagggt    180

tgctaggatc aatagtatag gctctggaaa gaagctggac accattttta atggaatcag    240

cctctttatt gttgagttct agaacagcca gtccaaccaa tgctcccacg catttggaat    300

tgagttccag ggctctgctg aatgccagac gagctttttc cagtttgtta agtttcacaa    360

agcaatgacc cattcctaaa cnaacttccg ctggacattc ctgggttaag tacctnnggc    420

cgngaccacg c                                                         431
```

<210> SEQ ID NO 123
<211> LENGTH: 504
<212> TYPE: DNA
<213> ORGANISM: Homo sapiens
<220> FEATURE:
<221> NAME/KEY: misc_feature
<222> LOCATION: (1)...(504)
<223> OTHER INFORMATION: n = A,T,C or G

<400> SEQUENCE: 123

```
actggctgtc ctctgaggca ccttggtgtc ttttccacaa tggtttattt tcctccagta     60

ggctagactg gcttccttat ttggcagttt cagggcagca tttcaaaagc aggaaggtgg    120

aagtggcaag gccccttgag gccctttctt cagagctcac acagtgtcac ctttaccaca    180

ttctattggt caaagcaact tccaggccag ccaaaattca aagggtgagg tagtagactc    240

tacctctttt ttcttttgag acagaattgc gctctattgc ccactctgga gtgcagtagc    300

agcctcatgg ctcactgcag cctcaacctc ctgggctcaa gcgatccttc catctcagcc    360

tcccgagtag ctaggaccac aggcacatac caccacagtc agctaattaa aacatttttt    420
```

ttggtagaag atgggttctc actttttttgc ccaagctgat catgaactcc tggccacntt 480
ngggcntttc aaggggnaac cccc 504

<210> SEQ ID NO 124
<211> LENGTH: 632
<212> TYPE: DNA
<213> ORGANISM: Homo sapiens
<220> FEATURE:
<221> NAME/KEY: misc_feature
<222> LOCATION: (1)...(632)
<223> OTHER INFORMATION: n = A,T,C or G

<400> SEQUENCE: 124
ggtacaaaca cagtaaagaa caacacagat accagtcctg cctttatcag gaaagacaaa 60
acaaaaacaa aaagtaaaca ttccagtaaa ggaatgatta gtgctattat gacaaggaaa 120
gcatagggaa ctattcgatc aaagaagaga ggttacagtt ccccaaatct agggtgtttg 180
gaaaggaaga atatccttag taaatgacat tgaagctaaa acctaaacta tgtatagcag 240
tcagctagaa aaaacaggca agaaagaata tttcaggtgg agagaaacac atgttttcag 300
gccaaaagct ggagaacaag gtgagtttaa agaactgana gaggtttagt gattacaatn 360
gttgaacaaa aggggggcat tgtggaatga atannaaaga ntggttttgt anattggaat 420
ctctgcagca aaactccatt cagaaggtat aagttcangc cttggtgggt tactttggna 480
aggccgtagt gggccaggag nttcatgntn cancttgggc caaaaagnng agaacccatt 540
ttttccaaaa anaatgnttt naatttacct ncntgggggg ggaatgnncn tngggtcctt 600
anttctttgg aanggtttaa attgnaaggt nc 632

<210> SEQ ID NO 125
<211> LENGTH: 496
<212> TYPE: DNA
<213> ORGANISM: Homo sapiens
<220> FEATURE:
<221> NAME/KEY: misc_feature
<222> LOCATION: (1)...(496)
<223> OTHER INFORMATION: n = A,T,C or G

<400> SEQUENCE: 125
acaagattag gagggggggaa aaacctgaac aaatcctgga acacacctat gtatttacgt 60
catgggaaaa ggggagagaa cacttcaaat atcaacaagt tctgcgccat taactcatta 120
atagctaaat ggccacacca aattgcatgt gaatgttaga acctctcaga tagccacaat 180
aagtccatat ttttttttaa aaaaaggaaa acacagaaat aactaccaac agtgtctgag 240
aagagagact aagttaacat acattgcatg tattgcaggc aaggcagagg catttttttta 300 aagcttttgc acagacttca tataatctta aaaaaaatat gcaggccttt gcaagatttg 360
acttgctgaa atccaaacaa ttttgactca tgaaaagtca taagacttca gctgaaaaaa 420
aagaaaaaag ttccagcctt agaccaaaaa aaaaaacctg gaanagtntg atagatttaa 480
cnanggtngg cacgct 496

<210> SEQ ID NO 126
<211> LENGTH: 631
<212> TYPE: DNA
<213> ORGANISM: Homo sapiens
<220> FEATURE:
<221> NAME/KEY: misc_feature
<222> LOCATION: (1)...(631)
<223> OTHER INFORMATION: n = A,T,C or G

<400> SEQUENCE: 126
ggtacacctt gttaccaaat aggttgttct cttccccacc cacctttgag cttttgctct 60
aaaatacatt caggttccaa gcctgaccat ccttgtttaa tctatcatac tcttccaggt 120
tttttttttt ggtctaaggc tggaactttt ttcttttttt tcagctgaag tcttatgact 180
tttcatgagt caaaattgtt tggatttcag caagtcaaat cttgcaaagg cctgcatatt 240
ttttttaaga ttatatgaag tctgtgcaaa agctttaaaa aaatgcctct gccttgcctg 300
caatacatgc aatgtatgtt aacttaagtc tctcttctca gacactgttg gtagttattt 360
ctgtgttttc cttttttaaa aaaaaatatg gacttattgt ggctatctga gagggtctaa 420
cattcacatg ccaatttggg ggtggncatt taactattaa tggagttaat gggcccaaaa 480
cttggtgata ttttnaaggg gtctcttccc ntttttccaa tgccgtaant cntttngggg 540
tggttccagg aatttgntcc aggntttttc ccccncctaa aatnttgaac cttgnccngg 600
cnggnccttt caaagggcna attnnanccn t 631

<210> SEQ ID NO 127
<211> LENGTH: 518
<212> TYPE: DNA
<213> ORGANISM: Homo sapiens

<400> SEQUENCE: 127
caggtactcg gtgcttccca acacctcctt attggaaaac agccaaggag atggtggcta 60
actggaggca tcacccagca gtggtggagc agtggagcaa ggtcatttgt gcactcactt 120
ccagattgct acgctttaca tatggtcctt catttcctgc atttaaagtt cccgatgaag 180
atgccagtct gatccctcca gaaatggata atgagtgtgt tgcacagaca tggtttcgct 240
ttttacacat gttaagtaat cctgtggatt tgagtaaccc agctattata agctctactc 300
ccaaatttca ggaacagttc ttgaatgtga gcggaatgcc gcaagaattg aatcagtatc 360
cctgccttaa acatctgcct caaatatttt ttcgtgccat gcgtggaatc agctgtctgg 420
tggatgcatt cttaggtatt tctagacccc gatcagacag tgctccccca acacccgtga 480
atagattaag tatgcctcaa agtgctgctg tcagtacc 518

<210> SEQ ID NO 128
<211> LENGTH: 865
<212> TYPE: DNA
<213> ORGANISM: Homo sapiens
<220> FEATURE:
<221> NAME/KEY: misc_feature
<222> LOCATION: (1)...(865)
<223> OTHER INFORMATION: n = A,T,C or G

<400> SEQUENCE: 128
accaaaggat agctgttctg tttaagtagg gacctctcat ggcctacagg ctttgacatc 60
tgagaatcaa actggagaac attccgaagc cgttcttata agtgtctcca tctctacctg 120
ggctgaaatg gaatgtgcaa atgtagccca gcctggtcct tgggtgttgc cagttgattg 180
atgactggga gccaaagtgg catctccttt gacctaaacg ggcgatgatg aaataaaact 240
caacagcctt tctctcatct tgcattgtga gatgcgaaat agagcgtgtc tctctgcctc 300
tcattttagg ctgaggccgt ccaaagcggc catgccccat gtttccacta gatggcgctg 360
acacttcagg catcaaccct catggcctct cagccttgca aaggcagcca cttaaagtcg 420
gtgtcctgtg tggggcacca agctgagctg cagacaccca gtaggcgcga ggcaaatgcg 480
tcccatttta agaggcttgt atttatgagc tctttgcttc ctccctccca ctatctttaa 540

```
agaattgctc tccatctcct ttggcaaagt tcctttgccc tttgncttat ttttgtgaaa    600

cccttcaagg tatttccagt ccatttgcat ccaatctggc atctttacng aanagcggtc    660

tcatatgcta ttggtggtaa cgtgggacta gtatttatgn ggttgagaac cacttggctg    720

tttgtcaagg aaaagtgtgc ccaaaaacca agaagtacct ttggccgnga accacgctta    780

aggccgaaat tctgnagata tncnntcaca cttggcgggc cggttcgaac cttgcatnta    840

aanggnccca atttggccct tatag                                          865
```

```
<210> SEQ ID NO 129
<211> LENGTH: 910
<212> TYPE: DNA
<213> ORGANISM: Homo sapiens
<220> FEATURE:
<221> NAME/KEY: misc_feature
<222> LOCATION: (1)...(910)
<223> OTHER INFORMATION: n = A,T,C or G

<400> SEQUENCE: 129
```

```
tactctttgt tttggcacac ttttcctgac aaacagccag tgttctcaac acataaatac     60

tagtccacgt taacaacaat agcatatgag accgctctcc gtaaagatgc cagattggat    120

gcaaatggac tggaaatacc ttggagggtt tcacaaaaat aagacaaagg gcaaaggaac    180

tttgccaaag gagatggaga gcaattcttt aaagatagtg ggagggagga agcaaagagc    240

tcataaatac aagcctctta aaatgggacg catttgcctc gcgcctactg ggtgtctgca    300

gctcagcttg gtgccccaca caggacaccg actttaagtg gctgcctttg caaggctgag    360

aggccatgag ggttgatgcc tgaagtgtca gcgccatcta gtggaaacat ggggcatggc    420

cgctttggac ggcctcagcc taaaatgaga ggcagagaga cacgctctat ttcgcatctc    480

acaatgcaag atgagagaaa ggctgttgag ttttatttca tcatcgcccg tttaggtcaa    540

aggagatgcc actttggctc ccagtcatca atcaactggc aacacccaag gaccaggctg    600

ggctacattt gcacattcca tttcagccca ggtagagatg gagaccttat aagaacngct    660

tcngaatggt ctncagtttt gaatctcaga tgtcaaaagc ctgtaagncc atgaaaggtc    720

cctacttaaa ccggaaccag ctatcctttg gnanctggcc gggccgggcc ggttcgaaaa    780

gggcgaaatt ccacaccact tgggcggccc gttacttaan ggaatcccga actttggnan    840

cccaagcntt ggcggtaaat catgggccat anctgggttt cctggggggg aaaatggtat    900

tcccttccca                                                           910
```

```
<210> SEQ ID NO 130
<211> LENGTH: 932
<212> TYPE: DNA
<213> ORGANISM: Homo sapiens
<220> FEATURE:
<221> NAME/KEY: misc_feature
<222> LOCATION: (1)...(932)
<223> OTHER INFORMATION: n = A,T,C or G

<400> SEQUENCE: 130
```

```
taccgcttgt ttatccaaat tttcctctgc aagtggagca tctgctagga tcaatagcag     60

cagtgttaag caggaagcta cattctgttc ccaaagggat ggcgatacct ctttgaataa    120

agccctatcc tcaagtgctg atgatgcgtc tttggttaat gcctcaattt ccagctctgt    180

gaaagctact tctccagtga aatctactac atctatcact gatgctaaaa gttgtgaggg    240

acaaaatcct gagctacttc caaaaactcc tattagtcct ctgaaaacgg gggtatcgaa    300
```

-continued

```
accaattgtg aagtcaactt tatcccagac agttccatcc aagggagaat taagtagaga    360

aatttgtctg caatctcaat ctaaagacaa atctacgaca ccaggaggaa caggaattaa    420

gcctttcctg gaacgctttg gagagcgttg tcaagaacat agcaaagaaa gtccagctcg    480

tagcacaccc cacagaaccc ccattattac tccaaatcaa aggccatcca agaaagatta    540

ttcaagcaag acacatcttc atctactacc catttagcac aacagctcaa gcaggaaccg    600

tcaaaaagaa ctagcatgtc ttcgtggccc gatttgacaa gggcaatatt atggaggtgc    660

agaaaaaggc nggaaactca aaaagcnaac cacctnggaa anccaaacng ggaaaacttc    720

acttgtcaag agcactcccc ttnaaaaaaa ccnccccaag gggtttnca aaaactcagt    780

cccnttccgg taaccngaaa aagggggacc cgaaaacccc cganacccng gcccaaaaat    840

tntaggacct tgccccggcg ggcccgntnc aaaangggcg aaatttttgg gaaaatccat    900

tnnncctngg cggggcnggt tttgaccatt cn                                  932
```

<210> SEQ ID NO 131
<211> LENGTH: 890
<212> TYPE: DNA
<213> ORGANISM: Homo sapiens
<220> FEATURE:
<221> NAME/KEY: misc_feature
<222> LOCATION: (1)...(890)
<223> OTHER INFORMATION: n = A,T,C or G

<400> SEQUENCE: 131

```
actagaattt ttggctggta tctggttttc ggtcaccttt tctgttactg gaagtgactg     60

agtttttgaa acaccttggt gtttttttgag gggagtgctc tgacagtgag tttcctgttt    120

ggtttctagt tgtttgcttt ttgagtttcc gccttttttct gcactccata tattgccctt    180

gtcaaatcgg ccacgaagac atgctagttc tttttgacgt tcctgcttga gctgttgtgc    240

taaatgggta gtagatgaag atgtgtcttg cttgaataat ctttcttgga tggcctttgt    300

atttggagta ataatggggg ttctgtgggg tgtgctacga gctggacttt ctttgctatg    360

ttcttgacaa cgctctccaa agcgttccag gaaaggctta attcctgttc ctcctggtgt    420

cgtagatttg tctttagatt gagattgcag acaaatttct ctacttaatt ctcccttgga    480

tggaactgtc tgggataaag ttgacttcac aattggtttc gatacccccg ttttcagagg    540

actaatagga gtttttggaa gtagctcagg attttgccct cacaactttt agcatcagtg    600

atagatgtag tagatttcac tggagaagta gctttcacag agctggaaat tgaggcatta    660

accaaagacg catcatcaag cacttgagga tagggcttta ttcaaagagg tatcggcatc    720

cctttgggga accagaatgg aagcttnctg cttaacactg ntgctatgga cctanccana    780

agctccactt tgcanangga aaatttggat aaaccagccg ganccttggc cgggaancac    840

gcttanggcc gaattccnca cacctgggcg gncggttacc taagggaacc               890
```

<210> SEQ ID NO 132
<211> LENGTH: 606
<212> TYPE: DNA
<213> ORGANISM: Homo sapiens
<220> FEATURE:
<221> NAME/KEY: misc_feature
<222> LOCATION: (1)...(606)
<223> OTHER INFORMATION: n = A,T,C or G

<400> SEQUENCE: 132

```
actcaggcac ttcacagttt acttgaaaga ggctttggaa aatagataaa gtgaaagaag     60

aataaataca tatttttaat aatgtaattt taaaaatcct ttataatcag gactaagtct    120
```

```
tggtttgcag aagctgtcac ttaccctgaa acacagtatc aaaagggaaa cttaaaacat    180

actgtttgat ttttttattt cctcttacaa tccatgtttt caggtagaat tatgactttc    240

cccccattgt tacacatttc tttacaaagg aggcctgtag aaattggaca cgatcatgct    300

tgagcatgtg agttagtcaa attatgagtc cctgcctatt gtccattaca caccgaatgt    360

taatttaaga accagaggca gaagttctgg cttcctgctt gaaacccaat tcttatatga    420

aaatttttaa aagccagaac ctagcagccc atctgntttt tctcttttgc cggngnattt    480

gganccttgg cgggaacacc cttangggn aattcngnnc acttgggggc cggtacttan    540

ggganccaac tttgggccca annttgggga aancagggcn anattngtnc ctggggnaaa    600

tggtnn                                                               606
```

```
<210> SEQ ID NO 133
<211> LENGTH: 606
<212> TYPE: DNA
<213> ORGANISM: Homo sapiens
<220> FEATURE:
<221> NAME/KEY: misc_feature
<222> LOCATION: (1)...(606)
<223> OTHER INFORMATION: n = A,T,C or G

<400> SEQUENCE: 133

ggtacttttc cttaatcttc ttcttcttct tcttgtcacc atccttcttt tcttcttcct     60

catcagaacc aacatcttca atttcaggtt tgtcttccga ctctttctct tctttttctt    120

tttcttcttc tttgtcttcc ttttcttcag cctcatcatc gcttacttct ttatcacgtt    180

ccttctccac aaaaagagta atgggatatc caataaactg agaatgtttc ttcacaatct    240

cctttattct tcgttcctcc aagtacttta aatttagtgg ttgctggagc acctaaaagt    300

cagattgtca tgttggaagc ctctgcagag aacattttac agcaggactt ttgccatgct    360

atcaaagtgg gagtgaaata tacccaacaa ataattcagg gcattcagca gttggtaaaa    420

gaaactggtg ttaccaagag gcacctcaga aggtatttac cccttcgcag agaatgngaa    480

atatactcat aaacctgcta tggagagact ctatgcagtt ttacagatac gagcatgaca    540

aggttcngga gatgaagctg taccaaataa gatagatccn gnggaccact aaangaaaat    600

tccgag                                                               606
```

```
<210> SEQ ID NO 134
<211> LENGTH: 598
<212> TYPE: DNA
<213> ORGANISM: Homo sapiens
<220> FEATURE:
<221> NAME/KEY: misc_feature
<222> LOCATION: (1)...(598)
<223> OTHER INFORMATION: n = A,T,C or G

<400> SEQUENCE: 134

tacntcacca tcccgtattt gctgctgtnc canaaggcat ngncaaattg agggtcatac     60

tngatagcan cagggtaaac tgtggctcca atttcaaaac ttncctttat gaacatcatc    120

accgangtat tattgatgca ggntccttct gngaagatga ggataggcag ctngctttta    180

tcttgcacat gttcannnan nctnttagcc accanntggc natccttcac ttccgagcgc    240

tcaaaccaga cgtgtggncn ggccttcacc atggntctct gaatcacacc catgagtccc    300

ccgtgcactt gacccaccat ggcataatan ccatcgctgg ccaagatgat cacatcgatc    360

ggtgaggnat gattggccac acagatgcca ccatttcttg gtctgntttc cctgtcatgg    420
```

-continued

```
taggtgatga tggctgtcag cgctcgcacg cagatccggt aacacattaa ctgaacatgt    480

ttactcatga actccttaaa cctcccattt ggcangtatc ccaccacagn tgtgcccacc    540

accagaaggc taatccctgt gaaagccagt gctatcctga gcggcancag aaagcagt      598
```

<210> SEQ ID NO 135
<211> LENGTH: 617
<212> TYPE: DNA
<213> ORGANISM: Homo sapiens
<220> FEATURE:
<221> NAME/KEY: misc_feature
<222> LOCATION: (1)...(617)
<223> OTHER INFORMATION: n = A,T,C or G

<400> SEQUENCE: 135

```
actgctttct gctgccgctc angatagcac tggctttcac agggattagc cttctggtgg     60

tgggcacaac tgtggnggga tacttgccaa atgggaggnt taaggagttc atgagtnaac    120

atgtncactt aatgtgttac cggatctgcg tgcgagcgct gacagccatc atcacctacc    180

atgacaggga aaacanacca agaaatggtg gcatctgngt ggccaancat acctcaccga    240

tcgatgtgat catcttggcc ancgatggct attatgccat ggtgngtcan gtgcacngcg    300

gactcatggg tgtgattnag agagccatgg ngaanngcct gcccacacgt ctggtttgag    360

cgctcggaag tgaatgatcg ncacctggtg gntaananac tgactganca tgtgcangat    420

aanngcnagc tggctatnct catcttccca gangganoct gcatcaatna tacatcgntg    480

atgatgttca aaaagggaag ttttgaactt ggagccacag tttaccctga tgctntcaag    540

tatgaccctg aatttgncga tgccttctgg aacagnagca aatncngtat ggngactanc    600

ctcggncgnn ancacgc                                                   617
```

<210> SEQ ID NO 136
<211> LENGTH: 610
<212> TYPE: DNA
<213> ORGANISM: Homo sapiens
<220> FEATURE:
<221> NAME/KEY: misc_feature
<222> LOCATION: (1)...(610)
<223> OTHER INFORMATION: n = A,T,C or G

<400> SEQUENCE: 136

```
cgtgccgtag gccggaatgt taccggctgt tggatctgcg gatgaggagg aggatcctgc     60

ggaggaggat tgtcctgaat tggttcccat tgagacgacg caaagcgagg aggaggaaaa    120

gtctggcctc ggcgccaaga tcccagtcac aattatcacc gggtatttag gtgctgggaa    180

gacaacactt ctgaactata ttttgacaga gcaacatagt aaaagagtag cggtcatttt    240

aaatgaattt ggggaaggaa gtgcgctgga gaaatcctta gctgtcagcc aaggtggaga    300

gctctatgaa gagtggctgg aacttagaaa cggttgcctc tgctgttnag tgaaggacag    360

tggccttaga gctattgaga atttgatcaa aagaaagggg aaatttnatt acatactggt    420

agagacnctg gattanccng accctggtgc cantggcttn tantgttttg ggttgaagct    480

tnaattaggg nnngtnttta acttggaggg ttnttacttt tgggggttca antttgggtt    540

aaacttttnn cnaaaaaaac cttgangcct tnttaatgan nnttttngca agttttttgc    600

canagccttt                                                           610
```

<210> SEQ ID NO 137
<211> LENGTH: 645
<212> TYPE: DNA
<213> ORGANISM: Homo sapiens

```
<220> FEATURE:
<221> NAME/KEY: misc_feature
<222> LOCATION: (1)...(645)
<223> OTHER INFORMATION: n = A,T,C or G

<400> SEQUENCE: 137

acaattccaa gtgcttatag ccaatataag catatttcat attagaaata gttatccata     60

tgttaacaag aaactatggt cctcaaatat gccaatttta gagtctaata actactgata    120

gtaactatgt aaatattttg gaataaacag ttatttacgc aagccacact tcagctgaga    180

tgatcactag acatctgttt ccagagcttc aacaatgtgt gcagcagaag gacgatcttt    240

agggtcttca ttagtgcata cagagaagag ttcaattact ttctggtatg attcatccag    300

ttcttccata ttaataggtg gcctagttcc caaggctgca tagtatgctt catcatcaaa    360

atcactttca tcaaaagttt tatcttcatc atcatcatca tttgaaagat taatgtgtgg    420

aaatccgata aaagtcatca tttcccacaa agtaagggcc aangccaaat atgtctggcc    480

tggccagtaa taacacccat tcttcttcac aggnttcttt tggggttnca atggnttctg    540

ggnccaatgg taaccaggnc ctaangggtc aggtcccggg cataattttc aatncccngg    600

gganaaaaag acctcctaaa nttnccagaa tttnaatngg ttcna                    645


<210> SEQ ID NO 138
<211> LENGTH: 612
<212> TYPE: DNA
<213> ORGANISM: Homo sapiens
<220> FEATURE:
<221> NAME/KEY: misc_feature
<222> LOCATION: (1)...(612)
<223> OTHER INFORMATION: n = A,T,C or G

<400> SEQUENCE: 138

ggtactcctg gtcacttaag atctgatact gaacattcta caaatgaagt tgggacttta     60

tgtcataaaa ctgatttaaa taatcttgaa atggccatta aggaagatca gattgcagat    120

aactttcaag gaatatcagg tcctaaagaa gacagcacaa gtataaaggt aattcagacc    180

aggattcttt tcttcatgag aattcgttac accaagaaga gagtcaaaaa gaaaatatgc    240

cttgtgggga aacagcagaa tttaaacaaa agcaaagtgt taacaaagga aaacaaggaa    300

aggagcaaaa tcaggactca cagacagagg cagaagagct acgcaaactt tggaaaaccc    360

atactatgca acaaactaaa cagcanaggg aaaatattca acaagtgtca caaanagaag    420

ctaagcataa aattacatct gctgatggac acatagaaag gtctgcactt ttaaaagaaa    480

agcanaggca tcgattacat aagttcttgg gtcttagagt tgggaaaacc aatgaggaaa    540

accgtttgga tnttaaggcc aggtgctacc aatgccaccg tntgccngag ggttaagaaa    600

cctnaatntt gg                                                        612


<210> SEQ ID NO 139
<211> LENGTH: 592
<212> TYPE: DNA
<213> ORGANISM: Homo sapiens
<220> FEATURE:
<221> NAME/KEY: misc_feature
<222> LOCATION: (1)...(592)
<223> OTHER INFORMATION: n = A,T,C or G

<400> SEQUENCE: 139

ggtactccac ttcttcctat tggaagatta acattattta ccaagaagga cttaagggag     60

taaggggcgc agattagcat tgctcaagag tatgtaaaaa aaaaaaaaaa aaaagaacca    120
```

-continued

```
aaccactgga aataatcaaa tgcaaaaagg taacaaattc ataactggaa agcaaagaga    180

agaacaagta tgatttggat gataaagcat tgttttaatg gtgaaaactt cacagatcac    240

taatgtttct agaggttaac ttcaagtggg caagctgggg tttttaggta gtcagtggcc    300

tagttcctaa agccacagta taggatctgt taaactgaat gtctgttgaa agtttggttt    360

agctgcttgg aggcttcctt ttaagacaaa ctgtatgtga ttaagttgtt tttgagggaa    420

ctgaagacct gatgtacccc tggccagata actgcctgat tctcagatat tattctctgg    480

gaaacatcta catacacagg agcttaaant ggcattatct cttgcctaaa ttcagagatn    540

ttttgnactt gccggnggcc gtcnaanggc gaatccgcac ctggcgccgt ac            592
```

<210> SEQ ID NO 140
<211> LENGTH: 618
<212> TYPE: DNA
<213> ORGANISM: Homo sapiens
<220> FEATURE:
<221> NAME/KEY: misc_feature
<222> LOCATION: (1)...(618)
<223> OTHER INFORMATION: n = A,T,C or G

<400> SEQUENCE: 140

```
ggtncttaca cgtaagattt tagcctatgg tcattttata aagatgactg ttaggattta     60

attcacattt aaagaaaatg agattcgtta tattatggtg tttttatgac ctataaaata    120

cttaccccta caaatttcca taaatgtagt ggttagtaaa gctttttttct tactgaaaaa   180

taatgccagg taaccaagta ttattccttc catcatttat ttaggaaaaa gttttatgta    240

ttagggtaaa gtggtagaag ttaacctaga atctaataat ctccaatcac ccattcctga    300

tctaataagt agccatgaga aaaaatctct agaaagaatc atacctctca aaaaataaaa    360

tatnaaacaa aggctgggtg cagtggctca cacctgtaat ctnagcactt cccngaagtt    420

gaggtgggca gatcgcttga gcctaggcat atcgcttgna gcctgggcaa ctgtggccaa    480

accggtcttn taccaaaaaa atcncnaaag tagcccggcc ttagggccat accacctnga    540

gcccagggan ggtnaagnct accttgganc ngtgattgga ncctgcccng gtggncgttc    600

gaaaagggcn naaatnnt                                                  618
```

<210> SEQ ID NO 141
<211> LENGTH: 551
<212> TYPE: DNA
<213> ORGANISM: Homo sapiens
<220> FEATURE:
<221> NAME/KEY: misc_feature
<222> LOCATION: (1)...(551)
<223> OTHER INFORMATION: n = A,T,C or G

<400> SEQUENCE: 141

```
ggtacttcaa actctcttaa cggtgatgct ctgacattca ctactacatt tactctgcaa     60

gatgtatcca atgactttga aataaatatt gaagtttaca gcttggtgca aaagaaagat    120

ccctcaggcc ttgataagaa gaaaaaaaca tccaagtcca aggctattac tccaaagcga    180

ctcctcacat ctataaccac aaaaagcaac attcattctt cagtcatggc cagtccagga    240

ggtcttagtg ctgtgcgaac cagcaacttc gcccttgttg gatcttacac attatcattg    300

tcttcagtag gaaatactaa gtttgttctg gacaaggtcc cctttttatc ttctttggaa    360

ggtcatattt atttaaaaat aaaatgtcaa gtgaattcca gtgttgaaga aagaggtttt    420

ctaaccatat ttgaagatgt tagtggtttt ggtgcctggc atcgaagatg gtgtgtcttt    480

tctggaaact ggatatctta ttggacttaa cccgatgatg agaancgcaa ggtaatttat    540
```

```
atagtacctg c                                                         551

<210> SEQ ID NO 142
<211> LENGTH: 601
<212> TYPE: DNA
<213> ORGANISM: Homo sapiens
<220> FEATURE:
<221> NAME/KEY: misc_feature
<222> LOCATION: (1)...(601)
<223> OTHER INFORMATION: n = A,T,C or G

<400> SEQUENCE: 142

cgaggtacat ggtctatgcc tcccaggaga cgttcgggat gaaattgtca gtgtaaaacc     60

agaaaaaatg catctcttct agaattgttt aaacccttac caaggaaaaa aaaggggtgt    120

taccaactga gatcgatcag ttcatccaat cacagatcat gaaacagtag tgttcccacc    180

taggagtgtt gggaagttgt gtttgtgttt caagcagaaa aactgagctc caagtgagca    240

cattcagctt tggaaactat attatttaat gtgggctagc ttgttttcaa attttaaaag    300

tttaaaaata aaatactttg cattctaagt tgccaataaa atagaccttc aagttatttt    360

aatgctcttt tctcactaat aggaacttgt aattccagca gtaatttaaa ggctttcaga    420

gagaccctga gtcttctctt caggttcaca gaacccgccg ncttttttggg tagaagtttt    480

ctactcagct agagagatct cctaagagga tcttttangc ctgagttgtg aangcaccnc    540

ngcaaacgca ttgccttcca nttggcacaa acnccggtna acggcttgtg ttaaaaaccg    600

c                                                                    601

<210> SEQ ID NO 143
<211> LENGTH: 515
<212> TYPE: DNA
<213> ORGANISM: Homo sapiens
<220> FEATURE:
<221> NAME/KEY: misc_feature
<222> LOCATION: (1)...(515)
<223> OTHER INFORMATION: n = A,T,C or G

<400> SEQUENCE: 143

ggtnncgtaa agaatatatc ttatctggag ctcagcctca atcatgtctt aacaaaatga     60

caggtctnan aaagggggag ctcaatagct caaaagtgac aagtcctttt cacagcaccg    120

ttctcagaac acctctgagt aacgtgtttg ccagtagcta ttctcactga tgcactgatg    180

gccctgaaga agcggatcca gtcacatagg aaaggaggct gtgttagtga aagcacatgg    240

aaggtgttgn tttagaaagg tagtcaggaa aaacattcag gaatagattt atacaccatt    300

attgnattat ttntaaattt tcattcactc ttctgtttgg atacttttgc taattaaccg    360

tcctatgtta atanccacca aagctataag tccatagtca gtaaaacatt ccccttgggc    420

tgtctgagct aaaagcantg gcatctccgn atgtnggaca tccnagaaat agnttggtac    480

ctgcccnggc cgnncgttct taaggctaat ccngg                               515

<210> SEQ ID NO 144
<211> LENGTH: 436
<212> TYPE: DNA
<213> ORGANISM: Homo sapiens
<220> FEATURE:
<221> NAME/KEY: misc_feature
<222> LOCATION: (1)...(436)
<223> OTHER INFORMATION: n = A,T,C or G

<400> SEQUENCE: 144
```

-continued

```
ggtaccgctc aggattccca tcccaagaca cccggtcctt aaaccgccca ctcatgggtt     60

ggaagggatc tatgtggtag tagaatacaa actgctcagg tcccccgtct agaggacgaa    120

aattccaggt cactgttaga gcatcaccca caggggcaaa gctggagaaa gtgcatttta    180

accgagcatc tgtcccatta acagcctcca gcacccggga ggtataaatt tccacagctg    240

ctataggcca aagagctgtg agctgtatgc caaggagaag aagcaccgca cgagtagagc    300

tcttgccata catgagggaa acccagcctt ggccccagag accggacggg gcagaccgag    360

ggctccaaca ccctgccaag gccactccgg gaggagcaag caccgcgttt tnccagagag    420

aggagtttga gttgag                                                    436
```

<210> SEQ ID NO 145
<211> LENGTH: 441
<212> TYPE: DNA
<213> ORGANISM: Homo sapiens

<400> SEQUENCE: 145

```
ggtacatccc cactatcatc cgccgggatg accccctccat catccccatc ctctacgacc     60

atgagcacgc aaccttcgag gacatccttg aggagataga gaggaagctg aacgtctacc    120

acaagggagc caagatctgg aaaatgctga ttttctgcca gggaggtcct ggacacctct    180

atctcctcaa gaacaaggtg gccacctttg ccaaagtgga gaaggaagag gacatgattc    240

acttctggaa gcggctgagc cgcctgatga gcaaagtgaa cccagagccg aacgtcatcc    300

acatcatggg ctgctacatt ctggggaacc ccaatggaga gaagctgttc cagaacctca    360

ggaccctcat gactccttat agggtcacct tcgagtcacc cctggagctc tcagcccaag    420

ggaagcagat gatcgagacg t                                              441
```

<210> SEQ ID NO 146
<211> LENGTH: 624
<212> TYPE: DNA
<213> ORGANISM: Homo sapiens
<220> FEATURE:
<221> NAME/KEY: misc_feature
<222> LOCATION: (1)...(624)
<223> OTHER INFORMATION: n = A,T,C or G

<400> SEQUENCE: 146

```
acgtctcgat catctgcttc ccttgggctg agagctccag ggtgactcgg aaggtgaccc     60

tataaggagt catgagggtc ctgaggttct ggaacagctt ctctccattg ggttccccca    120

gaatgtagca gcccatgatg tggatgacgt tcggctctgg gttcactttg ctcatcaggc    180

ggctcagccg cttccagaag tgaatcatgt cctcttcctt ctccactttg gcaaaggtgg    240

ccaccttgtt cttgaggaga tagaggtgtc caggacctcc ctggcagaaa atcagcattt    300

tccagatctt ggctcccttg tggtagacgt tcagcttcct ctctatctcc tcaaggatgt    360

cctcgaaggt tgcgtgctca tggtcgtana ggatggggat gatggaaggg gtcatcccgc    420

ngatgaatag tgggggatgt accttggccg ngaacacgct taagggccaa ttccannaca    480

cttgccggcc gttactaaag ggatnncaac tttngnacca aacttggcnn aaacaatggg    540

ccnaacttgg ttccntggng aaaatggttt cccntcaaat tccccccaan ttacnaccgg    600

aaccttaaag ggaaaacctt gggg                                           624
```

<210> SEQ ID NO 147
<211> LENGTH: 599
<212> TYPE: DNA
<213> ORGANISM: Homo sapiens
<220> FEATURE:
<221> NAME/KEY: misc_feature
<222> LOCATION: (1)...(599)
<223> OTHER INFORMATION: n = A,T,C or G

<400> SEQUENCE: 147

```
cgaggtacaa gcttttttttt ttttttttt ttttttttt cttttttttt ttttttttt     60
ttttttttt ttttttgaa cncanatcan tttattggca tggntttgtt tnaaaaaaag    120
gaaaagngnc aaanccaaaa nacanacttt gntaacaaat ncctgggggn ggctggacnt    180
ttttgcctaa tgctgngcaa anaggggggat cctggcccan acatccngct gattccttgg    240
nacaaggttg tntgcctggg cctaantgcn cctttttgaa tacttgnttg caaaccacac    300
nttccanttt aatttccagg ggcagntnat naccctnnat ccactgggtc cagccacgcc    360
cntcntttta accctttgc anacactgga gcttgntccg tcccagntca ctgnngnatg    420
cncttgcggn catttatgcc tgtcaaacct ctaaaactcn ttcccacctg gaagccatgg    480
angtagttcc taaaaaggct caacgngccg aagaacaana tgggccccgg cctggacaaa    540
actttttggc ngggttaaac aagttggcna ttttcccaag gnccanttgc ctnnnggcc    599
```

<210> SEQ ID NO 148
<211> LENGTH: 609
<212> TYPE: DNA
<213> ORGANISM: Homo sapiens
<220> FEATURE:
<221> NAME/KEY: misc_feature
<222> LOCATION: (1)...(609)
<223> OTHER INFORMATION: n = A,T,C or G

<400> SEQUENCE: 148

```
ggtacttaag taatccaaag ctcgatcctg atctgcatga attagcatca taaatgcatt     60
ccttttgcaa cttgcatcct tctcattcac cagaaaatca tgtatcagtt caggagcatc    120
aggtataaga tgttcaaaat ttctatagat ggtatagatg gccaaaacag catttcttct    180
aacatagctg tgtcgatgct ccaaacatgc acgaatagct ggcattaaag gttctagcaa    240
ttctgcttct ttcaatttgc aaagaaaacg aagagtagat cctcgaataa attcattagg    300
atgttgaaga tcctttctgt atgcatcaca tacaaggatc atctcatgta aaagtctccc    360
atctggagtt gttttaggaa caatttccca aaataccaga agtaatttct tgatagtgtg    420
atcctgaaga aggtagcaca naacgaatgg atggtcatca gaaagtncag gaagtttttc    480
accaattcag aatcataatg gattaccttt cttcaaagct tcagtctttg actttacttc    540
ttccttttc taaaatcatt ttttaagctt aatttccaaa tgggngggtc ttgaatccat    600
gggcncgtn                                                          609
```

<210> SEQ ID NO 149
<211> LENGTH: 589
<212> TYPE: DNA
<213> ORGANISM: Homo sapiens
<220> FEATURE:
<221> NAME/KEY: misc_feature
<222> LOCATION: (1)...(589)
<223> OTHER INFORMATION: n = A,T,C or G

<400> SEQUENCE: 149

```
actcaggtag aaccatcatg aaaatgaccc acagtgaact tatggaaaag ttcttaacag     60
attatttaaa tgacctccag ggtcgcaatg atgatgacgc cagtggcact tgggacttct    120
atggcagctc tgtttgtgaa ccagatgatg aaagtggcta tgatgtttta gccaaccccc    180
```

```
caggaccaga agaccaggat gatgatgacg atgcctatag cgatgtgttt gaatttgaat    240

tttcagagac ccccctctta ccgtgttata acatccaagt atctgtggct caggggccac    300

gaaactggct actgctttcg gatgtcctta agaaattgaa aatgtcctcc gcatatttcg    360

ctgcaatttt ccaaacgtgg aaattgtcac cattgcagag gcagaatttt atcggcaggt    420

ttctgcaagt ctcttggtct cttcttcaaa gacctggaac cttcaaccct gaaagtaagg    480

agctggtaga tctggtggaa ttcacgaacg aaatcaaact ctgctgggct cctctgtana    540

gtgctccacc cagtgattgg cctagacact ctgggagcaa ctggccccc               589
```

```
<210> SEQ ID NO 150
<211> LENGTH: 353
<212> TYPE: DNA
<213> ORGANISM: Homo sapiens

<400> SEQUENCE: 150

ggtacaaaga aattttggat agcaaaataa aggaatcttt acccatagat atagatcagc     60

tatcaggaag ggacttctgc cattcaaaga aaatgacagg aagtaacact gaggaaatag    120

actcaagaat ccgagatgca ggtaatgata gtgccagcac tgctcctagg agcactgagg    180

agtctctttc tgaagatgtg ttcacagaat cagaactttc ccctatacga gaggagcttg    240

tatcttcaga tgaactgcga caagataaat cttctggtgc gtcatcagaa tctgtgcaaa    300

ctgtcaatca ggctgaagta gaaagtctga cagtcaaatc agaatctact ggt           353
```

```
<210> SEQ ID NO 151
<211> LENGTH: 492
<212> TYPE: DNA
<213> ORGANISM: Homo sapiens
<220> FEATURE:
<221> NAME/KEY: misc_feature
<222> LOCATION: (1)...(492)
<223> OTHER INFORMATION: n = A,T,C or G

<400> SEQUENCE: 151

ggtacctact ggtgctgaaa aaaggaaaat tccggcttga aggaaaggag tttagaactc     60

tgaaaatttg gtgacattgt ttttccctga aagaaatgtg tgttggattt aacagatgaa    120

attatctgcc ctccaaaagt cctttagaag agccagtgca aggctgaaga ccaaagcgtc    180

aagaacacgc cagactctca gcttcctctg ctttgctcct ttgttgagga aatgcaaatg    240

caaagagctt cccgttaaaa acaaggagtg tctgagagcc acgtgttcaa cacgcttctc    300

ctgctgctga cccctctgca cctgcagagg cagtgagcac ccaacaggtg gcgccaaggc    360

gcccgtcaca cgctcacgtc ctctggccag cagccacgtt tattgaagga gtgtggcact    420

gcccatcatt ggatatgccc tcggccatga aggattccag tggttcacgc tgnccagtat    480

atacaaaaat gt                                                        492
```

```
<210> SEQ ID NO 152
<211> LENGTH: 597
<212> TYPE: DNA
<213> ORGANISM: Homo sapiens
<220> FEATURE:
<221> NAME/KEY: misc_feature
<222> LOCATION: (1)...(597)
<223> OTHER INFORMATION: n = A,T,C or G

<400> SEQUENCE: 152

ggtacataag cctaaacaat ttcacctagg taaaatattg atgtcataac caaactatat     60

ggccccgttt cataaaggtt actatattct atagagagtg aagaggtggc ctttctatcc    120
```

```
cagcttaccc tattcttgtt attgttcaaa ttctcctgaa gcttgcataa ctagctgcca    180

tcaggtaaat gctattggct agcagaagac tgcagttctg ttaatattag aaccagcagg    240

gggaacttgg gaacttgaca ttaaaaatct agaaacagaa ttttaggatg ggtctcgtta    300

gaaacctgaa ttgttaatgg acttaagtaa aaaccatccc aaagaatttg agctttaagg    360

tgataaccgt cttttcagag atcatagcac atgaagaacc catggacact acacagacta    420

tgaaccggta gcagaaaaag atctcgtgac taaagtgggg gatgacagca aaaaaaaaaa    480

ttaccaaagg aaaaaagttg agaatncagg aatattacca gatggtaaaa aatattatct    540

tangccaaat gaggcccttc ggattcccaa accttgcttc ttctcctttc gtcttgn       597
```

<210> SEQ ID NO 153
<211> LENGTH: 596
<212> TYPE: DNA
<213> ORGANISM: Homo sapiens
<220> FEATURE:
<221> NAME/KEY: misc_feature
<222> LOCATION: (1)...(596)
<223> OTHER INFORMATION: n = A,T,C or G

<400> SEQUENCE: 153

```
actggttgct acccattttt tcaagtctag gtgatggctg ctcctttcca acttgccttg     60

ttaaccagga tcctgaacaa gcatctactc ctgcagggct gaattccaca gctaaaaatc    120

tcgaaaacca tcagtttcct gcaaagccat tgagagagtc ccagagccac cttcttactg    180

attctcagtc ttggacggag agcagcataa acccaggaaa atgcaaagct ggtatgagca    240

atcctgcatt aaccatggaa aatgagactt aactcttcaa gcaagataaa ttcatacttt    300

ataaaagtat caatgctgta gatggatgga agaggcttcc cacaggaagg tgccaccagt    360

cagtttgtgc ctatgtccct ttggctggaa atgcagaata tgaattgatt aagttctctt    420

ccaagccatt gcttaaaata taacatgttt tgggatccaa tacacacatt ggtacaacta    480

acacaaattc ctattaaata ttaaaagtag ttctgggtta ttaatcaacg ggaaaaacat    540

tttttccaaa aaaacttgga ataaatccan ggaccagttt tancccaata tttggg        596
```

<210> SEQ ID NO 154
<211> LENGTH: 297
<212> TYPE: DNA
<213> ORGANISM: Homo sapiens

<400> SEQUENCE: 154

```
ggtacccagt ttcaaagctc tctggttttt tctaagaaat gaagcaagga taggaacccc     60

ttctcccaga acaggcctca aatctatctt caaaggtgac ccagcaatca gtgtcaatgc    120

ctttactgta gttaacctgg taatttcatt ctttagtctc tccaagaaaa tctgaagtgt    180

attaggcaag tcagaaccca aattgtctcc aaggttgcaa ataatttgtc ccatacagga    240

aatagccctt tccttgactt cctgatcaat gtcagctgct tttaatctct taatggt       297
```

<210> SEQ ID NO 155
<211> LENGTH: 594
<212> TYPE: DNA
<213> ORGANISM: Homo sapiens
<220> FEATURE:
<221> NAME/KEY: misc_feature
<222> LOCATION: (1)...(594)
<223> OTHER INFORMATION: n = A,T,C or G

<400> SEQUENCE: 155

-continued

```
ggtacttgaa ggagaacagt ttacatcggg cgttagccac cttgcaggag gagactactg     60

tgtctctgaa tactgtggac agcattgaga gttttgtggc tgacattaac agtggccatt    120

gggatactgt gttgcaggct atacagtctc tgaaattgcc agacaaaacc ctcattgacc    180

tctatgaaca ggttgttctg gaattgatag agctccgtga attgggtgct gccaggtcac    240

ttttgagaca gactgatccc atgatcatgt taaaacaaac acagccagag cgatatattc    300

atctggagaa ccttttggcc aggtcttact ttgatcctcg tgaggcatac ccagatggaa    360

gtagcanaga aaagagaaga gcagcaattg cccaggcctt agctggcgaa gtcaagtgtg    420

gtgcctncat ctcgtctcat ggcattgctg ggacaaggcc tgaagtggca gcacattcag    480

ggattgcttc ctcctggtat gaccatagaa tttggttcga ggcaaggcac tgtcaaagat    540

gtggaagaag aaaagtttct acacactgag caggcttata agttnggcag aaan          594
```

<210> SEQ ID NO 156
<211> LENGTH: 294
<212> TYPE: DNA
<213> ORGANISM: Homo sapiens

<400> SEQUENCE: 156

```
acaggatgca gtttctcagc tggattctga gctgatggac ataactaagc tttatgggga     60

atttgctgac ccatttaaac ttgcagagtg caaacttgca ataattcatt gtgccggtta    120

ttcagaccct atattggtgc agacactttg gcaagatatc atagagaaag aattgagtga    180

cagtgtgaca ttgagctcct cggatagaat gcatgctctt agtctcaaga ttgttctcct    240

tggcaaaatt tatgctggca caccacgctt ctttccttta gattttattg tacc          294
```

<210> SEQ ID NO 157
<211> LENGTH: 527
<212> TYPE: DNA
<213> ORGANISM: Homo sapiens
<220> FEATURE:
<221> NAME/KEY: misc_feature
<222> LOCATION: (1)...(527)
<223> OTHER INFORMATION: n = A,T,C or G

<400> SEQUENCE: 157

```
ggtactgatt gtcatcctga ctttggcatt ggcagctctt atattccgac gaatatatct     60

ggcaaacgaa tacatatttg actttgagtt ataatatggt tttgtgactt atgagctgtg    120

actcaactgc ttcattaaac attctgcatt gggtataatc taagaattgt ttacaaaaag    180

attattttgt atttaccctt cattcctttt tttgatcctt gtaagtttag tataaatata    240

tctagacatt cagactgtgt ctagcagtta cgtcctgctt aaagggacta gaagtcaaag    300

ttccttgtct cactatttga tctgctttgc agggaaataa cttgnttttt ctcatgtttc    360

atcttctttt tatgtaaatt tgtaatactt tcctatattg ccctttgaaa tttttggata    420

aaagatgatg gtttaagttc caatgagtat tactaggtac tcaataccac ttattggagt    480

cctggcccng ggcgggcgnt tcgaaanggc caaatncagc accactg                  527
```

<210> SEQ ID NO 158
<211> LENGTH: 617
<212> TYPE: DNA
<213> ORGANISM: Homo sapiens
<220> FEATURE:
<221> NAME/KEY: misc_feature
<222> LOCATION: (1)...(617)
<223> OTHER INFORMATION: n = A,T,C or G

<400> SEQUENCE: 158

```
ggtactgaaa aagaggcgtg aggtgctccc tgtggatata accaccgcta aagatgcatg     60

tgtcaacaac agtgctctcg gggagaagt ttatcgatta ccgcctcaga aagaggagac    120

acagtcctgc cctaacagtt tagaagataa caacttgcaa ttagaaaaat cagtttctat    180

acacacacca gtagtcagtc tctctcctca caaaaatctg cccgtggata tgcagctgaa    240

gaaggaaaag aaatgtgtga aactcatagg agttcccgct gacgctgagg ccttaagtga    300

aagaagtgga aacaccccta actctcccag gtcagtgtcc tcttttcctc caggcagcca    360

gcagacctct ccatctctcc tctctcgctg catgaactgt gctgnctgnt tctttatcta    420

ctttcttaca attgcatgca gtataattcc tcagtttcat ctacctacct tcaacttttn    480

cagaacttta agaaagactt aaactgattg caangggaaa ggactcttgg aataaggcaa    540

tcncattaaa aagttacncg tttctgggtt catgaaaggg atntcncagt ttaccccatn    600

tttgaaaggt ttatnng                                                   617
```

<210> SEQ ID NO 159
<211> LENGTH: 1002
<212> TYPE: DNA
<213> ORGANISM: Homo sapiens
<220> FEATURE:
<221> NAME/KEY: misc_feature
<222> LOCATION: (1)...(1002)
<223> OTHER INFORMATION: n = A,T,C or G

<400> SEQUENCE: 159

```
ggtaccagct tacctatttg attcagttgc tgttttctca ctctctatat ccatttgaaa     60

ttgatttatt ttagatgttg tatacttacg ttaggctttc tgttaatagt ggtttttctc    120

ctgttgacag agccaccgga ttatgacaca ggatgaggaa gattaaggat aatcaattga    180

ctaatttcat ttagaatatt atcaaacatt tcaactaggt atcagaaaaa ggctttcttt    240

cataagacta ttttaaatag aaattatttc aacaattaaa gtaatgttga ccatcccccct    300

ctcagctgaa taaagaaaaa tttagttcaa tttattgcaa tttaattaca atactacctt    360

cacaacattt tcatgtgttt taaataaata ttttttaatt ggctaaagga cattcaagca    420

aagaaatgct ttctttactt aaaatgtcta tctcatttgc tgctttttca ctaagccttt    480

actttgttaa taaaagtgtc cattgtgtga tgtttttgat tttacagttt gctaaatctt    540

attttcttgg agttgctttt tggtaacagc tccattgcta ctccccattt tattggttta    600

catcaatgca tgcttcgttg tgatccctca agatgtaaca cttggtatgc tcggntgagg    660

atatgaaaaa atactttccg aaaccaggga attcagtgga tgnttggttt atctggttgg    720

ataagaaaag tagggnccag ccttaagcag nacagaagcc nctggtanaa gcatagtcag    780

ggaacttttt ttaattcntt tangnctaag ggncaggagt ggattnnaaa gggaggagag    840

cccttattat ggcctatncc ccgntttgga gaaganoctt actgggaacc tggcccggcg    900

ggccgttcaa aagggcgaaa ttccgncacc tgggnggccg gttcttaagg ancccnactt    960

gggcccaaan nttggggaaa nnnggggcna aannggntcc cg                      1002
```

<210> SEQ ID NO 160
<211> LENGTH: 434
<212> TYPE: DNA
<213> ORGANISM: Homo sapiens
<220> FEATURE:
<221> NAME/KEY: misc_feature
<222> LOCATION: (1)...(434)
<223> OTHER INFORMATION: n = A,T,C or G

<400> SEQUENCE: 160

```
ggtacaagtc atcanggtca gcattctccc actttcaagt gcactaacaa ggctgctggg     60

atttccactg gagtgtcaac agcagtattc ttgttgcagg aactctcaga atttgggggt    120

ccataacagg tttagcctat gacccaggtc caaaagttcc agccttctct gccacctcca    180

gagctagctt caggttctgg tcaaagagct cacacctgat aggcatttct aaggaataga    240

atggattctt gagggcaaag tctgagtaaa tctcataaat ctttcggaga agagaatcta    300

ttccagcttg cctaggatct gctagaacca caaacttgat ccctgtcagt gtctggtagc    360

agtgcaattt gaatgtgtct gtctncagca tctcaatgcc tgagcttncc tgttcangag    420

acagntggna gcca                                                      434
```

<210> SEQ ID NO 161
<211> LENGTH: 652
<212> TYPE: DNA
<213> ORGANISM: Homo sapiens
<220> FEATURE:
<221> NAME/KEY: misc_feature
<222> LOCATION: (1)...(652)
<223> OTHER INFORMATION: n = A,T,C or G

<400> SEQUENCE: 161

```
acagactcca agggaagact gggctccaaa gccacatgcc tttgttggca gcgtcaagag     60

tgagaagact tttgtggggg gtcctcttaa ggcaaatgcc gagaacagga aagctactgg    120

gcatagtccc ctggaactgg tgggtcactt ggaagggatg ccctttgtca tggacttgcc    180

cttctggaaa ttaccccgag agccagggaa ggggctcagt gagcctctgg agccttcttc    240

tctcccctcc caactcagca tcaagcaggc attttatggg aagctttcta aactccaact    300

gagttccacc agctttaatt attcctctag ctctcccacc tttcccaaag gccttgctgg    360

aagtgtggtg cagctgagcc acaaagcaaa ctttggtgcg agccacagtg catcactttc    420

cttgcaaatg ttcactgaca gcagcacggt ggaaagcatc tcgctccagt gtgcgtgcag    480

cctgaaagcc atgatcatgt gccaaggctg cggtgcgttc tgtcacgatg actgtattgg    540

accctcaaag ctctgtgtat tgtgccttgt ggtgagataa taaattatgg ccatgggaaa    600

caaannanan nnnnnnnnaa aaaaaaagct tgnaccttgg ccgngaccac gc            652
```

<210> SEQ ID NO 162
<211> LENGTH: 638
<212> TYPE: DNA
<213> ORGANISM: Homo sapiens

<400> SEQUENCE: 162

```
ggtacttgaa gatttgcata aagccaacat tcgcaccgtc atggtcacag gtgacagtat     60

gttgactgct gtctctgtgg ccagagattg tggaatgatt ctacctcagg ataaagtgat    120

tattgctgaa gcattacctc caaaggatgg gaaagttgcc aaaataaatt ggcattatgc    180

agactccctc acgcagtgca gtcatccatc agcaattgac ccagaggcta ttccggttaa    240

attggtccat gatagcttag aggatcttca aatgactcgt tatcattttg caatgaatgg    300

aaaatcattc tcagtgatac tggagcattt tcaagacctt gttcctaagt tgatgttgca    360

tggcaccgtg tttgcccgta tggcacctga tcagaagaca cagttgatag aagcattgca    420

aaatgttgat tattttgttg ggatgtgtgg tgatggcgca aatgattgtg gtgctttgaa    480

gagggcacac ggaggcattt ccttatcgga gctcgaagct tcagtggcat ctccctttac    540

ctctaagact cctagtattt cctgtgtgcc aaaccttatc agggaaggcc gtgctgcttt    600
```

aataacttcc ttctgtgtgt ttaaattcat ggcattgt 638

<210> SEQ ID NO 163
<211> LENGTH: 1002
<212> TYPE: DNA
<213> ORGANISM: Homo sapiens
<220> FEATURE:
<221> NAME/KEY: misc_feature
<222> LOCATION: (1)...(1002)
<223> OTHER INFORMATION: n = A,T,C or G

<400> SEQUENCE: 163
acatataaat atatatataa aatgaacata gttcatgctt tcagataaaa tgagtagatg 60
tatatttaga ttaatttttt tagtcagaac ttcatgaaat ccacaccaaa ggaaaggtaa 120
actgaaattt cccttggaca tatgtgaaat ctttttgtct ttatagtgaa acaaagccag 180
agcatctttg tatattgcaa tatacttgaa aaaaatgaat gtattttttt ctccaaagaa 240
cagcatgttt cactcaatgg tgaaaaggtg gaaacattta tgtaacttta tgtgtatctg 300
tcttgatatc tactgacatt gtctatatga ggaaaatgat tactggtcat gctcctgtga 360 gtttttttggg aaggtagggt catttctccc tgcctgcttt gtgccaacta gcatgttgca 420
tctacatgca ttatgagtct ggttaggcat tactttaaac atacataaag agacagtagg 480
acattgtggc tgagtctacc cagctcaagg taaaggagaa tattgctaat tttttagcaa 540
actagaccag cattattact caaactaaaa atatcacacc tgaaaaattt aatttaggac 600
ctaaaatgtc tagattagct ttctgctttt tttatttgaa taactcattc agttgtgaat 660
gaattcctct ttaattggtg ccacagtcac caaatgacaa ggatttgcca ctttcccccc 720
aaatnggagt gcttgtaatt taggctctct accntnaaat cagtntaagg gaaccgtaat 780
tatgatggat tttttccaag atgaccagct ggggtgaaaa ccatttttct ttggccaatg 840
gcaaaactaa taagctttaa aaacttcccc tttatgggga aagttttaaa actgggaaag 900
gttangaacc naccngtgga aanccntgga agggaaaaaa anaaaggggn ccttggnccg 960
gaacaccctt aaggggaatt cancccattg ggggccnttc nt 1002

<210> SEQ ID NO 164
<211> LENGTH: 572
<212> TYPE: DNA
<213> ORGANISM: Homo sapiens
<220> FEATURE:
<221> NAME/KEY: misc_feature
<222> LOCATION: (1)...(572)
<223> OTHER INFORMATION: n = A,T,C or G

<400> SEQUENCE: 164
acagcatgca tttacaacca gcgctgatct agtctatttt gtcatataaa cttgaataca 60
aaaatccaat ttaaataaga ctagacttac tataatagta aacaaacaaa aacaaaaaac 120
aaaaaaaaaa aacacacaca gtagacttag tttgatactg attaatttta agagtaaact 180
catcctgtcc cctcttaata ctctactgca atttattgat ggctagaata tttactgact 240
taaaaaaggt attaaatact tgtatcatga aattacattc ttattaacaa taagacatac 300
tgtgtaagaa aatagctcat gtgtgaaatg tgtctgaaat gcattttttc cttacaacta 360
tcanaacatc cactcacact aaaatgaaac cactcccaac cccccctgaa aaaatgttna 420
gggaagacng ggtgggctgg gggaggagca agggaaggaa aagatttagc tatactaatt 480
acagcacagt gattaacaat gggtcaggac agaaccaaca gaattnggca aaaaanngcc 540

```
ctttaaacat ggntaccatt aaaaaccaac nn                                572

<210> SEQ ID NO 165
<211> LENGTH: 594
<212> TYPE: DNA
<213> ORGANISM: Homo sapiens
<220> FEATURE:
<221> NAME/KEY: misc_feature
<222> LOCATION: (1)...(594)
<223> OTHER INFORMATION: n = A,T,C or G

<400> SEQUENCE: 165

ggtactggcc tcctggcact ctgctttttc actgactggc tactgaagag caaggcagag    60

ctgggtggca tctcagaact ggcatctgga cctccctaac tgggccccgc tggtcccatt   120

tgctcattag aatttcctct cacatcagtg ggatacagaa ttcagtttct cccttgccag   180

gtccttggga tggttgaccc ctgcctctgc agtagccttt tgtgagtctg ctaaggtagc   240

tctcacacac ctcggctctg ggttgatac ctgagcctac aatagagccc tgaaatcaag    300

agcatagctt gagtgtgtga atatgatgtg tgcacatgct taatgagcgt gcaagtgtgc   360

acacgtttgt ggagaggagg gtgttctggc ctgagaaggt aaagaagagg catgtccagt   420

atgctttgca gggtgtgttt gctcttttcc atgcccatgc aacccagatt ggggtggagc   480

aggaaggagc tcttttctgt tcccaagcct cagaactctt gagctgtggc ttacttgctg   540

gcttcatcag gttcaagctn cgtgggccac actgctgctg ngccaagaag gtgt         594

<210> SEQ ID NO 166
<211> LENGTH: 434
<212> TYPE: DNA
<213> ORGANISM: Homo sapiens

<400> SEQUENCE: 166

gcgtcgcggc cgaggtacta taatggtccc catcttaatt tgaaagcgtt tgagaatctt    60

ttaggacaag cactgacgaa ggcactcgaa gactccagct tcctgaaaag aagtggcagg   120

gacagtggct acggtgacat ctggtgtcct gaacgtggag aatttcttgc tcctccaagg   180

caccataaga gagaagattc ctttgaaagc ttggactctt tgggctcgag gtcattgaca   240

agctgctcct ctgatatcac gttgagaggg gggcgtgaag gttttgaaag tgacacagat   300

tcggaattta catttaagat gcaggattat aataaagatg atatgtcgta tcgaaggatt   360

tcggctgttg agccaaagac tgcgttaccc ttcaatcgtt ttttacccaa caaaagtaga   420

cagccatcct atgt                                                     434

<210> SEQ ID NO 167
<211> LENGTH: 395
<212> TYPE: DNA
<213> ORGANISM: Homo sapiens

<400> SEQUENCE: 167

acaaagttaa gtttagccct tttctagaaa gtgatcttta aaattaaaat tgctcctctt    60

ttaaattcac caaatttatg tgtgggaagg caccaaaatg attttgtaag tgccactgca   120

atattccctt tcaagtgtgg cctaaatttc aatcttaagg atggaatgca tgtctgctcc   180

ttgttctgaa aaatataggc atctactaca ttttaaaaca cagtgaaaca tatacataag   240

cctataaaaa aagatttgtg caatttgaaa gcctgttaat tttttatgta gacataccta   300

cacacgaaag ggttaaattc acagccttac tagttccttg cttccagtat ttcaattggt   360

ctcctcccct cattattatt attactacta gtacc                              395
```

<210> SEQ ID NO 168
<211> LENGTH: 683
<212> TYPE: DNA
<213> ORGANISM: Homo sapiens
<220> FEATURE:
<221> NAME/KEY: misc_feature
<222> LOCATION: (1)...(683)
<223> OTHER INFORMATION: n = A,T,C or G

<400> SEQUENCE: 168

```
ggtacggtat tctaatcaat gcatttgaaa agtcagcaaa agcccacatt aattcctatt     60

acgcttgttt cttggttcaa tctcagcact ttcagcggct cttgtgcggc gattctgtct    120

tggacttatt tctgtgtctt gaagatcgtt tttatgtgat gcttcccagg cttcctcttc    180

ttctaaaaga tctcttatga tgtctgaact ggaactattg catgaatctg attctgatga    240

agaaagaact tcttgaatat caatacagct agaagaatcc tcttctctgt caggttccaa    300

ttcctctggg gagtccagct ttgattgaga aaagtggttt gttactgagg tcatattatc    360

ttcctgtccc atgcatacag aagatagctt ttctgtagat tcatcttctt ttgttattgt    420

tactgttttt tgtgacattc cagcaatttt cttgtatcct tttctagcct gatccaccag    480

aagctgaaat tcactcttat gttttttacg atatttactg tggatttcat ctatttcctt    540

ttctgnttgg tcctttgtaa aaaccattac actttcattg agtttactag cttcaagacg    600

catcctagtc ttctctatat tttcgatttc tcgaactatt tcagcagctg atttaggatg    660

caaagcatcg cattgggcat tgt                                            683
```

<210> SEQ ID NO 169
<211> LENGTH: 408
<212> TYPE: DNA
<213> ORGANISM: Homo sapiens
<220> FEATURE:
<221> NAME/KEY: misc_feature
<222> LOCATION: (1)...(408)
<223> OTHER INFORMATION: n = A,T,C or G

<400> SEQUENCE: 169

```
ggtacctttc tgaccacaat gaaataaacc tagaaatcaa taacaagagg aacttttaaa     60

gcagcacaaa taaatggaaa ttaaataaca tgattctgaa tgaccaatgg gtaatgaaga    120

aattaagaaa caaaatttaa atgtcttaaa atgagtgaaa acagaaacac aacatataaa    180

aatgtatggg atgcagcaag agcagtttta agagggaagt atttagtaat aaacacctac    240

atcaaaaaca agaaagatct ggctgggcaa ggtggctcac acctgtaatc ccagtgcttt    300

gggagcccaa ggcaggagga cgacttgatg ctgggtcaag accagcctgg gccatatata    360

tagcaagacc ttatctctaa aaaaaaaaaa nanaaaaaaa aagcttgt                 408
```

<210> SEQ ID NO 170
<211> LENGTH: 566
<212> TYPE: DNA
<213> ORGANISM: Homo sapiens
<220> FEATURE:
<221> NAME/KEY: misc_feature
<222> LOCATION: (1)...(566)
<223> OTHER INFORMATION: n = A,T,C or G

<400> SEQUENCE: 170

```
ggtaccaaca cagccaaaga ctgtaagaag gtagctgaag tcctctgcca aataggattg     60

aaaagctaaa atctttctct gtttctttct taagtaacaa ctggtctatt caagctcaac    120
```

```
cagagcatat aagagaaaaa actgactaac gagggggtct taaagagctt tgaaggacag    180

tttctagaaa gtagaaagat cactgagtaa attactgcac ctcctctacc ccacaaaaaa    240

aagggtgagg atgaatgtaa aagtgtagag caagctttca gacaacttca agtttgtttt    300

tggcgcttcc gtttgtaagc aatcaagatg gtgagagacg ctatcccaaa gaagaaagtc    360

tgtaggaacc agagtagctg agcccgacca cttgtgatgc ctttatgctt gcacaatact    420

atggcataca aggactctnc cacatgaatc agccaggcaa gccaataccc attgcaaagg    480

anggtgtgat gggngggcac caagtacctg tccgggcggc cctttaaaag gggaaattcc    540

ccacttgggg gcgggnttta gggnac                                          566


<210> SEQ ID NO 171
<211> LENGTH: 562
<212> TYPE: DNA
<213> ORGANISM: Homo sapiens
<220> FEATURE:
<221> NAME/KEY: misc_feature
<222> LOCATION: (1)...(562)
<223> OTHER INFORMATION: n = A,T,C or G

<400> SEQUENCE: 171

ggtacctttg caagcaggtg gccagtaaag ctgaggagaa tctgctcatg gtgctgggga     60

cagacatgag tgatcggaga gctgcagtca tctttgcaga tacacttact cttctgtttg    120

aagggattgc ccgcattgtg gagacccacc agccaatagt ggagacctat tatgggccag    180

ggagactcta taccctgatc aaatatctgc aggtggaatg tgacagacag gtggagaagg    240

tggtagacaa gttcatcaag caaagggact accaccagca gttccggcat gttcagaaca    300

acctgatgag aaattctaca acagaaaaaa tcgaaccaag agaactggac cccatcctga    360

ctgaggtcac cctgatgaat gcccgcagtg agctatactt acgcttcctc aagaagagga    420

ttagctctga ttttgaaggt gggagaattc atggccttag angaagtaaa gccangagcc    480

cccaaatgtc ttggacnaac ttctcaataa ctggcttttg agctgtacct gtcccgggng    540

ggcnctttaa aangnnnaat tn                                              562


<210> SEQ ID NO 172
<211> LENGTH: 617
<212> TYPE: DNA
<213> ORGANISM: Homo sapiens
<220> FEATURE:
<221> NAME/KEY: misc_feature
<222> LOCATION: (1)...(617)
<223> OTHER INFORMATION: n = A,T,C or G

<400> SEQUENCE: 172

acggtagaac tgctattatt catcctatgt gggtaattga ggagtatgct aagattttgc     60

gtagctgggt ttggtttaat ccacctcaac tgcctgctat gatggataag attgagagag    120

tgaggagaag gcttacgttt agtgagggag agatttggta tatgattgag atgggggcta    180

gtttttgtca tgtgagaaga agcaggccgg atgtcagagg ggtgccttgg gtaacctctg    240

ggactcagaa gtgaaagggg gctattccta gttttattgc tatagccatt atgattatta    300

atgatgagta ttgattggta gtattggtta tggttcattg tccggagagt atattgttga    360

agaggatagc tattagaagg attatggatg ccgttgcttg cgtgaggaaa tcttgatggc    420

agcttctgtt ggaacgangg tttatttttt gggtanaact gggattaaaa gctacatggt    480

taattctaag gccactcagg ntaaaaaanc nngcgagctt aaccctttga aaaangnggc    540

ccccntggcc cgaaacnccc ttaaggggca attccancaa cntggnggcc gttattangg    600
```

gatccgactt gggcccn 617

<210> SEQ ID NO 173
<211> LENGTH: 232
<212> TYPE: DNA
<213> ORGANISM: Homo sapiens

<400> SEQUENCE: 173
ggtaccagat gctagctggg cctggtgggt atccacccag acgagatgat cgtggaggga 60
gacagggata tcccagagaa ggaaggaaat accctttgcc accaccctca ggaagataca 120
attggaatta agcttttgta aagctttccc aaatcctttc atcattctac agttttatgc 180
tatttgtgga aagatttctt tctcaagtag tagtttttaa taaaactaca gt 232

<210> SEQ ID NO 174
<211> LENGTH: 987
<212> TYPE: DNA
<213> ORGANISM: Homo sapiens
<220> FEATURE:
<221> NAME/KEY: misc_feature
<222> LOCATION: (1)...(987)
<223> OTHER INFORMATION: n = A,T,C or G

<400> SEQUENCE: 174
gcggccgang tacttcacca tcactgactc catggacttg atcagccgcc gctggatgta 60
tccagtctca gcagtnttga cagccgtgtc aatgagcccc tcacgacccc ccatggngtg 120
gaaaaagaac tcagtgggtg tgaggccggc taggtaggag ttctccacaa agccacggct 180
ctcaggcccg tagtcatcct tgatgaagtg aggcactagt ccggtgcttg aagccaaatg 240
gaatccgctt gccctcgacg ttctgctgtc caacgacagc gatgacctgg gagatgttaa 300
tcttggaacc tttagctccg gacacgacca tanacttgaa gttgttgtat tcanacaggg 360
atttntgagc agaggagcca gtcttgtctc gggcatcgtt aagaatgcgg ttcacctgat 420
tctcaaacgt ctgccgcaga gtgttccctg nggngggctc cagctcattg ttgngngcct 480
tctcgatgac ctctattacg tcctgcttgn ncttcttaat agtgttctga atgtcctggt 540
aagncttaga atcagcantg gngtcccaan gcccatactt tgacctatag acagggaaaa 600
acatcagcaa accccttggg acctctaata nacatggaat ggaattataa ccccagagta 660
taancanggg caccanatnc aaggaggaaa gaaanggatn gtangacagn aagaagttnn 720
agaantcnnn nagacggctt ggaccctgnc cggcnggccg ttcaaanggc caattccann 780
ccactggtgg ccgnnacttn tggaaccgnc ttgganccaa acntggctaa aaanggccnt 840
agcnggttcc cggggcttaaa tggnatncgn tcccaattcc ncccaaatta cggcccgnaa 900
nccttaancn aaaancccgg ggggcctnan gaanggnnta acncccntta aatgggttng 960
ccncaaggcc cnntttcaan tngggan 987

<210> SEQ ID NO 175
<211> LENGTH: 574
<212> TYPE: DNA
<213> ORGANISM: Homo sapiens
<220> FEATURE:
<221> NAME/KEY: misc_feature
<222> LOCATION: (1)...(574)
<223> OTHER INFORMATION: n = A,T,C or G

<400> SEQUENCE: 175
actccccgcc ccctctgaaa gcatgtcaca tcatgtaaat ttgcttctaa catctgcttc 60

-continued

```
aaactgtctc tggactccaa atttggatgg gtcagcctct gcagaaagtt tgtgttgaga    120
tgctggaaga acagcagagc ctcctgcacc ctcagcaagg gaccagctcc caaaggaaag    180
gtccttgtgt gacatttgga gaatcttcct tcatccagac aactctactc gaagcaagac    240
gaaagcagga tgtggcagtt gcagtgagaa aggaaaggaa agatgggcag actctgcttt    300
ctggaaattt cttcacaaag tagagctcat gaactctgtg ctgtcttctg gtaacatatc    360
atcagtgttt gtattcatgg tgtggcacat ggatccatgg cattgggtaa atctggtggt    420
ttttacacat ggtcagaatg tgttcaaata catctcatga tggagacagt ncccaaggta    480
aatggttggt ttcagcattt taaaaaagac tcccttaaca tttatctcag aatcatgagc    540
ccttcttcta gttgacaatg gcaatggtcc cccn                                574
```

<210> SEQ ID NO 176
<211> LENGTH: 570
<212> TYPE: DNA
<213> ORGANISM: Homo sapiens
<220> FEATURE:
<221> NAME/KEY: misc_feature
<222> LOCATION: (1)...(570)
<223> OTHER INFORMATION: n = A,T,C or G

<400> SEQUENCE: 176

```
ggtacagata ttcattcagg agctccagga aactggattt gctctctaga gggcagctca     60
aagggcccat tcactcacaa tccacccaac ggcattcctg gcctccggtc acagcctcag    120
ccacggaagt cctgcagggt ttgtcagtct gtgggggtga gtgccctaac accatgaact    180
gcccactgct cccagaaaga aagaagaact tggaatatga gactccccag gtctcctgac    240
cctcttcctt cttggaatga gacccaggta gtgctcaggg gatttctggt gttggccatg    300
gacaagcaac cagtagtggg ctcactttag ggacgcaaac cacaaagccc acctcaggaa    360
gccaaatttc aactcttgcc ctggggcaaa cttctagcaa ccaggccaga ggcaaatgtc    420
agacaggata agggatgaca tnccatcaat caaagttgna aatgggaagg gacccancca    480
gtttgnaata aaggcnttaa actnggnacc tggcccggcc ggccgtttaa aggcgaattc    540
acacactggn gggccgtcta agggatccca                                     570
```

<210> SEQ ID NO 177
<211> LENGTH: 621
<212> TYPE: DNA
<213> ORGANISM: Homo sapiens
<220> FEATURE:
<221> NAME/KEY: misc_feature
<222> LOCATION: (1)...(621)
<223> OTHER INFORMATION: n = A,T,C or G

<400> SEQUENCE: 177

```
acagaagagg atgaagaaga ggatgaagag gaagaagaag agtcttttat gacatcaaga     60
gaaatgatcc cagaaagaaa aaatcaagaa aaagaatctg atgatgcctt aactgtgaat    120
gaagagactt ctgaggaaaa taatcaaatg gaggaatctg atgtgtctca agctgagaaa    180
gatttgctac attctgaagg tagtgaaaac gaaggccctg taagtagtag ttcttctgac    240
tgccgtgaaa cagaagaatt agtaggatcc aattccagta aaactggaga gattctttca    300
gaatcatcca tggaaaatga tgacgaagcc acagaagtca ccgatgaacc aatgggaaca    360
agactaacta tttagaaaca tttaagatgc cagtatttta catacaggtt ctggntttta    420
acactggatt aaaacttttt ggngtaaata aaaaatggga ccctttaggn ttttacccag    480
gaagaaagcc aaggtttggt aaaaattaaa aggtanccct tggggccggg gaanccacgg    540
```

ctttaagggg ccgaaaattt ccaagnacaa ccttggccng ggcccggnta ncttaaaggg 600
ggaatnccca agaccttnng g 621

<210> SEQ ID NO 178
<211> LENGTH: 403
<212> TYPE: DNA
<213> ORGANISM: Homo sapiens
<220> FEATURE:
<221> NAME/KEY: misc_feature
<222> LOCATION: (1)...(403)
<223> OTHER INFORMATION: n = A,T,C or G

<400> SEQUENCE: 178
actccttcct gagccgctgc aataagcttt ttgctgtgga atatgacgac agctagatac 60
tgtccctgcc acaagagctt ctggttataa atagacaaag actctaattt ctaattgacc 120
tcttttcttt ttcaggttta tacataaatt ttcgtcacct ttataaacag cgcagacggc 180
gctatggaca aaaaangaaa aagatccact aaaaagaaag atttagatgg cttcttgcca 240
gtttgagcct aatctgattc ttacagtttt accttcttga accaatgtaa aagttttttt 300
aatgttaaat gattaaattc tcagtgaggc tatcttcctt ttccccagta acattcctga 360
atttactgnt accttattgt aagtacctcg gtcgtgacca cgc 403

<210> SEQ ID NO 179
<211> LENGTH: 650
<212> TYPE: DNA
<213> ORGANISM: Homo sapiens
<220> FEATURE:
<221> NAME/KEY: misc_feature
<222> LOCATION: (1)...(650)
<223> OTHER INFORMATION: n = A,T,C or G

<400> SEQUENCE: 179
cgaggtacaa gctttttttt tttttttttt tttttttttg agccaaccag ctaaaggatc 60
actgcagcta aatacagata gagaagcaac aaagccaggc aaatacccat cagagacagt 120
gacaagagca gctgggggca cgggggaggc agaaggaaga gaaagaaggg gaggagcctc 180
cagagtccca gccccaaccc cctctgccat tggctacct tgctccccac aaatccctgg 240
ggttgaagtg aggaggacta caggctgggg tgaaaataca caaggacagc ccaacaaaat 300
acaacaagga ctagcatcag tctccccctt actccacccc caagaaaaat acccttattg 360
ngactagtat ttatgaaaat ctgtaagaga ctattctatg tagtggctct aatcccatat 420
cacagcaact gcctgngttg ggaacttttc aaatcagtga tttgcgggaa ccaaccggat 480
tttcagcttn ttacggngca tgcagcttta ccaaaacttg ggtaaagncc agncacattt 540
accttctgct tacatntaaa aagggtgang aaagagggaa gggaaaaagg ggttaagggc 600
taggtaaact tactggtnag cagctanatt caccatggtc ntttttttggg 650

<210> SEQ ID NO 180
<211> LENGTH: 639
<212> TYPE: DNA
<213> ORGANISM: Homo sapiens
<220> FEATURE:
<221> NAME/KEY: misc_feature
<222> LOCATION: (1)...(639)
<223> OTHER INFORMATION: n = A,T,C or G

<400> SEQUENCE: 180
acatacggct gtgcgataca ccagcattga attggttgga gagatgagtg aagtcgttga 60

-continued

```
tcgaaatcct cagttccttg accctgtgtt gggctatttg atgaaaggcc tgtgtgaaaa    120

gcccctggct tctgctgcag ccaaagccat tcataacatt tgctctgtct gccgagatca    180

catggctcag cactttaatg gactcctgga gattgcccgc tccctcgatt ccttcctgtt    240

gtctccagaa gctgctgtgg gcttgctaaa agggacagca cttgtcctag cccgattacc    300

tttggataag attaccgaat gtcttagtga actatgttct gttcaggtta tggcattgaa    360

aaagctgttg tctcaagagc ccagcaatgg catatcctca gatccacagt gttcttagat    420

cgccttgcag tgatatttag gcataccaat cccattgtgg aaaatggaca gactcatccg    480

tgtcagaaag tcatacagga aatatggnca gtttatccga gactctaaat aagcaccgag    540

ctgataatcg gattgtagag cgtgttcaag gtgcctgcgc tttgtggtcc tgngaagcna    600

angactgaac actgtgcagc nctagtccac aatgngaat                           639


<210> SEQ ID NO 181
<211> LENGTH: 644
<212> TYPE: DNA
<213> ORGANISM: Homo sapiens
<220> FEATURE:
<221> NAME/KEY: misc_feature
<222> LOCATION: (1)...(644)
<223> OTHER INFORMATION: n = A,T,C or G

<400> SEQUENCE: 181

acaagagagg ttccaggagg gggtgatagg cagaattttg gtccccatca ccttccctgc     60

ccagtgttat gcctatgaat gtgttacatt atgtggtaaa agggactttg cagatgtaac    120

taaaatttct aaaatagaga tattatcctg gattacctgg gggaacccag tgtaattaca    180

tgaaccctta aaaatggaag aggatgcagg agtcagattc aaaggaaggc ccaaggtgct    240

attgctgact tgaagataga ggggccatgt ggaaatcaag agaaggaagt gaatccttcc    300

agtgagcttg gaagagagca ccttgaggca cagatgagaa gcttggcctt acctgatgcc    360

ttgattttag cctggtgaga ccccgagcat ataaatttgc tgtgctatgc cacacttctc    420

acctacagaa acttagttta aagccactaa gtttgtggta atttggtggc tttaggcccc    480

ttgagggtag agatttatgg cttgtgttac aagtagaaga gcagtggaaa agttgggctt    540

tggtaattct ttcaagggtg aattgtagtt ctgggagtcc tatctanctt gggntcagaa    600

cnttgttggg cangncctgc tggggacttc ctggtttaac cttg                     644


<210> SEQ ID NO 182
<211> LENGTH: 609
<212> TYPE: DNA
<213> ORGANISM: Homo sapiens
<220> FEATURE:
<221> NAME/KEY: misc_feature
<222> LOCATION: (1)...(609)
<223> OTHER INFORMATION: n = A,T,C or G

<400> SEQUENCE: 182

ggtacagaaa agtcagatca aattggatat gtagacattg ctaaggattt tgaactctaa     60

gggcattgat aagctactca agggttttta gtaggggagt gacttgatta gacttattta    120

tttgttgaaa agtctgtgtg gctggtgtgt ggaaaataga atggattgaa aaggaactca    180

agtggagcat caagactcag ttaaggagtt aatctaggtt ggaaataatt gtagcttagg    240

cctggatgct ggcaataggg aaggggatgg attcatgaaa gaatgggata cttgagaaga    300

aatatttctg tgctggagaa gtagattggg gaagttcatg gcataaacat tataatggat    360

gctatgggca tagataacat aaacatgtag agaaagtaaa ggtgacctag ggcagaagcc    420
```

```
ttaggaaccc aaaatttaag agtagactga agagaaccgc tgtagaagtg ggaggaaanc    480

tgctcgtgtg ggtagacaag gagaccnttc aaaaggatca tcattacagt naaaagctgg    540

caactcggcg tcttggtgaa agtncctgcc cgcggccgtc naggcnatca gccatgcgcc    600

gtcttaggn                                                            609


<210> SEQ ID NO 183
<211> LENGTH: 401
<212> TYPE: DNA
<213> ORGANISM: Homo sapiens

<400> SEQUENCE: 183

ggtactcatc ctttgccagc aaagatgcac aactataact atggtggtaa cttacaggaa     60

aatccgagtg gccccagcct catgcatgga cagacctgga cttctcctgc ccaaggacct    120

ggatattcac aaggatacag gggacatatt agcacatcaa ctggcagagg cagaggcaga    180

gggttaccat actgagtatc tgtttttcct caggcacatc atttttatct ggaaagactt    240

ttctagctgc aatttaaggc agcaatccaa gagacttgaa taataataat tcaacaacag    300

ctttattttt atgtggagaa gggtcttgca tacaatagtt taaaaaagac aaaaaaaacc    360

tttgcttaaa ttcatgctgt tctaaaaact agatcgattg t                        401


<210> SEQ ID NO 184
<211> LENGTH: 423
<212> TYPE: DNA
<213> ORGANISM: Homo sapiens

<400> SEQUENCE: 184

ggcggcggat ggaggtcagc ggtggtgctc gctgcggttt ggaatcactt gctaggagtc     60

ttgtctctct gccacccagg acatcatggc agctcacctg gtaaagcgat gcacgtgcct    120

cctgagagaa gctgctcgtc aggcccctgc catggctcca gttggccgac tgagacttgc    180

ctgggtagcc cataagactc tgacttcctc agccacctca cccatttccc acctcccagg    240

ttccttgatg gagccggtgg agaaggaacg agcatctact ccctacatag agaagcaggt    300

ggaccacctc atcaagaagg ccacaaggcc agaggagctc ctggagctac ttggtggcag    360

tcacgacttg gacagcaatc aagcagcaat ggtactaccg gcgctacaaa gtgaagtcgt    420

acc                                                                  423


<210> SEQ ID NO 185
<211> LENGTH: 669
<212> TYPE: DNA
<213> ORGANISM: Homo sapiens
<220> FEATURE:
<221> NAME/KEY: misc_feature
<222> LOCATION: (1)...(669)
<223> OTHER INFORMATION: n = A,T,C or G

<400> SEQUENCE: 185

acccgcagct tgtccccatc ctcatattca tccaggcaaa tggcacagac atcatactgg     60

tctcccttct gatagtcatg tgtaggaatc tgtttcagtt gctctttggt aagtcgattc    120

cgctggagcc gtttccggtg ctggatacaa cgagctatca ttactgctcc catggccaaa    180

accagcagtc ccacaatccc tgtgaaaggg atgaggtaat agcccaaggg gaaggtattg    240

tctggaacca gaagcacccg agcccccttc tcgtagacaa agagggcacg caggtacaaa    300

gagagaaatt ttaaagctgg gtgtcagggg agacatcata tgtcggcagg ttctgtgatg    360
```

```
cccccctaagc ccgtaaaacc agcaagtttt tattagtgat ttccaaaagg gggaagggag    420
tgtatgaaat agggtggtgg gtcacaagag atcacatgct tnacaaggta ataaaaatat    480
cacaaggcaa aatggaggca gggttgagaa cacnggacca cattgaccaa gggcgaaatt    540
aaaaattgtg aagtgaagtt cnggccacgc antgncantg atacatctta tcaggagaca    600
ggntttgaga gcngaccanc agtctggncc aaaattaata agtgggaaat ttcttggcct    660
aataagccg                                                            669
```

```
<210> SEQ ID NO 186
<211> LENGTH: 638
<212> TYPE: DNA
<213> ORGANISM: Homo sapiens
<220> FEATURE:
<221> NAME/KEY: misc_feature
<222> LOCATION: (1)...(638)
<223> OTHER INFORMATION: n = A,T,C or G

<400> SEQUENCE: 186

ggtacatgtg cgttggcatt atggatcgat ttttacaggt tcagccagtt tcccggaaga     60
agcttcaatt agttgggatt actgctctgc tcttggcttc caagtatgag gagatgtttt    120
ctccaaatat tgaagacttt gtttacatca cagacaatgc ttataccagt tcccaaatcc    180
gagaaatgga aactctaatt ttgaaagaat tgaaatttga gttgggtcga cccttgccac    240
tacacttctt aaggcgagca tcaaaagccc ggggaggttg atgttgaaca gcacgcttta    300
gccaagtatt tgatggagct gactctcatc gactatgata tgggtgcatt atcatccttc    360
taaggtagca gcagctgctt cctgctgnct canaaggtct aggacaagga aaatggaact    420
taaagcagca gtattacaca ggatncncag agaatgaagt attggaagca tgcagcacat    480
ggccaaaaat gtggtgaaag aaatgaaaac ttacctaaat catcgccntc aagaataagt    540
ntgcagcngc aactcctgaa natcacttga ccccttagntg accttaaagc ccgnaaanac    600
cttgcctccc ccggaaggaa ggcctaggtt cccgggcc                            638
```

```
<210> SEQ ID NO 187
<211> LENGTH: 628
<212> TYPE: DNA
<213> ORGANISM: Homo sapiens
<220> FEATURE:
<221> NAME/KEY: misc_feature
<222> LOCATION: (1)...(628)
<223> OTHER INFORMATION: n = A,T,C or G

<400> SEQUENCE: 187

ggtacataga aattcattga ggtatataga tactcatctg tctaggcagt tcccaatttt     60
ctgaagaatg ttttacagca aaattttcta ttttctttta ttaaatagtg acacgtcaaa    120
caatgtcaca tccaaaacac tagtttcatc aatttctagc agtaataata gacttgctgt    180
aagtattgtt ttctgatgcc ataccccttgt catacatatt attaaatgac caatattatg    240
tatgaagtag acaaaaaaat ttactcaaac ttcattcaaa tcctaattgt gataattttt    300
gttttatatt taattataaa ccaaaataca tttgcatttt taagctaatt tgtctcaaaa    360
ttttgcttta tatttttgga tcaggttaaa gtcctgggga tcccctgaat gttattgccc    420
tcttggattg gtttttactt ctgagctata ccgtcaaaag acacataagc ttcaaaagtc    480
aagacaaacc tcatttgcca taaaaatcaa gatatagatg tctggtccga aactncttga    540
aaaacatttt aagcatcaat atgactggtt ccatgaactt aagtacttct taatgagtat    600
tctttctgaa gctgaaagaa gattgttt                                       628
```

<210> SEQ ID NO 188
<211> LENGTH: 654
<212> TYPE: DNA
<213> ORGANISM: Homo sapiens
<220> FEATURE:
<221> NAME/KEY: misc_feature
<222> LOCATION: (1)...(654)
<223> OTHER INFORMATION: n = A,T,C or G

<400> SEQUENCE: 188

```
cgaggtacaa ggtggactgt gcatgcctca aagaaaaccc agagtgccct gttctaaaac     60

gtagttctga atccatggaa aatatcaata gtggttatga gaccagacgg aaaaaagaat    120

aaaaagacaa agatatttca aaagaaaaag atacacaaaa tcagaatatt actttggatt    180

gtgaaggaac gaccaacaaa atgaagagcc cagaaactaa acaaagaaag ctttctccac    240

tgagactatc agtatcaaat aatcaggaac cagattttat tgatgatata gaagaaaaaa    300

ctcctattag taatgaagta gaaatggaat cagaggagca gattgcagaa aggaaaagga    360

agatgacaag agaagaaaga aaaatggaag caattttgca aggcttttgc cagacttgaa    420

aagagagaga anagaagaga acaagctttg gaaaggatca gcacagccna aactgaagtt    480

aaaactgaat gtaaagatcc cagattgcag tgatgctgag ttatttanga acnagccata    540

gaagaaaatg ctagcagcca acccctgcca agtaatagac taancgggga aaagttttct    600

cgagtaggac tacttggcag caccgtcgga gaccngactg tcacatggtt anan          654
```

<210> SEQ ID NO 189
<211> LENGTH: 650
<212> TYPE: DNA
<213> ORGANISM: Homo sapiens
<220> FEATURE:
<221> NAME/KEY: misc_feature
<222> LOCATION: (1)...(650)
<223> OTHER INFORMATION: n = A,T,C or G

<400> SEQUENCE: 189

```
ggtactttaa gataattgta ttgatctttt ttcagattcc ttgtattttt aataaagtaa     60

tcttaaataa aactcagata ggttaagtgt tagaaatttt aaacagctta cattgttagc    120

gtaaagttat cttttctttt ttcctaatca gagttcttga ccctttggtt attgagttta    180

aaacttcaat tgaaattcaa tagtatttat tttttaaaaa aatcactaaa ctgtgcctaa    240

agaacataac tgccatatta atgttttggt ttatatcctc tatagtaata gaaaaacatt    300

taatacttgt aatgctgatg tgttaatttg ataccagttg agtagaatgt gatcaatcca    360

gtttacaatc tatcatgagt attattaact aaaatctatg tgcttttcaa taggaatcat    420

tcttctcttg ctgnaacact tgccttaact tttangaaag nggtcatttt taaactgcac    480

tggnaagggt gaaagttang actcttggat ttggngaccg naatctgaag ccgaatantt    540

aaagggagaa aaagaaacca ggtctttttg ccaaaggctg ggaaccntat tcanctttgg    600

gnaagtaatt ggatatncca agggtgggan gacaagtctg aaaatcacng                650
```

<210> SEQ ID NO 190
<211> LENGTH: 699
<212> TYPE: DNA
<213> ORGANISM: Homo sapiens
<220> FEATURE:
<221> NAME/KEY: misc_feature
<222> LOCATION: (1)...(699)
<223> OTHER INFORMATION: n = A,T,C or G

<400> SEQUENCE: 190
accagctcta atctgtggcg tccagttttc tttctttttt tttttttctt ttttaatgtc 60
aaagtgaatg tctgaagttt tgtctttttt tctttgtcct tttccatctg cttcattctg 120
tggggataaa atacttgtgt ttaatcagaa caactggaac gcattgagga agggatggac 180
caaatcaata aggacatgaa agaagcagaa aagaatttga cggacctagg aaaattctgt 240
gggctttgtg tgtgtccctg taacaagtag gtgctgcctg cctgcctgaa gctttgattt 300
cccaaggccc atctccaagc cttgacaaag ctcattcctg ccaagctcat aggcaggatg 360
aagcatgtgg catgcagaaa cagatcaata cccgcttcaa tgcattcatc tcatagcata 420
gaagatatta accaggaagt tactgggtga tgcanttaaa aaatcaaggc catacctaca 480
ggtggaaagc nttcacntgt cagcnaacnt ttaattggat gaaccggttt caaccatttt 540
nccaaaaaag gtgtacctgg ggnnaagggg gtgggcccag tggcccccaa gtgggacctn 600
ttgaaaatga aaagggtggt tcntttccac tgggcccttt gggccttggt aaccaagncc 660
tcttccgcgg gggcaaggca antanccttg gcccggnan 699

<210> SEQ ID NO 191
<211> LENGTH: 378
<212> TYPE: DNA
<213> ORGANISM: Homo sapiens
<220> FEATURE:
<221> NAME/KEY: misc_feature
<222> LOCATION: (1)...(378)
<223> OTHER INFORMATION: n = A,T,C or G

<400> SEQUENCE: 191
acaaagattc cagacagact ttgttttttg gcttataaca atgtgtagat actacacaaa 60
gaatgaggat gtaattttca tttacaagca aaatgtgacc aaaatccctt ttcttcttaa 120
aattgaaaaa tgaaattctt gagaatacta attagtgacg gccaaatctt agactatttt 180
aaattagcca tggttaaaca taggtgagtt aaacattgtg cctttccaaa attaaggttt 240
gcagttagaa acataaacat ttgataaaac ttctcaaaat taattatgag tggcttattc 300
atgtcctttg gattccagac acacactana aaaagtaaac gttaaagagg tgatattttg 360
gaaagcatcc ctagtacc 378

<210> SEQ ID NO 192
<211> LENGTH: 624
<212> TYPE: DNA
<213> ORGANISM: Homo sapiens
<220> FEATURE:
<221> NAME/KEY: misc_feature
<222> LOCATION: (1)...(624)
<223> OTHER INFORMATION: n = A,T,C or G

<400> SEQUENCE: 192
acagtaaaaa gtaaacttcc ctccatccca ggcctgccag catccctgat gccgactttc 60
tgggtgtggc ctagggcccc tcagtgtaat gtaggggttg tgagcacaga ctttggtgcc 120
agtttgctag gttcgaatcc tgactccctc tttgtagctc tgtgcttcaa ttgaaatact 180
gtgcctcagt ttctccttta taaaggcagg gatcatgaga gtgcctgtcc cttgtgagca 240
ctatgaaagt gttagctgtt ctttaccaga ataaatgcat ttctatatct tcccatatgc 300
attttgttaa tttttaaagt atttcaaaca caaagtttga aacagaaaat tgtgtaacat 360
taactatgaa cttaccaccc agaatttaca aatgctgaca ttttgcaata tttatttcgg 420
atctattttt aagggggga accctgcagt tactgcttaa tcctctttcc accccaacct 480

```
tttattttta cacaaggagc catagtggtc atacttaagc tatttttttc agtaactnaa    540

tatattttgg aaganctccc tcctaggnca tanaagcttt gnccctttttt tttacagtgg   600

taaacctttn ggactaaagg gcng                                           624


<210> SEQ ID NO 193
<211> LENGTH: 348
<212> TYPE: DNA
<213> ORGANISM: Homo sapiens

<400> SEQUENCE: 193

actgctactt ctataaacgg acagccgtaa gactaggcga tcctcacttc taccaggact     60

ctttgtggct gcgcaaggag ttcatgcaag ttcgaaggtg acctcttgtc acactgatgg    120

atacttttcc ttcctgatag aagccacatt tgctgctttg cagggagagt tggccctatg    180

catgggcaaa cagctggact ttccaaggaa ggttcagact agctgtgttc agcattcaag    240

aaggaagatc ctccctcttg cacaattaga gtgtccccat cggtctccag tgcggcatcc    300

cttccttgcc ttctacctct gttccacccc ctttccttcc tttccacc                 348


<210> SEQ ID NO 194
<211> LENGTH: 627
<212> TYPE: DNA
<213> ORGANISM: Homo sapiens
<220> FEATURE:
<221> NAME/KEY: misc_feature
<222> LOCATION: (1)...(627)
<223> OTHER INFORMATION: n = A,T,C or G

<400> SEQUENCE: 194

ggtaccttct cagccagctg cagcaaagcc aaatggcaga gaagcagtta gaggaatcag     60

tcagtgaaaa ggaacagcag ctgctgagca cactgaagtg tcaggatgaa gaacttgaga    120

aaatgcgaga agtgtgtgag caaaatcagc agcttctccg agagaatgaa atcatcaagc    180

agaaactgac cctcctccag gtagccagca gacagaaaca tcttcctaag gatacccttc    240

tatctccaga ctcttctttt gaatatgtcc cacctaagcc aaaaccttct cgtgttaaag    300

aaaagttcct ggagcaaagc atggacatcg aggatctaaa atattgttca gagcattctg    360

tgaatgagca tgaggatggt gatggtgatg atgatgaggg ggatgacgag gaatggaagc    420

caacaaaatt agttaaggtg tccaggaaga acatccaagg gtgttcctgc aagggctggt    480

gtggaaacaa gcatgtgggt gcaggaagcc aaaagtcaga ctgtggtgtt ggctggtgct    540

tgtganccc ccaagtgtng gacccgccgc caaggcaagg aaaccttggg cccttttttaa    600

cgggcccngg aattcccaag gttcntt                                        627


<210> SEQ ID NO 195
<211> LENGTH: 405
<212> TYPE: DNA
<213> ORGANISM: Homo sapiens

<400> SEQUENCE: 195

ggtacaattc cacttatcca tactattcct ttataaaagg cagatttcag gtaagcttct     60

aaatgcatgc gtaatgtaga ggctaatatt ttctggcagt ccttggttcc tgaaatttga    120

acttcatatg tgttttaaac ttttgtcaaa atagtcatga aagatatgtt atttttgcat    180

aatgaggtaa tatatcaggg gcgggcactc ataagacagt ataaatccac ttgtctaaac    240

ttgcatgagg ctgtgtgcat tgtaaaatgc cataaagagt tttgggtcag tgaatatttt    300
```

-continued

```
gctgaaggaa taacacttac atttaactga gcacttttct gtaataaata ccaaagtagg    360

tttttgtagc tgtaaactgt gtacctgccc gggccggccg ctcga                   405
```

<210> SEQ ID NO 196
<211> LENGTH: 658
<212> TYPE: DNA
<213> ORGANISM: Homo sapiens
<220> FEATURE:
<221> NAME/KEY: misc_feature
<222> LOCATION: (1)...(658)
<223> OTHER INFORMATION: n = A,T,C or G

<400> SEQUENCE: 196

```
ggtgaaagga gttaaaacgc ccagtggtca ttaagtgaaa catcttttat caacctgcaa     60

aagctgcagc gttctctgcc aggtcaaatg ggcatgttta gaaaataaga gaagatggct    120

gagtatagct aatgaataaa tggttgtttc tttagaaaat taaacacaca cagagtgtaa    180

gaggagagga tacggccctc cctgaaggat aaagtccacc tggacggtgc cctgccctcg    240

cttctcacat taactgccca ggaatgtcat gctgattggt tcccggaagg gtgtttggca    300

aggggcagtg tatggagcta cgtgtagaag gagagaaatt tgtgtgtggc ttttgtaaat    360

tttgaccgat tgcagcaatt aaataagttg attactgngt tgatttaaat acttatgaaa    420

gctttcaaga cnaaaaataa acctttcacg ttacccccaa annaaaanan tnnnnnttta    480

nataaaaaaa acttggancg gnatgnggtt tcttggaaaa agtttggatg ccatttgcna    540

aattcttcnt tttnggtttn aaaattgaac ncaggnattn gggggganccc nttttggaaa    600

aancccataa gcttggtttn cttgnnnaaa ctttgnaant tngccccngg nttaattn      658
```

<210> SEQ ID NO 197
<211> LENGTH: 615
<212> TYPE: DNA
<213> ORGANISM: Homo sapiens
<220> FEATURE:
<221> NAME/KEY: misc_feature
<222> LOCATION: (1)...(615)
<223> OTHER INFORMATION: n = A,T,C or G

<400> SEQUENCE: 197

```
ggtacagaga aagaaataaa agatactgag aaagaggtgg atgacctaac agcagagctg     60

aaaagtcttg aggacaaagc agcagaggtc gtaaagaata caaatgctgc agaggaatcc    120

ttaccagaga tccagaaaga acatcgcaat ctgcttcaag aattaaaagt tattcaagaa    180

aatgaacatg ctcttcaaaa agatgcactt agtattaagt tgaaacttga acaaatagat    240

ggtcacattg ctgaacataa ttctaaaata aaatattggc acaaagagat ttcaaaaata    300

tcactgcatc ctatagaaga taatcctatt gaagagattt cggttctaag cccagaggat    360

cttgaagcga tcaagaatcc agattctata caaatcaaat gcacttttgg aagccnggtg    420

tcatgaaatg aaacccaacc ttcgggccat cgcagagtnt aaaaaggaag gaagaattgn    480

atttgcaccg gtagcagaat tggccaaaat acttntgaag ggaccggttt agaccaaaaa    540

anaannntan aaaaaaaann nttnacttgc ccggnggccc ttnaangggg attcncccat    600

gggggccttt tangg                                                     615
```

<210> SEQ ID NO 198
<211> LENGTH: 557
<212> TYPE: DNA
<213> ORGANISM: Homo sapiens
<220> FEATURE:
<221> NAME/KEY: misc_feature
<222> LOCATION: (1)...(557)
<223> OTHER INFORMATION: n = A,T,C or G

<400> SEQUENCE: 198

```
gggacctgca gttggtattg atcttggcac cacctactct tgtgtgggtg ttttccagca     60

cggaaaagtc gagataattg ccaatgatca gggaaaccga accactccaa gctatgtcgc    120

ctttacggac actgaacggt tgatcggtga tgccgcaaag aatcaagttg caatgaaccc    180

caccaacaca gtttttgatg ccaaacgtct gattggacgc agatttgatg atgctgttgt    240

ccagtctgat atgaaacatt ggccctttat ggtggtgaat gatgctggca ggcccaaggt    300

ccaagtagaa tacaagggag agaccaaaag cttctatcca gaggaggtgt cttctatggt    360

tctgacaaag atgaaggaaa ttgcagaagc ctaccttggg aagactgtta ccaatgctgt    420

ggtcacagtg ccagcttact ttaatgactc taacgtcagg ctaccaaaga tgctggaact    480

attgctggct caatgtacct nggccgcgaa cacgctaagg gcgaattnca cacacttggn    540

ggncgtctan tggatnc                                                   557
```

<210> SEQ ID NO 199
<211> LENGTH: 498
<212> TYPE: DNA
<213> ORGANISM: Homo sapiens

<400> SEQUENCE: 199

```
acaatgatgc ttctcacagc ttcaaagaca tgtctgaggc atcctaactg cgaatcagcc     60

cataaaaaca aagaaggagt atttgaccgt atgaaagtgg cattggataa ggtcattgaa    120

attgtgactg actgtaaacc gaatggagag actgacattt catctatcag tatttttact    180

ggaattaagg aattcaagat gaatattgaa gctcttcggg agaatcctta ttttcagtcc    240

aaagagaacc tttctgtgac attggaagtc atcttggagc gtatggagga ctttactgat    300

tctgcctaca ccagccatga gcacagagaa cgcatcttgg aactgtcaac tcaggcgaga    360

atggaactgc agcagttaat ttctgtgtgg attcaagctc aaagcaagaa aacaaaaagc    420

atcgctgaag aactggaact cagtattttg aaaatcagtc acagtcttaa tgaacttaag    480

aaagaacttc atagtacc                                                  498
```

<210> SEQ ID NO 200
<211> LENGTH: 615
<212> TYPE: DNA
<213> ORGANISM: Homo sapiens
<220> FEATURE:
<221> NAME/KEY: misc_feature
<222> LOCATION: (1)...(615)
<223> OTHER INFORMATION: n = A,T,C or G

<400> SEQUENCE: 200

```
ggtaccctct cttccagcac ccaggccagt attgagatcg attctctcta tgaaggaatc     60

gacttctata cctccattac ccgtgcccga tttgaagaac tgaatgctga cctgttccgt    120

ggcaccctgg acccagtaga gaaagccctt cgagatgcca aactagacaa gtcacagatt    180

catgatattg tcctggttgg tggttctact cgtatcccca agattcagaa gcttctccaa    240

gacttcttca atggaaaaga actgaataag agcatcaacc ctgatgaagc tgttgcttat    300

ggtgcagctg tccaggcagc catcttgtct ggagacaagt ctgagaatgt tcaagaattt    360

gctgctcttt gggatgtcac tcctcttccc ttggtattga aactgctggt ggagtcatga    420

ctgncctcat caagccgtaa taccaccatt cctaccaagc agaccacaga ccttcactac    480
```

-continued

```
ctatcttgac aaccagtctg gtggncttat tcanggttat gaagcgaccn gccttgccaa    540

ggataccacc tgnttggcaa gttttaactn caggcttcct tctggacccc aggngttccc    600

aaattgaagt ccttt                                                      615


<210> SEQ ID NO 201
<211> LENGTH: 256
<212> TYPE: DNA
<213> ORGANISM: Homo sapiens

<400> SEQUENCE: 201

actgcacttt ataaaagcat ggataatatt aaaggatcac aaaaggcagc attagcattc     60

tctatccagg tattattaaa tctttttatc ccatgccccc ctcaaatata ggagaattat    120

tatctgataa gcctgaaacg actttttta ataccataac ctaaaaagac acttcttaca    180

ggtgtatgca actttggtca gcagaaacac aatacgagcc tctggcctag ctaaggcact    240

ctattctgaa agtacc                                                     256


<210> SEQ ID NO 202
<211> LENGTH: 584
<212> TYPE: DNA
<213> ORGANISM: Homo sapiens
<220> FEATURE:
<221> NAME/KEY: misc_feature
<222> LOCATION: (1)...(584)
<223> OTHER INFORMATION: n = A,T,C or G

<400> SEQUENCE: 202

acttttcaat ctgatccatt atcttctcga ctctttctgg aggcactttc ccacgagttt     60

gcatcctttc ggccacattg tggtagaaat cctgagcaca ctctgactgt tcttcaatgc    120

ttagatccct tttgtaatgc attccttcca aaaacagctt ggtctgttta tagatttctt    180

ggcctgtctt gtggaaggtc ttgagaaatt ctatgaactc cttagacact ctatccgttt    240

caatgctggt ttgccggttt atggaaggac tgggagcttt tgcttcctga atttccttct    300

ttgatccgac cctggaagaa tgcactgaag aaattcttca ctgggggaac cctgccggtc    360

ttcttgntgg gtttcttttc ttcaaacttg gaaaatgtna aggattgggc ccctgggtgg    420

gttnactggt ngcaaaggct ttttttcttc cctgaggcnt tccgcagtcc annctctgaa    480

ttgntttgcc tggcttgngg acctggccga cacctanggg aaatccacca ctgggggccg    540

tctaaggganc cncntgggcc aacttggggn anntnggtan nntt                     584


<210> SEQ ID NO 203
<211> LENGTH: 608
<212> TYPE: DNA
<213> ORGANISM: Homo sapiens
<220> FEATURE:
<221> NAME/KEY: misc_feature
<222> LOCATION: (1)...(608)
<223> OTHER INFORMATION: n = A,T,C or G

<400> SEQUENCE: 203

ggtactctta tacacacctg ttttctccaa tgttctcctt tagtatggct ggtaattgtt     60

ttggtgattg ccaccccctc gagatgcctt gccataagtg ctctgttggc ctattttgaa    120

aacacagaat tctcatttag ttttctacaa aactttcttt acaaacacaa actattaaat    180

ctacaaatct ttgcatgcta aataaaaagt attaagatat tttagcaccc attagatgct    240

actcataaat catacatcct agttcattta taaccaccag tctatgttag tataatcatc    300

ctatgattgt aacatgcctn aaacacttaa ctccgaacac tttaatggaa agcccataca    360
```

cacaatttca gaacaggatt gtatgttaac aatgaatttt aataccactg ctttataaaa 420
ttaagttaaa tattcttacc actgnaatct gcatatcctg nccatatcat aggtcccata 480
ggtataccca ggataaacat attcggcata gcactatggt ttgaacacct ggcccggccg 540
gccggtncaa aaggcgaatt cancnactgg nggccggtnc natggatcca ncntcgnacc 600
aactttgg 608

<210> SEQ ID NO 204
<211> LENGTH: 621
<212> TYPE: DNA
<213> ORGANISM: Homo sapiens
<220> FEATURE:
<221> NAME/KEY: misc_feature
<222> LOCATION: (1)...(621)
<223> OTHER INFORMATION: n = A,T,C or G

<400> SEQUENCE: 204
ggtacctgaa gatcttgatt tgctacacga gctttctcta gggcattata gtaagaaact 60
gcttctttct ctcgctcctc tttttcctct ttaagccggt ctacctggcg cattaggtta 120
gtaataagaa gttctagctg ttcttgtctg tattgtagtt cattcacttc ttctttgagg 180
gtggtcttca tactctccat ttctgtcagc tcaatttgaa gagccagcat ctctgaagac 240
atgctttcct gcacacgttc agacattacg cgcagttcct ctgatttaca agagaggagt 300
tccttctgat gatctacttg gtgcttcagc tgcttttcac taagcctggc ttcatctaat 360
tccactttca gtttttctat cttaagtttt taagttcatt cacttcctgc catggcttct 420
gcttagttgt cttccnattt cttcaggtgc attttttggt ggtggttaat agcttcacat 480
tcgcaagctc aaactttcta acattcgact cttgagttca acttctcttt tgaangggat 540
attttcntgg tcataactct tangcatngg gcataattct taccacatta tccaatggat 600
ccggaattca ntttgccctn t 621

<210> SEQ ID NO 205
<211> LENGTH: 607
<212> TYPE: DNA
<213> ORGANISM: Homo sapiens
<220> FEATURE:
<221> NAME/KEY: misc_feature
<222> LOCATION: (1)...(607)
<223> OTHER INFORMATION: n = A,T,C or G

<400> SEQUENCE: 205
ggtaccacct atcataggta ttaccacaca atttcatgca tggtggcata ttttaactgg 60
ccttggttcc tatcttcaca tccttttcag tttgtataca agaacacttt acctgagata 120
taggccaaaa gtgaagtttc tctttggaat ctggccagtg atcctgtttg agcctctcag 180
gaagcattga tgaatcattc caccaagaaa acaaacaagc acctaccata gacctggcag 240
aataaataag gaaatcctta aagatctaca agttcaaata tgtcatgacc atcacagcag 300
aggagtgact ttctgactaa tgctgccacc cacacagaga ataaggagta gggcctgctg 360
ggtgtttagc tcatggcttt atcttatttg ccccctcctc tttcacgctc cagtttataa 420
aagaaacaga gatgatgtgt gtgtatgcct caaaatgcag aaacaggtgg gcttttctta 480
acanggtnac agtttgtgct gggtataaga aaataaccct ctttcttttn gccaagggtg 540
catgtgaatt atcccttctt aanattggtt aaataagcan tnncttanag cccccaaanc 600
nctntnn 607

<210> SEQ ID NO 206
<211> LENGTH: 572
<212> TYPE: DNA
<213> ORGANISM: Homo sapiens
<220> FEATURE:
<221> NAME/KEY: misc_feature
<222> LOCATION: (1)...(572)
<223> OTHER INFORMATION: n = A,T,C or G

<400> SEQUENCE: 206

```
acgcgtgacg tcactcacat agcaggaaga ctcacaacct ccatccagaa gcaccatttc     60

cccatccttg atgagttgat tatttttcac atagtgcaaa gtgtttgacc gattaccacc    120

agccaccaca ggtggatagg ctaaaatgtc tgcgccacga gcccggcatt caaattcaaa    180

cttagcataa agaaaggctt cttccacagg ggctttactg gtgaacatgg tttctatgaa    240

agcctgtgat gtcagcttcc cagcaatctg cattcgttca atttctgcag gagacttgat    300

cagccggagg cgctgtatca gctgctgaac accccgaacc ttgttcttgc tcttggcttt    360

ggcctcagtc aggggctgca tatagtcaga gtgaagctgt gcatgtgagg gccttatcca    420

ggtcatacca aaccatgttc gtctcagctt tcattttttg gtagaagatg ttgaaattct    480

tctagcgtat aggcttcgtc tactccagtt agagctattg gttccatcag tgccagantc    540

gnggaccatt ccaaaaggtt tnnactnggg ag                                  572
```

<210> SEQ ID NO 207
<211> LENGTH: 616
<212> TYPE: DNA
<213> ORGANISM: Homo sapiens
<220> FEATURE:
<221> NAME/KEY: misc_feature
<222> LOCATION: (1)...(616)
<223> OTHER INFORMATION: n = A,T,C or G

<400> SEQUENCE: 207

```
ggtacctgtc ccattcctaa aaggatttgt gggtaatgct ggcacttggt ggccaggaga     60

atcttctgac cccactctcc ctcctcttca gtcctgaaga ccccaagaac ccagttagga    120

tcccctggcc agaggtctct gtgactgcct ctggactcag cacgtgcagc agcttgggag    180

gatttgagcc agtctcaaaa acttttagcc ccagaatgag accagtgacc ccaagcagga    240

gggctgggat ctggagggaa gagagggggt ccaaggggac cctgtggctg aggccatgga    300

gaaccagtgc cagggcccaa gagacccatt tttccagtta tcagaggtga ctgacatctt    360

ctgccactgc cttgagttca gaaatttaaa aaagcttgca gcaagaaaat gccagtgtgc    420

aactgggtga ctaaagacca aagaaaaaca gttaaaaggg acagcttact tgctctctgt    480

ctcangttta acttctcacc tgaaatctct nataccctaa ttaacacaac caaagtctct    540

ttcatagata ggctactttt aagtttnact gcttctgtgg tgggctttgg gggctttgga    600

agtgggaatt ttttgg                                                    616
```

<210> SEQ ID NO 208
<211> LENGTH: 614
<212> TYPE: DNA
<213> ORGANISM: Homo sapiens
<220> FEATURE:
<221> NAME/KEY: misc_feature
<222> LOCATION: (1)...(614)
<223> OTHER INFORMATION: n = A,T,C or G

<400> SEQUENCE: 208

```
acacaacgtc atgaggttat tcgaaccaca gcgtcttcag aactttcaga gaaaccagct     60
```

```
gagtctgtca cttctaaaaa gacaggaccc cttagtgccc agccctctgt tgaaaaagag    120

aacttggcaa tagaaagtca atcgaaaact cagaaaaaag ggaagatgtc tcatgacaaa    180

aggaagaaat caagaagtaa agccataggc tcagatactt ctgacattgt gcacatttgg    240

tgtccagaag gaatgaaaac cagtgacatc aaggagttga atattgtttt gcctgaattt    300

gagaaaaccc acctagagca tcaacaaaga atagaatcta aagtttgtaa ggcagccatc    360

gccacatttt atgttaatgt taaagaacaa ttcatcaaaa tgcttaaaga aagccagatg    420

ttgacaaatc tgaaaaggaa gaatgctaag atgatttcag atatcgaaaa gaaaaggcag    480

cgtatgattg aagtccagga tgaactgctt cggntagagc cacagctgaa acaactncca    540

acaaaatatg atgaacttaa agagagaaag tctttccttt ggaaagcaca tatttcttat    600

ctaatttaaa canc                                                      614
```

```
<210> SEQ ID NO 209
<211> LENGTH: 610
<212> TYPE: DNA
<213> ORGANISM: Homo sapiens
<220> FEATURE:
<221> NAME/KEY: misc_feature
<222> LOCATION: (1)...(610)
<223> OTHER INFORMATION: n = A,T,C or G

<400> SEQUENCE: 209

acactgtttt gatggaagag gacattgtgg acacgaagta actggagatg gccttcagaa     60

tcagctgagc tgctgtctgc tttggaaaac cgttcctgcc gctgccgatg gatggaaatg    120

caatggattt cagcttctta tcatcagcca gggccaagca gtttttcact gtcttttcca    180

gaagttcttc acacttgtct gcaccccaaa ctggactatt acagtggatc acaaacttgg    240

caggcaggcc atggcctgcg ctgacagcag ctccagctac ttccaagggc ccgttctttt    300

tccggagttc caggacagct tccacaaact ccttgccacc tttcttctcc agcgtgtttc    360

ctaggtcatc tttaaggtca atgtcagcat tggtaggatt gattatggcc tncacctcaa    420

aagcccggct aaatactgat ttcactgnga ataanggtca acttttgggc canggaaaag    480

ctctttggtg gaaaaggact gtgaaaaccn tnggcaagng ggccctcggg tgggctttnn    540

gggcttgntg gcnttaaggg antnancngn gttttnggaa ttccggnccc tttttggccc    600

cnggttttta                                                           610
```

```
<210> SEQ ID NO 210
<211> LENGTH: 589
<212> TYPE: DNA
<213> ORGANISM: Homo sapiens
<220> FEATURE:
<221> NAME/KEY: misc_feature
<222> LOCATION: (1)...(589)
<223> OTHER INFORMATION: n = A,T,C or G

<400> SEQUENCE: 210

ggtacccagc tctaattact ggccgtagca gcatattgct taagaatttt gtagaactta     60

tttctcatca gcagctgtcc aaaggactga taaatagaga cagatcccag tcctggatac    120

tttctgtaaa tcctaatcgg agactcactt ctcagcaatg gaggctgaaa gtcttagtga    180

gactcagtaa attccttcag gccttggcag atggatccag taggttgaga gaaagtgaag    240

gacttcagga acagaaagaa aatccccatg ccactagcaa ctccattttt atcaactgga    300

aggaacatgc caacgaccag caacacatcc aggtttatga aaatggggggt tcacagccaa    360
```

```
atgtcagttc acagttcagg ctacggtatc tggttggagg actgagtggt gtggatgaag    420

gcctgncatc tactgaaacc tgaaaggatt attgngataa taattccttg ntnaatgaat    480

gctggttgaa ctgtacctgg ccggccggcc cttaaaggnc aattcngcca cttgggggcc    540

gactaaggga nccncttggg ccancntggg gnaacanggc aannttgtn                589


<210> SEQ ID NO 211
<211> LENGTH: 590
<212> TYPE: DNA
<213> ORGANISM: Homo sapiens
<220> FEATURE:
<221> NAME/KEY: misc_feature
<222> LOCATION: (1)...(590)
<223> OTHER INFORMATION: n = A,T,C or G

<400> SEQUENCE: 211

acgaactgta gcatcagcta caactgccat tgaaattcgt aggcaatcca gtagttatga     60

tgattcctgg aaaataacag atgaacaaag acagtattat gtaaatcagt ttaaaaccat    120

tcagcctgat ctaaacggat ttattccagg atctgcagct aaagagtttt ttacaaaatc    180

aaaacttcct attcttgaac tttctcatat ttgggaactc tcagactttg ataaagatgg    240

tgcattgaca ctggatgagt tttgtgctgc ttttcatctg gtggttgcta ggaagaatgg    300

ctatgattta ccagaaaaac ttcctgaaag cttaatgccc aaactgattg atttggaaga    360

ttcagcagat gttggggatc agccaggtga ggtaggttat tcaggctctt ctgctgaact    420

cctncaagca agtcccatcg atgccattac ttaacccgac ttggnctgac tgaatcaaac    480

cntgaccatg ggaaacatta nngacgcttt ttaagctaca aantttggnc ccattggttt    540

taaatttggc ccnattgnac cggaaccgga ntgggnattc cgnnccattn                590


<210> SEQ ID NO 212
<211> LENGTH: 614
<212> TYPE: DNA
<213> ORGANISM: Homo sapiens
<220> FEATURE:
<221> NAME/KEY: misc_feature
<222> LOCATION: (1)...(614)
<223> OTHER INFORMATION: n = A,T,C or G

<400> SEQUENCE: 212

ggtacattcc attactaaat gccacataac tgtttggata acataagaag agtgggtcat     60

tatatgatac caattagaag atattaggga tggtggaggc agtaatttct gggataagaa    120

ctataattta cagaataacc agacatcatc tgatctggtg aaacctgtgc attcccacaa    180

ttaggctttt tcacactttc tctctttaaa tgtgcaacac cttccccatc ccctctttac    240

ttgtagcaag ttgattttgc ttcttatatc ccgagaaagc aactaccacc aaatctacca    300

gtcaactcat ctatatttga acttaaagat ctttatgtta gaatggaatc tatccatgtt    360

ccagcttagg cgaagccctt ctgaagatat ccattccttc cttcctcatc aaattttcct    420

tcttgactag gattaaaaaa attcaaccag taggcataat ccgaaccttt ggnctcataa    480

tgaaaaggat agttaataag gctcatcaat tgggccgnaa ttttgntttg ggtcaagngt    540

tggccaaagc nncnnaaang gccccanttt tgggtaaaan tttttnaggg gttaaaancc    600

anggggntnc annn                                                      614


<210> SEQ ID NO 213
<211> LENGTH: 624
<212> TYPE: DNA
<213> ORGANISM: Homo sapiens
```

<220> FEATURE:
<221> NAME/KEY: misc_feature
<222> LOCATION: (1)...(624)
<223> OTHER INFORMATION: n = A,T,C or G

<400> SEQUENCE: 213

```
ggtacctctc ttgtcatcaa attttgccca gttatttaat gttggattcc tcaaggctca     60
gtcagcacct tttaagccac tctaaactcc cactaatgga taagctcatt tacttccaag    120
gcttcaatgg tcacaataca acactgctgg ctctccaact tatttttcta taaaataaaa    180
aataataaag gaacaacgta tttttctatt caagactttt tatctgagct tcagatacat    240
atatccaatt gcttacttga catctccact tagaggccag aggcatttaa actcaatacg    300
tcttaattca atctcatgat cttccctctg aaatctaatc tcctactctt ccctatctta    360
atgaaagaca acaccatccg tccctttaca ttaagtgctt cagcttatcc ctacatctat    420
ctcatcacta aagaacaggt attttcaccc ttttgagtat cattcaaatg cnttctactt    480
cttttccatt cntactggta cccccctang ggnaagntat taactttttc ctacctacng    540
ncccttttgn ancccttcca tcaantnttc cnaattgnga nggtnaattt ttnnaacccc    600
aanntggnca tacnnngtgg gnng                                           624
```

<210> SEQ ID NO 214
<211> LENGTH: 612
<212> TYPE: DNA
<213> ORGANISM: Homo sapiens
<220> FEATURE:
<221> NAME/KEY: misc_feature
<222> LOCATION: (1)...(612)
<223> OTHER INFORMATION: n = A,T,C or G

<400> SEQUENCE: 214

```
ggtacaagtc tgttaatacc ctatgtggtt tcattaggat aactttttac ctatccttga     60
ggtcatccat attcttacag gccttccagt caataatgga agagctcact ctatacaaaa    120
ccaatatgca aggcatgtgt ttgtccaagc aattggatgt gtgcagtagc caatttcatt    180
tactgcatta ctctttggcc tgggaaccct gtggtctgca ctacatgtga atggccttcc    240
acttcagtct taggcagatt tgacctttta ggggcagcaa tgctgaagga cacagcaatt    300
taaattataa tgtgtcaggc tgtgttttca cttcaaacat gtatgagtag tcagctgtaa    360
ttagagaaat gatgacttcc taagagttca gccacgcata attctagatt tcaagagcat    420
ctaagacttg tggattacct catggcatga gagtttcaga ctcagccntn tgagccagtc    480
nagggaaagt ggagtctgca acgcaaatga aaacctggct ttggggccaa nggacttggc    540
tttaaatggg ccccccttngg cctgggntttt cctcttttgg cnaaantttt ngtnnccaan    600
gaaagtaatn ag                                                        612
```

<210> SEQ ID NO 215
<211> LENGTH: 618
<212> TYPE: DNA
<213> ORGANISM: Homo sapiens
<220> FEATURE:
<221> NAME/KEY: misc_feature
<222> LOCATION: (1)...(618)
<223> OTHER INFORMATION: n = A,T,C or G

<400> SEQUENCE: 215

```
ggtactcggg aggctgatgc agcagaattg cttgaaccca agaggcggag gttgcagtga     60
gctgagaacg tgccattgca ctccagcctg ggcaagagag cgagactcca tctcaaaaaa    120
```

-continued

```
aaggtgagaa agataggtgt gaacatgagg tggcaggtgt gaagatagga aaggcaggct    180

caccccctgat gacatgcagt tagagagacg ggggcttccc tttcactttg gagagtaaag   240

agaaggctct gaggtatcaa cagcctgggc tgttgggaaa aggacaaaga atctgtgttt    300

cctgaacgcc aagaggaagt ctctttggtt gctgtgggct aactggtctc ctccagttcc    360

aagaggtcat ccacatattc cacaacttct ccctcatcat catccattat attttcctta    420

nccaaagtca tacaagcttc ntctggagtg gtggncacat ttaagaactg aactgnttta    480

agnctgggct ggaantgctc attcnanagg ccccantggn cctnngggan ctngccngcc    540

ggcccnttaa aggcgaattc cancanntgg gggccggttt tangggancc aacttgggnc    600

caacttggng aaatatgg                                                  618
```

<210> SEQ ID NO 216
<211> LENGTH: 595
<212> TYPE: DNA
<213> ORGANISM: Homo sapiens
<220> FEATURE:
<221> NAME/KEY: misc_feature
<222> LOCATION: (1)...(595)
<223> OTHER INFORMATION: n = A,T,C or G

<400> SEQUENCE: 216

```
ggtactccca ttcagggtga cgaagtgggc agaactggga gccatcttgc ccagcccctt     60

ggtgctatgt ttaccttgaa gcaatccttc ggccttagga ttggcctcta gtagttcatt    120

acactgacct agagctacct ctgataagag cagcagtcct gtattcttta ggcgagaggc    180

aaagcagtaa ttggcactct tggaagacat gtcagcaaag tagattcctt tcccaaacat    240

gtaacctgtg atgggagctt caggtggggc aattcgaagc ccatggctca agattcccac    300

ccagttactc atcctggaac catgccatag aagcatcctg ttatgaaggt cctctctgaa    360

ggcttctttc tcaccatcct tctcacttca aacaaatcca gcaaggtcat ggtataagtc    420

gctgtgtgtg ggaancatgg gtagaatgga aggtacctgg cccggccggc cnttcaaaag    480

ggccaaattc cagcacaatt ggnnggccgt tactaaggga tnccaacctt gggncccaaa    540

cnttggngga atcatgggcc naaactngtt ccctggnggn aaattgnaan cccnn         595
```

<210> SEQ ID NO 217
<211> LENGTH: 610
<212> TYPE: DNA
<213> ORGANISM: Homo sapiens
<220> FEATURE:
<221> NAME/KEY: misc_feature
<222> LOCATION: (1)...(610)
<223> OTHER INFORMATION: n = A,T,C or G

<400> SEQUENCE: 217

```
actgaaaact ttttttaaaa aaggtgatga tgaagtgcat tctgtagcag cagcgcagct     60

atgctttaaa ccacacaaaa ggctgtgtcc aggtgcagcc tccttcaccc ttcctgccca    120

cggtgaggat tgaataacca ggacttgggg atattgtttg ttgtcagggt tattctgtgt    180

ggtaaggaat atttgtttca catttataca ttttcttttt ccactcacgt aagtttctat    240

cttgagagca tagtccaaag tgcaaaactt ggtgtttaca aggaaaattg tcttccagaa    300

ctccactgtc atcactttca ccaaagtgga agtttgcatg aatatgctca gaatctaata    360

ttcaatgttc tgttacattg taagtgaagt ccagctcaaa atagatttaa tatattgaat    420

ttatttgnac cntngggcgg gaacacgcct aaggcgaaa ttncagcacc actggccggg    480

cggttcctaa ngggattccc aaactntggg nnccanactt nggcgnnaan cnatngggcc    540
```

taaaacttgg tttccccctng nngaaaattg ggttatnccg gttacaaatt tcccncncaa 600
atttccgggg 610

<210> SEQ ID NO 218
<211> LENGTH: 585
<212> TYPE: DNA
<213> ORGANISM: Homo sapiens
<220> FEATURE:
<221> NAME/KEY: misc_feature
<222> LOCATION: (1)...(585)
<223> OTHER INFORMATION: n = A,T,C or G

<400> SEQUENCE: 218
ggtacaattt gtaaatattt caaaggtcta ggagtcataa ctttttgttt tcatactgaa 60
aatgatgttg atcagagaaa ccaactgttt tgcttttcat tgctctgtga gaaatttgag 120
gattctgttt tgctgttagg taagctaaac tcagaaattg aaaaggaaaa gactggataa 180
acacaggatt ttcagtaaga aaacaacccc agtcttgtct tagaagccac ttgttgagga 240
gtctgttggg ggaaaaaaga ggatatgctt ttaaaggtag aacaaacctt cttctgtgtt 300
aaatcaaaag gatgttcaaa atccaccagg acagatgcta cttgggttta aatggagcca 360
tagatgatac aaagtcctct tggggctgaa aatcacttcc tatttgcatg gctttactaa 420
ctggtttctg ttttccatta tctttttcac agaaagtntt tggtcaagat tttttccagc 480
ctttnaaatt gaaaccggtc agtantttga cccctgnttg gntatttnnt ccagnaattn 540
aaattgnatt cnctggntcc aaaggcntta attccccttc cttng 585

<210> SEQ ID NO 219
<211> LENGTH: 599
<212> TYPE: DNA
<213> ORGANISM: Homo sapiens
<220> FEATURE:
<221> NAME/KEY: misc_feature
<222> LOCATION: (1)...(599)
<223> OTHER INFORMATION: n = A,T,C or G

<400> SEQUENCE: 219
acaggtcaca gatcctacaa tcctactgtg gcttgtgtct ctttttccga ggcacatcct 60
caaccttgga aaaataaact tttaaattga ttgagacttg cctcagtgat tttctttggt 120
gtatactctg tatcacttga atactttcca agtgaagaca tgctttataa tccagagtat 180
ggactgtttt ggccagatgt tttctatata ctggaaagaa atgtgtattc tgctgttgtt 240
gaatggcatg ttctataaat ctcaattaca tcaagttggt tgatagtctt gatgtcttct 300
atatctctgt ggattttcca tttgttctag tgattattga gagaaaggta ttgatatatc 360
tgcctataat tctggattta tctacttctc tttggagatt tctccatttt tgcttcatgt 420
attttggaag cccctacttc acccagcatn ggnctttctt gagccccttc caagaagtaa 480
ttttaaccac ccangnccca tccaacccct aaccccaang gnnaaccaac cgnnggcang 540
tnanttgggc ctaaccnggg gaacccattg ggggnccttn ggnattaggg ganaccnng 599

<210> SEQ ID NO 220
<211> LENGTH: 602
<212> TYPE: DNA
<213> ORGANISM: Homo sapiens
<220> FEATURE:
<221> NAME/KEY: misc_feature
<222> LOCATION: (1)...(602)
<223> OTHER INFORMATION: n = A,T,C or G

<400> SEQUENCE: 220

```
ggtacccatt taatataact atgatgcact taaattgaag ctatgccaca ggatagaaaa     60

tgaattacaa cttaaataca tgttggaagt gtaacactgt ttttcaaggt ttaaaaaaat    120

tcctaatgtc ttttagcctt ctttaatatt tttaggtaag gaaagtatgt ttggattttt    180

tcctctttgt aggtatatga gattgaaatg tgaagtattt ggacaacaaa cgtcaagcaa    240

tgggaagcca ttttgatttc ttgagtaatc ttgtaagcat taagtgaatg acaaagtagt    300

agtgtaactt atttcttatg gtataacttc agtcaattaa tataaggata gtttttgttg    360

tatgtacact aagtggtaat ataatngcca ttgaantata ctaatctttc tcttaanaga    420

ctattcnnct nttaattgnt tcctaatggg aacanttntg gcctaacccn gaaaaagggg    480

ganaaaggat tnccctgccc nggccgggcn tttccaaagg ggcanatttn cgnncacctt    540

ggnngcccgt tntctanngg aatccnannn tggtcccaan anttgggggg aatcttnggc    600

nn                                                                   602
```

<210> SEQ ID NO 221
<211> LENGTH: 573
<212> TYPE: DNA
<213> ORGANISM: Homo sapiens
<220> FEATURE:
<221> NAME/KEY: misc_feature
<222> LOCATION: (1)...(573)
<223> OTHER INFORMATION: n = A,T,C or G

<400> SEQUENCE: 221

```
acctaatgaa aagatctcca agaggtttgt ctcattctcc ttgggctgta aaaaagatta     60

atcctatatg taatgatcat tatcgaagtg tgtatcaaaa gagactaatg gatgaagcta    120

agattttgaa aagccttcat catccaaaca ttgttggtta tcgtactttt actgaagcca    180

atgatggcag tctgtgtctt gctatggaat atggaggtga aaagtctcta aatgacttaa    240

tagaagaacg atataaagcc agccaagatc cttttccagc agccataatt ttaaaagttg    300

ctttgaatat ggcaagaggg ttaaagtatc tgcaccaaga aaagaaactg cttcatggag    360

acataaagtc ttcaaatgtt gtaattaaag gcgattttga aacaattaaa atctgtgatg    420

tanggagtct ctctaccact ggatgaaaat atgactggga ctgcccttga ggcttggtac    480

cnttggcncc aanccccttgg gaaccccaaa aactntggaa gagaannggg gttttcctgn    540

caggcaacat attgcctttg gcctnctttg ggg                                 573
```

<210> SEQ ID NO 222
<211> LENGTH: 168
<212> TYPE: DNA
<213> ORGANISM: Homo sapiens

<400> SEQUENCE: 222

```
ccaccatctt ggaacgggag gcggagcaga gtcgactggg agcgaccgag cgggccgccg     60

ccgccgccat gaaccccgaa tatgactacc tgtttaagct gcttttgatt ggcgactcag    120

gcgtgggcaa gtcatgcctg ctcctgcggt ttgctgatga cacgtacc                 168
```

<210> SEQ ID NO 223
<211> LENGTH: 564
<212> TYPE: DNA
<213> ORGANISM: Homo sapiens
<220> FEATURE:
<221> NAME/KEY: misc_feature
<222> LOCATION: (1)...(564)
<223> OTHER INFORMATION: n = A,T,C or G

<400> SEQUENCE: 223
actgcagaca aaatctgctt ttagaggcaa gcggatttct gacaaagtaa ctgatccttt 60
ggatggcata aattcacttt ggggactagc cttattcttc ctctgaggtc cttcgttctt 120
caatttattc aattcatcaa tcaaaagtgt tctcttccca gttgcaatta gaagaagtct 180
ttctgcttca gcttcttcta ggggcccttt tccatgttct tcatcaacac agcagttaag 240
agcctggcta gcttgataga tcactgtctg ttgcatattt atttcgttat tgagttcctg 300
cattttctgt ttgatattaa cttgacaagg aaaggcatta ttttttttcat ccagttttga 360 agtaacatct tccttccgaa caatcacctg ctttattgat ggacgttctg tttctttgaa 420
tctttgagat ctatatgcat caatgctgta aagaagatca cgatcttcag aaccaaggct 480
atcacnagat tcaggtcgag ggacacgaag ttctttngaa tttcctgggt ttggactttc 540
atcacttctg ctggngcttt caan 564

<210> SEQ ID NO 224
<211> LENGTH: 277
<212> TYPE: DNA
<213> ORGANISM: Homo sapiens

<400> SEQUENCE: 224
acaaggctgg cggttgttgg gggacggttg agccttggga gggagggtca gggtctggac 60
aggagccgcg gccgccagat gggaaagaac acgtgggagc agtaatgtca agtgacactt 120
aaacccttag acgccgattc gttataacgc gaggaaatct aatcccacgt ccctaacggt 180
cttcggaagc gaagcagtgt caacagtccc tggtaaacac aagtagtatt acaagtcggg 240
agctcttcaa gtcttggatg agactgtaga gcggacc 277

<210> SEQ ID NO 225
<211> LENGTH: 589
<212> TYPE: DNA
<213> ORGANISM: Homo sapiens
<220> FEATURE:
<221> NAME/KEY: misc_feature
<222> LOCATION: (1)...(589)
<223> OTHER INFORMATION: n = A,T,C or G

<400> SEQUENCE: 225
ggtacctgga ggctcaacgg cagaagcttc accacaaaag cgaaatgggc acaccacagg 60
gagaaaactg gttgtcctgg atgtttgaaa agttggtcgt tgtcatggtg tgttacttca 120
tcctatctat cattaactcc atggcacaaa gttatgccaa acgaatccag cagcggttga 180
actcagagga gaaaactaaa taagtagaga aagttttaaa ctgcagaaat tggagtggat 240
gggttctgcc ttaaattggg aggactccaa gccgggaagg aaaattccct tttccaacct 300
gtatcaattt ttacaacttt tttcctgaaa gcagtttagt ccatactttg cactgacata 360
ctttttcctt ctgtgctaag gtaaggtatc caccctcgat gcaatccacc ttgggttttc 420
ttanggtgga atgtgatggt cagcaacaaa cttgcaacaa gactgggcct ttggttggta 480
ctttnnaaaa ggccncnttg atcccatttg agnaattncn cccggcccaa aaaaaggtcc 540
taangttggt aaaatttgca agctttttaa ggtttgccca aagnatgnt 589

<210> SEQ ID NO 226
<211> LENGTH: 636
<212> TYPE: DNA
<213> ORGANISM: Homo sapiens
<220> FEATURE:

-continued

<221> NAME/KEY: misc_feature
<222> LOCATION: (1)...(636)
<223> OTHER INFORMATION: n = A,T,C or G

<400> SEQUENCE: 226
ggtcaagaag catgccacct ccacaactcc tacctggacc tccagcgcag gtatgggaga 60
ccctcgatgt gcagagcctt cccctgggag aaggagctga aagacaaaca ccccagcttg 120
ttccaggcat tgctggagat ggatctgctg accgtgccaa ggaaccaaaa tgaatctgta 180
tcagaaatcg gtgggaagat atttgagaag gctgtaaaga gactctctag cattgatggt 240
cttcaccaaa ttagctctat cgtccccttt ctgacggatt ccagctgctg tggataccat 300
aaagcatcct actaccttgc agtcttttat gagactggat taaatgttcc tcgggatcag 360
ctgcaggggc atgttgnata agtttggttg gaggccnngg ggagtgagaa gctgcttcaa 420
tgaatcttgg gtataaacac taccaaggta ttgacaacta ccccctggac ttgggaactg 480
ncgtatgcct actacagcaa ccntggccnc caagaaaccc cttggaccag cacacacttg 540
gaaggngaat caggcctttt gttgaaacca tttgacttaa aggattgttg gaaatcttca 600
nggnaccttg cccggcgggc cctttnaaaa ggggna 636

<210> SEQ ID NO 227
<211> LENGTH: 451
<212> TYPE: DNA
<213> ORGANISM: Homo sapiens
<220> FEATURE:
<221> NAME/KEY: misc_feature
<222> LOCATION: (1)...(451)
<223> OTHER INFORMATION: n = A,T,C or G

<400> SEQUENCE: 227
acccaaaaac cacccccaac gccccccaac cctcaggcgt gcctgtgagt gtgtctgtgt 60
gtctcactct gactcaccca gacaactgac ttcagcagcc aaccttggtc attcccagaa 120
ccaccactgg ggggcatacg tgtggctaga ctgggggcgc ccgaatatct gtctctacaa 180
aaagtaaaaa aaaaattaat ggggtgtggt ggtggtgcgt gcctgtggta tcagctgctt 240
gggacgctgg ggcangagga tcacttgagc ccgagaattc aaggctacag tgagttaaga 300
ttacgccact gcactccatc ctgggtgaca gagcaagacc ttgtctcaag aaaaaatttt 360
taaatgagta aaattcaaaa aaaanaanaa aaanaaaagc ttgacacctg aaacatgggt 420
tactgcatat ggnacctngg cngagacacg c 451

<210> SEQ ID NO 228
<211> LENGTH: 408
<212> TYPE: DNA
<213> ORGANISM: Homo sapiens

<400> SEQUENCE: 228
ggtcccttat atggcagaat cttgcaggca gcatgtcgag tttgatatgc tggtgaagaa 60
tagaacccaa ggaatcattc ctttggcccc catatctaaa tcattgtgga cttgctcagt 120
agaatcttcc atggaatatt gtagaataat gtatgatata tttcctttca aaaagctggt 180
gaattttatt gtgagtgact ctggagcaca tgttttaaat tcttggactc aagaagacca 240
aaatttacag gggctaatgg cagcattagc cgctgttggg cctcctaatc ctcgggcaga 300
tccagagtgc tgcagtattc tgcatggcct tgttgcacag tggaaactct ctgcaaaatt 360
actgaatacc aacatgaggc tcgtacctgc cccgggccgg ccgctcga 408

<210> SEQ ID NO 229
<211> LENGTH: 270
<212> TYPE: DNA
<213> ORGANISM: Homo sapiens
<220> FEATURE:
<221> NAME/KEY: misc_feature
<222> LOCATION: (1)...(270)
<223> OTHER INFORMATION: n = A,T,C or G

<400> SEQUENCE: 229
ggtacacagc agcatcaaaa aggctattta caagagattt tcttcaacag aatccacttg 60
aaagcactga gaatttgcat cttagctaag agcagtttac caaggaacag ggccatctaa 120
gtgcctaact agcatttaaa gttgtcaagg ggtggggatg tgcaaattaa gcagcaaaag 180
attattatct tgttntgctt taagggaaag taatantggt cagaggggcc agttccaagg 240
gctggtccaa ggggggccgc tggtcttggt 270

<210> SEQ ID NO 230
<211> LENGTH: 425
<212> TYPE: DNA
<213> ORGANISM: Homo sapiens
<220> FEATURE:
<221> NAME/KEY: misc_feature
<222> LOCATION: (1)...(425)
<223> OTHER INFORMATION: n = A,T,C or G

<400> SEQUENCE: 230
ggtacattat ccaatttcag ggaaaaaaaa tacagttttc ttaccaaatt atccagtgta 60
tatgactggt tagaatttta agttttgatt tttactgaaa ttcagagtat gaaatgcaaa 120
cattcaggat aaaatgaatt cataattaca cacagttata tcaacttgca acaaagcagc 180
aaatatgagg gcctaacaca catctcgact ctccccttcc cttctgatcc ctcaaaaaaa 240
agtgcaaaat caaagagtca ctgcttggtc caaaaaaataa aatacattgt gtataaacat 300
ttgaaatctg atggaatcca gcttctattc cacaggttgt cttcagtaag aatcaacgtc 360
cgaagatgga actcagttcc agaagaatta attctacaat ctgattctgg tcctgccggg 420 cggnc 425

<210> SEQ ID NO 231
<211> LENGTH: 639
<212> TYPE: DNA
<213> ORGANISM: Homo sapiens
<220> FEATURE:
<221> NAME/KEY: misc_feature
<222> LOCATION: (1)...(639)
<223> OTHER INFORMATION: n = A,T,C or G

<400> SEQUENCE: 231
gcgtggttcg cggccgaggt actccaagaa gtctgtctgc cattgatagg gctggagcag 60
aggtgaagag tagaacaacg cttttcagaa agattggaga ctttagaagc ttggagaaga 120
tttcacggga agtcaaatca attacgatta tcggtggggg cttccttggt agcgaactgg 180
cctgtgctct tggcagaaag gctcgagcct tgggcacaga agtgattcaa ctcttccccg 240
agaaaggaaa tatgggaaag atcctccccg aatacctcag caactggacc atggaaaaag 300
tcagacgaga gggggttaag gtgatgccca atgctattgt gcaatccgtt ggagtcagca 360
gtggcaagtt acttatcaag ctgaaagacg gcaggaaggt ngaaactgac cacatagtgg 420
cagctgtggg cctggaaccc aatgttgagt tggccaagac tggtggcctg gaaatagact 480
cagattttng tggctttccg ggtaaatgca tnacttccag cacgctttta ccatcttggg 540

```
tggcangaaa atgctgcatt gcnttctacg atntaaaagt tgggnaagga ggccggttan    600

aacncccntg aacncccttt tgtgantggg aaaattgcn                           639


<210> SEQ ID NO 232
<211> LENGTH: 369
<212> TYPE: DNA
<213> ORGANISM: Homo sapiens

<400> SEQUENCE: 232

ggtactaaaa ggcctcaaaa taattagtga cagaaatagt gttattaatt tgctaagctc     60

aacaataagc aattccttaa ttaaaatctt cgagatataa atttgatgac tattctcttc    120

agaaatgaca tacctggatt atgttaatca tcacaagcct tattagtcac acatataaac    180

atggcctcat gcaatcattt gtctgtatat gttactctaa gttgcatgag cacaaggttt    240

aatatctata tctttaagaa aatacttgat attataaaca gagtaaaaga catgatatag    300

tagtgattac taaaaaaaaa aaattagcag cttaaatcta tctatatttg aaaaaacgta    360

gtcacaagt                                                            369


<210> SEQ ID NO 233
<211> LENGTH: 618
<212> TYPE: DNA
<213> ORGANISM: Homo sapiens
<220> FEATURE:
<221> NAME/KEY: misc_feature
<222> LOCATION: (1)...(618)
<223> OTHER INFORMATION: n = A,T,C or G

<400> SEQUENCE: 233

accctctctt ccagcaccca ggccagtatt gagatcgatt ctctctatga aggaatcgac     60

ttctatacct ccattacccg tgcccgattt gaagaactga atgctgacct gttccgtggc    120

accctggacc cagtagagaa agcccttcga gatgccaaac tagacaagtc acagattcat    180

gatattgtcc tggttggtgg ttctactcgt atccccaaga ttcagaagct tctccaagac    240

ttcttcaatg gaaaagaact gaataagagc atcaaccctg atgaagctgt tgcttatggt    300

gcagctgtcc aggcagccat cttgtctgga gacaagtctg agaatgttca agatttgctg    360

ctcttggatg tcactcctct ttcccttggt attgaaactg ctggtggagt catgactggc    420

ctcatcaagc gtaataccc attcctacca agcagacaca gaccttacta cctattctga    480

caaccagnct ggtgngctta ttcanggttt attaaaggca accttccctg acaaaggata    540

ccacctgctt ggcaaggttt gaactcccag gcctgccngg aaggaatgcn cggggggatt    600

nctggggggg ggnccncn                                                  618


<210> SEQ ID NO 234
<211> LENGTH: 603
<212> TYPE: DNA
<213> ORGANISM: Homo sapiens
<220> FEATURE:
<221> NAME/KEY: misc_feature
<222> LOCATION: (1)...(603)
<223> OTHER INFORMATION: n = A,T,C or G

<400> SEQUENCE: 234

accagatgga aaatgttttt ggtgatctgg ctgctgctta aagccagttt tccctaagaa     60

ctccaaaggc taaactctac taggggcaga gtgtgaggat agatttctaa tcagagaaaa    120

gtggcctcca ggagctttca tttatgtctt ctccagacca ggttttcctg ttatcttcct    180

ttaatcccct ttcaaccaac aggtgaagtt cttccagccc acagaggtag taatatcatc    240
```

```
ttttctatct cctcctctcc tttggccatg taatgaagca aaatattatt tatttagccc    300

aggcttgaga gccactgttt gtggacagtc ttcatctaga ttccataccc tggcctaggc    360

gaggtaaggc tctctggtta ttgccaggat ggagcccctc taccccangt ctgctgtang    420

gaatacccta attagttgan gcatgctttt ggaatcctgc atgttggcat atggctggnc    480

tatccttttt aaaanctctg ggtgggggna tctggatatn gattaagang ggacaaggag    540

cctttcttg gctaanggtt ncaatacctt tttgaatggg gccagccctc aggcttccca    600

ccc                                                                  603


<210> SEQ ID NO 235
<211> LENGTH: 328
<212> TYPE: DNA
<213> ORGANISM: Homo sapiens
<220> FEATURE:
<221> NAME/KEY: misc_feature
<222> LOCATION: (1)...(328)
<223> OTHER INFORMATION: n = A,T,C or G

<400> SEQUENCE: 235

gcgtgtcgcg gccgangnac atggacnaca ggtgangaac aggtgaacat ggaggttgta     60

gancccangg gagggggagt cacttggttt ggggcaaact tgctaaatgc aggaccacag    120

gaaccanctn ttcanctncc gtgaganttt ggctgcccan gccanttagg ggtgtgggcc    180

tgcacggnag acagttatcc ctttctantc tggctcgtgg gactntnnan ggantcantc    240

tgcaacagta agtggtgant tcttctgncc ancgtcagta ttttgatggt ggctttagac    300

ttgccagatn acactacntn acatcagt                                       328


<210> SEQ ID NO 236
<211> LENGTH: 352
<212> TYPE: DNA
<213> ORGANISM: Homo sapiens

<400> SEQUENCE: 236

ggtacacctg ttaggagctc tatcactctg aaagccaaaa gatagaatgc tcatttgagc     60

atttgcaaaa tgttctctat ttatattttt aaaaatctga tacatgtaag tttttctggc    120

agattctttt tgtatgttac aaaacaaaac atcaaaagct cagagtaaga taagaatccc    180

tttttcttag aaaggtcaag cagatacttc ttgacatcat gtcctttata caatggcata    240

ttgttcatat aaaaggtctc ttatcctata aaaatcttga caaaggcagc cttctaatcc    300

aatgcgtcca gtttccgttc tgcggactgc tacttgattg ttgcaaacaa gt            352


<210> SEQ ID NO 237
<211> LENGTH: 607
<212> TYPE: DNA
<213> ORGANISM: Homo sapiens
<220> FEATURE:
<221> NAME/KEY: misc_feature
<222> LOCATION: (1)...(607)
<223> OTHER INFORMATION: n = A,T,C or G

<400> SEQUENCE: 237

ggtacaaatg cgcttccagc aggaggtcat ggacagccct atggaagagg tcctgctggt     60

caatctttgt gaaggaacct tcttaatgtc ggttggtgat gaaaaagaca tcctgccacc    120

gaagcttcag gatgacatct tagactctct tggtcagggg atcaatgagt taaagactgc    180

agaacaaatc aacgagcatg tttcaggccc ctttgtgcag ttctttgtca agattgtggg    240
```

```
ccattatgct tcctatatca agcgggaggc aaatgggcaa ggccacttcc aagaaagatc    300

cttctgtaag gctctgacct ccaagaccaa ccgccgattt gtgaagaagt ttgtgaagac    360

acagctcttc tcacttttca tccaggaagc ccgagaagag caagaatcct cctgcaggct    420

atttccaaca gaaaatcttg aatatgagga acagaagaaa ccngaagaaa ccaagggaaa    480

aaactgtgaa ataagactgt ggtgaattag aatggctaga gctaccccca ttntnggctt    540

tagccctgcc aagtggcagg ntcancaact gtcagnttcc naatcctaat cntactttgg    600

gnnntgg                                                               607
```

<210> SEQ ID NO 238
<211> LENGTH: 391
<212> TYPE: DNA
<213> ORGANISM: Homo sapiens
<220> FEATURE:
<221> NAME/KEY: misc_feature
<222> LOCATION: (1)...(391)
<223> OTHER INFORMATION: n = A,T,C or G

<400> SEQUENCE: 238

```
acaaacttag aagaaaattg gaagatagaa acaagataga aaatgaaaat attgtcaaga     60

gtttcagata gaaaatgaaa aacaagctaa gacaagtatt ggagaagtat agaagataga    120

aaaatataaa gccaaaaatt ggataaaata gcactgaaaa aatgaggaaa ttattggtaa    180

ccaatttatt ttaaaagccc atcaatttaa tttctggtgg tgcagaagtt agaaggtaaa    240

gcttgagaag atgagggtgt ttacgtagac cagaaccaat ttagaagaat acttgaagct    300

agaaggggaa gttggttaaa aatcacatca aaaagctact aaaaggactg gtgtaaaana    360

aaaantgtna nnaaaaaaaa agcttgtcct n                                    391
```

<210> SEQ ID NO 239
<211> LENGTH: 466
<212> TYPE: DNA
<213> ORGANISM: Homo sapiens
<220> FEATURE:
<221> NAME/KEY: misc_feature
<222> LOCATION: (1)...(466)
<223> OTHER INFORMATION: n = A,T,C or G

<400> SEQUENCE: 239

```
gggagggaga cgggggagag agagaaaaaa aaaaaaaaaa aaaaaaaaag cttgtgttgg     60

tcccagcggt tcagctgagg tagggacgtg ccgtaggccg gaatgttacc ggctgttgga    120

tctgtggatg aggaagagga tcctgcggag gaggattgtc ctgaattggt tcccattgag    180

acgacgcaaa gcgaggagga ggaaaagtct ggcctcggcg ccaagatccc agtcacaatt    240

atcaccgggt atttaggtgc tgggaagaca acacttctga actatatttt gacagagcaa    300

catagtaaaa gagtagcggt cattttaaat gaatctgggg aaggaagtgc gctggagaaa    360

tccttagctg tcagccaagg cggagagctc tatgaaagag tggctggaac ttagaaacgg    420

tttgcctctt gcttgttcan tgaagtgagg aatgtgttta ctgggt                   466
```

<210> SEQ ID NO 240
<211> LENGTH: 616
<212> TYPE: DNA
<213> ORGANISM: Homo sapiens
<220> FEATURE:
<221> NAME/KEY: misc_feature
<222> LOCATION: (1)...(616)
<223> OTHER INFORMATION: n = A,T,C or G

<400> SEQUENCE: 240

```
ggtacaactc ttgctaatgg aatgctataa tgcacaaggt caaggattta ataaattcta     60

aaagtgtcta catatatcag tgataactgt attattagaa atataaatgt atagaaatat    120

aaagtatatg gtattaaaaa cagaccttgc taatataaac atatataaag tatgtcactt    180

ctcctgtaat aacagcataa agatcgatct acagtttgcc cttcgcctgg cactcttaaa    240

ccactcctcc aatggtcaat gttgaccttg aatcaacagc cgctgaaccc aggagacccc    300

acagatgtgt agattcagca cctanagggc ccccctaccc tctgtgctgt gtgttcccat    360

gactccagaa ataattaatc gcaacttgca ttattaagtc cacaggcaag ttttgaaatc    420

taactagaaa aagtagcagc aaaggccaaa ataccgcggg aatttgttaa gaaaagcaac    480

cagaatttct taaaatgctt tcanttcaag gtctgaatta aggtgacntt aggtcccacc    540

agcnttaacg nagttggggn atgttttgct gntggttttt naaaaaagaa gaatctgcna    600

taaacatgtc ctttgg                                                    616
```

<210> SEQ ID NO 241
<211> LENGTH: 598
<212> TYPE: DNA
<213> ORGANISM: Homo sapiens
<220> FEATURE:
<221> NAME/KEY: misc_feature
<222> LOCATION: (1)...(598)
<223> OTHER INFORMATION: n = A,T,C or G

<400> SEQUENCE: 241

```
ggtactctat gaatgtgtta cccaggagac cccagagatg ttgcctgcat acatagcaat     60

ggatcaggct ataagaagac ttgggagaag agaaatgtct gagacttctg aactttggca    120

gataaagttg gtgttagagt ttttcagctc ccgaagccat caggagcggc tgcagaacca    180

ccctaagcgg gggctcttta tgaactcgga attcctccct gttgtgaagt gcaccattga    240

taataccctg gaccagtggt tacaagtcgg gggtgatatg tgtgtgcacg cctacctcag    300

cgggcagccc ttggaggaat cacagctgag catgctggcc tgcttcctcg tctaccactc    360

tgtgccagct ccacaagcac ctgccaccta taggactaga agggagcaca agctttgctg    420

aactgntctt caaatttaac agcttaaaat gccagtgcga gctttgttga natggctcct    480

ttgcttcttg gaaatccaca gccatggtga tgtgaccgtg ttggccggga acctacctga    540

acgtgacttn tggcacaacg tgaccaacct naaacttaag catgttttaa gtttangg      598
```

<210> SEQ ID NO 242
<211> LENGTH: 565
<212> TYPE: DNA
<213> ORGANISM: Homo sapiens
<220> FEATURE:
<221> NAME/KEY: misc_feature
<222> LOCATION: (1)...(565)
<223> OTHER INFORMATION: n = A,T,C or G

<400> SEQUENCE: 242

```
acagagcttc gggtagcaga agaggaatgg cctatggaca tattgactct tatggggcag     60

atgatagtga ggaggagggg gctgggcctg ttgagcgacc gccagtgaga gggaaaactg    120

gcaagtttaa agatgataag ctgtatgacc cagagaaagg ggcaaggtct ttggctgggc    180

cacctccaca tttctctagt tttagccgtg atgtgagaga ggagcgagac aagttagacc    240

cagtccctgc agcaagatgc tcagctagca gagctgactt cctgccacaa agtagtgtgg    300

ccacacagtc gtcttctgaa ggcaagctgg ctacaaaagg tgacagctcg gagagggaga    360
```

-continued

```
gaagggagca aaatttacct gcacgttcca ncagggctcc tgtgagtatt tgtggtggtg    420

gggaaaacac ctnaaagaag tgcagaggaa cctgtggtca ggccccaaat cagaaacctg    480

gcaggtccaa ctgcgtgaaa cccaaaattt ttttttgatc ctgatgatga ntgaccatnt    540

ccncaccgta cctttggcgn gaaca                                          565
```

<210> SEQ ID NO 243
<211> LENGTH: 647
<212> TYPE: DNA
<213> ORGANISM: Homo sapiens
<220> FEATURE:
<221> NAME/KEY: misc_feature
<222> LOCATION: (1)...(647)
<223> OTHER INFORMATION: n = A,T,C or G

<400> SEQUENCE: 243

```
ggtacttgga atgggggctg ttttttggct ggtctgagtg caggactttg ctgctaggat     60

gcttaccaaa tagaaatttg actcagagcc tgtggctggg gaattgtcct caggaagtaa    120

aatggctcgc cagctttcct acctgcttgt ggatgcctca gatagcaatg gtcggacagg    180

acacttcagt gtgggaagca gcatccggtg aggctgtgct ctggcacagg gggatcctga    240

atctccccat ctcttctaag ctgacctgtc cacacattct gagggattaa gcttagagca    300

cctaagaaca gcagcctccc caggagaggc cagggaccaa agtggcagga atcctagaca    360

actctacgct tttctgcac taaccagctg ggtgactcta aacatgtcac ctccctntgg     420

cctnaacttt ctcatcgacc aaacgaanga gagtagactg ngctttcagc ttaagaccga    480

aaaccgtatc ttaacccttt tctggnacct tgcccggccg gccgttcnaa angggcaaat    540

tccnnacact gggcggccgt actaagggat cccacttngg gcccaaactt ggggtaaaca    600

tggcanaact ggtncctgng gnaaatggta anccgttcca aatcccc                  647
```

<210> SEQ ID NO 244
<211> LENGTH: 603
<212> TYPE: DNA
<213> ORGANISM: Homo sapiens
<220> FEATURE:
<221> NAME/KEY: misc_feature
<222> LOCATION: (1)...(603)
<223> OTHER INFORMATION: n = A,T,C or G

<400> SEQUENCE: 244

```
acaacattca gggctttctt tttttcttcg gcaagctctt cttcctcagc agttttcttt     60

tcatttacct cttcctgttc ctcttcactg tcagtttcta gaaatcgaga gtccatgcgg    120

aatctgtcat cggtgccaaa gtgcgactgt aaatccatga gcttctgtcc agctctgccc    180

tcaaactgag gtttaatttt gaacctatta ctgtcatctt cagaatcaga ttcgtcatca    240

tcactgctat caaacagctt ccctgatgtt ttacccatag actctttcac ccattcctct    300

cctggatggc tctgctcctg agtcgatgtc tcctctgttt cacattcact gtcagaaccg    360

aagatgatgt gcgttggctt atcctctgga tgaccatcca aattgccaga gcattatgca    420

ccagcttctt ctgcactctt tgctttttgc ctcgcttcca aggctgncaa acgcttcttn    480

attggcttca acatgcttat ctttagcact cacatttgac gaattactaa tngaaagggg    540

agaaaanagt tttggattcc ccgagngccc ttggatgana cctttgggga ttcttganaa    600

aag                                                                  603
```

<210> SEQ ID NO 245
<211> LENGTH: 640

<212> TYPE: DNA
<213> ORGANISM: Homo sapiens
<220> FEATURE:
<221> NAME/KEY: misc_feature
<222> LOCATION: (1)...(640)
<223> OTHER INFORMATION: n = A,T,C or G

<400> SEQUENCE: 245
actgggcacc attaatgagg atgcaggaga tcaggtggcc caggccttcg aagatatact 60
ggaacttgtg ctgctgaagg ctggcgctca tggcctcttc aatggcgctg atatctttgt 120
tgagcttgac caccaggggg tcataatcca tactttccac attagccaca atggcatagt 180
tcccctcctt tgcaagaggg ataagatagt ggaaacagtg aaccctcact tccagatgta 240
agacaagcaa gcagcggtca gccatatcct ggaacgattt ggcaagttca ctgagagtct 300
gcatgatctg ctctgacact ggggggagat ccgtgttcgt gtggctgctt gagcaggaga 360
aagcatctgg gatgtagaaa gattggaaga aagctgactt ttgttcgact tgccaaccat 420
tccaagcttt catgcntgtt ngccaaggct ttganggcac ttgaccgtca cgaaggatnc 480
ttgtggaagg antaatttat caccaaggtt ccaatagaac tttagactcc ttgncaaaac 540
tggccttatg aaaacttntt cntcnctctt ttggcctanc tgnttngggt tgngcctntt 600
cattccantt gggnaaaaat tcaaanattg ctggttcttn 640

<210> SEQ ID NO 246
<211> LENGTH: 608
<212> TYPE: DNA
<213> ORGANISM: Homo sapiens
<220> FEATURE:
<221> NAME/KEY: misc_feature
<222> LOCATION: (1)...(608)
<223> OTHER INFORMATION: n = A,T,C or G

<400> SEQUENCE: 246
cgaggtactg tcattgaagt ggaaccagcg gccttcgtga gttgcgtatg ctgtgtaatg 60
tccagaacca accccggaac catggtgcac caccacagcg gcgaggtcat acaggcagct 120
ctccgggcca ctgttctcag gctctagtaa gtagcatttc atgtctaggc ctctcagtgg 180
aaattctacg tatgtatcaa ctttatttct taaatatgct gtccaatgaa atcttttcaa 240
atgtaagcat agcaccttgg gtagtttttg aatccaaaac ttttttgtgg acttttgttt 300
ctttttgcat ttatggcaca tatataactc tgtctcatca agttcttcta agtcggtaaa 360
actgcgaaga caatctcgta acgaacaaac tggtccattt tcttgattct tagagcgctt 420
acttctgaac tgacttggaa tatctaatga aaggtctang gaatggatca aacttttaga 480
atctgcccca tatgaggcag ttacctcatt ttggagaagc ctccgaatat agccggacaa 540
cagtnaagct ccattatgna ccttggtacc ttgcagacag ngtaaaatnt cctgcaaaat 600 gntgaccg 608

<210> SEQ ID NO 247
<211> LENGTH: 632
<212> TYPE: DNA
<213> ORGANISM: Homo sapiens
<220> FEATURE:
<221> NAME/KEY: misc_feature
<222> LOCATION: (1)...(632)
<223> OTHER INFORMATION: n = A,T,C or G

<400> SEQUENCE: 247
acagaaagtc agagaacact tacagaactt ggaaaactca gctttcacag ctgacaggca 60

-continued

```
taagaaaaga aaacttttgg aaaactcaac actaaacagc aagttattaa aagtaaatgg   120

aagcaccact gccatttgtg ccacaggcct tcggaatttg gggaacacat gtttcatgaa   180

tgccatcctt cagtcactca gtaacattga gcagttttgc tgttatttca aagaactgcc   240

cgccgtggag ttaaggaatg ggaaaacagc aggaaggcgg acataccaca ccaggagcca   300

aggggataac aatgtgtctt tggtagaaga gtttagaaag acactctgtg ctttatggca   360

aggcagccag actgnattta gcccagagtc cttaatttat gttgtttgga agaatatgcc   420

caactttagg ggctatcaac agcaggacgc catgaatcat gcgctccttt tggaccccta   480

ccttggaact tcaggcggnt caacggggtt tccgctnaac attttgcagg gaaatctact   540

ttgctgcagt accaagtggt gctaaatgga catttntggt gcacggtntt ttcgagggnt   600

ntccaaatnn ggttactgcn tanttgggga aa                                 632
```

```
<210> SEQ ID NO 248
<211> LENGTH: 624
<212> TYPE: DNA
<213> ORGANISM: Homo sapiens
<220> FEATURE:
<221> NAME/KEY: misc_feature
<222> LOCATION: (1)...(624)
<223> OTHER INFORMATION: n = A,T,C or G

<400> SEQUENCE: 248

actccgaggg gcctggcgag gacatgtaga aagactgcgt tttccttttc aatcgggccc    60

ttttgttggc caacaccaga ctgcgccggc ttgaactgat gatttccgaa atgaacttct   120

tgcagtccac acacacctcc atggtgctcc agtcctccat caactctttg ggaaactgga   180

gttcttcatc tgatttgtcc atagacttag attttgagga gaacctggca atgctccgaa   240

gtggccgatg atgggcagtg gagggttttt ctgacctcat actactttcc cctctttgca   300

gagcagaagg tcccaatgaa aagataggaa gagtggagta tggtttggag ggcagcccgc   360

atctttttgc aacactgtga gcacaccggc ctnttacaga actgacaggt ataagaccaa   420

gtgaagaagg aaaaccttct ggttcggcaa ccaaagcaga gctttncttt tttcaagncg   480

tgtnaagnct ttatctggtg atattttcca ntntgcntta ccaggaccgg cgaatatgnt   540

ncttnttccc agtagacnag nattcnctgg gaccaaattc taaanaccgg acttnctgaa   600

gnggaggact gcttcgttta ggct                                          624
```

```
<210> SEQ ID NO 249
<211> LENGTH: 636
<212> TYPE: DNA
<213> ORGANISM: Homo sapiens
<220> FEATURE:
<221> NAME/KEY: misc_feature
<222> LOCATION: (1)...(636)
<223> OTHER INFORMATION: n = A,T,C or G

<400> SEQUENCE: 249

acagtaaaaa gtaaacttcc ctccatccca ggcctgccag catccctgat gccgactttc    60

tgggtgtggc ctagggcccc tcagtgtaat gtaggggttg tgagcacaga ctttggtgcc   120

agtttgctag gttcgaatcc tgactccctc tttgtagctc tgtgcttcaa ttgaaatact   180

gtgcctcagt ttctccttta taaaggcagg gatcatgaga gtgcctgtcc cttgtgagca   240

ctatgaaagt gttagctgtt ctttaccaga ataaatgcat ttctatatct tcccatatgc   300

attttgntaa tttttaaagt atttcaaaca caaagtttga aacagaaaat tgtgtaacat   360

taactatgaa cttaccaccc agaatttaca aatgctgaca ttttgcaata tttatttcng   420
```

-continued

```
atctattttt aanggggggga accctgcagt tactgnttaa tcctttccac ccacctttta    480

attttacacc angagcatag tggtcatacc tangctaatt ttttcagtac ctgatatatt    540

tggagaactc cttcctaggc ataaactttg nccctttttt taanagtggt taacctttgg    600

gacnaaaggg cttgaacaat tggcccatcc ctttgg                               636
```

<210> SEQ ID NO 250
<211> LENGTH: 669
<212> TYPE: DNA
<213> ORGANISM: Homo sapiens
<220> FEATURE:
<221> NAME/KEY: misc_feature
<222> LOCATION: (1)...(669)
<223> OTHER INFORMATION: n = A,T,C or G

<400> SEQUENCE: 250

```
ggtacataat ccggcagctc catggcatct cgcttctggt gctgtgcctc agccccaatc     60

agaaggttga aatgagtggc caaatgtctt cgcagcaaag tcttattggg tgggatgttc    120

aataactgag ccattgtttc tacgttaaaa cgaggctcta gaaccatgag cccaccatgg    180

acaccactgc ctctgagatt gggcgcatat tctgccaagt ccacggagcg cagccactcc    240

atcactcgat ggttagtcca cttctgaact tctgatgggg cgatggtatt ctcatcagat    300

ggccgcctcc gtagacagtt tggttcaaaa gttattgatc ctcaggacct ggatggccct    360

tttgatactg agatggtgta ncacacttac cacctttcag agacagtaag tcatcaacag    420

tcatgtaatg taacattcga ccatnaaccc ggccttnatt aaactgggtc ttatatttga    480

gggaaggncc atggcattcc aaccctntaa nggacccnnn ttggaaatcc actttcccat    540

gaatgggttc ntttttnaaa atcccanggc nttngaaagg ctaacttggg nggttcnttt    600

tcatgaaang aaagcctgga ttccaaggtc cctttttttaa aactttgtgg naaaccctgc   660

aaaaacntn                                                            669
```

<210> SEQ ID NO 251
<211> LENGTH: 670
<212> TYPE: DNA
<213> ORGANISM: Homo sapiens
<220> FEATURE:
<221> NAME/KEY: misc_feature
<222> LOCATION: (1)...(670)
<223> OTHER INFORMATION: n = A,T,C or G

<400> SEQUENCE: 251

```
actattcaag aggtgaagag aaatgtgtat gaccttacaa gtatccccgt tcgccaccaa     60

ttatgggagg gctggccaac ttctgctaca gacgactcaa tgtgtcttgc tgaatcaggg    120

ctctcttatc cctgccatcg acttacagtg ggaagaagat cttcacctgc acagacccgg    180

gaacagtcgg aagaacaaat caccgatgtt catatggtta gtgatagcga tggagatgac    240

tttgaagatg ctacagaatt tggggtggat gatggagaag tatttggcat ggcgtcatct    300

gccttgagaa aatctccaat gatgccagaa aacgcagaaa atgaaggaga tgccttatta    360

caatttacag cagagttttc ttcaagatat ggtgattgcc atcctgnatt ttttattggc    420

tcattagaag ctgcttttca agangccttc tatgtgaaag ccccgagata gaaagcttct    480

tgctatctan ctnccccntg atgnaaagtg tggtnaccca cgggttctgn gttaccaaat    540

gctttgggcc tgnaanccat tgggttcctt attctgggtc aaaaattttt taacccgggc    600

nttgggaact tgccaanggn ntccaccnga gccangaatt ttcactttgg gccaaaaaac    660
```

```
cttttgnggg                                                          670

<210> SEQ ID NO 252
<211> LENGTH: 498
<212> TYPE: DNA
<213> ORGANISM: Homo sapiens
<220> FEATURE:
<221> NAME/KEY: misc_feature
<222> LOCATION: (1)...(498)
<223> OTHER INFORMATION: n = A,T,C or G

<400> SEQUENCE: 252

acacagcaca ttctcttaag agaaaacagg aatgaacatt ctcagaaaca ttcacattgc    60

tcatcaaatg tagctttacc caaagtatat aggaaatggc aaaaacctaa cctagctgga   120

cattttatac aagtaagtca aagttcaaag gaatcatcct atctttattc tcagaaatcc   180

aatgttgaat atcacagttc ttctttaatg gaagcagaag attcagagtc cttgtctccc   240

aaaatgcctc agccagggtc agcacagaga gtggaatata aaaagcttaa ttgtgttaat   300

acatggaaga caacagttct cagtcaacct agccacaatt ttctgtcttg gccatctgta   360

agaaatgact accgtttgaa attcaacttt cacattcaaa aaaaagaaaa tcaattcagc   420

tttnagacac aaagcaaaac caaaacaaaa aaacnaatgg catagtctac atatttnacc   480

ccttgacaat tgggggaa                                                 498

<210> SEQ ID NO 253
<211> LENGTH: 433
<212> TYPE: DNA
<213> ORGANISM: Homo sapiens

<400> SEQUENCE: 253

acgtttcagt tcaagtgcaa aaaataacta tttgctgaat tctatttctt tcagttattt    60

tatttttaag ctgtgtttta ttgtgaagcg agacatccaa gtgtagaatt tcttatccca   120

aatgcagtat tgctccttgg ttacgcttcc tggggagaca ggggttgctg tgcttgagtt   180

caaagtcaag tccatcatac ggttagtaat ttcacctgtc tggggctgca gagtgggttc   240

actgttcatg tttggagctg ttggcaaagt aacggtgtct gagacattga gccctgtttc   300

caaaaggttt cttttctcac gcatttttgg tgatatggtg aggaaagagg taaaggaaga   360

atttgttggc aggataagtt aactggtgac ttgcattggt ggggtgaagt tggttgggcc   420

aatctttggt acc                                                      433

<210> SEQ ID NO 254
<211> LENGTH: 652
<212> TYPE: DNA
<213> ORGANISM: Homo sapiens
<220> FEATURE:
<221> NAME/KEY: misc_feature
<222> LOCATION: (1)...(652)
<223> OTHER INFORMATION: n = A,T,C or G

<400> SEQUENCE: 254

ggtacaaacc caggcctggg cctaggaaag ggcagaagaa aggcaaaggg tcccttggag    60

caggaaccca tccctctctg cttataccca gcacccctca tcccaggttc ctttcttcaa   120

cctccgcctg cctctgggaa cacagagcac caagaactga caaaccggga ccctccaggg   180

ccacagcgtg ggcagagtc caggcttctg tctccccgca gtgggagatc tggggagctc    240

agtgaacctc ctcaccctcc tgccagtatg aagttgggaa gcgccttctc tgtcccccag   300

aacagaacaa actcttgttc tctgtggttg gggaaaaggt gtgggggct tggacctagg    360
```

```
aagaagctga gctgaattcc tccagggccc aggtgaaacc cccaagggga gtttctgaga    420

cttctagact tggccattct ccactttttc cttccaatga ctccggtgaa gcagttaaaa    480

gtctnggctt agggcaactg gtaggacagt ngggaatttg ncccaagaca tttgngggtt    540

tcaaatnaag gtttcccaac accngaatca ttatatggan cctgccnggc nggccgttca    600

aagggcnaat tcngnccctt ggngggcgta ctaagggaac ccactttggg cc            652
```

<210> SEQ ID NO 255
<211> LENGTH: 605
<212> TYPE: DNA
<213> ORGANISM: Homo sapiens
<220> FEATURE:
<221> NAME/KEY: misc_feature
<222> LOCATION: (1)...(605)
<223> OTHER INFORMATION: n = A,T,C or G

<400> SEQUENCE: 255

```
ggtacgacag ttgtgtgggt ttattgggaa cctccaacat ctccacaaca atgtagtatt     60

gtggaaggcg ggtaagttta atgaacagtt tattcttaga aaggtttcca ataggatgag    120

ttgagtaatt ggaaagctgc aatgtttcac tgcttatcgt aggcagatgt tttatagact    180

gcttgcaacg ctgttgtcca agccaaaact taagttgctg aatccagggt atgattcgtt    240

tcatatcatc attcacagac ttctccatgt catccagagt ggcctggtca agtccataaa    300

gcatcaattg aaacattcca gaatgtaaat ctacaaaaat gtgcaggcac tctgaattac    360

cacagggctc caagatggga acaacaagag ctgggagtgc agtctctatg gaagagtttc    420

attggcattg aagcctctaa gaatggcctt cagttcttgg agcttctgat gagctcttgc    480

atggacactg gnaatcangg agttttctat tgataagtgg gccgatcttc atggctcttt    540

ctactaattt ggaatcanaa nttgcaaagg aggatcgtga aaaatttnna aggtttggaa    600

acatn                                                                605
```

<210> SEQ ID NO 256
<211> LENGTH: 654
<212> TYPE: DNA
<213> ORGANISM: Homo sapiens
<220> FEATURE:
<221> NAME/KEY: misc_feature
<222> LOCATION: (1)...(654)
<223> OTHER INFORMATION: n = A,T,C or G

<400> SEQUENCE: 256

```
acagttcaca agcttcaggc aaggggcagc ctgagactat ccgagtgatg ttgaggcaat     60

ccaggcacag caagtcattc agccacttct ccactgcatc cccaggggcc gtatcggatt    120

gactcctgga gggaaacctc atgcagtgtc cgcgctgatg ccaatctggc tgtcgtcgtg    180

gtcttattct cagcagtggt gctgacctgg ctctgggcgc tctgttgacg gagctgctga    240

attagcttga gggacagtga ccggccagtg ccctcatagc cattgatggt ggatgccatg    300

aaaacaaggt aggggccaag taggctcttc accaagggga gggggatggc ggcagcttca    360

tcaatcacaa ctagttcagc ctggcccagc ttcacagcat ctgcaggatg tatatactga    420

atagtctggc tgngtctcga aatacattca ctctgatcac tgntttggta aattcangaa    480

ttanagactg gataatctca taatccaaag gttcctgaaa nttgcanaac attnaaatcc    540

nttnaatncc aattcaaccc aattttgang ttttaanggc tttgggangg aaccaanaan    600

ttggggtacc ttggccggaa ccccccttaag gggnaattca gncacntggg gggn         654
```

<210> SEQ ID NO 257
<211> LENGTH: 594
<212> TYPE: DNA
<213> ORGANISM: Homo sapiens
<220> FEATURE:
<221> NAME/KEY: misc_feature
<222> LOCATION: (1)...(594)
<223> OTHER INFORMATION: n = A,T,C or G

<400> SEQUENCE: 257

```
actgctcttt tattacggta atacttgcta gtgggatttc tctcttcacc aaggctgcct     60

ttactgtgtg aaggacctgt cagtctggct gcagccaagt tggatggagt cctcattcga    120

agacttgact tagccatttc atgatgttca atttcagcct tttcatata  aaatattttt    180

ttaattgaat ttgcatcctt gaatacttga gagccaggct cattataagt tttggcattt    240

tttgcgagga gatctatatc tttggccatt gcatgaatac ttttgtagct tccattctgt    300

atcctctggg caatggtctt gagatctata ggctccttaa ttattgcata ataatctgga    360

tattgcactt tagaaggcaa gtttctgaaa aaagtcgcta atgagacgtn ctgatggatt    420

gnagctacca ctatggcttc aagaaactgc ttcaggaact ncttcaagta agctggagaa    480

aaatcttnag cactgggncc tggatgggct tggccatctt catcaataac ttcgncaatt    540

ggttctcntt ttgaaccaac ctcattnttg gtccaaggna ccttggncgg gaac          594
```

<210> SEQ ID NO 258
<211> LENGTH: 648
<212> TYPE: DNA
<213> ORGANISM: Homo sapiens
<220> FEATURE:
<221> NAME/KEY: misc_feature
<222> LOCATION: (1)...(648)
<223> OTHER INFORMATION: n = A,T,C or G

<400> SEQUENCE: 258

```
cgaggtacct tgctgtttat tccttagtct agcagcatcc ttagtttgta gtatatctta     60

cttagttgca actaaaaaaa attgctagcc taggctttaa ctgggagttt ctattatcta    120

gaaggttact gtgaaccttt cagaaaagtg gaaagcaacc aaaagagctg tctcaaagac    180

tgtgtccccc cagagtttgt ccagctctta ctgtagacac tctgaacagg cacggttatc    240

tcatgtccaa agctcataac agcacattag aagaaagtgg ggagcctgtt agaagcaggc    300

atattgatag tgtgggagaa gacatagcaa attacttagc agatatttta aaaattttaa    360

aatccaacag cagtctgagg caaatgattc tgnatacctc agggctgana gaatcacttt    420

atacatattt ggtatagccc tttcatttta tgaaagtgtt tacataccnn agactngatc    480

ctataataat accttatgaa tatactttac ttttcatcat ggaaaatgtg aatatactng    540

cntgatggtt aagaagaagg ccggagggtt cctaccntnc ntgaancctn ccttaaaaat    600

aatccnngtt taaanngtgg ncttggnaaa ttccttantt tcccaaaa                 648
```

<210> SEQ ID NO 259
<211> LENGTH: 224
<212> TYPE: DNA
<213> ORGANISM: Homo sapiens

<400> SEQUENCE: 259

```
ggtacttcaa aaagaacatc aggattaatg ttcctcagag tatgttctgc tgcttgaact     60

ttacttaatc ctgcttgatg aggttggaag aaaagtctat tcatattggc tagttccacc    120

ttgtcataat caaagagtag caacttacca atgccacatc ttgtcagcat ttcagcagtc    180
```

acactaccta ctccaccaac acctactatt gctacggcaa aggt 224

<210> SEQ ID NO 260
<211> LENGTH: 584
<212> TYPE: DNA
<213> ORGANISM: Homo sapiens
<220> FEATURE:
<221> NAME/KEY: misc_feature
<222> LOCATION: (1)...(584)
<223> OTHER INFORMATION: n = A,T,C or G

<400> SEQUENCE: 260
ggtacttcaa actctcttaa cggtgatgct ctgacattca ctactacatt tactctgcaa 60
gatgtatcca atgactttga aataaatatt gaagtttaca gcttggtgca aaagaaagat 120
ccctcaggcc ttgataagaa gaaaaaaaca tccaagtcca aggctattac tccaaagcga 180
ctcctcacat ctataaccac aaaaagcaac attcattctt cagtcatggc cagtccagga 240
ggtcttagtg ctgtgcgaac cagcaacttc gcccttgttg gatcttacac attatcattg 300
tcttcagtag gaaatactaa gtttgttctg gacaaggtcc ccttttttatc ttctttggaa 360 ggtcatattt atttaaaaat aaaatgtcaa gtgaattcca gtgttgaaga aagaggtttt 420
ctaaccatat tgaagaatgt tagtgggttt tggggccctg ggcatcgaag aatggtgtgg 480
ttcttttctg ggaaactgna taatcttaat tggacttaat ccagnatgat gaagaaaccg 540
caggaattcc cattnggaan gggataaatc tngcttaatt ggan 584

<210> SEQ ID NO 261
<211> LENGTH: 526
<212> TYPE: DNA
<213> ORGANISM: Homo sapiens
<220> FEATURE:
<221> NAME/KEY: misc_feature
<222> LOCATION: (1)...(526)
<223> OTHER INFORMATION: n = A,T,C or G

<400> SEQUENCE: 261
ggtacttgat gttctgcagc ttctgaaagg cttcctgata ctgctcaggg gtgtcaaggc 60
tgaagatgct cttccacact gcagtcaccc tctccacgaa agacccttcg gtgcccgtgt 120
tccaagtgtg gtaagaggag gagcttttgc cctctgaaag ctgcttttcc tccagatgcc 180
tggacagtag ctccagaagg caaaacacca atctctgacc ctgtagactt tcatgcagct 240
gcagggcttc ctgggctccc acccagttgt tggccagaag cagctcttgg gcacatctga 300
gagccaggga agcagacaac tcatcctctc ctacgatggc agccaactct gcagccgttc 360
taagtgatgc cgcatccccc tttttggcca aaactttggc tgcatcataa gcacaagtgg 420
cccctaaata gcatttggca gctacagcat agtggccatc tctttctagg acnggtcccc 480
agctgangna cctgcccggc gggcgcttct aaanggcgaa atcttg 526

<210> SEQ ID NO 262
<211> LENGTH: 703
<212> TYPE: DNA
<213> ORGANISM: Homo sapiens
<220> FEATURE:
<221> NAME/KEY: misc_feature
<222> LOCATION: (1)...(703)
<223> OTHER INFORMATION: n = A,T,C or G

<400> SEQUENCE: 262
cgaggtacag aggctgcaag aaggtggcat agagggctga aggtctgggt ggcagggcca 60

```
ctcctttaat aaaccaatgt catgctcaca ctcctattgc ctaccttggc atgctggatc    120

agctcacaga tgcaggatca agtcttgaaa gccaatcaga aaatccttca taggcttaca    180

aaggaccacc catggaacat tgtttcccgt aagactgaaa agacaaacta caccaaccac    240

caccactctt ctttttcctt tttggcccca tcaaaggaca tggagaaggt agacaagttt    300

tcttatccct acttttctaa ctcgaggatt ctccaaattt acatcagcag ctctaaggat    360

attcctcaca ggtcacaaac tgaaccaaaa atgaaaatcc tttctataaa actacacatt    420

ctttattcat acntatgact aaaggctact gaatggnacc tgccccggcc ggccgttcga    480

aagggccaan ttcaacacac ttggccggnc cgtactanat ggaatccnaa ctttgggacc    540

caagctttgg cggtaatcca tggccataa gcttggttnc ccgggggga aaattggtat    600

tnccgnttac caatttcccc accaaccntt cccaanccc gaaaccntta aaggggtaaa    660

anccttgggg gggccccaaa nggggtgggc cttaacttcc ann                      703


<210> SEQ ID NO 263
<211> LENGTH: 475
<212> TYPE: DNA
<213> ORGANISM: Homo sapiens
<220> FEATURE:
<221> NAME/KEY: misc_feature
<222> LOCATION: (1)...(475)
<223> OTHER INFORMATION: n = A,T,C or G

<400> SEQUENCE: 263

ggtacttgtt agcttacccc aaaataatac ctggtatacc ggacccaata tctgctgatt     60

gatctaacct aaatgaatac aaaccatttc agaaaaagat atacaataga ccacatatcc    120

aggtcatgaa aattaaagct ttcaggtcac ctagcttagt gactattgct tttctgaccc    180

tagactcttg aaagcctatt taaactggcc tctttctcca caccaaaact gataaaaagg    240

agactgatta tgagccagga tttacacaga gattctctat ataaggcata aaggtgaggg    300

gtgagagaga gagagagaga gagagagaga gagagagaga gagacgtgag ggagggagag    360

aaaagagaac agacngaaga tnagagaaag agaaaggtat acagtctggn gcctcaattc    420

cagtatgntg atttggcttc aacacccgng tacctggccc ggcnggccgn tngaa         475


<210> SEQ ID NO 264
<211> LENGTH: 601
<212> TYPE: DNA
<213> ORGANISM: Homo sapiens
<220> FEATURE:
<221> NAME/KEY: misc_feature
<222> LOCATION: (1)...(601)
<223> OTHER INFORMATION: n = A,T,C or G

<400> SEQUENCE: 264

ggtactacaa aaaccaagtg ctcgattacc acttaacatg ttcagcttga aatgactgct     60

acctttgcct tcaattcctt cccacacacc caggtataca aatatctttt ataccaagag    120

tccttgtgaa agtaaataga gggaactccc agggataagg gagggcaaaa aacaggaagc    180

acttgaagcc aaaatctgga gcaactttta agaaggaaga gacgtccgtc ctattttcat    240

atctctgcat ggatctccca tggagaactt gagttaaatg taatgattac acgtggcaga    300

aagacaactc tctagcacag tgtttctttc acataggctg ctacattcat tccataagct    360

caacaatttt aataaaaaat atttctgcta aatactttat attcatcatc ataaaaaatg    420

cacagccatt tgaaaaaaan ggcaattacc ctaaatgaat attgcccaaa gcacagatca    480

actttatata nggattcttt ccttggtctg aaaaatcgca ancggaactg gcagacttta    540
```

```
tttaccaacc atggattttg nccagcatgg agttaaattt antgctgtct ggagcaggaa    600

a                                                                    601


<210> SEQ ID NO 265
<211> LENGTH: 643
<212> TYPE: DNA
<213> ORGANISM: Homo sapiens
<220> FEATURE:
<221> NAME/KEY: misc_feature
<222> LOCATION: (1)...(643)
<223> OTHER INFORMATION: n = A,T,C or G

<400> SEQUENCE: 265

actatgaaag gcaggtttcc ttgtctggag gaaaaggtcc ttgagacacc acaggaaatt     60

cacaccgtaa gcagcgaggc tgtcagcttg ttggaagagg tcatcactcc ccggaaggac    120

ctgcctcctt tactcctcaa attgaatgag aggcctgccg aacgcctgga ttacctgggt    180

gtttcctatg gcttgacccc caggctcctc aagttctgga aacgagctgg atttgttcct    240

gtttatctga gacagacccc gaatgacctg accggagagc actcgtgcat catgctgaag    300

acgctcactg atgaggatga ggctgaccag ggaggctggc ttgcagcctt ctggaaagat    360

ttccgacggc ggtcctacct tgctctctac cagttcaata cctnggccgc gaccacctta    420

gggccaaatt cacacactgg cnggcgtact aatggatcca cttngttccc aacttggcgt    480

aatcatggca taactggttc gggngaaatg gtatccgtta caattcccac acatacaanc    540

cggaanntta agtgtaannc tgggtgctaa tgatgactac ttncttaatg ngttggctac    600

tgccgtttca tcgggaactt ntgccattgn tataatgcnc ccc                      643


<210> SEQ ID NO 266
<211> LENGTH: 582
<212> TYPE: DNA
<213> ORGANISM: Homo sapiens
<220> FEATURE:
<221> NAME/KEY: misc_feature
<222> LOCATION: (1)...(582)
<223> OTHER INFORMATION: n = A,T,C or G

<400> SEQUENCE: 266

actgtttacc agatctttgc agatgaggtg cttggttcag gccagtttgg catcgtttat     60

ggaggaaaac atagaaagac tgggagggat gtggctatta aagtaattga taagatgaga    120

ttccccacaa aacaagaaag tcaactccgt aatgaagtgg ctattttaca gaatttgcac    180

catcctggga ttgtaaacct ggaatgtatg tttgaaaccc cagaacgagt ctttgtagta    240

atggaaaagc tgcatggaga tatgttggaa atgattctat ccagtgagaa aagtcggctt    300

ccagaacgaa ttactaaatt catggtcaca cagatacttg ttgctttgag gaatctgcat    360

tttaagaata ttgtgcactg tgatttaaag ccagaaaatg tgctgctttg catcaacaga    420

accatttcct caggtgaagc tgtgtgactt ttggattgca cgcatcattg gtgaaaagta    480

ttcaggagac tgtggaggac tccactacta nccctgaagt cttcgagcaa ngtacaccgt    540

cctanaatgt ggcatgggag tatattatgg anctatgcca tt                       582


<210> SEQ ID NO 267
<211> LENGTH: 565
<212> TYPE: DNA
<213> ORGANISM: Homo sapiens
<220> FEATURE:
<221> NAME/KEY: misc_feature
<222> LOCATION: (1)...(565)
```

```
<223> OTHER INFORMATION: n = A,T,C or G

<400> SEQUENCE: 267

actttgggag gctgaggcgg gcagatcaca aggtcaggag ttcgagtccc agcctggcca     60

atatggtgaa accctgtctc tactaaaaat gcaaaaatta gccaggcatg gtggtgcatg    120

cctggagtcc cacctacttg ggctgaagc agaatggctt gacccaggag gtggaggttg    180

cagtgagcca agatcatgcc atggcactcc aacctgggtg acagagcaag actccatctt    240

aaaaaaaagt atactaatgt ccctcaagtt cttccatatg aggtaaaggg atccaagatt    300

aaggttgaaa ttcttaaact gttcaacaat tttgtggtgt catcaaaaaa ggaatatttc    360

atatatatta atttaacctc aatgatcaac attgttaaaa gtcagtatgg agaaagatca    420

ttctgacctc ttcagaaacc acctggtata tgaacattct gatcccanat tattttggga    480

nctaaggacn atggtgaaaa gaatcncnan attaaaagtt ctattttcna tggaccttng    540

gcccgngaac acncttaagg gccna                                          565


<210> SEQ ID NO 268
<211> LENGTH: 661
<212> TYPE: DNA
<213> ORGANISM: Homo sapiens
<220> FEATURE:
<221> NAME/KEY: misc_feature
<222> LOCATION: (1)...(661)
<223> OTHER INFORMATION: n = A,T,C or G

<400> SEQUENCE: 268

cgaggtacta caaaaaccaa gtgctcgatt accacttaac atgttcagct tgaaatgact     60

gctacctttg ccttcaattc cttcccacac acccaggtat acaaatatct tttataccaa    120

gagtccttgt gaaagtaaat agagggaact cccagggata agggagggca aaaaacagga    180

agcacttgaa gccaaaatct ggagcaactt ttaagaagga agagacgtcc gtcctatttt    240

catatctctg catggatctc ccatggagaa cttgagttaa atgtaatgat tacaccgtgg    300

cagaaagaca actctctagc acagtgtttc tttcacatag gctgctacat tcattccata    360

agctcaacaa ttttaataaa aaatatttct gctaaatact ttatatcatc atcataaaaa    420

atgcacagcc ttttgaaaaa angggcanta cccctaaatg aatattgcca agcacagatc    480

aacttatata ggattctttc cttggttctg aaaaatcgca accgaactgg cagactttaa    540

ttaacaacat tgatttggcc agcctggagt tnaatttant gcatgtcctg gaggcnggan    600

aaatgatcca gaagtaagca ccaccgnctg cngggnccan gttcaagaac ttaagccngg    660

g                                                                    661


<210> SEQ ID NO 269
<211> LENGTH: 643
<212> TYPE: DNA
<213> ORGANISM: Homo sapiens
<220> FEATURE:
<221> NAME/KEY: misc_feature
<222> LOCATION: (1)...(643)
<223> OTHER INFORMATION: n = A,T,C or G

<400> SEQUENCE: 269

actgatggga aggccaatat ttgatgcaat caccacagtg agggcagatg ccagttcaat     60

actgaagcca ctagagggtg tgatcggtgt cagatccttc cccatggtct ggataactct    120

tcttccccaa acccacagac caacacagat accaacacca ccatagagta gaagccatat    180

tggtgttgcc acttttgaag aaacatctcc tgtgccataa accaaatata aagcaaccag    240
```

```
aggcccaatg gcattgctta cgtcattgcc accatgggcg aatgacccaa agcaggctgt    300
aaggatctgc aggaactgga aganggagag agacttcagg gcttatcctg ggcataccat    360
tctttctaga agaaccctta ctttcttttc tgncacctaa acccatcttt gnctttgcac    420
ttatggctat cttaaaangc tnaatgaaag ncagacacng cattgcagta actggggnac    480
tgncatttna antcccttct tggagctgna ntaggcctgt cacttctcat ttcttngccn    540
ttggtaactt ttttgnncgg atgaatcnga gnatgcncat atgcntggat tganntactn    600
tatggcctaa gggtgnncgn ggtcctcant tcncttggan aga                      643
```

```
<210> SEQ ID NO 270
<211> LENGTH: 650
<212> TYPE: DNA
<213> ORGANISM: Homo sapiens
<220> FEATURE:
<221> NAME/KEY: misc_feature
<222> LOCATION: (1)...(650)
<223> OTHER INFORMATION: n = A,T,C or G

<400> SEQUENCE: 270

gggccacatc tgccagagcc tggagtctgc gaaggccggg acccggttcc ccggcccaca     60
gtgggggtgt gcaaacccga gagaactggg ttgcaaattc gtgaagaatc agcatcatgt    120
ttggcagctg agtattggag ccaggagcct gccatgaggt tttgagaaca gagtgctgtt    180
ttagagctgg cagcagcatc tcagcccaag agaaggttat attcccagag gatgtcagtc    240
ccaaggacca gtagctgcca tcagtttgga ttctgaaaac taactggcat caacactggg    300
tgtagaaaca tgcttgcctt atgtatcaga ggacatgctc agcaagatcc aagagatata    360
tttggcaact ttttctagaa aaggcacatt gggtatcatt cattacattc ttgagttttt    420
ttgggttttt tttttttttt tgaacagtct tgctgnattg ccangctgga atgtggtggc    480
caatcacanc ttattgcatc ctaatcaccc aggcctaagc aatcctcccc ttganctggg    540
actanggtta cagncacctg gtaaaatttt ttttgtgaac ggntcttatg tgccagctgg    600
nttaggttct nggntnaang gcctctgcta nnttcaaggc nagccatttg               650
```

```
<210> SEQ ID NO 271
<211> LENGTH: 620
<212> TYPE: DNA
<213> ORGANISM: Homo sapiens
<220> FEATURE:
<221> NAME/KEY: misc_feature
<222> LOCATION: (1)...(620)
<223> OTHER INFORMATION: n = A,T,C or G

<400> SEQUENCE: 271

ggtacacagg tcccaagctc tttaaggagc ccagtagtaa atcaaacaag ccgattattc     60
acaatgccat atcccattgc tgcctggctg gaaaagtgaa cgaaccccac aagaattcca    120
tattggagga gctggagaag tgtgatgcca atcactacat catactgttt cgtgatgctg    180
gctgccagtt cagggcgctt tactgctact atcctgatac tgaggaaatc tacaaactca    240
ctggcacggg gccaaagaac atcaccaaga aaatgatcga caaactgtat aaatacagct    300
cagaccgaaa acagtttaac ttgatcccag ccaaaaccat gtctgtcagt gtggacgcac    360
tcacaatcca caaccacctg tggnanccaa cggnctgcat gccaagaagg ccaaactcgt    420
aatgacccgg tgcactggcg tccaagggtg accagactcg taaatgatgc cttgtggtgg    480
atcaaaggtg cacgggggcc tanttantgg ttanctattt ggtcctgccg gcnggcgttn    540
```

aaagggaatt caccactggn ggcgtctaag gaccacttgn ccacttgnga anatggntan 600
gttctnggga aanttccccn 620

<210> SEQ ID NO 272
<211> LENGTH: 670
<212> TYPE: DNA
<213> ORGANISM: Homo sapiens
<220> FEATURE:
<221> NAME/KEY: misc_feature
<222> LOCATION: (1)...(670)
<223> OTHER INFORMATION: n = A,T,C or G

<400> SEQUENCE: 272
cgaggtactt tatattacta aatgtctgaa gacaaaagag caattggaaa tctctgtttc 60
ttgtttcgtc atacatagga aggcgacgtg atgcaaattt taacacaaga ttttattaaa 120
gacgggcaaa ttggtgaggc atacctgaat ttctggagat atacaaatgc gtgaggctgg 180
catcatatgc aaatgtggct ttacaaattg gttttatttt ctagctgtat ttaaagaggt 240
gttcaaaatt ccctactaat caagaagcac ccctgaaaaa actatgagat aagatagtgt 300
tattaatggt ttgcatctaa agaccaggaa acacattagc caatacagtc cacaatcggt 360
gaaatgctgc cgtgcnaaat gcacgtgcat atgcnttttt actatattcc ctnagagacc 420
gtaaaacaac naccaccacc aaaaaaaaac ngtgctcnta aatngnggac naacctttcc 480
aaaccaccgn cttactctta ctggggttta agggaattca ggaagcttcn tttanccana 540
aagctnaacc ccttcagttc ataanctttt nccttggaat aaggcctgnt ntggctacct 600
aaaaccaagt ctgggggaaa aggactcatt ccattattaa cnnttacncc taagggang a 660 ataagggnnt 670

<210> SEQ ID NO 273
<211> LENGTH: 688
<212> TYPE: DNA
<213> ORGANISM: Homo sapiens
<220> FEATURE:
<221> NAME/KEY: misc_feature
<222> LOCATION: (1)...(688)
<223> OTHER INFORMATION: n = A,T,C or G

<400> SEQUENCE: 273
acacaggtaa ccttatgcag cacattgtgc taaaagtatg gaacagttaa cactttcagc 60
cattactgaa aataaacatg tagaaactaa gcaacaagtt aaaatacagt aatgcacaac 120
ttaacaattt taagttttcc acatggagca ataaagcagg taactgaata atttaaggag 180
atgcaaatgg ccctcttcat tcttaattct cggcaattta ctcaggaaaa taaatttctg 240
gtcgcagccc gaacagttcc agtccgatct caccttgatg gaaagtcttc attatctgtg 300
cttgcccgag gacttatgaa tgnttcttct ctttcttttc ttctgaactg gccccgttct 360
ctttcttttc tatcctttct ttatcatgcc tggactcctt ttggcacccg aaggagaatt 420
taaccatctt ctcagaatta aatggaatca ctggcttttt cnttggcctg aagaatttga 480
cttanttttt tncttggctt tctcaattng attaagggga ttcnccaagg acttttactt 540
ttaaggtttt gnaaacccca atnggtncat tcttcccctt taccgctctt gggttaaanc 600
ccggggggac tttaccgggc cttggttgaa ngaacccntt ttcggtcttt tcngggcctt 660
ttaacttttt ctcnctttnn ctgggagn 688

<210> SEQ ID NO 274
<211> LENGTH: 674

<212> TYPE: DNA
<213> ORGANISM: Homo sapiens
<220> FEATURE:
<221> NAME/KEY: misc_feature
<222> LOCATION: (1)...(674)
<223> OTHER INFORMATION: n = A,T,C or G

<400> SEQUENCE: 274
atttaaacct ggtttggata tgcgcctgta tgaggaagat gatttggacc ggttagagca 60
gatggaagat tcagaaggga cagtgagaca gataggtgca ttctctgaag gcatcaacaa 120
tctgacgcac atgttaaaag aagatgacat gtttaaagat tttgctgccc gttcccccag 180
tgccagcatt acagatgaag actcaaacgt ttgaccgtag cacctggatg aacattagga 240
gtgcttagtc ttttttctac ttgcttttcc aaacactcac agtatataca acaggcagcg 300
gattgnctat tgnttgttgn tccaacttct gctgccagaa gtttaaacag aaagcaggaa 360
taatgtgccc attctgaagt tgccacaaaa aataagaccc tggtgaatga aaatataatt 420
ggttttcttc taattaatgg aaaaatctgg gatatattat atttaaaggt ggtgcattta 480
aagaatgagt attttacccc gaagtggttc ccttcatatt ccccggattg aaggatttga 540
nggaccgtac cnggatgggn atgaatttgg tacttcatgg tcacttgaac ccnctaagtn 600
ggccnttttt ggattcanaa tcatatgggg aacttcttta agccttcagg ggccncttaa 660
tgccnnncca cctn 674

<210> SEQ ID NO 275
<211> LENGTH: 638
<212> TYPE: DNA
<213> ORGANISM: Homo sapiens
<220> FEATURE:
<221> NAME/KEY: misc_feature
<222> LOCATION: (1)...(638)
<223> OTHER INFORMATION: n = A,T,C or G

<400> SEQUENCE: 275
ggtactggca tggcaccaac atttgctcag cttctggtga gggcctcagg aagcttacag 60
taaaggcgga aggtgaaggg ggagcaggca tatcacatgg cgagaaagag gggagaggtc 120
tcagactctt ttaaacaacc atatctatgt gaattgagtg agaactcact catcaccaag 180
gagatggtgc tgagccattc atgaaggatc ccctctcatg atccaaatac ttcccaccag 240
gctccacttc caacactggg aattacattt caacatgaga tttggagggg acgagcatcc 300
aaaccatatc agatggtgag acaggagaac tttgtgtgtc cagctgcact ggtctgaaga 360
tataactaag tccctggact ttttctcctt aattggagaa ttcctaatgt tcatgatcag 420
cctgantgac cagtggctga ctggcctgaa aggggagata aaacngacca cagctttctt 480
catagaccaa tttaaccttt attcatctgn gcagcagaag ggactggncc anatanccat 540
caggtaggng cttgaatatg ggtactttcc nanatacttg ccggccggcc ntttaaggca 600
attccaccaa tggggccgtc tannggatcc actcggnc 638

<210> SEQ ID NO 276
<211> LENGTH: 638
<212> TYPE: DNA
<213> ORGANISM: Homo sapiens
<220> FEATURE:
<221> NAME/KEY: misc_feature
<222> LOCATION: (1)...(638)
<223> OTHER INFORMATION: n = A,T,C or G

<400> SEQUENCE: 276

-continued

```
ggtacgtcag atctacagcg aacacaacta ctgccgcctt atcctctaaa tggggagcat     60

acccaggccg gaactgccat gtccagagct aggagagagg acctgccttc tctgagaaag    120

gaggaaagct gcctactaca gagggctaca gttggactca cagatgggct aggagatgcc    180

tcccaactcc ccgttgctcc cactggggac cagccatgcc aggccttgcc cctactgtcc    240

tcccaaacct cagtagctga gagattagtg gagcagcctc agttgcatcc ggatgttaga    300

actgaatgtg agtctggcac cacttcctgg gaaaagtgat gatgaggagc aaggacccac    360

cgttcctgca gacaatggtc ccattcccgc tctagtggga gatgatnntt agagaaagga    420

ctggcccagc tcttgcagtc atccactatg aaggatcctg taatgtgacc ccagttccac    480

actgatctca ccgctgatgc tgcagaacag anatttgatg acgaataggc ttggngntta    540

tgcctctatg aggaaagtat ctngacnaga aacttgaaac cangnttntg tttacagtct    600

ttgatggtcc atcatcatga nnngatgaac gccaaccg                            638
```

```
<210> SEQ ID NO 277
<211> LENGTH: 734
<212> TYPE: DNA
<213> ORGANISM: Homo sapiens
<220> FEATURE:
<221> NAME/KEY: misc_feature
<222> LOCATION: (1)...(734)
<223> OTHER INFORMATION: n = A,T,C or G

<400> SEQUENCE: 277

ggtacagaga tagatgaatg gaaatgggta agggaggtgt tcattcacat ccatctaact     60

gcaaaataca aaagtaagaa gtcattgaca tgaagcaacg acgaccaaga cgttctcaga    120

tctaaaggtg aatgatctca gtcagcctgg aaatgcacaa ggtggaaaaa taacataaaa    180

aagccataag accttgaaga acatcaatgt caaagataaa ttctaaagtc ccagagaaaa    240

aagaatggga atcaaattga cctcagacta tacgtgagaa acacggagag ccagaaaact    300

gtgatgttcc atcctcagag tttgaaggaa atatttgaag gctgaatttt acatccagct    360

taactatcaa ggcatgccaa gtcatgttat tcttaggcct tcaaggnctt ngccctttt     420

ctcngaaaag cccgaatttn aaatgctctt aaagaccgtt cttcaacccn gaagagaaaa    480

gaaanccngg gangggtgct cttgagatat ttcagtcncc cacaggttnc ccaaatnggg    540

cctaaggaaa ttccgaagag gtcncgaaat nttnacccat taccttcccc caatnggga     600

accccccgac agggntttan ccatnggggt taaagggttt ttgacccggg ggggccttgg    660

caaggtancc tggccccggg cgggcccntt cnaaangggc caaanttccn gnccccccttg   720

ggggggccgg tanc                                                      734
```

```
<210> SEQ ID NO 278
<211> LENGTH: 586
<212> TYPE: DNA
<213> ORGANISM: Homo sapiens
<220> FEATURE:
<221> NAME/KEY: misc_feature
<222> LOCATION: (1)...(586)
<223> OTHER INFORMATION: n = A,T,C or G

<400> SEQUENCE: 278

acatggtgaa tggaccacca cattttacag aaagcacagt gtttccaagg gaatctggga     60

agaattgcaa agtctgtatc tttagtaagg atgggacctt gtttgcctgg ggcaatggag    120

aaaaagtaaa tattatcagt gtcactaaca agggactact gcactccttc gacctcctga    180

aggcagtttg ccttgaattc tcacccaaaa atactgtcct ggcaacgtgg cagccttaca    240
```

```
ctacttctaa agatggcaca gctgggatac ccaacctaca actttatgat gtgaaaactg    300

ggacatgttt gaaatctttc atccagaaaa aaatgcaaaa ttggtgtcca tcctggtcag    360

aagatgaaac tctttgtgcc cgcaatgtta acaatgaagt tcacttcttt gaaaaccacc    420

aattttaaca caattgccaa ataaantgca tttgccaaaa attaatgact ttggattatc    480

accctggacc ccaaccatac caaggtggct ggctatgttn ccaggaagtn aangngcccc    540

cttatttggt agaatatatc agtancttgg gcgggaacac ccttan                   586
```

```
<210> SEQ ID NO 279
<211> LENGTH: 664
<212> TYPE: DNA
<213> ORGANISM: Homo sapiens
<220> FEATURE:
<221> NAME/KEY: misc_feature
<222> LOCATION: (1)...(664)
<223> OTHER INFORMATION: n = A,T,C or G

<400> SEQUENCE: 279

accaccgagg ctagcacagt caagcctcca gctaagctgg atccctgaag cctgctatca     60

tgcagacagg ctatgcggct gcctcggacc atgctaggcc acttgctggg gtgtcaacct    120

accaccaaag ggtcttttta gcaaacctca tggggaacag gaacattcct gttcatccct    180

ggccacaggc tgcagaccca gcactggccc ttgcgtgagt cagagcctgg ggctggccct    240

agccccttct actgacttcc tcatttaagc caattatata agctcacatt gatcagggag    300

ggagggaaag agctaaagag ggtcacacaa gtggctattt tccctgcagt gtttctgtgt    360

ggtgaaaata acccagtcca ctaaggggcg ggagtgaatg gatggctgga ttttccccaa    420

gctccttata gcctaatgtt gtcaggatgt gagtatgagg aatttagcct cttatagtga    480

aatgagtcca actctgggct ttgcttanan gaaagctncc gtcaggcttn ctataatatg    540

aaaagaagtc accattgggg aactagagac cccagacctt ttcatatgga tatttgagaa    600

tgtaatgcat ntangcctng tgctggaact ttaggcctnt aggcnggtta aaacacttga    660

tttt                                                                 664
```

```
<210> SEQ ID NO 280
<211> LENGTH: 448
<212> TYPE: DNA
<213> ORGANISM: Homo sapiens
<220> FEATURE:
<221> NAME/KEY: misc_feature
<222> LOCATION: (1)...(448)
<223> OTHER INFORMATION: n = A,T,C or G

<400> SEQUENCE: 280

actaccacag actgttgact tttagtttct taaagagaaa aattgccttt ttactagaaa     60

gcctttgtat attgcaattt ttctgtttgg gaaaatctaa ggatttactg tggttagtct    120

tacagaagaa atgtggattt gataaactag tgcctatgat tttaacttat gtttgatata    180

tagtagtaag ggttttatga atgttgatta ttttgtgcca acagcccaga attgtcactt    240

atatgtaagc agaaaacaat gagctctgct tccaaagtta tttaattttc tcagtgtttg    300

aatgttattt tttgtaagtg tgttaataaa agtgtaaaga attggaaaaa atataaatat    360

tcttaactca agcatttgct ggatcatttt tctacaaaac ttggttgtac tgngaacctg    420

tgtatcancg ttgtgtaaac ctagtacc                                       448
```

```
<210> SEQ ID NO 281
```

-continued

```
<211> LENGTH: 677
<212> TYPE: DNA
<213> ORGANISM: Homo sapiens
<220> FEATURE:
<221> NAME/KEY: misc_feature
<222> LOCATION: (1)...(677)
<223> OTHER INFORMATION: n = A,T,C or G

<400> SEQUENCE: 281

gcgtggcgcg gcccgaggta caccttcaca gggaatccgc aggcggggat cttcagtctc     60

ctttaacacc ggaaagtatc aacgggacag atgatgaaag aacacctgat gtgacacaga    120

actcagagcc aagggctgaa ccaactcaga atgcattgcc attttcacat agttcagcaa    180

tcagcaaaca ttgggaggct gaactggcta ccctcaaagg aaataatgcc aaactcactg    240

cagccctgct ggagtccact gccaatgtga aacaatggaa acagcaactt gctgcctatc    300

aagaggaagc agaacgtctg cacaagcggg taatttcagg gctgatgtct atagggattt    360

agggctaaca ggttttcttg atcagaagaa attttgcatg tagattcagc acagggatat    420

cttctagttc taggatgtca gaacatagat atgggttgna tgatatgcat ttggttgatt    480

aagaaaaata ttttccatag tttaatgaga atgaagaata taccccttttg aagcaacaaa    540

ncatgtgatt cccatattat catggggcta gngtatgcnc agtcctgccc ggcggcgtaa    600

ggcaatcagn cctggngccg tctnnggacc acttggccac tggngacagg caactgtctg    660

ggaatgncct ccatccc                                                   677


<210> SEQ ID NO 282
<211> LENGTH: 691
<212> TYPE: DNA
<213> ORGANISM: Homo sapiens
<220> FEATURE:
<221> NAME/KEY: misc_feature
<222> LOCATION: (1)...(691)
<223> OTHER INFORMATION: n = A,T,C or G

<400> SEQUENCE: 282

cgaggtacct tgctgtttat tccttagtct agcagcatcc ttagtttgta gtatatctta     60

cttagttgca actaaaaaaa attgctagcc taggctttaa ctgggagttt ctattatcta    120

gaaggttact gtgaaccttt cagaaaagtg gaaagcaacc aaaagagctg tctcaaagac    180

tgtgtccccc cagagtttgt ccagctctta ctgtagacac tctgaacagg cacggttatc    240

tcatgtccaa agctcataac agcacattag aagaaagtgg ggagcctgtt agaagcaggc    300

atattgatag tgtgggagaa gacatagcaa attacttagc agatatttta aaaattttaa    360

aatccaacag cagtctgagg caaatgattc tgtatacctc agggctgaga gaatcacttt    420

ataacatatt tgntatagcc ctttacattt tatgaagtgn tttacataca tcagagctgg    480

atcttataat aatacattat gaatataact ttaacttttc atcatgaaaa tgtgaattat    540

actgacctga tgttaagaan aangccggaa ggtttctaac atacctgaaa tctcccttaa    600

aataattcca ggtttaaang tggncttgga aanttcctta ctttccaaaa tntatgacct    660

gccgggggcn ntnnaaggng aatccnncct n                                   691


<210> SEQ ID NO 283
<211> LENGTH: 668
<212> TYPE: DNA
<213> ORGANISM: Homo sapiens
<220> FEATURE:
<221> NAME/KEY: misc_feature
<222> LOCATION: (1)...(668)
<223> OTHER INFORMATION: n = A,T,C or G
```

<400> SEQUENCE: 283

```
acatggttct gtgacatggc tggaggtggg cgttctggac aagtaaacaa tttactgggg     60
aggtgtctgt gtttcacact taggtcgcta agtttttagc caaggcttta gttgtcctcc    120
atgagcaatt gtagaaattg gaaatttgta atgatttttt atgagaaagg ccacgaatgt    180
gtgttactat tagagtatat ccacatattg tccagtcatg gaaaatggcc taaaagataa    240
tttacctgca aaacagaata ttatgcagct attaaaataa tgcatatgaa gatttgccat    300
agagtggaaa aatgcttgtt aggtaaaaat caaaaaaaca tgtaggaaac aaaattttac    360
atatttgatc tccactgtat aaataaataa aatggagaaa catttgagaa aaatcatcca    420
ataatggttg tctgtgggtg gtaaaagcaa ttgaaatgtc ttccttacac ttttaataat    480
ttttaaaaag tatgtaaaat gccaattatg acaatgctaa gctagatgaa catcccattc    540
aaattggaag cccatttaaa atttagaaag cncggttgga ttcccttctc tatccttttt    600
taaagcaaat ggcccannnc tggngnnttt ttgacccaac ctttcaaaat tnggctaact    660
ttntgaat                                                             668
```

<210> SEQ ID NO 284
<211> LENGTH: 777
<212> TYPE: DNA
<213> ORGANISM: Homo sapiens
<220> FEATURE:
<221> NAME/KEY: misc_feature
<222> LOCATION: (1)...(777)
<223> OTHER INFORMATION: n = A,T,C or G

<400> SEQUENCE: 284

```
acagtattta agggattttc cttttagctt ttcatctcca gtggcattaa acataaaaag     60
accctggcat tttttcacat acttgaatcc ctaaatgcac ctgtctttca ctttttgaga    120
cagactgaat atatctaaaa tttccagcaa taaaaaaaaa gcatttaact tgcaccaagc    180
aagaaaatat aaatacagtt aactgcatta agataatcac gttaaaattg ttactatgca    240
gcacagaact tcattcttat agtattcttg ggttcaacct ttgaatcaat tttaccactg    300
attaaataaa tgactcaaag acatctgtaa gtcatgctgc tgtgttttga aagtctttaa    360
ctaaattaag aatgcagaat ggatagtgat tattcaatta gaatttaagt aaggggatgg    420
tgatantana aggctggaaa atnccttaat ttttaaaaaa atcagaatag gcntttaaat    480
aggtaaaatc actttcaatt nttccccaaa acctgnangt ttcccggaaa aaaggtttta    540
aggctttnaa ggtggggaat gncccaaggt ttttaactta tnccatggaa gccanngcct    600
tgcatgggnn ccttagggna acccccngaa tcccnttccc aaaagggggg tttacccntt    660
tggaattnaa tttggggnaa ccttattngg nccttngggg nttaccttng gaaanaaaat    720
ttnnttttaa atnnttttcan ggggnnggaa atttaaaggc cttttttttt gggaaaa      777
```

<210> SEQ ID NO 285
<211> LENGTH: 692
<212> TYPE: DNA
<213> ORGANISM: Homo sapiens
<220> FEATURE:
<221> NAME/KEY: misc_feature
<222> LOCATION: (1)...(692)
<223> OTHER INFORMATION: n = A,T,C or G

<400> SEQUENCE: 285

```
ggtacaagct tttttttttt tttttttttt tttttttttt aaggatttac ttttcttaac     60
```

-continued

```
aagtgaacaa tttgcttcta agcgtcaatg aaaggcaaca cctccctnta atggccaaag    120

gaagagagtg gcagtaagct ggcttttcca atgngtcaca caatccttca tgccattaag    180

ttctccttgt tggaaaagaa attaggttgt tttgataact tagaaaagtt agttttagac    240

aacagtgact ttcagctaca aatacaaaat caaatccatg tatataaggc ttctgtaatc    300

gatgtcttag aggaacatct gctcattttc tccaagcccc agtcctataa atcaaggcaa    360

gtcaagtaat taagcttcaa ctattttggc agctttgcaa ttaaaatgag cnaagcacta    420

tatctatcct tcatatcngg atatattaaa ggtccaactt ggtacnccca atnttacatg    480

ccgagaggcc taaaatttnc nntttgggtt ccnggtttaa ttaaagncca taanggnctt    540

gcnacnaatc tttttcccct ncccaaggga aatttccctc nnattaccaa acccctgnct    600

caatttnttt ccccggnaat ttgaaaggcc gggtttntcc tttcaaaana aattttcccc    660

ggggattaan atttgggccc caatttctta nn                                  692
```

<210> SEQ ID NO 286
<211> LENGTH: 709
<212> TYPE: DNA
<213> ORGANISM: Homo sapiens
<220> FEATURE:
<221> NAME/KEY: misc_feature
<222> LOCATION: (1)...(709)
<223> OTHER INFORMATION: n = A,T,C or G

<400> SEQUENCE: 286

```
actgtgccag ggatattgag atgctctggg ggtgtattgt atacctgcca gttttcttca     60

tttctgaatt gagttttctt ttcttgatgt tggtttcctt catatcacct caaggtttag    120

atttgtgaag gaataagcat gatggaaata atagtcttga aaggagatat gttgtatata    180

atcaggagga agaggaagga aggacttacc catttttgata ttttgctgta ggtggccagt   240

tttgtttctc atagggaaat ctgacccacc tgtcatgttg gctcctaagg aactgctgtt    300

gtaagcggct catcaagagt tgaacttcac gtagccttgt tgggaatatg gaaaaggaag    360

aaagccacag gactgcccat tcagtcttgg gaagattggg atgattctgc acaagcaaaa    420

atgactgaag tttatgtata gacacacctc taccaatcca tcttcagctg actgaatgtt    480

gnatgatacc cttcttcaaa gcagangtag aatggtcang gttcacccat ggaattttct    540

acttaatttc gtttttngga atcaacttta ccnnaatncc aggtcccctt tnggaaaaaa    600

tccttaaatc ttttgctttt ttnaaaaaat aanttnggtt catanttaaa ggcccttggn    660

ttaanccang gttncnggtn ccnatttatt tgaacccttt gcccttana                709
```

<210> SEQ ID NO 287
<211> LENGTH: 231
<212> TYPE: DNA
<213> ORGANISM: Homo sapiens
<220> FEATURE:
<221> NAME/KEY: misc_feature
<222> LOCATION: (1)...(231)
<223> OTHER INFORMATION: n = A,T,C or G

<400> SEQUENCE: 287

```
acaagctttt tttttttttt tttttttttt ttttgtanag atgcgggtct cactatgttg     60

cccaggctgg tctcaaactc ctgggctcag gttctcctcc tgcctgggcc tcccaaagtg    120

ctgacatcac aggcgtgagc caccacaccc agcccctttg ggtgttttta aatataactt    180

tggcatttat aacaaatgca accacatgtt anatcttatt agaagtacct n             231
```

<210> SEQ ID NO 288
<211> LENGTH: 681
<212> TYPE: DNA
<213> ORGANISM: Homo sapiens
<220> FEATURE:
<221> NAME/KEY: misc_feature
<222> LOCATION: (1)...(681)
<223> OTHER INFORMATION: n = A,T,C or G

<400> SEQUENCE: 288

```
acctctcttt ccagcaccca ggccagtatt gagatcgatt ctctctatga aggaatcgac     60

ttctatacct ccattacccg tgcccgattt gaagaactga atgctgacct gttccgtggc    120

accctggacc cagtagagaa agcccttcga gatgccaaac tagacaagtc acagattcat    180

gatattgtcc tggttggtgg ttctactcgt atccccaaga ttcagaagct tctccaagac    240

ttcttcaatg gaaaagaact gaataagagc atcaaccctg atgaagctgt tgcttatggt    300

gcagctgtcc aggcagccat cttgtctgga gacaagtctg agaatgttca agatttgctg    360

ctcttggatg tcactcctct ttcccttggt attgaaactg ntggtggagt catgactgcc    420

tcatcaagcg taataccacc attcctacca agcagaccag accttnacta cctatctgac    480

accagcctgg ngngcttaat canggttatg aaaggcaaac gtgccatgac caangataca    540

acctggtttg gcaaggttga aactacaggc ttacctntgg accccgaggg gtcctnaaaa    600

tgaagtcctt ttgacattga gcccaggggt actcaaggnt ttgttnggca aaaancttgg    660

ccggaaccct angggaattn n                                              681
```

<210> SEQ ID NO 289
<211> LENGTH: 565
<212> TYPE: DNA
<213> ORGANISM: Homo sapiens
<220> FEATURE:
<221> NAME/KEY: misc_feature
<222> LOCATION: (1)...(565)
<223> OTHER INFORMATION: n = A,T,C or G

<400> SEQUENCE: 289

```
actcaaccta acttatagtt agcagctgga attctcaact cttccctgcc agcactatac     60

cacagtgtgg aagaaattag tcaaatgctt gttttcctgc ttctcttttc agctgttact    120

gtgctttgtt tgaaagtagt tttctctctc aaagccgttg cttatatcgt taagaatgaa    180

ggtttgtgtt taaaatttat tgcattgcaa agggtagttt cactgaagtc atgcaccatt    240

aaataagatg aaatatttgt atttattgtc ctacttccta agccgtaact tcttttcctc    300

tgtgaatttg cattgagtca ctcatgctac actacatcgc tttagtattt gagatggcat    360

ttatgtttcc tctcgtttat catgaaatgg ggtcagattc catcagattc cacctctgtc    420

aggtggactc ttgtctgcct tccatgatga gatttttttt tctccttccc tttctttaag    480

agaggctgcn gaactangng gcaatcaatt tggnaaccag tctctggntt tttttcatta    540

gtaatttcta tcatagttca ctggg                                          565
```

<210> SEQ ID NO 290
<211> LENGTH: 699
<212> TYPE: DNA
<213> ORGANISM: Homo sapiens
<220> FEATURE:
<221> NAME/KEY: misc_feature
<222> LOCATION: (1)...(699)
<223> OTHER INFORMATION: n = A,T,C or G

<400> SEQUENCE: 290

-continued

```
ggtacacaat tctgcatttc tctcttggta atgggatccc agttttattg caggaggcag     60

tgtgccagtc tcagtagatg gaacacgatt ggtctattca gccatgacaa ttctgttccc    120

tgctgtctta gctttgtttg cagctagagg tgcaatggta gctggctcgg gccaagggca    180

tctaagtgaa gatatgcaga gggagagagc aggaaacaga cttctgacga ggttttactt    240

tctgatagaa ggtgacaggt ccagctagtt tggcccttcc tcttcctcca cccctccttc    300

cttgaacgca gacatgattc ttggggatac agcagccatc ttgggaccat gaagtaacga    360

gcactgagat taaggcaaaa ggatcaagac gtgaccccta ccttcgtgga gttggtgaac    420

caataccatt aacccaccca tctccagaat ccatgctatg tggnaaaaca atcttctggt    480

tggttaaacc actgnaattc aaggtttncn ttncttgcaa ctgaatggaa gnccttttta    540

naaggtacct tgaccaaaat gccnaaggaa ncttggcctt tggaaattgg ancccgnaan    600

acctgggttt ttaagcccat tttggcnncn tttnggnaag ctttaagggt aaggcctgaa    660

cctttggccn aaagggggna actngggttc cccctttcc                           699
```

<210> SEQ ID NO 291
<211> LENGTH: 699
<212> TYPE: DNA
<213> ORGANISM: Homo sapiens
<220> FEATURE:
<221> NAME/KEY: misc_feature
<222> LOCATION: (1)...(699)
<223> OTHER INFORMATION: n = A,T,C or G

<400> SEQUENCE: 291

```
ggtacttggg gacttcaggc atacagcctg tccagaatat ggctatccta ctctcctact     60

cagaaagaga tcctgtccct ggaggctgta atttggagtt cgatttagat attgatccca    120

acatttactt ggagtataat ttctttgaaa cgactatcaa gtttgcccca gcaaacctag    180

gctatgcgag aggcgtagat cccccaccat gtgacgctgg gacagaccag gactccaggt    240

ggaggttgca gtatgatgtc tatcagtatt ttctgcctga gaatgacctc actgaggaga    300

tgttgctgaa gcatctgcag aggatggtca gtgtgcccca ggtgaaggcc agtgctctca    360

aggtggttac cctaacagct aatgataaga ccagtgtttc cttctctcct tccnggacaa    420

ggtgtcatat accatgtcat tggttgggac ccggttctaa atcatctgct ggctacattc    480

ctgntnacac ataccettgc aactttgang cnngaaaagg taagtggggc cttcctaagg    540

aaaaggnctt tccaaggggt cntcaatctt tttgncccgg ntnggntnct tnaattgggt    600

ntttggaccc cnaatttggg aaaccgaaat attnttnana ggctttannn nnggggaann    660

tntttnaaaa ccggntccnn nantggccct ttnaggtnn                           699
```

<210> SEQ ID NO 292
<211> LENGTH: 688
<212> TYPE: DNA
<213> ORGANISM: Homo sapiens
<220> FEATURE:
<221> NAME/KEY: misc_feature
<222> LOCATION: (1)...(688)
<223> OTHER INFORMATION: n = A,T,C or G

<400> SEQUENCE: 292

```
acagtcatcc cactacctgg ctatttcatt acttggtgct ctagacaagc tcccaagaac     60

tgactggatc ttggcttgtt ctgtttctgt cattgctaat ataatatgga aaacattgct    120

gaaaagaaca gagatggcca tggatatggc taggttaggt attcatatcc aaatatctga    180

actctaacct aatgtggata tgattctgta gcattatatt aaaagctatg atgatgcaat    240
```

```
gcaggaaata acctttcatt ctccccccta gaggatcacg acaggtgctt caatgcctgc    300

cttatctatg ggacagtagt gtgattctca gtgagaagtg aaggcctttg gggatttgag    360

tcaggaaagg gaacatggct aagtgcctgg aaactctggc aacagtctgc gggtagaatc    420

tacttggcct ctggataaga aaatctgtgc ttcantgaac ttaagnggtt tgggaaaatt    480

taacccagaa ttttnnanga agcataagtn cctggttcaa ganaaccagc ttacggaaca    540

tgcacattct taacatangc aacctttggc caatnaatcc catnggatgg ccccccttaag   600

ggaaagccat tttgggttct tggatcccaa cnttttaagt tcaaactttt tttttaagnt    660

tttagntcct nggcccccttt agnaaggn                                       688
```

```
<210> SEQ ID NO 293
<211> LENGTH: 572
<212> TYPE: DNA
<213> ORGANISM: Homo sapiens
<220> FEATURE:
<221> NAME/KEY: misc_feature
<222> LOCATION: (1)...(572)
<223> OTHER INFORMATION: n = A,T,C or G

<400> SEQUENCE: 293

ggtactgctc tgctaggcca gtgacaaatg gccatcagag atgtggctcg ggtcagcatt     60

gtccttcctg gtgcaggcca tggttttatc agagcactga ccaccctgtg gcactgtaac    120

aggtgaccat aggagacttg tgcctggaga acttggggcc actgtggtag gaacagcagg    180

ggttctggaa atggacacta atcctaggat tggaaccccg gcttgctgtc tgctctctgg    240

gtgtctcagc ctgtctccca cctgcctggg actgttttct cttgggtgga ttgggaagct    300

catgtgtggc ctcatctcac ggggtgaggt gaagactcaa tgaggcacta cctgggttcc    360

acggggtgtc cccgtgggt ctctcccccca gggtgtccct gcccccctgtg caagccagtt   420

tctgctgaat tacccagcca gctttgccaa accacctgac tttccttcag aagacttcag    480

gcngaaaaac agggttaaag acctacccct tctgaacttg gttcantgct antgcanaac    540

caagtccttc acaancttag gatcctatag gt                                 572
```

```
<210> SEQ ID NO 294
<211> LENGTH: 692
<212> TYPE: DNA
<213> ORGANISM: Homo sapiens
<220> FEATURE:
<221> NAME/KEY: misc_feature
<222> LOCATION: (1)...(692)
<223> OTHER INFORMATION: n = A,T,C or G

<400> SEQUENCE: 294

acttcacaag tgtatgaaaa tgatgtgacg ttaacggctg ataaaggcaa aacagaggac     60

actttcttca tgagcaacaa accccaaaga tacaaagaca agctaccaga tagtggtgat    120

tctatgctta ggatcagcac cattgcttca gccattgcag aggcatcagt taatactgat    180

ccttcccaac ttgctgcaat gatcaaggca ctttcaaata aaaccagaga caagactttt    240

caggaagatg agaaacaaaa ggactattct catgtgcgtc atttcttacc taatgattta    300

gaaaaaagta atggatccaa tgcacttgat atggagaaat accttaaaaa aacagaagtt    360

agtagatatg aaagtgcatt ggaaaacttt tcaagggcta gtatgtctga tacttgggat    420

ttatctttgc caaagaacaa actactcaag acattcattc cggtggactt aagtgctcta    480

gtggnaatgt gaaggccccn gaagaaaacn cagcagctat tgttatgttg aaaatggnga    540
```

-continued

```
gagtgagaat caagaggcnt ttagaancct aaacttctca aatccggttc caattgagag    600

aatacngggc cntanttgat gggaaaactg tccnttgcac caattccaga agtnggaccc    660

atnaaaactn cctaatttcc ctccnttgga gg                                  692
```

<210> SEQ ID NO 295
<211> LENGTH: 459
<212> TYPE: DNA
<213> ORGANISM: Homo sapiens
<220> FEATURE:
<221> NAME/KEY: misc_feature
<222> LOCATION: (1)...(459)
<223> OTHER INFORMATION: n = A,T,C or G

<400> SEQUENCE: 295

```
cgaggtacaa tgcaacaaaa tacaaaatac atgcttggtg aacattcgtt catatctaca     60

agacggcagc tagagattag gtttcaatac tgaccattta ctatcctaca agcaattagc    120

attacatcat aatatgccat caaggcaact ttttttatac tgaaaaaatc aaaataaaaa    180

ccgttatttg taaactttta tacgaaatgt aactcttcaa gtggaaataa aaaataaaat    240

ttgtctattt actattgaat acacatagga tttcaatttt cattataccg agaaaaaagc    300

tcttttgtgt tgggaaaata atgcttcaaa aaataattag tagaaaaacc cactagtata    360

atgntttgcc tttcaatgcc agcacagatt tgggaacata ctgaggatga aagttataga    420

cattcacagg tgaaatgtcc tgccnggcgg ccgtcgaaa                           459
```

<210> SEQ ID NO 296
<211> LENGTH: 677
<212> TYPE: DNA
<213> ORGANISM: Homo sapiens
<220> FEATURE:
<221> NAME/KEY: misc_feature
<222> LOCATION: (1)...(677)
<223> OTHER INFORMATION: n = A,T,C or G

<400> SEQUENCE: 296

```
taaagactac ctacacatag atatatgatt ccaaagtcat actttctcca tccccacatt     60

agccaagtga atacagggcc aaatgggttc ttggaatgat aataacaaag cattacaaag    120

tgggtcccct tggttccagc cttgtccaga gtttttggtt atatatttct atttattaca    180

atttaccttt taaattgtaa aataaacctt tgtgtggaca gagccaatgt ttcaatcttg    240

aatgagtaaa gaaaatactt tggaactgat cctcattttg aaattggttc taaattatta    300

tccatttcca atgtctgaaa ttctcttact tcctgctaaa actctctttc tgccaaagtt    360

gtttcgtaat ctgtctcaat gactataatg taaaattaaa gaagtaacca tgcttctcaa    420

ggggggaatt aaaagtggtt aatggatttt actcaggcta attggttggn cagaaattcc    480

taaggccaca gctttngggg ggtccgtgta natgtccagg anggcagnga cattagttcc    540

ttcttntgnt aatcccaaaa cttagaaacc nataatctta ccctggcatt tcctttntaa    600

aatggccagg ccnttggggg ggaccttggc cggaccccct tanggggaat ccnccactgg    660

gggccgtctt agggann                                                   677
```

<210> SEQ ID NO 297
<211> LENGTH: 574
<212> TYPE: DNA
<213> ORGANISM: Homo sapiens
<220> FEATURE:
<221> NAME/KEY: misc_feature
<222> LOCATION: (1)...(574)
<223> OTHER INFORMATION: n = A,T,C or G

<400> SEQUENCE: 297

```
accgtggtgt tagaatgatt gttatgtact gcagacaaaa tctgctttta gaggcaagcg      60

gatttctgac aaagtaactg atcctttgga tggcataaat tcactttggg gactagcctt     120

attcttcctc tgaggtcctt cgttcttcaa tttattcaat tcatcaatca aaagtgttct     180

cttcccagtt gcaattagaa gaagtctttc tgcttcagct tcttctaggg accctttttcc    240

atgttcttca tcaacacagc agttaagagc ctggctagct tgatagatca ctgtctgttg     300

catatttatt tcgttattga gttcctgcat tttctgtttg atattaactt gacaaggaaa     360

ggcattattt ttttcatcca gttttgaagt aacatcttcc ttccgaacaa tcacctgctt     420

tattgatgga cgttctgntt ctttgaatct ttgagatcta tatgcatcaa tgctgtaaag     480

aagatcacga tcttcagaac ccaggctatc accagattca actcgangga ccnagttctt     540

tggaattttc ctgggtttgg actttcatca cttn                                 574
```

<210> SEQ ID NO 298
<211> LENGTH: 535
<212> TYPE: DNA
<213> ORGANISM: Homo sapiens
<220> FEATURE:
<221> NAME/KEY: misc_feature
<222> LOCATION: (1)...(535)
<223> OTHER INFORMATION: n = A,T,C or G

<400> SEQUENCE: 298

```
ggtacattta gctttggaat gatggagaga cacagagata tatgtaaacg tcaagagaat      60

cactccactc cacgtctggg tccacaccct tccaggcttt gtctggaaca ttatgtggct     120

ggtgcctgat tccacagtga ggatgcagga gcccaggtgg tgatggataa agcattagga     180

gacaatcaag tgtcaggaat tggtcaataa gaacggctta aataatgatt taacaaggaa     240

gacgagtaaa aaacaatccc atttcatctt tagaaagaat taagtcacta aatgatttct     300

tctaagttgt tgccatttgc ttggatgaga tcttgaaggt tttccattct ttctccaccc     360

agttaagaac acattgacta gaaatttgtg acaagaatct agtaaaggcc ttttccctcc     420

tgctcctcat tatgccaatg caagaacact tatagcttcc tgngccaaag tatttgacat     480

ccatgncttc atcttggcct aacttctgna gtacctggcc gggccggccg ttcna          535
```

<210> SEQ ID NO 299
<211> LENGTH: 644
<212> TYPE: DNA
<213> ORGANISM: Homo sapiens
<220> FEATURE:
<221> NAME/KEY: misc_feature
<222> LOCATION: (1)...(644)
<223> OTHER INFORMATION: n = A,T,C or G

<400> SEQUENCE: 299

```
acatatttcc cgggataaga tcaccaggcc aggagcgaag ctatggaaga aaggggaagg      60

gctccccaac tttgacaaca acaatatcaa gggctctttg ataatcactt ttgatgtgga     120

ttttccaaaa gaacagttaa cagaggaagc gagagaaggt atcaaacagc tactgaaaca     180

agggtcagtg cagaaggtat acaatggact gcaaggatat tgagagtgaa taaaattgga     240

ctttgtttaa aataagtgaa taagcgatat ttattatctg caaggttttt ttgtgtgtgt     300

ttttgttttt attttcaata tgcaagttag gcttaatttt ttttatctaa tgatcatcat     360

gaaatgaata agagggctta agaatttgcc atttgcattc ggaaaagaat gaccagcaaa     420
```

-continued

```
agggttacta atacctctcc tttggggatt aatgctggtg ctgccgctga gtttcaagaa    480

ttaagctgca gaagactcag gagcaaagaa ccccatntta agggtggagt gtaccattcn    540

tcaaatgcca ctgggaagct gtttaancat ttggngtatt caaaaaaaaa aaaaaaaant    600

ttcttgccga ccctangnaa tcaccctggg cgtnttngan cann                     644
```

```
<210> SEQ ID NO 300
<211> LENGTH: 642
<212> TYPE: DNA
<213> ORGANISM: Homo sapiens
<220> FEATURE:
<221> NAME/KEY: misc_feature
<222> LOCATION: (1)...(642)
<223> OTHER INFORMATION: n = A,T,C or G

<400> SEQUENCE: 300

accttcccaa ccattagagt gagtcaccct agaagcaaat tctccagctc cagtgcatcc     60

tttagataac tgccactctg gtcactatct tatctacaac ctcatgagaa acctcagcca    120

gaaccaccca gctaagttgc ctctgaattc ctgagccaca gaaactggga gataatgttt    180

actgtttaag actttaaatt tggagtaatt tgctattcag ccatagaaag tgacactcat    240

ttcttcgtgc ccgacactgc tgtctctgtg gtttcacatc cctgtggtta aagctctcca    300

agggctcatc actaatttca ggataaaatc taaatccctt aacatagcat aggtttttta    360

caaactgcct cctgtgtgcc tctcagcccc atccggccca ctctgccttt cctncctgga    420

tcactccagc tactctgaaa catactgnac cttnctaaat gcngacagat aaaattggca    480

gacttttcat aggatgccca gtgaaatttg aatttcagat aaccatgaat aatgngtgtg    540

ggtatacaat atttgggaca tcctatacta aaaatattgc tgacncatat tcttcaaggt    600

attaatttaa tctgaaatcn catttaatan ggcatnttgg gc                       642
```

```
<210> SEQ ID NO 301
<211> LENGTH: 589
<212> TYPE: DNA
<213> ORGANISM: Homo sapiens
<220> FEATURE:
<221> NAME/KEY: misc_feature
<222> LOCATION: (1)...(589)
<223> OTHER INFORMATION: n = A,T,C or G

<400> SEQUENCE: 301

cgaggtaccg tattatgaac taacaaaata tttttgtttt acatcagtct taatagtccc     60

attttgctca attgggaata gtgctagctc tcttgtttga gaactgttac ttcaaaaaaa    120

atccaatgca aggtgctggt aagtcctctt cataacctta attaatactt gttagtgatt    180

tacagtaaaa ctgcttttag tgaagtatat tcacttggcc cataaacact gaaatagatg    240

aggtaatgat acattagtaa tgtagtaata aattagtatg ccaattctga caaaaaatta    300

ccaatagctc cccccacctt cacttacaag agggttcctg gtttgaaccc taacataccc    360

tagatataca tagcaattct gctgatagga aaaccaagtc ttagcacaca gctaataaat    420

gacaaacatg ggactagaat ttaagtctat actgccatga acctcatgag gaggagccaa    480

attgntaatt aagttgcact ctagttacca gcactaacan aacacaaacc aataacatgg    540

gtgtgggcta ttnanaaaaa ataactgggg gaaaacatta cttttntgg                589
```

```
<210> SEQ ID NO 302
<211> LENGTH: 577
<212> TYPE: DNA
<213> ORGANISM: Homo sapiens
```

```
<220> FEATURE:
<221> NAME/KEY: misc_feature
<222> LOCATION: (1)...(577)
<223> OTHER INFORMATION: n = A,T,C or G

<400> SEQUENCE: 302

ggtacttgaa atgttgctgg ttaaaagttt ttctgcttta ctcattcctt tgacagcatt     60

aatttgtgaa catttatatt cagttcagct gtatttatgg cacaagatct catttccaaa    120

atggcactaa ttttccttaa gtgtaacagc actctatttt tagcagtaat tatattttta    180

aaggttaatt tgtagaacaa atgttttaac tatacttttt ttctactcta tactccccag    240

ttacagtatt tacaaagggc tgaagtctat ataaaaaaat gatctttggc tgggcatggt    300

ggctcatgcc tgtaatccca gcactttggg aggtcgaggc aggcggatca cgaggttagg    360

agtttgagac cagcctgacc aacatgaaga aaccctgtct ctactaaaaa tacaaaatta    420

gccaggcatg gaggcaggcg cctgtaatcc caactactcg ggaggctgan gcagggagaa    480

tcgcttgaac ccgggaggcc gaaggtgccg tgagttgaga ntggccattg ccttcagcct    540

gggtgacaaa cgagtttcaa aaaaaaaaaa acatttt                             577


<210> SEQ ID NO 303
<211> LENGTH: 673
<212> TYPE: DNA
<213> ORGANISM: Homo sapiens
<220> FEATURE:
<221> NAME/KEY: misc_feature
<222> LOCATION: (1)...(673)
<223> OTHER INFORMATION: n = A,T,C or G

<400> SEQUENCE: 303

ggtacattta gcccatgagc ctggcacaga tccctatcta gacatgaggc cctttagaca     60

tgactttggc attgaccagc ctgttggcaa tgggtcgggg aggcagaggg gatgctcaca    120

ccagtaattc tcatcccctg aatgcttggg atcacctggg gagagttcac aaaatactgg    180

tgcaggggtc ccacctctga tgatgctgag tggtgggtct ggggtgtggc ccaggcatca    240

tgatgtttca ggcccccagg tgacttctta ggcagcccag ctaagcccct agagccttgc    300

aatttccccc aaatgacctc agagggcccg atttgaggga aatgcctaac ttcaggggcc    360

cgtaagaatc ccccagggag catgtgaaat gcagatacca ggcccacccc cagagatgag    420

ctgangtggg tcaaggggtg aaagtgcang gatcaagtgt ttttcacaag ctccatacct    480

tcaggaaatg gtgttgtggt ttgggcccgt anaaaacatt cttgagagtc ctggtgnctt    540

gtgccttggt gcaccttggg gtgggaatnc caatgggncc ttgncnttga ggaaggatgt    600

gccattaacc tggtaagggg aaacccgaaa ccggtttcaa cttgnccttg gcccaaccgg    660

ggacccttcn aaa                                                       673


<210> SEQ ID NO 304
<211> LENGTH: 426
<212> TYPE: DNA
<213> ORGANISM: Homo sapiens

<400> SEQUENCE: 304

ggtactgggc tcccatttat ttgaaatgtc caaaataggc aaatttgtag acgaaaagta     60

gatcagtggt ttcctgcagc tgaagtgtag gttgaaagtg gagcatgact gaatgccctt    120

tctaaaacaa gtaaacctat aattcatatt tccttaagaa aataaaaatt ttattaaatc    180

aagatttaat ttaccatgaa gaacacagag ttattattag tgcaagactt tattcatcct    240
```

```
ctccccagcc aaatcccaag aggatggcca cctttggaac tttttactgg cagcttactt    300

aacctaagtc agtctcctaa tctagtggtc tttgaaatgg ggatgtataa gacaaccatt    360

tgacacaggt agaaaacttt tactttttta agcccattcc cctggtaaac aatatatgta    420

cctgcc                                                               426


<210> SEQ ID NO 305
<211> LENGTH: 655
<212> TYPE: DNA
<213> ORGANISM: Homo sapiens
<220> FEATURE:
<221> NAME/KEY: misc_feature
<222> LOCATION: (1)...(655)
<223> OTHER INFORMATION: n = A,T,C or G

<400> SEQUENCE: 305

ggtacgagat tctgtgtgtc agccagttta ccctccagtg tgtcctgaag ggaaacaagc     60

ctgatttcca cctagcaatg cccacggagc aggcagaggg cttctacaac agcttcctgg    120

agcagctgcg taaaacatac aggccggagc ttatcaaaga tggcaagttt ggggcctaca    180

tgcaggtgca cattcagaat gatgggcctg tgaccataga gctggaatcg ccagctcccg    240

gcactgctac ctctgaccca aagcagctgt caaagctcga aaaacagcag cagaggaaag    300

aaaagaccag agctaaggga ccttctgaat caagcaagga aagaaacact ccccgaaaag    360

aagaccgcag tgccagcagc ggggctgagg gcgacgtgtc ctctgaacgg gagcccgtag    420

ctcaggaggc agaattcaat gtgttatcat tgggcagaac tggatcctga aaaattcaag    480

atgctaagca cctacactac tttaagaatt tggaactgaa catgaanaag aagacngaaa    540

ttagaatttg ggaacctgaa tagcttttgc aaaaacaccc aagggccggt taatcgtttc    600

tggtggtgct nnggtggaat gatncatggg ccttgccntg ggncaagggg cngnt         655


<210> SEQ ID NO 306
<211> LENGTH: 684
<212> TYPE: DNA
<213> ORGANISM: Homo sapiens
<220> FEATURE:
<221> NAME/KEY: misc_feature
<222> LOCATION: (1)...(684)
<223> OTHER INFORMATION: n = A,T,C or G

<400> SEQUENCE: 306

cgaggtacaa cacgcctcca tgtttcagca tctacgtcat gggcttggtt ctggagtgga     60

ttaaaaacaa tggaggtgcc gcggccatgg agaagcttag ctccatcaaa tctcaaacaa    120

tttatgagat tattgataat tctcaaggat tccacgtttg tccagtggag ccccaaaata    180

gaagcaagat gaatattcca ttccgcattg gcaatgccaa aggagatgat gctttagaaa    240

aaaagatttc ttgataaagc tcttgaactc aatatgttgt ccttgaaagg gcataggtct    300

gtgggaggca tccgggcctc tctgtataat gctgtcacaa ttgaagacgt tcagaagctg    360

gccgccttca tgaaaaaatt tttggagatg catcagctat gaacacatcc taacccagga    420

tatactctgt tcttgaacaa catacaaagt ttaaaggtaa cttgggggat ggctaccaaa    480

aggttaacac agtatttttc tcaaatgaac catgccttat tgcagaattc ttcntttttg    540

gaaagaacca ccggccaaaa cattccccaa cttntgtaaa agctggtggg gacctaatgg    600

ccgcccttaa ttctgacttt gaactggaaa nccttttaag naaaacttgg nggcttttnt    660

aacaaaatcc cgcgtanttt gnct                                           684
```

<210> SEQ ID NO 307
<211> LENGTH: 647
<212> TYPE: DNA
<213> ORGANISM: Homo sapiens
<220> FEATURE:
<221> NAME/KEY: misc_feature
<222> LOCATION: (1)...(647)
<223> OTHER INFORMATION: n = A,T,C or G

<400> SEQUENCE: 307

```
caggtcttgt atacacaagc gtccatgtct cacacaaata ttgatgtgat tattcttaag     60

tgttaaatca ttaacactta aatgacttca ttgggaatat tgagcagagg gactgtgctt    120

ctatgcactg ggcaaggcag tatttgctta ggaaactaat ttagtcatca gagatacttt    180

cctaaaaagg aaaaataaaa aacaaaatgg tgccactttg ggttgaagct actttgttag    240

gcttgaattc atttatatgt cttttgattc ttaaaaaaac aaaaaacatt ccattagaag    300

caccagtttt tttgctcaga ctttgtggat cagactctac actcaacaca ctctaatcta    360

cttaaaggta tacaaaatat gctgatcttt tttaaattat gatttcctga atttttttct    420

taagtcgtct caactgattt actcacttag cttcctttcc tcatcaccta gtataataga    480

atgnatgtta catttttatg aatggcaggt gtcattataa tctgnattga cttaaaaagg    540

ttcttcctca tgatgctaat angtttttgg atanttggga ggatacncat ttgacagttt    600

tgcattttat gnatgagccn gtatccatga cggggcacgg attatag                 647
```

<210> SEQ ID NO 308
<211> LENGTH: 660
<212> TYPE: DNA
<213> ORGANISM: Homo sapiens
<220> FEATURE:
<221> NAME/KEY: misc_feature
<222> LOCATION: (1)...(660)
<223> OTHER INFORMATION: n = A,T,C or G

<400> SEQUENCE: 308

```
acctttgttg ctataaacca gatggagact gtggtgctat tttgtatttt ttttttaatg     60

gaagggtgtt ggggtggcag tttttatcct tgaagacctc agatatgcta agtcaaccta    120

agcaaagtat actcggtgga accctagctc tgtggggtga tctgcaaaat agagtatcct    180

ggtcatgtaa gttcaggaaa tgctacagac tcaaggatta tttttgggga ttcaccatgc    240

acagcacaca ttgaaggctg aaaagtcctt gcagaaagga aactgactta actttgtttc    300

ttaaggatat ttgaccacaa aaccccttagt ctgcatcaca ccaacctgat gcctnctgga    360

acctgtgttc tgtanaatgc gtattagaaa atgttggaca acctgtttca ttatcagaag    420

tcccatttct gangacagtg gtctctgnct ggaaaataan ggtccagaat ctcaanttcc    480

agggaccagn caaggtctgg cacttntanc cagtaaaacc ccattgcata aatcttcatt    540

ccatcaaggg tataanttgc ttgngcccct tnacaaangg ggaaanaact cggaanaaag    600

gtnccttggg ccgggaacac ccttaagggc caaattccan acaattgnng gccgtaatna    660
```

<210> SEQ ID NO 309
<211> LENGTH: 401
<212> TYPE: DNA
<213> ORGANISM: Homo sapiens
<220> FEATURE:
<221> NAME/KEY: misc_feature
<222> LOCATION: (1)...(401)
<223> OTHER INFORMATION: n = A,T,C or G

<400> SEQUENCE: 309

-continued

```
ggtacacata tacacataac aagtgtagaa gtatatatta catacataca ctcactctgt     60

ctggtatagg ctaattttga agaactccca taagtttctg ctgcttctcc cataactgct    120

gccaccacca tcagaattca taatcaaacc taaccttttt gtttggggca ccaaatctga    180

agacaaaatt aatttgcacc agtaaacttc aagctgcttt ctttcttgaa aactaaacgt    240

ttaacgtata atgtctgttt ggatactgtt ccaaattgtt gattgcatgt ggttaatgtt    300

gcattagagc actttgcaat tgcataattc attaatgttt tgtgagcttg catttgtgag    360

ttattggatg atcagactga attttgcaag tatcacattg n                        401


<210> SEQ ID NO 310
<211> LENGTH: 502
<212> TYPE: DNA
<213> ORGANISM: Homo sapiens
<220> FEATURE:
<221> NAME/KEY: misc_feature
<222> LOCATION: (1)...(502)
<223> OTHER INFORMATION: n = A,T,C or G

<400> SEQUENCE: 310

acatgtttat ggggactcct aacacagggc tcccctcttt ttcactagga gtttcactta     60

cagctgacaa tctatggggg cggggggggg gcgcggcaaa aaagcaatga tggaccttgg    120

ctaatccccc cgaccccttt cttaacaata taggtagatg tctatcgtca gcttgcctct    180

ttgccaagac ctaggaggcg gctctgccat gagctgctgt gtgctgccct ccccaccttc    240

agcacactca tctacacaca cacaggtagc acccacctcg atgagaccgc cttgctctgg    300

cctgccccaa ccctggaagt tgaaaacata gagccattta tttctgcttc tactctctgn    360

gcccatgtct tgtccacgaa actttgctga acttccagga ccttacacct gaagccccac    420

aataacctgg atgttttgaa agccctngga aanccagttn taganaaagg accccccttaa   480

gccgaaacag ggcctgttaa aa                                             502


<210> SEQ ID NO 311
<211> LENGTH: 387
<212> TYPE: DNA
<213> ORGANISM: Homo sapiens

<400> SEQUENCE: 311

cgaggtacct tactcagagg ggctttgatt tttttcaagc acaaagcaag aagttccctg     60

gattctaaag cacactgtat ccaagttcct ggtggttgaa aatacctttg acattgtttg    120

cagaacgaaa tcgagacttg tttcggaata ccttggctga tgtccacttt acttcgcaaa    180

caggccacac aaatattggc aggatttgga cttatcggaa caccacactc acagcacaag    240

atgtgtccag ggctgcggtc ggtggattct gccatatact ccatcgttct gtatgcctta    300

agttttcgcg cctccagacc agccctggat ttgctgaaaa cccgcaacaa aatagacccc    360

ggctgtcccg tcagctgcca acctggt                                        387


<210> SEQ ID NO 312
<211> LENGTH: 654
<212> TYPE: DNA
<213> ORGANISM: Homo sapiens
<220> FEATURE:
<221> NAME/KEY: misc_feature
<222> LOCATION: (1)...(654)
<223> OTHER INFORMATION: n = A,T,C or G

<400> SEQUENCE: 312

ggtacaaaaa aatgcttctg gagatttctt tggcagaaat gcctttcatc tataatttca     60
```

```
tggagaactg ctttaattag cctaggtgaa aagtagtcct agcagtgtaa atatgtataa    120

ttagagtttt ctaatttcac tgtgagatct ctaacttttg agtggcaaac agatcaagtc    180

ttttgctcat agacttttct gtggggttat taaaatgcaa aagctttatt ttttttaata    240

atgccatact ccattagtgt cagatgatgg tatggaattt gttcccttgc tttcccccac    300

tgttactgct tcagtttata gattgccagc agagttcaga aatagagcag ggatttaccc    360

gttctttgct tggacatccc attttctttt gccagaccca tgttggcaat catgtatgaa    420

ctgngttata cttctcagtg ctttcttttt tctttttgat aagatggata tcaaaaatag    480

ttgctgtgcc aaaagtagta agccttcttc aagaagaaaa cccaatcttt ttctaataat    540

aatcctgnga aaatgcttca ttcattcatt taatttttaa gccaaaggtc accaaangct    600

gntgntttta actangaaat ttgaaatgnn agnnttaaag cnttttaaaa aaag          654
```

<210> SEQ ID NO 313
<211> LENGTH: 656
<212> TYPE: DNA
<213> ORGANISM: Homo sapiens
<220> FEATURE:
<221> NAME/KEY: misc_feature
<222> LOCATION: (1)...(656)
<223> OTHER INFORMATION: n = A,T,C or G

<400> SEQUENCE: 313

```
acagttctgt cctggcatca tcattcattg tagtatggtc aataggtgcc atgaaactca     60

gtagcttgct aaggacatga aaccgaagtt tcctgccttt gctggctttc ctatctactt    120

ttttgtggat tttgcttcgt aacttctgga ttgcaagcca ctgccttccc atggccacct    180

gatcgttggg atccaaggag ctggtcttcc gttctatgag ttctcgaagg agctggtggt    240

aaaagtcatc atcatcaaag atttcttcat ccaagtcctt cagatgagca ttagcagggg    300

cttgaggaag gatctccggt tcccctggca aactctctgg gacaggctga gctgctggct    360

caggtttgcc aagaactcga tagacagagc gcttggtctg tgtccttcga agtaatctct    420

ctttgnccat cagaatatgg tcgatctgag tcaaagattg aaccgttcaa angcaccaaa    480

acccttnccc agtttttcag aaacccagtt tggtcttatc gggccatttc tgaantgtgc    540

cggttcctgn aaactggtaa agtcggcaaa acgctttgcc atgaacttgg aatagncctc    600

catntccggt tncttttttgc anggaccctt ntttggtggn tgggtctttt tttttn        656
```

<210> SEQ ID NO 314
<211> LENGTH: 649
<212> TYPE: DNA
<213> ORGANISM: Homo sapiens
<220> FEATURE:
<221> NAME/KEY: misc_feature
<222> LOCATION: (1)...(649)
<223> OTHER INFORMATION: n = A,T,C or G

<400> SEQUENCE: 314

```
ggtacatgga ctggacctgc ctggagccca gcccagagca tctcctcagt gctcatctct     60

atccagtccc tgatgactga gaacccctat cacaatgagc ccggctttga acaggagaga    120

catccaggag acagcaaaaa ctataatgaa tgtatccggc acgagaccat cagagttgca    180

gtctgtgaca tgatggaagg aaagtgtccc tgtcctgaac ccctacgagg ggtgatggag    240

aagtcctttc tggagtatta cgacttctat gaggtggcct gcaaagatcg cctgcacctt    300

caaggccaaa ctatgcagga cccttttgga gagaagcggg gccactttga ctaccagtcc    360
```

```
ctcttgatgc gcctgggact gatacgtcaa gaaagtgctg gagaggctcc ataatgagaa    420

tgcagaaatg gactctgata gcagttcatc tgggacagag acagaccttc atgggagcct    480

ganggtttag accctggtcc atctcccttc cccacttaag aagtccagca gaatcctttc    540

cccancccan ggatggganan gcctgggnat ctccttccan aattgaagtc atcttgcaag    600

aaggcaagaa ccaagcagct tcgantccan ggtgtggaat gggggcctn                649
```

<210> SEQ ID NO 315
<211> LENGTH: 238
<212> TYPE: DNA
<213> ORGANISM: Homo sapiens

<400> SEQUENCE: 315

```
acctgcaggt ggtggcagcg ggtagccggg actcgggcgc cgcgctctac gtcttctccg     60

agttcaaccg gtatctcttc aactgtggag aaggcgttca gagactcatg caggagcaca    120

agttaaaggt tgctcgcctg gacaacatat tcctgacacg aatgcactgg tctaatgttg    180

ggggcttaag tggaatgatt cttactttaa aggaaaccgg gcttccaaag tgtgtacc      238
```

<210> SEQ ID NO 316
<211> LENGTH: 637
<212> TYPE: DNA
<213> ORGANISM: Homo sapiens
<220> FEATURE:
<221> NAME/KEY: misc_feature
<222> LOCATION: (1)...(637)
<223> OTHER INFORMATION: n = A,T,C or G

<400> SEQUENCE: 316

```
ggtactgtgt ttacatggtg agtggtcgtt accatccaac agcacaaggc acaaaaaatg     60

ggcatcaagc aaaccatgca taacgaggcc tggaaaccat caagaacagc cacaaaagag    120

gtcactcaga cctctgattc aaacttctgg tgtttgagtg acaagcatgc acgtttaggc    180

tctgcccaaa tatcagggag gatttccaat ctccacaaga gactggtttc acatatggcc    240

tttctcctgg ctgtcaaacc accagggttc ctccaaaaca aaatgagagc agctgttttg    300

ctgatcaacc aatcacacta gcagttctat ttcagtttaa aacaaccttg caggaataaa    360

ccacataaag actccgtggc taagggctgc tattacttac acctaccaag cgaacacaaa    420

cggctggctc ttctatggta acgcttcact ggcatgcaaa ccccaagggc cactgaatgg    480

aatgaatcca catgaacagc atacctggag caggaacatg ccttcacaag aagtgtcagg    540

agactaacct gtggttgcta acattnttgt gangaaaanc agggtagcag aagggtgggt    600

tgaagtnttg cctaatatnc ttaccatata tataaac                             637
```

<210> SEQ ID NO 317
<211> LENGTH: 505
<212> TYPE: DNA
<213> ORGANISM: Homo sapiens
<220> FEATURE:
<221> NAME/KEY: misc_feature
<222> LOCATION: (1)...(505)
<223> OTHER INFORMATION: n = A,T,C or G

<400> SEQUENCE: 317

```
ggtacattgg ccagactcat gcacaccaca tctgctgaca tctccttccg ttctgtgtac     60

tcattcagct gtcctgaagg atccatctcg aaatagacca gctctcctcc tgtcagggca    120

atcaccactt gtcgctggtt cactgcacac ttcacaattg ttttctttcc aggggtcttc    180

cactcattga ctctcttgtc tgctcgtatg tgccgaatgc catctggata gacctgcacc    240
```

```
aaggcatcat ctcctaataa ggagcaggac aaggtcgggg tggtccccag gaacccagag    300

tcagtcactt cttctacagt ttctccaatg gacaacacta gggtggcatt cacgaaagac    360

acaatgatgt aggcatcaaa ctcatcttca atgtgtcgac gcactgtcca nacagcgttg    420

gggttaccag gtanctcana aacagccatt tctgacacct naagtccatg gtttaaggac    480

ttttaaanat gatcngggnc ccctn                                          505
```

<210> SEQ ID NO 318
<211> LENGTH: 645
<212> TYPE: DNA
<213> ORGANISM: Homo sapiens
<220> FEATURE:
<221> NAME/KEY: misc_feature
<222> LOCATION: (1)...(645)
<223> OTHER INFORMATION: n = A,T,C or G

<400> SEQUENCE: 318

```
gcgtgtcgcg gccgaggtac atacaaactg gggttctgtc aatgacaaca aggactatgt     60

gttggttcat atcaaatcca agaatattag acaaccaaac atataacctt cttgtggttt    120

ctcttaatat gcagcattca ttatggtagt taggtccctt cactggtttt ctgcaagtct    180

gaagttgtgt ttcttgtgtc gttgcccgca tctccaccct cagagctgct tttgttttcc    240

tcttctttgc agtctttgtc atcttcatct cctggagatt tccgggactg tttagaggat    300

ttctttgaag tatatgactt tttccgtttt gagcctgctt tttcattctt tcttttgcct    360

tttccatctt cttctactct atcaccttct tcctcactgc ttgcatctgc agtatttcca    420

ccttctcctc agtttctgaa ganctctggt gctgaattgc ctggtaccag taaactttac    480

tnctgggtat tttctatttc cacaatcctt cgttaaatcc tttccgttgg ttgacttttc    540

aaactggcnt tggacctggc ccggccggcc gtcgaaaggc gaattccacc attggcggcc    600

gtactaatgg atcnacttgg ncccacctgg cgtaatatgg catan                    645
```

<210> SEQ ID NO 319
<211> LENGTH: 424
<212> TYPE: DNA
<213> ORGANISM: Homo sapiens

<400> SEQUENCE: 319

```
acttttccat aaagttctag tcacttctgt tggcctgagc caccagatta tgatgttgcc     60

agaattcact caatttgaat aaagatgaac agtatttgtt ttcttgtttc catgaattat    120

atcagtattc taaaacatcg cttcagaaag agaactgttt atttctgcag gcttcctgtc    180

cttttgtggt atggtttttt ggccttattt tcactggctt ttccttctcc aaactttgag    240

gcgtgatttc attcattgaa gaatcaatac atattttgtt tcaaaatgtt tgaaacaaaa    300

gacatagatg gtagactttt attaaaacat atatggatgt ggaaagcaca tatattaatg    360

cagtcatccc ttttcaggtg ggaagagagc aaaccagttg attttttaat tcatccttag    420

tacc                                                                 424
```

<210> SEQ ID NO 320
<211> LENGTH: 472
<212> TYPE: DNA
<213> ORGANISM: Homo sapiens
<220> FEATURE:
<221> NAME/KEY: misc_feature
<222> LOCATION: (1)...(472)
<223> OTHER INFORMATION: n = A,T,C or G

<400> SEQUENCE: 320
acgaagtcgg gcaacaagaa agcgaggagc agcgtgtatg cccttatcct cagcaagtga 60
gaacaaggca gatcacagca ccgacacaga agatggcctt ctcccatgtg ccagcggaga 120
atccccttcc agccaaatcc tcaggaagca gagcaccaca caagcagcat ttcttggttt 180
ctcatggtca tattcaaaag cgacttttaa atcagaaaat agaaaaagca tttgtggtag 240
gtctttttca aacccagaac acaagttggc taggaaaacg gaaagcttcc tctggcatcc 300
ctgtttggac tcctcctcct cttggaggag tttcctgaac cgcacacaca tcgcttcctc 360
accaagagag atgctcaact aggatctttt ttagtgtgcc agttacaaga cacatttaca 420
ggctatgttt ctaagacctc ttagtggcca acgangaagg agggtacctt cg 472

<210> SEQ ID NO 321
<211> LENGTH: 588
<212> TYPE: DNA
<213> ORGANISM: Homo sapiens
<220> FEATURE:
<221> NAME/KEY: misc_feature
<222> LOCATION: (1)...(588)
<223> OTHER INFORMATION: n = A,T,C or G

<400> SEQUENCE: 321
acctacctca caggtttgtt gtgaagacta aatgaagata atgcaataaa cggctgagac 60
ccatgccaag cacatggtaa aagtgtgtaa ttgcgtatta gcagcagcag ccagagcaat 120
agccaagggt caattaactc ccagtccagt gttcagttca tgattgtcca tgcattaaga 180
gccaaagcac ccccaaagcc atctcaccct gctgaagcag tctaaagtgc tcaactaagt 240
tggtgcatta atctctagac cagaggtcag cagacgtttt ctgtaaaggg ccagacagca 300
aacattttag gtctctgttg caactactca gctttgccct tgtgaatgaa agcagcaaga 360
caatatgtaa atgaatgggc cgtggcagat ttcatccaca ggggttccct gctttagact 420
gtgccgagag ccatangtct tgagttnaag tccaacctta ccacacttgc aangggtggt 480
ctttgaccaa gtcnnggaag gnntnccaaa agtcaaggcc cttaancctt taaaaaatgg 540
ggaataataa tgccttccnt caagagctgg tnaaacaatg gaagctgg 588

<210> SEQ ID NO 322
<211> LENGTH: 589
<212> TYPE: DNA
<213> ORGANISM: Homo sapiens
<220> FEATURE:
<221> NAME/KEY: misc_feature
<222> LOCATION: (1)...(589)
<223> OTHER INFORMATION: n = A,T,C or G

<400> SEQUENCE: 322
acagctaatt gaaagtatat aaaaatgtga attagtgtgg ttgcagctaa aagtatgagt 60
gatgtaacaa gaatgacgac gtaatgagtc aagtggtgag actagttcta taagcaccgt 120
aaggagtgcc agtcctaata catgaacttc atccatccct tgtatatcaa ggaggagact 180
gtggtcagag aatgtatttt gtaagctata gtttaaaaat attactcttc agaaatttgg 240
agcccaagca ggaattacag agattcctcc caacagaggc cctgagatct cccctgactg 300
ccacccaaag gatccacact tgcctctgat caaccagatt caggccaagg cttanaagag 360
ggaggaggca gtggccagaa gccagggact ctagaggaga gaaatgatgg cagatgtggg 420
gttcagaaaa aacacaagac gggaaagggg aagaagggga aaaaaaggaa gaaccaccac 480
tggtgangaa attgttnaan aaggccacnt ttgcttgang agtggccctt gnctttttca 540

```
ccttgcctgt gggcaaangc tggcaagtaa agacaagggc ttaaccctn              589


<210> SEQ ID NO 323
<211> LENGTH: 582
<212> TYPE: DNA
<213> ORGANISM: Homo sapiens
<220> FEATURE:
<221> NAME/KEY: misc_feature
<222> LOCATION: (1)...(582)
<223> OTHER INFORMATION: n = A,T,C or G

<400> SEQUENCE: 323

actgcttatg taaatcgttt atttttattt catcaaagcc tggcaagtat atgcattcca     60

atttaccatt ggcaaagctt tatttatttt taaggttgga tgttgaatta attttgtggg    120

aaaatgagat ttgtaagtag ttttctttct agataagata acataaacca agctttcaga    180

agttaaggat gatgaataat attgaaatga cttgttatat attgtaaggg ttcccttaag    240

tatcataatt aacaatttgt ggaaattgaa aaagcataaa ctgtgttatt tgattaagta    300

atatgttccc ttaaaattca ttttgaggtg tatgttatac acacagtaaa tttttgttca    360

ggaatgactt gctcattctg tgtttttaaa aataggaaat aaggcatagt gagtcatcat    420

tacatcaatt aaccnaaaaa atatttcatn ccctccgtca ctggaaatta tctacttcag    480

ncacctttct taatcctcgt gttaggaggg ccccgtttat gggccttttt taatttccat    540

gngccatatt gtccactacc cggcagtagc ccaaagctan ct                       582


<210> SEQ ID NO 324
<211> LENGTH: 180
<212> TYPE: DNA
<213> ORGANISM: Homo sapiens

<400> SEQUENCE: 324

acccgtcggc ggcacccacc aacaaccgcg ggatcttctg aattgtggct agcgagcaga     60

tgtttttgtg gccgcagaat ggcaggcgga ccgtggcgaa ggctctgccc tggttgaaca    120

tttctgtcac ttgggaaggc aggtagctgg tggaggccat gagcactttc ccgaagtacc    180


<210> SEQ ID NO 325
<211> LENGTH: 575
<212> TYPE: DNA
<213> ORGANISM: Homo sapiens
<220> FEATURE:
<221> NAME/KEY: misc_feature
<222> LOCATION: (1)...(575)
<223> OTHER INFORMATION: n = A,T,C or G

<400> SEQUENCE: 325

ggtacaaata ctgggaaaaa cctgctcttc tgcgttaagt gggagacaat gtcacaagtt     60

aaaagctctt attcctatga tgccccctcg gatttcatca atttttcatc cttggatgat    120

gaaggagata ctcaaaacat agattcatgg tttgaggaga aggccaattt ggagaataag    180

ttactgggga agaatggaac tggagggctt tttcagggca aaactccttt gagaaaggct    240

aatcttcagc aagctattgt cacacctttg aaaccagttg acaacactta ctacaaagag    300

gcagaaaaag aaaatcttgt ggaacaatcc attccatcaa atgcttgttc ttccctggaa    360

gttgaggcag ccatatcaag aaaaactcca gcccagcctc agagaagatc tcttaggctt    420

tctgctcaga aggatttgga acagaaagaa aagcatcatg taaaaatgaa agcccanaga    480

tgtgccactc ctgtaatcat cgatgaaatt ctaccctcta agaaaatgaa agtttctaac    540
```

acnaaaagaa ccngangaag aagcatgctc atcaa 575

<210> SEQ ID NO 326
<211> LENGTH: 584
<212> TYPE: DNA
<213> ORGANISM: Homo sapiens
<220> FEATURE:
<221> NAME/KEY: misc_feature
<222> LOCATION: (1)...(584)
<223> OTHER INFORMATION: n = A,T,C or G

<400> SEQUENCE: 326
accagcaatc ttagttacaa aataatactt ttcagtagtc tttcttgatg cacatttaaa 60
aaccagcaca actcctctag tgaaatggtc aatttccctt aaaaaacaac atctgaaatt 120
ataagacctg acaaatcata ttatatttca atattagact gctgtggctc tagaacaaca 180
gaaaagcgta actttcaaac agcttaggga aaaagcactg aaatgtagat gtcgtcaatc 240
agcctcaggc attattgatc ctgtgccatc cacacaccct taaggttttt cacagcactc 300
tgacggtatt atgtgtgttt tgcaaatgac gaatcaacag tatgctgaat aatcagcaat 360
gaaacacagg agataaatta aatgtgtttt tccaaatgtc agaatatcga ggttcccagg 420
agttggcaaa acttctcaag gtgggccatt cagactcang ctgtgcnggg ataaggcttc 480
cttaccgtan gtgaaccggt tgagaatatt ggttccncac acccnagaag ccatttaggc 540
atatactggg caaaaaagaa acctgaatnn aatgggacca atnt 584

<210> SEQ ID NO 327
<211> LENGTH: 573
<212> TYPE: DNA
<213> ORGANISM: Homo sapiens

<400> SEQUENCE: 327
ggtacctctc tgaagcacac agaagtagcg ccaggcagag ggtttgaagg atatgtattc 60
atcaagaagt aaacgcaaat ccaagatctc aaccacactt ggctcttaaa gatccaccaa 120
cttaaccctt atggcatgca tatgtgactt ctgcaagaag caacttgaaa acccaagaat 180
gccttgctct accacgtccc gcgactgcaa actcccttcc tctgaaacaa gcagccacag 240
ctttataaga aacatgccgg catgtagtcc atcctgggag gggagaaatc ttcaccactg 300
gctgcctttc agcaagttcc ccttgaaatc tgccggcagt ggaacagatc ccagatccca 360
acgctgtagc ttgggcgtcc tcccaccagg ggttccttgt tctgaaagct gccaccagtg 420
ttgttccgaa agatgcctct gcctttgtgg ggtcatcttc cattatgcct cctaacagga 480
aacaggcttc tatggaagag aagagtccca gccccctgac ctttccgctt tggtcttgga 540
ggatctgagt cacatctgcc atgttgccta aag 573

<210> SEQ ID NO 328
<211> LENGTH: 422
<212> TYPE: DNA
<213> ORGANISM: Homo sapiens
<220> FEATURE:
<221> NAME/KEY: misc_feature
<222> LOCATION: (1)...(422)
<223> OTHER INFORMATION: n = A,T,C or G

<400> SEQUENCE: 328
ggtactattt tgaagcgctg gaagaagaac tggtttgatc tgtggtcgga tggtcacctg 60
atctattatg atgaccagac tcggcagaat atcaaggata aggtccacat gccaatggac 120
tgcatcaaca tccgcacggg gcaggaatgt cgggatactc agcccccgga tggaaagtca 180

```
aaagactgca tgctccagat tgtttgtcga gatgggaaaa caattagtct ttgtgcagaa    240

agcacagatg attgcttggc ctggaaattt acactccaag attctaggac aaacacagcg    300

tatgtgggct ctgcagtcat gaccgatgag acatccgtgg tttcctcacc tccaccatac    360

acggnctatg ctgcaccggc ccctgagcag gcttatggct atgggccata cggtggtgcc    420

gt                                                                   422
```

<210> SEQ ID NO 329
<211> LENGTH: 467
<212> TYPE: DNA
<213> ORGANISM: Homo sapiens
<220> FEATURE:
<221> NAME/KEY: misc_feature
<222> LOCATION: (1)...(467)
<223> OTHER INFORMATION: n = A,T,C or G

<400> SEQUENCE: 329

```
ggtaccacta tccccacttt acagatgagg aaaaaacagg ctcaagagtg aagtccctcg     60

cttgcttagt atctcaaagc taagctgcaa gcaaagatgg ggctccaagg tctgtgtgac    120

ctgagctctt ggttatccaa tacttcaaaa ctgtcactta ggaaagaaga gaacattttt    180

agaaatagga gaaaacccaa cagccacagt gattgtcaaa gagctgaggg ggcatcagac    240

caggttcggg ggcaccagac caggttcagg gccactgcgt aactgccaat gccctgccca    300

gccccaggag acacgcagac tccactgccc tagacgagtg gccctgctgt taataaataa    360

ataaaggtca ggcacaatcc tacacaaagg ccccagaatt caaaccactg tcttgnttct    420

cagacttttg cttaagagcc nagtacctgc ccgggccggn cgctcga                  467
```

<210> SEQ ID NO 330
<211> LENGTH: 595
<212> TYPE: DNA
<213> ORGANISM: Homo sapiens
<220> FEATURE:
<221> NAME/KEY: misc_feature
<222> LOCATION: (1)...(595)
<223> OTHER INFORMATION: n = A,T,C or G

<400> SEQUENCE: 330

```
tcgagcggcc cccgggcagg tacatggccg ccgtcctgga atacctgaca gcggagattc     60

tggagctggc tggcaatgca gcgagagaca acaagaaggg acgggtcaca ccccggcaca    120

tcctgctggc tgtggccaat gatgaagagc tgaatcagct gctaaaagga gtcaccatag    180

ccagtggggg tgtgttaccc aacatccacc ccgagttgct agcgaagaag cggggatcca    240

aaggaaagtt ggaagccatc atcacaccac ccccagccaa aaaggccaag tctccatccc    300

agaagaagcc tgtatctaaa aaagcaggag gcaagaaagg ggcccggaaa tccaagaaga    360

ggcagggtga agtcagtaag gcagccagcg ccgacagcac aaccgagggc acacctgccg    420

acggcttcac agtcctnttc accaagagcc tcttncttgg ccagaagctg aaccttatta    480

cagggaaatc attaattagc cggctttgaa ggtggaggcc taaatcatcc taccaatgct    540

gcattgacct taaagatgac ctaggaacac gctggagaaa aaangtggnn aggat         595
```

<210> SEQ ID NO 331
<211> LENGTH: 421
<212> TYPE: DNA
<213> ORGANISM: Homo sapiens
<220> FEATURE:
<221> NAME/KEY: misc_feature
<222> LOCATION: (1)...(421)

<223> OTHER INFORMATION: n = A,T,C or G

<400> SEQUENCE: 331
acccaaaaac cacccccaac gccccccaac cctcaggcgt gcctgtgagt gtgtctgtgt 60
gtctcactct gactcaccca gacaactgac ttcagcagcc aaccttggtc attcccagaa 120
ccaccactgg ggggcatacg tgtggctaga ctgggggcgc ccgaatatct gtctctacaa 180
aaaaaaaaaa aaaaattaat ggggtgtggt ggtggtgcgt gcctgtggtg tcagctgctt 240
ggggcgctgg ggcaggagga tcacttgagc ccgagaattc aaggctacag tgagttaaga 300
ttacgccact gcactccatc ctgggtgaca gagcaagacc ttgtctcaag aaaaaatttt 360
taaatgagaa aaaaaaaann aaaanaaaaa aaaaaagctt gtacctcggc cgngaccacg 420
c 421

<210> SEQ ID NO 332
<211> LENGTH: 616
<212> TYPE: DNA
<213> ORGANISM: Homo sapiens
<220> FEATURE:
<221> NAME/KEY: misc_feature
<222> LOCATION: (1)...(616)
<223> OTHER INFORMATION: n = A,T,C or G

<400> SEQUENCE: 332
cgaggtacca ggctacatat ctcggtcagt agctggatcc tttgataatg aaggcattgc 60
tatttttgca cttcagttca catactattt atgggtaaaa tctgtaaaaa ctgggtcagt 120
tttttggaca atgtgctgct gcttatccta tttctatatg gtctctgctt ggggtggtta 180
tgtatttatc atcaatctta ttccactgca tgtatttgtg ttgttactga tgcagagata 240
cagcaaaaga gtctacatag catatagcac tttctacatt gtgggtttaa tattatcaat 300
gcagatacct tttgtgggat tccagccaat cagaacaagt gaacacatgg cagcttgcag 360
gtgctttgca ttgctgcaag cttaancttt cttgcagtat ctgagaaccg attaccaaac 420
caagagttcc agaccctttc nttttggggg atactacttc agngctgggt cctanggcat 480
tattgntatc nggtacattg cccctggatg gcngttantc ntgggaaccg ggatncaaaa 540
cccntccata tgctanggnt gncctaacct acaatngggg ctttttgac aaaaanntgg 600 atncctccgg ggccnn 616

<210> SEQ ID NO 333
<211> LENGTH: 650
<212> TYPE: DNA
<213> ORGANISM: Homo sapiens
<220> FEATURE:
<221> NAME/KEY: misc_feature
<222> LOCATION: (1)...(650)
<223> OTHER INFORMATION: n = A,T,C or G

<400> SEQUENCE: 333
ggtgggagag ctaagtctgc attatttttt ggaatcatta attaatttgc aatcacagag 60
tcttcaggaa aaaggcaagt tatcagctga agaaaatccc gatgactctg aagttccatc 120
atcatcagga attaactcta ccaaatccca agacaaagat gtcaatgaag gagaaacatc 180
agatggagtg aggaagtcag ttcacaaggt ctttgcttcc atgcttggag agaatgaaga 240
tgatgaggag gaagaggaag aagaggagga ggaggaggag gaggaagaaa cacctgagca 300
acccactgcg ggcgatgtat ttgtattgga gatggttctc aatcgtgaaa ccaagaaaat 360
gatgaaagag aaaaggcctc ggagtaaact tcccagagct ctgagaggtn tnatgggtna 420

```
ancctcnntt cgttttgnnt gaagagaacg tggngaggcn aatnttgngt gcctgggaat    480

nataaaaaca gctcttttgg cttatggcca tcttacttta ncctgatttt agggccnagg    540

ngcctngaaa atcntgccnt tgagtgatgc tggccttnaa tcccnggccc cnaaaaaggg    600

ttnactggcn aatttttggn nagcctttta ancggttttt ttgnttcaan               650
```

<210> SEQ ID NO 334
<211> LENGTH: 734
<212> TYPE: DNA
<213> ORGANISM: Homo sapiens
<220> FEATURE:
<221> NAME/KEY: misc_feature
<222> LOCATION: (1)...(734)
<223> OTHER INFORMATION: n = A,T,C or G

<400> SEQUENCE: 334

```
tgntatctga gaattcgcct ttcgagcggc gccgggcagg tacagattaa cttaacacaa     60

aaacccgaac ttcaaaatga aggtgtgtgg aggaaaggtg ctgctgggtc tccctacaac    120

tgttcatttc tttgtggggc agggggtagt tcctgaatgg ctgtggtcca atgactaatg    180

taaaacaaaa acagaaacaa aaaaaacaag gaactgtcat ttccacgaaa gcacagcggc    240

agtgattcta gcaggcctca gggccctggg cctggggagg ctacatgagg gggagcctca    300

gtcacaggat caacctgggg cccgaaggag cagggttccc tgcctctccc tctgcaacag    360

atcatcccat ccaacacaac ccccaaaatg ttgatgatga cgcaacatgg tcaaccctna    420

agacctttaa gaccaaacag agcagcatag gaaaaaaaaa accaaacgca ccaatttctg    480

catgtgtcaa tggtagggca ccattttnaa aaagtttggc ttaaacaagc tggctttact    540

tgganggacc taatnccaag cttaattcct ttggtaangg aaaaaaccct tgaaccccnn    600

tctnagctta aantcttaag gttaagtccn aaccanttaa aacnttctgg gttnccccctt    660

tccaagnttn aagccccctt ttccctnaac ctggggattg ggggnaattn accnggncnt    720

ttaaatttcc gngg                                                      734
```

<210> SEQ ID NO 335
<211> LENGTH: 492
<212> TYPE: DNA
<213> ORGANISM: Homo sapiens

<400> SEQUENCE: 335

```
acatccttca ccaccatgga atattttagt ctatgtagtc aaagtcttct ggaattccaa     60

aagttctatc aattttattt tcttcaaacc caaattttct tttggcccaa gattttattg    120

cgaatatgtt atgtatttct tccacaactt gcggatcaca gtctttgtat ttttctactt    180

ctgcctttag ctgttccctt tggtctcgaa gtgaagaaag ctcttttgct agcctggttc    240

gctcttccgt ttcacatcgg ccaattttag ctttctcaat gcttttctgt aggcttgcat    300

gcttttgact tccctcagac aactgagatt ccagaacctc caacttatgt ttccttgcat    360

gaagagcttt acttggaaaa gcccaataat aattagaagt tccgatcctc tcacagtcaa    420

ccataccatc atcaactaag ctttgaagga cttcttttac tgacatagca gtaatgcctt    480

tctctttggg gg                                                        492
```

<210> SEQ ID NO 336
<211> LENGTH: 732
<212> TYPE: DNA
<213> ORGANISM: Homo sapiens
<220> FEATURE:

<221> NAME/KEY: misc_feature
<222> LOCATION: (1)...(732)
<223> OTHER INFORMATION: n = A,T,C or G

<400> SEQUENCE: 336

```
ggtacatata aatgaatctg gtgttgggga aaccttcatc tgaaacccac agatgtctct     60
ggggcagatc cccactgtcc taccagttgc cctagcccag actctgagct gctcaccgga    120
gtcattggga aggaaaagtg gagaaatggc aagtctagag tctcagaaac tcccctgggg    180
gtttcacctg ggccctggag gaattcagct cagcttcttc ctaggtccaa gccccccaca    240
ccttttcccc aaccacagag aacaagagtt tgttctgttc tgggggacag agaaggcgct    300
tccaacttca tactggcagg agggtgagga ggttcactga gcttcccaga tctccactgc    360
ggggagacag aagcctggac ttttgcccaa cctgtggccc tggagggtcc cgggttgtca    420
attcttggtg ctcttgnggt tccagaagca agccggaagt ttgaaagaaa gggaaccttg    480
ggaatnaagg ggtgcttggg tattaanccn naaaagggat tggggttcct gnttccaang    540
gganccttt ggcctttctt tttggnctt tncttaaggc cccaggccct nggggtttgg    600
accttngccc cggngggccc aaggggccna aattcccacc ncanttgggg ggcccggtac    660
ttaangggga atcccaactt tgggncccca aactttnggg gnaaancntn gggccaaaac    720
tggtttcctn gg                                                         732
```

<210> SEQ ID NO 337
<211> LENGTH: 642
<212> TYPE: DNA
<213> ORGANISM: Homo sapiens
<220> FEATURE:
<221> NAME/KEY: misc_feature
<222> LOCATION: (1)...(642)
<223> OTHER INFORMATION: n = A,T,C or G

<400> SEQUENCE: 337

```
ggtacaacag tagaagaagc aacaacaata gtaaagccac aggaaattat gttggacaat     60
atagaagacc cttctcagga ggatctttgc agtgttgtcc aatctggaga aagtgaggag    120
gaagaggaac aagataccct tgaactggag ctagttttgg aaaggaaaaa agcagagttg    180
cgagccttgg aggaaggaga tggtagtgtg tcagggtcta gtccacgttc tgatatcagc    240
cagccagcat ctcaagatgg aatgcgtagg cttatgtcta aaagaggaaa atggaagatg    300
tttgttcgag ctaccagtcc agaatctacc agtaggagtt ctagtaaaac tggacgaaga    360
tctccagaaa atggagaaac tgcaattggt gctgaaaaat tcagaaaaaa tagatgagaa    420
ttcagataag agatggaagt agaagaatct tcagagaaat taaagtcctg ccnggccgnc    480
gttcnaangg cnaattncac acctggcggc cgtctagtgg attccacttg gtcccaactt    540
gcgnatctgg gatactggtt cttggngaat tgtntccgtt acaatcncnc acttcaancc    600
ggagcttaan gtaaacttgg ggcntannag tgctnactcc tt                        642
```

<210> SEQ ID NO 338
<211> LENGTH: 723
<212> TYPE: DNA
<213> ORGANISM: Homo sapiens
<220> FEATURE:
<221> NAME/KEY: misc_feature
<222> LOCATION: (1)...(723)
<223> OTHER INFORMATION: n = A,T,C or G

<400> SEQUENCE: 338

```
acataaacac acgcatatca caagtctagt caagaaagaa atacatagaa aaacaagata     60
```

-continued

```
gaattttaaa aataatttgc aagggaagtt ctcaatgctt cagttctaaa atattgtctt    120
cttttagaaa aatttaagac tggaataaca gattgttttt cctgcaatgc tgtaattact    180
gcaaatttat cagcaaagag gtaaacagca atgcaatttt tccttaagct tgaatacata    240
agggaacaat aaagaaacct gattagacct gaactaatta aaagtcacac cagtaatttt    300
caggccagct ctggtctcca ggtagaattc caggacaggt ttgnatcact gggtccattc    360
ccaacaggct ggataggaga gtctggagta attataagga taccaccttc ttctatcctg    420
ggctgccgac tggcattggg cttcacattc ccagaatacc ttctgngnga ataggccctt    480
ttcaggggga ccnggaagga aggaaaaagg gggctntggn aaacatnggg ggattctttg    540
gnaaaatttc tggcctggaa tngtggcnaa cctttggggc ttggggtntn ggaaaatgtc    600
caagggganct ttaangggnc ccttngaact cggagggnaa aatttaaccc ctangggccc    660
ttgggttnaa aaagggcttt atttggggga cccgggttnc ccttgnaaaa aatgccncca    720
ann                                                                  723
```

<210> SEQ ID NO 339
<211> LENGTH: 356
<212> TYPE: DNA
<213> ORGANISM: Homo sapiens

<400> SEQUENCE: 339

```
acaatagtgt aaaggtggtt tttaaaaaca tagccaggtg tggtggcacg tgcctttagt     60
tccagctact caggaggcta aggcaggagg attgcttgag cccaggctgt gtggttcacc    120
ataattgtgt ttgtgactag ctactgcact ccaacctggg caacatagtg ggacttcatc    180
tctaaaacaa aacaaaacaa aattacactt aagcactatt gtttaatttt taattgtcag    240
tttatcatta ttttgggtaa gacattctgg ggtttcttga atcttgtcca aaaaccagtt    300
gttttggaaa attgctttaa attgagcata tttatgtata ttggataaaa atgtcc        356
```

<210> SEQ ID NO 340
<211> LENGTH: 502
<212> TYPE: DNA
<213> ORGANISM: Homo sapiens
<220> FEATURE:
<221> NAME/KEY: misc_feature
<222> LOCATION: (1)...(502)
<223> OTHER INFORMATION: n = A,T,C or G

<400> SEQUENCE: 340

```
caggtacaat taactgtcac acagtcagat ataattcact ctgatgaggc cagagaaaga     60
aaacaaggca aagaaagggc tcatcttgtc cctttaggta atatccaaat atcccagcac    120
ggaaaccatc ttttcctcaa aggttatcta cacacgtggc ctgagaagaa aggcagtaag    180
cctttgggga gttggggaga aggaaggaaa agaaaacagg aggaggaaaa aggaagacct    240
cttttctgaa ccacaaatgc ctcatgctgc gcactccaag ctgaaataca gtatggtagg    300
tattctaagg gggaaaaaaa caactacatt tctttcctat tactgattcc tctctgcttc    360
acagacccag ctcggccaag tggaaaacgg ctgccatgag ttctgcagaa gctgcatgtc    420
ttgccctggc agtctgaagg tgaagcangc ttcanaggtg gacagctcaa ggagaattcc    480
cagaggncnc cnaaaagccc cc                                             502
```

<210> SEQ ID NO 341
<211> LENGTH: 243
<212> TYPE: DNA

<213> ORGANISM: Homo sapiens

<400> SEQUENCE: 341
acatcatcac cttcttggtc aagttttcca tccaacttaa ttttaggatt ctccggacaa 60
tcaacatttt cactgctttc tgctgcaatt ttctgttttg gattttcagt cacctcgttt 120
tgggcttcca ctgctgactt tctgtcagta gactttacct gctcttcttc cttaatttca 180
cttaaatctg tgttctgata cgttaactct tttttaacat ctttaagggt ttctacgggt 240
acc 243

<210> SEQ ID NO 342
<211> LENGTH: 669
<212> TYPE: DNA
<213> ORGANISM: Homo sapiens
<220> FEATURE:
<221> NAME/KEY: misc_feature
<222> LOCATION: (1)...(669)
<223> OTHER INFORMATION: n = A,T,C or G

<400> SEQUENCE: 342
tgaggtcaag cttttttttt tttttttttt tttttttttca gctttgttgt agttganatt 60
ctgatgttca cctaacaaag tccctgacaa aacagacttc cttcaatcca ggtcataatt 120
tgaaacgtta tacaataatg agatttaagt gatgaatgga aagaaaagaa ggagactgaa 180
aagatatcag aaatttctat tngtttttag attcagaaaa atataattac aggccaacat 240
gggtntgaca gagaggaagg acgtcagcag ttacttgaat gtaacccctt cccagcattt 300
ccaaagacct gcaatgngct cattgngatc caagggcctt gntacctagt ttctaggnga 360
tctacagant tgaaacaacc cagcacaact ttatttcttg gagaagatga acccttaact 420
ntgaaggtgc ntaaaggaaa tnttnaactg gtcacttcca tgggtccggt ttcaaagcca 480
caatcnttcc gattaaanta aaacctggga naaaagccaa cggngggcaa ncaaacgggn 540
gggattctac ntttggtaac ccattgaacc gggggcttcn ttttaaanan gtgntcattg 600
gtttggtttt anaacctaaa nccccttttt tnaaaaaant ggtgnaaatt ttccncntnt 660
aacccggtt 669

<210> SEQ ID NO 343
<211> LENGTH: 500
<212> TYPE: DNA
<213> ORGANISM: Homo sapiens
<220> FEATURE:
<221> NAME/KEY: misc_feature
<222> LOCATION: (1)...(500)
<223> OTHER INFORMATION: n = A,T,C or G

<400> SEQUENCE: 343
ggtacagggc agtgacatga gctttgacaa acagttcatg ctaggagtag agactgtgtc 60
ccaggactga gggatctgcc taagatcaag ggaaaaatct gaaagactcg tcctaacaaa 120
gtgtaaaact aaggttttat aagttcaagg gaactgacta ctgattagct gccagtgaaa 180
acaaaaatca acactctcag gtaacagaaa tcagaattgc tacaatgcat caccaacaat 240
gtccagctta caatttttaa ggacgactaa ataggagact cccagtttct agtctggcac 300
ataaggaggt cggcagtcat cacttcattc taacaagtaa aaagctgaac aaactaaaaa 360
atcaacaact cagccgggtg tggtggctca cgcctgtaat cccagcagtt tgggaggttg 420
aggcaggcgg atcatgaggt caggantttg agaccagtct ggcccacatg gnaaaacccc 480
ggtctactta aaanataaaa 500

<210> SEQ ID NO 344
<211> LENGTH: 483
<212> TYPE: DNA
<213> ORGANISM: Homo sapiens
<220> FEATURE:
<221> NAME/KEY: misc_feature
<222> LOCATION: (1)...(483)
<223> OTHER INFORMATION: n = A,T,C or G

<400> SEQUENCE: 344

```
ggtacttcgg ccaaaaacag gagcccattg tgacaggcat ctggcatcac tacaaaggac     60

ccctggggct ccatggcaac caggcaggca ctaaggatag aaggagagtc tgcggcagag    120

attccacaca tccggcacac atccttgagc tttttgctga ttgtctgtag tgaacattct    180

ccaaggagga tactccaatc tttaagctcc ccatggccaa gacgcccaag tcgcccgatt    240

acaactctcc agggtagaga tgtcatttgg acaatcccta tgcaccactc ccataacttc    300

tgtagtccaa ttttacgtgc agatacttta ctcctccgtg acctaacaaa taaagaaatg    360

gggaagggga aggggtccct agataaatca gagttattta tcacttataa gaccaacact    420

agaaatttcc aagaacctat ccatgctgna cctgccnggc ngccgtnnaa aggcgaantc    480

agc                                                                  483
```

<210> SEQ ID NO 345
<211> LENGTH: 667
<212> TYPE: DNA
<213> ORGANISM: Homo sapiens
<220> FEATURE:
<221> NAME/KEY: misc_feature
<222> LOCATION: (1)...(667)
<223> OTHER INFORMATION: n = A,T,C or G

<400> SEQUENCE: 345

```
ggtacaggag agaaggctct tatgaccgat acctacgaat ggatgactat tgcaggagaa     60

aggatgactc ttattttgac cgttacagag atagctttga tggacggggc cctccaggcc    120

cagaaagtca gtctcgtgca aaagagcgtt tgaaacgtaa ggaacggcgt agagaagagc    180

tttatcgtca atattttgag gaaatccaga gacgctttga tgccgaaagg cccgttgatt    240

gttctgtgat tgtggtcaac aaacagacaa aagactatgc tgagtctgtg gggcggaagg    300

tgcgagacct gggcatggta gtggacttga tcttccttaa cacagaagtg tcactgtcac    360

aagccttgga ggatgttagc aggggaggtt ctccttttgc tattgncatc acccacaaca    420

ccagatcacc gntcctgcac aggtcaacat catgtttgga accccgnaag aaccttgnaa    480

catgccccaa gncnatgcca tggtgctggt ggccanaaat ttttagccgt tccaggaatt    540

aattcccgga anaaggaacc tnagggnaat gccnaaccgg ccntcaaann gcccatgaaa    600

ccttcttgcg gaaaaaaaaa gggggcctna ggagggatcc ttggggcccc tttaancntt    660

caancnn                                                              667
```

<210> SEQ ID NO 346
<211> LENGTH: 754
<212> TYPE: DNA
<213> ORGANISM: Homo sapiens
<220> FEATURE:
<221> NAME/KEY: misc_feature
<222> LOCATION: (1)...(754)
<223> OTHER INFORMATION: n = A,T,C or G

<400> SEQUENCE: 346

```
actgaactac ttcattacca actcggccca gatattgaca tgcctgatga taacaaaaga     60

attagaaggg tgcgtctcct ggtggaagag ggctgtgaag atcgaattct ggtagcacat    120

gacatacata cgaaaacccg gctgatgaaa tatggaggtc acggctattc tcatatactc    180

accaatgttg ttcctaaaat gttgctgaga ggcataactg agaatgtgct tgataagatt    240

ctaatagaga accctaagca atggctaact ttcaaatagg atggttgctt atgaattcac    300

accttgagta taaaacttgc agagaacatt cagcgatttc cagtccactg tgagatatta    360

atcagttacc taggactaat gacagatcat ttccttctga tgagaactag gaggggtttg    420

ccttctctga gacccagcta ttacaactgg gccctntaag ggaggtactt aagcctaaat    480

tgagccccta ataatttnaa cttaacccaa anttaattnc cggaanttcc cttngggccg    540

ggaaaccacn ccttaagggg ccnaaatttc cagcnccaac ttgggcgggg ccggttactt    600

aanggggaat ncccaaactt tggggncccc aaanctttgg gcggaaaacc atngggccct    660

aaacctnggn tnccccnggg nggaaaaatn ggnaattccc ggtttnanaa atttccccnn    720

ccaanntttt tcnnaacccc ggnaagccnt taaa                                754
```

```
<210> SEQ ID NO 347
<211> LENGTH: 444
<212> TYPE: DNA
<213> ORGANISM: Homo sapiens

<400> SEQUENCE: 347

accgtctcga tcatctgctt cccttgggct gagagctcca ggggtgactc gaaggtgacc     60

ctataaggag tcatgagggt cctgaggttc tggaacagct tctctccatt ggggttcccc    120

agaatgtagc agcccatgat gtggatgacg ttcggctctg ggttcacttt gctcatcagg    180

cggctcagcc gcttccagaa gtgaatcatg tcctcttcct tctccacttt ggcaaaggtg    240

gccaccttgt tcttgaggag atagaggtgt ccaggacctc cctggcagaa aatcagcatt    300

ttccagatct tggctccctt gtggtagacg ttcagcttcc tctctatctc ctcaaggatg    360

tcctcgaagg ttgcgtgctc atggtccgta gaggatgggg atgatggagg ggtcatcccc    420

ggcggatgat agtggggatg tacc                                           444
```

```
<210> SEQ ID NO 348
<211> LENGTH: 693
<212> TYPE: DNA
<213> ORGANISM: Homo sapiens
<220> FEATURE:
<221> NAME/KEY: misc_feature
<222> LOCATION: (1)...(693)
<223> OTHER INFORMATION: n = A,T,C or G

<400> SEQUENCE: 348

ggtactttaa gaccctttgc cttaaagtac tataccaaca cagactttat agtatgttta     60

aaaatcccaa ctgcaagata cacaggatgc tgtaggcctg atttcctgtt gtagaacctc    120

cagccctgtg ttgaatgagg aggtgcaaat atatagaccc ttaagatcag accacagcag    180

gcattcaggt ggaggggatg aactccattc attccagctg tgcagtggga catctgcgcc    240

ctccgcatct cggctcattc ctcatctgag ccactcaaga gggcggtctg gtaagtgtca    300

tctgaattca gcttctgaat tccaatgatt tctccccttc cgtgtctctt catccgagtc    360

aaaaggcagt aaacaagaga atagttgacg gccacaatgc tgaaggcagc aggtagtgcc    420

agcagaaaca catggtgatg aacatgaagg tggcatcatc cttctggncc attcnggtgg    480

tncaaaaggt gggaacngga caaaccncaa ttttgccnaa ccangttccn tgnaaaatga    540
```

```
ttaaactggg tccggaaaaa gttccagcnc aatggnggtc ccggaaanat cnccntttng    600

ggggantctt acnccncctt ttgaaaaggg ctttccncng gaatgaanng aatnncttgg    660

nccaacggaa ggcccgtttg nggcntngta atn                                  693
```

<210> SEQ ID NO 349
<211> LENGTH: 299
<212> TYPE: DNA
<213> ORGANISM: Homo sapiens

<400> SEQUENCE: 349

```
cgaggtacat tctctaaaaa ttgttactga ctggtaagaa atagacctga gtttttattt     60

ctaacaccca atcactaaac cacggcagca agcactggcc accgatttaa tggattacga    120

cacaggaaac cccatcaggg ttctatgtaa tttagtgata ctcatgtcac taatattgag    180

cattatactt gatctgcatt atattgttga tatgcagagg ctaaactagt catcatttgc    240

tctttcatct atcagtagag tccaaagttg tttgcttgaa tggactacat gttaaaggt     299
```

<210> SEQ ID NO 350
<211> LENGTH: 622
<212> TYPE: DNA
<213> ORGANISM: Homo sapiens
<220> FEATURE:
<221> NAME/KEY: misc_feature
<222> LOCATION: (1)...(622)
<223> OTHER INFORMATION: n = A,T,C or G

<400> SEQUENCE: 350

```
actgtttacc agatctttgc agatgaggtg cttggttcan gccagttngg catcgtttat     60

ggaggaaaac atannaagac tgggagggat gtggctatta aagtaattga taagatgaga    120

ttccccacaa aacangaaag tcaactccnt aatgaagtgg ctatnttaca gaatntgcac    180

catcctggga ttgtaaacct ggaatgtatg tttgaaaccc canaacgagt ctttgtagta    240

atggaaaagc tgcatggaga tatgttggaa atgattctat ccnnngagaa aantctggct    300

tccagaacga attactnaat ncatgntcac acagatactt tgangccttt gaggaatctg    360

cattttaaga aatattggtg cnctggnatt taatancnna aaaagggctg cttgcatcaa    420

tagaanccat tncttaggtn aagctngtat nactntgnat tgcacccctc atttgcngaa    480

atgtcnttcn ngnnaactnt ggtacggaac tcctccatnc ttatcccngn aagttntccn    540

gagccanagg gtncnaccnt atcctatana nnagntcnnt cnggacntna tcnnctttng    600

ggnnccntag tggccctttn cc                                              622
```

<210> SEQ ID NO 351
<211> LENGTH: 574
<212> TYPE: DNA
<213> ORGANISM: Homo sapiens
<220> FEATURE:
<221> NAME/KEY: misc_feature
<222> LOCATION: (1)...(574)
<223> OTHER INFORMATION: n = A,T,C or G

<400> SEQUENCE: 351

```
gctttaacaa tagcagcaga caaaggtcac tacaaatttt gtgaactcct gattcatagg     60

ggagcccaca ttgatgttcg taacaaaaag ggaaatacgc cactttggct ggcatccaat    120

ggaggtcatt ttgatgttgt gcagttgcta gtgcaagcag gtgctgatgt ggatgcagca    180

gataaccgga aaatcacacc tcttatgtca gcatttcgca agggtcatgt aaaagttgtt    240
```

-continued caatatttgg taaaggaagt aaatcagttc ccttctgata tagaatgcat gagatacata 300
gcaacaatta cagataagga actgntgaaa aaatgtcatc aatgtgtcga aaccattgtg 360
aangctaaaa gaccacaagc tgcaaaagca aataaaatgc cagtntcttt taaggaactt 420
gatctggaaa agtcaganaa agacngaaac agctttgtgt aaagagaaaa gaangaaaga 480
gnaagaatag agaccgaagg actgagaata naacactagg atcgactcca gtaataagga 540
ttaattgnaa ntctaacttt nccctcatga ttgn 574

<210> SEQ ID NO 352
<211> LENGTH: 399
<212> TYPE: DNA
<213> ORGANISM: Homo sapiens

<400> SEQUENCE: 352
ggtacataat attccagtag gaaactgctt ccaagtttaa gcatgagctc cccaaactgg 60
agaaaacata ttttgctatt ctgagacaac aatcagaata cagactttgg attccaggtc 120
acagtttgct ttttagacaa ggtaaagcaa agaaagccac attgtgccat cttcagctcc 180
agtggcttta gcagtgactg tttgacataa aacatgtaag aattgcttgt tgggaagagt 240
gctttaggga cccactgttt tcatttcttc ttggagttta ccttgtttca gatgcagcca 300
tgggtaggtc agagatggac tgttggtgca ataaacccaa gaatcaatgt agcctcttaa 360
tcccatcaag atgtagtttg tagcagcaaa agtgtacct 399

<210> SEQ ID NO 353
<211> LENGTH: 727
<212> TYPE: DNA
<213> ORGANISM: Homo sapiens
<220> FEATURE:
<221> NAME/KEY: misc_feature
<222> LOCATION: (1)...(727)
<223> OTHER INFORMATION: n = A,T,C or G

<400> SEQUENCE: 353
ggtactttta cccatttcca gttccacctt tactttatca agtggaactt tctgtgggag 60
gacagcaatt taatggcaaa ggaaagacaa gacaggctgc gaaacacgat gctgctgcca 120
aagcgttgag gatcctgcag aatgagcccc tgccagagag gctggaggtg aatggaagag 180
aatccgaaga agaaaatctc aataaatctg aaataagtca agtgtttgag attgcactta 240
aacggaactt gcctgtgaat ttcgaggtgg cccgggagag tggcccaccc cacatgaaga 300
actttgtgac caaggtttcg gttggggagt ttgtggggga aggtgaaggg aaaagcaaga 360
agatttcaaa gaaaaatgcc cgccatagct gntcttgagg agctgaagaa agtaccgncc 420
ctggcttgna ttggaccgaa gttaaggcct anaatccaaa tgaaanaccn aaancccctt 480
ggtncaangc cnccagaccc anggccccat aattttttgg ccncngggg attcaaatnn 540 ccnttttaan ccncgacttg ggnccncnaa attcncgccn ggggccnaaa naaaggggta 600
naaaggggan ccccaanagt taccccttgnc ccngggcnng ggnccgtttt tnaaaanggg 660
gtcnaaantt cccatntcnc attggggggg gcccgttttc ttagggggaa tcccgagctt 720 tggggnc 727

<210> SEQ ID NO 354
<211> LENGTH: 411
<212> TYPE: DNA
<213> ORGANISM: Homo sapiens
<220> FEATURE:
<221> NAME/KEY: misc_feature
<222> LOCATION: (1)...(411)
<223> OTHER INFORMATION: n = A,T,C or G

<400> SEQUENCE: 354
ggtaccatag gtcatttctg gccgatagtc tgaatttaca gcccattgct ggtgaaagtt 60
tagtaatttt aaattgtttc tgtgagccca tgtaacactg acaaaattct ccatttcctt 120
ttccttcatc ccattctaat acaaagtttt ggattttaga accattgtca ctaggtgcct 180
tccattgcaa agtgagtgaa tttttggtcc gattggctat ccttggtgga ttaggtatat 240
caggttcaca gctcaaggtg gtaaagattt cagcctctga aggagttccc tttatagaat 300
tatattctgc ctggactttt gcatggtaat ccatggctgg cttgagatca tttaaagtga 360
tatttgnttc ttctctacat atacactttt ggatttccca tcttttccag t 411

<210> SEQ ID NO 355
<211> LENGTH: 331
<212> TYPE: DNA
<213> ORGANISM: Homo sapiens

<400> SEQUENCE: 355
ggtacttttc tctatctgat tcagccattt ctgccagagg gaaaaggtcg gcagaaaaga 60
tgtattgagt gaatagttaa ggataggatc tttgtccaaa aatttcagaa agattgagca 120
aatctgacgt attcattgag tgagtttctg tgttttcaaa ggtggaggag aaatttgtgc 180
tggaagtttt taagcctccg ttttcttgga aatcagtctg taacactggc aagtcttaag 240
atagtcccgt ttagactttg cagatgctga acctggctct gtaacgctgg gaagtcttaa 300
gatagtcctg tttagacttt gcaaaccctg t 331

<210> SEQ ID NO 356
<211> LENGTH: 678
<212> TYPE: DNA
<213> ORGANISM: Homo sapiens
<220> FEATURE:
<221> NAME/KEY: misc_feature
<222> LOCATION: (1)...(678)
<223> OTHER INFORMATION: n = A,T,C or G

<400> SEQUENCE: 356
ggtacttttt aattcagcac cttttcaaaa tatgtgctgg gatggattct tcttagggaa 60
agccccatat agaattctca ttttggagca tcatttttat atgctatctc cccagtgtat 120
cttctcaata tttataacac tttatgaaat aaatattggg ttgcctgtaa gaagagaaaa 180
atatagctct ttctgagaaa gagcatttgg cttgcagttt acagcaagag ctgaaattag 240
agaccatagg gatttccaag accaatttga ccagaaatac aaaaattctg atgtcaaaaa 300
ccctctcaca aaatttaaca ggtagaaatt attttagcag tatagcctga aatccagtgc 360
aacaaaaatg natcccaatt ctatgatatg ncataagtat gntctcttan ctggcttncc 420
ttacttggtc ctactcccta cttggacctt tngggaagaa aatggtcggc ccaancccat 480
ctttcaaatt ttcnaattcc ttaatatgga acccttagcc atggaataac caggggcntt 540
aaagttcccc ccatttaaat aatgnccctt aatntggnaa anggcttgaa ancctggncc 600
aaagggctgg ggtcttttaa gccctttgaa ggttaacctt caaaaggggg aaaaaaccnt 660
ttttttttta agttgggg 678

<210> SEQ ID NO 357
<211> LENGTH: 414
<212> TYPE: DNA

<213> ORGANISM: Homo sapiens
<220> FEATURE:
<221> NAME/KEY: misc_feature
<222> LOCATION: (1)...(414)
<223> OTHER INFORMATION: n = A,T,C or G

<400> SEQUENCE: 357
acaccgagaa ccataatgaa aaaaccttcc gtgtgttttg tcatgttttg ttccagggaa 60
gcagttgatg agtgctgtta ctaatgcttt ctcccagatc cattcagtgg tggagaggag 120
gaaaatgggc tggttggatg tggtcttggt gccttgcagt tactctgcac tggttatgca 180
tttaattctc ctcttttcta gttaaccttt tgccagtggg ttttccatag tctgggtatt 240
tgtccttata tcagttatac cacctaaggc aactgggtgc aaaatgcatt ctgttcactc 300
actgtctggg ccttccccac cctagtcttg gcacattcct tcaagaatgt agttaccgtc 360
tgcttgggaa gatgtcagtg caaatgtgaa gataatgggc atcggnaaac ccct 414

<210> SEQ ID NO 358
<211> LENGTH: 633
<212> TYPE: DNA
<213> ORGANISM: Homo sapiens
<220> FEATURE:
<221> NAME/KEY: misc_feature
<222> LOCATION: (1)...(633)
<223> OTHER INFORMATION: n = A,T,C or G

<400> SEQUENCE: 358
cgagggtact tcaaagaaag tcaaatccta agcctgccca ggcccaaaga caaagccagc 60
caggacctga ccacctgtat cctcttggtg gcaatctgct gaagccagat gagttctgct 120
ttttaattcc aatcctattc tgccactgaa actaggcctg ggcaaccact cttaatcatt 180
aacatatcaa aaggagtatc tcctctgaga aaagagcttt tctcaggttc tagaagctag 240
cttttacaaa agacgtcttc aaataggggc cgggtgcagt ggctcacgcc tataattttg 300
gcactttagg aggctgaggt gggaggattg cttgaggcca ggagtccaag accagcctgg 360
acaacgtagt gaaacatcta tttctaccaa aaaatttaaa aaaggaaaaa attatgtcct 420
aaaatattaa anggncatta aaanggccca ctngaacttg gaactttggg gaatctagtg 480
caacaacccc ttgccggana gaagaanctt naaccagctn ttgaattgcc nggtcaaant 540
ggtttatatt aaaaccgata ccactttttn ataatccttt ggnaaatnaa ctgtaagccn 600
tttttccctg aacggaccnt gcctgcccaa ttt 633

<210> SEQ ID NO 359
<211> LENGTH: 635
<212> TYPE: DNA
<213> ORGANISM: Homo sapiens
<220> FEATURE:
<221> NAME/KEY: misc_feature
<222> LOCATION: (1)...(635)
<223> OTHER INFORMATION: n = A,T,C or G

<400> SEQUENCE: 359
acagattctt ttagaagctg gggcagatcc taatgcaact actttagaag aaacgacacc 60
attgttttta gctgttgaaa atggacagat agatgtgtta aggctgttgc ttcaacacgg 120
agcaaatgtt aatggatccc attctatgtg tggatggaac tccttgcacc aggcttcttt 180
tcaggaaaat gctgagatca taaaattgct tcttanaaaa ggagcanaca agaaatgcca 240
ggatgacttt ggaatcacac ctttatttgt ggctgctcag tatggcaagc tagaaagctt 300
gagcatactt atttcatcgg gtgcaaatgt caattgtcaa gccttggaca aagctacacc 360
cttgtcattg ctgctcaaga gggacacacc aaatgtgtgg agcttttgct ctccagtggg 420
gcagatcctg atctttactg naatgangac agttggcagt ttcccnatca tgccagnttg 480
cccaaatngg gccntncaaa aatcttggac ttggtaatnc cccttaactn accgggncct 540 gggaccccttg gcttaaccaa agtnagncct tgttaattaa naaaggtttg ggggncttga 600
aaantgcttn naantnttct ccggaatggg ttcng 635

<210> SEQ ID NO 360
<211> LENGTH: 403
<212> TYPE: DNA
<213> ORGANISM: Homo sapiens
<220> FEATURE:
<221> NAME/KEY: misc_feature
<222> LOCATION: (1)...(403)
<223> OTHER INFORMATION: n = A,T,C or G

<400> SEQUENCE: 360
aggtgaaagt tcaccgagtg gtgctatggg cctgtccggg tgtcgctgta tgacctggct 60
tctgtggaca gctgtgagga gaactcagtg ctggagatca ttgcctttca ttgcaagagc 120
ccgcaccgac accgaatggt cgttttggag cccctgaaca aactgctgca ggcgaaatgg 180
gatctgctca tccccaagtt cttcttaaac ttcctgtgta atctgatcta catgttcatc 240
ttcaccgctg ttgcctacca tcagcctacc ctgaagaagc aggccgccct cacctgaaag 300
cggaggttgg aaactccatg ctgctgacgg gccacatcct tatcctgcta gggggggatct 360 acctcctcgt gggccaactg tggtacctng ggccggacca cgc 403

<210> SEQ ID NO 361
<211> LENGTH: 631
<212> TYPE: DNA
<213> ORGANISM: Homo sapiens
<220> FEATURE:
<221> NAME/KEY: misc_feature
<222> LOCATION: (1)...(631)
<223> OTHER INFORMATION: n = A,T,C or G

<400> SEQUENCE: 361
ggtacaagct tttttttttt tttttttttt tttttttttt cgtttttaaa aactcgggtt 60
ttatncaata gaatgttttn tagcanatgc ctnttgtttt aatatattaa aattttgcaa 120
agccntttga gctactgcct tagtctaccc actgtccttt ngttatgagg tanaggatnt 180
catgacacca tacacacaaa cccatcattg cctgtgaatg cacgtagggc canaattcct 240
cagttcccgc tcctctgagg gttgatactg ctgggaatgc caaccantnc acaagcanag 300
ggaagccccn tcaggcctnc aggaggagcc gcagcagggg gtccaattna aaccagcngc 360
aaaagagcct gacattttcc catccatnta tgaggaaagc cattttacag aacntggaca 420
tagggcactt gnttttccca cacnaanggg atgggaattt tctacctata gncattcctt 480
gnacttctgg anttactcan gaccanggnc caactaaang gcaaaaccct tttggntctt 540
taaccagaaa agcantnctn nggactgggg acctncccgg gnggccnttt aaaggngaat 600
ttccnnnntt ggggcggtnt aggggaccan g 631

<210> SEQ ID NO 362
<211> LENGTH: 660
<212> TYPE: DNA
<213> ORGANISM: Homo sapiens
<220> FEATURE:
<221> NAME/KEY: misc_feature
<222> LOCATION: (1)...(660)

<223> OTHER INFORMATION: n = A,T,C or G

<400> SEQUENCE: 362

```
ncnggtacct canttgnctg cttacgctnn anccagcatg tgtgagctag gtcatttnct     60
gcaagccagg caaccacacc agngtataan cctcaagcaa atgtnactcc naagcccnan    120
atgggactaa ggcctttgct gggctaggcg tggtgtaaan cccangcctg naagctnnta    180
cccaaccnta attagtntca ncttactntc aatatgtgca tantttcata aagcacacat    240
tnncatgagg aaaagangat ggtggtgaaa gggnaggggt gangggacat nttcaagtca    300
canaggctgn anaactcagc atgacttgtg gacggaccac aggncatnca gggnnacaac    360
acngacataa ctcaaccagt ggtnaacngn tctaaaccag ggtnaacagg agangggacc    420
aaangnaact tcctggattt ngctgcaagt ttaaaagata agttctacct tagctttaag    480
cttagnccct tatgggggca aaaaaanggn aaagtcaatt cttgccncaa atccaagctt    540
gggccngcca aaaaagggaa atnggggttn ttaggcccca aaacctnaat tgagntccca    600
aggnttcaag gcccaggcaa attgnaaagt tcctgccttn aaagcttggn ccaataaaaa    660
```

<210> SEQ ID NO 363
<211> LENGTH: 486
<212> TYPE: DNA
<213> ORGANISM: Homo sapiens
<220> FEATURE:
<221> NAME/KEY: misc_feature
<222> LOCATION: (1)...(486)
<223> OTHER INFORMATION: n = A,T,C or G

<400> SEQUENCE: 363

```
ggtaccttca accttctcta ttttaatctg aggggaaatt aagagaatct caaaagttac     60
tacagagttt gggtaggcta gatacattta ttaatagtaa aagcaaccat ggcaaaagca    120
accatactca ttcttgataa tgaaaggatc ttctatatac aaacctagca aattaaaaaa    180
aaatactaaa acaaagtgtc tgaagataat gaaaggcagt tcaattcatg taatgtcaag    240
taactttcaa ttgtaataga atcatttata ttcttatagt gccttacagc atattttatc    300
gttaatgaga aaatgaacca aaactatagt gctaaccctg aaaccttaaa ccgaacctta    360
caaagttaaa gactaagtgt tggtcagaag gaaaaggatg caccatgcat cttcacaggg    420
aaaaatgaaa atagcnaaga tggcagaaat gcctgaactc atgggtacct gcccggcggc    480
cgttng                                                               486
```

<210> SEQ ID NO 364
<211> LENGTH: 686
<212> TYPE: DNA
<213> ORGANISM: Homo sapiens
<220> FEATURE:
<221> NAME/KEY: misc_feature
<222> LOCATION: (1)...(686)
<223> OTHER INFORMATION: n = A,T,C or G

<400> SEQUENCE: 364

```
ggtgctcgga ataacttcct gcagcgacca acaggctaaa gagggggaag gtctggaggg     60
atccagcacc ggctcctcct ccggcaacca cggtgggagc ggcggaggaa atggacataa    120
acccgggtgt gaaaagccag ggaatgaagc ccgcgggagc ggggaatctg ggattcagaa    180
ctctgagacg tctcctggga tgtttaactt tgacactttc tggaagaatt ttaaatccaa    240
gctgggtttc atcaactggg atgccataaa caagaaccag gtcccgcccc ccagcacccg    300
agccctcctc tacttcagcc gactctggga ggatttcaaa cagaacactc ctttcctcaa    360
```

ctggaaagca attattgagg gtgccgaccg cgtcatcact gcagaaaccg tgcaaggcag 420
aacccgatca gaactaccaa ttccaccagc atgccgtatt cccacttggc ttattggtgg 480
ggaaatacct tgccngggcn ggnccgttca aangggcgna anttccagct cacttggccg 540
gccggtactt aatggggatc cnaaactttg gnaccccana cnttggggcg nnaatncatn 600
gggcaaaaat tggntnncnc tgggggnaaa atggtaatnc cggttcacaa nttcccccca 660
attttctann cccggaagct taaagg 686

<210> SEQ ID NO 365
<211> LENGTH: 639
<212> TYPE: DNA
<213> ORGANISM: Homo sapiens
<220> FEATURE:
<221> NAME/KEY: misc_feature
<222> LOCATION: (1)...(639)
<223> OTHER INFORMATION: n = A,T,C or G

<400> SEQUENCE: 365
ggtacatcct aaagcattct ggtacaaatg aaatggaact gcctcttgtg ggtctatttc 60
agaagtctgt tgtcagagtt cagttcacag gcatcaacca gaagcctagt gaggccgttt 120
gaaattctgg cccagattaa ttttttaaag ctgcatttgg agctttttaa agtcgagctg 180
tttccaaagg cttaactgaa gagtaactga tttcactgga aataaaagtc cacatgtgat 240
cccagctgga gtgtggtcat atttttcttg caaacctaga atgtcttggg gaacaaacgg 300
ctgtcacgtg tccccttcca aaaatgtctt aaacaccgga aaggagggca ggctaaggtg 360
tagcccttcc caccctgggt gccagggttg ggggtgctat aagtgaaata tcaaagcttg 420
aggcactaat attctgaatt tcagcctcaa agganggann gtntcnngaa tcnangaagg 480
aggggaagga cccaganacg gggaatggcc tggatgggat naatccanna cntggggnaa 540
agctggtttc ctgaataatg nggtcntggg gaccttgccc ggccggncgt tcnaaaggca 600
attccacccc atggnnggcc gttactaagg ggntccgcn 639

<210> SEQ ID NO 366
<211> LENGTH: 586
<212> TYPE: DNA
<213> ORGANISM: Homo sapiens
<220> FEATURE:
<221> NAME/KEY: misc_feature
<222> LOCATION: (1)...(586)
<223> OTHER INFORMATION: n = A,T,C or G

<400> SEQUENCE: 366
cgaggtacaa aattgcagat agtggcttac tgagtttaag atcaagatca gacttaaact 60
caacaagatc accaaaggta tttctactga gttttcctat gtcccacagt aagctgggtt 120
agagagaact caaattcctg atggaaaaca aaaccgaaca aaaaaactag aaaaaaaagg 180
tgttaaaaat gctgtgtaag ttgctgcaaa aggggaaaaa gaatagacac taactccatg 240
taattttaga catgcagctt ttgtgttttt ttttgttttt gttttttttt ttttgaaaaa 300
aaccagttta ttttgagatc agtgaaaaga gtctangcca cagaaaagaa cagctcttta 360
atgcaagtta aaatgtgtaa atgaatgacc cgggacactt gacaccttta gatgcagact 420
tcattcggca ctggttggct cagacttgcc ggcngccgtt naaaggcnat tcaccnctgc 480
ggccgtctan tnggtccaac ttgtccaact gnnaanaggn tanntgtctt gggaaannnt 540
nntncattcn cnntnaccga gctaagntag cgggngnntg nggnnn 586

<210> SEQ ID NO 367
<211> LENGTH: 628
<212> TYPE: DNA
<213> ORGANISM: Homo sapiens
<220> FEATURE:
<221> NAME/KEY: misc_feature
<222> LOCATION: (1)...(628)
<223> OTHER INFORMATION: n = A,T,C or G

<400> SEQUENCE: 367
gcttcctgag gagcaggcca gaacggaagt cttggtttta tttatagttg ataacttaca 60
tccggcctgc tcctcaggaa gcacagcagg gaggagacag agcccaaagg agacggcgac 120
aaaaatgccc aaacccctga gctaatgtgg tgactgagag caagcctaaa gctcccttct 180
gagctcccca gcagccaaag caaagagaga aacagggtcc tgcagcatga tgtcacagaa 240
aaccagggac cctggagcct gggttccaat aagaacctta cattctgacg ccttagattt 300
ctccctggaa aatggggaga aaaatactga attggttggg agggccatgc aacacaccca 360
gcacagtgtc tggatgcatt tcagaggccc caccagtcta gggtctacag aaagacagta 420
ccttnggccg ngaccacgct angggcgaat tccactcact ggcgggcggt tctaatggat 480
ccnacttcgg accaactttg gcgttatcat nggcataact tgnttcctgn gggaaaattg 540
gtatcccgnt tcaaattncc ccccanttct aancgaannc ttaangttta aacctggggg 600
ncaaataagn gcttacctcc tattgggn 628

<210> SEQ ID NO 368
<211> LENGTH: 618
<212> TYPE: DNA
<213> ORGANISM: Homo sapiens
<220> FEATURE:
<221> NAME/KEY: misc_feature
<222> LOCATION: (1)...(618)
<223> OTHER INFORMATION: n = A,T,C or G

<400> SEQUENCE: 368
acaattcata gggacgacca atgaggacag ggaatgaacc cggctctccc ccagccctga 60
tttttgctac atatggggtc tcttttcatt ctttgcaaaa acactgggct ttctgagaac 120
acggacggtt cttagcacaa tttgtgaaat ctgtgtagaa ccgggctttg caggggagat 180
aattttcctc ctctggagga aaggtggtga ttgacaggca gggagacagt gacaaggcta 240
gagaaagcca cgctcggcct tctctgaacc aggatggaac ggcagacccc tgaaacgaag 300
cttgcccctt ccaatcagcc acttctgaga acccccatct aacttcctac tggaaaagag 360
ggccttctca ggagcagtcc aagagtttca aaagatacgt gacaactacc atctagagga 420
aaggtgcccc ttagcagaga agcccagagc ttactctggt cgtttncaga nacaactgnt 480
ggcttgcttg ggatgccccc agcctttgan aggcccttac ccattgacct tttgccatcc 540
cttgggcatt aacttnnggc cttgggnttt aancttgntt gccttnaang gncaggtttt 600
gcttaanccg gntgnggc 618

<210> SEQ ID NO 369
<211> LENGTH: 443
<212> TYPE: DNA
<213> ORGANISM: Homo sapiens
<220> FEATURE:
<221> NAME/KEY: misc_feature
<222> LOCATION: (1)...(443)
<223> OTHER INFORMATION: n = A,T,C or G

<400> SEQUENCE: 369

```
gcagggcggg cngcggggtc ttggcgaacg gtcttcggaa gcggcggcgg cgcgatgacc     60

acgctacggg cctttacctg cgacgacctg ttccgcttca acaacattaa cttggatcca    120

cttacagaaa cttatgggat tcctttctac ctacaatacc tcgcccactg gccagagtat    180

ttcattgttg cagaggcacc tggtggagaa ttaatgggtt atattatggg taaagcagaa    240

ggctcagtag ctagggaaga atggcacggg caccgtcacg gctctgtctg ttgccccaga    300

atttcgacgc cttggtttgg ctgctaaact tatggaagtt actagaggag atttcagaaa    360

gaaagggtgg attttttgtg gatctctttg taagagtatc taaccaagtt gcaagtaaca    420

tgtaccttng gtcgcganna cgc                                            443
```

<210> SEQ ID NO 370
<211> LENGTH: 636
<212> TYPE: DNA
<213> ORGANISM: Homo sapiens
<220> FEATURE:
<221> NAME/KEY: misc_feature
<222> LOCATION: (1)...(636)
<223> OTHER INFORMATION: n = A,T,C or G

<400> SEQUENCE: 370

```
acatttgttt atttaaagca caggaaatga ataaaatgcc acctaaaaag tatctgcaat     60

gaataaatta tttccagtga agcactgcag atccacacac accagtctgc taacctttac    120

caaggccatg tccggtgggc ttgtgcttgt tccagttgac tcttccttga gacctttccc    180

ttctgtgcaa tgaccacagc attagagacc agtcctgcat gcgctggcct tcctcgtagg    240

catggcagac cacgtggatg agcagtgggc tggcatgcag taggcttnaa caaatggcac    300

ttcactgttt ccagtgaccc tgaaatgttt tacgtaagtg ggcctgggc tttaaagaaa    360

agagccaggg ttcctcaagc tgggcccctt tacttgaggc cagcttcagg aaatactggn    420

cttaaggagc cagcaacttg tccaggagtt ttgagccctt antttgaagg aaaatggccc    480

cttggngtcc ntgcaagcac cagnnatttc cgtgatngtg ancaagtnac cnnccttaag    540

ggaaggccaa tcccnctttg ggnggantcn agggcnctan tcctgtttgg aagggcttga    600

aggttgggaa tntttaaaat ggaggnntng gcttcc                              636
```

<210> SEQ ID NO 371
<211> LENGTH: 615
<212> TYPE: DNA
<213> ORGANISM: Homo sapiens
<220> FEATURE:
<221> NAME/KEY: misc_feature
<222> LOCATION: (1)...(615)
<223> OTHER INFORMATION: n = A,T,C or G

<400> SEQUENCE: 371

```
ggtacaagct tttttttttt tttttttttt tttttttttc tgttaaagaa tgctttatta     60

atacaaatac acacaaactc tgaagcacta anaaatttaa atatctatgt cacagcaaac    120

aggtggcaat tcaacatcca gggtcgacag aatgcttgaa gganactgca acagattgga    180

ttcccatggt gganagggca tnttcacagg tgaagggggg cccagctgaa acagcttttc    240

aagctctctc tcctcgtcaa ggatcatgag aggcactcca ctcaagggga ggtgcgcaat    300

ctggtgctct tcaggcaggt caaaactctc aaagtctaga ggattgaagg gaaagaattt    360

ttctatttct ggataggcat catctgaggc aggaacagag ctttttgctt taacagtctt    420

ctcagtcatc tttttggca aaaaagcttg gctggttttg tttganggg tccttgggct    480
```

-continued

```
ttacagactt ttctgnaact ctgttgacca gnttcccaaa gcctttttta gtaactttta    540

ggtaaggctt ntgggggcat taaacctttt tccaaacctg gggttgaaac ttggaaccnc    600

ctttaagggt ttgnt                                                     615


<210> SEQ ID NO 372
<211> LENGTH: 612
<212> TYPE: DNA
<213> ORGANISM: Homo sapiens
<220> FEATURE:
<221> NAME/KEY: misc_feature
<222> LOCATION: (1)...(612)
<223> OTHER INFORMATION: n = A,T,C or G

<400> SEQUENCE: 372

actttttttt tgttctagga atgagggtag gataaatctc agaggtctgt gtgatttact     60

caagttgaag acaacctcca ggccattcct ggtcaacgtt ttaagtagca tttccagcat    120

tcacacttga tactgcacat cangagttgt gtcacctttc ctgggtgatt tgggttttct    180

ccattcaagg agcttgtagc tctgagctat gatgctttta ttgggaggaa aggaggcagc    240

tgcagaattg atgtgagcta tgtggggccg aangtctcag cccgcagcta agtctctacc    300

taagaaaatg cctctgggca ttcttttgaa agtatagtgt ctgagctnat gctanaaaga    360

atcaaaaagc nagtgtggat ttttagactg naattaaatg aggcnaaang atttctattc    420

ccagtgggaa agaanacctt tctactgaag ttgtgggggg antatgttng aatgttagag    480

agaaccctta aggnntnctt tgattggccc ttggagaccg nttggannac atnncccgga    540

attnnantan aaattntttc nggnttnaag tttccccntg tngtngnann ccaacctngt    600

ttttgccccc cc                                                        612


<210> SEQ ID NO 373
<211> LENGTH: 638
<212> TYPE: DNA
<213> ORGANISM: Homo sapiens
<220> FEATURE:
<221> NAME/KEY: misc_feature
<222> LOCATION: (1)...(638)
<223> OTHER INFORMATION: n = A,T,C or G

<400> SEQUENCE: 373

ggtactcagt atttcaaatc atgaacacaa gattggaact tttggaaaaa tgggttcaag     60

ctttcctatt agccatggaa atgcaaagtt tagcagaagc aagcaattag gcagagaaca    120

aaaatgttaa gcatggtgtt gtctatctta ttgaagtggt tggaaatgaa agcttttaat    180

ttgatagatt tatcagtata aaattaggga aaccacgtgt ggggaatgaa tcaatttaga    240

gcttcgggaa ttgtgaggtg acttttgtaa cttttgttct gtgtgtgacc tgtgaaccac    300

tagatgtgat ctgcccttgt gggcaggtcc agcatagtta ggagttaggc tttancataa    360

aattctagct gcatctgagt ctcctgggat gggtgctctt tggctngttt tggcctgccn    420

gattggtgag atccagancc agctttttcc tgctgcttgg cccctnncaa ttaatttgtt    480

gggattgcca gtgcnagaan accttagttg taaagaattt taatcctacc ncgaccnagt    540

tccaaaangc ngggttttga atgtgggaan tttnnnaatt ttcccttana aagtctaaat    600

tttgtccngt tanactnttg gttttaaagg gaagggaa                            638


<210> SEQ ID NO 374
<211> LENGTH: 503
<212> TYPE: DNA
<213> ORGANISM: Homo sapiens
```

```
<220> FEATURE:
<221> NAME/KEY: misc_feature
<222> LOCATION: (1)...(503)
<223> OTHER INFORMATION: n = A,T,C or G

<400> SEQUENCE: 374

ggtacagatt aacttaacac aaaaacccga acttcaaaat gaaggtgtgt ggaggaaagg     60

tgctgctggg tctccctaca actgttcatt tctttgtgag gcagggggta gttcctgaat    120

ggctgtggtc caatgactaa tgtaaaacaa aaacagaaac aaaaaaaaca aggaactgtc    180

atttccacga aagcacagcg gcagtgattc tagcaggcct cagggccctg ggcctgggga    240

ggctacatga gggggagcct cagtcacagg atcaacctgg ggcccgaagg agcagggttc    300

cctgcctctc cctctgcaac agatcatccc atccaacaca acccccaaaa tgttgatgat    360

gacgcaacat ggtcaaccct caagaccttt aagacaaaac agagcagcat aggaaaaaaa    420

aaacaaaacg caccaatttc tgcatgtgtc aatggtaggg caccntttta aaaaagtctg    480

tctaaaacan nctntgttta ctt                                            503


<210> SEQ ID NO 375
<211> LENGTH: 611
<212> TYPE: DNA
<213> ORGANISM: Homo sapiens
<220> FEATURE:
<221> NAME/KEY: misc_feature
<222> LOCATION: (1)...(611)
<223> OTHER INFORMATION: n = A,T,C or G

<400> SEQUENCE: 375

ggtacaaaag ctgttgaact taatcccaaa tatgtgaaag ctctctttag acgtgcaaaa     60

gcccatgaga agctagacaa taagaaggaa tgtttagaag atgtcactgc tgtgtgtata    120

ttagaagggt tccaaaatca acaaagcatg ctgttagccg ataaagttct taaactcctt    180

ggaaaagaga aagccaaaga aaaatataag aatcgtgaac ctctgatgcc atctccacag    240

tttatcaaat cttacttcag ttctttcacg gatgatatca tttcccagcc catgcttaaa    300

ggagagaaat ctgatgaaga taaagacaag gaaggggagg ctttagaagt gaaagaaaat    360

tctggatact taaaggccaa acagttatgg aagaagaaaa ctacgatana atcataagtg    420

aatgcccana aaaaaaaatn atttaaaaaa aagcttgtcc ctgccggccg gccgttcnaa    480

agggcgaatt canctccctg gngggcggta ctannnggat ccaacnttgg gccaaccttg    540

gngnaaacan nggntatant gtttcctggg naaatggtnt ccngttncaa tccccnaatn    600

ntngngccgg g                                                         611


<210> SEQ ID NO 376
<211> LENGTH: 601
<212> TYPE: DNA
<213> ORGANISM: Homo sapiens
<220> FEATURE:
<221> NAME/KEY: misc_feature
<222> LOCATION: (1)...(601)
<223> OTHER INFORMATION: n = A,T,C or G

<400> SEQUENCE: 376

cgaggtcttt tctctctttc tgtcttcatc ccagatcaaa gaatcccgag ttaggatctg     60

gatgaaggat aagcccctga attgtcgatg ggctcacccc cacactgacc cagcatctga    120

acttgcttaa cagggagccg gggctaaact gcttcaccct gcctgagaac cagggagcac    180

tgcatttctc cacagggtgg aggagaagag gcagaataaa ccaagcctgg gacacctccc    240
```

-continued

```
tcctgtctag gtgtacagca cacaggttaa tactcttcac cctcatcctc tccgtcagca    300

ctatctgctc caacctcctc ataatccttc tcaagggcag ccatgtcctc acgggcctct    360

gaaaactcgc ctggaccaca aagtttgacc tgatgtatgc caagccgtgc ctttggtcac    420

tggnacctgg ccnggccggc cgttcaangg cgaattccac acactggcng gccgtactan    480

tggatccnaa ctnggaccag cttgngtaat catggcatnc tggttcctgg ggnaaatggt    540

atccgttaca attccnccan ntcnanccgg aacctaaagg gtaaacctgg ggngctaatn    600

a                                                                     601
```

<210> SEQ ID NO 377
<211> LENGTH: 621
<212> TYPE: DNA
<213> ORGANISM: Homo sapiens
<220> FEATURE:
<221> NAME/KEY: misc_feature
<222> LOCATION: (1)...(621)
<223> OTHER INFORMATION: n = A,T,C or G

<400> SEQUENCE: 377

```
ggtacaagct tttttttttt tttttttttt ttttttttg tctgttcaag aaccagtctg     60

ggatcttgta cccagctcta attactggcc gtagcagcat attgcttaan aattttgtag    120

aacttatttc tcatcagcag ctgtccaaag gactgataaa tagagacaga tcccagtcct    180

ggatactttc tgtaaatcct aatcggagac tcacttntna gcaatggagg ctgaaagtct    240

tagtgagact cagtaaattc cttnaggcct tggcagatgg atccagtagg ttgagagaaa    300

gtgaaggact tcaggaacag aaagaaaatc cccatgccac tagcaactcc atttttatna    360

actggaagga acatgccaac gaccagcaac acatccaggg tttatgaaaa tgggggttca    420

cagncnaaat gtcngntcca agttcaggct ncnggatttt ggtttggagg actgaatggt    480

gtggattaaa ggcttncatt ttcttgnaac cttgaaaggg tttttnggan aanaattcnt    540

tgntaatgna agctnggttt aaacttgacc tngcccgggn gggccnttca aaagggcgna    600

ttnccgcncn ttggggggcc g                                               621
```

<210> SEQ ID NO 378
<211> LENGTH: 327
<212> TYPE: DNA
<213> ORGANISM: Homo sapiens
<220> FEATURE:
<221> NAME/KEY: misc_feature
<222> LOCATION: (1)...(327)
<223> OTHER INFORMATION: n = A,T,C or G

<400> SEQUENCE: 378

```
acatctccga cagtatctgt ttcagcatct ttgcncttct gaagtctttn atacttgtgg     60

caaaagttcc tgaaactggc ctccangtgt ccctccacct gtgctggcac ttgggcgttt    120

ccacnaaact tcccaaacag ctcacaatcc tggctgactg ggacaataat tcagcaaact    180

ggctactcag acctggcacc aaatgtcctg tccaaaatgc tgttcactga accagtgctg    240

ggcgcccctg ggcagggtgg ctcgatcacc cgccacatnc acttggccgc cagaagccng    300

nggggaagga cctnggcgcg acnacgc                                         327
```

<210> SEQ ID NO 379
<211> LENGTH: 517
<212> TYPE: DNA
<213> ORGANISM: Homo sapiens
<220> FEATURE:
<221> NAME/KEY: misc_feature
<222> LOCATION: (1)...(517)
<223> OTHER INFORMATION: n = A,T,C or G

<400> SEQUENCE: 379
actcacaagt aagaaacttt ctctactgaa ggatactgtc acagagtttg ttgcagagca 60
tctatatata tatttattna tttattttaa aaaantaaac aacantgatg aacganccca 120
ggttcctaga accaattctc ttgattctct acttccacaa aataaagtgt atcatttggc 180
caagactaca gatgtgtttt tntttttca canatgcaag tgccatgcaa aaataaatta 240
aagaacagat accaaaacat acatgtgata aaactacana tggtagattt ttaaaggcat 300
ttatataaac ntaatttata aatacttctc tttntgcctt tatatacagt cncaaanctg 360
gntgttatac atntaggatt tcctntgcnt gaccttnggc cgtnacnacg nntaagggcc 420
gaattctgga agattccatc tacaattggc ggctcgtttn tancatncct ttntanggcc 480
caatttngnc cnntannnga gtcngattac aanntcn 517

<210> SEQ ID NO 380
<211> LENGTH: 351
<212> TYPE: DNA
<213> ORGANISM: Homo sapiens

<400> SEQUENCE: 380
acgctgtgga gggctgcagt gctcgtggat tcaaaatcac agagggctgg taaatggcag 60
cttctgtagg aataactgca gcaggagctg gaaatgtgta ggagggagga gacaggcatg 120
gtaacttaca tggcggtggg gataagccat ttcgatttaa agtgcccccc attaacacaa 180
agttcatctc ctcagctgaa cactgaaaga cttcaacata tctgtccttc atgttttttt 240
atgacacttc tgtgcagcca taaatgctct gtccgcagac ttcatctgga taaaggcatc 300
tcctgatggg cggccctggt gattcaaaac catgtgaacc ccatgagtac c 351

<210> SEQ ID NO 381
<211> LENGTH: 622
<212> TYPE: DNA
<213> ORGANISM: Homo sapiens
<220> FEATURE:
<221> NAME/KEY: misc_feature
<222> LOCATION: (1)...(622)
<223> OTHER INFORMATION: n = A,T,C or G

<400> SEQUENCE: 381
acacttccaa ttgtccatat aattaagctt tccacaatct tacacaccca tcatctcctg 60
aagatgctag caccgttcct gttatattcc aactcactcg ccagacctga gaattatgat 120
tatcgaactg agccactata tggatttcaa actttgttgg cccaccagag gaagtcagtt 180
ctttcctcac aggctttaat gtaaaaattc tcacatcttt ggtcgctatt gctagaatat 240
ggaaagatct tcccaaattt ggagcgaatg caatatcatg aacaggatca gtgactgtca 300
taagagtttc agcttttgca tatttcctgg tgttttcatt atattcaaaa atctgaacct 360
tggccattgc gttggggcta ctgncatcac tttctacggc gatcatgggg gaatgagcac 420
gagagctttg naggggtncc aagaaatnca cttccagctt agcttacttg aganctctgg 480
ctggnaaaga cccctnggct gagaattcnt aaccatctgg ggccctcaaa nantcttacc 540
tttccattng nggacaaggt ggttacttag aaccccnggn cttgggacca acttnccntt 600
cggtnncana gttttggtnt cc 622

<210> SEQ ID NO 382

<211> LENGTH: 509
<212> TYPE: DNA
<213> ORGANISM: Homo sapiens
<220> FEATURE:
<221> NAME/KEY: misc_feature
<222> LOCATION: (1)...(509)
<223> OTHER INFORMATION: n = A,T,C or G

<400> SEQUENCE: 382
ggtactctca tcccgccccc attcaggctg atagtaacag cctaggtaga gtcaacacat 60
aaaaaagtgt aattccaggg gaggaggatt agaataagga cacaaaggaa gggaggaaaa 120
tgttctttga ggctgaaatt ccattaattt ttcatagtat tgagtttata tttgccattg 180
catccttcaa tctttctaaa aaggaaatcc ccggaacata ataaaatctc ttctgtatag 240
aaaagctaca gctccacact aagaggaatg ccgtctgcct taaagaatgg aatcatcagt 300
gaccaagaat tacttccaag gagaaattca ttgatattaa aaccaaagcc agatccagct 360
cagcaaaccg acagccagaa cagtgatacg gagcagtatt ttagagaatg gtttccaaac 420
ccgccaacct gcacggtgtt atttctgcca cgtgtctctg gaacacacat taaactgtgg 480
aaactnnctn ctttccgctg ggggtcccc 509

<210> SEQ ID NO 383
<211> LENGTH: 380
<212> TYPE: DNA
<213> ORGANISM: Homo sapiens

<400> SEQUENCE: 383
acaattccac ttatccatac tattccttta taaaaggcag atttcaggta agcttctaaa 60
tgcatgcgta atgtagaggc taatattttc tggcagtcct tggttcctga aatttgaact 120
tcatatgtgt tttaaacttt tgtcaaaata gtcatgaaag atatgttatt tttgcataat 180
gaggtaatat atcaggggcg ggcactcata agacagtata aatccacttg tctaaacttg 240
catgaggctg tgtgcattgt aaaatgccat aaagagtttt gggtcaagtg aatattttgc 300
tgaaggaata acacttacat ttaactgagc acttttctgt aataaatacc aaagtaggtt 360
tttgtagctg taaactgtgt 380

<210> SEQ ID NO 384
<211> LENGTH: 317
<212> TYPE: DNA
<213> ORGANISM: Homo sapiens

<400> SEQUENCE: 384
ggtcccagac ccaagaccaa ccgatggagg aggaggaggt tgagacgttc gcctttcagg 60
cagaaattgc ccagttgatg tcattgatca tcaatacttt ctactcgaac aaagagatct 120
ttctgagaga gctcatttca aattcatcag atgcattgga caaaatccgg tatgaaagct 180
tgacagatcc cagtaaatta gactctggga aagagctgta tattaacctt ataccgaaca 240
aacaagatcg aactctcact attgtggata ctggaattgg aaatgaccaa ggctgacttg 300
gatcaataac ccttggt 317

<210> SEQ ID NO 385
<211> LENGTH: 275
<212> TYPE: DNA
<213> ORGANISM: Homo sapiens

<400> SEQUENCE: 385
acttttagtc cctgttttac aggggttaga atagactgtt aaggggcaac tgagaaagaa 60
cagagaagtg acagctaggg gttgagaggg gccagaaaaa catgaatgca ggcagatttc 120
gtgaaatctg ccaccacttt ataaccagat ggttcctttc acaaccctgg gtcaaaaaga 180
gaataatttg gcctataatg ttaaaagaaa gcaggaaggt gggtaaataa aaatcttggt 240
gcctggaaaa aaaaaaaaaa aaaaaaaaag ctgta 275

<210> SEQ ID NO 386
<211> LENGTH: 606
<212> TYPE: DNA
<213> ORGANISM: Homo sapiens
<220> FEATURE:
<221> NAME/KEY: misc_feature
<222> LOCATION: (1)...(606)
<223> OTHER INFORMATION: n = A,T,C or G

<400> SEQUENCE: 386
ggtacatgga tattcccaaa ccattccatt agaaaactgc cctccctgca cacacaacaa 60
aaacagcgct atttcctaca cctattggac tgaaagtgct tggaaatgga atggttttag 120
aatatgaaga agaacacaaa ccaagtagct gtgggttgaa cctggacgtg agctggctgc 180
agggccgttg ggtagaaaac cagcatctca taaacaggtc actacaaaaa taggaagagt 240
ataaaaatag aatatattat gtcactattt cgtcttctct ttatagtagc gtatcgtagg 300
agtgggacag gtggcctttc ccgaccctgc tacgctggct ggtgcccgac aaacctccac 360
tggatggttt gtcactggat ggtttgttgg ggtggtggtc acaggcgcaa aggacatgca 420
cacgggcacg ctcgctactg naacccagan gtgacttcag cntgaataaa ggngaaaagg 480
tccccatnta nctcnggaat tattncctnc ccaggnccta ttaaggggct ttntggcttt 540
tnaccancca agncccnccc cttgaaangc caaacttttt tgaaaaaaag gganccttgn 600 atngnc 606

<210> SEQ ID NO 387
<211> LENGTH: 339
<212> TYPE: DNA
<213> ORGANISM: Homo sapiens

<400> SEQUENCE: 387
accacttgca gtcaaatgaa ttccttcgaa atgtatttga acttggaccc ccagtgatgc 60
ttgatgctgc aacgcttaaa acgatgaaga tttctcgttt cgaaaggcat ttatataact 120
ctgcagcctt caaagctcga accaaagcta gaagcaaatg tcgagataag agagcagatg 180
ttggagaatt cttctagatt ttcagaactt gaagactatt ttctaatttc tatttttttt 240
tctatttcaa tgtatttaaa ctctagacac agtttttatc ctggattaac ttagataact 300
tttgtagcag tggttatatt gcttataatt taatgtacc 339

<210> SEQ ID NO 388
<211> LENGTH: 667
<212> TYPE: DNA
<213> ORGANISM: Homo sapiens
<220> FEATURE:
<221> NAME/KEY: misc_feature
<222> LOCATION: (1)...(667)
<223> OTHER INFORMATION: n = A,T,C or G

<400> SEQUENCE: 388
taccagttgt catcatagcc ggagatggac acttcaggag ggtagcgtac attcccatga 60
caccaatact acagttttcg gagtcacagt aagatacaca gaattacatc cgtaattaat 120

```
atgaatgcca acatgtcaag cagtaatttg ttacatggca aacaaaatca agaaagcaac    180

catcaaacaa aagagaccca tagcttcaga caaggcaaat cccaggatag catatgagaa    240

cagctgctgc ttcagcgaag ggtttctggc ataaccaatg ataaggctgc caaagactgt    300

tccaatacca gcaccagaac cagccactcc tactgttgca gcacctgcac caataaattt    360

ggcagcagta tcaatgtctc tgctgattgc actggtctga aactcccttt ggattagctg    420

agacacacca ttctgggccc cattaaatac cgtagagccc tctccagtcc tactagcctc    480

tggtcgagat aacactgatg cagaaattgg tctgtatgca actctggatc cagctcggat    540

cagagagggg gtgcaggcga gcttggcgca ggcgaacatc ttacactctt cgggactgcg    600

cggctggaga tattgggtga caggcgacgt gggctcctct cccgcttnct ctctttccag    660

gaagcgg                                                              667


<210> SEQ ID NO 389
<211> LENGTH: 613
<212> TYPE: DNA
<213> ORGANISM: Homo sapiens
<220> FEATURE:
<221> NAME/KEY: misc_feature
<222> LOCATION: (1)...(613)
<223> OTHER INFORMATION: n = A,T,C or G

<400> SEQUENCE: 389

ggtaccagtt gtcatcatag ccggagatgg acacttcagg agggtagcgt acattcccat     60

gacaccaata ctacagtttt cggagtcaca gtaagataca cagaattaca tccgtaatta    120

atatgaatgc caacatgtca agcagtaatt tgttacatgg caaacaaaat caagaaagca    180

accatcaaac aaaagagacc catagcttca gacaaggcaa atcccaggat agcatatgag    240

aacagctgct gcttcagcga agggtttctg gcataaccaa tgataaggct gccaaagact    300

gttccaatac cagcaccaga accagccact cctactgttg cagcacctgc accaataaat    360

ttggcagcag tatcaatgtc tctgctgatt gcactggtct gaaactccct ttggattagc    420

tgagacacac cattctgggc cccattaaaa taccgnagag ccttttcagt cctactagcc    480

tctggncgag ataacactga tgcanaaatg gnctgtatgc caactctgga tccacttcgg    540

ttcaaaaagg ggtgcaggca acttggccca ngcgaacatn tacacttttc gggactgccc    600

gnttggnnaa tgg                                                       613


<210> SEQ ID NO 390
<211> LENGTH: 278
<212> TYPE: DNA
<213> ORGANISM: Homo sapiens
<220> FEATURE:
<221> NAME/KEY: misc_feature
<222> LOCATION: (1)...(278)
<223> OTHER INFORMATION: n = A,T,C or G

<400> SEQUENCE: 390

actagtcctc tagaaatagg ttaaactgaa gcaacttgat ggaaggatct ctccacaggg     60

cttgttttcc aaagaaaagt attgnttgga ggagcaaagt taaaagccta cctaagcata    120

tcgtaaagct gttcaaaaat aactcagacc cagtcttgng gatggaaatg tagtgctcga    180

gtcacattct gcttaaagtt gtaacaaata cngatgagtt aaaaanannt cttttnttga    240

actctnanga aaancttgga ccttngccgn gaccacgc                            278


<210> SEQ ID NO 391
<211> LENGTH: 604
```

<212> TYPE: DNA
<213> ORGANISM: Homo sapiens
<220> FEATURE:
<221> NAME/KEY: misc_feature
<222> LOCATION: (1)...(604)
<223> OTHER INFORMATION: n = A,T,C or G

<400> SEQUENCE: 391

```
ggtctttttt tttttttttt tttttttgaa cacagatcac tttattggca tggctttgtt     60

ttaagaaaag gaaaagtgac aaagccaaga gacagactnt gctaacagat gcctgggggt    120

ggctggacat ttttgcctca tgctgtgcaa agagggggat cctggcccac acatcctgct    180

gattccttgg gacaaggttg tctgcctggg cctcactgca ccttcttgaa tacttgcttg    240

canaccacac cttccactct natctncagg tgcagctcat caccctngat ccactgggtc    300

cagccacgcc ccttcttctc acccttctga cacactggag cttgctccgt cccagtcact    360

gtgtcatgca cttgcggnca tctatgcctg nagatcctcc taaactcctt tccaacctgg    420

aagtccatga tgnantncct aaaagngctc accgtggcgg angatcatat ggtcancggc    480

ntgaacgaan tnttttggcg ggnttcanna agttgcccat ttttgcgcaa gggcccattg    540

gncgtnnagg gcccangtnc tttgcngnnc ccctnagggn gaatccccac nttggggccg    600

tntn                                                                 604
```

<210> SEQ ID NO 392
<211> LENGTH: 610
<212> TYPE: DNA
<213> ORGANISM: Homo sapiens
<220> FEATURE:
<221> NAME/KEY: misc_feature
<222> LOCATION: (1)...(610)
<223> OTHER INFORMATION: n = A,T,C or G

<400> SEQUENCE: 392

```
acgaggggag cgagacgaaa ggagaacggt gattattcat gacaggcctg atatcactca     60

tcctagacat cctcgagagg cagggcccaa tccttccaga cccaccagct ggaaaagtga    120

aggaagcatg tccactgaca aacgggaaac aagagttgaa aggccagaac gatctgggag    180

agaagtatca gggcacagtg tgagaggcgc tccccctggg aatcgtagca gcgcttcggg    240

gtacttattg gcacaaattc gggcagcctc cagggcttca gaggacagct gctcatattc    300

atctgacacc atgtggccac aaagcggaaa ctcatccact tttgcctttt tccgccccag    360

gtcaaaaatg cgaatcttgg catcagggac acctcggcag aagcgagact ttgggtgagc    420

ttgttttcca tctagggatg atgggagaca gtgacaaatc atccaccatt agatttttat    480

aaggagcgca caacccagac aacccaaatc cctttggatg tgccagttca caatagtggt    540

catgcctcca ttgagaatat aatggctctn gacttgccgg aaggcaaact taaggccata    600

atgggaccng                                                           610
```

<210> SEQ ID NO 393
<211> LENGTH: 314
<212> TYPE: DNA
<213> ORGANISM: Homo sapiens

<400> SEQUENCE: 393

```
ggtcccagac ccaagaccaa ccgatggagg aggaggaggt tgagacgttc gcctttcagg     60

cagaaattgc ccagttgatg tcattgatca tcaatacttt ctactcgaac aaagagatct    120

ttctgagaga gctcatttca aattcatcag atgcattgga caaaatccgg tatgaaagct    180
```

-continued

```
tgacagatcc cagtaaatta gactctggga aagagctgta tattaacctt ataccgaaca    240

aacaagatcg aactctcact attgtggata ctggaattgg aatgaccaag gctgacttga    300

tcaataacct tggt                                                      314
```

<210> SEQ ID NO 394
<211> LENGTH: 498
<212> TYPE: DNA
<213> ORGANISM: Homo sapiens
<220> FEATURE:
<221> NAME/KEY: misc_feature
<222> LOCATION: (1)...(498)
<223> OTHER INFORMATION: n = A,T,C or G

<400> SEQUENCE: 394

```
accagacctg tcaacgtcna tttctcggna aatttnttgg tatttttgaa tctncgtcca     60

gagaatgtaa aactccttca gncccagctt gccactcccg tccgaatcta gcatgtcaac    120

cataatttng aatcttcgtc cagagaatgt agaactcctt cagccccagc ttgccactcc    180

cgtccgaatc tagcatgtca accataattt tgcatgnctc gatgctgaag ccatctgact    240

ggatatcttg gcgctttgct agaacccttc tcaggatggt ctgcngctca aaggcanaga    300

tctccgnatc ctctcctgcc aactgggcaa acagnctcct gaatccatca tcaatgtcat    360

cctcgctgat gtcgaactct tcaagattgg cctcgatttc atcatcgaca gcttggtagt    420

cagctttctt ttcagaaaag acccggatgc agaaatcccc atccttgntg ggttcgaagg    480

tggaaggcac ganaatgt                                                  498
```

<210> SEQ ID NO 395
<211> LENGTH: 629
<212> TYPE: DNA
<213> ORGANISM: Homo sapiens
<220> FEATURE:
<221> NAME/KEY: misc_feature
<222> LOCATION: (1)...(629)
<223> OTHER INFORMATION: n = A,T,C or G

<400> SEQUENCE: 395

```
gccgcccgtc aagctgtcca catccctggc ctcagcccgc cacatcaccc tgacctgctt     60

acgcccagat tttcttcaat cacatctgaa taaatcactt gaagaaagct tatagcttca    120

ttgcaccatg tgtggcattt gggcgctgtt tggcagtgat gattgccttt ctgctcagtg    180

tctgagtgct atgaagattg cacacagagg tccagatgca ttccgttttg agaatgtcaa    240

tggatacacc aactgctgct ttggatttca ccggttggcg gtagttgacc cgctgtttgg    300

aatgcagcca attcgagtga agaaatatcc gtatttgtgg ctctgttaca atggtgaaat    360

ctacaaccat aagaagatgc aacagcattt tgaatttgaa taccagacca aagtggatgg    420

tgagataatc cttcatcttt atgaccaang gaggaattga gccaaccatt tgnatggttg    480

gatgggtgtg gttgcaattn ggtttactgg ggaaactggc cattangaaa agggntcctg    540

ggtaaaagaa tccctatggg ggccnnaacc tttgnttnaa agccntngcc ccaaaaangg    600

gntttttggg cggnatgttt cnaaaaacn                                      629
```

<210> SEQ ID NO 396
<211> LENGTH: 614
<212> TYPE: DNA
<213> ORGANISM: Homo sapiens
<220> FEATURE:
<221> NAME/KEY: misc_feature
<222> LOCATION: (1)...(614)
<223> OTHER INFORMATION: n = A,T,C or G

<400> SEQUENCE: 396

```
ggtacttggg cttctttcag ctgcttcaac agagtggcag caaccaagct ggagtccaag    60
ccccctgata aaaggcagcc aatccttctg tctgtcatca aacgtttctt tacagcatta   120
ttaaaaagga tcctgaggtt gttcttcaca gtttctatct caaaacctgg aaagagtttc   180
tccacattgt catagagggc gtgcaggggt tcatcccgac agtgatgata tttaaccatt   240
tccacggatg caactttgcc atttggcttt aaatccaaaa cttcatagtg tccaggaaga   300
aaaggctcca cttttaaaaa gggagtcgcg gagtgcttca atgtaacaag acctttaact   360
tctgaacata cagccaaaaa tcatctttct gncattgctt taaaccaang tctgactcca   420
tatggtatct cttacccagg aacccntttc ttaatgggca ggtantccag ttaaaaccaa   480
atggcaaacc ccanccantc caaccnttcc naaatggntt gggttnaaat nccttccttt   540
gggcataaaa gaattnaang ggnttnnttt tancctttcc ccttttgggc ccggggattt   600
cnaaaattcn aaaa                                                     614
```

<210> SEQ ID NO 397
<211> LENGTH: 588
<212> TYPE: DNA
<213> ORGANISM: Homo sapiens
<220> FEATURE:
<221> NAME/KEY: misc_feature
<222> LOCATION: (1)...(588)
<223> OTHER INFORMATION: n = A,T,C or G

<400> SEQUENCE: 397

```
acctgggcat aggaaggaac caggacaggg ctggggacag aaggtggtca cagtcatggt    60
ttcactctca gaaatatcct gggcctatgg cttaaggctt cgtggagcag ggagtggacc   120
ttgtggttat ttacaaggct gggccatata aaagcattgc aaacatggag tggagaggat   180
ccttggagat gagctggttc aatcactcct ctgaccaaca aggaaacaaa ggcccagaga   240
ggagaaggca gtgcctggcc agacgtggga cctgaaccca gccagggctc tgactcccag   300
tcccccagtc ccctctctac ctccttgctt ggctgagtct ttttttgata aaggccccag   360
acagcctctc cgacagtctc aggtcaggct ggggttataa atggagcagt ggactcagag   420
tcagaggccc agactctgnt cttgggcctt nacattacca agncttgcta ataaccacga   480
ggccctggtg tggaggggct gctctctttt aagctcagct cntatctgga acaggccaca   540
aagttncatg ggataanggn tgaggccnna gcccacagng tggaggnc                588
```

<210> SEQ ID NO 398
<211> LENGTH: 348
<212> TYPE: DNA
<213> ORGANISM: Homo sapiens

<400> SEQUENCE: 398

```
ggtactagcc ggacttggat tttctggaaa gatttcagtt gaggaacggg aacaaagatt    60
atgatagctt tccgaccacc accaacttca atttccttag ctgccgtaat attcagctcc   120
ctgagctgag ccttgaggtc cgagttcatc tccagctcca gaagagcttg ggagatgccg   180
gactcgaact cgtccggctt ctcgccattg ggcttcacga tcttggcgct cgaactgaac   240
atggctttct cctgggagaa cttgccgagc gccggcttag gaagagaccc aaatctcgcg   300
agagcacgtc aaaatccggc gtccgaaggc aagaggcgga aacagcgc                348
```

<210> SEQ ID NO 399

```
<211> LENGTH: 630
<212> TYPE: DNA
<213> ORGANISM: Homo sapiens
<220> FEATURE:
<221> NAME/KEY: misc_feature
<222> LOCATION: (1)...(630)
<223> OTHER INFORMATION: n = A,T,C or G

<400> SEQUENCE: 399

acatccaagt ttaaaattat cagcgaaatg gtccatgttt ttccaattac ctgctgacac     60

ggttctaagc taagtgaagg ggaagatctg agagcgtgct gtttgtggct gttgatgcat    120

attcgtgatg taacaggtcc tggggcctca ctttacccca tttgtaaaat ggggctaatg    180

tcacctgcct cttacctacc tcagagggat ttggtgaagc aaactgttaa tcttcgaaaa    240

cgaccatttc acttcttgga tatcaagtgc taacccagta tgttcttctt ttttatgtaa    300

gggacagctt tctccacaga gtcctttctg ctggtgagga cagcatttct gagcagggct    360

ttgttctcta tgtgcattag gacttttatc atgcccttgg tctatgtgta gttacttgac    420

agcatcaaat gccggctctt cctaatgncc ttcaaggttt catgaactaa caaccccacc    480

tttcancatg ggtctggccc ctgaatttgc tgngacttcc agaccacact ggttctacca    540

cctgaacagg ccnttaaagt tcccaanggt cancttcctt aattccttgg ttcccggtgt    600

atggggaact tggcctanaa aagggccncc                                     630


<210> SEQ ID NO 400
<211> LENGTH: 619
<212> TYPE: DNA
<213> ORGANISM: Homo sapiens
<220> FEATURE:
<221> NAME/KEY: misc_feature
<222> LOCATION: (1)...(619)
<223> OTHER INFORMATION: n = A,T,C or G

<400> SEQUENCE: 400

actgaacagg taagtcatcc ctcagccaga gattagtcta cttcttccat gcgtgatgtg     60

tcgtcatctc cttcaagggg tggcatttct tcagttacag cagcactggt atcatcagca    120

gtagggtcat cttcatcaat acccagacca agtttgatca tcctgtagat cctgttagca    180

tgtgtctggg gatcttccag actgaagcca gaagacagga gcgcagtttc ataaagcaag    240

atgaccagat ccttcacaga cttgtcgttc ttatcagcct ctgccttttg ccttaaggtc    300

tcaataatgg aatggtcagg gtttatctcc aggtgtttct ttgctgccat gtaacccatt    360

gntgagttgc tcttagggct tgagctttca tgattcgctc catgnttgct gccagccata    420

tgtgcttgtg acaatacagn atggagatgc accaatcggt tggacaaacc acctttcact    480

ttttcttcca tangctttca gatttgcaaa gttctaaact ttgggttttc ccttctgntc    540

ttttcctttt atctttggaa gtccaggctt nttggggacg ncctaagctt ccctnaatct    600

ttagtgtgga nnagncntn                                                 619


<210> SEQ ID NO 401
<211> LENGTH: 663
<212> TYPE: DNA
<213> ORGANISM: Homo sapiens
<220> FEATURE:
<221> NAME/KEY: misc_feature
<222> LOCATION: (1)...(663)
<223> OTHER INFORMATION: n = A,T,C or G

<400> SEQUENCE: 401

cgaggtactt gggcttcttt cagctgcttc aacagagtgg cagcaaccaa gctggagtcc     60
```

```
aagcccctg ataaaaggca gccaatcctt ctgtctgtca tcaaacgttt ctttacagca    120

ttattaaaaa ggatcctgag gttgttcttc acagtttcta tctcaaaacc tggaaagagt    180

ttctccacat tgtcatagag ggcgtgcagg ggttcatccc gacagtgatg atatttaacc    240

atttccacgg atgcaacttt gccatttggc tttaaatcca aaacttcata gtgtccagga    300

agaaaaggct ccacttttaa aaagggagtc gcggagtgct tcaatgtaac aagaccttta    360

gcttctgaac atacagccaa aaatccatct tctgcattgc tttaaacaaa ggtctgactc    420

catatgtatc tctacccagg aacactttct taatggcagt attcagtaaa accaatgcca    480

acccaccatt ccacatacca aatgggttgc tcaaatcctc cttggcataa agatgaaagg    540

ttatttnacc atncactttg gccgggattc aaattccaaa agccggtgca tttttntaan    600

ggtggaanaat tnncccttgn accnaanccc caaatccggg attttnttnc ctcnaatngn    660

tgg                                                                  663
```

<210> SEQ ID NO 402
<211> LENGTH: 673
<212> TYPE: DNA
<213> ORGANISM: Homo sapiens
<220> FEATURE:
<221> NAME/KEY: misc_feature
<222> LOCATION: (1)...(673)
<223> OTHER INFORMATION: n = A,T,C or G

<400> SEQUENCE: 402

```
ggtacgtgtc cagctctgaa gggcaaagtg cagaagatcc taatctggaa gtggggtcag     60

ccaccatctc ccacaccagt gcctcggcct ccagatgctg atcccaacac gccctcccca    120

aagcccttgg aggggcggcc agagcggcag ttctttgtga aatggcaagg catgtcttac    180

tggcactgct cctgggtttc tgaactgcag ctggagctgc actgtcaggt gatgttccga    240

aactatcagc ggaagaatga tatggatgag ccaccttctg gggactttgg tggtgatgaa    300

gagaaaagcc gaaagcgaaa gaacaaggac cctaaatttg cagagatgga ggaacgcttc    360

tatcgctatg ggataaaacc cgagtggatg atgatcaccg aatcctnaac cacagtgtgg    420

accagaaggg ccacgttcca ctacttggat ccaagtggcn ggacttaccc ttacgaatca    480

nggcnttttt ggaanaatga aggttttnga aaatccagga ataccnacct ggtcaagcng    540

anctttttgg naatcccnng ggagttnatt gaaggggtaa aggaaggcnn nacccagcca    600

agaaagcttt aagaaagggg naactttcgg aaattggaaa aggccttcan aacnccaacg    660

gttgttccac ngg                                                       673
```

<210> SEQ ID NO 403
<211> LENGTH: 616
<212> TYPE: DNA
<213> ORGANISM: Homo sapiens
<220> FEATURE:
<221> NAME/KEY: misc_feature
<222> LOCATION: (1)...(616)
<223> OTHER INFORMATION: n = A,T,C or G

<400> SEQUENCE: 403

```
ggtaccgatt atatcatctc agtcttgaat ttactcacgc tgattgttga acagataaat     60

acgaaactgc catcatcatt tgtagaaaaa ctgtttatac catcatctaa actactattc    120

ttgcgttatc ataaagaaaa agaggttgtt gctgtagccc atgctgttta tcaagcaatg    180

ctcagcttga agaatattcc tgttttggag actgcctata agttaatatt gggagaaatg    240
```

-continued

```
acttgtgccc taaacaacct cctgcacagt ctgcaacttc ctgaggcctg ttctgaaata    300

aaacatgagg cttttaagaa tcatgtgttc aatgtagaca atgcaaaatt tgtagttaaa    360

tttgacctca gtgccctgac tacaattgga aatgccaaaa actcgagtct ttaattgtaa    420

tggctttggt ttatccacag ttaggccctt tctcaataca tatttatgna tttcactggg    480

catggcaaca tggctggaaa aatcactgga tgtaaccaaa caggcctttt ttaanaaatg    540

ncncggntta accaaanaaa aaaaaaaaaa anaaagnttt gaccttcccg ggngggcctt    600

taaaaggnna attccn                                                    616


<210> SEQ ID NO 404
<211> LENGTH: 613
<212> TYPE: DNA
<213> ORGANISM: Homo sapiens
<220> FEATURE:
<221> NAME/KEY: misc_feature
<222> LOCATION: (1)...(613)
<223> OTHER INFORMATION: n = A,T,C or G

<400> SEQUENCE: 404

cagtgctggg cctaaaggag ataacattta tgaatggaga tcaactatac ttggtccacc     60

gggttctgta tatgaaggtg gtgtgttttt tctggatatc acattttcat cagattatcc    120

atttaagcca ccaaaggtta ctttccgcac cagaatctat cactgcaaca tcaacagtca    180

gggagtcatc tgtctggaca tccttaaaga caactggagt cccgctttga ctatttcaaa    240

ggttttgctg tctatttgtt cccttttgac agactgcaac cctgcggatc ctctggttgg    300

aagcatagcc actcagtatt tgaccaacag agcagaacac gacaggatag ccagacagtg    360

gaccaagaga tacgcaacat aattcacata atttgtatgc agtgtgaang agcagaaggc    420

atcttctcac tgggctgcaa atcnttatag cctttacaat ccggactttg ggaaatggt     480

atacctggat ctactctgnn tttanacctt tgggacntng gaaanntccc caaaanggga    540

aaggctttca aangtaaact ttgaacctga aaataagttt gttnaaacnc ctattgcaag    600

tttgtttttn gga                                                       613


<210> SEQ ID NO 405
<211> LENGTH: 605
<212> TYPE: DNA
<213> ORGANISM: Homo sapiens
<220> FEATURE:
<221> NAME/KEY: misc_feature
<222> LOCATION: (1)...(605)
<223> OTHER INFORMATION: n = A,T,C or G

<400> SEQUENCE: 405

ggtactgagg tgtaaaggga tttatatggg gacgtaggcc gatttccggg tgttgtaggt     60

ttctcttttt caggcttata ctcatgaatc ttgtctgaag cttttgaggg cagactgcca    120

agtcctggag aaatagtaga tggcaagttt gtgggttttt tttttttaca cgaatttgag    180

gaaaaccaaa tgaatttgat agccaaattg agacaatttc agcaaatctg taagcagttt    240

gtatgtttag ttggggtaat gaagtatttc agttttgtga atagatgacc tgtttttact    300

tcctcaccct gaattcgttt tgtaaatgta gagtttggat gtgtaactga ggcggggggg    360

agttttcagt attttttttt gtgggggtgg gggcaaaata tgttttcagt tctttttccc    420

ttaaggtctg ctagaatcct aaaggcaaat gactcaaggt gtaaccagaa aaccagaaaa    480

tcccattttc nggatatnng acccccccag gttancggtt attnaacttt naccnnttta    540

cctttaggct ttgggaaaaa atttnccttg gaaaaagggt tgggannacc ttttttnccc    600
```

-continued

```
ccccc                                                                605

<210> SEQ ID NO 406
<211> LENGTH: 255
<212> TYPE: DNA
<213> ORGANISM: Homo sapiens

<400> SEQUENCE: 406

ggtactacct gcggcctgtc tcccagcagg agtttgacaa gaacaccttg gatctcaggc     60

aacagaacgg aactgcctca tcacggaaga ccctctggaa tcaagaactc tacatccagc    120

aggacaactc agagaggaag cggaaacacc ttccagaccg acaggatggg cctgcagcca    180

agagtgagaa agcagccccc agaagtcagc actggttgca cagggacctg cgtgtgcggt    240

ttgtggacaa catgt                                                     255

<210> SEQ ID NO 407
<211> LENGTH: 601
<212> TYPE: DNA
<213> ORGANISM: Homo sapiens
<220> FEATURE:
<221> NAME/KEY: misc_feature
<222> LOCATION: (1)...(601)
<223> OTHER INFORMATION: n = A,T,C or G

<400> SEQUENCE: 407

ggtttttttt ttaagaggaa aacccggtaa tgatgtcggg gttgagggat aggaggagaa     60

tgggggatag gtgtatgaac atgagggtgt tttctcgtgt gaatgagggt tttatgttgt    120

taatgtggtg ggtgagtgag cccnattgtg ttgtggtaaa tatgtagagg gagtataggg    180

ctgtgactag tatgttgagt cctgtaagta ngagagtgat atttgatcag gagaacgtgg    240

ttactagcac agagagttct nccagtaggt taatagtggg gggtaaggcg aggttagcga    300

ggcttgctag aagtcntcat aaagctatta gtggnaagta gagtttgaag ccttgaaaag    360

aggatatgat nccactntga gtgcgttcgg tgtttgagtt ngctaggcag aatattantn    420

atgatgtaag cccgtggcca ttatgagant gactgccntg ttaagnttna nggggtttgg    480

atgangaatg gctngtaact actaaggcct atgntggctg gttnaanagn ttcnatntnc    540

nnantttann tcttgcttgt ctatgcagaa tnganctgnt attnatatgc ctcacnangg    600

g                                                                    601

<210> SEQ ID NO 408
<211> LENGTH: 630
<212> TYPE: DNA
<213> ORGANISM: Homo sapiens
<220> FEATURE:
<221> NAME/KEY: misc_feature
<222> LOCATION: (1)...(630)
<223> OTHER INFORMATION: n = A,T,C or G

<400> SEQUENCE: 408

ggtacaaaag gagtctcagg cttgaagagg ttatgtaact tgcctaaggt cacacagtta     60

agtggcagaa atgagataca aaccaaagtc tgtctaactc cagagttcac accatcatgt    120

tatagtgcca tcttcgtaca ttgagctcca tagagacagc gccggggcaa gtgagagccg    180

gacgggcact gggcgactct gtgcctcgct gaggaaaaat aactaaacat gggcaaagga    240

gatcctaaga agccgagagg caaaaatgtc atcatatgca ttttttgtgc aaacttgtcg    300

ggaggagcat aagaagaagc acccagatgc ttnagtcaac ttctnagagt ttctaagaaa    360
```

```
gtgctcanta gaggtggaaa gaccatgttt gcttaaagag anaggaaaat ttnaagatat    420

tggcaaagcg gacaaaggnc cgttttgaaa gangaaatga naacctatat cccttccaaa    480

gggggagacc caaanagaag tttcaaggat nccaatggca ccccaagaag gcntncttng    540

gccttcttnc tcttctgctc ntgagtattc ggcccaaaat tcaaagggag aacatcttng    600

gcctggccat tggtgatgtt ggcaaaaaag                                     630


<210> SEQ ID NO 409
<211> LENGTH: 614
<212> TYPE: DNA
<213> ORGANISM: Homo sapiens
<220> FEATURE:
<221> NAME/KEY: misc_feature
<222> LOCATION: (1)...(614)
<223> OTHER INFORMATION: n = A,T,C or G

<400> SEQUENCE: 409

cgaggtaccg ggatgcagca gtgatggctt ttggttgtat cttggaagga ccagagccca     60

gtcagctcaa accactagtt atacaggcta tgcccaccct aatagaatta atgaaagacc    120

ccagtgtagt tgttcgagat acagctgcat ggactgtagg cagaatttgt gagctgcttc    180

ctgaagctgc catcaatgat gtctacttgg ctcccctgct acagtgtctg attgagggtc    240

tcagtgctga acccagagtg gcttcaaatg tgtgctgggc tttctccagt ctggctgaag    300

ctgcttatga agctgcagac gttgctgatg atcaggaaga accagctact tactgcttat    360

cttcttcatt tgaactcata agttcagaag ctcctagaga ctacagacag acctgatgga    420

caccagaaca acctgaggag ttctgcatat gaatctctga tggaaattgt gaaaaacagt    480

gnccaaggat tggtaatcct gctgnnccag aaaaacgact tttggncatc atgggaacga    540

ctggcacang gtcttcaana tggagtcnca tatccgagcc cattccattg gaatnccgtt    600

caangacttn ntct                                                      614


<210> SEQ ID NO 410
<211> LENGTH: 611
<212> TYPE: DNA
<213> ORGANISM: Homo sapiens
<220> FEATURE:
<221> NAME/KEY: misc_feature
<222> LOCATION: (1)...(611)
<223> OTHER INFORMATION: n = A,T,C or G

<400> SEQUENCE: 410

cgaggtaccc atgttatgct ttcacctctc accccaatgg agtcacacag gcctgagttt     60

gaacagttaa cacagcttgg aagggacaca tgcctgattc ccatccttgg agaacaatat    120

catgctatga ggagtaggaa gggcaagaga tatgaaaaga acagaggaaa tgtggttcct    180

agaagtcaga aggcatcaag ggtccatcag tgtagaagtg gctggggcgg gagacgtaaa    240

cctcatccac ggtgttctgg ccagccaaca gtgggtcacc attcggcatg atttcttcaa    300

tctttacaca gtttctgaag atttccattg gctcagtgtt caaatgtctc agatcacagg    360

gcaaatctgg ctctggcact ggctgtgata caggtccttg gtctggctct ggcactgntt    420

gtgataccca tgcatagtgt gggctctatc acangctcca gagtggactt cagcacagac    480

tctagctttt ggccccagaa tccagccttg nctttaacca gtggctntta atncaggctg    540

acctctggct ntggcaccag ncctagttca gcttntaang ctccantttt gctntggttt    600

aagctccacn g                                                         611
```

<210> SEQ ID NO 411
<211> LENGTH: 590
<212> TYPE: DNA
<213> ORGANISM: Homo sapiens
<220> FEATURE:
<221> NAME/KEY: misc_feature
<222> LOCATION: (1)...(590)
<223> OTHER INFORMATION: n = A,T,C or G

<400> SEQUENCE: 411
ggtacccttg tctttaaaag gattccccct tataaggact cttcaagtaa atccacacat 60
atatagtcaa ctaatttttg acaaagacac caagaataca caatggggaa aggatagtgt 120
cttcaataaa cagtattgga aatactggat atccacatgc aaaagaatga aattggatga 180
aatatggtga aattatttta caccgtaccg gctccccaac gtgcacggca ggagctacgg 240
cccagcgccg ggcgctggcc acgtgcagaa atggagtttc atcatgttgt cctctcgaac 300
tcctgacctc aagtgatcca cccgcctcgc ccttccaaag tgctgagatt acaggaagag 360
tctaacctgt ctctgcaagc tcttgagtcc cgccaagatg atattttaaa acgtctgtat 420
gagttgaaag ctgcagttga tggcctctcc aagatgattc aaacccagat gcagacttgg 480
atgtaaccaa cataatccaa gcggatgagc ccacgacttt aaccaccaat gcgctggact 540
ttgaattcag tgcttgggaa ggatacgggc gctnaaagac atcggaacan 590

<210> SEQ ID NO 412
<211> LENGTH: 609
<212> TYPE: DNA
<213> ORGANISM: Homo sapiens
<220> FEATURE:
<221> NAME/KEY: misc_feature
<222> LOCATION: (1)...(609)
<223> OTHER INFORMATION: n = A,T,C or G

<400> SEQUENCE: 412
ggtacagaag atgctgtgga ctattcagac atcaatgagg tggcagaaga tgaaagccga 60
agataccagc agacgatggg gagcttgcag ccccttttgcc actcagatta tgatgaagat 120
gactatgatg ctgattgtga agacattgat tgcaagttga tgcctcctcc acctccaccc 180
ccgggaccaa tgaagaagga taaggaccag gattctatta ctggtgtgtc tgaaaatgga 240
gaaggcatca tcttgccctc catcattgcc ccttcctctt tggcctcaga gaaagtggac 300
ttcagtagtt cctctgactc agaatctgag atgggacctc aggaagcaac acaggcagaa 360
tctgaagatg gaaagctgac ccttccattg gctgggatta tgcagcatga tgccaccaag 420
ctgttgccaa gtgtcacaga actttttnca gaattttcga cctggaaagg tgttaccgtt 480
tttctacgtc tttttggacc agggaagaat gtnccatctg gtttggcgga ntgctcgaan 540
aaagaggaag aagaagcncc gggagctgat ccaggaagaa cnnatcccgg aagtggagtn 600 gctcantna 609

<210> SEQ ID NO 413
<211> LENGTH: 420
<212> TYPE: DNA
<213> ORGANISM: Homo sapiens

<400> SEQUENCE: 413
ggtaccgcca catcgctgac ttggctggca actctgaagt catcctgcca gtcccggcgt 60
tcaatgtcat caatggcggt tctcatgctg gcaacaagct ggccatgcag gagttcatga 120
tcctcccagt cggtgcagca aacttcaggg aagccatgcg cattggagca gaggtttacc 180

-continued

```
acaacctgaa gaatgtcatc aaggagaaat atgggaaaga tgccaccaat gtgggggatg    240

aaggcgggtt tgctcccaac atcctggaga ataaagaagg cctggagctg ctgaagactg    300

ctattgggaa agctggctac actgataagg tggtcatcgg catggacgta gcggcctccg    360

agttcttcag gtctgggaag tatgacctgg acttcaagtc tcccgatgac cccagcaggt    420
```

<210> SEQ ID NO 414
<211> LENGTH: 621
<212> TYPE: DNA
<213> ORGANISM: Homo sapiens
<220> FEATURE:
<221> NAME/KEY: misc_feature
<222> LOCATION: (1)...(621)
<223> OTHER INFORMATION: n = A,T,C or G

<400> SEQUENCE: 414

```
acatagtttt atagtagcca cagtaacttc cagtgactgg caaatttctt tgcatcagct     60

ggcatgtgtg gtgaatggaa ttcccatgaa cagctcttac atccttccgc tttccttcta    120

caggcctcgg tcttgtttcc aaaggtgact gcagtgagga tgtaaggtcc atgacctcta    180

gggataatgc catccactca ggaagaaaga tgctgagaaa ctctagggat atctaagttt    240

acatcacagg gggagaatca attgtggagg ttttaagaag acatttgaat ttttgcccct    300

aatcaagaag tgttttgcca tctggtttac attcaataac tagttggctc atcatttgca    360

gaaataaact ttcctctaga ttaggaaact tcatcatgag atctgagata tactggtttg    420

gaaaggttnc tcagttctct tggctttcna agtccccggc cttggaatgg ggtnaaggcc    480

cattggangc ncattnaatt ggccttgggg taaaggaaac tttggantgg cgnccaaatt    540

nnaacccggg tgggccattn nttttnacnc ggtaaattaa ggntgggccc cggaaaattt    600

ggttttccgg aanannttn g                                               621
```

<210> SEQ ID NO 415
<211> LENGTH: 619
<212> TYPE: DNA
<213> ORGANISM: Homo sapiens
<220> FEATURE:
<221> NAME/KEY: misc_feature
<222> LOCATION: (1)...(619)
<223> OTHER INFORMATION: n = A,T,C or G

<400> SEQUENCE: 415

```
acaagctttt tttttntttt tttttttttt tttttttaaa gatcaacaaa cattttatta     60

attctgattc cttttatcat gtgctttttt atacaaagca ctttnaaatn cattacatta    120

tcttaaatat ataataggag tttctttcgg attcagttta aaaatgacaa atagcattcg    180

ttgcgcccaa gttagaatta caccaaaatt accatgngct ggcacatacc atcatcccac    240

tggtggctgg aaaactgggt tgcaggagtg tctgcactga gatgggccac caccccagtg    300

gccatatagg tatagatgag ggaaggatgg actanaanca agctgggctt tcngggtcgt    360

ctatantcct ttttcacttc attccgtttt ccccattgng cnttgaaccc agggaatctn    420

nttgacccat ccttggagct nttaaaaagg acctgngttn aaggtgccnc cntttgaaaa    480

ggggccccct ttgnatnaan tgggccgttg aaaaaggccc tttngatttg gancccaang    540

acngggaaat ttcacttngg cattaacnan tgtcnccgaa atnttcnctn ngntatgaac    600

tttantaana tngnttngn                                                 619
```

<210> SEQ ID NO 416
<211> LENGTH: 611

<212> TYPE: DNA
<213> ORGANISM: Homo sapiens
<220> FEATURE:
<221> NAME/KEY: misc_feature
<222> LOCATION: (1)...(611)
<223> OTHER INFORMATION: n = A,T,C or G

<400> SEQUENCE: 416
ggtacactaa ggtatgagct gaagctttag gttctccgtg cttccctcaa gacctccttc 60
ttgctaacag aagcagtagg caattgctgc agtgcgtttc tcaccctgcc aataggtctg 120
tctgtatctc tgttaaggaa aatagcctgg tccctcctgg cagtgcttgg aagcttgatg 180
ctaattttta tatagcgtgg caagctgacc agcagtgcca ggccttgatc tgtattctgc 240
actatccctt tacttggttc ctggcactga atggtctcca gccctgaaga atcacgtgtg 300
atcacagcag ctgacctggg ctttctcccc gagaggaagg ggcatgtcat ttttatttga 360
cagagggaaa atgggaactg ccttgactgc ctttgntgng ctttcccgcg taagaaagca 420
ctgngtttaa actgtgcaat acactngctt tgccatngat gtaaatgtaa gaaaatccct 480
anctttaaaa cctantggtt tgaacnttat tatatnaaan actttttaac ctattnngna 540
atttngggnc cttgccggta agntttnggg ggggnaaacn ngttncaaaa ggaaaggtcc 600
tttaactttn g 611

<210> SEQ ID NO 417
<211> LENGTH: 609
<212> TYPE: DNA
<213> ORGANISM: Homo sapiens
<220> FEATURE:
<221> NAME/KEY: misc_feature
<222> LOCATION: (1)...(609)
<223> OTHER INFORMATION: n = A,T,C or G

<400> SEQUENCE: 417
caggtactga gacatcacat tactggccag tgttggcaaa gaaactgcca caaacaccat 60
gagaaggcag gcaattttat actcttcttc tggactaatg ttttccgatt tttgtgaaga 120
aagagctacg accaatgcag gatcaatctc acaaggtaat ccggcagctg atgataactc 180
atacacattc attgcaacct tcatatcagt ttcccttgga atgtgatcct taaaatcttc 240
aattgaactt acaagaaaag gaatgtggta ggataacaca tctctaagtg cttcttgtgc 300
caatgatcgg aaggataaaa ttacaccaat tattgtcatc ctcttcaaga cactgtcaac 360
agatgataat cttttaaaca gtgcagccat ctggtctggt ttgtcaaagc tggtcctcat 420
ttgtgttaac acatcaacat tctccaccac aagtttctta agttcaagca accttgtgat 480
gaaatatgcc acataaggct ttcacttaga aacntcatac catatgggcc taataagtct 540
ggataatgac ctcattctga natggtcaga atattcntnt gcattggaan gtaaatcaat 600
ttctggagg 609

<210> SEQ ID NO 418
<211> LENGTH: 643
<212> TYPE: DNA
<213> ORGANISM: Homo sapiens
<220> FEATURE:
<221> NAME/KEY: misc_feature
<222> LOCATION: (1)...(643)
<223> OTHER INFORMATION: n = A,T,C or G

<400> SEQUENCE: 418
ggtactcccg attgaagccc ccattcgtat aataattaca tcacaagacg tcttgcactc 60

```
atgagctgtc cccacattag gcttaaaaac agatgcaatt cccggacgtc taaaccaaac    120

cactttcacc gctacacgac cgggggtata ctacggtcaa tgctctgaaa tctgnggagc    180

aaaccacagt ttcatgccca tcgtcctaga attaattccc ctaaaaatct ttgaaatagg    240

gcccgtattt accctatagc acccnctcta ccccctctag agcccactgt aaagctaact    300

taggcattaa ccttttaagt taaagattaa gagaaccaac acctctttac agngaaatgc    360

cncaactata tactacccgt atggcccacc atanttacct ccnatactnc ctacactatt    420

tncttatnaa cncancttna naatattaat ctcataatta ccagctanct ttncttaacc    480

aatgnccnat tanaaattaa anntattatn taccatactc cntgtnntcn nnataatgta    540

nngnananat tggnntcggc ttcaatttat nnggtcccaa aaatgcctan gcttaactcn    600

gnactngtnc gggcggcncg ttngnaaagg ggctgaaatt cng                      643
```

```
<210> SEQ ID NO 419
<211> LENGTH: 607
<212> TYPE: DNA
<213> ORGANISM: Homo sapiens
<220> FEATURE:
<221> NAME/KEY: misc_feature
<222> LOCATION: (1)...(607)
<223> OTHER INFORMATION: n = A,T,C or G

<400> SEQUENCE: 419

accagaatat ggacacattc caagctttct tgtcgatgct tgcacatctt tagaagacca     60

tattcatacc gaagggcttt ttcggaaatc aggatctgtg attcgcctaa aagcactaaa    120

gaataaagtg gatcatggtg aaggttgcct atcttctgca cctccttgtg atattgcggg    180

acttcttaag cagtttttta gggaactgcc agagcccatt ctcccagctg atttgcatga    240

agcacttttg aaagctcaac agttaggcac agaggaaaag aataaagcta cactgttgct    300

ctcctgtctt ctggctgacc acacagttca tgtattaaga tcttctttaa ctttctcagg    360

aatgtttctc ttagatccag tgagaataag atggacagca gcaatcttgc agtaatattt    420

gcaccgaatc ttctttagaa caagtgaagg ccntgaaaag atgcttntac ccccggaaaa    480

gaagcttcca atacnggntt gaanaagnac cttgggcggg aacacnctta nggnggaaat    540

tcngnccact tggnggccgt actaangggn nccaacttng gnccaacttt ggggaaacan    600

ggcanaa                                                              607
```

```
<210> SEQ ID NO 420
<211> LENGTH: 494
<212> TYPE: DNA
<213> ORGANISM: Homo sapiens

<400> SEQUENCE: 420

ggtacatgag aacatatatt tattgcatga ttttctagat acacagtcta tgcattattc     60

atatacattt attttagcct aaagtggttt tcaaatccag ttcttcaagc cataaatgac    120

caagatccaa gcaatctgaa tttgtttttg tgattatttg actggaatgc ttcttaagtg    180

gaataactat actccgttat ccacccgatt tcctaatgta attgaaagat tttctatttt    240

gccacacact tggagacaat aagggttttt agttttatct actcttctat tgaagttaaa    300

gaaagaaaaa aagatttttt tatttgtatt aatgaaaagc tttagtttaa aataaggaga    360

tccagaataa aaagaagaga ctgatctctt caattattgt catctgtagc caccagcaca    420

tcactcttat gtaatcccca aaggcttggc atgccgtaag tgtgtggtgg ggtagactgc    480

tgccggggaa tcgt                                                      494
```

<210> SEQ ID NO 421
<211> LENGTH: 366
<212> TYPE: DNA
<213> ORGANISM: Homo sapiens

<400> SEQUENCE: 421
ggtaccaagg ttattgatca agtcagcctt ggtcattcca attccagtat ccacaatagt 60
gagagttcga tcttgtttgt tcggtataag gttaatatgc agctctttcc cagagtctaa 120
tttactggga tctgtcaagc tttcataccg gattttgtcc aatgcatctg atgaatttga 180
aatgagctct ctcagaaaga tctctttgtt cgagtagaaa gtattgatga tcaatgacat 240
caactgggca atttctgcct gaaaggcgaa cgtctcaacc tcctcctcct ccatcggttg 300
gtcttgggtc tgggtttcct caggcatctt ggctaagtga ccgcacagga ccaacggcac 360
agccac 366

<210> SEQ ID NO 422
<211> LENGTH: 418
<212> TYPE: DNA
<213> ORGANISM: Homo sapiens
<220> FEATURE:
<221> NAME/KEY: misc_feature
<222> LOCATION: (1)...(418)
<223> OTHER INFORMATION: n = A,T,C or G

<400> SEQUENCE: 422
ggtacaagag tgtttcatga aatccgtttt taaaatgaac atctctgtgt gccacagttc 60
ctaggactgg ggcaaggaca cagtgtcaag tcttgttttg aggatgagtc tctgaagaga 120
cagaattcct gccagaatgc gcacagaaca taagtcagcc aagtgtgtcg tgccagggat 180
actttgactt tggtttgctg ctgctgctag ggatattggg agggttatcc tttccaggtt 240
gtaggagagg gttgtgggta aaggtctgtc gtaaaggacc cctggctgct agctccaact 300
gattccgcat gcgttgttca cgctctcnca gctgacgccg tcatttcagc atttttccag 360 cctttttga aagctctcta ggaagccttt ccgtggaggt aatttgtcca ggtcatgt 418

<210> SEQ ID NO 423
<211> LENGTH: 374
<212> TYPE: DNA
<213> ORGANISM: Homo sapiens

<400> SEQUENCE: 423
ggtctattct gcatatagag aactgagggc tttccctgag aaacagttga gttgtgttgc 60
caaccagaat ggctcgcaag ctgactgtga gctcggaaat ccttttaaaa gaaattcaaa 120
tgtcactttt tatttggttt taagtacacc tgattttcat gacaaatacg gtaatgctgt 180
attagctagt ggagccactt tctgtattgt tacatggaca tatgtagcaa cacaagtcgg 240
aatagaatgg aacctgtccc ctgttggcag agttacccca aaggaatgga ggaatcaagt 300
aatcatccca actggtgtaa taatgaattg tttaaaaaac agctcataat tgatgccaaa 360
ttaaagcact gtgt 374

<210> SEQ ID NO 424
<211> LENGTH: 610
<212> TYPE: DNA
<213> ORGANISM: Homo sapiens
<220> FEATURE:
<221> NAME/KEY: misc_feature
<222> LOCATION: (1)...(610)

<223> OTHER INFORMATION: n = A,T,C or G

<400> SEQUENCE: 424
ggcggagctt gaggaaaccg cagataagtt tttttctctt tgaaagatag agattaatac 60
aactacttaa aaaatatagt caataggtta ctaagatatt gcttagcgtt aagtttttaa 120
cgtaatttta atagcttaag attttaagag aaaatatgaa gacttagaag agtagcatga 180
ggaaggaaaa gataaaaggt ttctaaaaca tgacggaggt tgagatgaag cttcttcatg 240
gagtaaaaaa tgtatttaaa agaaaattga gagaaaggac tacagagccc cgaattaata 300
ccaatagaag ggcaatgctt ttagattaaa atgaaggtga cttaaacagc ttaaagttta 360
gtttaaaagt tgtaggtgat taaaataatt tgaaggcgat cttttaaaaa gagattaaac 420
ccgaagggtg attaaaagac cttgaaatcc atgaccgcag ggagaattgc gtcatttaaa 480
gcctagttaa cgcatttcct aaaccccaga ccaaaaatgg ggaaggatta attgggagtg 540
gtaggatgaa ccaanttggg ngaagatgaa gttggaagtg gaaactggaa aaccgaaagt 600 ncctcggccc 610

<210> SEQ ID NO 425
<211> LENGTH: 368
<212> TYPE: DNA
<213> ORGANISM: Homo sapiens

<400> SEQUENCE: 425
ggtataagtt cagagagaaa gattccttcc caaggtcatg cagctagtaa atgatagaat 60
caggattcat agcatcacta taggggtca atatttacac aaaaaaggaa agtcacaagc 120
ctgtttaaaa tgaagtgacc accttttctt gcatagacta aataactcga actggcattt 180
ttaggttgga aagacagctg aattagtagt taagtctgat agccaagtaa gttttaaaaa 240
ccaaagcatc caggatgcac acccctgcac catttgctgt gcgaattaat agttctgtct 300
ctctctctct ttcttttttc tttttattct ttgagatgga ttttcgctct tgtcgcccag 360
gctggagt 368

<210> SEQ ID NO 426
<211> LENGTH: 630
<212> TYPE: DNA
<213> ORGANISM: Homo sapiens
<220> FEATURE:
<221> NAME/KEY: misc_feature
<222> LOCATION: (1)...(630)
<223> OTHER INFORMATION: n = A,T,C or G

<400> SEQUENCE: 426
actaccacag cctttaagtg acattgattt ataacttggt cacaattcac tgcatttagg 60
aaaaccagca ttcttatctg gtcagtgctc gcttcttagc aacccctaat taaatttaat 120
tcatctctaa atcttagctt caactttatt caattacatt tggctgacgg ctgttttcta 180
aaacccttaa gtgttgacca taaatgcaaa acttccagta tctgttgggt tttattagca 240
gatgctgctt ttatttaaaa aaaaccgaca gtataactgt cataattatg gaaggcactg 300
cttccgataa ttatattcta ttaaaaaaac accatttata gtgaactctg tcactgataa 360
ataaacaata aatatctcag tgccaaaagg acagaaagct ctcccctaag attaacactt 420
tggccaaaat ttggtagcat attattcttt aaagtctgac aaactgagtc tgcaactaaa 480
cacctgaaac tggtctcttt caatgggctt tggaagaacc aaaataccaa gaactaaatg 540
gaggcttatg gggaagggn cgaggaaata aatatctaag cnttggcttc tggccctctt 600
tcataaannc ctgaggtaca tattangctn 630

<210> SEQ ID NO 427
<211> LENGTH: 224
<212> TYPE: DNA
<213> ORGANISM: Homo sapiens

<400> SEQUENCE: 427
ggtgggaggg tggtgtccac tgcccagttc cgtgtcccga tgcccagcgc cagcgccagc 60
cgcaagagtc aggagaagcc gcgggagatc atggacgcgg cggaagatta tgctaaagag 120
agatatggaa tatcttcaat gatacaatca caagaaaaac cagatcgagt tttggttcgg 180
gttagagact tgacaataca aaaagctgat gaagttgttt gggt 224

<210> SEQ ID NO 428
<211> LENGTH: 543
<212> TYPE: DNA
<213> ORGANISM: Homo sapiens
<220> FEATURE:
<221> NAME/KEY: misc_feature
<222> LOCATION: (1)...(543)
<223> OTHER INFORMATION: n = A,T,C or G

<400> SEQUENCE: 428
ggacgctctc agctctcggc gcacggccca gcttccttca aaatgtctac tgttcacgaa 60
atcctgtgca agctcagctt ggagggtgat cactctacac cccaagtgc atatgggtct 120 gtcaaagcct atactaactt tgatgctgag cgggatgctt tgaacattga aacagccatc 180
aagaccaaag gtgtggatga ggtcaccatt gtcaacattt tgaccaaccg cagcaatgca 240
cagagacagg atattgcctt cgcctaccag agaaggacca aaaaggaact tgcatcagca 300
ctgaagtcag ccttatctgg ccacctggag acggtgattt tgggcctatt gaagacacct 360
gctcaagtat gacgcttctg agctaaaagc ttccatgaag ggctgggga accgacgagg 420 actctctcat tgagancatc tgnttcagaa cccaacccag gaagctgcan ggaaantaac 480
cagagtctac caagggaaat gtaccctnng gnccgngaac cacgcttaan gggcgaaatt 540
cca 543

<210> SEQ ID NO 429
<211> LENGTH: 346
<212> TYPE: DNA
<213> ORGANISM: Homo sapiens

<400> SEQUENCE: 429
actatctttt cattcagtcc cttaagcagc ttactcttca atgccaacaa aactttattt 60
tttaaatagt cttaaaagtg cttaagggag ttctggttcc tctttttagc ctgcacagtt 120
taagatcaat ggtaaaggta ggaaataatc ataagggcac tggaagaagg aatgagtcta 180
aataatgtat aatgactgtt ccgccatacc aattttgtca tggtgattat tcactaattt 240
tataggagag tgtattgaga tctgctacag cttcttggat ctttgaagca ctgctgaatt 300
acatacacaa agcagagcag atgtcagcac ctgattaatc agtacc 346

<210> SEQ ID NO 430
<211> LENGTH: 605
<212> TYPE: DNA
<213> ORGANISM: Homo sapiens
<220> FEATURE:
<221> NAME/KEY: misc_feature
<222> LOCATION: (1)...(605)

<223> OTHER INFORMATION: n = A,T,C or G

<400> SEQUENCE: 430
ggtggcgcgg ccgaggtaca gctggtgctt ctgccttacc ccatcctctc ctctcagatt 60
caccgaggac tgttcaggtg gtaacattct cttagggtag ggaactctgc agagggagag 120
ctgaggaggt tccggccata gttgtttgta atcttagggc tctgggcttg gctgaaacat 180
gacggtattg cttggtttca ggcttgacac tgccaggcgc ctattgcttg acctctgttt 240
aaatgaggga cttcaagact agacagcatg gctcttttca gtttattgca tgaaggagtt 300
acactagtcc aagttaaaag cggaccccaa atggttacat tatacaagct gtgaggtttt 360
taaacctgtg acaagggaga gaagggaaat tctactcatt gcaaggaaat cctcacttaa 420
gcttcagtga gccacaagca cttaaaaccc atgaaccttc agctgatcgt ccttagccag 480
tccaatctct acgaggaact ggcatatgtc ttgcgttggc accctgtagc tgaattactt 540
ctcatattcn gatgctaatt ncagacctgn ccggcggccg tcaaaggcna atccacnact 600 gnggn 605

<210> SEQ ID NO 431
<211> LENGTH: 430
<212> TYPE: DNA
<213> ORGANISM: Homo sapiens
<220> FEATURE:
<221> NAME/KEY: misc_feature
<222> LOCATION: (1)...(430)
<223> OTHER INFORMATION: n = A,T,C or G

<400> SEQUENCE: 431
acactaccaa cagatcaaag aaacccctcc ggccagtgag aaagacaaaa ctgctaaggc 60
caaggtccaa cagactcctg atggatccca gcagagtcca gatggcacac agcttccgtc 120
tggacacccc ttgcctgcca caagccaggg cactgcaagc aaatgccctt tcctggcagc 180
acagatgaat cagagaggca gcagtgtctt ctgcaaagcc agtcttgagc ttcaggagga 240
tgtgcaggaa atgaatgccg tgaggaaaga ggttgctgaa acctcagcag gccccagtgt 300
ggttagtgtg aaaaccgatg gaggggatcc cagtggactg ctgaagaact tccaggacat 360
tatgcaaaag caaagaccaa aaaanaaann nnaaaaaaaa aagcttgtac ctnggccgng 420
accacgctaa 430

<210> SEQ ID NO 432
<211> LENGTH: 479
<212> TYPE: DNA
<213> ORGANISM: Homo sapiens
<220> FEATURE:
<221> NAME/KEY: misc_feature
<222> LOCATION: (1)...(479)
<223> OTHER INFORMATION: n = A,T,C or G

<400> SEQUENCE: 432
acaagctttt tttttttttt tttttttttt ttggaacgta ggctttctct tgtctttatt 60
ctggggagga ggaatcctcc tcatcatctt cctcatcttc atcattgaac gaacaggggg 120
tctcgcctcg ggactcggag cagtgagagg ccgcactgct ggactggtga ctgtttgggg 180
ccaggaactg cccagttgct aaggccactt ctgcatccaa gcataaccct tggtttacac 240
ttgactgggg taaggtggca ccagtggtca ggtctaaatt tgaaactgat tgggtagaag 300
ttcagaagta gtccctgatt taaccaagaa ggtcctgtgg agatatctgn gatataacct 360
tctaaagcct ttggcaccag ggatttcgca agttttcaan atcctccaga gagcatttgc 420

```
ctgacttcag gcnaaacgac attcccatnc gctttangac cttgggcgng accacgcta     479


<210> SEQ ID NO 433
<211> LENGTH: 600
<212> TYPE: DNA
<213> ORGANISM: Homo sapiens
<220> FEATURE:
<221> NAME/KEY: misc_feature
<222> LOCATION: (1)...(600)
<223> OTHER INFORMATION: n = A,T,C or G

<400> SEQUENCE: 433

ggtacccaac aataccaccg accaggagct gcaacacatt cgcaacagcc tcccagacac      60

agtgcggatt aggcgggtgg aggagcggtt ctcagccttg ggcaatgtca ccacctgcaa     120

tgactacgtg gccttggtcc acccagactt ggacagggag acagaagaaa ttctggcaga     180

tgtgctcaag gtggaagtct tcagacagac agtggccgac caggtgctag taggaagcta     240

ctgtgtcttc agcaatcagg gagggctggt gcatcccaag acttcaattg aagaccagga     300

tgagctgtcc tctcttcttc aagtccccct tgtggcgggg actgtgaacc gaggcagtga     360

ggtgattgct gctgggatgg tggtgaatga ctggtgtgcc ttctgtggcc tggacacaac     420

cagcacagag ctgtcagtgg tggagagtgt cttcaagctg aatgaagccc agcctagcac     480

cattgccacc agcatgcggg attccctcat tgacagcctc acctgagtca ccttccaagt     540

tgttccatgg gctcctggct ctggactgtg gccaaccttc tncacattcc gccaatctgt     600


<210> SEQ ID NO 434
<211> LENGTH: 417
<212> TYPE: DNA
<213> ORGANISM: Homo sapiens

<400> SEQUENCE: 434

ggtaccaacg cgctaagaaa tcagctccaa ttcgaagtgc acctgttccc cccaaagatt      60

gcacacctcc tacccgcttc tccttgagtg ctgggctgtc atccccaagg gcaagacgag     120

aagcacagct ccggaactca gccaggccca ggattggcag atactcgtga tttaggctat     180

tgtcattagc aatcttctgc tccactttct tcactactgg caaaacccag ggatggcagt     240

catccgtgcg atatgctccc actcccaggt tgaccttgcg ggggtccgga tcctccctga     300

agtcggcagt gagcttgaag accaggacag gctgggcctg cggaacctcg gcaaagactg     360

acggaggtgc catatcgaga gactaggaat caagagattt caccccacgc ccggagc        417


<210> SEQ ID NO 435
<211> LENGTH: 672
<212> TYPE: DNA
<213> ORGANISM: Homo sapiens
<220> FEATURE:
<221> NAME/KEY: misc_feature
<222> LOCATION: (1)...(672)
<223> OTHER INFORMATION: n = A,T,C or G

<400> SEQUENCE: 435

ggcagagaac gatgtggaca atgagctctt ggactatgaa gatgatgagg tggagacagc      60

agctggggga gatggggctg aggcccctgc caagaaggat gtcaagggct cctatgtctc     120

catccacagc tctggctttc gtgacttcct gctcaagcca gagttgctcc gggccattgt     180

cgactgtggc tttgagcatc cgtcagaagt ccggcatgag tgcatccctc aggccattct     240

gggaatggat gtcctgtgcc aggccaagtc gggcatggga aagacagcag tgtttgtctt     300
```

-continued

```
ggccacactg caacagctgg agccagttac tgggcaggtg tctgtgctgg tgatgtgtca    360

cactcgggag ttggcttttc aagatcagna aggaatatga gcgcttcttt taatacatgc    420

ccaatgtcaa aggttgctgg tttttttggt gggctggcta tcaagaaagg atgaagaagg    480

tgctgaanaa anaactgccc natattcgtc ctgggggact tcaagcccgt atnctaancc    540

tggcttcgaa ataagancct taancttaaa cncataaaca ctttatttgg atgaatgngn    600

taanancttg aacagtngac atncttcgga tgtcnggaaa ttttncnatg accccccana    660

annggncntgn tt                                                       672
```

<210> SEQ ID NO 436
<211> LENGTH: 469
<212> TYPE: DNA
<213> ORGANISM: Homo sapiens

<400> SEQUENCE: 436

```
ggtacaagct tttttttttt tttttttttt ttttttataa aagcatttta ttgaacacat     60

tctggaggta agttagaacc aaaacaaaat ttgggattgg ggtggggatt ctgttttgat    120

gatttagatt tgggaaaact ttggattctc gtgtcagcag gggccatgct gtgggaaacc    180

tgaaggctga tttgaagcag aatatagaac tgcggcacgg gagaccaggg gctgggaatg    240

gggctctcct gggaaccaaa gaatgtggtt ctgcaattgg cttggtctag actactctcc    300

agaaaaggat aaaacatggc ttgagcaact gcctagaaga ggcaatctcc atgggctggg    360

ttgctgcact tggaaggcag tgacttgcag caggttctta gctcttgaag ctcttccggg    420

aggaggaggt ggtggagaca aatttgacgc tggggctgct acccccgcc                469
```

<210> SEQ ID NO 437
<211> LENGTH: 457
<212> TYPE: DNA
<213> ORGANISM: Homo sapiens

<400> SEQUENCE: 437

```
actgaggcat cttcttcagc atctgggaca ggtcccgcat ggtgggtctt ctctccagta     60

ttcattctct tgctagaaga aaaatctttc agagaccggg gtgacttctg ggacacctct    120

gcgatgtgct tgtggcgcag tgctatccac aggtcgtcgt cctcgtccag gagcacctcc    180

ttcacccgtg cctccccgat gccgctggtc tcatacttgt atacatcatt ttcgataggc    240

agcagatcat aactcatagc ctgaaaagtc aattcatgga gcacagggga gctggggtca    300

aagcctcgat ccaggatcag gagctgggag cgtgccttgt ctgggccctc cccattgtt    360

ggatcatcag ctttataggc atcgagcttg tcctggatta gctgagccag cagggcattg    420

tccttgtatt ccccccgata ccgcatagcc gggtacc                             457
```

<210> SEQ ID NO 438
<211> LENGTH: 731
<212> TYPE: DNA
<213> ORGANISM: Homo sapiens
<220> FEATURE:
<221> NAME/KEY: misc_feature
<222> LOCATION: (1)...(731)
<223> OTHER INFORMATION: n = A,T,C or G

<400> SEQUENCE: 438

```
accaattatt cagaatcaaa tggatgcact tcttgatttt aatgttaata gcaatgaact     60

tacaaatggg gtaataaatg ctgccttcat gctcctgttc aaagatgcca ttagactgtt    120

tgcagcatac aatgaaggaa ttattaattt gttggaaaaa tattttgata tgaaaaagaa    180
```

```
ccaatgcaaa gaaggtcttg acatctataa gaagttccta actaggatga caagaatctc    240

agagttcctc aaagttgcag agcaagttgg aattgacaga ggtgatatac cagacctttc    300

acaggcccct agcagtcttc ttgatgcttt ggaacaacat ttagcttcct tggaaggaaa    360

gaaaatcaaa gattctacag ctgcaagcag ggcaactaca ctttccaatg cagtgtcttc    420

cctggcaagc actggtctat ctctgaccaa agtggatgaa agggaaaagc aggcagcatt    480

agaggaagaa caggcacgtt tgaaagcttt aaaggaacag cgcctaaaag aacttgcaaa    540

gaaacctcat acctctttaa caactgcagc ctctcctgta tccacctcag caggagggat    600

aatgactgca ccagccattg acatattttc taccccctagt tcttctaaca gcacatcaaa    660

gctgnccaat gatctgcttg anttgcagca gccaactttt cacccatctg tacctttggg    720

ccgngaacac g                                                          731
```

```
<210> SEQ ID NO 439
<211> LENGTH: 470
<212> TYPE: DNA
<213> ORGANISM: Homo sapiens

<400> SEQUENCE: 439

ctgcgagcca ggattcccga tccagagaca atggccccga tgggatggag cccgaaggcg     60

tcatcgagag taactggaat gagattgttg acagctttga tgacatgaac ctctcggagt    120

cccttctccg tggcatctac gcctatggtt ttgagaagcc ctctgccatc cagcagcgag    180

ccattctacc ttgtatcaag ggttatgatg tgattgctca agcccaatct gggactggga    240

aaacggccac atttgccata tcgattctgc agcagattga attagatcta aaagccaccc    300

aggccttggt cctagcaccc actcgagaat tggctcagca gatacagaag gtggtcatgg    360

cactaggaga ctacatgggc gcctcctgtc acgcctgtat cgggggcacc aacgtgcgtg    420

ctgaggtgca gaaactgcag atggaagctc cccacatcat cgtgggtacc               470
```

```
<210> SEQ ID NO 440
<211> LENGTH: 353
<212> TYPE: DNA
<213> ORGANISM: Homo sapiens
<220> FEATURE:
<221> NAME/KEY: misc_feature
<222> LOCATION: (1)...(353)
<223> OTHER INFORMATION: n = A,T,C or G

<400> SEQUENCE: 440

ggtacattga agagaacaag tatagcagag ccaaatctcc tcagccacct gttgaagaag     60

aagatgaaca cttcgatgac acagtggttt gtcttgatac ttataattgt ggatctacat    120

tttaaaatat caagagatcg tctcagtgct tcttccctta caatggagaa gttttgcttt    180

tctttgggct ggaggaagag catcctatgg tgtgtcaaaa ggcaaagtgt gttttgagat    240

gaaggttaca gagaagatcc cagtnaggca tttatatcnn nngatattga catacatgaa    300

gttcgnattg gctggncact actcnnntgg aatgntcttg gngaanaana att           353
```

```
<210> SEQ ID NO 441
<211> LENGTH: 647
<212> TYPE: DNA
<213> ORGANISM: Homo sapiens
<220> FEATURE:
<221> NAME/KEY: misc_feature
<222> LOCATION: (1)...(647)
<223> OTHER INFORMATION: n = A,T,C or G
```

<400> SEQUENCE: 441
acattattga tgaacgcagt gactctgaag aataatcaga ggatgacatg ggagagccca 60
atggcttcat tgattgccca tccctgtgag gacagggaaa tgggagcttg tgggattctg 120
gggatgacag aggtgagtga ggtgaagccc taggggatgg tgaatggtag ctccggatcc 180
ctggtgagga gcttcctctt aagtctgagt tactgagagg gaagagggag aagctgggtg 240
aggctagcat cgtcgacctt ggggaatccg ggctgggga ctgttcacaa gaagagccag 300
acaagaccct actgttctta ggtgcagaca ggattatgaa acctgaagct cccagggacc 360
ccaacaaatt ttcaaaccct gagaatgaag gagtgtgtgt gactgtgaga gtgtgtgtgt 420
gtgtgtgtgg tgtgaggtat gcgctcctta agaaaatgga aataaaccaa ccaatgagac 480
agacagacag acagagactc acttatccaa gtgttctgtc cagtcctctg aatccggttc 540
caagtcgcaa gaccctttga gctccaagtc catacagagc ccggcaaaat gctccggccc 600
gctgctcggc tcttgtgacg atctgagtac ctcgggccgn gaccacg 647

<210> SEQ ID NO 442
<211> LENGTH: 1002
<212> TYPE: DNA
<213> ORGANISM: Homo sapiens
<220> FEATURE:
<221> NAME/KEY: misc_feature
<222> LOCATION: (1)...(1002)
<223> OTHER INFORMATION: n = A,T,C or G

<400> SEQUENCE: 442
acagaagttg aagtgaaatc tactgaggag gcttttgaag ttttctggag aggccagaaa 60
aagagacgta ttgctaatac ccatttgaat cgtgagtcca gccgttccca tagcgtgttc 120
aacattaaat tagttcaggc tcccttggat gcagatggag acaatgtctt acaggaaaaa 180
gaacaaatca ctataagtca gttgtccttg gtagatcttg ctggaagtga aagaactaac 240
cggaccagag cagaagggaa cagattacgt gaagctggta atattaatca gtcactaatg 300
acgctaagaa catgtatgga tgtcctaaga gagaaccaaa tgtatggaac taacaagatg 360
gttccatatc gagattcaaa gttaacccat ctgttcaaga actactttga tggggaagga 420
aaagtgcgga tgatcgtgtg tgtgaacccc aaggctgaag attatgaaga aaacttgcaa 480
gtcatgagat ttgcggaagt gactcaagaa gttgaagtag caagacctgt agacaaggca 540
atatgtggtt taacgcctgg gaggagatac agaaaccagc ctcgaggtcc agttggaaat 600
gaaccattgg ttacctgacg tgggtttgca gagttttcac cnttgncgtc atgcgaaatt 660
ttggatatca acgatgagca gacactttcc angctgattg gaagccctta gagaaacgac 720
ttacttacga caaatggatg attggtgagt ttaacaaacc atntaaagct tttaaagctt 780
ttgtaccaga aattggcaat gctggtttaa gtnaaggaaa anccccctgcc anggggaact 840 taatggaaan ggggaaaaag atttngnccc aaattggaat tnaaccnccc gaaaaaaaaa 900
annnnnnaaa aaagancttg gncgggaacc ccccttaggg gaattcnncn ccttgggggc 960
cnntnntaan ggacccantt ggnccaaaat ttggggaaan tg 1002

<210> SEQ ID NO 443
<211> LENGTH: 486
<212> TYPE: DNA
<213> ORGANISM: Homo sapiens

<400> SEQUENCE: 443
acattagtct taattgactt attacataat cgattcgtgt ctagttttga gagctttaag 60

-continued

```
ttctcaatta tagttctttg aaaactgaat agcaaataac aatatgatta acttcatatt    120

tattatttca acgatctttt ttataaccga gtttaatttt taaattaaat ttctaaaata    180

gattaccaat attaaaatac cttaagatat ttatctttag caataatagg caatattaaa    240

gttgtattaa cttttaaatt aagtaagagt atttggtgga tgccttgggt ctgaaagtcg    300

atgaaggacg cgattacctg cgataagctt cgtggagttg gaaataaact atgatacgga    360

gatttccgaa tggggtaacc taactgagca aacctcagtt gcattttgat gaatccatag    420

tcaaattagc gagacacgtt gcgaattgaa acatcttagt agcaacagga aaagaaaata    480

aatacc                                                               486
```

<210> SEQ ID NO 444
<211> LENGTH: 625
<212> TYPE: DNA
<213> ORGANISM: Homo sapiens
<220> FEATURE:
<221> NAME/KEY: misc_feature
<222> LOCATION: (1)...(625)
<223> OTHER INFORMATION: n = A,T,C or G

<400> SEQUENCE: 444

```
gagggatgca cgttgcctta gccgagcttc ggagagaagc ctgatatgta acccaggcag     60

gtgggagcct cagtctgtcg ggctgaggtc tggcatctac aaagcctctt ggccgtgttc    120

tgaacttgaa gcctggagga gttctctgct cagcacagcc aaggaacaga attagaagaa    180

aaggaaccct ggcctgaggc aggtgacaaa cattaccacc ccagctgtgc acgatgcagc    240

agatgcaacc agatgttcac agaaggagag gaaatgtatc ttcaaggctc caccgtttgg    300

catcccgact gtaagcaatc tacgaagacc gaggaaaagc tgcggcctac caggacatcc    360

tcggaaagta tttattctag gccaggctcc agtattcctg gctcaccagg tcatactatc    420

tatgcaaaag tagacaatga gatcctggat tacaaggatt tagcagccat tccgaaggtc    480

aaggcaattt atgacattga acgtccagat cttattacct atgagccttt ctacacttcg    540

ggctatgatg acaaacagga gagacagagc cttggagagt ctccgaggac tttgnctnct    600

acttcatcag cagaagggta cctcg                                          625
```

<210> SEQ ID NO 445
<211> LENGTH: 1002
<212> TYPE: DNA
<213> ORGANISM: Homo sapiens
<220> FEATURE:
<221> NAME/KEY: misc_feature
<222> LOCATION: (1)...(1002)
<223> OTHER INFORMATION: n = A,T,C or G

<400> SEQUENCE: 445

```
accacaactc ccaggatttt cctggatcaa accttgtatc tcttctgcaa gtattgtgta     60

tattggtctg agagacgtgg accctcctga acattttatt ttaaagaact atgatatcca    120

gtatttttcc atgagagata ttgatcgact tggtatccag aaggtcatgg aacgaacatt    180

tgatctgctg attggcaaga gacaaagacc aatccatttg agttttgata ttgatgcatt    240

tgaccctaca ctggctccag ccacaggaac tcctgttgtc gggggactaa cctatcgaga    300

aggcatgtat attgctgagg aaatacacaa tacagggttg ctatcagcac tggatcttgt    360

tgaagtcaat cctcagttgg ccacctcaga ggaagaggcg aagactacag ctaacctggc    420

agtagatgtg attgcttcaa gctttggtca gacaagagaa ggagggcata ttgnctatga    480
```

```
ccaacttcct actcccagtt caccagatga atcagaaaat caagcacgtg tgagaattta    540

ggggacactg tgcactgaca tgtttcacaa caggcattcc agaattatga ggcattgagg    600

ggatagatga atactaaatg gttggctggg tcaatactgn cttaatgaga acatttacac    660

attctcacaa ttggtaaagg ttcccctcta ttttggtgac caatactact ggaaatggaa    720

tttggntttt tgcagttcac agggtantaa tatggctcag taccttnggc cgcgaacacg    780

cttaagggcn aattccacac acttgggcgg ccgttcttaa nggatccgaa ctnggancca    840

agcnttggcg taaacatggg cnataantgg tttctggggg gaaatggtat ccggttacaa    900

tttcccccca nattccnaac ccggaagncn tnaagggtaa aacccggggg gccctaangg    960

ggngctaact ccaaatnaaa tgggttgngc ttaatggccc nt                      1002
```

<210> SEQ ID NO 446
<211> LENGTH: 367
<212> TYPE: DNA
<213> ORGANISM: Homo sapiens

<400> SEQUENCE: 446

```
ggtacaaaag agtatgggct cacaagaaga tgattcagga aacaaaccat ccagttattc     60

ttgaaactaa catccatcct gagctaaaca agagaaacta ccatcttggc cagtgacaag    120

tgttcggagg gcagcagaga ggaccaagcc tgtgtcacct ggagactaag aaattaagtt    180

ttgttttgac atcttcagtc ctgtgtgctt tcagaaaacc attttctctg caaagaaagg    240

aaacagattt gcaaacttta aagtctgtcg tggatttatt tatcctcaga ttattgttac    300

tgcattaaat ctaccttttt gttttaagtt gcttgaaaaa aaaaaaaaaa aaaaaaaaaa    360

aaaaagc                                                              367
```

<210> SEQ ID NO 447
<211> LENGTH: 754
<212> TYPE: DNA
<213> ORGANISM: Homo sapiens
<220> FEATURE:
<221> NAME/KEY: misc_feature
<222> LOCATION: (1)...(754)
<223> OTHER INFORMATION: n = A,T,C or G

<400> SEQUENCE: 447

```
actcttgggg tggaaaagat ctacacataa caagttcaga aaccacagtg ataaactaac     60

ctaagaaaat cgtttaactt ttatctacct gaaacacaaa attaaaaggc aacctataaa    120

ctggaaaaaa atatttgcat caaatataac aaaagattat caatatcctt aagatgtaaa    180

tggcttttgc aaaacaatca atagaaaaat gactaggaat tagaaaatca tacacacaca    240

cacacacaca cacacgcaca cacacacaca ccacaaatgg ccaattgaca catggtagag    300

atgttcagtc accagcagac aaagcaatgt tcacatccac agggaaagca gactcgatcc    360

gtcggaggag caaaggtttt caatgtnata aagcccggtt ctgaggaaan angggaaggc    420

atcagggttt ncctcaccca gtgaagaaca cctaattnga aaaaaatccc ttcccttgct    480

tggggccagt tttaaccaat tatggaaccc ttgaaagtct ttaaagaagt ttnaaccagt    540

caatttncct ttcttcngaa atggtatggt atttcaggca tttcccaaag gaggtttanc    600

canccggacc gttgaaaaaa ggtcntggaa ccttccnagg gnaaagttca tttgccaagg    660

gtnttaattt ttcttaagga agggaaaaaa aaaaancttg naaaaatncc ctnngattgn    720

ccccattggn aancccggnn atnggtttaa aatt                                754
```

-continued

<210> SEQ ID NO 448
<211> LENGTH: 551
<212> TYPE: DNA
<213> ORGANISM: Homo sapiens

<400> SEQUENCE: 448

```
accagaaccg agttcgggat actcacaggc tcatcactca gatgcagctg agcctggcag     60
aaagtgaagc ttccttggga aacactaaca ttcctgcctc agaccactac gtggggccaa    120
atggctttaa aagtctggct caggaggcca caagattagc agaaagccac gttgagtcag    180
ccagtaacat ggagcaactg acaagggaaa ctgaggacta ttccaaacaa gccctctcac    240
tggtgcgcaa ggccctgcat gaaggagtcg gaagcggaag cggtagcccg gacggtgctg    300
tggtgcaagg gcttgtggaa aaattggaga aaaccaagtc cctggcccag cagttgacaa    360
gggaggccac tcaagcggaa attgaagcag ataggtctta tcagcacagt ctccgcctcc    420
tggattcagt gtctcggctt cagggagtca gtgatcagtc ctttcaggtg gaagaagcaa    480
agaggatcaa acaaaaagcg gattcactct caagcctggt aaccaggcat atggatgagt    540
tcaagcgtac c                                                          551
```

<210> SEQ ID NO 449
<211> LENGTH: 398
<212> TYPE: DNA
<213> ORGANISM: Homo sapiens

<400> SEQUENCE: 449

```
accttcaaca ggcatctcaa cagccccatc accaacacct gtgtgcaagg catagccatc     60
acgcggaaaa gtctcaggac tcagaactac accataaatg caggatcttt ttatttcata    120
taaaaatgat caatgtgaaa aaagccaaac tgtatgctgg ttttacagac tccgaccctt    180
cctgacagtc gtcttgtctg gccaggctgg gggcccagca ttcctggaag ggagagacag    240
cccggcatct cagtatttca ttgggacaac aagctggatg tggcagggaa agctgagagc    300
gccaaggtcc ccttgcttta tcccaagctc ggagggacgc agcctggcat ggctctggcc    360
tagcagccag gtgacatggc caggcacctt cctgtacc                            398
```

<210> SEQ ID NO 450
<211> LENGTH: 672
<212> TYPE: DNA
<213> ORGANISM: Homo sapiens

<400> SEQUENCE: 450

```
accttattag aaagcgacgg caaactatgt gccagcagcc gcggtaatac ataggtcgca     60
agcgttatcc ggaattattg ggcgtaaagc gtccgtaggt tttttgctaa gtctggagtt    120
aaatgctgaa gctcaacttc agtccgcttt ggatactggc aaaatagaat tataaagagg    180
ttagcggaat tcctagtgaa gcggtggaat gcgtagatat taggaagaac accaataggc    240
gaaggcagct aactggttat atattgacac taagggacga aagcgtgggg agcaaacagg    300
attagatacc ctggtagtcc acgccgtaaa cgatgatcat tagttggtgg aataatttca    360
ctaacgcagc taacgcgtta aatgatccgc ctgagtagta tgctcgcaag agtgaaattt    420
aaaggaattg acgggaaccc gcacaagcgg tggagcatgt ggtttaattt gattctacgc    480
gtagaacctt acccactctt gacatcttct gcaaagctat agagatatag tggaggttaa    540
cagaatgaca gatggtgcat ggttgtccgt cagctcgtgt cgtgagatgt taggttaagt    600
cctgcaacga gcgcaaccct tttctttagt tactaatatt aagttaagga ctctagagat    660
```

actggctgga cc 672

<210> SEQ ID NO 451
<211> LENGTH: 554
<212> TYPE: DNA
<213> ORGANISM: Homo sapiens
<220> FEATURE:
<221> NAME/KEY: misc_feature
<222> LOCATION: (1)...(554)
<223> OTHER INFORMATION: n = A,T,C or G

<400> SEQUENCE: 451
acacgctgcc aaagtaattc ctgctcatcc atgccctgtc tctgtctctt ttagagtcat 60
accttatttg agtataggtt gcttaatttt gctagacttc ctgaaaacac taaggtggag 120
tatcagaagt gattttagtc acagttctgc gggagagctt agaataacat cctcctttgg 180
gaggtggtct tgggtgcgtg gatgttggta tacagtcttt attgtaagtc tgatacaaaa 240
tgctaataaa tttaatgttt ttcttcctta atttattggc atagttcttc aggtagcacc 300
tcatttttat taatgatatt gggattaact atgaacaagc tatatgtaga catttgcatt 360
taaggacatt gcagtggttc aaagatccca tcattgcagc ttgnatcctt tagatccaat 420
cggaaacttc tggagcttac attaaatgct catttgagct aaatagnaat ctggtnaacc 480
aganttgggc aatactttta aaganactgg ggacnattan ggntaganng ggctatttcc 540
cctttnaggg nggg 554

<210> SEQ ID NO 452
<211> LENGTH: 566
<212> TYPE: DNA
<213> ORGANISM: Homo sapiens
<220> FEATURE:
<221> NAME/KEY: misc_feature
<222> LOCATION: (1)...(566)
<223> OTHER INFORMATION: n = A,T,C or G

<400> SEQUENCE: 452
acaaataaat tgtatgcttt ccggataagt gacatgttta tatggtgata aagggaatta 60
taatgctctt aactcttatg tagtatgttc tcatcaaaat caccaagcat gagaacactg 120
tttagtctca ttcatcactc agcacagcct ctttctgtcc acttcagggc caagtctttg 180
ccatggcccc acataacgtg taaattagct tcagggatca aaaatctttg aaaacccagt 240
ttgctgagcc ttgaaggaag cctttagacc cagcttcaat gaagtcacag ctccctgagg 300
gtcctggtgg actggaggcg gcctcccaag cctgggagct gtgtgcctgg atggtctcac 360
tggggtgatg acccaagctc atggctccct ctcaacctct aacccttctt aacacaagtc 420
acccctggnc ccctgagcac tcctgaagtc cctttgaaag gacatttcta ggctnctaag 480
angcctggtt ccttcagctg gcaccctnan tttaccagcc nggnangcag gntttccaan 540
ttntgctggg tnaanaaanc ccgncc 566

<210> SEQ ID NO 453
<211> LENGTH: 688
<212> TYPE: DNA
<213> ORGANISM: Homo sapiens
<220> FEATURE:
<221> NAME/KEY: misc_feature
<222> LOCATION: (1)...(688)
<223> OTHER INFORMATION: n = A,T,C or G

<400> SEQUENCE: 453
ggtactccta cttcattttt gaaggcttgt aactgctgag gtgtaggtgc tgtcacattc 60

```
aacattttca ctgccacatc accatgccac tttcccttgt agactgttcc aaatgatcca    120

gatccaattc tttgtcccac tgtaatctgc ccatcaggaa tctcccaatc atcactcgag    180

tcccgtctac caagtgtttt cattcgattc ctgtcttctg aggatgaaga tgacttcctt    240

tctcgctgag gtcctggaga tttctgtaag gctttcacgt tagttagtga gccaggtaat    300

gaggcagggg gggtagcaga caaacctgtg gttgatcctc catcaccacg aaatccttgg    360

tctctaatca agtcatcaat attgacaggt tctattgtgt ttatatgcac attggggagc    420

tgatgaggat cggnctcgtt gcccaaattg aattccatga tcttcatctg ctgggccgaa    480

nggctgngga aatggaatgg gttttgaaga gaccgactgg tgagaattgg ggcccaatan    540

aatcnaggcg ggtgccgaaa gggatgatcn cantgtaggc agtctttggt aaggaccctn    600

ttctgnggga ttgggggggt taannacttg gggacaaccg caaatcaant ggcctattaa    660

nccttaggga aattntanct gccngggg                                       688
```

```
<210> SEQ ID NO 454
<211> LENGTH: 565
<212> TYPE: DNA
<213> ORGANISM: Homo sapiens
<220> FEATURE:
<221> NAME/KEY: misc_feature
<222> LOCATION: (1)...(565)
<223> OTHER INFORMATION: n = A,T,C or G

<400> SEQUENCE: 454

actggctgcg aggcgccagt cgatcaatgt atgacaggag ctgagacttg gccacaccag     60

gatcccccat cagacagatg ttgatgttgc cccggatttt catgcctcga ggagactggt    120

ccacaccccc gactagcagg agcagcagtg ccttcttcac atcttcatgc ccgtatattt    180

ctggggcgat tgaagctgcc agcttttcgt agaaaatcct cctctgcaat ttgcctcagc    240

tcctccctgg tgagctctcc agccccagac tcatcatcct cactcttgtt catcttcaca    300

atccgatggg cttccaggta ggtttctgag agtaaaccct gtacttgatg cactttgcac    360

agacagggtg tgttgaatag gcattatttt ataaggaaaa gaagtctgtg gtgactggtt    420

tgaaataaag tggtaatggt gatggagggc agntcttttg gatttgcctg gtantgctga    480

tgggagacng gagaccacct ngggcgcgaa cacgcttaag gggganaatt cngcacactg    540

gggggccgta ctataggngn ccnnc                                          565
```

```
<210> SEQ ID NO 455
<211> LENGTH: 566
<212> TYPE: DNA
<213> ORGANISM: Homo sapiens
<220> FEATURE:
<221> NAME/KEY: misc_feature
<222> LOCATION: (1)...(566)
<223> OTHER INFORMATION: n = A,T,C or G

<400> SEQUENCE: 455

acagtcctga ttgcatcata attgtggttt ccaacccagt ggacattctt acgtatgtta     60

cctggaaact aagtggatta cccaaacacc gcgtgattgg aagtggatgt aatctggatt    120

ctgctagatt tcgctacctt atggctgaaa aacttggcat tcatcccagc agctgccatg    180

gatggatttt gggggaacat ggcgactcaa gtgtggctgt gtggagtggt gtgaatgtgg    240

caggtgtttc tctccaggaa ttgaatccag aaatgggaac tgacaatgat agtgaaaatt    300

ggaaggaagt gcataagatg gtggttgaaa gtgcctatga agtcctcaag ctaaaaggat    360
```

```
ataccaactg ggctattgga ttaagtgtgg ctgatcttat tgaatccatg ntgaaaaatc    420

tatccaggat tcatcccgng tcaacnatgg tnaaagggga atgtatggca ttggagaaat    480

gaanctttcc tngnccottc cntgnatccc ncaanggncc cggggattna acnagcggtt    540

ttnaancccn aanctttaag ggnggg                                         566
```

<210> SEQ ID NO 456
<211> LENGTH: 559
<212> TYPE: DNA
<213> ORGANISM: Homo sapiens
<220> FEATURE:
<221> NAME/KEY: misc_feature
<222> LOCATION: (1)...(559)
<223> OTHER INFORMATION: n = A,T,C or G

<400> SEQUENCE: 456

```
ggtcctggcc tcagcccgcc acatcaccct gacctgctta cgcccagatt ttcttcaatc     60

acatctgaat aaatcacttg aagaaagctt atagcttcat tgcaccatgt gtggcatttg    120

ggcgctgttt ggcagtgatg attgcctttc tgttcagtgt ctgagtgcta tgaagattgc    180

acacagaggt ccagatgcat tccgttttga gaatgtcaat ggatacacca actgctgctt    240

tggatttcac cggttggcgg tagttgaccc gctgtttgga atgcagccaa ttcgagtgaa    300

gaaatatccg tatttgtggc tctgttacaa tggtgaaatc tacaaccata agaagatgca    360

acagcatttt gaatttgaat accagaccaa agtggatggt gagataatcc ttcatcttta    420

tgacaaagga ggaattgagc caacaattgn atgttggatg gtgggttgca tttggtttac    480

tggatactgg catagaaagt ggtnctggga gaaaaaccta tgggggcaga ncnttttttta    540

agcctggcca ananaggnt                                                 559
```

<210> SEQ ID NO 457
<211> LENGTH: 552
<212> TYPE: DNA
<213> ORGANISM: Homo sapiens
<220> FEATURE:
<221> NAME/KEY: misc_feature
<222> LOCATION: (1)...(552)
<223> OTHER INFORMATION: n = A,T,C or G

<400> SEQUENCE: 457

```
gttacgacaa aatttaagag gaataacaaa tacaaatttt ctgttaagaa cggaaaggtg     60

caaactagca gagtcaatac tggtaaccag aaggcactaa tccaaacaca taaatttcaa    120

aagctggtta tattatggaa taccatatat actggccttt gccagtttgg gatttctgca    180

atagcaataa gcctcgtttc tgtttccaat tataacaaca aaaagatgag ttactaatga    240

acattccact acagaagtct aggctatgtt gataaattga aaacttatct agactactct    300

gtctaagagc aataaaaagt aaacactctt ttatccagca gcactaggaa acagggtgaa    360

tttaccaaga taaattaggt tggggatacc tactgccaac ttgtgcggtt gtcgaattca    420

ctgnaatatg tattcctctt attgatagag ctcttgaatg naaaccacct anaagtgagg    480

ggaaaagctt caggatcatg gnccacaatt atgntatagn gcttttngng ggtngagccn    540

aaccccgntn cc                                                        552
```

<210> SEQ ID NO 458
<211> LENGTH: 561
<212> TYPE: DNA
<213> ORGANISM: Homo sapiens
<220> FEATURE:
<221> NAME/KEY: misc_feature
<222> LOCATION: (1)...(561)
<223> OTHER INFORMATION: n = A,T,C or G

<400> SEQUENCE: 458

```
accccaacaa tcttcaagcc acagtccaag agaagtctca ggaaagcaga cgtagaggaa     60

gaatccttag cactcaggaa acgaacacca tcagtaggga aagctatgga cacacccaaa    120

ccagcaggag gtgatgagaa agacatgaaa gcatttatgg gaactccagt gcagaaattg    180

gacctgccag gaaatttacc tggcagcaaa agatggccac aaactcctaa ggaaaaggcc    240

caggctctag aagacctggc tggcttcaaa gagctcttcc agacaccagg cactgacaag    300

cccacgactg atgagaaaac taccaaaata gcctgcaaat ctccacaacc agacccagtg    360

gacaccccag caagcacaaa gcaacggcca agagaaacct caggaaagca gacgtagagg    420

aagaattttt agcactcagg aaacgaacac catnagcagg ccaagccntg gncaccccaa    480

aaccngcngt nagtggttga gnaaaaattt cncccanttt tgggnaactt ccggngcaaa    540

nttnggcccn tntttggnaa a                                              561
```

<210> SEQ ID NO 459
<211> LENGTH: 468
<212> TYPE: DNA
<213> ORGANISM: Homo sapiens
<220> FEATURE:
<221> NAME/KEY: misc_feature
<222> LOCATION: (1)...(468)
<223> OTHER INFORMATION: n = A,T,C or G

<400> SEQUENCE: 459

```
ggtacctcga catcctgaac actggataaa aaagttgatt aaatccagaa gtgcgatgtc     60

cctgtcttgt ttatatgatt caatccagtc atccaccacg gactgcattg cacttttccc    120

cagtttcacc acctcaaata atgtgacagg ctccccttcc ccattctgtt gagggtgtcc    180

attagctctt ccacggcctg ctcctctaat tccagcttca attctgctct tctcacctgg    240

agattttcga ggtttcttat ttgtagatgg aggccggcca ggacgacccc tttttctttt    300

tcctttgacc tctgtttctt caagctcgct gccagcatcg gaatgggcag tagtttcatt    360

agttgaatcc tgtaacactg gtaattctga agtaatcatt gctggagagg cctttcacaa    420

tgcagcaaaa taatcaagtg ctgnacctgg ccgggccggg cgctcgaa                 468
```

<210> SEQ ID NO 460
<211> LENGTH: 566
<212> TYPE: DNA
<213> ORGANISM: Homo sapiens
<220> FEATURE:
<221> NAME/KEY: misc_feature
<222> LOCATION: (1)...(566)
<223> OTHER INFORMATION: n = A,T,C or G

<400> SEQUENCE: 460

```
acttcttgca tgttgtcaca tgttgctgtg agaatcaggt gctgcctata tggctccact     60

gggagagggc agatggaagc cgtcgcctca tctgtcgtgg aacgtgtgct gtgcacctcc    120

tccctttgct gatcttaatc tctgtccttt tactgtaata aactgtaact gtgagcctaa    180

cagctttcct gagtctagtg agtccttcta gcaaatgaaa ggagggtggt cttggagacc    240

tatgaacttg cacctgcccc cgtcgttttg aggtctggca cagggaggga ggctggtctc    300

tttggagggg gtcttcatcc attggggtcg ggtccaactc tggaggccca cgtccttgcc    360

agctccagtc tctctcccct ctcagtcccg acgctgtcac cttgtgccct ctgtctgtgg    420
```

-continued

```
atcctgggaa gagctgntct ctctgctcac agctgaatan gagacatgcc cattagctga    480

ggcgcttgca tgcttgtact actcgattgn caaangtnca agngntccca nnncnccccg    540

ggtctatgga naannggggg gnanan                                         566


<210> SEQ ID NO 461
<211> LENGTH: 570
<212> TYPE: DNA
<213> ORGANISM: Homo sapiens
<220> FEATURE:
<221> NAME/KEY: misc_feature
<222> LOCATION: (1)...(570)
<223> OTHER INFORMATION: n = A,T,C or G

<400> SEQUENCE: 461

ggtactatag catagcctgc ctttgctggt gtgtggcgat taggcctggt ggaactgcca     60

tcaataaatc aagcgtgatc agggtgagga acagggaaga aggaaatgtg gggaaatggg    120

atgaacatca ggtggatcac agagatgcag tcatggggggt caggtgtggt atccggaata    180

atgtgggagg ctggattgaa gtccgggcca ggaacaatgg taattgtggg acttaacaaa    240

aagtgagaac agctgaagga gtcagggagc agaaagtata tgcgtcaggt gtgaggaaga    300

aaatagattt tggaagttat gagaaatgta gagagtgagt tgagcatagt ttgtgatttt    360

gagggcctct aatagtatta aagcagtggc agcccgctac accgcagaca tganggctag    420

gctaaaacag taagggccaa gttgtttgca cagaaaggct tcagggtgcc ggtcctggct    480

cttgggtaag aattttggac cggacttaac catgcctaag gaaggggaag gagttgtngt    540

tttgtnaggg gacccaggtt tgggaaaann                                     570


<210> SEQ ID NO 462
<211> LENGTH: 573
<212> TYPE: DNA
<213> ORGANISM: Homo sapiens
<220> FEATURE:
<221> NAME/KEY: misc_feature
<222> LOCATION: (1)...(573)
<223> OTHER INFORMATION: n = A,T,C or G

<400> SEQUENCE: 462

cgaggtacca ccagtatatg gaatgttagg gaaaaacttt gttccagttc cttttttttt     60

tctttctact ttcaagttta agtgaaccat actgaaatga ccaacaagtc tgcctgtaaa    120

gttacatgtc atgattgtgt tgttaaatga ttatgggggga gaaaatgaag taaatgttgc    180

tgatgatccc catatttatt gatcatatta aggttgttta tatagtttgg aaatgaccag    240

ccccctaagc agtgtttgat taacttatgc taatcagatg attactcata tattctgcta    300

attttctagc tttattcttg ttatttggaa aaattattag ccaaatgcct tcctaggtgg    360

atccagttgg aagatatgtc cagaaacctg aagaaaaatt gacgctgcct ttgtgtgctg    420

gattgctcta cttgattaga tcatgatata tcaaggntga atttttagag ggaaaattaa    480

ttctgatatc ttattggatc ccttgataag ntttttcctg gatttttttt tttccccaaa    540

gaatttttca tttgngncct ngcccggcgg gcc                                 573


<210> SEQ ID NO 463
<211> LENGTH: 574
<212> TYPE: DNA
<213> ORGANISM: Homo sapiens
<220> FEATURE:
<221> NAME/KEY: misc_feature
<222> LOCATION: (1)...(574)
<223> OTHER INFORMATION: n = A,T,C or G
```

<400> SEQUENCE: 463
accatatcct gtgtttgaat caaacccgga gttcttctat gtggaaggct tgccagaggg 60
gattcccttc cgaagcccta cctggtttgg aattccacga cttgaaagga tcgtccacgg 120
gagtaataaa atcaagttcg ttgttaaaaa acctgaacta gttatttcct acttgcctcc 180
tgggatggct agtaaaataa acactaaagc tttgcagtcc cccaaaagac cacgaagtcc 240
tgggagtaat tcaaaggttc ctgaaattga ggtcaccgtg gaaggcccta ataacaacaa 300
tcctcaaacc tcagctgttc gaaccccgac ccagactaac ggttctaacg ttcccttcaa 360
gccacgaagg gaagagaggt ttncttttga ggcctggaaa tgcccaaaat cacnggcctt 420
aaaacaggaa ggttggaaaa tctctttcaa tgagaaaatg tggggnaact cttgggcctt 480
aaacaagctg tgaaaggtgc ccggtcccgg taatttgggg ccttttcccg gaagacnttt 540
ttgtggaaag gnttacctga ngggggggcc cttt 574

<210> SEQ ID NO 464
<211> LENGTH: 458
<212> TYPE: DNA
<213> ORGANISM: Homo sapiens

<400> SEQUENCE: 464
ggtactgccg ctcggagatc tttacttgtt tttactttga acatgagcag agaaaagaca 60
aagaaaaaga tggccatggc aaagctgatc cgatacacag ctttataacc aaccagcaca 120
tcacaatctt tatctgcatt tatatcagcc tcatggattt taaatccccc ttcacaaaat 180
ccaggaatct tcttcaagta agtttccatc tcttttctct gcatgatata ggatacgaca 240
gtgctcagga ggagaatgaa agcataaatg aggcgagtca ccgtggaatt cttactgtta 300
ggacagcaac tacacagcaa acatgaggca ccgctgcaga ggcatggaac ccagctggcg 360
agggagaaga cacccagcac agcccccatg gtgacgccag tgatggaggt ggccggtcct 420
gaggctgctt tctaacacgg tggtaactgc cagctgag 458

<210> SEQ ID NO 465
<211> LENGTH: 580
<212> TYPE: DNA
<213> ORGANISM: Homo sapiens
<220> FEATURE:
<221> NAME/KEY: misc_feature
<222> LOCATION: (1)...(580)
<223> OTHER INFORMATION: n = A,T,C or G

<400> SEQUENCE: 465
gcggccgang tacttcacca tcactgactc catggacttg atcagccgnc gctggatgta 60
tncagtctca gnagtnttga cagccgtgtn aatgagcccc tcacgacccc ccatggngtg 120
gaaaaagaac tcagtgggtg tgaggccggc taggtaggag ttctncacaa agccacggct 180
ctnaggcccg tagtcatcct tgatgaagtg aggcagagtc cggtgcttga agccaaatgg 240
aatccgcttg ccctcgacgt tctgctgtnc aacgacagcg atnacctggg agatgttaat 300
cttggaacct ttagctccgg acacgaccat anacttgaag ttgttgtatt canacaggga 360
tttctgagca gaggagccag tcttgtctcg ggcatcgtta agaatgcggg tcacctgatt 420
ctcaaacgtc tgncgcagan tggtccctgg ggngggctcc agctcattgt tgngngnctt 480
cttnatgacc tctantacgt cctgnttggg gcttttaana gggcctgaat gncccgggaa 540
ggnnttanaa ttncnatggg gttcccaagg ccanacttnn 580

<210> SEQ ID NO 466
<211> LENGTH: 566
<212> TYPE: DNA
<213> ORGANISM: Homo sapiens
<220> FEATURE:
<221> NAME/KEY: misc_feature
<222> LOCATION: (1)...(566)
<223> OTHER INFORMATION: n = A,T,C or G

<400> SEQUENCE: 466

```
caagcctttt tttttttttt tttttttttt gggcatgcct gtgttgggtt gacagtgagg     60

gtaataatga cttgttggtt gattgtagat attgggctgt taattgtcag ttcagtgttt    120

taatctgacg caggcttatg cggaggagaa tgttttcatg ttacttatac taacattagt    180

tcttctatag ggtgatagat tggtccaatt gggtgtgagg agttcagtta tatgtttggg    240

attttttagg tagtgggtgt tgagcttgaa cgctttctta attggtggct gcttttaggc    300

ctactatggg tgttaaattt tttactctct ctacaaggtt ttttcctagt gtccaaagag    360

ctgntcctct ttggactaac agtaaattta cnagggggat ttaaagggtt ctgggggcca    420

aatttaaagg ttgaactaag aattctatct tggaccaacc agnttttcac cangcctcgg    480

gaaggtttgg ccgcctntac ctattaaact tncccctatt ttgggaccta naccgggngg    540

ggctcctttt aacngggcnt aagggg                                         566
```

<210> SEQ ID NO 467
<211> LENGTH: 597
<212> TYPE: DNA
<213> ORGANISM: Homo sapiens
<220> FEATURE:
<221> NAME/KEY: misc_feature
<222> LOCATION: (1)...(597)
<223> OTHER INFORMATION: n = A,T,C or G

<400> SEQUENCE: 467

```
gcgtggtccg gccgaggtac gtgatgccct tacagctgaa aaatccaaga ttgagacaga     60

aatcaagaac aagatgcaac agaaatcaca gaagaaagca gaacttcttg ataatgaaaa    120

accagctgct gtggttgctc ccattacaac gggctatacg gtgaaaatca gtaattatgg    180

atgggatcag tcagataagt ttgtgaaaat ctacattacc ttaactggag ttcatcaagt    240

tcccactgag aatgtgcagg tgcatttcac agagaggtca tttgatcttt tggtaaagaa    300

tctaaatggg aagagttact ccatgattgt gaacaatctc ttgaaaccca tctctgtgga    360

aggcagttca aaaaaagtca agactgatac agttcttata ttgtgtagaa agaaagtgga    420

aaacacaagg tgggattacc tgacccaggt ttgaaaangg agtgcaaaga aaaaggagaa    480

gcccttncta tgacactgga accagaatcc tngtnagggg attgatgaaa ggtcttaaga    540

aaaatttttg aagaangnga cattgatttt gaagcgnacc ctttattnan gcttggg      597
```

<210> SEQ ID NO 468
<211> LENGTH: 562
<212> TYPE: DNA
<213> ORGANISM: Homo sapiens
<220> FEATURE:
<221> NAME/KEY: misc_feature
<222> LOCATION: (1)...(562)
<223> OTHER INFORMATION: n = A,T,C or G

<400> SEQUENCE: 468

```
ggtactggat aaagggctga catcaagagc aaacagaagt cttttcctag tgcatatgca     60

aactggccaa ttccttccaa ctgaatgcat atttgccaga tgttactgtt catggagcaa    120
```

```
atagtgggac ttggctttga gaaggctaga aaagatgtaa cttggtaggt gtgttcacca    180

gacgtgatgg cttggaggcc tgggtgctcc atcatcagct cctctcccat ttcctcagtt    240

tcaagacagg taaccaaata ccaattttct tgacttgtgt attcttcaag tatagatgtc    300

acaatctctc tcagttcttc tgggtttgtt ttaatatgtt tttcgtgaag atcctcaacc    360

tccagcccag cagcccctgt aaccagttca ttaaggatca tggcagcttg cttccggtaa    420

accacagatt gatggtaaag ttccataaag tgatccacaa gcnaataaaa gattnccata    480

ataaccaagt agcttgacaa acctggctna agagcntgaa gaatctctta tccgtgaaga    540

aaccggaata tcttctntng gg                                             562
```

<210> SEQ ID NO 469
<211> LENGTH: 533
<212> TYPE: DNA
<213> ORGANISM: Homo sapiens
<220> FEATURE:
<221> NAME/KEY: misc_feature
<222> LOCATION: (1)...(533)
<223> OTHER INFORMATION: n = A,T,C or G

<400> SEQUENCE: 469

```
cgaggtacca ataccaccaa ttttgtagac atcctggaga ggcaggcgca agggcttgtc     60

agttggacga gttggtggta ggatgcagtc cagagcctca agcagcgtgg ttccactggc    120

attgccatcc ttacgggtga ctttccatcc cttgaaccaa ggcatgttag cacttggctc    180

cagcatgttg tcaccattcc aaccagaaat tggcacaaat gctactgtgt cggggttgta    240

gccaattttc ttaatgtaag tgctgacttc cttaacaatt tcctcatatc tcttctggct    300

gtagggtggg ctcagtggaa tccattttgt taacaccgac aattagttgt ttcacaccca    360

gtgtgtaagc cagaagggca tgctctcggg tctgccattc ttggagatac cagcttcaaa    420

ttcaccaaca ccagcagcaa caatcaggac agcacaagtc aggctgagat gtcctgnaat    480

catgnttttg ataaagctct gggtcctggg ccatcaatga tagccatagt acc           533
```

<210> SEQ ID NO 470
<211> LENGTH: 672
<212> TYPE: DNA
<213> ORGANISM: Homo sapiens
<220> FEATURE:
<221> NAME/KEY: misc_feature
<222> LOCATION: (1)...(672)
<223> OTHER INFORMATION: n = A,T,C or G

<400> SEQUENCE: 470

```
ggtacaccat ataaacagca gatgaagtcg gagagatagt ctaatacact tagatcatgt     60

tccaccacaa tgatatatct atctggattt attagagatc gtatagtaat agcagccttt    120

aaacgctgct tgacatctag gtaactagaa ggctcatcaa acatgaaaat atcagctttc    180

tgtatgcaaa cgacagcaca agcaaatctc tgcaactctc ctcctgaaag atcttcaaca    240

tttcgttctt ttaggtgggt taaatcaagc tgctgacata caattgcctg tgtctttgtt    300

tcatcttttc ggtccaaaat agatcccact gtcccctttg cagccttagg aatctggtct    360

acatattgag gtttgatgat ggcttttagg tcatcttcta gaatctttgg aaagnaattt    420

tgnaattcag atccacngaa ataagtcaaa atcttctggc agtcaaggan gatcatcgga    480

cctgncccgg ccggccgntt cgaaaggcca aattccagca cacttggccg gccggtactt    540

agnggaatcc nagcttcggg ancccangcn ttggcgnnaa tcatngggca taactgggtt    600
```

-continued

```
ccctgggggg aaaaatggta atcccggtta ccaanttcnc cccnacatac cnaacccgga    660

agccttanan gg                                                        672


<210> SEQ ID NO 471
<211> LENGTH: 387
<212> TYPE: DNA
<213> ORGANISM: Homo sapiens

<400> SEQUENCE: 471

cgaggtgagc tttgaaacaa ctgatgagag cctgaggagc cattttgagc aatggggaac     60

gctcacggac tgtgtggtaa tgagagatcc aaacaccaag cgctccaggg gctttgggtt    120

tgtcacatat gccactgtgg aggaggtgga tgcagctatg aatgcaaggc cacacaaggt    180

ggatggaaga gttgtggaac caaagagagc tgtctccaga gaagattctc aaagaccagg    240

tgcccactta actgtgaaaa agatatttgt tggtggcatt aaagaagaca ctgaagaaca    300

tcacctaaga gattattttg aacagtatgg aaaaattgaa gtgattgaaa tcatgactga    360

ctgagacctg cccgggccgg ccgtcga                                        387


<210> SEQ ID NO 472
<211> LENGTH: 241
<212> TYPE: DNA
<213> ORGANISM: Homo sapiens

<400> SEQUENCE: 472

ggtacgaatc gtctcctggc actgtgcagg cccacagctg acggcgatga cctccttcac     60

cagcttcttc tccttgagcc gcacagcctc ctccaccgcg atctcacaga aggggttcat    120

ggagtgcttc acaccatccg tgaccacacc ggtcctgtca ggcttcactc ggatcttcac    180

ggcgtagtcg atgaccctct tgacagctac gagcacgcgc agctccgcca tcttcccgcc    240

g                                                                    241


<210> SEQ ID NO 473
<211> LENGTH: 470
<212> TYPE: DNA
<213> ORGANISM: Homo sapiens

<400> SEQUENCE: 473

ggtactagtt cactatcggt gtctgattag tatttagcct taccgggtgg tcccggcaga     60

ttcagacagg gtttcacgtg ccccgcccta ctcaggatac atctatgaga ttttatgatt    120

tcgtatacag gaatatcacc ttctatgttg aagctttcca acttcttcta ctatcataaa    180

attttgtaac tcaatgtaag atgtcctaca accccttttt acaggtttgg gctctttcgc    240

tttcgctcgc cactactgac gaaatcatta tttattttct tttcctgttg ctactaagat    300

gtttcaattc gcaacgtgtc tcgctaattt gactatggat tcatcaaaat gcaactgagg    360

tttgctcagt taggttaccc cattcggaaa tctccgtatc atagtttatt tccaactcca    420

cgaagcttat cgcaggtaat cgcgtccttc atcgactttc agacccaagg              470


<210> SEQ ID NO 474
<211> LENGTH: 637
<212> TYPE: DNA
<213> ORGANISM: Homo sapiens
<220> FEATURE:
<221> NAME/KEY: misc_feature
<222> LOCATION: (1)...(637)
<223> OTHER INFORMATION: n = A,T,C or G

<400> SEQUENCE: 474
```

```
acctcttcct gataagattg aagtaaaaac tggtgaggaa gatgaagaag aattcttttg      60

caaccgcgcg aaattgtttc gtttcgatgt agaatccaaa gaatggaaag aacgtgggat     120

tggcaatgta aaaatactga ggcataaaac atctggtaaa attcgccttc taatgagacg     180

agagcaagta ttgaaaatct gtgcaaatca ttacatcagt ccagatatga aattgacacc     240

aaatgctgga tcagacagat cttttgtatg gcatgccctt gattatgcag atgagttgcc     300

aaaaccagaa caacttgcta ttaggttcaa aactcctgag gaagcagcac tttttaaatg     360

caagtttgaa gaagcccaga gcattttaaa agccccagga acaaatgtag ccatggcgtc     420

aaatcaggct gcagaattgt aaagaaccca caagtcatga taacnaggat atttgcaaat     480

ctgatgctgg aaacctgatt ttgaatttca ggntgcaaga aagaaagggc ttggtggcat     540

tgaaccactg ntcattaaga atgcttcact gctaaaaatg ngattatgcc aaattaancc     600

agcaataaga ctcgtggccc ccttaactga actgttt                              637
```

```
<210> SEQ ID NO 475
<211> LENGTH: 647
<212> TYPE: DNA
<213> ORGANISM: Homo sapiens
<220> FEATURE:
<221> NAME/KEY: misc_feature
<222> LOCATION: (1)...(647)
<223> OTHER INFORMATION: n = A,T,C or G

<400> SEQUENCE: 475

ggtacaagcc atagtggaaa gaatgaatct ctccctaaaa tagcagttgc aaaagcagaa      60

agggggagac agagaatatg gaaccccaca gatgcaactg aacctagcat tattaacagt     120

aaattttttg agcctgccca aaggccacat gttatcagca gctgaagagc atctacagaa     180

accagctgca aggacaaaaa cagaacaact gatttggtgg agagatccga taacacgaag     240

ttgggaaata ggtaaaataa taacttgggg gagaggttat gcttgtgttt ctccaggcca     300

atatcaatag cctatttgga taccatcaag acacctgaaa ccttatcgtg agccagatgc     360

tgaggaatag actccgggag ggatcctgag aaccccccag ttgcagccat gtttgagact     420

gatgctgagg aggactccaa ctgtcacgag cacagccccc atctggggac agatcaagaa     480

gctgtcacag atggaagaag aaaaccttga ggaaagcagg acaatcggtc ccatgagtaa     540

aatctgatgg tagctataaa ccggttttan cacnccatgn tattctttng ttaaggctga     600

cncngagaac aattatacct antggggata tttatcatct tggtngg                   647
```

```
<210> SEQ ID NO 476
<211> LENGTH: 665
<212> TYPE: DNA
<213> ORGANISM: Homo sapiens
<220> FEATURE:
<221> NAME/KEY: misc_feature
<222> LOCATION: (1)...(665)
<223> OTHER INFORMATION: n = A,T,C or G

<400> SEQUENCE: 476

accttattag aaagcgacgg caaactatgt gccagcagcc gcggtaatac ataggtcgca      60

agcgttatcc ggaattattg ggcgtaaagc gtccgtaggt tttttgctaa gtctggagtt     120

aaatgctgaa gctcaacttc agtccgcttt ggatactggc aaaatagaat tataaagagg     180

ttagcggaat tcctagtgaa gcggtggaat gcgtagatat taggaagaac accaataggc     240

gaaggcagct aactggttat atattgacac taagggacga aagcgtgggg agcaaacagg     300
```

-continued

```
attagatacc ctggtagtcc acgccgtaaa cgatgatcat tagttggtgg aataatttca    360

ctaacgcagc taacgccgtt aaatgatccc gcctgagtag tatgctcgca agagtgaaat    420

ttaaaggaat tgacgggaac ccgcacaagc cggtggaaca tgtgggttaa tttgattcta    480

cgccgtagaa ccttacccac ttcttggaca tcttctgcaa agctatngga gatatagtgg    540

anggttaaca gaatggcccg aaggtgcatg ggtggccgca gctcgtgtcg tgagaaggta    600

nggtnaagtc ctgnaacgag cgccaaccnt ttctttagta ctaatattaa gttaaggact    660

ntagn                                                                665
```

<210> SEQ ID NO 477
<211> LENGTH: 319
<212> TYPE: DNA
<213> ORGANISM: Homo sapiens

<400> SEQUENCE: 477

```
cgaggtactt ttcaattatg ttaacgtaaa atactcgtaa cgaatgtagt atgagtttaa     60

agtgagcttt tcagatccta taagtgcatc ctaagtaatg acaggcttta agataaggaa    120

tatatgcatt ttgttaaggc agaaatctca taaaatttca tgaaaaacca tggtcaatcc    180

aatgatgcac tttttaagac aagtttgtct ggaaactgga agggtcaaaa gacaacaaaa    240

aagcacacac caaaaaacct cactttaagc aaatctataa cttgaaaaaa aaaaagccta    300

agaatattct gagagtggt                                                 319
```

<210> SEQ ID NO 478
<211> LENGTH: 419
<212> TYPE: DNA
<213> ORGANISM: Homo sapiens

<400> SEQUENCE: 478

```
acccacgatg atgtggggag cttccatctg cagtttctgc acctcagcac gcacgttggt     60

gcccccgata caggcgtgac aggaggcgcc catgtagtct cctagtgcca tgaccacctt    120

ctgtatctgc tgagccaatt ctcgagtggg tgctaggact aaggcctggg tggcttttag    180

atctaattca atctgctgca gaatcgatat ggcaaatgtg gccgttttcc cagtcccaga    240

ttgggcttga gcaatcacat cataaccctt gatacaaggt agaatgggct cgctgctgga    300

tggcagaggg cttctcaaaa ccataggcgt agatgccacg gagaagggac tccgagaggt    360

tcatgtcatc aaagctgtca acaatctcat tccagttact ctcgatgacg ccttcgacc     419
```

<210> SEQ ID NO 479
<211> LENGTH: 312
<212> TYPE: DNA
<213> ORGANISM: Homo sapiens

<400> SEQUENCE: 479

```
acatcctgga gacctgaaga attctgttga agtcgcactg aacaagttgc tggatccaat     60

ccgggaaaag tttaataccc ctgccctgaa aaaactggcc agcgctgcct acccagatcc    120

ctcaaagcag aagccaatgg ccaaaggccc tgccaagaat tcagaaccag aggaggtcat    180

cccatcccgg ctggatatcc gtgtggggaa aatcatcact gtggagaagc acccagatgc    240

agacagcctg tatgtagaga agattgacgt gggggaagct gaaccacgga ctgtggtgag    300

cggcctggta cc                                                        312
```

<210> SEQ ID NO 480
<211> LENGTH: 640

-continued

<212> TYPE: DNA
<213> ORGANISM: Homo sapiens
<220> FEATURE:
<221> NAME/KEY: misc_feature
<222> LOCATION: (1)...(640)
<223> OTHER INFORMATION: n = A,T,C or G

<400> SEQUENCE: 480
ggtaccaaca attcctccta ccagtggctg agcatactct gcagagtcag cctgcagcac 60
tgtggtgact tctcttggac tcaggtgatt aacttcgctg ctgctatagc gaactggggt 120
ttcctcatgg tccactgctt ttgcaggaag aaactgcttc attcctttcc accaacctgc 180
ccggccccag taaggtaagt cataggtgcc ttcagttttt ttctttctgt ttctccagtg 240
ccaagcacac actaatatga gaatgagagt agtgaggacc atgaccagca cagggacaag 300
aactgcagcc agcgctacat ctttggttac atttggagtt acggtagtat ttctgatatc 360
aggactggca gttgtttgtt ctgtctgtgc aggaaattca ttgctactgc gaagttgtag 420
tggttgcgta aattttgggg cacgaccttt ggctattttg gaggggctgt agtggttttg 480
aggncattgc tgttncnaag aggtggaggt tgagtaagtt ttggangacn actttangaa 540
taaactgaca tccgagcagt tcattttcat ggcaatttct gctgccatgg gtaaggatta 600
ctctaataaa cgtgccataa ttggtggcaa aagtattccc 640

<210> SEQ ID NO 481
<211> LENGTH: 501
<212> TYPE: DNA
<213> ORGANISM: Homo sapiens

<400> SEQUENCE: 481
ggtacatttc cttgtagact ctgttaattt cctgcagctc ctggttggtt ctggagcaga 60
tgatctcaat gagagagtcc tcgtcggttc ccagcccctt catggaagct tttagctcag 120
aagcgtcata ctgagcaggt gtcttcaata ggcccaaaat caccgtctcc aggtggccag 180
ataaggctga cttcagtgct gatgcaagtt cctttttggt ccttctctgg taggcgaagg 240
caatatcctg tctctgtgca ttgctgcggt tggtcaaaat gttgacaatg gtgacctcat 300
ccacaccttt ggtcttgatg gctgtttcaa tgttcaaagc atcccgctca gcatcaaaag 360
ttagtatagg ctttgacaga cccatatgca cttgggggtg tagagtgatc accctccaag 420
ctgagcttgc acaggatttc gtgaacagta agacattttg aaaggaagct gggcccgtgc 480
gcccgagagc tgaaagcgtc c 501

<210> SEQ ID NO 482
<211> LENGTH: 306
<212> TYPE: DNA
<213> ORGANISM: Homo sapiens

<400> SEQUENCE: 482
ggtacctata cagggatggc tcccacgcat ccctcagtga ccccaaaccc atctccactt 60
acactcaggc actcccagga cctgacagct actccccgtt atcgtccttc agttcgaagc 120
cctggccaat ctaccagccc acatgacgca gttacctggc catttctcca cggttcccgt 180
gagggcccca cacccagccg cacaagagcc cctcctgcat tccgtcctca cacacaggcc 240
tgtgtatgca cttgctactg tcacactctt gctagcagaa gaggcccctg taatggccga 300
tatccc 306

<210> SEQ ID NO 483

<211> LENGTH: 663
<212> TYPE: DNA
<213> ORGANISM: Homo sapiens
<220> FEATURE:
<221> NAME/KEY: misc_feature
<222> LOCATION: (1)...(663)
<223> OTHER INFORMATION: n = A,T,C or G

<400> SEQUENCE: 483

```
acagaatttc ttatttcttg aagactctgt ggttgaccac ttcttcatta gttacctgca     60

gcaagacacc ttccatttta ctaccaacac cactgaagga accaagaaaa gctttattaa    120

tgatcacttg gcttgcctca gctgttgaaa tgaagcactt tacagtcttt gtggcagcag    180

aatatacttg tccatggttc atatcaatgc catggcaaat aggaagaagc tcagtatcgg    240

ctcctcccac cataaccccc acttcctcca ctgcctcctg gaccatagtt tcctccacca    300

tatggtcccc ccatgttcct gctaccacca aagtttccac tcttcacacg ggccaagtca    360

gaaagaccat gacataaaga gagatggcga aactgaaacg gattatttct tttgncttca    420

aaacatctca tcaatttatc actcatccat tctacctggg acttagaaaa ctccaccaca    480

ttgtaactga cattatttag gagtgccaat gagtaaacac ccaatcctgn atctttagtc    540

cctccaaatc tggatccaag aagtttagcc aggttccaaa cttntggctg ntgggggcca    600

ctgntattaa cacattttca ttancttgaa nnggttccag gacanttggc anaacttgtt    660

ant                                                                  663
```

<210> SEQ ID NO 484
<211> LENGTH: 228
<212> TYPE: DNA
<213> ORGANISM: Homo sapiens

<400> SEQUENCE: 484

```
cttgggtctg aaagtcgatg aaggacgcga ttacctgcga taagcttcgt ggagttggaa     60

ataaactatg atacggagat ttccgaatgg ggtaacctaa ctgagcaaac ctcagttgca    120

ttttgatgaa tccatagtca aattagcgag acacgttgcg aattgaaaca tcttagtagc    180

aacaggaaaa gaaaaaaaaa aaaaaaaaaa aaaaaaaaag cttgtacc                228
```

<210> SEQ ID NO 485
<211> LENGTH: 672
<212> TYPE: DNA
<213> ORGANISM: Homo sapiens
<220> FEATURE:
<221> NAME/KEY: misc_feature
<222> LOCATION: (1)...(672)
<223> OTHER INFORMATION: n = A,T,C or G

<400> SEQUENCE: 485

```
acggagccct ctgaaaaatg acaaagatgg tatgatgtat ggcccaccag tggggactta     60

ccatgacccc agtgcccagg aggctgggcg ctgcctaatg tctagtgatg gtctgcctaa    120

caagggcatg gaattaaagc atggctccca gaagttacaa gaatcctgtt gggatctttc    180

tcggcaaact tctccagcca aaagcagcgg tcctccagga atgtccagtc aaaaaaggta    240

tgggccgccc catgagactg atggacatgg actagctgag gctacacagt catccaaacc    300

tggtagtgtt atgctgagac ttccaggcca ggaggatcat tcttctcaaa accccttaat    360

catgaggagg cgtgttcgtt cttttatctc tcccattccc agtaagagac agtcacaaga    420

tgtaaagaac agtagcactg aagataaagg tcgccttcct tcactcatca aaaagaaagg    480

cgcttgatta aagcatttca atttcctatg gccccatctt ttnttcacag gtccngggat    540
```

antcaaggtc tattncctta agaagagaat tnccttccan gggnccttc cnaggtcccc 600 aatagtttna aaaactggnc ctggtnggta anccttttann aaagcccttg gttaaaancc 660
cnaaananng ng 672

<210> SEQ ID NO 486
<211> LENGTH: 637
<212> TYPE: DNA
<213> ORGANISM: Homo sapiens
<220> FEATURE:
<221> NAME/KEY: misc_feature
<222> LOCATION: (1)...(637)
<223> OTHER INFORMATION: n = A,T,C or G

<400> SEQUENCE: 486
ggtacaatag agctttggat ctgatacaag aatttagaaa tataaaacaa aataactata 60
aaagttagga ggcatttgaa tggcatttcc ttagaagaac ctgctaactc tgtatcattc 120
tgatgtggat tcctagtcat gtggggtgaa atgcatattt ttccccccttt gctggatcac 180 tggcctttct tcaaaagcta taatgccatg aacacacatc ctaggagtct ctataatgtt 240
aacagaagct ccaaatacca agccaatcaa agatgggaga gggcagggga accataaagg 300
cgaagggtcc aaaggtggct gttactgaga acttgccctt tccaaaatgt gaaagtcata 360
gtgcttcttg cttgttctca gcttaaactt gttaactgag ttaatttgtt tcttcagtgc 420
attctgtgca gctgaaatgg aggggaatgt ggctaagacg gtgtangtgg angccaagtc 480
actgggttta gaaccgttca agggttggca gtggtggncc ccactggcca cagcagaagg 540
ggttgaccac cctgggttgg gactgggggg tncccggann cccccggatn ttggngccca 600
attttaaaga agttncccca aaaacttttt aacttng 637

<210> SEQ ID NO 487
<211> LENGTH: 618
<212> TYPE: DNA
<213> ORGANISM: Homo sapiens
<220> FEATURE:
<221> NAME/KEY: misc_feature
<222> LOCATION: (1)...(618)
<223> OTHER INFORMATION: n = A,T,C or G

<400> SEQUENCE: 487
ggtacctctt cccatgactg cacccagctc caggggccct tgggacagcc agagctgggt 60
ggggacagtg ataggcccaa ggtcccctcc acatcccagc agcccaagct taatagccct 120
ccccctcaac ctcaccattg tgaagcacct actatgtgct gggtgcctcc cacacttgct 180
ggggctcacg gggcctccaa cccatttaat caccatggga aactgttgtg ggcgctgctt 240
ccaggataag gagactgagg cttagagaga ggaggcagcc ccctccacac cagtggcctc 300
gtggttatta gcaaggctgg gtaatgtgaa ggcccaagag cagagtctgg gcctctgact 360
ctgagtccac tgctccattt ataaccccag cctgacctga gactgtcgga gaggctgtct 420
ggggccttta tcaaaaaaag actcagccaa gacaaggagg tanagagggg actgggggac 480
tgggagtcaa aacccctggc tggggttaag tccacgtntg gcnagcactg gctttttctt 540
ttgggccttg gttccttgtg ggcaaagaat gatgaccnct attttcagga cttttccttc 600
ngttncaagg tttttntg 618

<210> SEQ ID NO 488
<211> LENGTH: 618
<212> TYPE: DNA

<213> ORGANISM: Homo sapiens
<220> FEATURE:
<221> NAME/KEY: misc_feature
<222> LOCATION: (1)...(618)
<223> OTHER INFORMATION: n = A,T,C or G

<400> SEQUENCE: 488
ggtacagtcg tctgaagaag ctctgagggc ggcaggacca gccagcagca gcccaagctt 60
ccctccatcc ccctttaccc tctttgctgc agagaaactt aagcaaaggg gacagctgtg 120
tgacatttgg agagggggcc tgggacttcc atgccttaaa cctacctccc acactcccaa 180
ggttggagcc cagggcatct tgctggctac gcctcttctg tccctgttag acgtcctccg 240
tccatatcag aactgtgcca caatgcagtt ctgagcaccg tgtcaagctg ccctgagcca 300
cagtgggatg aaccagccgg ggccttatcg ggctccagcc atctcatgag gggagaggag 360
acggagggga gtagagaagt tacacagaaa tgctgctggc caaatagcaa agacaacctg 420
ggaaaggaaa ggtctttgtg ggataatcca tatgttaatt attcaacttc atcaatcact 480
ttatttattt tttttctaac ttcttggaga cttaatttac tgntttatta gggtgaaaac 540
tggcnttcta ngtagggttt tnttatccca ggactacctt gggttttaan ttaaaaaaaa 600
aaagaaatgg ntnaaaaa 618

<210> SEQ ID NO 489
<211> LENGTH: 624
<212> TYPE: DNA
<213> ORGANISM: Homo sapiens
<220> FEATURE:
<221> NAME/KEY: misc_feature
<222> LOCATION: (1)...(624)
<223> OTHER INFORMATION: n = A,T,C or G

<400> SEQUENCE: 489
naggtnctga tgattctcca natccangta tagaatatga ncncgnnctn cgaaantggn 60
gtganttgat tcctggggct gagtatcgat gtttatgnca tggaaaacna gcttattggt 120
atttctcaga gagactacac acaatactat gatcatattt ctaaacagna ggaagaaatt 180
cgcanatgca tacaagactt tttcaagaaa cacatacagt acaagctttt ntnctattta 240
attgntgtnt ttttttgtgg taacnngaaa gtttattnnt gtctgaaagc ttttataagt 300
atttaaatnn acnnagtaat gaactattca attgctgnaa tcggtcaaaa tttncnaaag 360
ncgcacacaa antnntatcc ttgnncacgn anctncatac actgnccctn gccaaacacc 420
cttgccggga accaatcngc atgacatttc tgggccggtt aaatnttata aagccaaggg 480
cccnggcact ggttaaggng ggccttanac cttttagggg agggcccnaa taccctnccn 540
cttaaacntc tgggggggngg tananatttc ttataggnac cgnccccttta aatcnattgn 600 cantttttnng nccctttggt tttt 624

<210> SEQ ID NO 490
<211> LENGTH: 620
<212> TYPE: DNA
<213> ORGANISM: Homo sapiens
<220> FEATURE:
<221> NAME/KEY: misc_feature
<222> LOCATION: (1)...(620)
<223> OTHER INFORMATION: n = A,T,C or G

<400> SEQUENCE: 490
ggtacctctt cccatgactg cacccagctc caggggccct tgggacagcc agagctgggt 60
ggggacagtg ataggcccaa ggtcccctcc acatcccagc agcccaagct taatagcccc 120

```
ccccctcaac ctcaccattg tgaagcacct actatgtgct gggtgcctcc cacacttgct    180

ggggctcacg gggcctccaa cccatttaat caccatggga aactgttgtg ggcgctgctt    240

ccaggataag gagactgagg cttagagaga ggaggcagcc ccctncacac cagtggcctc    300

gtggttatta gcaaggctgg gtaatgtgaa ggcccaagag cagagtctgg gcctctgact    360

ctgagtccac tgctccattt ataaccccag cctgacctga gactgtcgga aggctgtctg    420

gggcctttat caaaaaaaag actnagccaa acaaggaggt agagagggga ctgggggact    480

gggagtcana gccctggctg ggttcangtc cacgttgggc aggcacttgc ttttcttttt    540

nggnctttgg ttccttgttg gcaaaagagt gattgaaccc cttattttca agggcttttc    600

nctnatgttn cangntttnn                                                620
```

```
<210> SEQ ID NO 491
<211> LENGTH: 630
<212> TYPE: DNA
<213> ORGANISM: Homo sapiens
<220> FEATURE:
<221> NAME/KEY: misc_feature
<222> LOCATION: (1)...(630)
<223> OTHER INFORMATION: n = A,T,C or G

<400> SEQUENCE: 491

acatttcctt gtagactctg ttaatttcct gcagctcctg gttggttctg gagcagatga     60

tctcaatgag agagtcctcg tcggttccca gccccttcgt ggaagctttt agctcagaag    120

cgtcatactg agcaggtgtc ttcaataggc ccaaaatcac cgtctccagg tggccagata    180

aggctgactt cagtgctgat gcaagttcct ttttggtcct tctctggtag gcgaaggcaa    240

tatcctgtct ctgtgcattg ctgcggttgg tcaaaatgtt gacaatggtg acctcatcca    300

cacctttggt cttgatggct gtttcaatgt tcaaagcatc ccgctcagca tcaaagttag    360

tataggcttt gacagaccca tatgcacttg ggggtgtaga gtgatcaccc tccaagctga    420

gcttgcacag gaattccgtg aacagtagac attttgaagg aagcttnctt gaggcccaat    480

gtgttcaacc caaccgggaa aactnttncg ggtagaagtg aaatccgaag ttgctattgc    540

ttccagaata acctgggncn tnccccnaaa actttaaaac gttcccacct tgggcgggaa    600

cccncttaan gggggaattc ccgnccncng                                     630
```

```
<210> SEQ ID NO 492
<211> LENGTH: 412
<212> TYPE: DNA
<213> ORGANISM: Homo sapiens
<220> FEATURE:
<221> NAME/KEY: misc_feature
<222> LOCATION: (1)...(412)
<223> OTHER INFORMATION: n = A,T,C or G

<400> SEQUENCE: 492

acactaccaa cagatcaaag aaacccctcc ggccagtgag aaagacaaaa ctgctaaggc     60

caaggtccaa cagactcctg atggatccca gcagagtcca gatggcacac agcttccgtc    120

tggacacccc ttgcctgcca caagccaggg cactgcaagc aaatgccctt tcctggcagc    180

acagatgaat cagagaggca gcagtgtctt ctgcaaagcc agtcttgagc ttcaggagga    240

tgtgcaggaa atgaatgccg tgaggaaaga ggttgctgaa acctcagcag gccccagtgt    300

ggttagtgtg aaaaccgatg gaggggatcc cagtggactg ctgaagaact tccaggacat    360

tatgcaaaag caaagaccan aaaaaaaaan nnaaaaaaaa aaagcttgta cc            412
```

<210> SEQ ID NO 493
<211> LENGTH: 633
<212> TYPE: DNA
<213> ORGANISM: Homo sapiens
<220> FEATURE:
<221> NAME/KEY: misc_feature
<222> LOCATION: (1)...(633)
<223> OTHER INFORMATION: n = A,T,C or G

<400> SEQUENCE: 493

```
acactggcca gtgtgttttt ggcgattaaa cataatcctg tgaatcagat taattcactt     60

gctgagtgtt catttgcggc atccctctgt tgggtcttgg gggccctcca cgacctcgtg    120

gggctccccg tggtccactc tgcccagagc ctcgcttgaa attctgctga tatccatccc    180

gttgatagcc agagtaatcc cggggagcac tgaactgaga ctgtgtataa ccactgtttg    240

gagtgttaga gaatgaaggg cggtaaccat natatcctcc tctgaatcca ttggcagggc    300

cccggtatcc attcatcaag cctctagcac cacgggagcc ttcacgagac gcaccacgac    360

tattgtaata ggggctgatt gctacgtgga aatncagtgt tctgctgaag aagctgctgg    420

tgggtaccag tcacttgatg ggactggtct gggggaaccc atggtaaagt gcccaaccac    480

tggttgnaac ttgtcttgct tgaanctctg gttggtctac cttggggaag cttgactaaa    540

aaaacttttg gtataaattg ggctgggacc ccctangggn gcaaccctgg gccanntttt    600

tcctnannct taaaaagggg ggggnatgaa ggn                                 633
```

<210> SEQ ID NO 494
<211> LENGTH: 609
<212> TYPE: DNA
<213> ORGANISM: Homo sapiens
<220> FEATURE:
<221> NAME/KEY: misc_feature
<222> LOCATION: (1)...(609)
<223> OTHER INFORMATION: n = A,T,C or G

<400> SEQUENCE: 494

```
acttaaaagg taaagtagta accaaagaga aaatccagga agccaaagat gtctacaaag     60

aacatttcca agatgatgtc tttaatgaaa agggatggaa ctacattctt gagaagtatg    120

atgggcatct tccaatagaa ataaaagctg ttcctgaggg ctttgtcatt cccagaggaa    180

atgttctctt cacggtggaa aacacagatc cagagtgtta ctggcttaca aattggattg    240

agactattct tgttcagtcc tggtatccaa tcacagtggc cacaaattct agagagcaga    300

agaaaatatt ggccaaatat ttgttagaaa cttctggtaa cttagatggt ctggaataca    360

agttacatga ttttggctac agaggagtct cttcccaaga gactgctggc ataggagcat    420

ctgctcactt ggttaacttc aaaggaacag atacagtagc aggacttgct ctaattaaaa    480

aatattatgg aacgaaagat nctgttccag ctattctggt ccacagcaga acacagtacc    540

ttggccgnga cnacnctaag gcgaaatccg ccactggggg gccgttataa nggatcccnc    600

ttnggaccn                                                            609
```

<210> SEQ ID NO 495
<211> LENGTH: 606
<212> TYPE: DNA
<213> ORGANISM: Homo sapiens
<220> FEATURE:
<221> NAME/KEY: misc_feature
<222> LOCATION: (1)...(606)
<223> OTHER INFORMATION: n = A,T,C or G

<400> SEQUENCE: 495

```
ggtaccaagc tatctttgat aataccacta gtctgacgga taaacacctg gacccaatca     60
gggaaaatct gggaaagcac tggaaaaact gtgcccgtaa actgggcttc acacagtctc    120
agattgatga aattgaccat gactatgagc gagatggact gaaagaaaag gtttaccaga    180
tgctccaaaa gtgggtgatg agggaaggca taaagggagc cacggtgggg aagctggccc    240
aggcgctcca ccagtgttcc tggatcgacc ttctgagcag cttgatttac gtcagccaga    300
actaaccctg gatgggctac ggcagctgaa gtggacgcct cacttagtgg ataaccccag    360
aaagttggct gcctcagagc attcagaatt ctgtcctcac tgataggggt tctgtgtctg    420
cagaaatttt gtttcctgta cctgccnggc ggncgctcaa agggcgaatt cacacactgc    480
ggccgtacta gtggatccaa ctcggaccaa cttggcgtaa tatggcatac tgtttctgng    540
ggaaatgtat ccgtccaatt cncccacata cganccganc ntaaaggtaa gcttggggcc    600
tataat                                                               606
```

<210> SEQ ID NO 496
<211> LENGTH: 279
<212> TYPE: DNA
<213> ORGANISM: Homo sapiens

<400> SEQUENCE: 496

```
ggtactcaat gatgctggtc agcgacttcc acgggagaaa atcttgctga atgtccgtga     60
aatccttccc atatttttcc agggcttcct cgaaaaggtt ggcctctgat gcagaccact    120
cctccatctc gtccctgcag agcacgggcc cgccctgcgg caccagcgcc gagatggcct    180
tggagatgtc gtagatgttc ttgtggagag tatccatggc gtggaacagg gtgatgtctc    240
gggaggcagc tgcggcgctc atgtgcaggc tgggctgtc                           279
```

<210> SEQ ID NO 497
<211> LENGTH: 633
<212> TYPE: DNA
<213> ORGANISM: Homo sapiens
<220> FEATURE:
<221> NAME/KEY: misc_feature
<222> LOCATION: (1)...(633)
<223> OTHER INFORMATION: n = A,T,C or G

<400> SEQUENCE: 497

```
ggtacacaac agggcaaaag ctttttcgca agtcataaaa ttgagttgaa aataacttgt     60
tgattcagct acaggaagac aactaacaat taacaggctc atgaatattt atgaataaag    120
tgccactaat tttattgtaa taagatataa atagaataaa tcctgacatg gatagtagct    180
tctgtgttct ctccatcctg agaacagaag ggccataaaa aaacaaagaa gcattaccaa    240
aggggagttc tagacccaca cggggaactc ctaatacaaa agcaacaaga aagacangta    300
agactttaaa agttgcagaa gtcctaagaa tagcgccaat gtagtaggcc ctttttaaca    360
acaacaaana ataaaaataa gagagagaga gaaattagaa atttangaag ttcattaaat    420
aactggtact tatattcaag ggaatttatt agtggccagc ctantggggg acccagcntn    480
taggaaaaga cccttgaaaa ggaccttccc ncacctggga canaaggata gnaccgaccc    540
cccagggaag nccgccntgg aaangggatc cnaacttgan gctttttagg gtttcaaaan    600
tccttgctng gccccaangg gcaggntttn ntn                                 633
```

<210> SEQ ID NO 498
<211> LENGTH: 601
<212> TYPE: DNA

<213> ORGANISM: Homo sapiens
<220> FEATURE:
<221> NAME/KEY: misc_feature
<222> LOCATION: (1)...(601)
<223> OTHER INFORMATION: n = A,T,C or G

<400> SEQUENCE: 498

```
acattcttca gaacagtttt ggtcgtttaa aaaaaatcac acatttataa gcagtgattt     60
caatcatgtt taaaaacaaa aatattaaac aaattcattt cctaatccag atgatacaga    120
atccaagaaa tttctgtagg cacttcactt tccatagaac ttcttgttca gcaggtatat    180
gagaaggttt acattcactt taaccttatc aaacattttc attacagcta ctccttcata    240
ttgcatctga agtaaatcct gaatattgag ttgcaccttt tccatctcaa caccaaggaa    300
ttttgatctt acatcgaaaa tgcctacatc ttcagtagct atgatatcaa atgtaacatt    360
cttaaactgg tttgtttgaa gatcatctat atctagcagg acacctttct catgcagctt    420
tgctgcagtg tacaaactgc aggctccatc ctcgtgggct cgcactatgt gcgcttttaa    480
aaaatattat ttctaataaa tctttgaagt taaaataccg ttctttcagt tggnccaaaa    540
aaaaannnnn nnnanganag aanngnaang aaagtggggt gnnnttgggg nggaaaaacn    600
n                                                                    601
```

<210> SEQ ID NO 499
<211> LENGTH: 293
<212> TYPE: DNA
<213> ORGANISM: Homo sapiens

<400> SEQUENCE: 499

```
ggtactcaag cttttgacct catgccttgt gtagtaaaaa aggatttggg ggttttgttt     60
ggttcctgag agggttgtgt tttgtttttg tttcctttttg tttatgtttt ggcctttcct   120
ctttgtcttt ccatgtagac cagatatttg aaagggcaga cgatggctag aggtgtaatg    180
tgcagcttgt ttatacggta ttttgggaaa cttaccttgg atgggaaatc gaatcgtgga    240
ttcaccaggc cggtgctggc acactcaccc tcgccctttc cctccggttc agt           293
```

<210> SEQ ID NO 500
<211> LENGTH: 630
<212> TYPE: DNA
<213> ORGANISM: Homo sapiens
<220> FEATURE:
<221> NAME/KEY: misc_feature
<222> LOCATION: (1)...(630)
<223> OTHER INFORMATION: n = A,T,C or G

<400> SEQUENCE: 500

```
gggtactcat gaattcaagc cacagagtgg agcagagatc aaagaagggt gtgaaacaca     60
taaggttgcc aacacaagtt cttttcacac aactccaaac acatcactgg gaatggttca    120
ggcaacgcca tccaaagtgc agccatcacc caccgtgcac acaaaagaag cattaggttt    180
catcatgaat atgtttcagg ctcctacact tcctgatatt tctgatgaca aagatgaatg    240
gcaatctcta gatcaaaatg aagatgcatt tgaagcccag tttcaaaaaa atgtaaggtc    300
atctggggct tggggagtca ataagatcat ctcttctttg ncatctgctt ttcatgtgtt    360
tgaagatgga aacaaagaaa attatggatt accacagcct aaaaataaac ccacaggagc    420
caggaccttt ggagaacgct ctgtcacaga cttncttcaa acccaaggag gaagtgcctn    480
atgctgaaaa gttttggatg actcaactgg atggggtatt ccctgnaacc aaaacctggn    540
acccaagtcc ttaaaanccn nggagactta cattntgntg nacaatttgg gttaaaccnn    600
```

ttcncaaagc tttccatggg ggcanggccc 630

<210> SEQ ID NO 501
<211> LENGTH: 240
<212> TYPE: DNA
<213> ORGANISM: Homo sapiens

<400> SEQUENCE: 501
acatctgaaa taccccccaa acccagaaag cttttcaaca gctaggttgt ccaagaactt 60
ggaaaattca ccttctgatg tcctccaaga cagattccat tttttataca ccttatttgc 120
tcagacctgt aacttcagcc tggagtgaac acagacacct agttttcctc aaactcctct 180
tgggctttag agagaaggtg ctggcccttt gagccaagca ggttattggt tagtagtacc 240

<210> SEQ ID NO 502
<211> LENGTH: 481
<212> TYPE: DNA
<213> ORGANISM: Homo sapiens
<220> FEATURE:
<221> NAME/KEY: misc_feature
<222> LOCATION: (1)...(481)
<223> OTHER INFORMATION: n = A,T,C or G

<400> SEQUENCE: 502
ggtacctgtt cttctatcca aacctttcaa ttcatgctac ctgattcatt tatttgacat 60
agatcttagg cccacttgaa ctcttttctt gtttatctag catagcacaa acgtttttcc 120
agtcttcttt atcaacacta atgcctctta attgcatcag tatttcctat tggaaaatac 180
atctgttcca gaaaaacatt tggcattcct gaataatttc caaatgtttt taatccaaag 240
aaaaaggttt aaagcttatt tccctttctt atacacacct gaataaaatt gatgtgcatg 300
ttttagggat caattaccta actgttcctt ggtctattta tgtataagaa tgctttttaa 360
agcacatgtc tcattttaaa tgacgcacaa actgaagatg ttaataaaat ttaagagtaa 420
tacaatgaaa aatattantn ttnnanatan aaaagcttgg acctgccngg gcggccgntc 480
g 481

<210> SEQ ID NO 503
<211> LENGTH: 643
<212> TYPE: DNA
<213> ORGANISM: Homo sapiens
<220> FEATURE:
<221> NAME/KEY: misc_feature
<222> LOCATION: (1)...(643)
<223> OTHER INFORMATION: n = A,T,C or G

<400> SEQUENCE: 503
ggtactgcat tatttgagaa gctgctcaac ttgcaaaatc agttttcctc tcaataaaat 60
tatagctcta atgtttgcat ataagggaag tagttatcat gttagtaata cctctaatag 120
tataaacccc accccaaaat tagccagtaa tcctgtagga aggtacaagt ctcagactaa 180
gtttttagcc acttgtcaaa ttcagtttta aatgcttaga aaacactgag gacacctatt 240
gaggagggag gggggaaggt cacctgtaaa ggagtccaaa gtatgtgctg gagcagatga 300
tgacaaagac agaacatcta agaagataga catggaggaa agggagtagt atttccacac 360
actatgacat tgaaaattca atcatttatg ataggatttt gatccactgc cattactacc 420
ttgtgggaaa aatctnccaa tgaaaaggtt gaaaaattca ttctccaaaa attggcccng 480
ttttaangag aaaattttag agcagcaccn ttaaaccatg ccgggaactt tggtttaaca 540
aaatatngtg gggccccaaa aagctcctgt tgcttttagg cctcnagaga tttacccaga 600
acttaaaggn ttncnctggc cttgttcctt aangttgaaa acc 643

<210> SEQ ID NO 504
<211> LENGTH: 624
<212> TYPE: DNA
<213> ORGANISM: Homo sapiens
<220> FEATURE:
<221> NAME/KEY: misc_feature
<222> LOCATION: (1)...(624)
<223> OTHER INFORMATION: n = A,T,C or G

<400> SEQUENCE: 504
ggtactgcat tatttgagaa gctgctcaac ttgcaaaatc agttttcctc tcaataaaat 60
tatagctcta atgtttgcat ataagggaag tagttatcat gttagtaata cctctaatag 120
tataaacccc accccaaaat tagccagtaa tcctgtagga aggtacaagt ctcagactaa 180
gtttttagcc acttgtcaaa ttcagtttta aatgcttaga aaacactgag gacacctatt 240
gaggagggag gggggaaggt cacctgtaaa ggagtccaaa gtatgtgctg gagcagatga 300
tgacaaagac agaacatcta agaagataga catggaggaa agggagtagt atttccacac 360
actatgacat tgaaaattca atcatttatg ataggatttt gatccactgn ccattactac 420
cttgtgggaa aaatccttca caatgaaaag ggttgaaaaa ttcattcttc caaaattggc 480
ccnngtttta aggagaaaat nttagagccg ccccttaanc ctgcccggaa cttggntta 540 ccaaatntca gggngncccc aaaancttct gntgccttta ngncntncan agacttnacc 600
cnngaacttc naggntttnc ctng 624

<210> SEQ ID NO 505
<211> LENGTH: 652
<212> TYPE: DNA
<213> ORGANISM: Homo sapiens
<220> FEATURE:
<221> NAME/KEY: misc_feature
<222> LOCATION: (1)...(652)
<223> OTHER INFORMATION: n = A,T,C or G

<400> SEQUENCE: 505
acaagctaca aatgcttgtt cagcagctga ggggcactct tgagtagcgt gtctgaagag 60
tgaataaaaa tccatataaa acaaatattc aaatagtttc cataggaaca cagataagtg 120
tgacccatat cctagtcttc catatggctg catcatggcg accctactct tacaaagaca 180
tttcaaaact agcagtaatt aagttacatg gtccccccaa atcccttaat tcaagctaaa 240
cttgcagtta acagctacca gagtgctatc tacacattaa tactagcccg aagcacaggc 300
tgctctgtgg cgtttcatcc cactctccca ggcacaagac acaggcaggg tgctggcatc 360
ctgttcctct acttcgggtg gggaaagtcg gggttctgga attgctgcat gagttgccac 420
gcaggccctg acatcacata gtaanatcgt ccggcctttt gggaaaccca ttgnacctan 480
aaggcancna gcaaccagtg gtaagccgcc ccaaggtttt cnaaagagcc tttccaatna 540
ccccccatgc cnttttaang gcnnggttac caagggcttn aaaaaatccg atttnanggg 600
ccnttacaag gttggggccc ccanaatgcn cggatngnaa aaaanacctt tt 652

<210> SEQ ID NO 506
<211> LENGTH: 545
<212> TYPE: DNA
<213> ORGANISM: Homo sapiens
<220> FEATURE:
<221> NAME/KEY: misc_feature
<222> LOCATION: (1)...(545)
<223> OTHER INFORMATION: n = A,T,C or G

<400> SEQUENCE: 506

```
acaagctttt tttttttttt tttttttttt tttttttatc taaaagtgcc caggtgggct     60
taaggctgcc anactgcacg cacatctaca gcaacaaggg cttctattcc atctacaact    120
tggatcgggg gaaaagggag atgtaggaga ggaaggaaaa aagaggggaa aaatatacca    180
ccaaccctcc cccacaaaaa aagggaaaaa aaaaaatccc accacaggga gatctatgtg    240
ccaagcataa tggaagagtg tgctccccaa acagatggtt ttgcacaggc taatgttctg    300
ctggttttcc ttagagacct attttgaaaa agtttaaaaa gacaggagat ttcaaaataa    360
ttcaatcctg gcagaaattc aaactccaaa actaggagca aaatcatcct tcactgaatt    420
aattcctttt ctctttctct tttcttaaac attttattca ttttatagaa agatttcttt    480
ttttggntgc ntttggtcca atcntttgga nantggttga aggagtacct tggncgngan    540
ccccc                                                                545
```

<210> SEQ ID NO 507
<211> LENGTH: 625
<212> TYPE: DNA
<213> ORGANISM: Homo sapiens
<220> FEATURE:
<221> NAME/KEY: misc_feature
<222> LOCATION: (1)...(625)
<223> OTHER INFORMATION: n = A,T,C or G

<400> SEQUENCE: 507

```
acctgtctct ctgccttctg gaggctctct aggattggaa aagttcaaga aacccgaggg     60
aagctgggac tgtgaattgt gcctagtgca gaataaggca gactctacca aatgtttggc    120
atgtgaaagt gcaaagccag gcacaaaatc tgggtttaaa ggctttgaca catcttcctc    180
atcttcgaac tcagcagcct cctcatcctt caaatttggt gtctcatcat cctcttctgg    240
gccttctcag actttaacaa gcactggaaa ttttaaattt ggagatcagg gaggattcaa    300
aataggtgtg tcatctgatt ctgggtctat aaaccccatg agtgaaggct ttaaattttc    360
taaaccaata ggagatttta aatttggagt ttcatctgaa tctaagcccg aagaagttaa    420
aaaagatagt aagaatgata atttttaagt ttggacttct ttggtttaac cacccagttt    480
ctttaacttc atttcaattg ggtatctaa tcttggacag gaagaaaaag aaagangaac    540
ctggcccaaa tctttcctnt gcaggntta nccttnggac ccttggccgc naaccaccct    600
aagggggaa ttccnnacac tgggg                                           625
```

<210> SEQ ID NO 508
<211> LENGTH: 612
<212> TYPE: DNA
<213> ORGANISM: Homo sapiens
<220> FEATURE:
<221> NAME/KEY: misc_feature
<222> LOCATION: (1)...(612)
<223> OTHER INFORMATION: n = A,T,C or G

<400> SEQUENCE: 508

```
ggtcgaagac agaggttcag gtcgttccag gggtagagga ggcatgaagg atgaccgtcg     60
ggacagatac tctgcgggca aaaggggtgg atttaatacc tttagagaca gggaaaatta    120
tgacagaggt tactctagcc tgcttaaaag agattttggg gcaaaaactc agaatggtgt    180
ttacagtgct gcaaattaca ccaatgggag ctttggaagt aattttgtgt ctgctggtat    240
```

```
acagaccagt tttaggactg gtaatccaac agggacttac cagaatggtt atgatagcac    300

tcagcaatac ggaagtaatg ttccaaatat gcacaatggt atgaaccaac aggcatatgc    360

atatcctgct actgcagctg cacctatgat tggttatcca atgccaacag gatattccca    420

ataagacttt agaagtatat gtaaatgnct ggttttcata attgctcttt atattgggng    480

gtatctgacc agatagtatt ttaagaaaca tgggaattgc anaaatgact gnagtgcaan    540

agtaattntn gggcactttt cgtttttaag ntggaaattc nctacanttc ctgaaccant    600

ttanggtttt tt                                                        612
```

<210> SEQ ID NO 509
<211> LENGTH: 473
<212> TYPE: DNA
<213> ORGANISM: Homo sapiens
<220> FEATURE:
<221> NAME/KEY: misc_feature
<222> LOCATION: (1)...(473)
<223> OTHER INFORMATION: n = A,T,C or G

<400> SEQUENCE: 509

```
cttgggtctg aaagtcgatg aaggacgcga ttacctgcga taagcttcgt ggagttggaa     60

ataaactatg atacggagat ttccgaatgg ggtaacctaa ctgagcaaac ctcagttgca    120

ttttgatgaa tccatagtca aattagcgag acacgttgcg aattgaaaca tcttagtagc    180

aacaggaaaa gaaaataaat aatgatttcg tcagtagtgg cgagcgaaag cgaaagagcc    240

caaacctgta aaaaggggtt gtaggacatc ttacattgag ttacaaaatt ttatgatagt    300

agaagaagtt ggaaagcttc aacatagaag gtgatattcc tgtatacgaa atcataaaat    360

ctnatagatg tatcctgagt agggcggggc accgtgaaac cctgtctgaa tctgccggga    420

ccaccccggt aaggctaata ctaatcanac accgatagtg aactagtacc tng           473
```

<210> SEQ ID NO 510
<211> LENGTH: 632
<212> TYPE: DNA
<213> ORGANISM: Homo sapiens
<220> FEATURE:
<221> NAME/KEY: misc_feature
<222> LOCATION: (1)...(632)
<223> OTHER INFORMATION: n = A,T,C or G

<400> SEQUENCE: 510

```
ggtacctatg tggattccaa gagcctgata gcattcttgt ccttcagagc ctccctggca     60

aacaattacc atcacacaaa gccatacttt ttgtgcctcg gcgagatccc agtcgagaac    120

tttgggatgg tccgcgatct ggcactgatg gagcaatagc tctaactgga gtagacgaag    180

cctatacgct agaagaattt caacatcttc taccaaaaat gaaagctgag acgaacatgg    240

tttggtatga ctggatgagg ccctcacatg cacagcttca ctctgactat atgcagcccc    300

tgactgaggc caaagccaag agcaagaaca aggttcgggg tgttcagcag ctgatacagc    360

gcctccggct gatcaagtct cctgcagaaa ttgaacgaat gcagattgct gggaagctga    420

catcacaggc tttcatagaa accatgttna ccagtaaaag cccctgtgga agaaccnttc    480

tttatgctaa gtttgaattt gaatgcccgg ctcgtggcgc agacatttta acctattcan    540

cttgtggtgg cttggnggta attcggncca aacactttgc ncttttgtga aaaaaaatcn    600

cctcttcang gttggggnaa nggggctttt gg                                  632
```

<210> SEQ ID NO 511
<211> LENGTH: 616

<212> TYPE: DNA
<213> ORGANISM: Homo sapiens
<220> FEATURE:
<221> NAME/KEY: misc_feature
<222> LOCATION: (1)...(616)
<223> OTHER INFORMATION: n = A,T,C or G

<400> SEQUENCE: 511
acagaaccta aaggtttcac tgaatgcgaa atgacgaaat ctagcccttt gaaaataaca 60
ttgtttttag aagaggacaa atccttaaaa gtaacatcag acccaaaggt tgagcagaaa 120
attgaagtga tacgtgaaat tgagatgagt gtggatgatg atgatatcaa tagttcgaaa 180
gtaattaatg acctcttcag tgatgtccta gaggaaggtg aactagatat ggagaagagc 240
caagaggaga tggatcaagc attagcagaa agcagcgaag aacaggaaga tgcactgaat 300
atctcctcaa tgtctttact tgcaccattg gcacaaacag ttggtgtggt aagtccagag 360
agtttagtgt ccacacctag actggaattg aaagacacca gcagaagtga tgaaagtcca 420
aaaccaggaa aattccaaag aactcgtgtc cctcgagctg aatctggtga tagcccttgg 480
ttctgaagat cgtgacttct ttacagcatt gatgcatata gatctcaaag attnanagaa 540
acnggaatgt ccatcaataa acnaggtgat tgttnggaag gaagatgttc tttttaaaaa 600
tnaatgtttn atntng 616

<210> SEQ ID NO 512
<211> LENGTH: 619
<212> TYPE: DNA
<213> ORGANISM: Homo sapiens
<220> FEATURE:
<221> NAME/KEY: misc_feature
<222> LOCATION: (1)...(619)
<223> OTHER INFORMATION: n = A,T,C or G

<400> SEQUENCE: 512
ggtaccggtc tttctcaaat atcatcagca ccctcaatcc cactgctaaa cgacatttgg 60
tcctcgcctg ccactatgac tccaagtatt tttcccactg gaacaacaga gtgtttgtag 120
gagccactga ttcagccgtg ccatgtgcaa tgatgttgga acttgctcgt gccttagaca 180
agaaactcct ttccttaaag actgtttcag actccaagcc agatttgtca ctccagctga 240
tcttctttga tggtgaagag gcttttcttc actggtctcc tcaagattct ctctatgggt 300
ctcgacactt agctgcaaag atggcatcga ccccgcaccc acctggagcg agaggcacca 360
gccaactgca tggcatggat ttattggtct tattggattt gattggagct ccaaacccaa 420
cgtttcccaa ttttttttcca aactcagcca ggtggttcga aagacttcaa gcaattgaac 480
atgaacttca tgaattgggt tgcttcaagg atcactcttt tggaagggcg ggatttnccg 540
aaatacnggt tttggaggng tgaatcaggg atgaccntat tcccttttta anaaaaaggg 600
gttcccntnt gcntntgnn 619

<210> SEQ ID NO 513
<211> LENGTH: 175
<212> TYPE: DNA
<213> ORGANISM: Homo sapiens

<400> SEQUENCE: 513
ggtacatcct cggccgggag tccccactgt ctctctacaa tgaggagctg gtgagcatga 60
acgtgcaggg tgattatgag ccaactgatg ccaccgggtt catcaacatc aattccctca 120
ggctgaagga atatcatcgt ctccagagca aggtcactgc caaatagacc cgtgt 175

<210> SEQ ID NO 514
<211> LENGTH: 597
<212> TYPE: DNA
<213> ORGANISM: Homo sapiens
<220> FEATURE:
<221> NAME/KEY: misc_feature
<222> LOCATION: (1)...(597)
<223> OTHER INFORMATION: n = A,T,C or G

<400> SEQUENCE: 514

```
actagttact gcatctgatt ttacagacag agaagagtca aggcccagag agcagacagc     60

tcaccccaac atcacacagc agtcagctgc gaggggcttg gtgctactca gatttctcct    120

aagaatgttt ggaaacaacc tgagggagag ttaagtaata aaggaaaatc acaaacagag    180

acagagaccc agaaagggac tcacgggaat aaaagcagaa agtgacagag atacatagag    240

atgatgagac agagacagag agatcagaga tagggttcag aaaaaaagaa gagagaggct    300

gggcacagtt gctcacgcca gtaatcccag cactttgaga ggcggagatg ggaggatctc    360

ttgagcccag gagtttgaga ccagcctgga cagcatagta agaccccatc tttatttaaa    420

aaaaagtttt attaatttaa aaaaaatgcc nagagagata accccccnta gaaggttgga    480

aagccaaaag ctttttgggg gcttaaaagn accccaaccc ggnccnggga ganaggtttt    540

tttttgaggg aanaatccgg ttcttggcca ngcttaanng gcctatttcc aaaaaac       597
```

<210> SEQ ID NO 515
<211> LENGTH: 574
<212> TYPE: DNA
<213> ORGANISM: Homo sapiens
<220> FEATURE:
<221> NAME/KEY: misc_feature
<222> LOCATION: (1)...(574)
<223> OTHER INFORMATION: n = A,T,C or G

<400> SEQUENCE: 515

```
ggtacactgg ttgatatgaa gattgaattt ggtgttgatg taaccaccaa agaaattgtt     60

cttgctgatg ttattgacaa tgattcctgg agactctggc catcaggaga tcgaagccaa    120

cagaaagaca aacagtctta tcgggacctc aaagaagtaa ctcctgaagg gctccaaatg    180

gtaaagaaaa actttgagtg ggttgcagag agagtagagt tgcttttgaa atcagaaagt    240

cagtgcaggg ttgtagtgtt gatgggctct acttctgatc ttggtcactg tgaaaaaatc    300

aagaaggcct gtggaaattt tggcattcca tgtgaacttc gagtaacatc tgcgcataaa    360

ggaccagatg aaactctgag gattaaagct gagtatgaag ggatggcat tcctactgta    420

tttgtggcag tggcaggcag aagtaatggt tngggaccag tgatgtctgg gaacactgca    480

tatnccgtta tnagctggcn tcncttanac caactgggga agttcaggat gtgtgggctt    540

ctctttgact nccaatggnc ttggctntca accn                                574
```

<210> SEQ ID NO 516
<211> LENGTH: 450
<212> TYPE: DNA
<213> ORGANISM: Homo sapiens
<220> FEATURE:
<221> NAME/KEY: misc_feature
<222> LOCATION: (1)...(450)
<223> OTHER INFORMATION: n = A,T,C or G

<400> SEQUENCE: 516

```
aaaaaggcgt aaagcggaaa gcagatacta ccacccctac acctacagcc atcttggctc     60

ctggttctcc agctagccct cctgggagtc ttgagcctaa ggcagcacgg cttcccccta    120
```

```
tgcgtagaga gagtggtcgc cccatcaagc ccccacgcaa agacttgcct gactctcagc    180

aacaacacca gagctctaag aaaggaaagc tttcagaaca gttaaaacat tgcaatggca    240

ttttgaagga gttactctct aagaagcatg ctgcctatgc ttggcctttc tataaaccag    300

tggatgcttc tgcacttggc ctgcatgact accatgacat cattaagcac cccatggacc    360

tcagcactgt caagcggaag atggagaacc gtgattaccg ggatgcacag gagtttgctg    420

ctgatgtacc tcgggcgcga acacgcttan                                      450
```

```
<210> SEQ ID NO 517
<211> LENGTH: 611
<212> TYPE: DNA
<213> ORGANISM: Homo sapiens
<220> FEATURE:
<221> NAME/KEY: misc_feature
<222> LOCATION: (1)...(611)
<223> OTHER INFORMATION: n = A,T,C or G

<400> SEQUENCE: 517

actcctctga ggactacatt aagtcaggag ctcttcttgc ctgtggcata gtgaactctg     60

gggtccggaa tgagtgtgac cctgctctgg cactgctctc agactatgtt ctccacaaca    120

gcaacaccat gagacttggt tccatctttg ggctaggctt ggcttatgct ggctcaaatc    180

gtgaagatgt cctaacactg ctgctgcctg tgatgggaga ttcaaagtcc agcatggagg    240

tggcaggtgt cacagcttta gcctgtggaa tgatagcagt agggtcctgc aatggagatg    300

taacttccac tatccttcag accatcatgg agaagtcaga gactgagctc aaggatactt    360

atgctcgttg gcttcctctt ggactgggtc tcaaccacct ggggaagggt gaggccatcg    420

angcaatcct ggctgcactg gaaggtgngc anaaccnttt cgcanttttg nccacacacc    480

tggnggatgt gtgngcctat tcncgctttt ggnanatgcc tnaagggcna caaattggtc    540

caatttgnnn nnaacctttg cctccaaaga aagggggaaa naaaagtttc ccccnanngg    600

gggcgggccc c                                                         611
```

```
<210> SEQ ID NO 518
<211> LENGTH: 395
<212> TYPE: DNA
<213> ORGANISM: Homo sapiens

<400> SEQUENCE: 518

ggtgatttat ctaatcagaa ctcttcagat caggcaaatg aagaatggga aacagcttct     60

gaaagcagtg atttcaatga gaggcgagag agggatgaaa aaaaaaatgc tgacttgaat    120

gcacaaacag ttgtaaaggt tggagagaat gttctacctc caaagaggga aattgcaaag    180

agaagttttt ctagtcagag accagtagat cgtcagaatc gacgtggcaa caatggtcca    240

cccaaatcag gaaggaattt ctcaggtcct agaaatgaaa ggagaagtgg cccaccatca    300

aaaagtggga agagagggcc atttgatgac cagcctgcag gcacaactgg ggttgacctc    360

atcaatggca gctctgcaca ccatcaggaa ggagt                               395
```

```
<210> SEQ ID NO 519
<211> LENGTH: 626
<212> TYPE: DNA
<213> ORGANISM: Homo sapiens
<220> FEATURE:
<221> NAME/KEY: misc_feature
<222> LOCATION: (1)...(626)
<223> OTHER INFORMATION: n = A,T,C or G
```

<400> SEQUENCE: 519
ggtaccgaaa gcacagtaat cactggtgtc gatattgtca tgaaccatca cctgcaggaa 60
acaagtttca caaaagaagc ctacaagaag tactgatttt aaaaactaat aacttaaaac 120
tgccacacgc aaaaaagaaa accaaagtgg tccacaaaac attctccttt ccttctgaag 180
gttttacgat gcattgttat cattaaccag tcttttacta ctaaacttaa atggccaatt 240
gaaacaaaca gttctgagac cgttcttcca ccactgatta agagtggggt ggcaggtatt 300
agggataata ttcatttagc cttctgagct ttctgggcag acttggtgac cttgccagct 360
ccagcagcct tcttgccact gctttgatga cacccaccgc aactgtctgn ctcatatcac 420
gaacagcaaa gcgacccaaa ngtggatagt ctgagaagct nttcaacaca catnggcttt 480
gccaggaanc ntttntacca tgggagcntt cccngacttt tagnaaatta agggcntttt 540
tcacttttta acccaaacgg ggaaaaattt ttnctttaag ttaanaaact tgcnntgcaa 600
tggaanccgn ngggaatcca atacgg 626

<210> SEQ ID NO 520
<211> LENGTH: 322
<212> TYPE: DNA
<213> ORGANISM: Homo sapiens

<400> SEQUENCE: 520
ggtacccaag catctagtct ggaactgaca gagataaata gagaaaatgt tccaaagtct 60
ggcacgcccc agcttaggct gccattcgct gcaaggttga acacccccat gggccctgga 120
cgaactgtcg tcgttaaagg agaagtgaat gcaaatgcca aaagctttaa tgttgaccta 180
ctagcaggaa aatcaaagga tattgctcta cacttgaacc cacgcctgaa tattaaagca 240
tttgtaagaa attcttttct tcaggagtcc tggggagaag aagagagaaa tattacctct 300
ttcccattta gtcctgggat gt 322

<210> SEQ ID NO 521
<211> LENGTH: 613
<212> TYPE: DNA
<213> ORGANISM: Homo sapiens
<220> FEATURE:
<221> NAME/KEY: misc_feature
<222> LOCATION: (1)...(613)
<223> OTHER INFORMATION: n = A,T,C or G

<400> SEQUENCE: 521
ggtaccatcc tcatctcggt gggatgtgca gttttctgtg cccttatcgt ctggttcttt 60
gtatgtccca ggatgaagag aaaaattgaa cgagaaataa agtgtagtcc ttctgaaagc 120
cccttaatgg aaaaaaagaa tagcttgaaa gaagaccatg aagaaacaaa gttgtctgtt 180
ggtgatattg aaaacaagca tcctgtttct gaggtagggc ctgccactgt gcccctccag 240
gctgtggtgg aggagagaac agtctcattc aaacttggag atttggagga agctccagag 300
agagagaggc ttcccagcgt ggacttgaaa gaggaaacca gcatagatag caccgtgaat 360
ggtgcagtgc agttgcctaa tgggaacctt gtccagttca gtcaaagccg tcagcaacca 420
aataaactnc agtggccact accagtatca caccgtgcat aaaggattcc gggctgtanc 480
ttgcccggcc ggccgtntaa aggcgaattc cagncacttg ggggccgntc taaagggatn 540
ccactttggn ccaacnttgg gggaatctng ggcaaantng tccctgngna aatggtatcc 600
gtcaaatncc cnn 613

<210> SEQ ID NO 522
<211> LENGTH: 319
<212> TYPE: DNA
<213> ORGANISM: Homo sapiens

<400> SEQUENCE: 522
accagggagg catgacattg cttttgttga atttgaaaat gatgggcagg ctggagctgc 60
cagggatgct ttacagggat ttaagatcac accgtcccat gctatgaaga tcacctatgc 120
caagaaataa catttgggat agtcgtcttt aaaagacttg gtgttattta cagtgtttgt 180
tttgataaca tttggctggg tcattttaat agttagagat gaggaggagt aaaagtgaaa 240
tttttgtgaa ggacttaaat tatccagtgt ttctttagcc ttggtgaact atgaaatacg 300
aaggccttaa ttttgtacc 319

<210> SEQ ID NO 523
<211> LENGTH: 589
<212> TYPE: DNA
<213> ORGANISM: Homo sapiens
<220> FEATURE:
<221> NAME/KEY: misc_feature
<222> LOCATION: (1)...(589)
<223> OTHER INFORMATION: n = A,T,C or G

<400> SEQUENCE: 523
acagcgcgcg gctctacacg cttgggtagc gggataagtc actgttttct ttatttcttt 60
aaaaaaaaaa aagttctgtt gcaaacgact gctgttggat tctgagggtg gggagggaga 120
gagagggagg gagagggagt gaagagcctg ccctcctata tggattcttc agggccctcc 180
acatctgagg tggctcattc ccatcacaca cagattgtcc tggtgttcat ttcaaggcca 240
gtgttcagca gcagcgtttg gaaagcaggt tctgtgggac cccccgcccc gcccccacac 300
tccttcatag cagcagtagt ggcttctcca tcctgntttc tgcaacattc tatacaaaac 360
tgtgctgtga ccttgcggta agcctggatc tggcaaagag aatcaaatga aaccccttct 420
ttctcttttc gtccacaact ctgtanaact ntntgnaccc ttaccccttt ccaccttttg 480
gattnaattt taaggccgtg nanctttggc cggaacaccc ttagggcnaa ttcnnnccat 540
tgggggccgt ctaagggann ccaattggnc caanttgggn aacanggnn 589

<210> SEQ ID NO 524
<211> LENGTH: 621
<212> TYPE: DNA
<213> ORGANISM: Homo sapiens
<220> FEATURE:
<221> NAME/KEY: misc_feature
<222> LOCATION: (1)...(621)
<223> OTHER INFORMATION: n = A,T,C or G

<400> SEQUENCE: 524
ggtacattgg agagatctcg cctactgccc tgcggggtgc ctttggcact ctcaaccagc 60
tgggcatcgt tgttggaatt ctggtggccc agatctttgg tctggaattc atccttgggt 120
ctgaagagct atggccgctg ctactgggtt ttaccatcct tcctgctatc ctacaaagtg 180
cagcccttcc attttgccct gaaagtccca gatttttgct cattaacaga aaagaagagg 240
agaatgctaa gcagatcctc cagcggttgt ggggcaccca ggatgtatcc caagacatcc 300
aggagatgaa agatgagagt gcaaggatgt cacaagaaaa gcaagtcacc gtgctagagc 360
tctttagagt gtcagctacc cgacagtcca tcatcatttc cattgtgctc cagctctntc 420
gcagcttctt gggatcaatg ctgngttcta atactcacca ggaatcttca aggatgcagg 480

-continued

```
tggttaaaaa ncccatttat gccncctttg ggcccggtgn gggtnaaacc anacttnccn    540

nggaggnncc tnttttnnng ggggaanggc cngaaaaaag gncttcgcct ttaaanngcc    600

cttggaggga agnttttttt n                                               621
```

<210> SEQ ID NO 525
<211> LENGTH: 384
<212> TYPE: DNA
<213> ORGANISM: Homo sapiens

<400> SEQUENCE: 525

```
acagcacttt gagaggacat cactagacaa gtaatacaca catggcctgc aggaggtcaa     60

gggcggcgag ggggctgggc aggggacatt tttgtgactt ccactgttat tatatttcac    120

gacaacagca gcagcacaaa tggtgtgctc accactggag aatgagagct gctgagtctt    180

gaggatggcg agacagcctt cctgcatttg ctgctttagt ttctgcttta gagctaagtt    240

ttatacagag aataaaatga ccatcttctc ttacaaacac gatgatgtat gaccccacac    300

aacacaaggt attatgaagt atctgaaact gaggataatc tgactgaaga tgcttgccga    360

gagggtacct cggccgcgcc acgc                                            384
```

<210> SEQ ID NO 526
<211> LENGTH: 621
<212> TYPE: DNA
<213> ORGANISM: Homo sapiens
<220> FEATURE:
<221> NAME/KEY: misc_feature
<222> LOCATION: (1)...(621)
<223> OTHER INFORMATION: n = A,T,C or G

<400> SEQUENCE: 526

```
actgtagctc cccatgagat gtgatgagta tgccttcacc cttggtgtca tactggggtc     60

ttccggcacg tcccagcatc tgcagaatgt ccagtgctcc cagttctgtc caacgcccct    120

tctctggact gtacaatgtc actgacggat cctgccagct gtttgtgtat gggggctgtg    180

acggaaacag caataattac ctgaccaagg aggagtgcct caagaaatgt gccactgtca    240

cagagaatgn cangggtgac ctggccacna gcangaatgc agcggattcc tctgcccaag    300

tgcttnagaa ggcagnattc tgaagactac tncagcgata tgttcaacta tgangaatac    360

tgcacngtna accgcattna ctgggntttg ncngtgcatc cttcnacgct ggtaccttcg    420

gcccgggacc acgcttaagg gcgaatncan gnactactgg ccgggtcgtt actantngaa    480

tccgagnttc gnnaccaagc tttgcgtaaa atattgggca taagttggnt ttctgngnga    540

aaaatggtan atcngttnan aattcccnaa tatatncanc cngtnccttt aattntaaat    600

ccgggggtnn taantnantn n                                               621
```

<210> SEQ ID NO 527
<211> LENGTH: 611
<212> TYPE: DNA
<213> ORGANISM: Homo sapiens
<220> FEATURE:
<221> NAME/KEY: misc_feature
<222> LOCATION: (1)...(611)
<223> OTHER INFORMATION: n = A,T,C or G

<400> SEQUENCE: 527

```
acagctcatc cacttcctca tctgtaaacc gatcccccat ggttgtcagc agctctctta     60

ggtaatcttc ctgaatggtg cctgttgctt cttcatcaaa gcaagcaaag gcgtttctga    120

tgacatcttc aggatctgtg ccatttaact tctcaccaaa catggtcagg aacatggtga    180
```

```
aattgatggg ccctggggcc tcattcatca tggcatcaag gtatgcatca gtgggattct    240

tccctagaga agcaagcata tcatgcaaat cttccttgtc gatgaagcca tctctgttct    300

gatcaatcat gttgaaggcc tctttgaact cctgaatctg tgattggtca aacatggcaa    360

acacattgga tgttgcacgc tgagggcgct tcttggtggt cttggtcttt gcctttttgc    420

ttcgacatgg tggntggtta attncgacgc ccaaacacca gaacccgggg ccancctgcg    480

cganaacgca accaaaacct tnggccggaa cacccttaag gggaaatccc nncactgggg    540

ggccgtataa nggganccna nttnggacca aacttggngg aaaaangggc aaaanngttc    600

ctgnggaaan n                                                         611
```

<210> SEQ ID NO 528
<211> LENGTH: 593
<212> TYPE: DNA
<213> ORGANISM: Homo sapiens
<220> FEATURE:
<221> NAME/KEY: misc_feature
<222> LOCATION: (1)...(593)
<223> OTHER INFORMATION: n = A,T,C or G

<400> SEQUENCE: 528

```
acaagctttt tttttttttt tttttttttt taggtagtgg gtgttgagct tgaacgcttt     60

cttaattggt ggctgctttt aggcctacta tgggtgttaa attttttact ctctctacaa    120

ggttttttcc tagtgtccaa agagctgttc ctctttggac taacagttaa atttacaagg    180

ggatttagag ggttctgtgg gcaaatttaa agttgaacta agattctatc ttggacaacc    240

agctatcacc aggctcggta ggtttgtcgc ctctacctat aaatcttccc actattttgc    300

tacatagacg ggtgtgctct tttagctgnt cttaggtagc tcgtctggtt tcggggggtct   360

tanctttggc tctccttgca aaggtatttc tagntaattc attatgcnna aagnatangg    420

gtaagccctg ctatataagc ctgggtataa attttcancc tttcctttgn ggaccctngg    480

ccggaacacc ctaagggcga aatccancca ctgggggccg tactaaaggg atcccaactt    540

gggnccaact tggnnnaaac cggggcanaa nngtccctgg ggnaaatggn anc           593
```

<210> SEQ ID NO 529
<211> LENGTH: 251
<212> TYPE: DNA
<213> ORGANISM: Homo sapiens

<400> SEQUENCE: 529

```
accattggtg gccaattgat ttgatggtaa gggagggatc gttgacctcg tctgttatgt     60

aaaggatgcg tagggatggg agggcgatga ggactaggat gatggcgggc aggatagttc    120

agacggtttc tatttcctga gcgtctgaga tgttagtatt agttagtttt gttgtgagtg    180

ttaggaaaag ggcatacagg actaggaagc agataaggaa aatgattatg agggcgtgat    240

catgaaagac c                                                         251
```

<210> SEQ ID NO 530
<211> LENGTH: 601
<212> TYPE: DNA
<213> ORGANISM: Homo sapiens
<220> FEATURE:
<221> NAME/KEY: misc_feature
<222> LOCATION: (1)...(601)
<223> OTHER INFORMATION: n = A,T,C or G

<400> SEQUENCE: 530

-continued

```
acagtataaa atgtttccat aggaacacaa aagaaactgt cactagtggc ctgctgtcag     60

atggcttcta attcatcagt tagccatttt taggacacta gtccagctta ttgctacaat    120

cttcaagttg ttctagtcac ccaaattata atgaattcaa tgtataccag aatttaccaa    180

taaaggctca aagagttata taatatacac caatatacac aaaacagcta ttctgagtaa    240

aatgaatatt ccatacttaa ataagaacca agaatagtaa ttttaggcta ctctattatc    300

cttgtgattg gtatttttaa aattttgagc aaagtgcaca gtgaatgaaa cagtcagcag    360

acacgatcct tctgtgaact ctcaaattcc tgccttagaa tcacgtcacc tgagaaatga    420

gaacctttga gacctggtgc atatcaaata gcttcacatg tcaaaccaca ggggccgctt    480

ggangccatt ctngggcaca ggangncaac tggttcnttn aaaatggnnc ccttncctgt    540

gcangggccc tgtgttaaag gccccaaaac cggcctcngg ggaaacaagg ttgntaatta    600

a                                                                    601
```

```
<210> SEQ ID NO 531
<211> LENGTH: 607
<212> TYPE: DNA
<213> ORGANISM: Homo sapiens
<220> FEATURE:
<221> NAME/KEY: misc_feature
<222> LOCATION: (1)...(607)
<223> OTHER INFORMATION: n = A,T,C or G

<400> SEQUENCE: 531

ggtacaagct tttttttttt tttttttttt ttttttttct cagccttgga tttcttctta     60

gcttccttct gctttaagct cttggtctct tgtttccgct natttctggc ctgcccttgg    120

atagtagtct gacactctcc ccgttgaacc ttctgcctca tcttcttctt gcttttagca    180

atctttgctt tatcctcctc attcaatgtt tcttgggcct ccagtttctt tagggggcgg    240

ttgtctgtct tgttcaatag ctcagtgatt ttgaccttag gtggccgacc tcgaccccgt    300

ttcaccttgg ggacttcctt agtcttagcc ttctcagtgt ttcaaggtcg accccgtttg    360

ccagtaattg cctgaatcct cgacgggatc tcctctgctg aaagctgcac ccactgcaag    420

ccctttggcg ngnctctttt cttcaaagaa atctccaaca nggcatacgg ggactgaanc    480

ttaanngctt nttggnggaa actgggnacc tggccgggca ngggcctntg ttttacctnc    540

tggnaatnaa aagggaaaat ncaaaanttt accctnttna ccnngtttnt ggggtngggg    600

gaaaang                                                              607
```

```
<210> SEQ ID NO 532
<211> LENGTH: 608
<212> TYPE: DNA
<213> ORGANISM: Homo sapiens
<220> FEATURE:
<221> NAME/KEY: misc_feature
<222> LOCATION: (1)...(608)
<223> OTHER INFORMATION: n = A,T,C or G

<400> SEQUENCE: 532

ggtactgaac aggtaagtca tccctcagcc agagattagt ctacttcttc catgcgtgat     60

gtgtcgtcat ctccttcaag ggtggcattt tcttcagtta cagcagcact ggtatcatca    120

gcagtagggt catcttcatc aatacccaga ccaagtttga tcatcctgta gatcctgtta    180

gcatgtgtct ggggatcttc cagactgaag ccagaagaca ggagcgcagt ttcataaagc    240

aagatgacca gatccttcac agacttgtcg ttcttatcag cctctgcctt ttgccttaag    300

gtctcaataa tggaatggtc agggtttatc tccaggtgtt tctttgctgc catgtaaccc    360
```

-continued

```
attgttgagt ngctcttagg gcttgagctt tcatgattcg ctccatgttt gctgtccagc    420

catatgtgct tgngacaatc agcatggaaa ntcaccaatc cggttgacac aaccacnttt    480

cactttttct ccaaanngcc tttcatgant ttcnnanggt ntcaaacttt gggttttcnc    540

ntnccgggtc ntttcncntt ttaaaccctt nggaattccn gccttttttg ggacnnacnn    600

taagnttt                                                             608
```

<210> SEQ ID NO 533
<211> LENGTH: 593
<212> TYPE: DNA
<213> ORGANISM: Homo sapiens
<220> FEATURE:
<221> NAME/KEY: misc_feature
<222> LOCATION: (1)...(593)
<223> OTHER INFORMATION: n = A,T,C or G

<400> SEQUENCE: 533

```
acacatttgc tgatggcttc tcaaaacctg agccgagaat agggtctgat agcccagcca     60

agtttaaaag cagacacaca cgaatgtagt atcgttgtgc ctgaaatgac cattctgggt    120

tgtttagaat ccagaatcat caaaagccat gtggtatgag gaagtaataa atatcctctt    180

gaatcttctt accctatttt gcacaaatgg atggctgcat gaacagctct tgtaaattgc    240

tctgagtcca caccaataga aacctgcact cattctatag ctacagaggg tttgttggct    300

taaggggact ttatcatctc agcattaatt tccctttttaa agctattctc aaggttggac    360

tgtctcagag ataaacaaag aggaatcctt ttggcttaga agccaactgg cttactcaga    420

cttcctccct tcctactcca attcccacac taccatanta tcntcttgac tagaaaatca    480

attatttacc tgacataagg gcaagtctat tctttttcca nnccttgccc tnggggcctt    540

ggnaanaaaa atccntgcct ttttggaana agttttggga cnngcttagg ttt           593
```

<210> SEQ ID NO 534
<211> LENGTH: 608
<212> TYPE: DNA
<213> ORGANISM: Homo sapiens
<220> FEATURE:
<221> NAME/KEY: misc_feature
<222> LOCATION: (1)...(608)
<223> OTHER INFORMATION: n = A,T,C or G

<400> SEQUENCE: 534

```
ggtacacttc tgtttatatt taaacaacaa agaaaaaagc atctacacac ttaaaaaatt     60

aattcaatat tcctaaatct attttaactc attttaaaat actacataca gaagccagaa    120

tgcagggtta agaatggaat aaggtgggga gaagaagggg accacgaaga aaaacactta    180

gacaattact tgtctgttgt gggtaaagca acaggaatcc tgggagatac aagaaatcag    240

taacaacttt gctcataact gatattttcc cctcatgttt gtttttaata acgtccatat    300

gggtgctctc tgtatgctcc cttcactggc ctagcaggag gggccttnag cgacggcctg    360

gtcccattcc agtccgtcct ggccataagc ttcataagaa tcttgaacct ncccatgtcc    420

atagtcataa tattctgagt ccccttgact ctggctgnaa ataancttcg tagccttnga    480

actttggtct gcgnatgnat natcatatnc ctaatcntca naagnttntn gngcccgaag    540

ttggnggcaa gggttctttn ggaanccccct tnccngcctt tggggnctgg acncnctnan    600

agnggggg                                                             608
```

<210> SEQ ID NO 535

```
<211> LENGTH: 603
<212> TYPE: DNA
<213> ORGANISM: Homo sapiens
<220> FEATURE:
<221> NAME/KEY: misc_feature
<222> LOCATION: (1)...(603)
<223> OTHER INFORMATION: n = A,T,C or G

<400> SEQUENCE: 535

acaaagtgac ccctcgctcc tgccaccggt ttgagcaagc gttctacacc tatgacacgt     60

cttcacctag tatcttgaca ttgacagcca ttcgccacca tgtccttgga actatcacca    120

ccgacaaaat gatggatgtc actgtgacta tcaagtcttc catcgacagt gaacccgcct    180

tggtcttagg ccctctgaag tctgtgcagg agctgcggag ggagcagcag ctggctgaga    240

tcgaggcccg caggcaggag agggagaaaa acggcaatga ggaaggtgaa gaaagaatga    300

ccaagcctcc cgtgcaggag atggtagatg agttacaagg cccccttctcg tatgatttct    360

cttactgggc gcnggnctgg agagaaaatt actgnttcac ngtcatctna agaactgctc    420

ttttatcccc ctttcaatgg aaagcncgtt gntcangtgg gaagaaagct tgcncaaggg    480

aaanttggat tcgagatncn ccgggaaaag gccaggcctg gtttttaaaa agggcccnaa    540

tncccccccgg nanttgnaaa gggaatccna aattggtctt ccntnngaaa aggggncaag    600

ttn                                                                  603


<210> SEQ ID NO 536
<211> LENGTH: 581
<212> TYPE: DNA
<213> ORGANISM: Homo sapiens
<220> FEATURE:
<221> NAME/KEY: misc_feature
<222> LOCATION: (1)...(581)
<223> OTHER INFORMATION: n = A,T,C or G

<400> SEQUENCE: 536

ggtactcctg ggaggctttt gacagccacg ggcaggagag cagcggccag cttccccgagg     60

agctctttct gctgctccag tctttggtca tggctaccca cgaaaaggac acggaagcca    120

tcaagtcgct gcaggtggag atgtggccac tgttgactgc tgagcagaac cacctccttc    180

acctcgttct acaagaaacc atctccccct caggacaggg agtctgatcc atcccattca    240

cccagtgact tctttttgcc caggcctgga ctttttgcat cagtcacgtt aaccagatga    300

ctttgcctgt taccaaacct catgcatcca cgtttgcgtc tggggaggaa taaaaagaca    360

tcgttcccgc ttctgcgttt tgntattcct actgccgcca taggaattat ttcgtggctg    420

aacgttaccc agcancccga gaacactttt ggatagaatt ngagttgagg acattggctg    480

gcttttaaaa ancccnnctt ggaaatngna atncctttcg ntcctttctc cggnggttcc    540

ncctnanggn anttttggtt cgctttgntn caaagngagg g                        581


<210> SEQ ID NO 537
<211> LENGTH: 568
<212> TYPE: DNA
<213> ORGANISM: Homo sapiens
<220> FEATURE:
<221> NAME/KEY: misc_feature
<222> LOCATION: (1)...(568)
<223> OTHER INFORMATION: n = A,T,C or G

<400> SEQUENCE: 537

ggtacggact actcccctca catgcgtcct acctgtgaaa ctctgggaag caggaaggcc     60

caagacctgg tgctggatac tatgtgtctg tccactgacg actgtcaagg cctcatttgc    120
```

```
agaggccacc ggagctaggg cactagcctg acttttaagg cagtgtgtct ttctgagcac    180

tgtagaccaa gcccttggag ctgctggttt agccttgcac ctggggaaag gatgtattta    240

tttgtatttt catatatcag ccaaaagctg aatggaaaag ttaagaacat tcctaggtgg    300

ccttattcta ataagtttct tctgtctgtt ttgtttttca attgaaaagt aattaaataa    360

cagatttaga atctagtgag agcctcctct ctggtgggtg gtggcattta agggtcaaac    420

cancnanaaa tgcttggtgc tggttnaaaa agctcangtg gctgctgtgg tggctnatgc    480

ctgnaatcca acattntggg aaggccaagc cggaaaactg ttgngccnng anttaaaata    540

anctgggcac ntacaanntt cgtttnna                                        568
```

```
<210> SEQ ID NO 538
<211> LENGTH: 598
<212> TYPE: DNA
<213> ORGANISM: Homo sapiens
<220> FEATURE:
<221> NAME/KEY: misc_feature
<222> LOCATION: (1)...(598)
<223> OTHER INFORMATION: n = A,T,C or G

<400> SEQUENCE: 538

ggtttttttt ttttttngtt catgtctttt attaactcat acagttactt gtcttctggt     60

ttgttgaaac agtaagtcag acaacntttg ccacaataat gtctgtcaaa gtgacttgcc    120

ataaanaccc cancaccaca ttcatcataa gggcactctt gacgaaggcg actaattttg    180

ccattctatt tcaggacagc cagctaaacc ttctntctct tgtgcttatt cttcttggga    240

gtggtgtaag acttcttctt ccttttctta gcaccaccac gaagtcttaa cacatgatga    300

agantagact ccttttgaat attgtagtcn gacaagagtn catacatcat accaacttnn    360

tanatacaca gctcagttaa ttagcttgat ggcacagtta tngttnggaa nagagangag    420

tgcancatan gnangagtga ngnggngatt cccacaattt tctnagaacn gaanagtagg    480

nngaattagt aggtactgga aatgaaatnn ggcttagcct gnctggntta gaaanaagaa    540

ttcnaagccc tttgtcaana nttntcaaaa agtnacttta ngcctatntt gcgggnag      598
```

```
<210> SEQ ID NO 539
<211> LENGTH: 607
<212> TYPE: DNA
<213> ORGANISM: Homo sapiens
<220> FEATURE:
<221> NAME/KEY: misc_feature
<222> LOCATION: (1)...(607)
<223> OTHER INFORMATION: n = A,T,C or G

<400> SEQUENCE: 539

ggtacaggct ttaacagaaa ttcaggagtt catcagcttt ataagcaaac aaggcaattt     60

atcatctcaa gttcccctta agagacttct gaacacctgg acaaacagat atccagatgc    120

taaaatggac ccaatgaaca tctgggatga catcatcaca aatcgatgtt tctttctcag    180

caaaatagag gagaagctta cccctcttcc agaagataat agtatgaatg tggatcaaga    240

tggagacccc agtgacagga tggaagtgca agagcaggaa gaagatatca gctccctgat    300

caggagttgc aagttttcca tgaaaatgaa gatgatngac agtgcccgga agcagaacaa    360

tttctcactt gctatgaaaa ctactgaagg agcttgcata aagagtcaaa aaaccagaga    420

cgaattggct ggtgagctgg ggtgccaaac tactggcgnc tggagcccct tacccgggag    480

cccgggnccc anggnttggt cttganncag gggcttcaat tggccttgaa aacnagtctt    540
```

```
ttttggttgg attagnaacn cacngtgtca agctncttta agccaaaaat tntccnggnt    600

tttnccg                                                              607


<210> SEQ ID NO 540
<211> LENGTH: 432
<212> TYPE: DNA
<213> ORGANISM: Homo sapiens
<220> FEATURE:
<221> NAME/KEY: misc_feature
<222> LOCATION: (1)...(432)
<223> OTHER INFORMATION: n = A,T,C or G

<400> SEQUENCE: 540

ggtactgatc attctatttc cccctctatt gatccccacc tccaaatatc tcatcaacaa     60

ccgactaatc accacccaac aatgactaat caaactaacc tcaaaacaaa tgataaccat    120

acacaacact aaaggacgaa cctgatctct catactagta tccttaatca tttttattgc    180

cacaactaac ctcctcggac tcctgcctca ctcatttaca ccaaccaccc aactatctat    240

aaacctagcc atggccatcc ccttatgagc gggcgcagtg attataggct ttcgctctaa    300

gattaaaaat gccctagccc acttcttacc acaaggcaca cctacacccc ttatccccat    360

actagttatt atcgaaacca tcagcctact cattcaacca atagccctgg ccgncctcgg    420

ncgtgaccac gc                                                        432


<210> SEQ ID NO 541
<211> LENGTH: 597
<212> TYPE: DNA
<213> ORGANISM: Homo sapiens
<220> FEATURE:
<221> NAME/KEY: misc_feature
<222> LOCATION: (1)...(597)
<223> OTHER INFORMATION: n = A,T,C or G

<400> SEQUENCE: 541

gggtaccggc gtgtcaaaaa aatgtcagat gacgaggacg atgacgagga ggaatatggc     60

aaggaggaac atgaaaaaga agctattgcg gaagaaatct tccaggatgg ggaaggggaa    120

gaagggcagg aggccatgga ggcccccatg gctcctccag aggaggagga agaagatgat    180

gaggagtcag atattgacga cttcattgtg gatgatgatg gacagcctct gaaaaaacct    240

aagtggcgga aaaagcttcc tggatacaca gacgcggccc tgcaagaagc ccaggaaatc    300

ttcggtgtgg actttgacta tgatgaattt gagaaataca atgagtatga tgaagaactg    360

gaggaagagt atgagtatga ggatgatgan gctgatggtg aaatccgatg ccccccccaga    420

agaccaccca gaaacngtgt tgagcccntn ggagcntttt ttgaaatggt ttganncccn    480

gtngggcttt naaagccnnc nccttacnna ttnggggcct tngantcccn gcccttncct    540

gccttnaaag ggtccanntt ccgttncttc ccagtcangg ggnttaaaaa tnatnan       597


<210> SEQ ID NO 542
<211> LENGTH: 577
<212> TYPE: DNA
<213> ORGANISM: Homo sapiens
<220> FEATURE:
<221> NAME/KEY: misc_feature
<222> LOCATION: (1)...(577)
<223> OTHER INFORMATION: n = A,T,C or G

<400> SEQUENCE: 542

gcccaaggct cagccagtct ctatttaaga aaatttaaca aatacgagta accctgtccc     60

aatcactgaa tctctagtta ctactcttag aaacacctgt ggcttcttgg ccctcctgtt    120
```

```
gcccgctctg aatctctctg cagtctacaa aatcgcccca gtcaactctc cacttggagg    180

gaattgtcca gtgtggcccc tagaattgag tcacccccta gataccaact gtctgacccc    240

gaggagctct gtaagtccct gctcctcctc ttccctttgg ggctggtgct gccactcagc    300

aataatcctc ttttctctgt gctttcttag gtccctgtcc tctgtctttg aggctggtta    360

ggaagcaaga gtcctgatct ttcatgctgc acaatatgag catgcaaaaa gctttttcca    420

gcagaacatg ttccctcgtc tccagttgcc cggaaaagga atttggggga tcaaagaact    480

tagcttggnc taccccatgg ttgagttctg gccttggaaa ancccaagcc aagtnangga    540

ccnagacctt ggccggaaac cnttaagggc aattccn                             577
```

<210> SEQ ID NO 543
<211> LENGTH: 607
<212> TYPE: DNA
<213> ORGANISM: Homo sapiens
<220> FEATURE:
<221> NAME/KEY: misc_feature
<222> LOCATION: (1)...(607)
<223> OTHER INFORMATION: n = A,T,C or G

<400> SEQUENCE: 543

```
tcgagcggcc gtccggcagg tacattattg ggcctcattt gcccagcaac ggggcatcca     60

gattgagtgc agtcagggcc atgtcttcac tcgggggact cancaggctt atacctcaag    120

caggcacagt gatgcggcgc cttatctctg attggagtgt tacccanatg gtgagtgacc    180

taagtcaggt gaccgttcac ctgatggcct cacccactga agagaatgct gatcactgtc    240

ttgatccctt ggtaacaaag acccacctgc tgagcttgtc ctccctcacc taccaacggn    300

ntancaattc gcacagctga cgaggagctc tctgntcgtg atggggatcc tacctttcat    360

acanatcagc tgcacttagt nnanttacng atttctggac aaactaccaa tcganacatt    420

gcctttgggt aattgatggg tccctnggcc gngacaanct taggggcgaa tttccatnca    480

actgggcggg ccgntactan cngnatccta nctttgggac ctaatcttgt tgtanccatg    540

gcnttacntg tacctctggg taatcntatc cngtnaanta tccnnanctt tactngccng    600

anntnng                                                              607
```

<210> SEQ ID NO 544
<211> LENGTH: 570
<212> TYPE: DNA
<213> ORGANISM: Homo sapiens
<220> FEATURE:
<221> NAME/KEY: misc_feature
<222> LOCATION: (1)...(570)
<223> OTHER INFORMATION: n = A,T,C or G

<400> SEQUENCE: 544

```
acttgggctt ctttcagctg cttcaacaga gtggcagcaa ccaagctgga gtccaagccc     60

cctgataaaa ggcagccaat ccttctgtct gtcatcaaac gtttctttac agcattatta    120

aaaaggatcc tgaggttgtt cttcacagtt tctatctcaa aacctggaaa gagtttctcc    180

acattgtcat agagggcgtg caggggttca tcccgacagt gatgatattt aaccatttcc    240

acggatgcaa ctttgccatt tggctttaaa tccaaaactt catagtgtcc aggaagaaaa    300

ggctccactt ttaaaaaggg agtcgcggag tgcttcaatg taacaagacc tttagcttct    360

gaacatacag ccaaaaatcc atcttctgtc attgctttaa acaaaggtct gactccatat    420

gtatctctac ccaggaacac tttcttattg gcagtatcca gtaaaacaaa tgcnaacaca    480
```

-continued

```
ccatccaaca tacaaattgn ttgctcaatt cctcctttgg cataaagatg aaggattatc    540

tcaccaatcc acttttggnc tggnattcaa                                      570


<210> SEQ ID NO 545
<211> LENGTH: 330
<212> TYPE: DNA
<213> ORGANISM: Homo sapiens

<400> SEQUENCE: 545

accgtccagg atctccaggt catagccatc agccagacac cagttgacgc ttgtctcctt     60

agtcttcccg gattgccttt tggaatcata tatgctgact ctgccaacct tggggtggtt    120

gacaataaag ggatgtcgta gtccatcctc aaatgcactc ccatctcttg tcacacgaca    180

gcaaatagca cgggtcagat gcccttggct gaaaaggtaa cccaatgtga cagatttgag    240

ataaatgggc tgcaggaagt gggtcaacag tgccccttgc aggcccagca cgttccagcg    300

taggattttg tcactacagg acatggtacc                                      330


<210> SEQ ID NO 546
<211> LENGTH: 589
<212> TYPE: DNA
<213> ORGANISM: Homo sapiens
<220> FEATURE:
<221> NAME/KEY: misc_feature
<222> LOCATION: (1)...(589)
<223> OTHER INFORMATION: n = A,T,C or G

<400> SEQUENCE: 546

ggtaccagag gcactgtgga tgggccacgg aatgaattgt cccgggtctc caaaaagaac     60

atttttcttc tatttaagaa gctctgctcc ttccgttacc gcagggatct actgagactc    120

tcctatggtg aggccaagaa agctgcccgt gactacgaga cggccaagaa ctacttcaaa    180

aaaggcctga aggatatggg ctatgggaac tggattagca aacccagga ggaaaagaac    240

ttttatctct gcccagtata gtatgctcca gtgacagatg gattagggcg tgtcatacta    300

gggtgtgaga gaggtaggtc gtagcattcc tcatcacatg gtcaggggat ttttttttt    360

cctttttttt ttctttttaa gccataattg gtgatactga aaactttggg gttcccattt    420

atcctgcttt ctttgggatt gctaagcaag gncttggcca agcccccct tttttcccc    480

caaggngaaa agnccnaaan cctaanaagn tatcctttct ttttanccca aggcttccct    540

tagcccttgg nccncctggg ggncccnttc ctttaaaang tttnggttt                589


<210> SEQ ID NO 547
<211> LENGTH: 613
<212> TYPE: DNA
<213> ORGANISM: Homo sapiens
<220> FEATURE:
<221> NAME/KEY: misc_feature
<222> LOCATION: (1)...(613)
<223> OTHER INFORMATION: n = A,T,C or G

<400> SEQUENCE: 547

ggtaccaggt ttaaatgtag tcttctggag aagtattttt gacattgagc tctgggacag     60

gacaccttgg gtttgtggac tgcagcccac tatgatgtta ttacttctct ggccaggcct    120

ccagtggaag tgcacaggca ctcccaatgt tgttaatgct ctgtcttcca tttgttctgg    180

aatcctacgt gttggtctgt ggttccatgc attagctgtt tgtaaataat gcatttgcat    240

actgaaaaag gaatgccacc tgccacagtt gatggtgagg aagctccttt gacgtggtgc    300

aattttgatg agatgtctct ggggacacga ggatgcccta atgatgctga cttgtcatgg    360
```

```
ttgcagcatt tgaacttttg gtgttaaaaa naaaaaacctg tnagtctgga accctggcaa   420

cattttacaa ccctngnatt tttaaaagaa ggcntttctt attaaaaaaa ttcnnaaacn   480

ccaccagnnc ctattgggtc aaaccaattc ctncncttnt ggggccnctg gttttttaaa   540

ggggcctttg ctngaancaa ttggnantcc cangggtttc ganaaaaant gaaatggttt   600

tnnnccnccc tcc                                                      613
```

<210> SEQ ID NO 548
<211> LENGTH: 578
<212> TYPE: DNA
<213> ORGANISM: Homo sapiens
<220> FEATURE:
<221> NAME/KEY: misc_feature
<222> LOCATION: (1)...(578)
<223> OTHER INFORMATION: n = A,T,C or G

<400> SEQUENCE: 548

```
ggtacatatg tattttacaa tatacttacc atgagtttag aaaaatttga attcccacca    60

ttctatacca accaaccaca accccactgt ctacattccc cagccagaag acttagaatc   120

catgcttgag ccaaagcctc cattaaaacc actgcccgac cctgcattgg atgctgatcc   180

ccaaccaatt gctgcaccag aattagagcc actataagag ttatttccag aaccgaaggc   240

ctggtttggc tccctctgca tgttgccttg gttttggtta ttacccgatg ggcctgactg   300

gttctgctgg ctggctaaca tgcccatcat accccaactg ctctgtantg ctgcctgggc   360

ggcagccatc atggctggat taatgctgaa cgcacccaag ttcatccacc accatattac   420

tacctttgat ggttnccaaa ncaagtcacc cctntggtta ttaccaaatc caccctggat   480

cccaaagccc cctgggatta ccccccaaan tttcncttnt ttntaaatng ccaatgntta   540

tggggcttaa ggtcngcntt ngatttttga accctgnt                           578
```

<210> SEQ ID NO 549
<211> LENGTH: 620
<212> TYPE: DNA
<213> ORGANISM: Homo sapiens
<220> FEATURE:
<221> NAME/KEY: misc_feature
<222> LOCATION: (1)...(620)
<223> OTHER INFORMATION: n = A,T,C or G

<400> SEQUENCE: 549

```
ggtacgcatg tcacttccca tcatggaacc actcatggtt gctggtggaa cgccaggatt    60

agcttcataa cctatgccac caccacctcc tagaggtgga aatttctggc ctcctgaacc   120

atagggatct cccatgttca ttgctcctcc gccacccatt cgcatgtctc tttcccgtgg   180

atccatgtag cccattcggc tgtaactttc ctctctttgg cgcctcattt gttcttccat   240

ctcacgttga cgaatcatca tctcttcctc tcttctacgt cgntcctcct cttgcctcaa   300

ttgcatttct ttacgtttct gcatttcttg attgtgaaag ttcttccatg cgtcttaatt   360

cttcctgtcg tctcatcaga tcttggcgca aaagatttgc ctgatgttca tgatanggca   420

ttttccattt cacttttcca atttggnctt ttggcanctt ttcanngntg tntttcaaac   480

ttnggtncct tttggctggg nttttcccat ntcnatncan atgagnnttg nnntgggngg   540

ggagnantgg tngggnccta nnctgtccgg cccntntnaa angggcgnaa tttcnnaagc   600

cncatgggng ggccggtant                                               620
```

<210> SEQ ID NO 550

<211> LENGTH: 577
<212> TYPE: DNA
<213> ORGANISM: Homo sapiens
<220> FEATURE:
<221> NAME/KEY: misc_feature
<222> LOCATION: (1)...(577)
<223> OTHER INFORMATION: n = A,T,C or G

<400> SEQUENCE: 550
acctatgttt cacctcctgg aaatgaagag gaagaatcaa aaatcttcac cactcttgac 60
cctgcttctc tggcttggct gactgaggag gagccagaac cagcagaggt cacaagcacc 120
tcccagagcc ctcactctcc agattccagt cagagctccc tggctcagga ggaagaggag 180
gaagaccaag ggagaaccag gaaacggaaa cagagtggtc attccccagc ccgggctgga 240
aagcagcgca tgaaggagaa agaacaggag aatgaaagga aagtggcaca gctagctgaa 300
gagaatgaac ggctcaagca ggaaatcgag cgcctgacca gggaagtaga ggcgactcgc 360
cgagctctga ttgaccgaat gggtgaatct gcaccaagca tgaaccaatt ggggagcatc 420
aagtccccca cttgggccac acttacccac cttttccaga agtggcttct gnctaccttt 480
nacttanngc catggtgggn accttaattc ccattcccca gggggaagnt ttgaattacc 540
aaagggaagg gtttnacctn gttttagaaa ttngccc 577

<210> SEQ ID NO 551
<211> LENGTH: 573
<212> TYPE: DNA
<213> ORGANISM: Homo sapiens
<220> FEATURE:
<221> NAME/KEY: misc_feature
<222> LOCATION: (1)...(573)
<223> OTHER INFORMATION: n = A,T,C or G

<400> SEQUENCE: 551
ggtacaaacc atcttctact gtgacttctt ctacttgtat gtgaccaaag tccttaaggg 60
aaagaagtta agtcttccaa tgccaatctg aggaccttca gagacagtct acgccttaac 120
aagcacatga aggaaactat tttgaatgtt ctctttggca acttatccat aatttgggat 180
caaatgttaa aaccagaaaa gtgtttagtg tggatttcag caaaacctga tcatcccacc 240
cagaagacct tctcatcaat agatcgccct taaagaccca ttgtaaggtc ataaaaaacc 300
tcggccaact gcacaaagat ggtgcctcac tgcaacaaga aaccttaagg tgtcttaccg 360
acgaaataaa aaacataaat gattgntctc caaaggcctg agggcaagac tcatgatgag 420
caagtcaacc cccaatctgg aacaatggcc ttctnttaaa atgncccact taagacccgt 480
taaaatatta ggganctggc ccggcggccc tttaaanggc naattcngnc nctggnggcc 540
ntacttangg gaccaacttn ggnccangtt ngg 573

<210> SEQ ID NO 552
<211> LENGTH: 581
<212> TYPE: DNA
<213> ORGANISM: Homo sapiens
<220> FEATURE:
<221> NAME/KEY: misc_feature
<222> LOCATION: (1)...(581)
<223> OTHER INFORMATION: n = A,T,C or G

<400> SEQUENCE: 552
ggtacattca ggaataatca tatcactggt tacatacaac tctcatgcaa agaaaaccct 60
caaaaaacaa acaaaaaaaa ccctcagtta gttgttttct taagtctaat taatccaaac 120
taataatagc catttaatta gcaatctgta aatcagagag gtatagaaat tcagcagcta 180

```
aactgtattt tccacctata gcactgctgc tactcaaact attttcttca cgtattagaa    240

gaattcatag gcattgatgg tcaaaataag aatttcaaca tagcagcaaa tgacagaaga    300

gtgagagaaa gagctcctaa tgtggtgaca gtcttaatga tcctttaaaa ggtagaagat    360

tgngtgcgta tgtgtggaaa ggagtaggaa agaaaagcat gaggttaaga caggtattta    420

aagggaatgg cgagatagct accttagaat atttattttt ttaaaaaact gctctgaaat    480

ctgcccagtg tacctgcccg gcngncnttc naagggcnaa ttttgncnna tntnnttcan    540

cttggcgggc cgtnnacctg gntttttaan ggccccantt c                        581
```

```
<210> SEQ ID NO 553
<211> LENGTH: 575
<212> TYPE: DNA
<213> ORGANISM: Homo sapiens
<220> FEATURE:
<221> NAME/KEY: misc_feature
<222> LOCATION: (1)...(575)
<223> OTHER INFORMATION: n = A,T,C or G

<400> SEQUENCE: 553

ggtactgccc ttggaacctt tgctgagggc tttgtaattc ctagttaaaa tccatttgta     60

atattgtttc tgtaaagcac tcatttccat tcttaaaatc tgctcaacct tggcaggaag    120

agatttttcc acatctttct taactcggcg taacagaaat ggctcaagct ccttgtgaag    180

gcttgcataa ccatattctc tccctttgcc atgttcttct tcaaaatctt cccaggaaga    240

aaacttttct ggcataatga aatgtagcaa agaccagagc tctttgaggg aattctgtag    300

aggagttcca gtgataagga gacgatgatt ggatttaaaa tctattaaag ttttatacag    360

aagggagtca tcattcttta atcggtgtgc ttcatcaaca cctataaatg cccaatttaa    420

gaccttccag ggaatgcctt aaaataatag aaaaacagta ttttgagaga aaaaccggaa    480

ttcaaattta gcccttccat ttaatctgac tcaattatta aaatgaaatn naaattaaaa    540

accaactttg gcctaatttt caaataaaaa atcgn                              575
```

```
<210> SEQ ID NO 554
<211> LENGTH: 548
<212> TYPE: DNA
<213> ORGANISM: Homo sapiens
<220> FEATURE:
<221> NAME/KEY: misc_feature
<222> LOCATION: (1)...(548)
<223> OTHER INFORMATION: n = A,T,C or G

<400> SEQUENCE: 554

acggaggact ccattaataa catggaaatc tccactctga aagcgattca ccatttctgt     60

cagcaagtca ggccatttct gtggaaaatc ttctctgcca ataatgctaa ttgcatcact    120

taactgcttc tgaatttgct ctgggctgct aagcatcaag tgcactatgt tggctttaat    180

ggccactcga tcggcttcac aaattttgtt tggttcatct tcaacaattc tccagttcct    240

tttaatatag tttttgaatg ttactgaagc acatactttg ataacattat cctgggactt    300

ctccagtaat gtcaaaagca acagtggata attctgattt ccttcaacag attcaagaaa    360

tttctcagct ggacgtcgga tggcaggatc aggatcaagt gttttcttta aatattctgt    420

tagtgtttgc agatttgcat cgctgagttc cattgctata ggatctcgtg gggatacaga    480

aaccgaggaa ggaaccccag ccgcggaccg taactngcac taccccgcta cctngggcgc    540

gaaacacg                                                             548
```

<210> SEQ ID NO 555
<211> LENGTH: 576
<212> TYPE: DNA
<213> ORGANISM: Homo sapiens
<220> FEATURE:
<221> NAME/KEY: misc_feature
<222> LOCATION: (1)...(576)
<223> OTHER INFORMATION: n = A,T,C or G

<400> SEQUENCE: 555

```
actccctgca taacaagaga ttattttgga gacagttgat aaaaaccata catccttttt     60

attgttaagt cataaagagg tatcaaaatt aaaagcaaaa attacagggt aagacttaac    120

aaaactacta ggagcgtcaa aggaagtgaa aatgggacta ggcgcggggc aatatgaatt    180

aatgaacatg ggaaggacaa ggatggggag aacagtgagc atgtgctgaa gatactaggg    240

gagaggatct ggtgaaaaat ttgatcttag acaagcgcct aggtaaagaa ataatgggat    300

aagatttcta aaccccacta tgtgcttaag agtcatcctc gccattggcg ctgnctctgn    360

catcctctcc ttctcacctc tttttcatca tccttgatca actccagctt ggcatncccc    420

cgatcttcat tatcattaat cttccagtan gncccccttc ttagcanaag taatntgnac    480

ccccttana attcattttt ccatttgnct aaattttttt tccnggacnn gtnggnntgg    540

gcccttttng nnntaaaant tttaantctt acnggg                              576
```

<210> SEQ ID NO 556
<211> LENGTH: 613
<212> TYPE: DNA
<213> ORGANISM: Homo sapiens
<220> FEATURE:
<221> NAME/KEY: misc_feature
<222> LOCATION: (1)...(613)
<223> OTHER INFORMATION: n = A,T,C or G

<400> SEQUENCE: 556

```
ggtacctctt cccatgactg cacccagctc caggggccct tgggacagcc agagctgggt     60

ggggacagtg ataggcccaa ggtcccctcc acatcccagc agcccaagct taatagccct    120

ccccctcaac ctcaccattg tgaagcacct actatgtgct gggtgcctcc cacacttgct    180

ggggctcacg gggcctccaa cccatttaat caccatggga aactgttgtg ggcgctgctt    240

ccaggataag gagactgagg cttagagaga ggaggcagcc ccctccacac cagtggcctc    300

gtggttatta gcaaggctgg gtaatgtgaa ggcccaagag cagagtctgg gcctctgact    360

ctgagtccac tgctccattt ataaccccag cctgacctga nacttgtcgg aaaagctgtc    420

ttggggcctt ttatnaaata aaaagacttn agncnatgac aanggangt ttaagaangg    480

gacttgnggg gaantnggaa gnnannaanc ccttggttgg ggtttaagnn nccccacgtt    540

tggcccaggc angtggcttt ttccttnttg ggnccttngg tnncnttgng ggacanaagg    600

nnntttgnac ccc                                                       613
```

<210> SEQ ID NO 557
<211> LENGTH: 607
<212> TYPE: DNA
<213> ORGANISM: Homo sapiens
<220> FEATURE:
<221> NAME/KEY: misc_feature
<222> LOCATION: (1)...(607)
<223> OTHER INFORMATION: n = A,T,C or G

<400> SEQUENCE: 557

```
acctggatga aaagcagagg gaccccagaa tcgaagcgag caaagtgctg ctgtgccatg     60
```

```
gggagctgcg gagcaagagt ggacataaac tttacatttt cctgtttcaa gacatcttgg    120

ttctgactcg gcccgtcaca cggaacgaac ggcactctta ccaggtttac cggcagccaa    180

tcccagtcca agagctagtc ctagaagacc tgcaggatgg agatgtgaga atgggaggct    240

cctttcgagg agctttcagt aactcagaga aagctaaaaa tatctttaga attcgcttcc    300

atgacccctc tccagcccag tctcacactc tgcaagccaa tgacgtgttc cacaagcagc    360

agtggttcaa ctgtattcga gcggccattg ccccttcca gtcggcaggc aagtccacct    420

gaactgcagg gcctggccgg agctgtacga aaaatgtgaa ggggaaccac cctttgcgag    480

gaactnacag cccaaaggaa ggcattcaca gtttcagtgg tacttcaggt agaaagttga    540

tgaaaaccct taccagantg tggcttttgg cattgcaaat ggcagaggcc agcaagaact    600

taaannt                                                              607
```

<210> SEQ ID NO 558
<211> LENGTH: 355
<212> TYPE: DNA
<213> ORGANISM: Homo sapiens
<220> FEATURE:
<221> NAME/KEY: misc_feature
<222> LOCATION: (1)...(355)
<223> OTHER INFORMATION: n = A,T,C or G

<400> SEQUENCE: 558

```
acaaagacaa agaaacaaac tacattggca tttaagccaa tcaaaaaagg aaagaagaga     60

aatccctggt ctgattcaga atcagatagg agcagtgacg aaagtaattt tgatgtccct    120

ccacgagaaa cagagccacg gagagcagca acaaaaacaa aattcacaat ggatttggat    180

tcagatgaag atttctcaga ttttgatgaa aaaactgatg atgaagattt tgtcccatca    240

gatgctagtc cacctaagac caaaacttcc ccaaaactta gtaacaaaga actgaaacca    300

cagaaaagtg tcgtgtcaga ccttgaagct gatgatgtta agggcagtgt acctn         355
```

<210> SEQ ID NO 559
<211> LENGTH: 597
<212> TYPE: DNA
<213> ORGANISM: Homo sapiens
<220> FEATURE:
<221> NAME/KEY: misc_feature
<222> LOCATION: (1)...(597)
<223> OTHER INFORMATION: n = A,T,C or G

<400> SEQUENCE: 559

```
acccgcaaaa cgggacatag tatgtgacaa tctgcatcga tcatggacta ctaaatgcct     60

ttacatagaa gggctctgat ttgcacaatt tgttgaaaaa tcacaaaccc atagaaaagt    120

aagtaggcta agttggggag gctcaaacca ttaagggtta aaaatacatc ttaaacattg    180

gaaagctctt ctagctgaat ctgaaatatt accccttgtc tagaaaaagg ggggcagtca    240

gaacagctgt tccccactcc gtggttctca aaatcataaa ccatggctac tcttgggaac    300

cacccggcca tgtggtcgcc aagtagagca agcccccttt ctcttcccaa tcacgtggct    360

gagtgtggat gacttttatt ttaggagaag ggcgattaac actttttgac agtattttgn    420

tttgccctga tttgggggat tgntttgttt ttggtgggtt gttttggaaa aacnggttat    480

aaactgggtt tttgnangnt ttgggatttt aaagcccnaa ataaaaaann nnanaaaaaa    540

aaagnctttg gnctttgggc cggaaaccct taangggcna attccagcca ccttggg       597
```

<210> SEQ ID NO 560

<211> LENGTH: 559
<212> TYPE: DNA
<213> ORGANISM: Homo sapiens
<220> FEATURE:
<221> NAME/KEY: misc_feature
<222> LOCATION: (1)...(559)
<223> OTHER INFORMATION: n = A,T,C or G

<400> SEQUENCE: 560

```
gactttgagg caagtgtggg ccactgtggt ggcagtggag gtggggtgtt tgggaggctg     60

cgtgccagtc aagaagaaaa aggtttgcat tctcacattg ccaggatgat aagttccttt    120

ccttttcttt aaagaagttg aagtttagga atcctttggt gccaactggt gtttgaaagt    180

agggacctca gaggtttacc tagagaacag gtggttttta agggttatct tagatgtttc    240

acaccggaag gtttttaaac actaaaatat ataatttata gttaaggcta aaaagtatat    300

ttattgcaga ggatgttcat aaggccagta tgatttataa atgcaatctc ccttgattta    360

aacacacaga tcacacacac acacacacac acacaaaccn tntgcctttg atgttacaga    420

ttttantccg ttnattttta aggatagagc ctttatnggt gnnnanaaaa caatctggan    480

taaaaaaaac ncnccngcc ttgnatttng ncttnntngg ggtttcccca aanccattnn    540

nnttgncagg ctnggggng                                                 559
```

<210> SEQ ID NO 561
<211> LENGTH: 569
<212> TYPE: DNA
<213> ORGANISM: Homo sapiens
<220> FEATURE:
<221> NAME/KEY: misc_feature
<222> LOCATION: (1)...(569)
<223> OTHER INFORMATION: n = A,T,C or G

<400> SEQUENCE: 561

```
ggtacaagct tttttttttt tttttttttt tttttttact ttttgggana naggctagga     60

ggaggaaggg gtgaaaacag cgtctcactg gagtctcaaa agtgtatgaa tcttctggta    120

gtgcaaggat gggataagat ggccagggaa gtcagatgga aaatccccaa gattcttttt    180

gctactgatt tctataatta aaatatgaca tatgtaaggg actagtgcat gatattcaat    240

aaatgtcagt tgtctttcct aactaggttc ctcacaggct aggttatgcc tanatatcat    300

catcctcctt tcagggaatg aagctcacct agaaaactag ggaactaaaa gtgcaatatg    360

gtttgggtaa tgcagttggt tagctgctcc ccatcctccc aactcactat tccagggagg    420

ggctgaaaac agaaatggct cccctgaagc tanntagcat ggcatgcana gtcncatgaa    480

aggtttgggc tggaattttt aagccaagnc ctntttttttg gaaaaaaatn ttgggaaaaa    540

ancccnnccc tnctgnttcn nagctgttt                                      569
```

<210> SEQ ID NO 562
<211> LENGTH: 597
<212> TYPE: DNA
<213> ORGANISM: Homo sapiens
<220> FEATURE:
<221> NAME/KEY: misc_feature
<222> LOCATION: (1)...(597)
<223> OTHER INFORMATION: n = A,T,C or G

<400> SEQUENCE: 562

```
cgaggtacgg atgctacttg tccaatgatg gtaaaagggt agcttactgg ttgtcctccg     60

attcaggtta gaatgaggag gtctgcggct aggagtcaat aaagtgattg gcttagtggg    120

cgaaatatta tgctttgttg tttggatata tggaggatgg ggattattgc taggatgagg    180
```

```
atggatagta atagggcaag gacgcctcct agtttgttag ggacggatcg gagaattgtg    240

taggcgaata ggaaatatca ttcgggcttg atgtggggag gggtgtttaa ggggttggct    300

agggtataat tgtctgggtc gcctaggagg tctggtgaga atagtgttaa tgtcattaag    360

gagagaagga agagaagtaa gcccgagggc cgtctttgat tgtgtagtaa ggggtggaag    420

gtgattttat ccggaatggg aagtgatnct aaggggggtt gtttganncc cttttcntgc    480

cntaaantgg angtngaatt ccnnntnngg cncncatana ttanaggcca aaatnaaatt    540

gaanggnnaa aaaancttnn anggggggga ctgntnnntg agaacccccc taaaatn       597
```

<210> SEQ ID NO 563
<211> LENGTH: 574
<212> TYPE: DNA
<213> ORGANISM: Homo sapiens
<220> FEATURE:
<221> NAME/KEY: misc_feature
<222> LOCATION: (1)...(574)
<223> OTHER INFORMATION: n = A,T,C or G

<400> SEQUENCE: 563

```
acgccaagaa ccgtattctt tgccacaggg ttttatgtgg gacactttag acttgagtga     60

tgccgaagtg ctcaaggagt tatacacgtt gttaaatgag aattacgtag aagatgatga    120

caatatgttc cgatttgact attcacccga gttcctgttg tgggctctgc gtccaccagg    180

ctggctcctg cagtggcact gtggggtcag agtgtcttca aataaaaaac tggtcgggtt    240

cataagtgcc atcccagcaa acattcggat ttatgacagt gtgaagaaga tggtagaaat    300

caactttctt tgtgttcata agaagttgag atcgaaacgg gtagccccag tgctaatccg    360

agagatcact agaagagtga acctggaagg gatcttccag gctgtgtcaa aaagcacact    420

ctccanncct cngggccctg cattcctgcg cttntntnna gacactttcc ctttctattt    480

tactgnggtg actttttcaa acgctgtnac cccaaccctt anantttttn gcccttggcg    540

gnntatnggt taaanatcac ccttcccngg gttt                                574
```

<210> SEQ ID NO 564
<211> LENGTH: 600
<212> TYPE: DNA
<213> ORGANISM: Homo sapiens
<220> FEATURE:
<221> NAME/KEY: misc_feature
<222> LOCATION: (1)...(600)
<223> OTHER INFORMATION: n = A,T,C or G

<400> SEQUENCE: 564

```
ggtacagaat atttctaata aacctaaatt taatcacagt taaaatttct caaaagtatt     60

ttcaagtgct caagaatatt aaagtttggg gggaaatacc taagtcataa ataagcaagt    120

attccctcca agattcacta attgggataa aagtctcagg gtaagcccac aagaatggtc    180

tgcaataaag aaaaatcagg tctgtgtaga gtaatttctg ccatctttag cagaaaagcc    240

aaaaacattc tgagccaaat aaaagcaaag atcttttgat tcagcgcctt ttgttgtgtt    300

agttttaatt tctaacttct caacatgtta tagctcagaa attcccatat gcttactatc    360

tgtaataagg aactataacg ttaaagaaaa aattcagaga ccgtgatcat tttccatcat    420

aggtctggct ctctttggta gaaacagatc aagacttact ttatttttct cttccccncc    480

ngaagaaaan gggggggttta atggcnttta cccttgnnaa anaacccncg ngggtttaac    540

cttnaaattn ggnggggtaa aanancctaa ngntnagccc tttttnanaa ctnggggnaa    600
```

<210> SEQ ID NO 565
<211> LENGTH: 600
<212> TYPE: DNA
<213> ORGANISM: Homo sapiens
<220> FEATURE:
<221> NAME/KEY: misc_feature
<222> LOCATION: (1)...(600)
<223> OTHER INFORMATION: n = A,T,C or G

<400> SEQUENCE: 565
accatcggcc atgtggacca cgggaagacc acactgactg cagccatcac gaagattcta 60
gctgagggag gtggggctaa gttcaagaag taccaggctg tttgtgatcg tatcagccgc 120
tatgtgaaac agcctttacc tgatgagttt ggcagctcac ccttggagcc aggggcctgc 180
aatggctcca ggaacagctg tgaaggagaa gatgaggaag aaatggagca tcaggaagaa 240
ggcaaagagc agntttnana aacagaaggc agnggggaag atgagccagg aaatgacccc 300
agtgagacca cccaaaagaa gatcaaaggc cagccctgcc caaaaaggct tntttaccnt 360
cagtcttgtg aactcctatg gaacagctga cataaatttc actttgcagc tnatggaaaa 420
ctacntaaac tcaantnttc ganctacact tggncntgga tttgtgacnt ttgaaaactn 480
tggaganttt tnctatgnnt gtgcncnnaa atttntaggg nttntccnat aaatctctgt 540
tanccttttt gggnaccntt tcnaagnaag atntnangnc cctanggncc nttnaaaaan 600

<210> SEQ ID NO 566
<211> LENGTH: 576
<212> TYPE: DNA
<213> ORGANISM: Homo sapiens
<220> FEATURE:
<221> NAME/KEY: misc_feature
<222> LOCATION: (1)...(576)
<223> OTHER INFORMATION: n = A,T,C or G

<400> SEQUENCE: 566
ggtactgaac aggtaagtca tccctcagcc agagattagt ctacttcttc catgcgtgat 60
gtgtcgtcat ctccttcaag ggtgtttttc tttatttttg ttaatattaa aaagtctgta 120
tggcatgaca actactttaa ggggaagata agatttctgt ctactaagtg atgctgtgat 180
accttaggca ctaaagcaga gctagtaatg ctttttgagt ttcatgttgg tttattttca 240
cagattgggg taacgtgcac tgtaagacgt atgtaacatg atgttaactt tgtggtctaa 300
agtgtttagc tgtcaagccg gatgcctaag tagaccaaat cttgttattg aagtgttctg 360
agctgtatct tgatgtttag aaaagtattc gttacatctt gtagggatct actttttgaa 420
ctttttcatt ccctgnaggt gacaantctg catggacctg ccccgggcgg cccttnaaan 480
ggcgaanttc annncantgg ngggcnntct tngggnnccn ncctggncca aatntggggg 540
ancngggnca anctnttccn tggggaaatg gntccc 576

<210> SEQ ID NO 567
<211> LENGTH: 427
<212> TYPE: DNA
<213> ORGANISM: Homo sapiens

<400> SEQUENCE: 567
ttttggcagt aaatcaattt tatttgtgtt cacagaacat actaggcgat ctcgacagtc 60
gctccgtgac agcccaccaa cccccaaccc tctacctcgc agccacccta aaggcgactt 120
caagaagatg gaaggatctc acggatctca ttcctaatgg tccgccgaag tctcacacag 180
tagacagacg gagttgagat gctggaggat gcagtcacct cctaaactta cgacccacca 240
ccagacttca tcccagccgg gacgtcctcc cccacccgag tcctccccat ttcttctcct 300
actttgccgc agttccaggt gtcctgcttc caccagtccc acaaagctca ataaatacca 360
agagacctgc atttacagca gggggaacat ctcacaccct tgcataagtt aaaataaata 420
ttaccgt 427

<210> SEQ ID NO 568
<211> LENGTH: 616
<212> TYPE: DNA
<213> ORGANISM: Homo sapiens
<220> FEATURE:
<221> NAME/KEY: misc_feature
<222> LOCATION: (1)...(616)
<223> OTHER INFORMATION: n = A,T,C or G

<400> SEQUENCE: 568
acaagagtga tggcaatgtg actggaacag aaatagtttc taccaggcac acaaaagctc 60
ctgtaagccc cgtagttccg tcctgcaaag ggcctcagtg ggaaccaggt ctgcagaccc 120
gagtgggcag agagacgggt ggaagcaggt gccccagatg gtcccgcagg cgtcaccgtc 180
tggtttggag accttaaggg agttgtgctt caaacttctc tcccagggtc tcaggtggag 240
actagggagt ttgacctaaa ggtcctccaa ggagaggcca aggtcttgga gacagatctg 300
gtttaccatc ttttaacaaa aggcaaatgt cttctcttct tcagaaagag tcattaacac 360
taaaattctt ttcttnngaa gtttcttctt ttccgatgcc atcttccaag tttgnnccca 420
agaatgaaag gcgtcttttn ccnaagggtc aagggtttcc attcacnttg ggccccattg 480
naaaagggac tggttccttt tggggggttg ggncccggac cccccaaana aggnaanggn 540
ttttgtnccc aagcctttnt tcccngggg n gggaagggna anaacctttg ggcccgngna 600
acccacctta angggg 616

<210> SEQ ID NO 569
<211> LENGTH: 582
<212> TYPE: DNA
<213> ORGANISM: Homo sapiens
<220> FEATURE:
<221> NAME/KEY: misc_feature
<222> LOCATION: (1)...(582)
<223> OTHER INFORMATION: n = A,T,C or G

<400> SEQUENCE: 569
acagaatata acgcagcttg gcaggatgca tacggccctg cgcaggggaa agtatttcaa 60
atcagctggc aggttcaagc ctttctgcac tgtagacttt ccacactctg gaaaagaagc 120
aaacaaacaa accccaaaga acccccgaaa aaaacaaaaa ccatccggga ggtgcatgag 180
tccaatggga atgcaaccgt gatgccgctg tcctatgccc agtgacagca caggtcacgt 240
aagttacagc aggggagggg tagctcaagc tacagaggat tattgtcata ttgctaagac 300
agcataaatc cattcaaaaa aaaaaaaaaa aatccaaacc agggtaagta aagaaaggaa 360
aaccaaatct atacagcatt tacaacaaat aaatctctag ccagctgggg gtaaaatatg 420
catctatgta tagactatgt gtagggtaag aaaagctttt aatatnggtt anaaagaggn 480
cctttgatta aaggccttgg cccgaacncc cttaaggnnn aattcnagnc nattgggggc 540
cggtcnaagg ggatccaacn tgggnccaaa nttggngaat nn 582

<210> SEQ ID NO 570
<211> LENGTH: 557
<212> TYPE: DNA

<213> ORGANISM: Homo sapiens
<220> FEATURE:
<221> NAME/KEY: misc_feature
<222> LOCATION: (1)...(557)
<223> OTHER INFORMATION: n = A,T,C or G

<400> SEQUENCE: 570

```
ccgggcaggt acttcttgcc tttaagatag gcaccaggaa atctttcaag gatctcatag     60

tcactctcca atttatagag ggctgacaat ctggcttcca ttaaaatgag taatcgtcct    120

ctggcaacat ctttaatttt cacatattgc atttctggat taacacacac agcaaggtta    180

ctaggtagag tccagggagt ggttgtccaa gcaactaaag atacagtttc atcttcttcc    240

aaagggaaag ttacaaatac tgaaggatct tgaacatcct tataattctg gtgtgactcg    300

aagttggaaa gtggagtgtt acatgccgta gagaagggca tgactttcac acctctataa    360

acaaggcctt tatcatagag ttggttgaag acccaccaga ctgattccat gaattgtgga    420

tacagagttt tatagtcatt ggcaaagtna atncatcggc aagttgctac aggagacttc    480

actnannnaa atctcatcnc aatnnntgga ctnatggata cctnggannc ccntttngcc    540

caatctgggc ctngatn                                                   557
```

<210> SEQ ID NO 571
<211> LENGTH: 382
<212> TYPE: DNA
<213> ORGANISM: Homo sapiens

<400> SEQUENCE: 571

```
acactgctct cttcctggca attgacagtg gtaaccctcc cgctacgggc actgggactt     60

tgctgataac cctggaggac gtgaatgaca atgccccgtt catttacccc acagtagctg    120

aagtctgtga tgatgccaaa aacctcagtg tagtcatttt gggagcatca gataaggatc    180

ttcacccgaa tacagatcct ttcaaatttg aaatccacaa acaagctgtt cctgataaag    240

tctggaagat ctccaagatc aacaatacac acgccctggt aagccttctt caaaatctga    300

acaaagcaaa ctacaacctg cccatcatgg tgacagattc agggaaacca cccatgacga    360

atatcacaga tctcagggta cc                                             382
```

<210> SEQ ID NO 572
<211> LENGTH: 621
<212> TYPE: DNA
<213> ORGANISM: Homo sapiens
<220> FEATURE:
<221> NAME/KEY: misc_feature
<222> LOCATION: (1)...(621)
<223> OTHER INFORMATION: n = A,T,C or G

<400> SEQUENCE: 572

```
acaagctttt tttttttttt tttttttttt ttttttgcc atttattgcc atgttttaaa      60

attcgtgcaa aatatntgaa gccctggaca gagaatacaa agtgatattt tcccaagaaa    120

cntaaaacta ggaaaagggg tgggggacat tttcccacca nagctncccc cacgccaggc    180

cccaagcagg gtgaggcctn caacccggcc agctgagcag ggaggactaa gagctacaat    240

ctggaccang gaaggagggg tggaatttgc aacagngtnt taactaccaa cgagaggaaa    300

gccagtcaac tgtacaacct cttgcggagc ggggaaggtg actaccngaa caagacatgc    360

tgcctgccct gtgcttgtgg gctgcaaagt gggnntccaa taagtggttc catgaacgag    420

gacaggagtt tttganccctt gnggatcaac aaaangttna ctgacatccn tttctgcctt   480

tccctttcct ggnnctttta anccatgtca acnntgacan acncctntng atggtccctt    540
```

tggnagtcct aatnaggctg atttttggan nantnaatnt ttttttggaa cncaaggnga 600
acntttttgg ngaattttng g 621

<210> SEQ ID NO 573
<211> LENGTH: 296
<212> TYPE: DNA
<213> ORGANISM: Homo sapiens
<220> FEATURE:
<221> NAME/KEY: misc_feature
<222> LOCATION: (1)...(296)
<223> OTHER INFORMATION: n = A,T,C or G

<400> SEQUENCE: 573
ggtactcatt gtgctctttg gtgcctttcc tttcctacag aaaaggaagt gatctatacc 60
aaggtttgca gggaagtcaa atgttctcaa cctttcatgc cctctggtta ctcatctggc 120
ttgcaaaata atttggatcc ggacagattt ccagtatttt caagtccgct gctttcccgc 180
aaagctcggc ctaacctgga gctagttagg tccgcaggcg ccaccgncgg cgcactccgg 240
agaagaagct ccttcttcag ccgcccagga gagttcctcg agaaagatgc cgccgc 296

<210> SEQ ID NO 574
<211> LENGTH: 616
<212> TYPE: DNA
<213> ORGANISM: Homo sapiens
<220> FEATURE:
<221> NAME/KEY: misc_feature
<222> LOCATION: (1)...(616)
<223> OTHER INFORMATION: n = A,T,C or G

<400> SEQUENCE: 574
ggtactccaa cgccaccctg tgcagaaatg agagaagaca gtgctagagt ctatgaaaac 60
gtgggcctga tgcaacagca gaaaagtttc agatgagaaa acctgccaaa acttcagcac 120
agaaatagat gtggactttc accctctccc taaaaagatc aagaacagac gcaagaaagt 180
ttatgtgaag acagaatttg gatttggaag gcttgcaatg tggttgacta ccttttgata 240
agcaaaattt gaaaccattt aaagaccact gtattttaac tcaacaatac ctgcttccca 300
attactcatt tcctcagata agaagaaatc atctctacaa tgtagacaac attatatttt 360
ataggaattt gtttgaaatt gaggaagcag ttaaattgtg cgctgtattt tgcagattat 420
ggggattcaa attctagtaa taggcttttt tattttattt ttataccctt aaccaggtta 480
attttttttt ttcctcattg gtnggggatg atgagaagaa atgattnggg aaaattaagt 540
accaacgnac tagaaaagtg agaaccattc tatttcccnt ntggttccng gagnggataa 600
ttcatttgan ggcttn 616

<210> SEQ ID NO 575
<211> LENGTH: 614
<212> TYPE: DNA
<213> ORGANISM: Homo sapiens
<220> FEATURE:
<221> NAME/KEY: misc_feature
<222> LOCATION: (1)...(614)
<223> OTHER INFORMATION: n = A,T,C or G

<400> SEQUENCE: 575
ggtacaaaca ttttacaaaa aagaacatta ccaatatcag tggcagtaag ggcaagctga 60
agaataaata gactgagttt ccgggcaatg tctgtcctca aagacatcca aactgcgttc 120
aggcagctga aacaggcttc tttcccagtg acaagcatat gtggtcagta atacaaacga 180

```
tggtaaatga ggctactaca taggcccagt taacaaactc ctcttctcct cgggtaggcc    240

atgatacaag tggaactcat caaataattt aaacccaagg cgataacaac gctatttccc    300

atctaaactc atttaagcct tcacaatgtc gcaatggatt caagttactt gcaaacgatc    360

ccgggttgtc atacagatac ttgnttttta cacataacgc tatgccatcc cttncttcac    420

tgcccagtca ggtttcctgn tgttggaccg aaaggggatc cttttaaaaa tgcttcnttc    480

aagacagaag tgagaaagaa aggagaccct gaggccagan ctattaaaac ttgtgngtcc    540

ccaaaaggaa ggggaaaggn agaattgaaa ggaaacggnt ctttngccca ggatnggaan    600

cgggactacn ttgg                                                      614
```

```
<210> SEQ ID NO 576
<211> LENGTH: 596
<212> TYPE: DNA
<213> ORGANISM: Homo sapiens
<220> FEATURE:
<221> NAME/KEY: misc_feature
<222> LOCATION: (1)...(596)
<223> OTHER INFORMATION: n = A,T,C or G

<400> SEQUENCE: 576

acatcaagac ttttggaaca gcgatcgtaa tcaatcctga gaaagacaaa gacatggtcc     60

aagacctgtt ggacttcaag gacaaggtgg accacgtgat cgaggtctgc ttccagaaga    120

atgagcggtt cgtcaacctg atgaaggagt cctttgagac gttcatcaac aagagaccca    180

acaagcctgc agaactgatc gcaaagcatg tggattcaaa gttaagagca ggcaacaaag    240

aagccacaga cgaggagctg gagcggacgt tggacaagat catgatcctg ttcaggttta    300

tccacggtaa agatgtcttt gaagcatttt ataaaaaaga tttggcaaaa agactccttg    360

ttgggaaaag tgcctcagtc gatgctgaaa agtctatgtt gtcaaagctc aagcatgagt    420

gcggtgcagc cttcaccagc aagctggaag gntgttcaag gacatggagc tttcaangac    480

atcatggtca tttcaagcca gcntatgcag natcngagtg cttcaggcct atagacctac    540

agggacatct nccatggctt ctngccacat aacnccatgg aangccttac cccaaa        596
```

```
<210> SEQ ID NO 577
<211> LENGTH: 617
<212> TYPE: DNA
<213> ORGANISM: Homo sapiens
<220> FEATURE:
<221> NAME/KEY: misc_feature
<222> LOCATION: (1)...(617)
<223> OTHER INFORMATION: n = A,T,C or G

<400> SEQUENCE: 577

ggtaccacaa ctcccaggat tttcctggat caaaccttgt atctcttctg caagtattgt     60

gtatattggt ctgagagacg tggaccctcc tgaacatttt attttaaaga actatgatat    120

ccagtatttt tccatgagag atattgatcg acttggtatc cagaaggtca tggaacgaac    180

atttgatctg ctgattggca agagacaaag accaatccat ttgagttttg atattgatgc    240

atttgaccct acactggctc cagccacagg aactcctgtt gtcgggggac taacctatcg    300

agaaggcatg tatattgctg aggaaataca caatacaggg gttgctatca gcactggatc    360

ttgttgaagt caatcctcag ttggccacct cagaggaaga ggcgaagact acagctaacc    420

tggcagtaga tgtgattgct tcaagctttt ggtcagacca gaagaangaa ggcatattgg    480

ctatgaccaa ctttctactc ccagttcacc agatgaatca gaaaatcaag cncctgtgan    540

aaattaggag acacttngcc ctggcatgtt tacaaaaagg ctttnngaaa tntgangcct    600
```

```
ttaggggaaa aaataaa                                                617

<210> SEQ ID NO 578
<211> LENGTH: 409
<212> TYPE: DNA
<213> ORGANISM: Homo sapiens

<400> SEQUENCE: 578

ggtacatgca gaattgtcaa ctacagggaa tgaaaagttc aaaaagtaga tcctacaaga     60

tgtaacgaat acttttctaa acatcaagat acagctcaga acacttcaat aacaagattt    120

ggtctactta ggcatccggc ttgacagcta aacactttag accacaaagt taacatcatg    180

ttacatacgt cttacagtgc acgttacccc aatctgtgaa aataaaccaa catgaaactc    240

aaaaagcatt actagctctg ctttagtgcc taaggtatca cagcatcact tagtagacag    300

aaatcttatc ttccccttaa agtagttgtc atgccataca gactttttaa tattaacaaa    360

aataaagaaa aacatccttg aaaatatatt atcagaggaa ttgtagagt                409

<210> SEQ ID NO 579
<211> LENGTH: 619
<212> TYPE: DNA
<213> ORGANISM: Homo sapiens
<220> FEATURE:
<221> NAME/KEY: misc_feature
<222> LOCATION: (1)...(619)
<223> OTHER INFORMATION: n = A,T,C or G

<400> SEQUENCE: 579

ggtactattt tatatccaga aagtcttctc tatgtagaga agtcagagag actagatgct     60

ttcactaggg aatgtcttcc cacccagcca tcacaaatgt ggacaatcac tgcatccaca    120

tctgtaggca tatttctatg gaagtttaat tgacagctat attcattatt tattttacaa    180

tttcattttt ctacaccttt gagatttatg aatgcagttt tttcttaaaa tttattttaa    240

cttgacagta tgtttttagt tcccccaatt taattaatgg accatgtgca tatatatggg    300

agtgtgctta catgttaata atttacttgc atacttatga gaatttcaca ttggaattca    360

taatggtaaa acaacataca tctgccaata tacgtttttt ctgntggttt aagagaagat    420

aactgacagc tttacctact tcctacagat gcatctaaac ccagatttac tgagaagaag    480

tgtattggac tctgagtgga aaaagagtat ggtgtttttt ggttttaagn tctgctctag    540

anccataatt ngnaaaaaat tttaggnctt aanctggtnc cctaaaattg gnnanccaaa    600

ngttnaatga aanggctgc                                                 619

<210> SEQ ID NO 580
<211> LENGTH: 632
<212> TYPE: DNA
<213> ORGANISM: Homo sapiens
<220> FEATURE:
<221> NAME/KEY: misc_feature
<222> LOCATION: (1)...(632)
<223> OTHER INFORMATION: n = A,T,C or G

<400> SEQUENCE: 580

ggtacaaaca ttttacaaaa aagaacatta ccaatatcag tggtagtaag ggcaagctga     60

agaataaata gactgagttt ccgggcaatg tctgtcctca aagacatcca aactgcgttc    120

aggcagctga aacaggcttc tttcccagtg acaagcatat gtggtcagta atacaaacga    180

tggtaaatga ggctactaca taggcccagt taacaaactc ctcttctcct cgggtaggcc    240
```

-continued

```
atgatacaag tggaactcat ataacaacgc tatttcccat ctaaactcat ttaagccttc    300

acaatgtcgc aatggattca gttacttgca aacgatcccg ggttgtcata cagatacttg    360

ntttttacac ataacgctgt gccatccctt ccttcactgn cccagtcagg tttcctgttg    420

gtggaccgaa aggggatcat tttaagaaat gcttccttna agacagaaag tgagaaagaa    480

aaggagaccc ttgaggncag gaactaatta aacctggtgt ggtgccccaa aagggaaggg    540

ggaaaggccg gaanttgnaa nggataaccg nttcntttng cccagggant cnggaaccgt    600

ggctcgcttt gggcttggac annccccaaat cc                                 632
```

<210> SEQ ID NO 581
<211> LENGTH: 607
<212> TYPE: DNA
<213> ORGANISM: Homo sapiens
<220> FEATURE:
<221> NAME/KEY: misc_feature
<222> LOCATION: (1)...(607)
<223> OTHER INFORMATION: n = A,T,C or G

<400> SEQUENCE: 581

```
acataagtga tggagtatca atgctggtgg ttgaggtgga gaaggaattt agttccttga     60

attttctttg ttctcctctg tgttccttct tggccaggta acccctgcta tatcataaga    120

tttcatctgc gagaaaagga ggaattcttc tacagctccc ctgctcaact ttcaggagat    180

tttgacccat gtgctgttaa tcaccgaaat tttttaagga ggcttctcct ggcatgaaag    240

agttggtatt gtgtcccgaa ttggttggtt cttggtctca ctgacttcaa aaatgaagcc    300

gcggaccctc gcggtgagtg ttaacagctc ttaaggtggc acgtctggag tttgttcctt    360

ctgatgttcc ggatgtgttc agagtttctt ccttctggta ggttcctggc ctcgcttggc    420

ttcaggaatg aagctgcaga ccttctcggt nagtgntaca agctcttaan gcaggccgtc    480

tggaagttgt tcgttcctcc tggggctcgt ggtcttgctg gctttaggag tcaagtncaa    540

accttnaggg tgagtgtaca ntcatanaag cagtgtngnc ccaanaatna ncnttnaaaa    600

gccaacn                                                              607
```

<210> SEQ ID NO 582
<211> LENGTH: 603
<212> TYPE: DNA
<213> ORGANISM: Homo sapiens
<220> FEATURE:
<221> NAME/KEY: misc_feature
<222> LOCATION: (1)...(603)
<223> OTHER INFORMATION: n = A,T,C or G

<400> SEQUENCE: 582

```
actgtattct ccatatgtag ctcggatgcg gagggctgtg agattccgca gtaaccttcg     60

atactcaaag taactcagct gggggctcca attattgctt ggatgctcat ttaacctgaa    120

tgtgtaagtc ttggtgagcc cacaaggcag tgtcttgcca agtggcatca agggagctgt    180

gatccgtaga ccagcacctt ccagaatcac atcatgggca gatgggtgtc tgcctcctct    240

gtccacacgg tagtcaaagg acaggctttg accatagctc acctgttgat tcccaagaaa    300

tttggcagga gccacaaaat agacagggtc tagtcgttgg gctgagctaa acacatcttg    360

atgggcgctg tgaccattgg agctttgcag gagacccatt tcgttggaca gccttccagc    420

catcaacatc ttgatgaaag gtanaagtga tcttatggac actgnattct gcanaactgc    480

ggcaacttgg ctgaatgcca tagcagaacc ctgggtacct tnggccggaa cacgcttang    540

gcgaattcag cccacttggg gccgtctann ggnanccact ttgggcccan cttggggaan    600
```

```
ant                                                                603

<210> SEQ ID NO 583
<211> LENGTH: 535
<212> TYPE: DNA
<213> ORGANISM: Homo sapiens
<220> FEATURE:
<221> NAME/KEY: misc_feature
<222> LOCATION: (1)...(535)
<223> OTHER INFORMATION: n = A,T,C or G

<400> SEQUENCE: 583

ggtacacaca ggaccgcctg gggctaaagg aaatggacaa tgcaggacag ctagtgtttc    60

tggctacaga aggggaccat cttcagttgt ctgaagaatg gttttatgcc cacatcatac   120

cattccttgg atgaaacccg tatagttcac aatagagctc agggagcccc taactcttcc   180

aaaccacatg ggagacagtt tccttcatgc ccaagcctga gctcagatcc agcttgcaac   240

taatccttct atcatctaac atgccctact tggaaagatc taagatctga atcttatcct   300

ttgccatctt ctgttaccat atggtgttga atgcaagttt aattaccatg gagattgttt   360

tacaaacttt tgatgtggtc aagttcagtt ttagaaaagg gagtctgttc cagatcaagg   420

gccagaactg tgcccaggcc caaaggagac actaactaaa gtagtgagat agattctaan   480

ggcaaacatt ttccaggctt gccatatttc aagcaanaag ggccnaagcc tgagg        535

<210> SEQ ID NO 584
<211> LENGTH: 524
<212> TYPE: DNA
<213> ORGANISM: Homo sapiens
<220> FEATURE:
<221> NAME/KEY: misc_feature
<222> LOCATION: (1)...(524)
<223> OTHER INFORMATION: n = A,T,C or G

<400> SEQUENCE: 584

acaactctct taaaagagta tggataacta tattttctgg attctggagg ttgataacca    60

tatgcactta acattatatt ctataaacat taagtagtgc cagttatgag attcccagtt   120

cttactaaat tgtattagca ggagctggta attacttgta ttatcacatg taactaataa   180

tttgaactat acttgaagga ccgtgttgat gtcaggtatt tacagtggtt ggaagatagc   240

agtattatta gcataagctg catacgtaat attcagtaac tgccatatta tataacaaat   300

ttacattcgc aaattcagta tcctgttaaa gtgtcatatt cttgtaatct gcattctcca   360

ggagttttat gtgtttaata gatgaattta ttttatttnt aaaggtattc aaatgntttc   420

agccncntat aggagaaata cccaagtata ttctagttcc ttnatgtccc tgnaccctcg   480

gccgngacca cgctaaaggg cgaaatncaa ncncactggn nggn                    524

<210> SEQ ID NO 585
<211> LENGTH: 618
<212> TYPE: DNA
<213> ORGANISM: Homo sapiens
<220> FEATURE:
<221> NAME/KEY: misc_feature
<222> LOCATION: (1)...(618)
<223> OTHER INFORMATION: n = A,T,C or G

<400> SEQUENCE: 585

actgactata atcaaactcc gaataccatt aaaattaagc tatgcagtcg gaacgtgggt    60

gataacgtcc acgctcgcga ggggaacaac ccagatcgtc agctaaggtc ccaaaattgt   120
```

```
gttaagtgag aaaggttgtg agatttcata aacaactagg aagttggctt agaagcagcc    180

acctttaaa gagtgcgtaa ttgctcacta gtcaagagat cttgcgccaa taatgtaacg    240

ggactcaaac acaataccga agctacgggc acattatgtg cgttaggaga gcgttttaat    300

ttcgttgaag tcagaccgtg aggactggtg gagagattaa aagtgagaat gccggcatga    360

gtaacgattc gaagtgagaa tcttcgacgc ctattgggaa aggtttcctg ggcaaggttc    420

gtccacccag gggttagtca gggcctanga tgaggcanaa atgcatagtc gatggacaca    480

ggttaatatt cctgtacctt cggncgngaa cacgctaagg gccgaattnc agcacacttg    540

gcgggnggtc ctagtnggat cccanctntg ganccaactt nggggtaatc ntgggcttan    600

ctggttccct ggtgaaat                                                   618
```

<210> SEQ ID NO 586
<211> LENGTH: 337
<212> TYPE: DNA
<213> ORGANISM: Homo sapiens

<400> SEQUENCE: 586

```
acaagctttt tttttttttt tttttttttt tgtttcaagt tttaatcaaa gcttgtatat     60

aagattactt tattcctgca tcttctcaat ggtttcttcc ttgtatttgc ccttttcctt    120

tcctacttgg cgagatttgg ctttccgttc gaggatcttt ttgcggtctt tgtccagttt    180

tagcctagtg ataaccacct tgctggggtg aatgcctacg tggacagttg tgccattagc    240

cttttcccgc tgcacccgtt caatgtagat aacatatttc ttcctgtaaa cctggactac    300

tttgccaatt tgctgacctt tatagtgtcc acgtacc                              337
```

<210> SEQ ID NO 587
<211> LENGTH: 656
<212> TYPE: DNA
<213> ORGANISM: Homo sapiens
<220> FEATURE:
<221> NAME/KEY: misc_feature
<222> LOCATION: (1)...(656)
<223> OTHER INFORMATION: n = A,T,C or G

<400> SEQUENCE: 587

```
cgaggtacaa gctttttttt tttttttttt tttttttttct gaggagtggc atggagttct     60

ttaatttgga aggcaaaagg ttacatttaa tgaaaggcag aggctggatt aataaatgtt    120

tgttanaaag ttgttctgac acacagtgaa ctctgggctt ttctcctgca taaaaagcag    180

agctagcagt aagtgcaaat ntgaagaaaa tccatgtgtc caataagctg ccatctccan    240

aactcttatc caggaaattc aaagagtgaa cattctttta gtctcctact cctcaattaa    300

gtaaatgaga atgattcagc caacaaagtt catgacaaca aggtgcagga tggtgctggc    360

aaanagaaaa tnagcaaagg ctcgctctgg ggagatgcct tggaaatccn ntttgntctg    420

ngggttgatc tgnattcttc agggnaaacc cgctagggat gaaacttccc acccnaagan    480

aatgaaaccc cgaaagaaaa agangtttaa aggggaaagg ncccccngan ggagaccagt    540

tacccgaact tggaacnncc ccggcaagca attttttcnc ggcagggtnc cctggcccng    600

ggcggccntt tnaaaagggg gcaattncca ngncacttgg gggggcgttt tttnng         656
```

<210> SEQ ID NO 588
<211> LENGTH: 586
<212> TYPE: DNA
<213> ORGANISM: Homo sapiens
<220> FEATURE:
<221> NAME/KEY: misc_feature
<222> LOCATION: (1)...(586)
<223> OTHER INFORMATION: n = A,T,C or G

<400> SEQUENCE: 588
actcaaacac agggggggttg tcatttatgt caagaactga tacaatcaca gtgccagtgg 60
cagtcagcct ccttggcaag ccttgatcca cagctttcaa agagagggtg tatactgcct 120
ggagttctct gtccaaaggt ttttctaact gaataattcc agataattcg ttaatggaga 180
actgcccatc agcagagtca atcagtgagt ataaaatctt ccgatttaat cctgcgtcgg 240
catctgtggc ctgcactctt gtcagcagcg ttcccggctc tgtgttttca aacacggtga 300
tggcataagg atcggcagag aattcggggg cattatcgtt cacgtcttct agcgtgagca 360
caatactggc ttggtagaat cttcctcctc catctgtggc cctgacgaga agatgataaa 420
cagcttgctc ctnacgatca aaggggggtt gacgttttca agtcacctgg nctggattaa 480
tttgaatttt ctgcacctga cccaatacgg taagtattca gcgtaaccgg atgttgcgtt 540
gacanaaact gatgacattt tccgaaggac tnttaggaaa aggtga 586

<210> SEQ ID NO 589
<211> LENGTH: 645
<212> TYPE: DNA
<213> ORGANISM: Homo sapiens
<220> FEATURE:
<221> NAME/KEY: misc_feature
<222> LOCATION: (1)...(645)
<223> OTHER INFORMATION: n = A,T,C or G

<400> SEQUENCE: 589
acaagcagta ttagaaaatc tttttggcaa gggagagaaa taaatacaaa tggaatgcta 60
catttttaaa ttagcaaact gtctcaggaa tgataaaggt atcagtaaag tagcaagggg 120
ataactttaa aacattattt gtctggggct caaaaaacac tcaaaacaat ttatttaaag 180
gttgcacaag agctatgtcc aggcatttac gcttatggga agtaaaatta aaagaggata 240 ctttttttccc aaggagaatt tctttaaaac caagcacatt gctaaatagc aacattatac 300
tcggtaaaca ataattggca acaaaataag tttaatattc tgcccaaacc agtcccagat 360
actgtttaat aaccaagata caaactaatt ttgttgnaac aagcctagac caattttatc 420
aaacatgtcc ttggttagat atccaatttc atttaacgtt tttgnaagct canttgacag 480
ccagtcnagt ccttnatacn gacccagttc cntggggttg gcacaaagtg ggnttggacc 540
atacccacca ttcaaaaagg cgcatntngg ttcttggccc aaaaaatccn ggnaaaaaaa 600 agggangggga aattattnaa gggnccccttg ggnggnaatg ggcnc 645

<210> SEQ ID NO 590
<211> LENGTH: 464
<212> TYPE: DNA
<213> ORGANISM: Homo sapiens

<400> SEQUENCE: 590
ggttcttgac gaggctgcgg tgtctgctgc tattctccga gcttcgcaat gccgcctaag 60
gacgacaaga agaagaagga cgctggaaag tcggccaaga aagacaaaga cccagtgaac 120
aaatccgggg gcaaggccaa aaagaagaag tggtccaaag gcaaagttcg ggacaagctc 180
aataacttag tcttgtttga caaagctacc tatgataaac tctgtaagga agttcccaac 240
tataaactta taaccccagc tgtggtctct gagagactga agattcgagg ctccctggcc 300
agggcagccc ttcaggagct ccttagtaaa ggacttatca aactggtttc aaagcacaga 360

-continued gctcaagtaa tttacaccag aaataccaag ggtggagatg ctccagctgc tggtgaagat 420
gcatgaatag gtccaccagc ttgtacctgc cgggcggccg ttcg 464

<210> SEQ ID NO 591
<211> LENGTH: 387
<212> TYPE: DNA
<213> ORGANISM: Homo sapiens
<220> FEATURE:
<221> NAME/KEY: misc_feature
<222> LOCATION: (1)...(387)
<223> OTHER INFORMATION: n = A,T,C or G

<400> SEQUENCE: 591
ggaagacgga ggtcctcttt ccttgcctaa cgcagccatg gctcgtggtc ccaagaagca 60
tctgaagcgg gtggcagctc caaagcattg gatgctggat aaattgaccg gtgtgtttgc 120
tcctcgtcca tccaccggtc cccacaagtt gagagagtgt ctccccctca tcattttcct 180
gaggaacaga cttaagtatg ccctgacagg agatgaagta aagaagattt gcatgcagcg 240
gttcattaaa atcgatggca aggtccgaac tgatataacc taccctgctg gattcatgga 300
tgtcatcagc attgacaaga cgggagagaa tttccgtctg atctatgaca ccaagggtcg 360
ctttgctgta cctnggccgc gacacgc 387

<210> SEQ ID NO 592
<211> LENGTH: 648
<212> TYPE: DNA
<213> ORGANISM: Homo sapiens
<220> FEATURE:
<221> NAME/KEY: misc_feature
<222> LOCATION: (1)...(648)
<223> OTHER INFORMATION: n = A,T,C or G

<400> SEQUENCE: 592
ggtacaaaca ttttacaaaa aagaacatta ccaatatcag tggtagtaag ggcaagctga 60
agaataaata gactgagttt ccgggcaatg tctgtcctca aagacatcca aactgcgttc 120
aggcagctga aacaggcttc tttcccagtg acaagcatat gtggtcagta atacaaacga 180
tggtaaatga ggctactaca taggcccagt taacaaactc ctcttctcct cgggtaggcc 240
atgatacaag tggaactcat caaataattt aaacccaagg cgataacaac gctatttccc 300
atctaaactc atttaagcct tcacaatgtc gcaatggatt cagttacttg caaacgatcc 360
cgggttgtca tacagatact tgntttttac acataacgct gtgccatccc ttccttcact 420
gncccagtca ggtttcctgt tgntggaccg aaaggggata cattttanga aaatgctttc 480
ttcaagacag aaatgagaaa gaaanggaga accctgaggc caggaatcta ttaaaccctg 540
ggggtngnnc nccaaaaggg aagggggnaa aggccnggaa tttgaaaagg ntaaaaccgn 600
ttccttttgn gncccaggga attagggaaa ccttgactna cntttggg 648

<210> SEQ ID NO 593
<211> LENGTH: 625
<212> TYPE: DNA
<213> ORGANISM: Homo sapiens
<220> FEATURE:
<221> NAME/KEY: misc_feature
<222> LOCATION: (1)...(625)
<223> OTHER INFORMATION: n = A,T,C or G

<400> SEQUENCE: 593
ggtacttaaa atcagagtca aaaaatggtt ttaagtttta atactcttaa ttagctccct 60
gctttatact gtaactccac agaagacata gggccaccta ggattcacag gaaggagcag 120

```
ctctgattct tacatggctg gctccgatgc cccacagca ggcctcttcc tccccaagtt    180

tttcctctcc atttcaaaaa agcactattt tatcttcaca tccaagagct ggttggtttg    240

gtttgtttct ttggaaacca ataaaagaag caattttttc ctgttctttt tactcacatc    300

tacctatcag agcggctatt tccttcgaca gttcagtagc acacaggctg acttggccac    360

atggactcat gaatgcatgc attcagaccg catattgcta ccaaatggga atgtgggaat    420

atgctatgca cctcaggttg agaaatgacc aagaaaatca agatctaaag ggtgatata    480

taatatatat atatatcaat gctattattc ataaaaacct tggttagtaa taaaaaaaat    540

tgctttggtt naaatattga atattataag ctggcttctc atgggttgga aaaaataagt    600

ctttntgnaa aagccggggc ctttt                                          625
```

```
<210> SEQ ID NO 594
<211> LENGTH: 586
<212> TYPE: DNA
<213> ORGANISM: Homo sapiens
<220> FEATURE:
<221> NAME/KEY: misc_feature
<222> LOCATION: (1)...(586)
<223> OTHER INFORMATION: n = A,T,C or G

<400> SEQUENCE: 594

ggtacccaga caaaacccgg ccacgtgtaa gtcagatgct gattttgact ccatttcaag     60

gtcaaggcca tggtgctcaa cttcttgaaa cagttcatag atactacact gaatttccta    120

cagttcttga tattacagcg gaagatccat ccaaaagcta tgtgaaatta cgagactttg    180

tgcttgtgaa gctttgtcaa gatttgccct gtttttcccg ggaaaaatta atgcaaggat    240

tcaatgaaga tatggcgata gaggcacaac agaagttcaa aataaataag caacacgcta    300

gaagggttta tgaaattctt cgactactgg taactgacat gagtgatgcc gaacaataca    360

gaagctacag actggatatt aaaagaagac taattagccc atataagaaa aagcagagag    420

atcttgctaa gatgagaaaa tgtctcagac cagaagaact gacaaaccag atgaaccaaa    480

tagaaataag catgcaacat gaacagcttg gaananaagt tttcanggnc tagtggaaga    540

ataccccggc gtggtattga acnacttgct caagagttaa gaattt                   586
```

```
<210> SEQ ID NO 595
<211> LENGTH: 613
<212> TYPE: DNA
<213> ORGANISM: Homo sapiens
<220> FEATURE:
<221> NAME/KEY: misc_feature
<222> LOCATION: (1)...(613)
<223> OTHER INFORMATION: n = A,T,C or G

<400> SEQUENCE: 595

acagaaggtt gacgaaaatt cttactgagc aagaaataac cttgttgtaa ttactaaaat     60

ttgagaaatg tgattcttga ctggaaaaat agatgtgtcg tggaggccga atgtttgcac    120

caaccaaaac ctggcgccgt tggcatcgta gagtgaacac aacccaaaaa cgatacgcca    180

tctgttctgc cctggctgcc tcagccctac cagcactggt catgtctaaa ggtcatcgta    240

ttgaggaagt tcctgaactt cctttggtag ttgaagataa agttgaaggc tacaagaaga    300

ccaaggaagc tgttttgctc cttaagaaac ttaaagcctg gaatgatatc aaaaaggtct    360

atgcctctca gcgaatgaga gctggcaaag gcanaatgag aaaccgtcgc cgtatccagc    420

gcaggggccc gtgctcatct ataatgagga tnaatggtat catcaaggcc tttagaaaca    480
```

```
tcctggaaat acctctgctt aatggtaagc caagcttgac cattttgaan ncctgttctg    540

gtgggccttt tgggacgttc tggatttgga cttgaaaggc ttttccggaa ttnnatgaaa    600

tgnccnncgg ccc                                                      613


<210> SEQ ID NO 596
<211> LENGTH: 616
<212> TYPE: DNA
<213> ORGANISM: Homo sapiens
<220> FEATURE:
<221> NAME/KEY: misc_feature
<222> LOCATION: (1)...(616)
<223> OTHER INFORMATION: n = A,T,C or G

<400> SEQUENCE: 596

gcgtgggtcg cggccgaggt acaagaacac tccttgggcg tccttgctgt tttgtttgtg     60

aagttttcta tgcccagtgt tcctgacttc gaaacgctat tctcacaggt tcagctcttc    120

atcagcactt gtaatgggga gcacattcga tatgcaacag acacttttgc tgggctttgc    180

catcagctaa caaatgcact tgtggaaaga aaacagcccc tgcgaggaat tggcatcctt    240

aagcaagcca tagacaagat gcagatgaat acaaaccagc tgacctcaat acatgctgat    300

ctctgccagc tttgtttgct agcaaaatgc tttaagcctg ccttccatat cttgacgtgg    360

atatgatgga tatctgtaaa gagaatggag cctatgatgc aaaacacttt ttatgntact    420

attattatgg agggatgatt atactgggct gaaagaactt tgaaagactc tctactttta    480

tgaacaggct atactacttc tgcatggcgg cagtcatatc atgtgggaac atttaaaagn    540

ntatttanng gcttgaatac ctggcaaaga cctgnccggc gccgttcaaa ggggaattca    600

ccacttggng gcgtnt                                                   616


<210> SEQ ID NO 597
<211> LENGTH: 631
<212> TYPE: DNA
<213> ORGANISM: Homo sapiens
<220> FEATURE:
<221> NAME/KEY: misc_feature
<222> LOCATION: (1)...(631)
<223> OTHER INFORMATION: n = A,T,C or G

<400> SEQUENCE: 597

accagatggc ttttcagaca gaggttggaa accatcccac ttttgaggat atgcaggttc     60

tcgtgtctag ggaaaaacag agacccaagt tcccagaagc ctggaaagaa aatagcctgg    120

cagtgaggtc actcaaggag acaatcgaag actgttggga ccaggatgca gaggctcggc    180

ttactgcaca gtgtgctgag gaaaggatgg ctgaacttat gatgatttgg gaaagaaaca    240

aatctgtgag cccaacagtc aatccaatgt ctactgctat gcagaatgaa cgcaacctgt    300

cacataatag gcgtgtgcca aaaattggtc cttatccaga ttattcttcc tcctcataca    360

ttgaagactc tatccatcat actgacagca tcgtgaagaa tatttcctct gagcattcta    420

tgtccagcac acctttgact atagggggaa aaaaacccga aattcaatta ctatgaaccg    480

acagcaaggc acaaagctcg aatncccaag cccttgaaac aagtggtaac cagcttttca    540

ccacancacc aaccnncaaa cnccccaggg anttacgccc aaggtacctt nggccgggaa    600

cccncttang gggnaattcn cgncccttgg g                                  631


<210> SEQ ID NO 598
<211> LENGTH: 630
<212> TYPE: DNA
<213> ORGANISM: Homo sapiens
```

<220> FEATURE:
<221> NAME/KEY: misc_feature
<222> LOCATION: (1)...(630)
<223> OTHER INFORMATION: n = A,T,C or G

<400> SEQUENCE: 598

```
cgaggtgctt cgtcttcggt ttttctcttc cttcgctaac gcctcccggc tctcgtcagc     60
ctcccgccgg ccgtctcctt aacaccgaac accatgcctt caattaagtt gcagagttct    120
gatggagaga tatttgaagt tgatgtggaa attgccaaac aatctgtgac tattaagacc    180
atgttggaag atttgggaat ggatgatgaa ggagatgatg acccagttcc tcctcctcct    240
cctcctgaag atgatgagaa caaagaaaag cgaacagatg atatccctgt ttgggaccaa    300
gaattcctga aagttgacca aggaacactt tttgaactca ttctggctgc aaactactta    360
gacatcaaag gtttgcttga tgttacatgc aagactgttg ccaatatgat caaggggaaa    420
actcctgagg agattcgcaa gaccttcaat atcaaaaatg actttccctc ttttttgta     480
agcaatggct ggctaagtta atgggccagg taacntttag tgacctttta aaaagtttgg    540
ccattggnaa atnaaaccac ttgcaaaaaa gttttntgga atagaatttc cnaatatttt    600
ccttttcat gagtgggaac tgggnaaagg                                       630
```

<210> SEQ ID NO 599
<211> LENGTH: 359
<212> TYPE: DNA
<213> ORGANISM: Homo sapiens

<400> SEQUENCE: 599

```
ggtacctacc tcaggagcag agatttgata ttcgagtgct gggcttaggt ctgctgataa     60
atctagtgga gtatagtgct cggaatcggc actgtcttgt caacatggaa acatcgtgct    120
cttttgattc ttccatctgt agtggagaag gggatgatag tttaaggata ggtggacaag    180
ttcatgctgt ccaggcttta gtgcagctat tccttgagcg agagcgggca gcccagctag    240
cagaaagtaa aacagatgag ttgatcaaag atgctcccac cactcagcat gataagagtg    300
gagagtggca agaaacaagt ggagaaatac agtgggtgtc aactgaaaag actgatggt     359
```

<210> SEQ ID NO 600
<211> LENGTH: 589
<212> TYPE: DNA
<213> ORGANISM: Homo sapiens
<220> FEATURE:
<221> NAME/KEY: misc_feature
<222> LOCATION: (1)...(589)
<223> OTHER INFORMATION: n = A,T,C or G

<400> SEQUENCE: 600

```
acccagggac acaaacactg tggaaggctg cagggacctc tgcctaggaa agccaggtat     60
tgtccaaggt ttctccccat gtgacagtct gaaatatggc ctcgtaggaa gggaaagacc    120
tgaccgtccc ccagcccgac acccataaag ggtctttgct gaggaggatt agtaaaagag    180
gaaggcctct ttgcagttga gataagagga aggcatctgt ctcctgctcg tccctgggca    240
atggaatgtc tcggtttaaa acccgattgt atattctatc tactgagata ggagaaaact    300
gccttagggc tggagatgag acatgctggt ggcaatactg ctctttaatg cattgagatg    360
tttatgtatg tgcacaaaaa agcacagcgc ctttttcttt acctcgttta tgatgcagag    420
acatttgttc acatgttttc ctgctgactc tctcccacta ttaccctatt gcctgccaca    480
tctccttttc gaaanggtag agataatgat caataaatac tgagggactn aganactggg    540
```

-continued

```
ccgcgtaagt cctaatatct gaacgccagt ccctggccca nttttttnt              589


<210> SEQ ID NO 601
<211> LENGTH: 240
<212> TYPE: DNA
<213> ORGANISM: Homo sapiens

<400> SEQUENCE: 601

acatctgaaa taccccccaa acccagaaag cttttcaaca gctaggttgt ccaagaactt     60

ggaaaattca ccttctgatg tcctccaaga cagattccat tttttataca ccttatttgc    120

tcagacctgt aacttcagcc tggagtgaac acagacacct agttttcctc aaactcctct    180

tgggctttag agagaaggtg ctggcccttt gagccaagca ggttattggt tagtagtacc    240


<210> SEQ ID NO 602
<211> LENGTH: 621
<212> TYPE: DNA
<213> ORGANISM: Homo sapiens
<220> FEATURE:
<221> NAME/KEY: misc_feature
<222> LOCATION: (1)...(621)
<223> OTHER INFORMATION: n = A,T,C or G

<400> SEQUENCE: 602

ggtacctttt acatacaaga aattaaatga gagaaaaaat aactgtagtt acaccatatc     60

acttacaaga atggagaatc tgcttataag tcaaactaga attagaactt atttcttaga    120

ctgcttcata aaaactaaca taccactact ttttaattat ttatttattt gctaaagaac    180

aaaaatttaa gtatgaaaaa caaccaactg attcacccaa ctcagtaagt ttgactcacg    240

ttttctggtt caacaccaat gtcttcacaa aatttctcca tgccttcagg gcctacaaca    300

tcatcagttc ctgcatattc atagaaccat tccaagcacc ttttacttga aaaggcttct    360

tcttcagtct ttattctagt cgaatcatat tttctataca tgctatcatg tctacttttc    420

ttggcagata aatcatctcc agaagcaggt cttctctttt tccttggtgg catcacttta    480

ttaaagcagt ctgaagaact gnaagaaccg agacttcttg gtttggcgac gncttggnca    540

nggctctggt anggtcaanc ttattaangg ngngggaaaa ccttntgaan atttgccccn    600

gttganagat gaaaagtcnn g                                              621


<210> SEQ ID NO 603
<211> LENGTH: 655
<212> TYPE: DNA
<213> ORGANISM: Homo sapiens
<220> FEATURE:
<221> NAME/KEY: misc_feature
<222> LOCATION: (1)...(655)
<223> OTHER INFORMATION: n = A,T,C or G

<400> SEQUENCE: 603

acttataatt ggcagtggag gaagggaaca tacgctggcc tggaaacttg cacagtctca     60

tcatgtcaaa caagtgttgg ttgccccagg aaacgcaggc actgcctgct ctgaaaagat    120

ttcaaatacc gccatctcaa tcagtgacca cactgccctt gctcaattct gcaaagagaa    180

gaaaattgaa tttgtagttg ttggaccaga agcacctctg gctgctggga ttgttgggaa    240

cctgaggtct gcaggagtgc aatgctttgg cccaacagca gaagcggctc agttagagtc    300

cagcaaaagg tttgccaaag agtttatgga cagacatgga atcccaaccg cacaatggaa    360

ggctttcacc aaacctgaag aagcctgcag cttcattttg agtgcagact tccctgcttt    420

ggttgtgaaa gggcancggg cttgcaactt ggnaaaaggg tgaatggttg ccaaagaagc    480
```

```
caaagaaana aggncctgca aagcntgtan cctttgggcc gggaaccacg cttaangggc    540

cnaaattcca agnacaactt ggccgggccc gttacctaaa ngggatccca actttngggn    600

acccaaaacn ttngggngna aatcatnggg ncnaaaantt tggtttccct gngng         655


<210> SEQ ID NO 604
<211> LENGTH: 490
<212> TYPE: DNA
<213> ORGANISM: Homo sapiens
<220> FEATURE:
<221> NAME/KEY: misc_feature
<222> LOCATION: (1)...(490)
<223> OTHER INFORMATION: n = A,T,C or G

<400> SEQUENCE: 604

acaacacacg aattccactc taaacttgaa cgcaaagcta tgttcctctc tgcctcatgg     60

cagtgggcca cagcatcctt caatctttta gttgagcgat acaactccac tagccggatg    120

ttcacatgga cgtcatcagg tcttacataa agttctgact gaatcaagtc aaaaagttta    180

ttccatccat cttcaccttc acaatctaga agctgttcct ttagtttata aattgcagga    240

cttcctggga aaagttttgc tgctctttcg acccagtatt ttgctcttcc atcaggtaac    300

atcattttta caaagcaatt ctgcaatctt caacacaaga tcttttgtgt tgggtttaat    360

tccactgaac gcctgtaaca ttnaacggnt ttctctgtgt tttcttccat tcataaagan    420

gacccagaaa tctgtgagct ttgggatccc tctctcgcac attaaatgta agtacctngg    480

gncgcgacca                                                           490


<210> SEQ ID NO 605
<211> LENGTH: 612
<212> TYPE: DNA
<213> ORGANISM: Homo sapiens
<220> FEATURE:
<221> NAME/KEY: misc_feature
<222> LOCATION: (1)...(612)
<223> OTHER INFORMATION: n = A,T,C or G

<400> SEQUENCE: 605

acagaaggtt gacgaaaatt cttactgagc aagaaataac cttgttgtaa ttactaaaat     60

ttgagaaatg tgattcttga ctggaaaaat agatgtgtcg tggaggccga atgtttgcac    120

caaccaaaac ctggcgccgt tggcatcgta gagtgaacac aacccaaaaa cgatacgcca    180

tctgttctgc cctggctgcc tcagccctac cagcactggt catgtctaaa ggtcatcgta    240

ttgaggaagt tcctgaactt cctttggtag ttgaagataa agttgaaggc tacaagaaga    300

ccaaggaagc tgttttgctc cttaagaaac ttaaagcctg gaatgatatc aaaaaggtct    360

atgcctctca gcgaatgaga gctggcaaag gcaaaatgag aaacccgtcg ccgtatccag    420

ccgcaggggc ccgtgcatca tctataatga ggataatggg tatcatcaag gccttcagaa    480

acatccctgg aattactctg cttaatgnaa gcaagctgac atttttgaac cctgcttctg    540

ggnggcctgt nggactttct gcatttggac tgaaantgct tttcggaagt ttantaantg    600

gacctnngcc cc                                                        612


<210> SEQ ID NO 606
<211> LENGTH: 577
<212> TYPE: DNA
<213> ORGANISM: Homo sapiens
<220> FEATURE:
<221> NAME/KEY: misc_feature
<222> LOCATION: (1)...(577)
```

<223> OTHER INFORMATION: n = A,T,C or G

<400> SEQUENCE: 606

```
gactttgagg caagtgtggg ccactgtggt ggcagtggag gtggggtgtt tgggaggctg     60
cgtgccagtc aagaagaaaa aggtttgcat tctcacattg ccaggatgat aagttccttt    120
ccttttcttt aaagaagttg aagtttagga atcctttggt gccaactggt gtttgaaagt    180
agggacctca gaggtttacc tagagaacag gtggttttta agggttatct tagatgtttc    240
acaccggaag gtttttaaac actaaaatat ataatttata gttaaggcta aaaagtatat    300
ttattgcaga ggatgttcat aaggccagta tgatttataa atgcaatctc cccttgattt    360
aaacacacag atacacacac acacacacac acacacacac aaaccttctg cctttgatgt    420
tacagattta atacagttta tttttaaaga tagaatcctt ttataggtga gaaaaaaaca    480
atctgggaag aaaaaaccac acaagacatt gatcagcctg ttngcgtttc canangtctt    540
tgattggcag catggttnca aggaaantag gtacctc                             577
```

<210> SEQ ID NO 607
<211> LENGTH: 312
<212> TYPE: DNA
<213> ORGANISM: Homo sapiens

<400> SEQUENCE: 607

```
ggtaccaggc cgctcaccac agtccgtggt tcagcttccc ccacgtcaat cttctctaca     60
tacaggctgt ctgcatctgg gtgcttctcc acagtgatga ttttccccac acggatatcc    120
agccgggatg ggatgacctc ctctggttct gaattcttgg cagggccttt ggccattggc    180
ttctgctttg agggatctgg gtaggcagcg ctggccagtt ttttcagggc aggggtatta    240
aacttttccc ggattggatc cagcaacttg ttcagtgcga cttcaacaga attcttcagg    300
tctccaggat gt                                                        312
```

<210> SEQ ID NO 608
<211> LENGTH: 614
<212> TYPE: DNA
<213> ORGANISM: Homo sapiens
<220> FEATURE:
<221> NAME/KEY: misc_feature
<222> LOCATION: (1)...(614)
<223> OTHER INFORMATION: n = A,T,C or G

<400> SEQUENCE: 608

```
ggtgcaactt ccttcggtcg tcccgaatcc gggttcatcc gacaccagcc gcctccacca     60
tgccgccgaa gttcgacccc aacgagatca aagtcgtata cctgaggtgc accggaggtg    120
aagtcggtgc cacttctgcc ctggccccca agatcggccc cctgggtctg tctccaaaaa    180
aagttggtga tgacattgcc aaggcaacgg gtgactggag gggcctgagg attacagtga    240
aactgaccat tcagaacaga caggcccaga ttgaggtggt gccttctgcc tctgccctga    300
tcatcaaagc cctcaaggaa ccaccaagag acaaagaaac agaaaaacat taaacacagt    360
gggaatatca cttttgatga gattgtcaac attgctcgac agatgccggc accgatcctt    420
agccagagaa ctctctggaa ccattaaaga gatctgggga ctgcccagtc agtgggctgn    480
aatggtgatg gcccgcatnc ttatgacttc atcgatgaca tcaacagtgg tgctgtggaa    540
tgcnagccgg ttaanccnaa ggaaacttta atnanggtca ttgcactggn aaaaaaaaaa    600
nnaananaaa ggnt                                                      614
```

-continued

<210> SEQ ID NO 609
<211> LENGTH: 609
<212> TYPE: DNA
<213> ORGANISM: Homo sapiens
<220> FEATURE:
<221> NAME/KEY: misc_feature
<222> LOCATION: (1)...(609)
<223> OTHER INFORMATION: n = A,T,C or G

<400> SEQUENCE: 609

```
ggtactgagc acccctgttg tcaagaaagt gggagtaaca tctgtaggag gttctttaac     60
tggtgggcca aatatataaa caactctgtt aacgttgtga cacatgcgag gtataagcct    120
agccagaaaa ataagtgatt cccagtcagg ttcatcttta ctggagattc cacacacgta    180
attgtaggaa cgacagtcac cctgcacacc tacagtttta attggcagca agaaggcatt    240
cagtgaatgc agactggtaa tttgcatcag cttctcctga tcctcttctg ttgtgcaggc    300
tttgactctc tgtaataggg tatgtggctt tttaacactt gcagaaaaat cagctactat    360
tttcaaaata ttgttggttt caggaaagtc cttacaaata taaggttctt cagcacatat    420
tactctgatt gccaggccag gacctggaaa tggatgcctg gaaactaact cttctggaag    480
tccaagttct cttggccaaa attctcactt catctttatg aaaatctttc agaggtctat    540
acttttcctc ctttttaact ttctgaatga ctcttgggna tttggaangg tttgatgagt    600
tcactttnc                                                             609
```

<210> SEQ ID NO 610
<211> LENGTH: 254
<212> TYPE: DNA
<213> ORGANISM: Homo sapiens
<220> FEATURE:
<221> NAME/KEY: misc_feature
<222> LOCATION: (1)...(254)
<223> OTHER INFORMATION: n = A,T,C or G

<400> SEQUENCE: 610

```
accattggtg gccaattgat ttgatggtaa gggagggatc gttgacctcg tctgttatgt     60
aaaggatgcg tagggatggg agggccgatg aggactagga tgatggcggg caggatagtt    120
cagacggttt ctatttcctg agcgtctgag atgttagtat tagttagttt tgttgtgagt    180
gttaggaaaa gggcatacag gactaggaag cagataagga aaatgattat gagggcgtga    240
tcatgaaaga cctn                                                       254
```

<210> SEQ ID NO 611
<211> LENGTH: 687
<212> TYPE: DNA
<213> ORGANISM: Homo sapiens
<220> FEATURE:
<221> NAME/KEY: misc_feature
<222> LOCATION: (1)...(687)
<223> OTHER INFORMATION: n = A,T,C or G

<400> SEQUENCE: 611

```
ggtacaagga tgccatccat ttctataaca agtctctggc agagcaccga accccagatg     60
tgctcaagaa atgccagcag gcagagaaaa tcctgaagga gcaagagcgg ctggcctaca    120
taaaccccga cctggctttg gaggagaaga acaaaggcaa cgagtgtttt cagaaagggg    180
actatcccca ggccatgaag cattatacag aagccatcaa aaggaacccg aaagatgcca    240
aattatacag caatcgagct gcctgctaca ccaaactcct ggagttccag ctggcactca    300
aggactgtga ggaatgtatc cagctggagc ccgaccttca tcaaggggtt atacacggaa    360
```

```
agccgctgca ctggaagcga tgaaggacta cacccaaaag cccatggatg tgtacctgcc    420

cgggccggcc gctcgaaagg ggcgaaattn agcacactgg ccggccggta cttagtggga    480

tncnancttc ggtaccaaac ntngcggnaa tcatgggcat ancnnggttc ctngggngga    540

aaattggtaa tnccgtttac natttcccca ccaacttccn aacccggaaa ccttnaagng    600

gaaanccntg gggnggccta atgggngggc ttactcncct taattggctt gggcttaatg    660

ggccccttttt caatngggaa acctnnt                                       687
```

<210> SEQ ID NO 612
<211> LENGTH: 673
<212> TYPE: DNA
<213> ORGANISM: Homo sapiens
<220> FEATURE:
<221> NAME/KEY: misc_feature
<222> LOCATION: (1)...(673)
<223> OTHER INFORMATION: n = A,T,C or G

<400> SEQUENCE: 612

```
gactgatgtt ggtgtcctgc agcgccacgt ttcccgccac aaccaccgga acgaggatga     60

ggagaacaca ctctccgtgg actgcacacg gatctccttt gagtatgacc tccgcctggt    120

gctctaccag cactggtccc tccatgacag cctgtgcaac accagctata ccgcagccag    180

gttcaagctg tggtctgtgc atggacagaa gcggctccag gagttccttg cagacatggg    240

tcttcccctg aagcaggtga agcagaagtt ccaggccatg gacatctcct tgaaggagaa    300

tttgcgggaa atgattgaag agtctgcaaa taaatttggg atgaaggaca tgccgcgtgc    360

agactttcaa cattcatttt gggttcaagc acaagtttct ggccagccga cgtggtcttt    420

ngcaccatgt ctttgatgga gagccccgan aaaggatggc tnaaggaccg aatcacttta    480

tncaggcttt tggacangcc tnttcaggag tnaccctgga caaacttgta cctttgggnc    540

ggngaacacc ncttaagggc naatttcang cacactggcg ggccgtaatt aagggaatcc    600

aacttnggna nccaancttg gggnaaancn tgggcataan ngttccctgn ggnaaatngt    660

attccctncc aat                                                       673
```

<210> SEQ ID NO 613
<211> LENGTH: 279
<212> TYPE: DNA
<213> ORGANISM: Homo sapiens

<400> SEQUENCE: 613

```
ggtacaaaag gagacaatcc atccccgaaa gtcatataag atgaactctt cctgtgcaga     60

tatcctgctc tttgcctcct ataagtggaa tgtctcccgg ccctcattgc tggctgactc    120

caaggatgtg atggacagca ccaccaccca gaaatactgg attgacatcc agttgcgctg    180

gggggactat gattcccacg acattgagcg ctacgcccgg gccaagttcc tggactacac    240

caccgacaac atgagtatct acccttcgcc cacaggtgt                           279
```

<210> SEQ ID NO 614
<211> LENGTH: 653
<212> TYPE: DNA
<213> ORGANISM: Homo sapiens
<220> FEATURE:
<221> NAME/KEY: misc_feature
<222> LOCATION: (1)...(653)
<223> OTHER INFORMATION: n = A,T,C or G

<400> SEQUENCE: 614

```
gtttccacaa acttcgtgga tcaaaacgag gtcttccagt tctgcgggtc agaaggctga     60
```

```
cccggggctc aaatctgggt gtcggcagtc ctgcactcct tctggaggct ctaggggaga    120

attcatttct ggccttttca tttttagagg ctgaccgtaa ttcttgactt caggctcctc    180

catcttcaga gccagctgtg ggtagttgaa tctttttccc gtcacctcat tgaggcctcc    240

cctctcctgc ctccctccac cacttttttt ttttttgag acagggtctt gctgtgttgc    300

ccaggctgga gtgcagtggc ctggtcatgg catcaaggct cactgcagcc tggacctcct    360

ggttcaagtg atcctcttgt ctcagtcccc tgagacaatc ccccacgccc agctacatat    420

tttttgtgga tacagggtct cattctgntg cctagcttgt ctggaactcc tgggctcaag    480

ggatcttgga gccttaaccc tnctaaagtg cttgggaata taggcatgag tcactggacc    540

ttgggnccga ccaccttaan ggccgaattt cagcacaatt ggcgggccgg tacttagggg    600

annccaactt tgggaccaac ntgggngnaa tcatgggccn aactggttnc cng           653
```

<210> SEQ ID NO 615
<211> LENGTH: 676
<212> TYPE: DNA
<213> ORGANISM: Homo sapiens
<220> FEATURE:
<221> NAME/KEY: misc_feature
<222> LOCATION: (1)...(676)
<223> OTHER INFORMATION: n = A,T,C or G

<400> SEQUENCE: 615

```
acatgtgaag attttttggc agcttagcgt ggaaaccatt gatcaccctg ctctcatttc     60

tacctgttct gtgttggcaa gggagagtgc ccaaatgagc aagatatcgc agcaaaacag    120

cactccaggg gtgaacggaa ttagtgttat ccatacccag gcacatgcca gcggcttaca    180

gcaggttcct cagctggtgc ctgctggccc tgggggagga ggcaaagctg tggctcccag    240

caagcagagc aaaaagagtt cgcccatgga tcgaaacagt gacgaagtat cggcaacgcc    300

gagagaggaa caacatggct gtgaaaaaga gcccggttga aaagcaagca gaaagcacaa    360

gacacactgn agagagtcaa tcagctcaaa gaagagaatg aacggttgga aagcaaaaat    420

caaattgctg accnanggat taagtgtacn gaagcatgcc aacgccttag ctnatgggcc    480

tggctnctat cagcttggga acccnaaagn accagttttt ccangaatcc ccagaccgaa    540

ngggnccaag gggnccaacg ttcgggactt gaaangggaa aaaaaacttg ganctggca     600

aggacttggg cttncnaaat tgganccgan cccaanggat gaanaacccc ttcaagaaaa    660

ccagcttcct ttctng                                                    676
```

<210> SEQ ID NO 616
<211> LENGTH: 694
<212> TYPE: DNA
<213> ORGANISM: Homo sapiens
<220> FEATURE:
<221> NAME/KEY: misc_feature
<222> LOCATION: (1)...(694)
<223> OTHER INFORMATION: n = A,T,C or G

<400> SEQUENCE: 616

```
ggtaccttct agatcttgga gttgatatga atgaaccaaa tgcctatgga aatacacctc     60

ttcatgtagc ctgctataat ggacaagatg ttgtagtgaa tgaacttata gactgtggtg    120

ctattgtgaa tcaaaagaat gaaaaaggat ttactccttt gcactttgct gctgcatcaa    180

cacatggagc attgtgttta gagcttctag ttggcaatgg ggccgatgtc aatatgaaga    240

gtaaagatgg gaaaacccca ctacacatga ctgctctcca cggtagattc tcccgatcac    300
```

-continued

```
aaaccattat ccagagtgga gctgtaatcg actgtgagga taagaatgga aatacccctt    360

tgcacatagc aacacggtat ggccatgaan ctgctgatca acacttctta ataccagtgg    420

gtgctgaccc ttgcaaannc gtgggcatac cttggaatgg ttccccttc catttggca    480

agcccttaaa ccggnttttt caagaattac tggcnnaaaa accttcnttc ttttanggaa    540

ttnganattn gaaanccccc aanggaattt tngccnggac cttgggntaa catgccantt    600

gnnacttgga agggnaattt gggaanggcc tnaaaccttt tnggngnaaa cctggggccn    660

aacntttatt aaaangggcc caatttnggg gaan                                694
```

<210> SEQ ID NO 617
<211> LENGTH: 554
<212> TYPE: DNA
<213> ORGANISM: Homo sapiens
<220> FEATURE:
<221> NAME/KEY: misc_feature
<222> LOCATION: (1)...(554)
<223> OTHER INFORMATION: n = A,T,C or G

<400> SEQUENCE: 617

```
cgaggtaccg caagggaaag atgaaaaatt ataaccaagc ataatatagc aaggactaac     60

ccctatacct tctgcataat gaattaacta gaaataactt tgcaaggaga gccaaagcta    120

agacccccga aaccagacga gctacctaag aacagctaaa agagcacacc cgtctatgta    180

gcaaaatagt gggtagattt ataggtagag gcgacaaacc taccgagcct ggtgatagct    240

ggttgtccaa gatagaatct tagttcaact ttaaatttgc ccacagaacc ctctaaatcc    300

ccttgnaaat ttaactgtta gtccaaagag gaacagctct ttggacacta ggaaaaaacc    360

ttgtagagag agtaaaaaat ttaacaccca tagtaggcct aaaaagcagc caccaattaa    420

gaaagcgttc agactatatc tattgcgcca ggtttcaatt tctatcgcta tactttattt    480

gggtaaaatg ggtttggctt aagggtggct nggaagaaag gtggaatngg aactgcccgg    540

gcnggccgct ngaa                                                      554
```

<210> SEQ ID NO 618
<211> LENGTH: 305
<212> TYPE: DNA
<213> ORGANISM: Homo sapiens

<400> SEQUENCE: 618

```
acatgtgttc acaagggtta ctcctcaaaa cccccagttc tcactcatgt ccccaactca     60

aggctagaaa acagcaagat ggagaaataa tgttctgctg cgtccccacc gtgacctgcc    120

tggcctcccc tgtctcaggg agcaggtcac aggtcaccat ggggaattct agcccccact    180

ggggggatgt tacaacacca tgctggttat tttggcggct gtagttgtgg ggggatgtgt    240

gtgtgcacgt gtgtgtgtgt gtgtgtgtgt gtgtgtgttc tgtgacctcc tgtccccatg    300

gtacc                                                                305
```

<210> SEQ ID NO 619
<211> LENGTH: 604
<212> TYPE: DNA
<213> ORGANISM: Homo sapiens
<220> FEATURE:
<221> NAME/KEY: misc_feature
<222> LOCATION: (1)...(604)
<223> OTHER INFORMATION: n = A,T,C or G

<400> SEQUENCE: 619

```
acactctcat agtcactgaa agtaatatac actgacctgc aaaagtcaga tgggaagaca     60
```

-continued

```
taaaggacct catctttggt tattagtggg tgaaaagaat ctccatctgt tccattaatc    120
atattgcact tgtctgttat ccaccagtca agtgacgttt tcccattcca ttccacaatt    180
tttgtaaagt taaggtaact gtcttctcca gttagaaaaa catagtctcc atcattagtc    240
ccatttttct catagaatag gccaaaatag ggagagatat cggcctgaa aacatggata     300
agggacaaga tttcatcttt gtagccccag agcaattcgt caactgtgtg agtcacaaag    360
agcttctgct gataggcttt caacatggcc tcgatgatct ccctgaggaa gtgcacctgg    420
gaccactcta tgacagtcaa tacaggaata tttaatggtc taattaagtn aaattttaag    480
ggctncaaca gattgggtct cgttcaaaac cataggcctt gttgctaaca gcaganattg    540
gtggttcatt atctncaaat ggaaaattng ctttggttct ggagtncctg naagggtatg    600
gncc                                                                 604
```

<210> SEQ ID NO 620
<211> LENGTH: 571
<212> TYPE: DNA
<213> ORGANISM: Homo sapiens
<220> FEATURE:
<221> NAME/KEY: misc_feature
<222> LOCATION: (1)...(571)
<223> OTHER INFORMATION: n = A,T,C or G

<400> SEQUENCE: 620

```
ggtactgtga acatgacttt cagatgctct ttgccccttg ctgtcatcag tgtggtgaat     60
tcatcattgg ccgagttatc aaagccatga ataacagctg gcatccggag tgcttccgct    120
gtgacctctg ccaggaagtt ctggcagata tcgggtttgt caagaatgct gggagacacc    180
tgtgtcgccc ctgtcataat cgtgagaaag ccagaggcct tgggaaatac atctgccaga    240
aatgccatgc tatcatcgat gagcagcctc tgatattcaa gaacgacccc taccatccag    300
accatttcaa ctgcgccaac tgcgggaagg agctgactgc cgatgcacgg gaactgaaag    360
ggggaactat actgncttcc atgccatgat aaaatggggg tcccattgng gtgcttgcca    420
cggccatcaa ggcgctgtga cctatggcaa catgcatgtg gacatttggt gnncagtgta    480
aaccttntga atgcatataa gaagctgcgn ttggactatt accgtntggg ngtgtcctga    540
tcggntnaag ggaggctgtn taaagcggng g                                   571
```

<210> SEQ ID NO 621
<211> LENGTH: 581
<212> TYPE: DNA
<213> ORGANISM: Homo sapiens
<220> FEATURE:
<221> NAME/KEY: misc_feature
<222> LOCATION: (1)...(581)
<223> OTHER INFORMATION: n = A,T,C or G

<400> SEQUENCE: 621

```
acattcggcc tgagggccag gacagtgctt tctcctggac ggacctgctg ctgaagaata     60
attctgagct gcttaacaac ctgggcaact tcatcaacag agctgggatg tttgtgtcta    120
agttctttgg gggctatgtg cctgagatgg tgctcacccc tgatgatcag cgcctgctgg    180
cccatgtcac cctggagctc cagcactatc accagctact tgagaaggtt cggatccggg    240
atgccttgcg cagtatcctc accatatctc gacatggcaa ccaatatatt caggtgaatg    300
agccctggaa gcggattaaa ggcagtgagg ctgacaggca acgggcagga acagtgactg    360
gcttggcagt gaatatagct gccttgctct ctgcatgctt caccttacat gcccacggta    420
```

-continued

```
gtgcccaatc agcccactgc actccactca gctgagtatc ngntgacaac ttctgngacc    480

ttggccggac acctaaggca atcaccatgg cgcgtctang gaccactcga ccacttgcga    540

acatggcnat ggtctgngaa tgnccgtaat tccncanntc a                        581


<210> SEQ ID NO 622
<211> LENGTH: 644
<212> TYPE: DNA
<213> ORGANISM: Homo sapiens
<220> FEATURE:
<221> NAME/KEY: misc_feature
<222> LOCATION: (1)...(644)
<223> OTHER INFORMATION: n = A,T,C or G

<400> SEQUENCE: 622

actgtttacc agatctttgc agatgaggtg cttggttcag gccagtttgg catcgtttat     60

ggagaatttg caccatcctg ggattgtaaa cctggaatgt atgtttgaaa ccccagaacg    120

agtctttgta gtaatggaaa agctgcatgg agatatgttg gaaatgattc tatccagtga    180

gaaaagtcgg cttcagaacg aattactaaa ttcatggtca cacagatact tgttgctttg    240

aggaatctgc attttaagaa tattgtgcac tgtgatttaa agccagaaaa tgtgctgctt    300

gcatcagcag agccatttcc tcaggtgaag ctgtgtgact ttggatttgc acgcatcatt    360

ggtgaaaagt cattcaggag atctgtggta ggaacttcag catacttacc cctgaagttc    420

ttcngagcca angtacaacc gntccctana tatgtggnca gtgggagtta tcatctatgt    480

gagcctnaat ggcacatttc ctttaatgng gatgaagatt taatgnccaa tccaaaaggc    540

tgganttatg naccctnggc cgaccccctt angggggaatt ccannnnntt gggggggcgt    600

tctaaggggn nccancttgg gcccaacntg ggggaancat ggcn                     644


<210> SEQ ID NO 623
<211> LENGTH: 662
<212> TYPE: DNA
<213> ORGANISM: Homo sapiens
<220> FEATURE:
<221> NAME/KEY: misc_feature
<222> LOCATION: (1)...(662)
<223> OTHER INFORMATION: n = A,T,C or G

<400> SEQUENCE: 623

acaaagagct actccataaa ttacatcttg ccaaggtggg agattgcatg ggagactccg     60

gtgacaaacc cttaaggcgc aataatagct atacttccta taccatggca atatgtggca    120

tgcctctgga ttcattccgt gccaaagaag gtgaacagaa gggcgaagaa atggagaagc    180

tgacatggcc taatgcggac tccaagaagc gaattcgaat ggacagttac accagttact    240

gcaatgctgt gtctgacctt cactcagcat ctgagataga catgagtgtc aaggcagaga    300

tgggtctagg tgacagaaaa ggaaagtaat gggctctcta gaagaatggt atgaccagga    360

taagcctgaa gtctctctcc tctttcagtt cctgcaganc cttacagcct gctttgggtc    420

attcgcccat ggtggcaatg acgtaagcca tgccatttgg gcctctgggt gctttatatt    480

tgggttatga cccnngagan gttcttcaaa agtggcaaca ccaatattgg nttctactct    540

antggngggg gttgggatct gnggttggtc tgtggggttt ggggaaaaaa aagttttccc    600

naccttgggg aaaggatttg ccnccgttac accctttaag ggtttngtat ttgactngna    660

tn                                                                   662


<210> SEQ ID NO 624
<211> LENGTH: 682
```

<212> TYPE: DNA
<213> ORGANISM: Homo sapiens
<220> FEATURE:
<221> NAME/KEY: misc_feature
<222> LOCATION: (1)...(682)
<223> OTHER INFORMATION: n = A,T,C or G

<400> SEQUENCE: 624

```
acaccaagca tgggactttg aaataccaga cagactgtgc ccctaataat ggttacttta     60
tgatcccttt gtatgataag ggggatttca ttctgaagat tgagcctccc ctagggtgga    120
gttttgagcc gacgaccgtg gagctccatg tggatggagt cagtgacatc tgcacaaagg    180
gtggggacat caactttgtc ttcactgggt tctctgtgaa tggcaaggtc ctnagcaaag    240
ggcagcccct gggtcctgcg ggagttcang tgtctctgag aaacactggg acccgaagca    300
aagatccagt ncacagttac acagnctgcg gaaagtttgc attttttaaa gttctgcctg    360
gagaatatna aaatcctngt actcatccaa cctggggcgt tgaaagaagc aagcaccacn    420
gtnccntgtt accaactcca atgccaatgn cggncagtcc ccttcatagt tgctggnnta    480
ccaatngtgg tcttggcntn tgtcccnaaa ttgattnggn gaagcccctt gtaanggccc    540
taaagtttcn tnntcntttt cttctttant ttcctnnang aaggaanncc ttgggttnca    600
ntggntnacc tgngcctggg gttccaancc nnataccnan nntcttgggg tatttngcct    660
acccggtntc nnaaaaanat gg                                             682
```

<210> SEQ ID NO 625
<211> LENGTH: 502
<212> TYPE: DNA
<213> ORGANISM: Homo sapiens

<400> SEQUENCE: 625

```
acatttcctt gtagactctg ttaatttcct gcagctcctg gttggttctg gagcagatga     60
tctcaatgag agagtcctcg tcggttccca gccccttcat ggaagctttt agctcagagg    120
cgtcatactg agcaggtgtc ttcaataggc ccaaaatcac cgtctccagg tggccagata    180
aggctgactt cagtgctgat gcaagttcct ttttggtcct tctctggtag gcgaaggcaa    240
tatcctgtct ctgtgcattg ctgcggttgg tcaaaatgtt gacaatggtg acctcatcca    300
cacctttggt cttgatggct gtttcaatgt tcaaagcatc ccgctcagca tcaaagttag    360
tataggcttt gacagaccca tatgcacttg gggggtgtag aagtgatcac cctccaagct    420
gagcttgcac aggaatttcg tgaacagtag acattttgaa ggaactgggc ccgtgcgccg    480
aagagctgaa aaccgtccca cc                                             502
```

<210> SEQ ID NO 626
<211> LENGTH: 935
<212> TYPE: DNA
<213> ORGANISM: Homo sapiens
<220> FEATURE:
<221> NAME/KEY: misc_feature
<222> LOCATION: (1)...(935)
<223> OTHER INFORMATION: n = A,T,C or G

<400> SEQUENCE: 626

```
acattcatca aagaggaatt tgtcacccaa ggccatgtgc ttttcagtgg aaaggaagga     60
gggaaacctc taaggccgca cggtgggccc acggagctag cacgtgggcg ggactgaagg    120
ctagatgctg ggattgaggt ggggaactag agatgactct aaggcaggaa catctgtacc    180
ttcgggccgc ganccacgcc taagggccga aattcagcac actggccggg cccgttacct    240
```

-continued

```
aagtgggaat cccgaagctt cgggtaccca aagcctttgg gccgtaaaat caattgggtc    300

caattaagcc ttggnttttc ccttgggggg tggnaaaaat ttgggtttaa ttcccggctt    360

tcaaccaaan ttttcccaac canccaaacc antttanccn aaaacccccn gggaaaaggc    420

cnttttaaaa aggttggtta aaaaaggncc ccttnggggg ggttnggccc cttaaaattg    480

gaaantttgg aaacccttna aaccnttnaa nccattttta aaattttggc ccgttttggc    540

cggcctttta aactttgggc ccccnggttt tttttcccaa agttcccggg ggaaaaaanc    600

cttgggtncc nttggnccca aaccnttggc cantttnaaa ttggnaaatt cnggggcncn    660

aaacggcccc ccgggggnna aaaaaaggcc cngggttttg gccggtaant tnggggcccc    720

cttttttttc ccggcttttc cctttgggtt tnaacttgga acttcnnttt tgggncnttg    780

gggnccnttt cggggttttn cggncaaaac cggggatntc aagntttanc ttcaaaaggg    840

ccgggaaata ncngggtttt cccccngaaa tccgggggnn aaacccccgg gaaaaaacct    900

ttttggacca aaaggcccnc naaanggccc ggaan                               935
```

```
<210> SEQ ID NO 627
<211> LENGTH: 680
<212> TYPE: DNA
<213> ORGANISM: Homo sapiens
<220> FEATURE:
<221> NAME/KEY: misc_feature
<222> LOCATION: (1)...(680)
<223> OTHER INFORMATION: n = A,T,C or G

<400> SEQUENCE: 627

ggtaccacaa ctcccaggat tttcctggat caaaccttgt atctcttctg caagtattgt     60

gtatattggt ctgagagacg tggaccctcc tgaacatttt attttaaaga actatgatat    120

ccagtatttt tccatgagag atattgatcg acttggtatc cagaaggtca tggaacgaac    180

atttgatctg ctgattggca agagacaaag accaatccat ttgagttttg atattgatgc    240

atttgaccct acactgactc cagccacagg aactcctgtt gtcgggggac taacctatcg    300

agaaggcatg tatattgctg aggaaataca caatacaggg ttgctatcag cactggatct    360

tggtgaaagt caatcctnag ttggccacct nagaggaaga ngccaagact acagctaacc    420

tggcagtaga tgngantgct tcaagctttt gggcagacca ganaaaggan ggcntattgg    480

ctattgaccc actttctant tccaagttan cccgaaggaa tccgaaaatc nagcccctgt    540

gganaaattt tggggaaact tggcncctgn ctggtttacc aacaggggct ttcccnaaat    600

ttttanggcc tttngggggn ttnanngaaa ccctaaaggg gtnnnctggg gccaaaaccg    660

gccttaanng ggnaaacttt                                                680
```

```
<210> SEQ ID NO 628
<211> LENGTH: 637
<212> TYPE: DNA
<213> ORGANISM: Homo sapiens
<220> FEATURE:
<221> NAME/KEY: misc_feature
<222> LOCATION: (1)...(637)
<223> OTHER INFORMATION: n = A,T,C or G

<400> SEQUENCE: 628

acttgtaggg tggaggtgtc ggtcaaagac cttctttatg atatcaagaa atagacatgt     60

aacaaccatg aggattatgg caaaccaagc agaaccactt gacaggagct gaataaacac    120

aaaatacata ttctgggagc ccaaaaatgg ccagagaatc cctccataaa acaaggaaaa    180

tacaaaataa aatataatag atccccaggt aacgagatgg ttgatccaag tccaaaaatg    240
```

```
agtttccaga gccatcttta ctgtgactgt aataaccatg actgtgaaga ccaaagtgcc    300

aaatgtccag tttccaaaca tctggcattt ccaagcagag atgtatcttt ccctattagt    360

aaataggatc naaaaagaaa ataaaggcat gactgaaccc aggatggtcc aataaagaaa    420

tggtttaata cttaagaagg cggttttact aatggctcga taaaggtggc ttaatttggn    480

acacatgaag gnctacatgc ttgttccaaa agactntttn tcnnaattgg tngggaagta    540

aaccaatttt ggttaaagtc agggnccttg gccggacccn cttanggcga attccnnccn    600

ctgggggccg tcttagggga ncaacttggg cccaact                             637
```

<210> SEQ ID NO 629
<211> LENGTH: 446
<212> TYPE: DNA
<213> ORGANISM: Homo sapiens
<220> FEATURE:
<221> NAME/KEY: misc_feature
<222> LOCATION: (1)...(446)
<223> OTHER INFORMATION: n = A,T,C or G

<400> SEQUENCE: 629

```
acttctcatg tccatggtta atgaaaggca gccatttgtt ttgcgctgtg ctgttctcta     60

ttgtttccag tgtttcttgt ataaaaacca aaaaggacaa ggagaaatcg tgtcaacact    120

tttaccttct accattgatg caacaggtaa ttcagtttca gctggccagt tattatgtgg    180

aggtttgttt tctactgatt cactttcaaa ctggtgtgct gctgtggccc ttgcccatgc    240

gttgcaagaa aatgccaccc agaaagaaca gttgctcagg gttcaacttg ctacaagtat    300

tggcaaccct ncagtttctt tacttcaaca gtgcaccaat attctttcac agggtgataa    360

agatcgacag acggggaaac naaatacnaa ccaagaagtg gattattaat ggtgctttgg    420

accttggncg ngancacctt anggcc                                         446
```

<210> SEQ ID NO 630
<211> LENGTH: 635
<212> TYPE: DNA
<213> ORGANISM: Homo sapiens
<220> FEATURE:
<221> NAME/KEY: misc_feature
<222> LOCATION: (1)...(635)
<223> OTHER INFORMATION: n = A,T,C or G

<400> SEQUENCE: 630

```
actagatatt gtgcctgcaa gtcataaaaa aaaaaaaaaa aaaagaaaaa aatgaaagaa     60

tgcctttccc cttcagacaa aagaattact tttttcattt ttcttaaaaa aagaggaaaa    120

gttataacac gaaacctaaa ttgacttgca aaggaatacc atgtaacaaa tggcttgaag    180

tagtctatca aaaaattggg gagattttta tttaatagtg agtcagcaag gcatttttttg    240

ttgtttaaaa aaaatctcat ttccttacag aaacagtttt tagtttttaa tgaacttgta    300

aacnaaaaag ctcccatttc aaaataaaaa cnaaatccca gatcatatta atgnttacng    360

ggggtacctt tatctaagca acatacntac ctgttcagtt gtaagangt aactaaattt     420

ctgngaccaa natgcntttt ttttaatacc cngaacnttn ttgaggtaat gcnnaatcct    480

aangggaaac tagnngnccc taagntttct taagcnttcc tttaaaagcn gggaattnta    540

gccccattaa ccggccnagn ttttntatgc ctaaancctg gaantttggn gntnccatta    600

atgggttgna acaaaanccc ccntttnaaa ngttn                               635
```

<210> SEQ ID NO 631

<211> LENGTH: 694
<212> TYPE: DNA
<213> ORGANISM: Homo sapiens
<220> FEATURE:
<221> NAME/KEY: misc_feature
<222> LOCATION: (1)...(694)
<223> OTHER INFORMATION: n = A,T,C or G

<400> SEQUENCE: 631

```
actcatctta tactgaaaga acgtggtggc tctaaatatg aagctgcaaa gaagtggaat     60

ttacctgccg ttactatagc ttggctgttg gagactgcta gaacgggaaa gagagcagac    120

gaaagccatt ttctgattga aaattcaact aaagaagaac gaagtttgga aacagaaata    180

acaaatggaa tcaatctaaa ttcagatact gcagagcatc ctggcacacg cctgcaaact    240

cacagaaaaa cccgtcgtta cacctttaga tatgaaccgc tttcagagta aagctttccg    300

tgctgnggct nacaacatgc cagacaggtc gcaacctccc agcagtagga caaccacttn    360

agaaggagcc ctcggtacac ctggatacac cattcaaaat tctgntccan ggccaactct    420

ttaagccttt ctttgatgtg aaagatgccc tttcagnctt tggnaacttc cagaacgttc    480

caancccacn gaaaaaggga aacccggtan ccttngccgg gaaccccccct taaggggcga    540

aattccannn cacttggggg gnccgttnct aaaggggatc ccaaacttng ggncccaaan    600

nttgggggga aancangggg ccanaaanng gntcccctgg gggnaaaaat ggntatnccg    660

gttcnaaaan ttcccccccn aanatttngg ggcn                                694
```

<210> SEQ ID NO 632
<211> LENGTH: 252
<212> TYPE: DNA
<213> ORGANISM: Homo sapiens

<400> SEQUENCE: 632

```
acggccatct tccagctgct tgcctgcaaa gatgagcctc tgctggtcgg ggggaatgcc     60

ttccttatcc tggatcttgg ccttcacatt ttcgatggtg tcactgggct ccacctcaag    120

ggtgatggtc ttgccggtaa gggttttcac gaagatctgc attttgacct gttagcggat    180

accaggatcc tgccaatcac caaccacgtc cacccacagg gacacaaaca agctcaccca    240

acaaagccaa cc                                                        252
```

<210> SEQ ID NO 633
<211> LENGTH: 631
<212> TYPE: DNA
<213> ORGANISM: Homo sapiens
<220> FEATURE:
<221> NAME/KEY: misc_feature
<222> LOCATION: (1)...(631)
<223> OTHER INFORMATION: n = A,T,C or G

<400> SEQUENCE: 633

```
ggtactgttg attcaacaac aaaccttaat gggtgatgag cttttgcata ccaatatgaa     60

tttgtcagca cttctgaaaa ctggccatca tttttcaaat tcacaatttg ctggatgtca    120

gggaacaata ggaagaagaa tgagcgtcaa ttttcatgtc ttcctttgct tcttcactgg    180

ccttccatag aagtagtcag aaaaaaacaa agcaccatca accacacttc acaaacaatt    240

catgttggcc taagctttgc tcaacattca tatgacagaa gatagaataa tgaaaaggaa    300

ctgctggcat cactttcccc ataatattac ataaaaatgg acagcacatt aaataaacat    360

tctgntatta atcattaaat atattaacac caaaaatcat gtataaaatt aggaaataaa    420

tgtcctgccc ggccggncgc tcaaggccaa atncagncac tggcgggcgg tctagtggat    480
```

ccnactcgga ccaacttggc gtaacatngn catactggtt cctgggggaa atggtaatcc 540
nttacaantc ncacactnac anccggaanc taaggggtaa acttgggtgc ctaagaggng 600
nctacntnca ttaatgngtg gcncnttgcc c 631

<210> SEQ ID NO 634
<211> LENGTH: 561
<212> TYPE: DNA
<213> ORGANISM: Homo sapiens
<220> FEATURE:
<221> NAME/KEY: misc_feature
<222> LOCATION: (1)...(561)
<223> OTHER INFORMATION: n = A,T,C or G

<400> SEQUENCE: 634
gtgaaattgg tgagtttggt ggtgatttcc cggtgcctgc aatgaactcc tggtgaaatg 60
taggcgaggt tggaaagtag ctgggacaga caggagattt cctgaagttt ggagataaac 120
acgtggtaga gactggggag taacacagtg aaagtgggga gcttggtggt gatccctggg 180
atcctggaaa tgactggggc tgaaatgtgg gcgtggttgg agagtagctg ggacagacag 240
gagggtttgt aagggctggt ggtgaagacg tgagagagac tggcgaggat ctcactgagg 300
tctctgactt tctaggtgtt tctggggtgt gggagacata caacagctga aaactggaca 360
tagttggaca gcactgggac agaaaggaga tcgtgatggg tgggggtgac tgtctattgt 420
gccaacagan taccaaaagt atatcagacc gtttgctttc nttgaatggc ctctggctnt 480
caaaagcgna tggtangaca ctcagagtat tctnctaagc nttgataata cactgnttat 540
nctgcntgtg tctanctgcn c 561

<210> SEQ ID NO 635
<211> LENGTH: 630
<212> TYPE: DNA
<213> ORGANISM: Homo sapiens
<220> FEATURE:
<221> NAME/KEY: misc_feature
<222> LOCATION: (1)...(630)
<223> OTHER INFORMATION: n = A,T,C or G

<400> SEQUENCE: 635
accgaggctg ctaaagctgc cagtcacaac ccagcatgtc aactggttcc tcatgctctg 60
tttggtgtgg aaattcacat gtgccctgac actgaggaag caattgctta aaatcacttt 120
ccaataacag ctgataaaat attttgcagg tttgtcatgc aaggtttatt tattaggtgg 180
ctattcaaag tttgtatagc aaccacttaa gcagaactaa attaatattc actgagcact 240
gtaacgatgg aagagggctt ttcctaaggg ttgggttggg agttgtgctt ctgtgaaatt 300
aacatctctc actcattgcc aagattctct gcttaaaaat attagttttc tgtgctggtg 360
ccaaaatagc aatttaagcn aatgtagtgc cagaatgaca catgaacctn ggactnaggg 420
aacagttncc tgctgnggag taccttgggc gngaacacgc ttanggcgaa ttccacacac 480
tgcgggcgta ctaanggatc caactnggna ccancttggc gaatcatggc atactggttc 540
ctggggaaaa tggtatccgt tacaatcncn cacntaccag ccggaaccta annggnaaac 600
tgggggccta atggngacta cntcattant 630

<210> SEQ ID NO 636
<211> LENGTH: 640
<212> TYPE: DNA
<213> ORGANISM: Homo sapiens
<220> FEATURE:

<221> NAME/KEY: misc_feature
<222> LOCATION: (1)...(640)
<223> OTHER INFORMATION: n = A,T,C or G

<400> SEQUENCE: 636
actcctattg ccgccagtgg ggcctgtgga atgagtgtgc atggaggccc tcctgtgctg 60
ggggaatgag cccagagaac agcgaagtag cttgctccct gtgtccacct gtgggtgtag 120
ccaggtatgg ctctgcaccc ctctgccctc attactgggc cttagtgggc cagggctgcc 180
ctgagaagct gctccaggcc tgcagcagga gtggtgcaga cagaagtctc ctcaattttt 240
gtctcagaag tgaaaatctt ggaaaccctg caaacagaac agggtcatgt ttgcaggggt 300
gacggccctc atctatgagg aaaggttttg gatcttgaat gtggtctcag gatatcctta 360 tcagancttta nggtgggtgc tcanaataag gcangcattt gangaaaaat cttgggttct 420
ctttacagtg cccacttctt acacaccctt gaggcaagga atgcttgctt acaagtacct 480
tgggcgggaa cacgcttang gccaaattca acacacttgc cggccgtact aaagggatcc 540
ancttnggan ccaacttggn ggaaacatgg cnaaatggtt ccntggggaa atgnaatccg 600
ttcaattccc nnaantntca accggaacct taagggtaan 640

<210> SEQ ID NO 637
<211> LENGTH: 470
<212> TYPE: DNA
<213> ORGANISM: Homo sapiens
<220> FEATURE:
<221> NAME/KEY: misc_feature
<222> LOCATION: (1)...(470)
<223> OTHER INFORMATION: n = A,T,C or G

<400> SEQUENCE: 637
acctggtgac cttgaatgtg attaggactg ggagctccgt gaggccagag acctatgttc 60
atttagccta cataaaagac actcaataaa tagctggtaa aataacaaat gaataaatac 120
atatcatcaa gggttggggt cagtagacag cagtgcccaa gctggcatcc gtcaggaagt 180
gtgggccttt gtgttttgat gctacacatg tctatggagg gccacttctt ctgtaagtct 240
gtggggcctc agcataccca ataggcagca agtttcagta tttcccagtt gtatgtcctc 300
atggtggggc tatgtctccc ccaccacgtc ccctctcatc aggctagact ttaacatcca 360
tcaatcatgt cttgagtctt gctccttcct cttggcttan tcatgtgact acngatcaan 420
atcntggcct aatggtttaa gtgtnccang taccttnggc cgggcccacg 470

<210> SEQ ID NO 638
<211> LENGTH: 391
<212> TYPE: DNA
<213> ORGANISM: Homo sapiens
<220> FEATURE:
<221> NAME/KEY: misc_feature
<222> LOCATION: (1)...(391)
<223> OTHER INFORMATION: n = A,T,C or G

<400> SEQUENCE: 638
actggaacat caagttaaat acaaatactc agaactaacc actgtccaac aacagctaat 60
tagggagacg ctcatatcat ggctgcaagc tcagatgctg aatccccaac cagagaagac 120
ctttatacga aataaagccg cccaagtctt cgccttgctt tttgttacag agtatctcac 180
taagtggccc aagttttttt ttgacattct ctcagtagtg gacctaaatc caaggggagt 240
agatctctac ctgcgaatcc tcatggctat tgattcagag ttggtggatc gtgatgtggt 300
gcatacatca gaggaggctc gtaggaatac tctcataaaa gataccatga gggaacagtg 360
cattccaaat ctggtggaat catggnacct n 391

<210> SEQ ID NO 639
<211> LENGTH: 329
<212> TYPE: DNA
<213> ORGANISM: Homo sapiens

<400> SEQUENCE: 639
acatgctgac ccaccaggaa ctagcctccg atggggagat tgaaactaaa ctaattaagg 60
gtgatattta taaaacaagg ggtggtggac aatctgttca gtttactgat attgagactt 120
taaagcaaga atcaccaaat ggtagtcgaa aacgaagatc ttccacagta gcacctgccc 180
aaccagatgg tgcagagtct gaatggaccg atgtagaaac aaggtgttct gtggctgtgg 240
agatgagagc aggatcccag ctgggacctg gatatcagca tcacgcacaa cccaagcgca 300
aaaagccatg aactgacagt cccagtacc 329

<210> SEQ ID NO 640
<211> LENGTH: 764
<212> TYPE: DNA
<213> ORGANISM: Homo sapiens
<220> FEATURE:
<221> NAME/KEY: misc_feature
<222> LOCATION: (1)...(764)
<223> OTHER INFORMATION: n = A,T,C or G

<400> SEQUENCE: 640
gcggccgagg tacttcacca tcactgactc catggacttg atcagccgcc gctggatgta 60
tccagtctca gcagtcttga cagccgtgtc aatgagcccc tcacgacccc ccatggcgtg 120
gaaaaagaac tcagtgggtg tgaggccggc taggtaggag ttctccacaa agccacggct 180
ctcaggcccg tagtcatcct tgatgaagtg aggcagagtc cggtgcttga agccaaatgg 240
aatccgcttg ccctcgacgt tctgctgtcc aacgacagcg atgacctggg agatgttaat 300
cttggaacct ttagctccgg acacgaccat agacttgaag ttgttgnatt cagacaggga 360
tttctgaagc agaaggaacc agtcttggct tgggcattcg gtaanaaatgc gggtcacctg 420 aatcttcaaa acgtctggnc cgcaaaatgg ttcccctggg ggttggggct tccancntta 480
attggtgggg gngccctttn ttggaaggaa ccctctaatt aacggtcctt ggctttgggc 540
ctttccttaa ataaggggtn ctngnaaagg gccctngggn aaaggncntt aaaaaaatcc 600
nccaatnggg agnncccccc aanggcccca atnngtnttg ganccttttaa aannccccggg 660 ggaaaaaacc ttttngncaa aaacccccnt ttggggnccc ttttaaanaa aacccttggg 720
aatgggggaa tttnttnncc cccaaaanag gtttnaaaac ccgg 764

<210> SEQ ID NO 641
<211> LENGTH: 540
<212> TYPE: DNA
<213> ORGANISM: Homo sapiens
<220> FEATURE:
<221> NAME/KEY: misc_feature
<222> LOCATION: (1)...(540)
<223> OTHER INFORMATION: n = A,T,C or G

<400> SEQUENCE: 641
ggtacagtag ccatgaacta catacagtga cgcctctaga aacgtggtta gtgcaactga 60
ggaaggaatt tttaatctta tgtgatttta attggcttaa ctttaaacag ccgcatgtgg 120
ttactgtatt ggatagcaca gccctagagc ctgaagaaag caaaccaaag aacaccagct 180

```
gggtcccaaa cagaaggcag aaagggtaga accatccacc tcaactattc cagccccatc    240

agaaggcacc aggaacaggg caagagaaaa aggcaaaaac ccacccagcc catgaaaatt    300

cactcctcaa ccacccagca catcaaactg gaacaccaca ctatttcctg aaaaaatata    360

ttattatttt ctagaccaag gagatatata tatatagaac cagcacaatt ccacatcctc    420

atatatttgg actgtaaaaa acttgttcgc aantttttaa agacantnaa ggcagctagc    480

gggtaagtaa aaactgggag gtatgaaaca gagaaggaga gctttantta tnaaaaaaaa    540
```

<210> SEQ ID NO 642
<211> LENGTH: 608
<212> TYPE: DNA
<213> ORGANISM: Homo sapiens
<220> FEATURE:
<221> NAME/KEY: misc_feature
<222> LOCATION: (1)...(608)
<223> OTHER INFORMATION: n = A,T,C or G

<400> SEQUENCE: 642

```
ggtactagtg agaagaggga atatgcattg cagttcagca aagccggaat tctgtgttga     60

acagatgtct gtctccctag tgtgtgactc acaccttgtg gctgccttca gagcgccacc    120

tccagatcag atggggacac acaacccctg gatatgtttc attgtcagat tttgtgcttg    180

attttaagaa tggaattgtg ggtatctttc ctttttttta atgtatctta actgttgcct    240

gtcagtgttt acaaactagt gcgttgacgg caccgtgtcc aagtttttag aacccttgtt    300

agccagaccg aggtgtcctg gtcaccgttt caccatcatg ctttgatgtt cccctgtctt    360

tccctcttct gctctcaaga caaaggttaa ttaaggacna agatgaagtc actgtaaact    420

aatctggcat tggtttttac cttccttttc tttttcagtg cagaaaatta aaagttangt    480

attaaagcac ccgtaaaaaa aaataactnt antacaaana aaagcttgtn caagctttnt    540

tttttntntn tttttttttt ttatttcccc ggncaaaaaa gttttttnan tcaaantcaa    600

gggttnan                                                             608
```

<210> SEQ ID NO 643
<211> LENGTH: 669
<212> TYPE: DNA
<213> ORGANISM: Homo sapiens
<220> FEATURE:
<221> NAME/KEY: misc_feature
<222> LOCATION: (1)...(669)
<223> OTHER INFORMATION: n = A,T,C or G

<400> SEQUENCE: 643

```
acagagtcat ttacatagat tatgttgtgc tttgtgttta ttctccacac tttcagtcca     60

tattctgtcc tgtatatgtt tcccattttt ccaggcattt tagttccagg ccagactctg    120

ccaatatcac cagttgcaac agctccaggt ctcctgtggg ttttcgtttg accatgcgta    180

gcaggctggc ctttaaatcc ccatcttttc atgacacctt gaaaaccttt accaatagtt    240

ttggctgtga catccacata ctgtcctgga cgaaagtgag cagcataaag aggagtgcct    300

ggtttaattg cagcattatc tgttatatta aagattttaa ctgtctgttt cggcggcaat    360

ccaagttccc ggtaaaattc caatatggat gtagctttac gaaaacgtga tcaggttttc    420

cttctacaga cagggttgcc atttttcatt acaggtttcc ttttgacgta tattttaaga    480

catgacagtc ttgnacacta gaattatggt ttaagtttcc tttggnatta agagatatat    540

aaccctttca aaacaatctg gtccttaaaa aatntcaata atggaatgaa ttttcttaaa    600

aaaggggaga atccaccnnt gcacctgctt tggnnttaan aaaatatggg taaacattta    660
```

```
cttccntnn                                                          669


<210> SEQ ID NO 644
<211> LENGTH: 572
<212> TYPE: DNA
<213> ORGANISM: Homo sapiens
<220> FEATURE:
<221> NAME/KEY: misc_feature
<222> LOCATION: (1)...(572)
<223> OTHER INFORMATION: n = A,T,C or G

<400> SEQUENCE: 644

acaagctttt tttttttttt tttttttttt tttttttttc atattcacta nttgngacat     60

ntaactgctc aangatttct tgaatacgtt tttcaatttg ancctngtca ccttttcctt    120

ttaanagcat ggcatcgtct ttggncacaa ngacctntcc aacttttcct aagtcatgag    180

gctgaacgtc ttcaanattc agggtcaatc cctnttctcc aaacacctac aaaaagagtt    240

aaacgtaaac ctgttgtagg ttacagtttn tgccattata ccaagttnat taatacncca    300

tgcaananaa tcatcaaaat actttatttc tttgaaatga gagattttaa natcactgtt    360

agtccanaac aagacttgag tatagtctnt ttcactgnat ttccaaattc tcaattttca    420

caactggggt aattattacc agcnttactt gnnaaaaaaa cnttcnaagg tcacacttac    480

tgggaanagc caggacaana ncataggccn ttgactntta agtcctanaa tcccttggna    540

catacncttt tacctttnaa actgnngctt gg                                  572


<210> SEQ ID NO 645
<211> LENGTH: 690
<212> TYPE: DNA
<213> ORGANISM: Homo sapiens
<220> FEATURE:
<221> NAME/KEY: misc_feature
<222> LOCATION: (1)...(690)
<223> OTHER INFORMATION: n = A,T,C or G

<400> SEQUENCE: 645

ttgtgagacc ctcttcattc tggtgttgtc cttgaaccaa cagcatcccc tggaacgccc     60

caagcaagac caaggcagat actatgaggc aggcagcaca gggcccaaat caagaattgg    120

tgcagtcgaa tcagggctgt gggagaggcc ctatgtattc cggattccca gggcttgctc    180

taattcttgt cgtctctgct gcaccttgga gtagaagtat cggcacacag cctcctgagc    240

ccagggctgg aagtagaact cagctcggcg ctcctcctct gggttaccca ccacatcagt    300

cattgtcttg aggtccctgc actgggactg aagccagtca ttgatgaaac cctgagggtc    360

tctggccaaa cttaacatga actcccgctg agtcttcagc tggttgatgg gtttctattg    420

gctcatggat cttggtggct aaagtaccaa tcttctggtg gcccggcant gggacagcag    480

aaaaagaaat catcttgggg ctttcaaggn ggcattcact ttnaccatca atggcataac    540

aagctggcct ttttctnaac attcgggtca acactgatga cattgaataa nganaatagg    600

ttntggnggc attaaccang natggaaccn cttagggact ttgaaactta tcnntgagac    660

ttaananttn tgnggacctt gccgaacncg                                     690


<210> SEQ ID NO 646
<211> LENGTH: 770
<212> TYPE: DNA
<213> ORGANISM: Homo sapiens
<220> FEATURE:
<221> NAME/KEY: misc_feature
<222> LOCATION: (1)...(770)
```

<223> OTHER INFORMATION: n = A,T,C or G

<400> SEQUENCE: 646

```
cgaggtacat tccgctcacg gatctcagct tccagatggt ggatgaactg gaggcagtgc     60
ccaacatccc cctggtgccc gatgaggagc tggacgcttt gaagatcaag atctcccaga    120
tcaagagtga catccagaga gagaagaggg cgaacaaggg cagcaaggct acggagaggc    180
tgaagaagaa gctgtcggag caggagtcac tgctgctgct tatgtctccc agcatggcct    240
tcagggtgca cagccgcaac ggcaagagtt acacgttcct gatctcctct gactatgagc    300
gtgcagagtg gaggggagaa catccgggag cagcaagaaa gaagtgtttc anaaaagcttt    360
ctcccttgac atcccgtgga gcttgcanaa tgcctgaccc aacttcgtgt tggtggaaac    420
ttccagaact tgtncacaag catttcccgc ttgacccatt caatttaagg gaagaatgaa    480
tgaagtcttc cnggggcttt ttattggggt tttctggaat ggtcattcan tccacttnaa    540
gcccncttgg gaatttnaag cccgaggttt caaaatcttg tanccttggc ccngggccgg    600
gccggttcca aaggggcgaa atttccagcn cacttgggng ggccggtact tannggggat    660
cccaacttcg gnncccaacc ttggnggnaa ancatngggc ctanctnggt tccncgggng    720
gaaaatggta ttnccgttcc aatttccccc canntttnna accggagctt               770
```

<210> SEQ ID NO 647
<211> LENGTH: 454
<212> TYPE: DNA
<213> ORGANISM: Homo sapiens
<220> FEATURE:
<221> NAME/KEY: misc_feature
<222> LOCATION: (1)...(454)
<223> OTHER INFORMATION: n = A,T,C or G

<400> SEQUENCE: 647

```
acttggaatc ctccaggaag ggcttcagga cctggttggg gaagaccttc atcaggatct     60
tgtgtttccg cagctggtgt cgcataagaa gcttgtcctc tgcactcaga gccacattct    120
ggcagacggc tatcattcgg ttgtcctgga aaactgctgc tatctcccgg cggagaagcc    180
tgatgaggcc tatctcctcc tgtgggggc tgggaggaga tggcacgtat cttccaagta     240
tgttctgaaa attaaacagg gtaacctatt tttgatgtta tttcaaactg ctatattcat    300
ctatgtctag ttaaaaacaa tttttggttt attcacttac ataatgttct tatagtgata    360
ttttttccac ttattccana agtgttaggt gattattcta cacttcttgn gcccattcta    420
tggagaataa agatggtcct nggccgcgac cacc                                454
```

<210> SEQ ID NO 648
<211> LENGTH: 532
<212> TYPE: DNA
<213> ORGANISM: Homo sapiens
<220> FEATURE:
<221> NAME/KEY: misc_feature
<222> LOCATION: (1)...(532)
<223> OTHER INFORMATION: n = A,T,C or G

<400> SEQUENCE: 648

```
ggtacatgtg ggagaaaaac ttaagtgtga tgagtgtggt aaggaattca gtcagggcgc     60
tcatctacag acccatcaga aagtccacgt gatagagaaa ccatacaaat gtaagcaatg    120
tgggaaaggt ttcagtcgta gatcagcact taatgttcat tgcaaggtcc acacggcaga    180
gaaaccttat aattgtgagg agtgtgggag ggccttcagt caggcctctc atcttcagga    240
ccatcagaga ctccacactg gggagaagcc attcaaatgt gatgcatgtg gtaagagctt    300
```

```
cagtcggaat tcacatcttc aatcccatca aagagttcat acaggagaga aaccatacaa    360

atgtgaggag tgtggtaagg gcttcatttg tagctcaaat ctttacattc atcagagagt    420

ccacacagga gaaaaaccct ataaatgtga ggaatgtggt aaaggcttta gtcggncttc    480

aagtcttcag gcccatcagg gagttcacac tggagagaag tcatacatat gt            532
```

<210> SEQ ID NO 649
<211> LENGTH: 493
<212> TYPE: DNA
<213> ORGANISM: Homo sapiens

<400> SEQUENCE: 649

```
ggtacaaaat tgttggaatt tagctaatag aaaaacatag taaatattta caaaaacgtt     60

gataacatta ctcaagtcac acacatataa caatgtagac aggtcttaac aaagtttaca    120

aattgaaatt atggagattt cccaaaatga atctaatagc tcattgctga gcatggttat    180

caatataaca tttaagatct tggatcaaat gttgtccccg agtcttctgc aatccagtcc    240

tcttagaaat tggtttctct ctttgggaga ttcagactca gaggcagcca gaggggacag    300

gtcaagagct gaaataatca cataactact ctaattttct tcattctatt gactgtgtca    360

agttatagac acagccaaag tgtttttctt ctgcctctga tgatttgaga agatgaagaa    420

catgagcaat ttctcattgc ttaaagaaaa acttggcaca taagaggctg agtgtagtag    480

agtatctgtc ctg                                                       493
```

<210> SEQ ID NO 650
<211> LENGTH: 693
<212> TYPE: DNA
<213> ORGANISM: Homo sapiens
<220> FEATURE:
<221> NAME/KEY: misc_feature
<222> LOCATION: (1)...(693)
<223> OTHER INFORMATION: n = A,T,C or G

<400> SEQUENCE: 650

```
gagactttgg atccttcctg aggacgtgga gaaaacttgc tgctgagaag gacattttga     60

aggttttgtt ggctgaaaaa gctgtttctg gaatcacccc tagatctttc ttgaagactt    120

gaattagatt acagcgatgg ggacacagaa ggtcacccca gctctgatat ttgccatcac    180

agttgctaca atcggctctt tccaatttgg ctacaacact ggggtcatca atgctcctga    240

gaagatcata aaggaattta tcaataaaac tttgacggac aagggaaatg ccccaccctc    300

tgaggtgctg ctcacgtctc tctggncctt ggctgtggcc atattttccc nccggggtat    360

gaacggnttc tttttccgcg gactctttcg caacccnttt ggcaggcccc attcaatgct    420

gaatggcaac ctggtngctg cactggtggc tgctttattg ggactgggtn aaggaactta    480

ntccggttgn aatgcttgat nccgggnccc ttnggtaatt gggcnttttn tgnggactnt    540

tggncaaggt ttgggnccca tgtanccttg ggccggnaac acccttangg gcnaanttcc    600

gcncacttgg ccgggccgta ctanagggaa tcccaacttg gnacccaacn ttggggnaaa    660

catnggcana actggttccc gggggaaaa tgg                                  693
```

<210> SEQ ID NO 651
<211> LENGTH: 678
<212> TYPE: DNA
<213> ORGANISM: Homo sapiens
<220> FEATURE:
<221> NAME/KEY: misc_feature
<222> LOCATION: (1)...(678)

<223> OTHER INFORMATION: n = A,T,C or G

<400> SEQUENCE: 651

```
ggtacgaagt ttgttaccac agtagagata atttagtaga aaaatgcttt gaggcttcag     60
tatttgtaag attttgcatt agccagatgc taggttgttg aaggcatttc agtgttgata    120
ataacctgag cagacttctt tacaaatggg atctgtttct atatgtgtat atgcccactt    180
accattcaga gagactggtc tttctctttg tcttccttca cattgctgtg tcagttctac    240
acctagtctt ttcagcactt agcaaattca aattttgatt tttttgtcag cttagttcac    300
tttaaggcat attggcatgg tgtgtgaaag tgatgttttg ccccagtatt gaggactttt    360
agatccnaat aatgactcat taaatataat tatgttttaa gtatacctga atttctggta    420
gcttaaaatg ttaattctca ggaatgattt tctcacactt ttggggtggc taataataaa    480
agcactggtt tattctcaaa actccttttt tcaaaattag ggagagagcn naagtggaca    540
ttttatgtga acccctttgn aaaanatgggg gntngantgc ngagaaacca atggagtttt    600
ngntgcnaaa aggtttttttc ccgnaangta aaattggaat aantggcnat tgaggaccct    660
tgnnctgccc ggcggcnn                                                   678
```

<210> SEQ ID NO 652
<211> LENGTH: 676
<212> TYPE: DNA
<213> ORGANISM: Homo sapiens
<220> FEATURE:
<221> NAME/KEY: misc_feature
<222> LOCATION: (1)...(676)
<223> OTHER INFORMATION: n = A,T,C or G

<400> SEQUENCE: 652

```
ggtacaagct tttttttttt tttttttttt tttttttgtg tttaaatgca ttttattttt     60
agacaaccta catgacatgt ttttcttaaa aacaatgcct ccactccaaa taaatcacag    120
tcaaaataaa tgaagagctc aagatgacat cagtcccatt tgtcttaagt cctggtgttg    180
tgtggatgac aagcagaagc cagttatgat gacaggtgat agatccaaaa taattgccac    240
atttgttaac atttttccat ttctaaacca tccttaaaga aaatcatata tggggtcaca    300
ccatcctcac ggtagtccaa tagagcaacc atgccatctg gattcatgtt ttcaccaata    360
aagaactggt aagtttttga aattagcaag ggatgtgctt gatttgttct gcaacccctg    420
gcataaaaag gtttactctt tctnggctct ggtctttaag gttncctttg aatggattca    480
tgtaaccttt gatgtaccct ggcccggccg gccaagggac ntgtaaaagn gccccaatcc    540
acccganaan aaataagggg tttnttccgc gnttangane tcctttggac cttttttaan    600
cttgcctgnn ggaaattaat ctggccnttt acctnggana atagaaaata ntttttcccg    660
naaccttgaa cttcnn                                                     676
```

<210> SEQ ID NO 653
<211> LENGTH: 468
<212> TYPE: DNA
<213> ORGANISM: Homo sapiens

<400> SEQUENCE: 653

```
tcgagcggcc ccgggcaggt actccagcat tggttatagt catgggaaag gaaggtgtcc     60
acggaggcac acttaacaag aaagcatatg aactcgcttt atacctgagg aggtctgatg    120
tgtaagcagc ctctccccat ctacctagca actgtcttca tcaacaaccc taattatggt    180
cacaatgcta ccaaactgta gatggtagct aatttttctt tacctatttt ctaatgtcat    240
```

```
gattcctgtt tgcccaatgg atcatttgta tgttaaccac tgtatgtaac caacccttat    300

ctggcaacat aattgcagca caataatgat ttgcatgata ccttgaaatt ggggggaggg    360

ggcatgccaa gttgggcatc actttgtctt agcaattaat gggatattga ttactaaaat    420

aagttaatat taaacaaggt gccggttgta ccttggccgg gaacacgc                 468


<210> SEQ ID NO 654
<211> LENGTH: 612
<212> TYPE: DNA
<213> ORGANISM: Homo sapiens
<220> FEATURE:
<221> NAME/KEY: misc_feature
<222> LOCATION: (1)...(612)
<223> OTHER INFORMATION: n = A,T,C or G

<400> SEQUENCE: 654

actgaagagc ccatggatac tacttctgca gttatccatt cagaaaattt tcagacattg     60

cttgatgctg gtttaccaca gaaagttgct gaaaaactag atgaaattta cgttgcaggg    120

ctagttgcac atagtgattt agatgaaaga gctattgaag ctttaaaaga attcaatgaa    180

gacggtgcat tggcagttct tcaacagttt aaagacagtg atctctctca tgttcagaac    240

aaaagtgcct ttttatgtgg agtcatgaag acttacaggc agagagaaaa acaagggacc    300

aaagtagcag attctagtaa aggaccagat gaggcaaaaa ttaaggcact cttggaaaga    360

acaggctaca cacttgatgt gaccactgga cagaggaagt atggaggacc accttcagat    420

tccgtttatt caggtcagca gccttctgtt ggcacctgag atatttgtgg ggaaagatcc    480

caagagatct atttgaggat gaacctggtn cantaatttg agaaaacctn gacctatatg    540

gggatcntcg tctaatgatg ggatcccttc actgggcttn aataaanggt ntgccgttgg    600

caantttttg nc                                                        612


<210> SEQ ID NO 655
<211> LENGTH: 608
<212> TYPE: DNA
<213> ORGANISM: Homo sapiens
<220> FEATURE:
<221> NAME/KEY: misc_feature
<222> LOCATION: (1)...(608)
<223> OTHER INFORMATION: n = A,T,C or G

<400> SEQUENCE: 655

ggtactttgt cctggaggaa gggcacgact acacttcttc caaggggcag aacatggtgt     60

gcggcggcat gggctgcaac aatgattccc tggtgcagca gatatttaac gcggcgcagc    120

tggacaacta tacccgaata ggcttcgccc cctcgtcctg gatcgacgat tatttcgact    180

gggtgaagcc acagtcgtct tgctgtcgag tggacaatat cactgaccag ttctgcaatg    240

cttcagtggt tgaccctgcc tgcgttcgct gcaggcctct gactccggaa ggcaaacaga    300

ggcctcaggg gggagacttc atgagattcc tgcccatgtt cctttcggat aaccctaacc    360

ccaagtgtgg caaaaggggg acatgctgcc tatagtctgc agttaacatc ctccttggcc    420

atggcaccag ggtcngaacc acgtactaca atgaanccac aggtggcaaa atgttcctcg    480

tgccttctgt ggattaaact gggaccatgg cttgtcctag nccttttgcng ncttaaccaa   540

cacttgattg canttgggag taaatggcaa gcctccagag cncactgtnt tgctgaggac    600

tccgcgcc                                                             608


<210> SEQ ID NO 656
```

-continued

```
<211> LENGTH: 659
<212> TYPE: DNA
<213> ORGANISM: Homo sapiens
<220> FEATURE:
<221> NAME/KEY: misc_feature
<222> LOCATION: (1)...(659)
<223> OTHER INFORMATION: n = A,T,C or G

<400> SEQUENCE: 656

accaaactga ccaatgggct gcaagaggtt tagattattg ctacccacaa aattctgagc     60

caaattgata atggtcatca ttagtgacat ctcgccatga tgataagaag acatttcagc    120

cactgatcca gctaattggg caacctttac ttctcgcttg tcattccgtt tgaagcaagt    180

aaacaaaacc tttctctgac ctggtttcaa accatccacc atagaaggga tagatctctc    240

gttatcagaa tttgagaaca agataagttc cttgttgatg aagtcattat atgtcagata    300

tgtggtagtt tgtccataca agtaatcctc aggaagccca agtaactttc gttgtcttct    360

atcctccatg aaattagtta accattcctt tcgatcatct atctgttttt tgctaaaggc    420

caggctgata gcagcatcat cttcaggacc agaatatttg aactggatac gatgtctttt    480

catatctgca aagtatcttt acttcctttg atgtgctggt gcccaaacct ttgnaatatt    540

ggcttttcat ttttatgatt gggagtagaa ctcttncact cttcaaattc aggaangctt    600

naaaatgcct ttcttgcttg gtttagancc tttccatggg agtgataaat cctccgaaa     659


<210> SEQ ID NO 657
<211> LENGTH: 676
<212> TYPE: DNA
<213> ORGANISM: Homo sapiens
<220> FEATURE:
<221> NAME/KEY: misc_feature
<222> LOCATION: (1)...(676)
<223> OTHER INFORMATION: n = A,T,C or G

<400> SEQUENCE: 657

ggtacagaat tatataattc taacgcttaa atcatgtgaa agggttgctg ctgtcagcct     60

tgcccactgt gacttcaaac ccaaggagga actcttgatc aagatgccca accctgtgat    120

cagaacctcc aaatactgcc atgagaaact agagggcagg tcttcataaa agccctttga    180

accccttcc tgccctgtgt taggagatag ggatattggc ccctcactgc agctgccagc     240

acttggtcag tcactctcag ccatagcact ttgttcactg tcctgtgtca gaacactgag    300

ctccaccctt ttctgagaag ttattacagc cnagaaagtg tgggctgaaa aatgggtggg    360

ttcatggttt tggattaatg gatctttttg gatgggaaag actatatttt gggacctcat    420

cttttcccag gatgacccag aagctanaac ctgctaaaag gattcttgga acntgaaggg    480

tattaatacn aacccnntca tggnggnatc ctnggaacct gccgggaaga aggccnttgg    540

cccgtttaat gcnccggtgc tnaacaagtc tgnttcttgn ntttcacttc ancttggggc    600

cctggaatca nctggcnctg gtgnncagtt taactatgnc ttgntggaac ccctaaggcc    660

ttangcctta ccaaag                                                    676


<210> SEQ ID NO 658
<211> LENGTH: 646
<212> TYPE: DNA
<213> ORGANISM: Homo sapiens
<220> FEATURE:
<221> NAME/KEY: misc_feature
<222> LOCATION: (1)...(646)
<223> OTHER INFORMATION: n = A,T,C or G

<400> SEQUENCE: 658
```

```
ggtacaatgg aacaaacaac aagaacacac ctgtctatgt gtcctcacca acctgggaga     60

atcacaatgc tgtgttttcc gctgctggtt ttaaagacat tcggtcctat cgctactggg    120

atgcagagaa gagaggattg gacctccagg gcttcctgaa tgatctggag aatgctcctg    180

agttctccat tgttgtcctc cacgcctgtg cacacaaccc aactggaatt gacccaactc    240

cggagcagtg gaagcagatt gcttctgtca tgaagcaccg gtttctgttc cccttctttg    300

actcagccta tcagggcttc gcatctggaa acctggagag agatgcctgg gccattcgct    360

attttgtgtc tgaagcttcg agttcttctg tgcccatcct tctccaagaa cttcggctct    420

acaatgagag agtcnggaat ctgactgntg gttggaaaag aacctgagaa catcctgcaa    480

gtcctttcca gatgagaaaa tcgtgccgat tacttggtcc aatcccccgg ccaaggagcc    540

cnaattgtgg ccagcaccnt tttaacctga cttttgagga tggcnggtat ntgaaacatg    600

gtnaccgatc tggcctgana ctgactnngn ncnntnaanc ctaaan                   646
```

<210> SEQ ID NO 659
<211> LENGTH: 673
<212> TYPE: DNA
<213> ORGANISM: Homo sapiens
<220> FEATURE:
<221> NAME/KEY: misc_feature
<222> LOCATION: (1)...(673)
<223> OTHER INFORMATION: n = A,T,C or G

<400> SEQUENCE: 659

```
actgtgtcca acagctgaag gaatttgagg ggaagacttt agtgtcagtc accaaagaag     60

gcctggaact tccagaggat gaagaagaga aaaagaagca ggaagagaaa aaaacaaagt    120

ttgagaacct ctgcaaaatc atgaaagaca tattggagaa aaaagttgaa aaggtggttg    180

tgtcaaaccg attggtgaca tctccatgct gtattgtcac aagcacatat ggctggacag    240

caaacatgga gcgaatcatg aaagctcaag ccctaagaga caactcaaca atgggttaca    300

tggcagcaaa gaaacacctg gagataaacc ctgaccattc cattattgag accttaaggc    360

aaaaggcaga ggctgataag aacgacaagt ctgtgaagga tctggtcatc ttgctttatg    420

aaactgcgct cctgncttct ggcttcagtc tggaagatcc cagacacatg ctaacaggat    480

ctcagggatg atcaaacttg gtctgggtat tgatgaagat gaccctactg ntgatgatcc    540

catgcttgct gnaactgaag aaatgcccnc ccttgaagga gataccaccc ctnacgcctg    600

ggaanaagtn actaactttg gcttanggat nnttaccngt cagaccttgg ncggaccccc    660

ttagggcnaa tcc                                                       673
```

<210> SEQ ID NO 660
<211> LENGTH: 580
<212> TYPE: DNA
<213> ORGANISM: Homo sapiens
<220> FEATURE:
<221> NAME/KEY: misc_feature
<222> LOCATION: (1)...(580)
<223> OTHER INFORMATION: n = A,T,C or G

<400> SEQUENCE: 660

```
acaaaacgcc acattctcac ttgtattggg agctgaaaaa tgggatcaca tggacgcagg     60

acggggaaca acacacactg gggcttttcg ggagacagag cgttaagaaa aacagctgat    120

gcatgctggg cttaatacct aggtgacggg ttgacaggtg cagcaaacca ccatggcact    180

cgtttacctt agtaacaaat atacacatcc tgcccatata ccccagaact tagaaacaga    240
```

```
acgaaacaaa agaaaacgag aaagcaatag caaatcgcta gcgggaaaac aaattttcaa    300

actcagaaaa tgacagacca atttttgctt caaatcatgg ttcttaaccc aggtgccata    360

aggtcaggat aaagaatttg attacatatt gtaaataaga catgcagcaa atgaccagaa    420

aaattattcc caacatatgt gtgtcttcga attcaatggt gacgctatct accgggacat    480

aacattagat tccaaagggc cgagtnncac aagactgncc tnccatacta ataacnatga    540

aagccctacg ttgggtttac ctgcttttnt ancagctggg                          580
```

<210> SEQ ID NO 661
<211> LENGTH: 710
<212> TYPE: DNA
<213> ORGANISM: Homo sapiens
<220> FEATURE:
<221> NAME/KEY: misc_feature
<222> LOCATION: (1)...(710)
<223> OTHER INFORMATION: n = A,T,C or G

<400> SEQUENCE: 661

```
ggtacatata aatgaatctg gtgttgggga aaccttcatc tgaaacccac agatgtctct     60

ggggcagatc cccactgtcc taccagttgc cctagcccag actctgagct gctcaccgga    120

gtcattggga aggaaaagtg gagaaatggc aagtctagag tctcagaaac tcccctgggg    180

gtttcacctg ggccctggag gaattcagct cagcttcttc ctaggtccaa gccccccaca    240

ccttttcccc aaccacagag aacaagagtt tgttctgttc tgggggacag agaaggcgct    300

tcccaacttc atactggcag gagggtgagg aggttcactg agctccccag atctcccact    360

gcggggagac agaaacctgg actctgcccc acgctgtggc cctggagggt cccggttgnc    420

agttcttggt gctctgtgtt cccagaggca agccggaggt ttgaaagaaa ggaacctggg    480

atgaaggggt gctgggtata aaccagaaaa gggatngggt tcctgnttcc aangggaccc    540

ctttggcctt tcttctggcc tttcctaagg cccaggnctg gggnttggnc ccttgggccg    600

ngaaccacgc ttaagggccg aaattccagc acacttggcc ggccggtacc tagtgggatc    660

ccaactttgg gtccaaactt tggcgtaaat catngggcct aacttngttn               710
```

<210> SEQ ID NO 662
<211> LENGTH: 411
<212> TYPE: DNA
<213> ORGANISM: Homo sapiens

<400> SEQUENCE: 662

```
ccaaaatctg gaatgttcat agtgtcctca atgtccttca ttccctggta gacaaatcca     60

acatcaaccg acagttggag gtatacacaa gcggaggtga ccctgagagt gtggctgggg    120

agtatgggcg gcactccctc tacaaaatgc ttggttactt cagcctggtc gggcttctcc    180

gcctgcactc cctgttagga gattactacc aggccatcaa ggtgctggag aacatcgaac    240

tgaacaagaa gagtatgtat tcccgtgtgc cagagtgcca ggtcaccaca tactattatg    300

ttgggtttgc atatttgatg atgcgtcgtt accaggatgc catccgggtc ttcgccaaca    360

tcctcctcta catccagagg accaagagca tgttccagag gaccacgtac c             411
```

<210> SEQ ID NO 663
<211> LENGTH: 633
<212> TYPE: DNA
<213> ORGANISM: Homo sapiens
<220> FEATURE:
<221> NAME/KEY: misc_feature
<222> LOCATION: (1)...(633)
<223> OTHER INFORMATION: n = A,T,C or G -continued

<400> SEQUENCE: 663
ggtacttggt tttaatgctc gtcagcgaaa agcctttctt aatgcaatta tgcgatatgg 60
tatgccacct caggatgctt ttactaccca gtggcttgta agagacctgc gaggcaaatc 120
agagaaagag ttcaaggcat atgtctctct tttcatgcgg catttatgtg agccgggggc 180
agatggggct gagacctttg ctgatggtgt cccccgagaa ggcctgtctc gccagcatgt 240
ccttactaga attggtgtta tgtctttgat tcgcaagaag gttcaggagt ttgaacatgt 300
taatgggcgc tggagcatgc ctgaactggc tgaggtggag gaaaacaaga agatgtccca 360
gccagggtca ccctccccaa aactcctaca ccctccactc caggggacac gcagcccaac 420
actcctgcac ctgtccacct gctgaagatg gataaaatng aaggaaaata cctcaaagaa 480
ganagagctn gaaggagaaa aggaggttaa actacagccc tgaactgcca tgatgactgc 540
ccggcggccg tcaaaggcna atcaaccatn gcgccgtnta atggntcaac tnggaccant 600
tgcnaacatg cnaacttgtc ctgggaaatg nnc 633

<210> SEQ ID NO 664
<211> LENGTH: 598
<212> TYPE: DNA
<213> ORGANISM: Homo sapiens
<220> FEATURE:
<221> NAME/KEY: misc_feature
<222> LOCATION: (1)...(598)
<223> OTHER INFORMATION: n = A,T,C or G

<400> SEQUENCE: 664
gcgtggtgcg gcccgaggta ctgggtccaa atgctggaga agttacacaa ggctttgcag 60
ctgcgctcaa atgtggactg accaaaaagc agctggacag cacaattgga atccaccctg 120
tctgtgcaga ggtattcaca acattgtctg tgaccaagcg ctctggggca agcatcctcc 180
aggctggctg ctgaggttaa gccccagtgt ggatgctgtt gccaagactg caaaccactg 240
gctcgtttcc gtgcccaaat ccaaggcgaa gttttctaga gggttcttgg gctcttggca 300
cctgcgtgtc ctgtgcttac caccgccaag gccccttgg atctctttgg ataggagttg 360
tgaatagaag cagcacatca cacttgggtc actgcagaac ttgaanttga cattggcagg 420
catcnaggat natccatgag tcaccagtct nagccatgtg taggcgtatg acactgcaaa 480
tatttacata ccttcctggg attctatctc tggaagttnn ggtgattttc tttttcatgg 540
naanattaan taaactncat tatttgcaac anntgttaat cntcagggtg tctgaagg 598

<210> SEQ ID NO 665
<211> LENGTH: 658
<212> TYPE: DNA
<213> ORGANISM: Homo sapiens
<220> FEATURE:
<221> NAME/KEY: misc_feature
<222> LOCATION: (1)...(658)
<223> OTHER INFORMATION: n = A,T,C or G

<400> SEQUENCE: 665
acccaaaagc agtgcaggac ctctgcagct ggagaatctg gagcctggct tgtgggaaga 60
gcagcatcat tgtggcagcc gatgagagca ccatcagctg ggcccatca ccgacctttg 120
gggaactggg ctacagggat cacaagccca agtcttccac tgcagcccag gaggtgaaga 180
ctctgcatgg cattttctca gagccggtcg ccatgggcta ctcacactcc ttggtgatag 240
caagagatga aagtgaaact gagaaagaaa agatcaagaa actgccagaa tacagccccc 300

-continued

```
aaaccctctg atgctccaga gactcctccg actccacacc tctcatggca gctgcatttc    360

catgtgcact gggaccggaa agtcaaacna ggaatttaaa aaagccaaag tggacccaaa    420

ggtgcctttt tatttaaact tcctganggt ncggtttacc agtgatccaa cggtnactac    480

cttttttttct ggttgctttc caaagaccct ttttttctct taatggccaa ataaaaaacc    540

tgnttcgaan tggcntaaca nttctaccaa gaggccnaaa ccttttacca ttaagggggt    600

tttttcttct tctntctgaa acccttncca aaaactcntt tccgtttaat nnntnngg      658
```

<210> SEQ ID NO 666
<211> LENGTH: 349
<212> TYPE: DNA
<213> ORGANISM: Homo sapiens

<400> SEQUENCE: 666

```
gcggcggcgg gggaagcagc gtgagcagcc ggaggatcgc ggagtcccaa tgaaacgggc     60

agccatggcc ctccacagcc cgcagtatat ttttggagat tttagccctg atgaattcaa    120

tcaattcttt gtgactcctc gatcttcagt tgagcttcct ccatacagtg gaacagttct    180

gtgtggcaca caggctgtgg ataaactacc tgatggacaa gaatatcaga gaattgagtt    240

tggtgtcgat gaagtcattg aacccagtga cactttgccg agaaccccca gctacagtat    300

ttcaagcaca cttgaaccct cagcccctga atttattctc ggttgtacc                349
```

<210> SEQ ID NO 667
<211> LENGTH: 768
<212> TYPE: DNA
<213> ORGANISM: Homo sapiens
<220> FEATURE:
<221> NAME/KEY: misc_feature
<222> LOCATION: (1)...(768)
<223> OTHER INFORMATION: n = A,T,C or G

<400> SEQUENCE: 667

```
ggtggcgagg tggaggccca ggactctgac cctgcccctg ccttcagcaa ggcccccggc     60

agcgccggcc actacgaact gccgtgggtt gaaaaatata ggccagtaaa gctgaatgaa    120

attgtcggga atgaagacac cgtgagcagg ctagaggtct ttgcaaggga aggaaatgtg    180

cccaacatca tcattgcggg ccctccagga accggcaaga ccacaagcat tctgtgcttg    240

gcccgggccc tgctgggccc agcactcaaa gatgccatgt tggaactcaa tgcttcaaat    300

gacaggggca ttgacgttgt gaggaataaa attaaaatgt ttgctcaaca aaaagtcact    360

cttccaaagg cccgacataa gatcatcatt cttggatgaa acaagaacag cattgacccg    420

acggagccca agcaagccnt tgaaggaaga acccatggga aaatctactt ttaaaaaacca    480

cttcgntttc gncccttttgc nttggaaatg gcttttngga ttaagaaaca attngaagcc    540

ccaatttaan tnccccgctt ggggccaatc ccnttccngg taaccttggn cccngggccn    600

ggcccggttt cnaaaanggg ccnaaaattt ccaagcacca ctttgggnng ggncccgntn    660

ncttaanggg gatcccaaac tttgggnacc ccanncottg nggcgnaaaa ncaatgggcc    720

ataaannggg gttcccctgg ggngnaaaaa tgggnattnc ccccncnc                 768
```

<210> SEQ ID NO 668
<211> LENGTH: 659
<212> TYPE: DNA
<213> ORGANISM: Homo sapiens
<220> FEATURE:
<221> NAME/KEY: misc_feature
<222> LOCATION: (1)...(659)
<223> OTHER INFORMATION: n = A,T,C or G

<400> SEQUENCE: 668

```
ggtacagtat cctctccaga catttgcaat tggcatggaa gacagccccg atttactggc     60
tgctagaaag gtggcagatc atattggaag tgaacattat gaagtccttt ttaactctga    120
ggaaggcatt caggctctgg atgaagtcat attttccttg gaaacttatg acattacaac    180
agttcgtgct tcagtaggta tgtatttaat ttccaagtat attcggaaga acacagatag    240
cgtggtgatc ttctctggag aaggatcaga tgaacttacg cagggttaca tatattttca    300
caaggctcct tctcctgaaa aagccgagga ggagaagtga gaggcttctg agggaactct    360
atttggttga tgttctccgc gcagatcgaa ctactgctgc ccatggtctt gaactgagaa    420
gtccatttct agaacatcga ntttcttnct aatacttggc tttgccccag aaatgagaaa    480
ttccaagaat gggatngaaa aacattttct gaganaaacc ntttgaggat tccaatctga    540
taccaaagag aatctttggc gaccaaanaa accttnatga tnggaaacct tngntaaaaa    600
tnctggttaa aattnnngga atccttnact tngggtnata atccngangg caaannccc     659
```

<210> SEQ ID NO 669
<211> LENGTH: 409
<212> TYPE: DNA
<213> ORGANISM: Homo sapiens
<220> FEATURE:
<221> NAME/KEY: misc_feature
<222> LOCATION: (1)...(409)
<223> OTHER INFORMATION: n = A,T,C or G

<400> SEQUENCE: 669

```
acgtgccgcg gaaatgctcc gctagcaatc gcatcatcgg tgccaaggac cacgcatcca     60
tccagatgaa cgtggccgag gttgacaagg tcacaggcag gtttaatggc cagtttaaaa    120
cttatgctat ctgcggggcc attcgtagga tgggtgagtc agatgattcc attctccgat    180
tggccaaggc cgatggcatc gtctcaaagt aaggttgggg gctcacattt gggcagagtg    240
agtggactag gactgctcca gaggcgtggt cttaacgttg tccttttccc ctggttctag    300
gaacttttga ctggagagaa tcacagatgt ggaatatttg tcataaataa ataatgaana    360
aaaaannnnn nnnnnnaaaa aaaaaaactt gtcctcggcc ggaccacgc                409
```

<210> SEQ ID NO 670
<211> LENGTH: 741
<212> TYPE: DNA
<213> ORGANISM: Homo sapiens
<220> FEATURE:
<221> NAME/KEY: misc_feature
<222> LOCATION: (1)...(741)
<223> OTHER INFORMATION: n = A,T,C or G

<400> SEQUENCE: 670

```
accgctgtaa gactgccaag aagtcagagg aggagattga ctttcttcgt tccaatccca     60
aaatctggaa tgttcatagt gtcctcaatg tccttcattc cctggtagac aaatccaaca    120
tcaaccgaca gttggaggta tacacaagcg gaggtgaccc tgagagtgtg gctggggagt    180
atgggcggca ctccctctac aaaatgcttg gttacttcag cctggtcggg cttctccgcc    240
tgcactccct gttaggagat tactaccagg ccatcaaggt gctggagaac atcgaactga    300
acaagaagag tatgtattcc cgtgtgccag aatgccaggt caccacatac tattatgttg    360
gggtttgcat atttgatgat gcgtcgttac caggatgcca tcgggtcttc gccaacatcc    420
tnctctacat ccagaggacc nagaagcatg ttncagaagg acccacgtac ctttggccgn    480
```

```
gaccacgcct aagggccaaa attncaacac actggccngg ncggttacct aagtggaatc    540

cnaaccttcg gnanccaaag ctttggccgt naatccatng ggccataagc ttggttccct    600

gggggggaaa attggtaatn ccggttcacn aatttcccca ccaacnttcc naaacccggn    660

aagcctttaa agnggtnaaa accntggggg tggccnnaaa ggggggggac ctnaacttnc    720

atttaaatng gggttggccn c                                              741
```

<210> SEQ ID NO 671
<211> LENGTH: 699
<212> TYPE: DNA
<213> ORGANISM: Homo sapiens
<220> FEATURE:
<221> NAME/KEY: misc_feature
<222> LOCATION: (1)...(699)
<223> OTHER INFORMATION: n = A,T,C or G

<400> SEQUENCE: 671

```
ggtacagcag gaattacaac tactacctca ccgagaactc ctccaccact gactgttcag     60

gatcccttat gtcctgcagt ttgtccctta gaagaattat ctccagatag tattgatgca    120

catacgtttg attttgaaac tattccccat ccaaacatag aacagactat tcaccaagtt    180

tctttagact tggattcatt agcagaaagt cctgaatcag attttatgtc tgctgtgaat    240

gagtttgtaa tagaagaaaa tttgtcgtct cctaatccta taagtgatcc acaaagccca    300

gaaatgatgg gtggaatcac tttattcatc agttatcaat gcgatagaca gtagacgaat    360

gcagggatca aatgtatgtg gtaaggaggg attttggaga tcatacttct ctgaatgtcc    420

agttggaaag atgtagagtt gttgcccaag actctcactt cagtatacca accattaagg    480

aagaccttgg cacttttaga accattgtac ctggcccggc cggccggttc naaanggccg    540

aanttccagc acacttggcn ggccgttact tagtgggatt ccgagcttcg ggacccaagc    600

nttggcggta atcatngggc catagctggt tcccngngtg naaattggta ttccggttac    660

caattcccca ccacnnttcc ancccggnaa ccntaaagt                           699
```

<210> SEQ ID NO 672
<211> LENGTH: 377
<212> TYPE: DNA
<213> ORGANISM: Homo sapiens
<220> FEATURE:
<221> NAME/KEY: misc_feature
<222> LOCATION: (1)...(377)
<223> OTHER INFORMATION: n = A,T,C or G

<400> SEQUENCE: 672

```
actgaagctg aaatgcagga agtggtggca aaggtttatt ccagagaagc caggaagccg     60

gtcatcaccc agcctctgag agcagttact ggggtcaccc aacctgactt cctctgccac    120

tccccgctgt gtgactttgg gcaagccaag tgccctctct gaacctcagt ttcctcatct    180

gcaaaatggg aacaatgacg tgcctacctc ttagacatgt tgtgaggaga ctatgatata    240

acatgtgtat gtaaatcttc atgtgattgt catgtaaggc ttaacacagt gggtggtgag    300

ttctgactaa aggttacctg ttgtcgtgat ctgaaaaaaa aaannnnnaa aaaaaaaaac    360

ctnggccgnn accacgc                                                   377
```

<210> SEQ ID NO 673
<211> LENGTH: 650
<212> TYPE: DNA
<213> ORGANISM: Homo sapiens
<220> FEATURE:
<221> NAME/KEY: misc_feature
<222> LOCATION: (1)...(650)
<223> OTHER INFORMATION: n = A,T,C or G

<400> SEQUENCE: 673

```
cgaggtactt gattggacca gatggtgagt ttctagatta ttttggccag aacaagagga     60
agggagaaat agctgcttca attgccacac acatgaggcc atacagaaaa aagagctagc    120
caaagcagtg ttgctggatg cagtattctc ttgctaagag gaaggaaact gtctcgcata    180
ggagcctata taaatataaa catatatacg tgcactctac agaatggcct tcataccatg    240
agaacatttc tgttttggat ggggatgtta cccttgcgtt caaccaaaat tgattcttgg    300
aactgtaaag attacaaccc aaagtctccc aggaagctgt ggggagacca gaggatcaag    360
ctgaagtgaa accagtgaaa aacccacctg tggaaggcat ggcggggcca ggcacaccag    420
tgcattcctg cctgcgaaca ggcctccaca actttgccgc ttttcatcgc ttgggccctt    480
gctaaatagc tgtgggactg aattcacaga aaagaatnta tttccatagg ctcttgctgg    540
ctcttcttga gtcttttntct ttgagtcttg gnggctatac cgncgaatag ggcttggcat    600
tanagtgatg cttgaacttt agttcctata angattnctn tcgattgcta               650
```

<210> SEQ ID NO 674
<211> LENGTH: 705
<212> TYPE: DNA
<213> ORGANISM: Homo sapiens
<220> FEATURE:
<221> NAME/KEY: misc_feature
<222> LOCATION: (1)...(705)
<223> OTHER INFORMATION: n = A,T,C or G

<400> SEQUENCE: 674

```
ggtacaagct tttttttttt tttttttttt ggtgaaaaga tatatatata tatatattca     60
gaattaggca gctggactca gtttagatga tcccaatttt gttggcaaca tccaaagcat    120
cgtaatcagg agccagtcga acatatgcct tcttctctcc atcaggccga atcagggtgt    180
tgaccttggc cacatcaatg tcatacagct tcttcacagc ctgtttaatc tggtgcttgt    240
tggctttaac atccacaatg aacacaagtg tgttgttgtc ttctatcttc ttcatggcag    300
actcagtggt cagcggaaac ttgatgatag catagtggtc aagcttgttt ctcctgggag    360
cgctcttccg aggatatttg ggctgtctcc ggagtcgcag tgtcttcggc cgcccgaagg    420
nggggtgacg tgccggatct tcttcttttt ggggctgtgg accacctttc aacactgcct    480
ttttgggccn ttnaaagccc ttngctttgg ctttagcttt taggaagggg ccaggaacct    540
tnccttnttc gcttttcgga acctgccccg gccgggccgt tcnaaaaggg cnnaatttcc    600
aacncacttg gcngggccgn tactaagggg atnccaanct ttggnancca anctttggcg    660
naaancttgg ggcnataact ggnttcccgg ngngnaaaaa tgntt                    705
```

<210> SEQ ID NO 675
<211> LENGTH: 622
<212> TYPE: DNA
<213> ORGANISM: Homo sapiens
<220> FEATURE:
<221> NAME/KEY: misc_feature
<222> LOCATION: (1)...(622)
<223> OTHER INFORMATION: n = A,T,C or G

<400> SEQUENCE: 675

```
ggtaccctaa ttttccttgc acccatgcct gtccaatcag atgactctgg gaaacgccaa     60
acaggctgaa tcaatgtctt tgtgtggttt ttttcttcca gattgttttt ttctcaccta    120
```

```
taaaaggatc tatctttaaa aataaactgt attaaatctg taacatcaaa ggcagaaggt    180

ttgtgtgtgt gtgtgtgtgt gtgtgtgtat ctgtgtgttt aaatcaaggg gagattgcat    240

ttataaatca tactggcctt atgaacatcc tctgcaataa atatactttt tagccttaac    300

tataaattat atattttagt gtttaaaaac cttccggtgt gaaacatcta agataaccct    360

taaaaaccac ctgttctcta ggtaaacctc tgaggtccct actttcaaac accagttggc    420

accaaaggat tcctaaactt caacttcttt aaagaaaaga aaggaactta tcatctggca    480

tgtgagaatg caacctttc tcttnctgca cgcagctnca acacccactc atgcacacag    540

tggccacctt gctaaagtct gttgaacagc ctgcggcgcg tcaagngatc accactgcgc    600

gtctatgacc actcgacact gc                                              622
```

```
<210> SEQ ID NO 676
<211> LENGTH: 620
<212> TYPE: DNA
<213> ORGANISM: Homo sapiens
<220> FEATURE:
<221> NAME/KEY: misc_feature
<222> LOCATION: (1)...(620)
<223> OTHER INFORMATION: n = A,T,C or G

<400> SEQUENCE: 676

cgaggtgcac aggcaccact aataatcaga cctgattctg gaaaccctct tgacactgtg     60

ttaaaggttt tggagatttt aggtaagaag tttcctgtta ctgagaactc aaagggttac    120

aagttgctgc caccttatct tagagttatt caaggggatg gagtagatat taataccttta    180

caagagattg tagaaggcat gaaacaaaaa atgtggagta ttgaaaatat tgccttcggt    240

tctggtggag gtttgctaca gaagttggca agagatctct tgaattgttc cttcaagtgt    300

agctatgttg taactaatgg ccttgggatt aacgtcttca aggacccagt tgctgatccc    360

aacaaaaggt ccaaaaaggg ccgattatct ttacatagga cgccagcagg gaatttggta    420

cactggaaga aggaaaagga gaccttgagg aatatggtca ggatctcttc atctgcttca    480

gaatggcang tgacaaaagc tatctttgta aaaaaaaaaa aaaaacctgc cgccgncgtc    540

aangccaatt caccctgcgg cgtctatgac cactgnccac tgcnatntgc tactgtnctg    600

ggaatgatcg tncatcncan                                                620
```

```
<210> SEQ ID NO 677
<211> LENGTH: 691
<212> TYPE: DNA
<213> ORGANISM: Homo sapiens
<220> FEATURE:
<221> NAME/KEY: misc_feature
<222> LOCATION: (1)...(691)
<223> OTHER INFORMATION: n = A,T,C or G

<400> SEQUENCE: 677

cgaggtactg ggtccaaatg ctggagaagt tacacaaggc tttgcagctg cgctcaaatg     60

tggactgacc aaaaagcagc tggacagcac aattggaatc caccctgtct gtgcagaggt    120

attcacaaca ttgtctgtga ccaagcgctc tggggcaagc atcctccagg ctggctgctg    180

aggttaagcc ccagtgtgga tgctgttgcc aagactgcaa accactggct cgtttccgtg    240

cccaaatcca aggcgaagtt ttctagaggg ttcttgggct cttggcacct gcgtgtcctg    300

tgcttaccac ccgccaagcc cccttggatc tcttggatag gagttggtga atagaagcag    360

gcagcatcac actggggtca ctgacagact tgaactgaca ttttggcaag gcatcgaaag    420

gatgtattcc atgaagtcac cagtcttaaa cccatgtggt aagccggtga tggaaccact    480
```

gtnaaatcaa ttttaacatg aacctttcnt gnggatttct taatctcggt gcaagttttt 540
aagggtgaat ttttcttttt ctncatgggg gtaatgattt tnagatgaaa acctttccag 600
ttgatttttg tccaaancaa tnatggttaa atatccctcc agggnntttt ncttgaagga 660
aattggtnct ttgaggtttt agcttnccgg a 691

<210> SEQ ID NO 678
<211> LENGTH: 667
<212> TYPE: DNA
<213> ORGANISM: Homo sapiens
<220> FEATURE:
<221> NAME/KEY: misc_feature
<222> LOCATION: (1)...(667)
<223> OTHER INFORMATION: n = A,T,C or G

<400> SEQUENCE: 678
cgaggtactt gattggacca gatggtgagt ttctagatta ttttggccag aacaagagga 60
angggagaaa tagctgcttc aattgccaca cacatgaggc catacagaaa aaagagctag 120
ccaaagcagt gttgctggat gcagtattct cttgctaaga ggaaggaaac tgtctcgcat 180
aggagcctat ataaatataa acatatatac gtgcactcta cagaatggcc ttcataccat 240
gagaacattt ctgttttgga tggggatgtt acccttgcgt tcaaccaaaa ttgattcttg 300
gaactgtaaa gattacaacc caaagtctcc caggaagctg tggggagacc agaggatcaa 360
gctgaagtga aaccagtgaa gagcccacct gtggaaagga catggcgggg cgaggcacaa 420
ncagtgcatt cctgcctgcg aacagncctn cacactttgc cgctttcatc gcttgggcct 480
tggtaaatac tgtggactga atttccagaa aagaatntat ttcataggnt cttnttgctt 540
tcttgagtct tgtctttgag tcttggggnt aanacagtcn aatanggctt tgcnttcaag 600
tgancttgaa cctaagttcc tntaangana tcctttcnat gctatgaaag gaattttgtt 660 nggggaa 667

<210> SEQ ID NO 679
<211> LENGTH: 302
<212> TYPE: DNA
<213> ORGANISM: Homo sapiens
<220> FEATURE:
<221> NAME/KEY: misc_feature
<222> LOCATION: (1)...(302)
<223> OTHER INFORMATION: n = A,T,C or G

<400> SEQUENCE: 679
cgaggtactg atggggaagt gccggcgctt cttggatgaa ctagatgcgg ttcagatgga 60
ctgagcttgg atgcttctga ggcaagctga agctttgggt tctgactgac ccaccctaca 120
ggactgctga acagagagcc cagtgtgact agggatcctg agttttctgg gacaattcca 180
gctttaatca atacattttg ttaaatgtgc cataaaatga gactttttac gcctttataa 240
ggccttagat gtaaataaac tcacccaaac aaaaaaaaaa aaaanaaaaa aaaaaagctt 300
gt 302

<210> SEQ ID NO 680
<211> LENGTH: 649
<212> TYPE: DNA
<213> ORGANISM: Homo sapiens
<220> FEATURE:
<221> NAME/KEY: misc_feature
<222> LOCATION: (1)...(649)
<223> OTHER INFORMATION: n = A,T,C or G

<400> SEQUENCE: 680
ggtacgtgct caggaaatta aaaacaaaaa tcaaggaatt gaacaacaca tgtgaacccg 60
ttgtaacaca accgaaacca aaaattgaat cacccaaact ggaaagaact ccaaatggcc 120
caaatattga taaaaaggaa gaagatttag aagacaaaaa caattttggt gctgaacctc 180
cacatcagaa tggtgaatgt taccctaatg agaaaaattc tgttaatatg gacttggact 240
agataacctt aaattggcct attccttcaa ttaataaaat atttttgcca tagtatgtga 300
ctctacataa catactgaaa ctatttatat tttctttttt aaggatattt agaaattttg 360
tgtattatat ggaaaaagaa aaaaagctta agtctgtagt ctttatgatc ctaaaaggga 420
aaattgcctt ggtaactttc agattcctgt ggaattgtga attcatacta agctttctgg 480
gcagtctcac catttgcata ctgaggatga aactgacttt ggcntttgga gaaaaaaact 540
gtcctgccgg cggccgtcaa aggcaattca ccctgcggcg tntanggacc actnggacca 600
ctgggaantg gctactgtcc tggaatgtnc cgtccatccc aatcaccgg 649

<210> SEQ ID NO 681
<211> LENGTH: 722
<212> TYPE: DNA
<213> ORGANISM: Homo sapiens
<220> FEATURE:
<221> NAME/KEY: misc_feature
<222> LOCATION: (1)...(722)
<223> OTHER INFORMATION: n = A,T,C or G

<400> SEQUENCE: 681
cgaggtacca ccagagggaa agctggggcg gagggatttg ttcgtgttga cccgagatta 60
tgtgctgaag tctgcagagc tggcaaaagc tggagggtgc aaacatttca acttgctatc 120
ctctaaagga gctgataaat caagcaattt tttatatcta caagttaagg gagaagtaga 180
agccaaggtt gaagaattaa aatttgatcg ttactctgta tttaggcctg gagttctgtt 240
atgtgatagg caagaatctc gcccaggtga atggctggtt agaaagttct ttggctcctt 300
accagactct tgggccagtg ggcattctgt gcctgtggtg acccgtgggt tagagcaatg 360
ctgaacaatg tgggtgagac caagagacaa gcagatggaa ctgctggaga acaaggccat 420
ccatgacctg ggaaaagcg catggctctn tnaagccatg acccccattg gagaaatggg 480
ttttattggc aacccttaca cccattaccc aaatcngnaa tttcanggtc taaaaaaaag 540
tcancctggt ttaactttgg ngggttacta atccttaggc ttcanttcca atcaggaaat 600
gatggggcct ntggattaag gggttcaaaa cccgggtttc cctttggann cttcggggnc 660
ntttggnaaa ataaaaattt gnnncccntnt tttaacttga atnaaaattt ngggggggc 720 cn 722

<210> SEQ ID NO 682
<211> LENGTH: 530
<212> TYPE: DNA
<213> ORGANISM: Homo sapiens

<400> SEQUENCE: 682
ggtacttgcc tttagtttat caggggatgt gtaaggagct tcaggagcat aaatcctgaa 60
aatatcagca aggcagcagg ctaccagtaa gcgaacatcc ttatcaggat gcttgaggaa 120
aaaatctgaa gcaagatgta aagctaggtt taaataaagc tccttttctt cttcagagtc 180
ctggtccata tccataaaag ttttcacaac catctataca aaaataaaaa atcaaataat 240
gaaatgctcc atgtaaaact acagtcatgt gaaataaagg tcatgttaat tgctaaggtt 300

```
aacttcaaat gaatatactt tcatttttct gcagaaagtc tctatttgag agaacacaat    360

tctcctaaaa ctacaaagta aacttctatt taaaagactt actaaaatat tttttcattt    420

acccaaaata tctgctaacc agatttttaa agattaaatt gcccttatgt agtagtcatt    480

attggaagaa ttccaataga atatttgtgg aaacttctgg tctcacttgt              530
```

<210> SEQ ID NO 683
<211> LENGTH: 745
<212> TYPE: DNA
<213> ORGANISM: Homo sapiens
<220> FEATURE:
<221> NAME/KEY: misc_feature
<222> LOCATION: (1)...(745)
<223> OTHER INFORMATION: n = A,T,C or G

<400> SEQUENCE: 683

```
ggtacctgtc tttccttatt ccctcatcct tagtggatca tttgtatctc ctgccttatg     60

agaacctttt gacagaagat gagacaacca tatctgatga tgtggatatc gctcgggatg    120

tcatatgtct tataaaatgc ctccggctga ttgaagagtc agtaactgtg gatatgtcag    180

ttataatgga aatgagttgt tataacctac agtctccgga aaaggctgca gagcagattc    240

tggaagatat gatcactatt gatgtagaaa atgtgatgga ggatatttgt agtaaactgc    300

aagagattag gaacccaatc catgcaattg gactacttat acgggaaatg gattatgaaa    360

cagaagtgga aatggaaaag ggattcaatc cagctcacct ttgaatattc gaatgaatct    420

tacccagctc tatggtagta acacagcagg gtatattgtg tgccagangg gtgcattaaa    480

atccgccagt acctgcccng gccggccgnt cgaaanggcc naatttccac acactgggcg    540

ggccgttact angggggaatc ccaagctttg gganccaagc nttggncgta atcatgggcc   600

ataanctngg tnccctgggn ngaaaatngg taatccggtt aacaattncc ccnccaactt    660

tcccnacccg gnaaccctta aaggggtaaa aaccctgggg gggncccaaa gggagggggc    720

cttaaccttc ccctttaaat tggcn                                          745
```

<210> SEQ ID NO 684
<211> LENGTH: 628
<212> TYPE: DNA
<213> ORGANISM: Homo sapiens
<220> FEATURE:
<221> NAME/KEY: misc_feature
<222> LOCATION: (1)...(628)
<223> OTHER INFORMATION: n = A,T,C or G

<400> SEQUENCE: 684

```
ggttggagac ccgagaaccg gaggctggag agcaaaatcc gggagcactt ggagaagaag     60

ggaccccagg tcagagactg gagccattac ttcaagatca tcgaggacct gagggctcag    120

accttcgcaa atactgtgga caatgcccgc atcgttctgc agattgacaa tgcccgtctt    180

gctgctgatg actttagagt caagtatgag acagagctgg ccatgcgcca gtctgtggag    240

aacgacatcc atgggctccg caaggtcatt gatgacacca atatcacacg actgcagctg    300

gagacagaga tcgaggctct caaggaggag ctgctcttca tgaagaagaa ccacgaagag    360

gaagtaaaag gcctacaagc ccagattgcc agctctgggt tgaccgtgga ggtagatgcc    420

cccaaatctn aggacctcgc aagatcatgg cagacattcc ggcccaatat gacaactggc    480

tcggaagaac cnagangact ngacaagtcc ttgccggccg ncgtcnaagg caattcacca    540

ctgnggcgtc tatgatccac tgnncactgg gantgctact gtctggaatg ttcgtnatcc    600
```

```
cactcacgac tagnactggc tagggata                                      628


<210> SEQ ID NO 685
<211> LENGTH: 758
<212> TYPE: DNA
<213> ORGANISM: Homo sapiens
<220> FEATURE:
<221> NAME/KEY: misc_feature
<222> LOCATION: (1)...(758)
<223> OTHER INFORMATION: n = A,T,C or G

<400> SEQUENCE: 685

gcgtgggtcg cggcccgagg tacggagcaa atgttttatt taataagtta taagatacaa     60

tttacagtcg gcgtttgatt ccagtttngg cttccgtggt ccaacttaac acaccccgtg    120

ggcccttcac aataagcttc cggctggtcc actttctgta ngggtgggct tttaccccaa    180

cactngccca gatctacacc tgccacaaga ntggccactt tctnaggact aagcagcaaa    240

acctaaaggn ctgcctgcca gaccacacta cacatttggg ctcaggcaac gtccctgaca    300

ctttaacctc attccaaagc cagctcaggt ctgcaggaag gcaggcaaaa ttccctacac    360

ctcatttctg gatttctgca ccacacagnt ctnactggtt ctgcccatgg tgaaaagacc    420

ccaataagct gntggccttn tttccccaac cattcccaac tttnagggcc aagancccca    480

agaggttcaa tctggcctgc tggacctggc cggcnggccg ntnnaaangg ccaaantcca    540

ncacaattgg gnggncggta ctaaagggga acccaacttn gggnccaaac tttggggnaa    600

acatggggnn naannggggnn ccngggngn aaaatngnna ncccntttcc aaattncccn    660

ccaannttttn naacccggaa accttaaang ggnaaaancc cggggggggcc caaagggggg    720

ggccnannnn cccnttaaan ggggnngggc cccccnn                             758


<210> SEQ ID NO 686
<211> LENGTH: 697
<212> TYPE: DNA
<213> ORGANISM: Homo sapiens
<220> FEATURE:
<221> NAME/KEY: misc_feature
<222> LOCATION: (1)...(697)
<223> OTHER INFORMATION: n = A,T,C or G

<400> SEQUENCE: 686

ggtacagatt gggcggaatg tggagaaggt tggccacagt ccagagccag gagcccatgg     60

aacaacttgg aaggtgactc aggtgaggct gtcaatgagg gaatcccgca tgctggtggc    120

aatggtgcta ggctgggctt cattcagctt gaagacactc tccaccactg acagctctgt    180

gctggttgtg tccaggccac agaaggcaca ccagtcattc accaccatcc cagcagcaat    240

cacctcactg cctcggttca cagtccccgc cacaaggggg acttgaagaa gagaggacag    300

ctcatcctgg tcttcaattg aagtcttggg atgcaccagc cctccctgat tgctgaagac    360

acagtagctt cctactagca cctggtcggc cactgctgtc tgaagacttc caccttgagc    420

acatctgcca gaatttcttc tgnctcctgt ccaagtctgg gtggaccaag gncacgtagt    480

catttcaagt ggtgacattg cccaaggctt aaaaccgttc ttcaaccgnc taatctgcac    540

ttggtctggg aaggttgttg ccaatgtgtg caacttctgg ggccgnggta ttgtngggac    600

cttgcccggc cggccgttca aagggcaatt ccanccaatg ggggccgtac tangggaacc    660

ancttgggnc caacttgggg naanatgggc nnaacgn                             697


<210> SEQ ID NO 687
<211> LENGTH: 668
```

<212> TYPE: DNA
<213> ORGANISM: Homo sapiens
<220> FEATURE:
<221> NAME/KEY: misc_feature
<222> LOCATION: (1)...(668)
<223> OTHER INFORMATION: n = A,T,C or G

<400> SEQUENCE: 687

```
acataataac ctcatcaact aacttttaaa ttaactgaat ggctattatg tatttattac     60

tcaataccag tccattacct aatataagag cactaagagt atttaatcat tacctatttt    120

aatttatttt ataggtgaaa aacactgatg tcaagttagg ttgaggaact tatattcaag    180

gtcctccagc taactgtcga cacaacaatg actagaacta attgtcaggt ctcctgataa    240

ttagtccact gttctttcta ttctaccata aggttgttag gatgaagaat actgcagttt    300

tactgcataa atattctgaa gtcagactta ctctaaggca ttcttccttc agaatacagg    360

ctaaagcaga attttacaag ctactgcttc tttttttttt ttttttttta ataaacacag    420

aacattttgn tcaaaccaaa tctaactcag aagtgnaaat aatgnaagcc aatcactatt    480

aaaaggcnga atttcctaaa gggaaaanta ccatttaacc aacctttcta aagtaaacat    540

cctttccang ggactgggga tttagnctta cacttgaagg cttcctggga cctgggcggn    600

acccttangg cnattcancc atgggggcgg tctanggnnc cacttgggcc annttggnna    660

attnggcn                                                             668
```

<210> SEQ ID NO 688
<211> LENGTH: 375
<212> TYPE: DNA
<213> ORGANISM: Homo sapiens

<400> SEQUENCE: 688

```
acatcaattc agtgagaaaa ggtgtgtagg gagccataag tctgcaaaga gaaagcagaa     60

cactaaacaa ggtttctagg gccatgacac aatcctccat cccattttca ccctttaatc    120

ttctgcggtt cattctaaca taccaattgg tcagaatatc tacaaacttg accaggcgag    180

gcaccacagt ataaagccta taagctgcca tttcagtctc aaagaagcca atgagagact    240

gcatgaagga caggatccac cggtctgtaa tgttggggct ttctctaacc gtgttctcat    300

tgtagagaaa ttctatttct tcctccttct ggagcctcag aacgttctgg attaagaagc    360

gataggcatt gtacc                                                     375
```

<210> SEQ ID NO 689
<211> LENGTH: 582
<212> TYPE: DNA
<213> ORGANISM: Homo sapiens
<220> FEATURE:
<221> NAME/KEY: misc_feature
<222> LOCATION: (1)...(582)
<223> OTHER INFORMATION: n = A,T,C or G

<400> SEQUENCE: 689

```
ggtaccaaaa gttaaatgac ttacctgggc tgtttagaaa ctctctacct agaaagattt     60

ccattaccgt cagatgttag gagaggatct aacataggaa aggtcaccag ttgtcacaga    120

aaaagccaaa gaacttaggt ctagtgcccc tttgccactg acaaactaat aacaccctct    180

agacatcctc aagtccttct ccttgctcag gaattttctt ctaccaggtc ttttctacca    240

acttctctgt ataactacat cttactcatc tttcaaagcc cgactcagtt gccccttcca    300

tctagaaaac tttccagacc aaactatccc agcacatggt tatgatctct caaacctctg    360
```

-continued

```
tgtttcccca tccctgttgc ccgttaaatt ctgccacaag ctcagaccga ctctctattt    420

ggcttatttg tgtctaatcc attgagttct cctccaaagc agagatcatg cttcactcat    480

ttctgcatct ncaggacctt atgaatgaat gaatgtgtga attataagga ttactaaagc    540

cncagggcct gactcaaagc caggacccta gtaggngctt gg                       582
```

<210> SEQ ID NO 690
<211> LENGTH: 812
<212> TYPE: DNA
<213> ORGANISM: Homo sapiens
<220> FEATURE:
<221> NAME/KEY: misc_feature
<222> LOCATION: (1)...(812)
<223> OTHER INFORMATION: n = A,T,C or G

<400> SEQUENCE: 690

```
actaaagcgg atgggaatgt cgtttggcct ggagtcaggc aaatgctctc tggaggatct     60

gaaacttgcg aaatccctgg tgccaaaggc tttagaaggt tatatcacag atatctccac    120

aggaccttct tggttaaatc agggactact tctgaactct acccaatcag tttcaaattt    180

agacctgacc actggtgcca ccttacccca gtcaagtgta aaccaagggt tatgcttgga    240

tgcagaagtg gccttaacaa ctgggcagtt cctggcccca aacagtcacc agtccagcag    300

tgcggnctnt nactgnttcg agtcccgaag cgaagacccc ctggtcgttc aatgatgaan    360

atgaaggaan atgatgaagg agggattccc tncttcccaa gaattaaaga ccangaagaa    420

agccctacct tttcaaatat ggtgaatgcc tcaatggtgt ggtttggtaa ntgggtgaag    480

cctcnttggg ttttttgaaa atggaattgg ctttcaagtc cttttggccc tttgggtttg    540

gcacttgggg ngggttcaan nggaaaaanc tttngnggaa aacnccccat ttaggcccaa    600

attcnccatt gaaanggctt tgaaaaatgn atttggnaaa ttgnaaaagg ttnaaccctt    660

aangggggna attgnaaaan tnttgggccc aaccngaacc ccnttnnaan gggnttttnc    720

cccaannaaa agcctggcnt tttttgaggg gaaaaaaanng gggggataaa ncccccttaaa  780

aaaatttgcc cnnntnnaag ngccaccntt tt                                  812
```

<210> SEQ ID NO 691
<211> LENGTH: 691
<212> TYPE: DNA
<213> ORGANISM: Homo sapiens
<220> FEATURE:
<221> NAME/KEY: misc_feature
<222> LOCATION: (1)...(691)
<223> OTHER INFORMATION: n = A,T,C or G

<400> SEQUENCE: 691

```
acctactata atacagtagc taacatgtat tgagcacaga tttttttttgg taaaactgtg   60

aggagctagg atatatactt ggtgaaacaa accagtatgt tccctgttct cttgagcttc    120

gactcttctg tgctctattg ctgcgcactg ctttttctac aggcattaca tcaactccta    180

aggggtcctc tgggattagt taagcagcta ttaaatcacc cgaagacact aatttacaga    240

agacacaact ccttccccag tgatcactgt cataaccagt gctctaccgt atcccatcac    300

tgaggactga tgttgactga catcatttta tcgtaataaa catgtggctc tattagctgc    360

aagctttacc aagtaattgg catgacatct gagcacagaa attaaggnaa aaaaccaaag    420

caaaacaaat acatgggctg aaantaactt gatgccaagc ccaaggcact gatttctggg    480

natttgaact tanggcaaat cagagctaca cagacgccta cagaaggttc aggaagangc    540

agaagccttc aatttgaaag aaatttattg gcaccaaagt aagggccgga tnaaccttta    600
```

```
ggcnttttta nggagggcct tttaaaaagg ntccttggcc ggaacncntt anggngaatt    660

ccancentgg gggccgtatt aagggacccg n                                   691


<210> SEQ ID NO 692
<211> LENGTH: 271
<212> TYPE: DNA
<213> ORGANISM: Homo sapiens

<400> SEQUENCE: 692

cgaggtactg ctgctaccac tggaagcgct gcgcctcttt cgggttttgt cccggccgcg     60

atccttctca ctcgactcct tggtggcccc tttatctttt gagcgatcct tggacttctc    120

atctgagcgg tctttgcgtt tggtaggtga aggagcccta gtgctggact ttttattatg    180

agaaacgatc cctaatcgat tgcaatttac gccgaagagc agcatcttcc ctccgccgcc    240

acctcctcct gctttcctca gccgccgagg c                                   271


<210> SEQ ID NO 693
<211> LENGTH: 730
<212> TYPE: DNA
<213> ORGANISM: Homo sapiens
<220> FEATURE:
<221> NAME/KEY: misc_feature
<222> LOCATION: (1)...(730)
<223> OTHER INFORMATION: n = A,T,C or G

<400> SEQUENCE: 693

cgaggttttt ttttgccgca catgaaacat tattttaatt ggtttaaagt ccctttataa     60

agagtgctac atggtttaga taaaggaaac atataactat tgagttacag gggattttat    120

taattataaa atgcaatcaa tttaaattac gtaggtttaa gactagtccc ttggataagc    180

cccaagcgaa tttgtcttca gattattaaa attagtgctg taaatcaggg tgggcaattc    240

acagcctttc tgaactgact gaactagagc ttgcagtgaa gtgttctgct gagactgagc    300

accttacaga tatttttctc cagaagatgg tgctgggtaa taaaatcatc acaattaggg    360

gaatggttaa gtggtctcta ctgnggcaaa tgccaactgn tggaattcac tttattgtag    420

aaaaacccaa actgagactc ttaagttttg gttaacaatg nggttctggg atgaaaccaa    480

ctactggggc actgnccagg taggaaacca ttctttcact ggggtttcag cataaatggg    540

aactggatgt tnaaaggcng ggaattaacc ctttttaggc caaaagaaaa agcttaantg    600

gggntttacc aangggntcc ctggggctta aattcaannn tgggncctac anngnccnna    660

ancccctggnt aaacccggat taaccettta acctgggaac ccaaccttta aangggggt   720

tttaaaaggg                                                           730


<210> SEQ ID NO 694
<211> LENGTH: 700
<212> TYPE: DNA
<213> ORGANISM: Homo sapiens
<220> FEATURE:
<221> NAME/KEY: misc_feature
<222> LOCATION: (1)...(700)
<223> OTHER INFORMATION: n = A,T,C or G

<400> SEQUENCE: 694

cgaggttaca aaccacaaag acattggaac actataccta ttattcggcg catgagctgg     60

agtcctaggc acagctctaa gcctccttat tcgagccgag ctgggccagc caggcaacct    120

tctaggtaac gaccacatct acaacgttat cgtcacagcc catgcatttg taataatctt    180
```

-continued

```
cttcatagta atacccatca taatcggagg ctttggcaac tgactagttc ccctaataat    240

cggtgccccc gatatggcgt ttccccgcat aaacaacata agcttctgac tcttacctcc    300

ctctctccta ctcctgctcg catctgctat agtggaggcc ggagcaggaa caggttgaac    360

agtctaccct cccttacagg gaactactcc accctggagc cttcgtagac acaccttgga    420

gtttttttcga aatatgggtt gggtttttgg gctctttggg tgaattaaaa taaaatttaa    480

atgccttcac gctgngatag gtgccacatg aactaccgag nttcngaaaa agaagggaga    540

actgacactt cttanngntt gcagactntt aangggccct taggactant ngggcttttg    600

ggggtaaaag gtncccttna agaancccng nacctggccn ggggggcgtt naaangggga    660

attcnanccn ctgggggccg tactaagggg acccactnng                          700
```

```
<210> SEQ ID NO 695
<211> LENGTH: 690
<212> TYPE: DNA
<213> ORGANISM: Homo sapiens
<220> FEATURE:
<221> NAME/KEY: misc_feature
<222> LOCATION: (1)...(690)
<223> OTHER INFORMATION: n = A,T,C or G

<400> SEQUENCE: 695

ggtacagatg gcactgacaa tcccctttct ggtggggatc agtatcagaa catcacagtg     60

cacagacatc tgatgctacc agattttgat ttgctggagg acattgaaag caaaatccaa    120

ccaggttctc aacaggctga cttcctggat gcactaatcg tgagcatgga tgtgattcaa    180

catgaaacaa taggaaagaa gtttgagaag aggcatattg aaatattcac tgacctcagc    240

agccgattca gcaaaagtca gctggatatt ataattcata gcttgaagaa atgtgacatc    300

tccctgcaat tcttcttgcc tttctcactt ggcaaggaag atggaagtgg ggacagagga    360

gatggcccct ttcgcttagg tggccatggg ccttcctttc cactaaaagg aattacncga    420

acagcaaaaa gaaggtcttg agatagtgaa aatggtgatg atatctttag aaggtgaaga    480

tgggttggat gaaatttatt cattcatgag agtctgagaa aactgngccg tcttcaagaa    540

aattgagagg cttccattca cttggncctg ccgactgacc atggctccaa ttggctataa    600

ggttgcagcc tttaatcgat ttncngggna gggttaaaag cttggnccgt tgggttccaa    660

acctaaaaaa aannnnnnnn aaaaaaanant                                    690
```

```
<210> SEQ ID NO 696
<211> LENGTH: 688
<212> TYPE: DNA
<213> ORGANISM: Homo sapiens
<220> FEATURE:
<221> NAME/KEY: misc_feature
<222> LOCATION: (1)...(688)
<223> OTHER INFORMATION: n = A,T,C or G

<400> SEQUENCE: 696

ggtacagaaa tgaggcgtcg cagaatagag gtcaatgtgg agctgaggga aagctaagaa     60

ggatgaccag atgctgaaga ggagaaatgt aagctcattt cctgatgatg ctacttctcc    120

gctgcaggaa aaccgcaaca accagggcac tgtaaattgg tctgttgatg acattgtcaa    180

aggcataaat agcagcaatg tggaaaatca gctccaagct actcaagctg ccaggaaact    240

actttccaga gaaaaacagc cccccataga caacataatc cgggctggtt tgattccgaa    300

atttgtgtcc ttcttgggca gaactgattg tagtcccatt cagtttgaat ctgcttgggc    360

actcactaac attgcttctg ggacatcaga acaaaccaag gctgtggtag atggaggtgc    420
```

```
catcccagca ttcatttctc tggtggcatc tccccatgct cacatnagtg aacaagctgt    480

ctgggctcta ggaaacattg caggtgatgg cttcaatggt nccagacttg ggtanttaag    540

acctggccgg ccggccgttc aaaaggccaa ntccacacct tggcggccgt ctanngg atc   600

caactnggac caacttgggg naacatggca aactggttct tggggaaatg gttccgttcc    660

aattccccaa tttcaccgag gctaaagg                                        688


<210> SEQ ID NO 697
<211> LENGTH: 732
<212> TYPE: DNA
<213> ORGANISM: Homo sapiens
<220> FEATURE:
<221> NAME/KEY: misc_feature
<222> LOCATION: (1)...(732)
<223> OTHER INFORMATION: n = A,T,C or G

<400> SEQUENCE: 697

gcgggtcgcg gccgaggtac tcccgattga agcccccatt cgtataataa ttacatcaca     60

agacgtcttg cactcatgag ctgtccccac attaggctta aaaacagatg caattcccgg    120

acgtctaaac caaaccactt tcaccgctac acgaccgggg gtatactacg gtcaatgctc    180

tgaaatctgt ggagcaaacc acagtttcat gcccatcgtc ctagaattaa ttcccctaaa    240

aatctttgaa atagggcccg tatttaccct atagcacccc ctctaccccc tctagagcca    300

aaaaaaaaaa aaaaaaaaaa aaaaaaagct tgtaccatct cccagtcctg gaggctggcc    360

atgtgagacc caggtattgc agggctggtt gcttctgagg ctgaggtgtg tcccgtcttg    420

ctccaggccc ttcccagctg gtcttctccc tacatttgca gacngatggc catccgaagn    480

tgacatcatc tcctttgggg ctggctctgg gnccattggg aattaatggt ttanagacng    540

aattcactgg ggtgcttaag cttgggcttc aaaccggtag gnttaaacnn nnttnctttc    600

ttagccttcc aagtaactng atnccnggct taanccccctg ggcccanccc aaagttcccc   660

ctttttttaan gggcctcttt ttaatngggt taaggnccnc tggaaggatt cntnttaact   720

nggaaancnt na                                                         732


<210> SEQ ID NO 698
<211> LENGTH: 651
<212> TYPE: DNA
<213> ORGANISM: Homo sapiens
<220> FEATURE:
<221> NAME/KEY: misc_feature
<222> LOCATION: (1)...(651)
<223> OTHER INFORMATION: n = A,T,C or G

<400> SEQUENCE: 698

cgaggtgcca cgtaatgtcc cgtagttcgc tcatcccgtc catgccagat ggattgtggg     60

gaaggtgatt gggacaaaaa tgcaaaagac tgctaaagtg agagtgacca ggcttgttct    120

ggatccctat ttattaaagt attttaataa gcggaaaacc tactttgctc acgatgccct    180

tcagcagtgc acagttgggg atattgtgct tctcagagct ttacctgttc cacgagcaaa    240

gcatgtgaaa catgaactgg ctgagatcgt tttcaaagtt ggaaaagtca tagatccagt    300

gacaggaaag ccctgtgctg gaactaccta cctggagagt cccgttgagt tcggaaacca    360

cccagctaag caaaaatctg gaagaactca atatctcttc agcacagtga agcgggagtg    420

gaagaaggat ctaaagggaa aaactgacat gtttatgtta tggaaaaaga aattttctaa    480

gttcatcaca actgngtcag ttcttgngng ttatgaatac taaaccaatg aataanggct    540
```

```
actatggttt tacaaaaaaa nnnaataaaa anaactgnct gccggggcgt naaggnaatn    600

accatgngcg tntntggnnc acttggccac ntgggannggg cnantgtctg g             651


<210> SEQ ID NO 699
<211> LENGTH: 709
<212> TYPE: DNA
<213> ORGANISM: Homo sapiens
<220> FEATURE:
<221> NAME/KEY: misc_feature
<222> LOCATION: (1)...(709)
<223> OTHER INFORMATION: n = A,T,C or G

<400> SEQUENCE: 699

actgtagcat attaataccc tgtgaactgc aaaaaaccaa atacatttac agtagtattg     60

gtcaccaaaa tagaggggaa actttacaat tgtgagaatg tgtaaatgtt ctcattaagg    120

cagtattgac ccagacaacc atttagtatt catctatccc ctcaatgcct cataattctg    180

gaatgcctgt tgtgaaacat gtcagtgcac agtgtctcct aaattctcac acgtgcttga    240

ttttctgatt catctggtga actgggagta ggaagttggt catagacaat atgccctcct    300

tctcttgtct gaccaaagct tgaagcaatc acatctactg ccaggttagc tgtagtcttc    360

gcctcttcct ctgaggtggc caactgagga ttgacttcaa caagatccag tgctgatagc    420

aaccctgnat tgggtattcc tcagcaatat acatgccttc tcgatanggt aagtcccccg    480

acacaggagt tnctgtggct tggagcccgt gtaggggcaa atgcntnaat atcnaaactt    540

caaatggaat gggcttttgg ctcttgccaa tcancngaac caaangttcg ntccctgaac    600

cntttggaaa cccagttnat tcaanttntn tcangggaaa aaacctggga atcnaagnct    660

tttaaaaaaa aaggttcnga ngggncnccg tttttnaacc aaaaaaccc                709


<210> SEQ ID NO 700
<211> LENGTH: 656
<212> TYPE: DNA
<213> ORGANISM: Homo sapiens
<220> FEATURE:
<221> NAME/KEY: misc_feature
<222> LOCATION: (1)...(656)
<223> OTHER INFORMATION: n = A,T,C or G

<400> SEQUENCE: 700

ggtcagaacc taaaggtttc actgaatgcg aaatgacgaa atctagccct ttgaaaataa     60

cattgttttt agaagaggac aaatccttaa aagtaacatc agacccaaag gttgagcaga    120

aaattgaagt gatacgtgaa attgagatga gtgtggatga tgatgatatc aatagttcga    180

aagtaattaa tgacctcttc agtgatgtcc tagaggaagg tgaactagat atggagaaga    240

gccaagagga gatggatcaa gcattagcag aaagcagcga agaacaggaa gatgcactga    300

atatctcctc aatgtcttta cttgcaccat tggcacaaac agttggtgtg gtaagtccag    360

agagtttagt gtccacacct agactggaat tgaaagacac cagcagaagt gatgaaagtc    420

caaaaccagg aaaattccaa agaactcgtg tcctcgagct gaatctggtg atagccttgg    480

tctgaagatc gtgacttctt tacagcattg atgcatatag atctcaaaga ttnaagaacn    540

gaacgtcntc ataagcagtg atgtccgaag ganatgtctt aaactgntga aaaatancct    600

tcttgcagta ttcaccgaaa gcggactatc caatattcnc nacgggttta ctgcnn        656


<210> SEQ ID NO 701
<211> LENGTH: 716
<212> TYPE: DNA
<213> ORGANISM: Homo sapiens
```

<220> FEATURE:
<221> NAME/KEY: misc_feature
<222> LOCATION: (1)...(716)
<223> OTHER INFORMATION: n = A,T,C or G

<400> SEQUENCE: 701

```
ggtaccttga cagggacgag aggtcgaagg agttgccagc cccatctttg aatgaacatt      60

cagtcagatc gaaaggtggg caggcatact gcgttcgcca ctcaaacaag taggaacaat     120

ctgaagtctc ctttagaaat actggccgct gggtgccgcg gtcacagtag aagaagatgg     180

ctgtggagcg ctgataaacc ttatggcaag tgtccccccc gtgaagttca tttttaacaa     240

gccattttca taagttagct tctgagtcag gagacctgcc actttgtgaa atccctgcgg     300

ttcccgcttt tcctgacatg aggagaccac cttggacttg ncacttgtgg gggcagacgt     360

ctgaggaaaa gctttccaca gaccccgaaa gtaataaagt gtattcgcca gcgctnacga     420

atggtgtcgt tgaagcccaa gggcttnang tcatacaagt tgccatgccc ttgggtcttt     480

caccttacaa gttgncccn ttcacttttg acaacgggac caggctttca caagttttcc     540

aantaacccg taccttgccc nggccggccg ttnnaaangg gcnaattcca nncacttggn     600

ggccgtacta aggggatccc aactttggac ccaacttggn gnaaanatng ggcntaactg     660

gttccctggg gnaaaatgtt tcccgttcaa aattcccncn aantttgagc cggaag         716
```

<210> SEQ ID NO 702
<211> LENGTH: 707
<212> TYPE: DNA
<213> ORGANISM: Homo sapiens
<220> FEATURE:
<221> NAME/KEY: misc_feature
<222> LOCATION: (1)...(707)
<223> OTHER INFORMATION: n = A,T,C or G

<400> SEQUENCE: 702

```
tgnatntgtc agcggcgcag tgtatggtat ctgnagaatt cgcctttcga gcggcgccgg      60

gcaggtactc atcttatact gaaagaacgt ggtggctcta aatatgaagc tgcaaagaag     120

tggaatttac ctgccgttac tatagcttgg ctgttggaga ctgctagaac gggaaagaga     180

gcagacgaaa gccattttct gattgaaaat tcaactaaag aagaacgaag tttggaaaca     240

gaaataacaa atggaatcaa tctaaattca gatactgcag agcatcctgg cacacgcctg     300

caaactcaca gaaaaaccgt cgttacacct ttagatatga accgctttca gagtaaagct     360

ttccgtgctg tggtctcaca acatgccaga caggtcgcag cctcccagca gtaggacaac     420

cacttcagaa ggagccctcg ttacacctgg atacaccatc aaaattcctg tccaaggaca     480

aactcttnaa gccttccttt gatgtgaagg atgcacttgc agccttggaa acttcangac     540

gtccagccac agaaaaggaa ccgagtcctn ggccgcgacc ccctaaggca attcacacac     600

tggcggcgtc tagggaccac ttgggccaac ttgngaactg gctactggtc tgggaatgtn     660

ccgtacatcc ncaatnaccg actaagtaac tgggctnngg gctatcn                   707
```

<210> SEQ ID NO 703
<211> LENGTH: 703
<212> TYPE: DNA
<213> ORGANISM: Homo sapiens
<220> FEATURE:
<221> NAME/KEY: misc_feature
<222> LOCATION: (1)...(703)
<223> OTHER INFORMATION: n = A,T,C or G

<400> SEQUENCE: 703

-continued

```
acctgccaga attagcaaga gctttcttta agaagacatt tgtcaaactc aacaaattga     60

aggttaacac cttaagagtt gtagttactg accagaaata tggacagact tcttagactt    120

ggaggaggta tgcctggact gggccagggg ccacctacag atgctcctgc agtggacaca    180

gcagaacaag tctatatctc ttccctggca ctgttaaaaa tgttaaaaca tggccgtgct    240

ggagttccaa tggaagttat gggtttgatg cttggagaat ttgttgatga ttataccgtc    300

agagtgattg atgtgtttgc tatgccacag tcaggaacag gtgtcagtgt ggaggcagtt    360

gatccagtgt tccaagctaa aatgttggat atgttgaaca gacaggaaag cccgaaatgg    420

ttggttggtt ggtatcacaa gtcaccctgg ctttggttgg tggctttctg gtgtggatan    480

tcaacacttn agcagagctt ttgaagcctt ttccggaaaa nagctttggc antgggttgt    540

ggatcccttt canaatggta aaaggaaagg ttggtaattg atgccttcan aatggancaa    600

ggctaaatna agggcttagg acttgaaccc ggacaanaan tttaaattng gncccttaaa    660

caagcctttt ntcnggcttt attttggctt accnnctttt tnn                      703
```

<210> SEQ ID NO 704
<211> LENGTH: 683
<212> TYPE: DNA
<213> ORGANISM: Homo sapiens
<220> FEATURE:
<221> NAME/KEY: misc_feature
<222> LOCATION: (1)...(683)
<223> OTHER INFORMATION: n = A,T,C or G

<400> SEQUENCE: 704

```
cgaggtactg agggatagga gagtatatgg gtttggcacc acagggtggg taggcaaaac     60

aatttggttg ataaggctca gatcctgaac taacctgtaa gggcttgtct ggttcgagga    120

caggtgaaat gggggaattg taagtagagt ttataggctt taaaaggcca tgctgtagca    180

ggcgagtgat aacaggcttt aatcttttta aagcatgctg tgggatggga tattggcatt    240

gagcggggta agggtgatta ggttttaatg agatggtaag gggtccatga tcggtcacca    300

aggagggagt agaggtatct tatacttgtg ggttaaggtg gggggataca agaggaggac    360

gcanaggagg ctttggattg ggaaaaaagg gcaccaatga gatgtaccnt aatccaggaa    420

tagtcaggga aacnnatagt tanttaaaag tgtctcggct aatangggac tgggcagtgg    480

ggatactaaa aaggatgctt aaaaagtatg nctaagttgc accnnattna ngagtttaaa    540

aaggttaaaa acttgctggn aatcctanca ccnttttgga gcnagaaaac aggcccttna    600

aanaaggtat ntgaatggga accccntntt aaaaggggcg gcntaatttc cctgnaaagt    660

cttnaactnt nnaaggccct acn                                            683
```

<210> SEQ ID NO 705
<211> LENGTH: 463
<212> TYPE: DNA
<213> ORGANISM: Homo sapiens

<400> SEQUENCE: 705

```
ctgaaagtcg atgaaggacg cgattacctg cgataagctt cgtggagttg gaaataaact     60

atgatacgga gatttccgaa tggggtaacc taactgagca aacctcagtt gcattttgat    120

gaatccatag tcaaattagc gagacacgtt gcgaattgaa acatcttagt agcaacagga    180

aaagaaaata aataatgatt tcgtcagtag tggcgagcga aagcgaaaga gcccaaacct    240

gtaaaaaggg gttgtaggac atcttacatt gagttacaaa attttatgat agtagaagaa    300

gttggaaagc ttcaacatag aaggtgatat tcctgtatac gaaatcataa aatctcatag    360
```

atgtatcctg agtagggcgg ggcaccgtga aaccctgtct gaatctgccg ggaccacccg 420
gtaaggctaa atactaatca gacaccgata gtgaactagt acc 463

<210> SEQ ID NO 706
<211> LENGTH: 651
<212> TYPE: DNA
<213> ORGANISM: Homo sapiens
<220> FEATURE:
<221> NAME/KEY: misc_feature
<222> LOCATION: (1)...(651)
<223> OTHER INFORMATION: n = A,T,C or G

<400> SEQUENCE: 706
actatagcat ctgtggaaaa tcttagaaaa aaacattttc tcccccaccc tctctcttcc 60
ctgttaagac catcccaaaa tgcttcaagt aaaaaataac aagtttaagg ggttaagcac 120
ttttaaagtc tgattaaggg ggtgggggga aaaaagagta actaccagcc atttctccaa 180
tggacatctc ttccacagac ctcaacgtga gaactgctct agtttctata aactgtaaac 240
ctgtggtggt ctgattatcc tgatattgga ttttcttgtt ttctgttaca ccttgagtca 300
tttgccttta ggattctaga cagacctaag ggaaaaagaa ctgaaaacat attttgcccc 360
cacccccaca aaaaaaaata ctgaaaactc ccccccgcct cagttacaca tccaaactct 420
acatttacaa aacgaattca gggtgaggaa gtaaaacagg tcatctattc acaaaactga 480
aatacttcat taccccaact aaacatacaa actgnttaca gattgctgaa atggctcaat 540
ttggctatca aattcatttg ggtttcctca aatcgngtaa aaaaaaaaaa aaaaaaagct 600
tggncctngg ccgnaacacn cttangggca aatccanccc ctgggnggcc g 651

<210> SEQ ID NO 707
<211> LENGTH: 625
<212> TYPE: DNA
<213> ORGANISM: Homo sapiens
<220> FEATURE:
<221> NAME/KEY: misc_feature
<222> LOCATION: (1)...(625)
<223> OTHER INFORMATION: n = A,T,C or G

<400> SEQUENCE: 707
ggtggcggct cgggacggag gacgcgctag tgttcttctg tgtggcagtt cagaatgatg 60
gatcaagcta gatcagcatt ctctaacttg tttggtggag aaccattgtc atatacccgg 120
ttcagcctgg ctcggcaagt agatggcgat aacagtcatg tggagatgaa acttgctgta 180
gatgaagaag aaaatgctga caataacaca aaggccaatg tcacaaaacc aaaaaggtgt 240
agtggaagta tctgctatgg gactattgct gtgatcgtct ttttcttgat tggatttatg 300
attggctact tgggctattg taaaggggta gaaccaaaaa ctgagtgtga gagactggca 360
ggaacccgag tctccagtga gggaggagcc aggagaggac ttcctgcaca cgtcgcttat 420
attgggatga cctgaagaga aagttgtcgg agaaactggc agcacagact tcaccagcac 480
catcaagctg ctgaatgaaa atcatatgtc cctcgtgang ctggatctca aaagatgaaa 540
atctgcttga tgttgaaatc aattcgtgaa ttaactcaca agttgcgtga cacatttgta 600
aatcngcaaa cacntnaaac tgggn 625

<210> SEQ ID NO 708
<211> LENGTH: 209
<212> TYPE: DNA
<213> ORGANISM: Homo sapiens

<400> SEQUENCE: 708

```
actgttccat ctggaagtca agattggtgc cacctaagtg ggttcctgct gcaaggaact      60

taaggacatc ctcctccttc atttgcagga catcaagggc tccggacatt gtgaaagttt     120

ccctttaagt tacgacggga atccagaaca acgccgtatg gacccctctg caggtagcac     180

ggaaaaaaaa aaaaaaaaaa gcttgtacc                                       209
```

<210> SEQ ID NO 709
<211> LENGTH: 643
<212> TYPE: DNA
<213> ORGANISM: Homo sapiens
<220> FEATURE:
<221> NAME/KEY: misc_feature
<222> LOCATION: (1)...(643)
<223> OTHER INFORMATION: n = A,T,C or G

<400> SEQUENCE: 709

```
ggtactcctt agagccagtt gctgtagaac tcaaatctct gctgggcaag gatgttctgt      60

tcttgaagga ctgtgtaggc ccagaagtgg agaaagcctg tgccaaccca gctgctgggt     120

ctgtcatcct gctggagaac ctccgctttc atgtggagga agaagggaag ggaaaagatg     180

cttctgggaa caaggttaaa gccgagccag ccaaaataga agctttccga gcttcacttt     240

ccaagctagg ggatgtctat gtcaatgatg cttttggcac tgctcacaga gcccacagct     300

ccatggtagg agtcaatctg ccacagaang ctggtgggtt tttgatgaag aaggagctga     360

actactttgc aaaggccttg gagagcccag agcgaccctt cctggccatt ctnggcggac     420

taaagttgca gaccagatcc agctcatcaa taatatgctg gacaaaagtc aatgagatga     480

ttattggtgg tggaatggct tttaccttcc ttaangngct caacaccatg gagattggca     540

cttctctggt tgatgaaaaa gggncccaga ttgcaaagac tnatgtccaa actgagaaaa     600

agggntgaan ataccttgcc tgtgctttgc nctgttncaa ttg                       643
```

<210> SEQ ID NO 710
<211> LENGTH: 390
<212> TYPE: DNA
<213> ORGANISM: Homo sapiens

<400> SEQUENCE: 710

```
ggtactcttc tagcatttag atctacactc tcgagttaaa gatgggggaaa ctgagggcag      60

agaggttaac agatttatct aaggtcccca gcagaattga cagttgaaca gagctagagg     120

ccatgtctcc tgcatagctt ttccctgtcc tgacaccagg caagaaaagc gcagagaaat     180

cggtgtctga cgattttgga aatgagaaca atctcaaaaa aaaaaaaaaa gaaaagagaa     240

aaaaaagact agccagccag gaagatgaat cctagcttct tccattggaa aatttaagac     300

aagttcaaca acaaaacatt tgctctgggg ggcagggaaa acacagatgt gttgcaaagg     360

taggttgaag ggacctctct cttaccaagt                                      390
```

<210> SEQ ID NO 711
<211> LENGTH: 683
<212> TYPE: DNA
<213> ORGANISM: Homo sapiens
<220> FEATURE:
<221> NAME/KEY: misc_feature
<222> LOCATION: (1)...(683)
<223> OTHER INFORMATION: n = A,T,C or G

<400> SEQUENCE: 711

```
cgaggtcaag aaggcagccc gagaagaaac gggaggacaa agctaagaag aagcacgaca      60
```

ggaaatccaa acgcctggat gaggaggagg aggacaatga aggcggggag tgggaaaggg 120
tccggggcgg agtgccgttg gttaaggaga agccaaaaat gtttgccaag ggaactgaga 180
tcacccatgc tgttgttatc aagaaactga atgagatcct acaggcacga ggcaagaagg 240
gaactgatcg tgctgcccag attgagctgc tgcaactgct ggttcagatt gcagcggaaa 300
acaacctggg agagggcgtc attgtcaaga tcaagttcaa tatcatcgcc tctctctatg 360
actacaaccc caacctggca acctacatga agccagagat gtgggggaag tgcctggact 420
gcatcaatga gctgatggat atcctgtttg caaatcccaa catttttgnt gggggagaat 480
attcttggaa gaaaagtgag aacctgcaca acgctgaccc agcccttgcg tgtccctggc 540
ttgcatnctn acttttggtg ggaaccnaat gggttaaaga aattanccca ataatgccaa 600
atacttgacc cttanttccc aaaaatacct tgcccgggcg ggcccnttca aaagggccaa 660
attccancnc ccttgggggc ccg 683

<210> SEQ ID NO 712
<211> LENGTH: 605
<212> TYPE: DNA
<213> ORGANISM: Homo sapiens
<220> FEATURE:
<221> NAME/KEY: misc_feature
<222> LOCATION: (1)...(605)
<223> OTHER INFORMATION: n = A,T,C or G

<400> SEQUENCE: 712
ggtacaagct tttttttttt tttttttttt tttctaaaca atagtgcttt attgataaaa 60
ggttagttta aatggataca aaattgctgt gtaaaataag tgttttcaaa atacatttct 120
ataggtagag actatgtctt agtaaaagag cagttatcta ttatcaaaag tatctattta 180
natttgggta gtaaaaccaa aggggatcag aagtgtanca gtgtgggtcc tccctccctg 240
catagctgtt accaggaggc agcgtgcctg aagtacttgg aggaacgaag aataaaggag 300
attgtgaaga aacattctca gcttattgga tatcccatta ctctttttgt ggagaaggaa 360
ccgtgataaa gaagtaagcg atgatgaggc tgaagaaaag gaagaccaag aagaagaata 420
ngaanaagaa gagaaagagt cggaagacaa acctgaaatt gaanatgttg gtctgatgag 480
gaagaaaaaa gaaggtggtg cnagaagaan anaagaagat taggaaagtc ctgccggcgg 540
ccgtcaangc aatccaccct gcggcgtcta ngaccactgn ncactgngat atgctctgtc 600 tggna 605

<210> SEQ ID NO 713
<211> LENGTH: 376
<212> TYPE: DNA
<213> ORGANISM: Homo sapiens

<400> SEQUENCE: 713
ggtaccaagg ttattgatca agtcagcctt ggtcattcca attccagtat ccacaatagt 60
gagagttcga tcttgtttgt tcggtataag gttaatatgc agctctttcc cagagtctaa 120
tttactggga tctgtcaagc tttcataccg gattttgtcc aatgcatctg atgaatttga 180
aatgagctct ctcagaaaga tctctttgtt cgagtagaaa gtattgatga tcaatgacat 240
caactgggca atttctgcct gaaaggcgaa cgtctcaacc tcctcctcct ccatcggttg 300
gtcttgggtc tgggtttcct caggcatctt ggctaagtga cccgcacagg accaacggca 360
cagccacacc gacctg 376

<210> SEQ ID NO 714
<211> LENGTH: 378
<212> TYPE: DNA
<213> ORGANISM: Homo sapiens

<400> SEQUENCE: 714
cgaggtacca aggttattga tcaagtcagc cttggtcatt ccaattccag tatccacaat 60
agtgagagtt cgatcttgtt tgttcggtat aaggttaata tgcagctctt tcccagagtc 120
taatttactg ggatctgtca agctttcata ccggattttg tccaatgcat ctgatgaatt 180
tgaaatgagc tctctcagaa agatctcttt gttcgagtag aaagtattga tgatcaatga 240
catcaactgg gcaatttctg cctgaaaggc gaacgtctca acctcctcct cctccatcgg 300
ttggtcttgg gtctgggttt cctcaggcat cttggctaag tgaccgcaca ggaccaacgg 360
cacagccaca ccgacctg 378

<210> SEQ ID NO 715
<211> LENGTH: 310
<212> TYPE: DNA
<213> ORGANISM: Homo sapiens
<220> FEATURE:
<221> NAME/KEY: misc_feature
<222> LOCATION: (1)...(310)
<223> OTHER INFORMATION: n = A,T,C or G

<400> SEQUENCE: 715
acttttgagt gtgtgtgtgc atgtgtgtgt gtgtgtgtgt gtgtgtgtat gtgagagatt 60
ctgtgatctt ttaaagtgtt actttttgta aacgacaaga ataattcaat tttaaagact 120
caaggtggtc agtaaataac aggcatttgt tcactgaagg tgattcacca aaatagtctt 180
ctcaaattag aaagttaacc ccatgtcctc agcatttctt ttctggccaa aagcagtaaa 240
tttgctagca gtaaaagatg aagttttata cacacagcan aaaaaaaaaa aaaaaaaaaa 300
agcttgtacc 310

<210> SEQ ID NO 716
<211> LENGTH: 624
<212> TYPE: DNA
<213> ORGANISM: Homo sapiens
<220> FEATURE:
<221> NAME/KEY: misc_feature
<222> LOCATION: (1)...(624)
<223> OTHER INFORMATION: n = A,T,C or G

<400> SEQUENCE: 716
ggtaccgatt gccaggctgt ggtctcctcc cagtgtgaca cggctgtagc catctgacac 60
agctctgcta accacctcag ccagttcctg gttggcaaga cccactgagc gtggattcac 120
tatcaggttg ttgtagagat catctttggg gactggagta aaattcaaat ctccaaagtc 180
ttttaggtgg cagcccaaac tggagagcct tttcatcaag ccagcttctc ttatggcagc 240
gggaccatgc tccactccgt ttcttttctg tccttgtgag aacggggctc ctatcacagc 300
cacggagtgg acggatttct tcaggatgga atgcactcgc gtctggagga gacgcgagag 360
gctgccctta gggacatgat cccgcagcac tgagaatctc caaggcagag gctccacatg 420
gccggggtgt tgaaggtctc aaacataatc tgagtcatct tctctctgtt ggccttgggg 480
ttcaaggggg cctcggcaca gcactgggtg ctcttncggg ccacgcgcac ttgtgtaaaa 540
gtgngtgcca nactttcatg cgnccaattg gngaccatcc tctnatggga ctgccggggc 600
cgttnaaggg gaatcaccnt ggng 624

<210> SEQ ID NO 717
<211> LENGTH: 652
<212> TYPE: DNA
<213> ORGANISM: Homo sapiens
<220> FEATURE:
<221> NAME/KEY: misc_feature
<222> LOCATION: (1)...(652)
<223> OTHER INFORMATION: n = A,T,C or G

<400> SEQUENCE: 717

```
cgaggtacaa aaattagctg ggtgtcgtga tgggtgcctg taatcacagc tatgtgggag     60

gctgaggcag gagaattgct tgaacctggg aggcgaaggt tgcagtgagc caagatcacg    120

tcactgcact ccagcctctt tgacagagtg cgactctgtc tcagaaaaaa aaaaaaaaga    180

aagaaaagag attacatatt atttagaaaa cagcagctaa acagtctttg ggtctctggc    240

aaagatgaag tgagccagtc ttcttccgac taaatcacca actggacaaa gttctcagct    300

ggaaaacact ccccttctgg gatcctgcgc ccagaagtgg tagcaagaac ttcttggaat    360

agaatggagc agaaccttcc tgagcctgag gaaccaacaa aaagtcaaag aatgaactct    420

ttcgaacaca aaataaaatt tctcaaagcc caggtcatgc tttttctgta aatctttatc    480

cctgcgtcag tatggacatg acatagtcca gagagaaaat tctcagccta ccttatgcnc    540

aagaaaatgc catgatgccg ccagcttgtt gatgcccnag gacantgctn ttganggccg    600

gaaaataggn ctgcagcngg gaaccaaagg ctgttnncct gnttcttaaa ag            652
```

<210> SEQ ID NO 718
<211> LENGTH: 544
<212> TYPE: DNA
<213> ORGANISM: Homo sapiens
<220> FEATURE:
<221> NAME/KEY: misc_feature
<222> LOCATION: (1)...(544)
<223> OTHER INFORMATION: n = A,T,C or G

<400> SEQUENCE: 718

```
cacagaggga gtgaggtgca tttgcagtca gctttcgctc accactaaga tggatgcaga     60

gcatccggaa ctcaggagtt acgctcagag ccaaggttgg tggacgggag agggcgagtt    120

caatttttcc gaagtctttt ctccagttga ggatcatcta gactgcggtg ctggcaaaga    180

cagcttagaa aaacaagaag aaagcatcac agtgcagact atgatgaaca ccttacggga    240

caaagccagc ggagtgtgca tagactctga gtttttcctc accacagcca gtggagtgtc    300

tgtcctgccg cagaatagaa gctctccgtg cattcactac ttcactggaa cccctgatcc    360

ttccaggtcc atattcaagc ttttcatctt tggtgatgac gtaaaacttg tccccaaaac    420

acaagtctcc ctgttttggg ggatgacgac ccttgccaaa aaggagcctc gggttncagg    480

agaaaccnga accggccggc attgaacctg taccttgncc gggccggccg nttcnaangg    540

gcga                                                                 544
```

<210> SEQ ID NO 719
<211> LENGTH: 626
<212> TYPE: DNA
<213> ORGANISM: Homo sapiens
<220> FEATURE:
<221> NAME/KEY: misc_feature
<222> LOCATION: (1)...(626)
<223> OTHER INFORMATION: n = A,T,C or G

<400> SEQUENCE: 719

-continued

```
accaaagaaa agctgaacag gaaaatgaga agagaagaaa tgtagaaaat gaagtttcta     60

cattaaagga tcagttggaa gacttaaaga aagtcagtca gaattcacag cttgctaatg    120

agaagctgtc ccagttacaa aagcagctag aagaagccaa tgacttactt aggacagaat    180

cggacacagc tgtaagattg aggaagagtc acacagagat gaacaagtca attagtcagt    240

tagagtccct gaacagagag ttgcaagaga gaaatcgaat tttagagaat tctaagtcac    300

aaacagacaa agattattac cagctgcaag ctatattaga agctgaacga agagacagag    360

gtcatgattc tgagatgatt ggagaccttc aagctcgaat tacatcttta nagaggaggt    420

gaacatctca acataatctc gaaaaagtgg aaggagaaag aaaagagctc aagacatgct    480

taatcactca gaaaaggaaa gaatatttag agatagattt aactacaact taaatcnttc    540

acacggtaga ccagangtaa tgaccccagt accaagctcg ttactgcaac atcattnttg    600

agaggcaagc ttggcatggg taaaaa                                          626
```

<210> SEQ ID NO 720
<211> LENGTH: 469
<212> TYPE: DNA
<213> ORGANISM: Homo sapiens
<220> FEATURE:
<221> NAME/KEY: misc_feature
<222> LOCATION: (1)...(469)
<223> OTHER INFORMATION: n = A,T,C or G

<400> SEQUENCE: 720

```
ggtactcttt agcattaaat tacatcgtgc atatacaact acacccattt agatttgcct     60

tggaatataa tttcaaggcc ttaaatatta aaaataattt tataactatt tcatagttta    120

attggctctt aaatagtttt gctagggagg aaacattttg tgttctttaa gaaattgata    180

tgtgtaaatg tgttcactta aatcttgaga aaacctaagg atgaagtctg ttgttttgtt    240

tttcctaaaa aaggaaaaaa gaaccaaaga aaaatgttga agaacaagaa tatttaccat    300

taaaaagaag aaacattatc caacaaaaag gagacatata gatttgaaaa cacttatttt    360

actgncttca acaacaacaa caaacagata ggcaggggaa gtccagagga ctcagaattg    420

aagcagctct atacaataat gaaggtggac ctgccgggcg ggcgctcga                469
```

<210> SEQ ID NO 721
<211> LENGTH: 644
<212> TYPE: DNA
<213> ORGANISM: Homo sapiens
<220> FEATURE:
<221> NAME/KEY: misc_feature
<222> LOCATION: (1)...(644)
<223> OTHER INFORMATION: n = A,T,C or G

<400> SEQUENCE: 721

```
acaaggtcaa tctcacttcg agtgaccaca atccggacca gggtggagtc atctgtgcca     60

gcacctttca tagcatagta gagcctctca gcaaagaagg cagggcggtt cagggcacac    120

tgcaagatgg tcttcaaacc actttctaca tatccggaaa actcacggct cacactgctt    180

aacaagtctc gattagccat cctagaataa gcctccatgg tagctctcag ctgaggaaag    240

cttcttgtgg caaggatcat gttaaagcaa gattcatcgg tccctagtct cccctcacca    300

gcttgataga gacgctgagc atcttcctga gccatttggt ggtttatact ctggttctca    360

tcacgatttc cctggcacat ggacacaagt aaacgttcaa aatgtcctga tgtatctgac    420

ctaatgncct tttcaaggtc tcgtccaaat tctgactgat aacatctgac aatttctcgg    480

atttcctgat ttggtcttgn gcacaaaatc ttcaatcaat acaccgttcc tgagttcctg    540
```

```
ntncctgcat tgntttccga agcttcaggc atcgnaatcc taggangctt gaaaaggccn    600

ggatcagttn ttcctattcn cttactttga ttgaaacntt gata                    644


<210> SEQ ID NO 722
<211> LENGTH: 510
<212> TYPE: DNA
<213> ORGANISM: Homo sapiens
<220> FEATURE:
<221> NAME/KEY: misc_feature
<222> LOCATION: (1)...(510)
<223> OTHER INFORMATION: n = A,T,C or G

<400> SEQUENCE: 722

cgaggtcgga gatctcgccg gctttacgtt cacctcggtg tctgcagcac cctccgcttc     60

ctctcctagg cgacgagacc cagtggctag aagttcacca tgtctattct caagatccat    120

gccagggaga tctttgactc tcgcgggaat cccactgttg aggttgatct cttcacctca    180

aaaggtctct tcagagctgc tgtgcccagt ggtgcttcaa ctggtatcta tgaggcccta    240

gagctccggg acaatgataa gactcgctat atggggaagg gtgtctcaaa ggctgttgag    300

cacatcaata aaactattgc gcctgccctg gttagcaaga aactgaacgt cacagaacaa    360

gagaagattg acaaactgat gatcgagatg gatggaacag aaaataaatc taagtttggt    420

gccaacgcca ttctgggggt gtcccttgcc gctgcaaagc tggtgccgtt gagaangggg    480

tcccctgtac ctgccnggcg gccgtcgaaa                                     510


<210> SEQ ID NO 723
<211> LENGTH: 640
<212> TYPE: DNA
<213> ORGANISM: Homo sapiens
<220> FEATURE:
<221> NAME/KEY: misc_feature
<222> LOCATION: (1)...(640)
<223> OTHER INFORMATION: n = A,T,C or G

<400> SEQUENCE: 723

ggtaccaagc gtatcagcat tcacctcctt gcctcacatg ccagtgggct caatcacaac     60

cctgcctgtg aatctgtaat tgactcctca acatttggag aaggcaaagc tccaggtccc    120

ccttttcctc aaactcttgg catagccaac gtggccaccc gcctctcttc catccagctg    180

ggccagtctg agaaggagag acctgaggag gccagggagc tggactcatc tgatagggat    240

attagttcag ctactgacct ccagccagat caggctgaga ctgaagatac agaagaagaa    300

ctagtagatg gtttggaaga ctgntgtagc cgtgatgaga atgaagagga ggagggagac    360

tcagagtgct cctcattaag tgctgctccc ccagcgaatc ggtggccatg atctctagaa    420

ctgtatggaa attctgacca aaccccttc caatcatgag aaaagttgtc cgaccagcct    480

catctacagc tctttccaac gttcccctac catctatttt ggcactcggg atgaaaaant    540

ggagaaactt tcctgggaac cnangaagtt gcttcnatgg aagatgagcn cagggacccc    600

aacattgcaa ccnaccattg gacggncccc tttaaatang                          640


<210> SEQ ID NO 724
<211> LENGTH: 593
<212> TYPE: DNA
<213> ORGANISM: Homo sapiens
<220> FEATURE:
<221> NAME/KEY: misc_feature
<222> LOCATION: (1)...(593)
<223> OTHER INFORMATION: n = A,T,C or G
```

<400> SEQUENCE: 724

```
ggtacctgcg cgccctcgac gtcaatgtgg ccttgcgcaa aatcgccaac ttgctgaagc     60
cagacaaaga gatcgtgcag gacggtgacc atatgatcat ccgcacgctg agcactttta    120
ggaactacat catggacttc caggttggga aggagtttga ggaggatctg acaggcatag    180
atgaccgcaa gtgcatgaca acagtgagct gggacggaga caagctccag tgtgtgcaga    240
agggtgagaa ggaggggcgt ggctggaccc agtggatcga gggtgatgag ctgcacctgg    300
agatgagagt ggaaggtgtg gtctgcaagc aagtattcaa gaaggtgcag tgaggcccag    360
gcagacaacc ttgtcccaag gaatcagcag gatgtgtggg ccaggatccc cttttgcaca    420
gcatgaggca aaaatgtcca ccacccccag cattgttagc agatctgctc ttgctttgca    480
cttttctttc ttaaacaaac ctgcataagt gatctgtgtt agaaaaactg ccggcggcca    540
agcaatcacc atgcgcgtct atgaccactn nncactgcna tatgctantg tct           593
```

<210> SEQ ID NO 725
<211> LENGTH: 606
<212> TYPE: DNA
<213> ORGANISM: Homo sapiens
<220> FEATURE:
<221> NAME/KEY: misc_feature
<222> LOCATION: (1)...(606)
<223> OTHER INFORMATION: n = A,T,C or G

<400> SEQUENCE: 725

```
acngcagctg ctccacggcc ccagcacgaa atgtatcaca ggcagcaatg aggacactga     60
agccattctc taacaaccag aaggaaatct tggcaagatt agtagatttc cccactccat    120
taacgccgca gaaggtgacg acataagggc gctggcgacg ctgggcatcc atgatgtccc    180
ggagcatgtc tacacgacgc tgtggctgca gaatctgcac cagggactcc tgtagggctt    240
gctttactgt ggaagtcacc gtgctgaacg tccccatcac cttcccttcc aacttgttgg    300
caacagattc acagagctgg acggcaatgt ctgcagccac gttcttagca atgagatgat    360
cacgcatctt gtccagcaca gattccatgt cttcacgact caagctcttt gaacccacaa    420
ggcccttcag cataccaaac atgccaccca gtgttccttg gtcgcactan gtttggtaga    480
gttttgagca gcccttcgtc atcaanctgt gcatccagat ctgaactgcc ccagaccagc    540
cttgaatagg tgatgcctaa caggagctag ggtcatgngg tggagactgg cgncacctag    600
gcaatc                                                               606
```

<210> SEQ ID NO 726
<211> LENGTH: 594
<212> TYPE: DNA
<213> ORGANISM: Homo sapiens
<220> FEATURE:
<221> NAME/KEY: misc_feature
<222> LOCATION: (1)...(594)
<223> OTHER INFORMATION: n = A,T,C or G

<400> SEQUENCE: 726

```
accacatcat ccatgctgac atctaccgct ggtttaacat ttcgtttgat atttttggtc     60
gcaccaccac tccacagcag accaaaatca cccaggacat tttccagcag ttgctgaaac    120
gaggttttgt gctgcaagat actgtggagc aactgcgatg tgagcactgt gctcgcttcc    180
tggctgaccg cttcgtggag ggcgtgtgtc ccttctgtgg ctatgaggag gctcggggtg    240
accagtgtga caagtgtggc aagctcatca atgctgtcga gcttaagaag cctcagtgta    300
aagtctgccg atcatgccct gtggtgcagt cgagccagca cctgtttctg gacctgccta    360
```

```
agctggagaa gcgactggag gagtggttgg ggaggacatt gcctgcagtg actggacacc    420

caatgcccag ttatcacccg ttcttgcttc nggatggcct caaccacgct gataacccga    480

gacctcaatg gggaacctgt cctcggcgga cacctaggca atcacacact gcggccgtct    540

agtgatccac tcgaccactt gcgatatgga tantgtctgg taatgatcgt acat          594


<210> SEQ ID NO 727
<211> LENGTH: 665
<212> TYPE: DNA
<213> ORGANISM: Homo sapiens
<220> FEATURE:
<221> NAME/KEY: misc_feature
<222> LOCATION: (1)...(665)
<223> OTHER INFORMATION: n = A,T,C or G

<400> SEQUENCE: 727

gcgtggtcgc gccgaggtgc cgtcaaggag tagaaattgg tatgcttaga agcagattct     60

aaaagcagtt tctcttcaga acatcttttt tcataccact tgataagcat cttgaaacac    120

catggctgta gctgcagtaa aatgggtgat gtcaaagaga actatcttga aacatttatt    180

tccagtccaa aatggagctt tatattgtgt ttgtcataaa tctacgtatt ctcctctacc    240

agatgactat aattgcaacg tagagcttgc tctgacttct gatggcagga caatagtatg    300

ctaccaccct tctgtggaca ttccatatga acacacaaaa cctatccctc ggccagatct    360

gtgcataata atgaagaaac acatgatcaa gtgctgaaaa ccagattgga agaaaaagtt    420

gaacaccttg aggaaagacc tatgatngaa ccacttancc aaatggtcnt tactactaag    480

cacccgtggn attcctcatg gacngnntac agatgtcnta agaatctgaa tcctccaaag    540

accgatgatg ccganggtcc tggggggatc aaaagaaaag ggncccattt gcatttggna    600

aaagccanct gggggttccn tattttttgt aaggaataat gntaaaaatc tttctntttt    660

anaag                                                                665


<210> SEQ ID NO 728
<211> LENGTH: 624
<212> TYPE: DNA
<213> ORGANISM: Homo sapiens
<220> FEATURE:
<221> NAME/KEY: misc_feature
<222> LOCATION: (1)...(624)
<223> OTHER INFORMATION: n = A,T,C or G

<400> SEQUENCE: 728

ggttacccag gcagtatctc tagagtcctt aacttaatat tagtaactaa agaaaagggt     60

tgcgctcgtt gcaggactta acctaacatc tcacgacacg agctgacgac aaccatgcac    120

catctgtcat tctgttaacc tccactatat ctctatagct ttgcagaaga tgtcaagagt    180

gggtaaggtt ctacgcgtag aatcaaatta aaccacatgc tccaccgctt gtgcgggttc    240

ccgtcaattc ctttaaattt cactcttgcg agcatactac tcaggcggat catttaacgc    300

gttagctgcg ttagtgaaat tattccacca actaatgatc atcgtttacg gcgtggacta    360

ccagggtatc taatcctgtt tgctccccac gctttcgtcc cttagtgcaa tatataacca    420

gttagctgcc ttcgcctatt gggntcttcc taatatctac gcattccacc gcttcactag    480

gaattccgtt acctctttat aatctatttg gcagtatcca agcggctgaa gttgagctta    540

acatttactt cagacttaca aaaactacgc gcttacgccc aatattccga tacgttgcac    600

natgattacc ggggtgtgcc aaaa                                           624
```

<210> SEQ ID NO 729
<211> LENGTH: 449
<212> TYPE: DNA
<213> ORGANISM: Homo sapiens

<400> SEQUENCE: 729

```
actgacacac aaagtgcctt cactggacct tacagttctc actgccgttg gactccagtc     60
cagctttggg gctggggaca agtcggcctc gcttgaccct caggccctct ctggggctgt    120
cagtcggact tctctcagga agattattga ctgggacgga tttcgtggtg ggttctcgga    180
ggatggtgcc tgaatctact gggctccgct gagcaacttt gaccttttgt gatctgctgc    240
caccagctgt tggtttggag gactctgcaa gattttcttt gccgagactc agtggggata    300
gcgctaactt ctgtgcaacc aggcgggggc tggtcccagt tgccatggtt gttcttcgca    360
ggatatatgg gctaagtctt tcctgtcggg atgtcagcaa accctttctt tacaacttct    420
ggaagtccct ctggctcaaa ctcagtacc                                      449
```

<210> SEQ ID NO 730
<211> LENGTH: 646
<212> TYPE: DNA
<213> ORGANISM: Homo sapiens
<220> FEATURE:
<221> NAME/KEY: misc_feature
<222> LOCATION: (1)...(646)
<223> OTHER INFORMATION: n = A,T,C or G

<400> SEQUENCE: 730

```
actcattaat cagggagcct caatcttagt aaaagattac attttgaaga ggacacctat     60
tcatgcagca gcaacaaatg gtcattcaga atgcttacgg ctattaatag gaaatgcaga    120
accacagaat gcagtggata ttcaagatgg aaatggacag acgcctctga tgctatctgt    180
tctcaacggg cacacagact gtgtttactc attgctgaac aaaggagcaa atgtagatgc    240
caaagataag tggggaagga cagcgttgca tagaggggca gttacaggcc atgaagaatg    300
tgtagatgca ttacttcaac atggtgctaa gtgcttactt cgggatagca ggggcccgga    360
cgcctataca cctgtctgct gcctgtggac acattggtgt tcttggagcc cttttgcagt    420
cagcagcatc tatggatgca aatccagcca cagcagacaa tcatggatat ccgnacttac    480
tgggcttgta caatggtcac gagacatgtg tagaactgnt tttagaacag gaagttttcc    540
agaaaacgga aggaaatgct tttagtccat tgcattgngc cgtgataaat gccaccaaag    600
ggctgttaaa ngttaattga tcnttanggg ccacattggg aacccc                   646
```

<210> SEQ ID NO 731
<211> LENGTH: 639
<212> TYPE: DNA
<213> ORGANISM: Homo sapiens
<220> FEATURE:
<221> NAME/KEY: misc_feature
<222> LOCATION: (1)...(639)
<223> OTHER INFORMATION: n = A,T,C or G

<400> SEQUENCE: 731

```
acagacttgt ttttgagtgt tgagtagcag ggacaaaata agggaatgtt attttttaag     60
aaaattcatt ttcattgttg tctccttcct tttctgtgaa agtcctcata ctgagaaatt    120
tgtatatttt atattaaatc acttactatt gatttttgtt gtgattttca aaggtggatt    180
cccacagata aaatcttggc tattgcccaa aacatagtaa agggtcacgt gtgacttttt    240
ataataggaa gaaaattctg cctttgtgag tgcacatgtc cacatttcat ccctccttcc    300
```

-continued

```
ctcaaaaccc tagagagggg cattaaagaa ttgttgatgt atatgcaatg tctgttaaag    360

catgcactat gtatttcatc ctcatttatt gggtctggga ctgaagtttt taacccacat    420

ggacctaacc tactttttgg gataaaattc tctgtttggt acaggcaaaa ttctggtatg    480

gcgtgaatgc catgggtcat tctgaatata tttttctgg aatttatcat acacgatgtt     540

gcaatacgtg ctttggtttt taatttgaag ccaacttttc tactgttgaa agacattttt    600

gccaactggn ccttctanaa tggagtctaa gttaggncg                           639
```

<210> SEQ ID NO 732
<211> LENGTH: 538
<212> TYPE: DNA
<213> ORGANISM: Homo sapiens
<220> FEATURE:
<221> NAME/KEY: misc_feature
<222> LOCATION: (1)...(538)
<223> OTHER INFORMATION: n = A,T,C or G

<400> SEQUENCE: 732

```
ggtactcgtc ccttcaaaca gtaaacaaga aagtgcagac agtgctgcca gagacaggag     60

gattttcaca tgagactgaa aaagccgaca cacccttaca actaagtcat ggtcgagtcg    120

gacctgccat ccacctccac cagtccctgg aacccggcag gtcagagttt tctctaattc    180

tattccccgg catcaagtga acactagaac tcacacggaa ggccccgagc aaccactggc    240

ctcggggctg ggtgcaccca ctcctcaccc agggagattg tcacaaaaca cgctaggggg    300

cagagacgct gtaaactgga cacacacgga acacaatgcc ctttccactt acacagcgtg    360

gggatgataa aaaggaatct tttgagcaag tctataattt tacagaattt agaggtggga    420

aagatggcca attttccttc tttatgcctg gggcagacca cctgcttctg gggtaaagtg    480

tttgagaagg aaaaagaccc tgnacctgcc nngggcggcg ctcgaaaggc caattcna      538
```

<210> SEQ ID NO 733
<211> LENGTH: 351
<212> TYPE: DNA
<213> ORGANISM: Homo sapiens

<400> SEQUENCE: 733

```
cgaggtaccc tatggcctat gttgactata agactgtgct gcagattgat gataatgtga     60

cgtcagccgt agaaggcatc aacagaatga ccagagctct catggactcg cttgggcctg    120

agtggcgcct gaagctgccc tcaatcccct tggtgcctgt ttcagttcag aagaggtgga    180

attccttgcc ttcggagaac cacaaagaga tggctaaaag caaatccaaa gaaaccacag    240

ctacaaagaa cagagtgcct tctgctgggg atgtggagaa agccagagtt ctgaaggaag    300

aaggcaatga gcttgtaaag aagggaaacc ataagaaagc tattgagaag t             351
```

<210> SEQ ID NO 734
<211> LENGTH: 625
<212> TYPE: DNA
<213> ORGANISM: Homo sapiens
<220> FEATURE:
<221> NAME/KEY: misc_feature
<222> LOCATION: (1)...(625)
<223> OTHER INFORMATION: n = A,T,C or G

<400> SEQUENCE: 734

```
cgaggtacaa tccttgacct tgtgcattat agcattccat tagcaagagt tgtaccatcc     60

ttcatccaaa tggcaacatc acagagctcc tcctgaagga aggtttcgca cgctgtgtgg    120
```

-continued

```
actggtcgat tgcagtttac acccggggcg cagaaaagct gagggcggca gagaggtttg    180

ccaaagagcg caggctgaga atatggagag actatgtggc tcccacagct aatttggacc    240

aaaaggacaa gcagtttgtt gccaaggtga tgcaggttct gaatgctgat gccattgttg    300

tgaagctgaa ctcaggcgat tacaagacga ttcacctgtc cagcatccga ccaccgaggc    360

tggagggggga gaacacctag gataagaaca agaaactgcg tcccctgtat gacattcctt    420

acatgtttga ggccccggga atttcttcga aaaaagctta ttgggaaaaa gtcaatgtga    480

cngtggacta cattagacca ccagcccagc cacagagaca gtgctgcctt tcaaacgtcc    540

tgccgggcgg ccgtcaaagg cnattcacca tggcggcgtc tatggaccac tcggaccact    600

gggaactggc tactgtctgg gaatg                                          625
```

<210> SEQ ID NO 735
<211> LENGTH: 677
<212> TYPE: DNA
<213> ORGANISM: Homo sapiens
<220> FEATURE:
<221> NAME/KEY: misc_feature
<222> LOCATION: (1)...(677)
<223> OTHER INFORMATION: n = A,T,C or G

<400> SEQUENCE: 735

```
actttctatg agaagcgtat gaccacagaa gttgctgctg acgctctggg tgaagaatgg     60

aagggttatg tggtccgaat cagtggtggg aacgacaaac aaggtttccc catgaagcag    120

ggtgtcttga cccatggccg tgtccgcctg ctactgagta aggggcattc ctgttacaga    180

ccaaggagaa ctggagaaag aaagagaaaa tcagttcgtg gttgcattgt ggatgcaaat    240

ctgagcgttc tcaacttggt tattgtaaaa aaaggagaga aggatattcc tggactgact    300

gatactacag tgcctcgccg cctgggcccc aaaagagcta gcagaatccg caaacttttc    360

aatctctcta aagaagatga tgtccgccag tatgttgtaa gaaagccctt aaatanngaa    420

ggtaagaaac ctaggaccaa agcaccaaga ttcaanngtc ttggtactcc acgtgtcctg    480

cagcacaaac cggcggtgta ttgctntnna aaaaccagcg taccttnggc cgngaacacc    540

cttanggccg aatttccagn ccacttggcn ggccgntnct aatgggaatc cancttcggt    600

acccannctt ggcggaatca tgggcatanc ttggttccct gggtgaaaat ggtattccgt    660

tcaaaattcc nccaann                                                   677
```

<210> SEQ ID NO 736
<211> LENGTH: 651
<212> TYPE: DNA
<213> ORGANISM: Homo sapiens
<220> FEATURE:
<221> NAME/KEY: misc_feature
<222> LOCATION: (1)...(651)
<223> OTHER INFORMATION: n = A,T,C or G

<400> SEQUENCE: 736

```
ggtactattg aagaactggc tccaaatcaa tatgtgatta gtggtggagt agctattctt     60

aattctacaa ccattgaaat ctcagagctt cccgtcagaa catggaccca gacatacaaa    120

gaacaagttc tagaacccat gttgaatggc accgagaaga cacctcctct cataacagac    180

tatagggaat accatacaga taccactgtg aaatttgttg tgaagatgac tgaagaaaaa    240

ctggcagagg cagagagagt tggactacac aaagtcttca aactccaaac tagtctcaca    300

tgcaactcta tggtgctttt tgaccacgta ggctgtttaa agaaatatga cacggtgttg    360

gatattctaa gagacttttt tgaactcaga cttaaatatt atggattaag aaaagaatgg    420
```

-continued ctcctaggaa tgcttggtgc tgaatctgct aaactgaata atcaggctcg ctttatctta 480
gagaaaatag atggcaaaat aatcattgga aataagccta agaaagaatt aattaaaggt 540
ctgattcaga ngggatatga ttcggatcct gtgaaggcnt ggaaagaaac ccannaaang 600
gttcngatta agaaaaaaat naanaagagn gccancaaag gaacttgaaa n 651

<210> SEQ ID NO 737
<211> LENGTH: 404
<212> TYPE: DNA
<213> ORGANISM: Homo sapiens

<400> SEQUENCE: 737
cgaggtactg tgtggccacc atgccatgtc tagagccagg ctcccgttgt tggccatgcc 60
ttgctttgag gctttggctc tgcacgagac gccgcagaga acgtcttgat gcctcgctcc 120
ccttatcctc accacttcct tcttaggggt ggaaatgctg gatcaaaggg tcttcacgtt 180
ttctgacttt tccacgcatg gggttagcct gtgctccgga gaccctgtga gcacacatgt 240
ccccagcgca gcttgtgact cctgcctctc tgaccccgcc aggtggatta caaagctgac 300
gagtggctga tgaagaacat ggatcccctg aatgacaaca tcgccacact gctccaccag 360
tcctctgaca agtttgtctc ggagctgtgg aaggatggta cctg 404

<210> SEQ ID NO 738
<211> LENGTH: 250
<212> TYPE: DNA
<213> ORGANISM: Homo sapiens

<400> SEQUENCE: 738
acatcaaaga ttacatgaaa tcaatcaaag ggaaacttga agaacagaga ccagaaagag 60
taaaaccttt tatgacaggg gctgcagaac aaatcaagca catccttgct aatttcaaaa 120
actaccagtt ctttattggt gaaaacatga atccagatgg catggttgct ctattggact 180
accgtgagga tggtgtgacc ccatatatga ttttctttaa ggatggttta gaaatggaaa 240
aaaaaaaacc 250

<210> SEQ ID NO 739
<211> LENGTH: 582
<212> TYPE: DNA
<213> ORGANISM: Homo sapiens
<220> FEATURE:
<221> NAME/KEY: misc_feature
<222> LOCATION: (1)...(582)
<223> OTHER INFORMATION: n = A,T,C or G

<400> SEQUENCE: 739
acagtaagga caaccccaac ctgctgttca acatgtgtgg cttcgagtgc cgcatcctgc 60
ctaagtgccg caccagctat gaggagttca cccacaagga cggggtctgg aacctgcaga 120
atgaggttac taaggagcgc acagctcagt gtttcctgcg tgtggacgat gagtcaatgc 180
agcgcttcca caaccgcgtg cgtcagattc tcatggcctc tgggtccacc accttcacca 240
agattgtgaa taagtggaat acagctctca ttggccttat gacatacttt cgggaggctg 300
tggtgaacac ccaagagctc ttggacttac tggtgaagtg tgagaacaaa atccagacac 360
gtatcaagat tggactcaac tccaagatgc caagtcggtc cccccggttg tgttctacac 420
ccctaaggag ttgggtggac tcggcatgct ctcaatgggc catgtgctca tncccca atc 480 cgacctcagg tgggtccaaa cagacngatg taggtatcac acactttcgt tcaggaatga 540

```
gccttgaaga agaccactta ttcccacttg nacctcggcc gg                   582


<210> SEQ ID NO 740
<211> LENGTH: 576
<212> TYPE: DNA
<213> ORGANISM: Homo sapiens
<220> FEATURE:
<221> NAME/KEY: misc_feature
<222> LOCATION: (1)...(576)
<223> OTHER INFORMATION: n = A,T,C or G

<400> SEQUENCE: 740

ggtaggacac cgaacccctg attcagacag caaaaaccac gctgggctcc aaagtggtca    60

acagttgtca ccgacagatg gctgagattg ctgtgaatgc cgtcctcact gtagcagata   120

tggagcggag agacgttgac tttgagctta tcaaagtaga aggcaaagtg ggcggcaggc   180

tggaggacac taaactgatt aagggcgtga ttgtggacaa ggatttcagt cacccacaga   240

tgccaaaaaa agtggaagat gcgaagattg caattctcac atgtccattt gaaccaccca   300

aaccaaaaac aaagcataag ctggatgtga cctctgtcga agattataaa gcccttcaga   360

aatacgaaaa ggagaaattt gaagagatga ttcaacaaat taaagagact ggtgctaacc   420

tacaatttgt cagtggggct ttgatgatga agcaaatcac ttacttcttc agaacacttg   480

ccttgcggtt ccttggtagg aggacctgaa attgagctga ttgccatcgc aacaggangg   540

cggatcgccc cagttctcaa gctnacagcc gagaan                             576


<210> SEQ ID NO 741
<211> LENGTH: 579
<212> TYPE: DNA
<213> ORGANISM: Homo sapiens
<220> FEATURE:
<221> NAME/KEY: misc_feature
<222> LOCATION: (1)...(579)
<223> OTHER INFORMATION: n = A,T,C or G

<400> SEQUENCE: 741

accttatctg aaactcttgc acttccccaa ccagggcaga aatgaggtgg gagaagtttg    60

actaaaatga gggatggggg aaagtaaaag atgttttttt ttttttgaga ctcgctttgt   120

cacccaggct ggagtgcaat ggcacaatct caactcaccg caacctccgc ctcccgggtt   180

caagcgattc tcctgcctca gcctcccgag tagttgggat tacaggcgcc tgcctccatg   240

cctggctaat tttgtatttt tagtagagac agggtttctt catgttggtc aggctggtct   300

caaactccta acctcgtgat ccgcctgcct cgacctccca aagtgctggg attacaggca   360

tgagccacca tgcccagcca aagatcattt ttttatatag acttcaccct ttgtaaatac   420

tgtactgggg gagtatagag tagaaaaaaa gtttagttaa aacatttgtt tacaaattaa   480

cctttaaaaa tntaattact gctaaaaata gaaggctgtt ncccttaagg aaaattagng   540

ccattttgga aatganactt gggccataaa tncaggtgg                          579


<210> SEQ ID NO 742
<211> LENGTH: 578
<212> TYPE: DNA
<213> ORGANISM: Homo sapiens
<220> FEATURE:
<221> NAME/KEY: misc_feature
<222> LOCATION: (1)...(578)
<223> OTHER INFORMATION: n = A,T,C or G

<400> SEQUENCE: 742

ggtactttgg gatgctttac taggtgtttt ccattagaat tagaccttga ttttaaatcc    60
```

```
aagcaagctt gaagcccctt ggcttacagc atttgcctgc tgaatactaa acactcacat    120

ggcaagagtt gctctggaga ggtagggcca gaggaatgct gctgcactgc caactcaggc    180

acatgcttag ctgtaaaggg aagcgaggtg aagtcgtcct gcagcgtatt agagtaaaag    240

tctacccctc tgaagcacta ttaagcgctt aaccgtatat ttaaatacta ccatgtgcta    300

tctactgagg aagattcatg ttcaattatt tggaaataat gcaagcatcc actaagggcc    360

tttaagcttt ctttgattat aattaaggtt cattttaagt tntttttttt ctttcaacca    420

gtgtgccatc tccaatattt ctatagtata ccaaccaccc caggaatgca ctttaacaat    480

atcagggatt tatataacca aatagtttca aatccaacaa aattcccttt atgaactttc    540

gctttttaag actactgatg ggtacctgcc gggcggcc                            578
```

```
<210> SEQ ID NO 743
<211> LENGTH: 592
<212> TYPE: DNA
<213> ORGANISM: Homo sapiens
<220> FEATURE:
<221> NAME/KEY: misc_feature
<222> LOCATION: (1)...(592)
<223> OTHER INFORMATION: n = A,T,C or G

<400> SEQUENCE: 743

ggtctttaga aagttccatg attctgcata tactgtttga actgaatcat gatgtcttta     60

gaaagtatat gcagaatcag aatgttccgg gaaatattga gttaactgtg aatatcctga    120

caatgggcta ttggccgaca tatgtgccta tggaagttca tttaccacca gagatggtaa    180

aacttcagga gattttcaag acattttacc taggcaaaca tagtggcagg aaacttcagt    240

ggcagtcaac cctaggacac tgtgtgttaa agcagaattt aaagagggta aaaaggaact    300

ccaggtctct ctttttcaaa cactggtgct gctaatgttt aatgagggag aggagttcag    360

tttagaagag atcaagcagg caactggaat agaaggatgg agagttaagg agaacactgc    420

agtcattagc ctggtggcaa aagctagagt tctggcgaaa aaatnccaan ggccaaagac    480

ctttgaanat ggtgacaagt tcanttngta atngatgatt caaaccttaa actttcagga    540

tnaaggatca atcaaatnca aaaaaaaaaa nnnaaaaaaa agcttgttcc ga            592
```

```
<210> SEQ ID NO 744
<211> LENGTH: 578
<212> TYPE: DNA
<213> ORGANISM: Homo sapiens
<220> FEATURE:
<221> NAME/KEY: misc_feature
<222> LOCATION: (1)...(578)
<223> OTHER INFORMATION: n = A,T,C or G

<400> SEQUENCE: 744

ggtaccaaac atagccctta ggcctgggct aggctctcaa aggtctttcc cagaaatgga     60

ggcagcagta gcttcaaaca ggcacaaaaa cagccaggag gaggcagcat ccactccatg    120

aaggcctaag acaatgaaag gaagccagag caacagacca ccttgggatc cggggagaag    180

ggtaaatggg caaaagggtt gtatttcctg atgctctcag aacatcagac cacaccatgt    240

gaatttaagc aggactattt taagtgggga aacaatacta gaagcatttg gtgtattttc    300

ctggcactca cctcctaggt aagcaggaga gcgggacact caggagttgt gactaaactc    360

acacttaagc tgcctgtcca gaccgtcccc ttggctgaac acaacactga aattgtggca    420

gtgtctgttg cnccagtgga cctncactta ctaatgagta tgtaaaacag angagccaca    480
```

```
gtgaggcntt tcacaaaacc canggctctt gggggaaaaa cgggtttcca ccttctgnct    540

tttggtgctg gaaagtncct gaggganaag aagtttgn                            578


<210> SEQ ID NO 745
<211> LENGTH: 581
<212> TYPE: DNA
<213> ORGANISM: Homo sapiens
<220> FEATURE:
<221> NAME/KEY: misc_feature
<222> LOCATION: (1)...(581)
<223> OTHER INFORMATION: n = A,T,C or G

<400> SEQUENCE: 745

acagatcagg caactgtgga aaatctaaac gaactgcgcc aagatctgtc aaaattccga     60

aatgaaataa gggatttacc tggctttcgg acttctaaat atgctatgtt ttatccaaga    120

aattaaccat tttctaaatc atggagcgaa taattttcaa taacagatcc aaaagactat    180

attgcataac ttgcaatgaa attaatgaga tatatattga aataaagaat tatgtaaaag    240

ccattcttta aaatatttat agcataaata tatgttatgt aaagtgtgta tatagaatta    300

gtttttttaaa ccttctgtta gtggcttttt gcagaagcaa aacagattaa gtagatagat    360

tttgttagca tgctgcttgg ttttcttact tagtgcttta aaatgttttt ttttatgttt    420

aagaaggggc agttataaaa tggacacatt gcccaaaaag gttttggaaa antggaagac    480

ccagcaaatg gtanggcttg acctccttca caaggataca cttggaaata tagaaagtta    540

tgtttaaata tctctggttt aggagttcac atatagttaa g                        581


<210> SEQ ID NO 746
<211> LENGTH: 506
<212> TYPE: DNA
<213> ORGANISM: Homo sapiens
<220> FEATURE:
<221> NAME/KEY: misc_feature
<222> LOCATION: (1)...(506)
<223> OTHER INFORMATION: n = A,T,C or G

<400> SEQUENCE: 746

ggtacaagct tttttttttt tttttttttt tttttttttt taggtagtgg gtgttgagct     60

tgaacgcttt cttaattggt ggctgntttt aggcctacta tgggtgttaa attttttact    120

ctctctacaa ggntttttcc tantgtccaa agagctgttc ctntttggac taacagttaa    180

atttacaagg ggatttaaag ggttctgtgg gcaaatttaa agttgaacta agattctatc    240

ttggacaacc agctntcacc aggctcggta ggtttgtcgc ctctacctat aaatcttccc    300

actattttgc tacatanacg ggtgtgctct tttanctgtt cttaggtanc tcgtctggtt    360

tcgggggtct tanctttggc tctccttgca aagttatttc tagttaattc attatgcana    420

aggnataggg gttaagtcct tgctatatta tgcttgggta taattttcat ctttnccttg    480

cggnacctgc ccggccggcc gtttna                                         506


<210> SEQ ID NO 747
<211> LENGTH: 454
<212> TYPE: DNA
<213> ORGANISM: Homo sapiens

<400> SEQUENCE: 747

ggtactttgg cttcaatgat tggcaacttc tacaggggcc agtcttttga actggacaac     60

cttacaagta tatgagtatt atttataggt agttgtttac atatgagtcg ggaccaaaga    120

gaactggatc cacgtgaagt cctgtgtgtg gctggtccct acctgggcag tctcatttgc    180
```

```
acccatagcc cccatctatg gacaggctgg gacagaggca gatgggttag atcacacata    240

acaatagggt ctatgtcata tcccaagtga acttgagccc tgtttgggct caggagatag    300

aagacaaaat ctgtctccca cgtctgccat ggcatcaagg gggaagagta gatggtgctt    360

gagaatggtg tgaaatggtt gccatctcag gagtagatgg cccggctcac ttctggtatc    420

tgtcaccctg agcccatgag ctgcctttta gggt                                454


<210> SEQ ID NO 748
<211> LENGTH: 569
<212> TYPE: DNA
<213> ORGANISM: Homo sapiens
<220> FEATURE:
<221> NAME/KEY: misc_feature
<222> LOCATION: (1)...(569)
<223> OTHER INFORMATION: n = A,T,C or G

<400> SEQUENCE: 748

ggtaccagct ggcacaggag cagggggcat ggcacctctg ttgtttatgc ccatagcacc     60

tcccatagcc atctgaccca tccgaatctc ctgctctctc gcatcaggga aggttccctt    120

gaatccttcc tgctgtcgcc gcatcatttc ttcttgctgc cgccgcatct cttcttcacg    180

gcgcctgcgc tcttcctcct gcctgagctc cagttgcttt cgtttttgca cctcttggtt    240

gtgcagctct tccatcctcc gaagttcttc ttggcgcctc atcaaatcct gtctcattag    300

catgacctgg tgctcatggc gtgcagcttc catctccatc tccagcttct cacgagcctc    360

cttgatgttg cggtccactt ggtcctgctg ctgcttctcc atctcaatga gtgccttnca    420

gcgcatggca tattcatact caaaggaacc aggctgtgca aatctgggtg gctgctctcg    480

ttccttgtga aatgctggtt ttataaccag cttcnttgga agccctcttc atcaatctaa    540

cctggtccat gggctccaca gtcacaagg                                     569


<210> SEQ ID NO 749
<211> LENGTH: 428
<212> TYPE: DNA
<213> ORGANISM: Homo sapiens

<400> SEQUENCE: 749

acatggatat tcccaaacca ttccattaga aaactgccct ccctgcacac acaacaaaaa     60

cagcgctatt tcctacacct attggactga aagtgcttgg aaatggaatg gttttagaat    120

atgaagaaga acacaaacca agtagctgtg ggttgaacct ggacgtgagc tggctgcagg    180

gccgttgggt agaaaaccag catctcataa acaggtcact ccactggatg gtttgtcact    240

ggatggtttg ttggggtggt ggtcacaggc gcaaaggaca tgcacacggc cacgctacgc    300

tactgtaacc aagaggtgac ttcagccatg aataaggtga agaggttaca catctaccta    360

cggaatataa taacatacaa tgacttataa agtgactaca tgcatatgag caagcaaagt    420

acctcggc                                                             428


<210> SEQ ID NO 750
<211> LENGTH: 569
<212> TYPE: DNA
<213> ORGANISM: Homo sapiens
<220> FEATURE:
<221> NAME/KEY: misc_feature
<222> LOCATION: (1)...(569)
<223> OTHER INFORMATION: n = A,T,C or G

<400> SEQUENCE: 750
```

-continued

```
acctgccaga attagcaaga gctttcttta agaagacatt tgtcaaactc aacaaattga     60

aggttaacac cttaagagtt gtagttactg accagaaata tggacagact tcttagactt    120

ggaggaggta tgcctggact gggccagggg ccacctacag atgctcctgc agtggacaca    180

gcagaacaag tctatatctc ttccctggca ctgttaaaaa tgttaaaaca tggccgtgct    240

ggagttccaa tggaagttat gggtttgatg cttggagaat ttgttgatga ttataccgtc    300

agagtgattg atgtgtttgc tatgccacag tcaggaacag gtgtcagtgt ggaggcagtt    360

gatccagtgt tccaagctaa aatgttggat atgttgaagc agacaggaag gccggagatg    420

gttgttggtt gggtatcaca gtcaccctgg ctttggttgn tggctttctg gtgtggatat    480

caacactcag cagagctttg aagccttgtc gganagaact tgtggcaagt ggttgtggat    540

cccattcaga gtgtaaaagg aaaggttgt                                      569
```

```
<210> SEQ ID NO 751
<211> LENGTH: 568
<212> TYPE: DNA
<213> ORGANISM: Homo sapiens
<220> FEATURE:
<221> NAME/KEY: misc_feature
<222> LOCATION: (1)...(568)
<223> OTHER INFORMATION: n = A,T,C or G

<400> SEQUENCE: 751

acctgaagct caggaggaga tgaaagaagt agccaaacac ccaaagaatc ctgaggttgg     60

cttgaagcct gtgtggtata gtcccaaagt tttcattgaa ggtgctgatg cagagacttt    120

ttcggagggt gagatggtta catttataaa ttggggcaac ctcaacatta caaaaataca    180

caaaaatgca gatggaaaaa tcatatctct tgatgcaaag ttgaatttgg aaaacaaaga    240

ctacaagaaa accactaagg tcacttggct tgcagagact acacatgctc ttcctattcc    300

agtaatctgt gtcacttatg agcacttgat cacaaagcca gtgctaggaa aagacgagga    360

ctttaagcag tatgtcaaca agaacagtna gcatgaagag ctaatgctag gggatccctg    420

ccttaaggat tttgaaaaaa ggagatatta tacaacttca gagaagagga ttttcatatg    480

tgatcaacct tatgaacctg taacccatgt agttgcaagg aancccgtgt gtttgatata    540

cattcctgat ggcacacaan gaaatgcc                                       568

<210> SEQ ID NO 752
<211> LENGTH: 312
<212> TYPE: DNA
<213> ORGANISM: Homo sapiens

<400> SEQUENCE: 752

accgccaggg atgtcccttc cagccctggg atggactaga ggagcacagc caagccctga     60

gtgggaggct gcgggccatt ctccagaatc agggaaactg aaggatgggc ctcagtctct    120

aaggaaggca gagacctggg ttgagcagca gaataaaaga tcttcttcca agaaatgcaa    180

acagaccgtt caccaccatc tccagctgct cacagacacc agcaaagcaa tgtgctcctg    240

atcaagtaga ttttttaaaa atcagagtca attaatttta attgaaaatt tctcttatgt    300

tccaagtgta cc                                                        312

<210> SEQ ID NO 753
<211> LENGTH: 334
<212> TYPE: DNA
<213> ORGANISM: Homo sapiens

<400> SEQUENCE: 753
```

```
ggtacaagcg tctgcagcag actgtggcgg gcgaaggagc aggattccag ggcgctgttg     60

ggcttggtca cgaacgccag cagcaggggt gcaagggcct tggggaaata gtcctgctgc    120

accatgtggt tcagcgccat caggggggccg tacagttttt tcccacggga caaaaaatgc    180

ctaaggaagg gagaacataa taaaggggtt tctttctctc cctctttctt tcacattaag    240

acctacactt aaatattttc catagaaaac catcttccta attgtctttt gaatgaaatt    300

ctgacttggt gccacaagga ctaatacccg ccga                                334
```

<210> SEQ ID NO 754
<211> LENGTH: 533
<212> TYPE: DNA
<213> ORGANISM: Homo sapiens
<220> FEATURE:
<221> NAME/KEY: misc_feature
<222> LOCATION: (1)...(533)
<223> OTHER INFORMATION: n = A,T,C or G

<400> SEQUENCE: 754

```
ggtcgccgcc actgtccggc cacagcctaa cgctcttcgc tgtcgtttgc ggtctcgcgc     60

agggcggccc cggttctggt gtttggcgtc ggaattaaac aaccaccatg tcgagcaaaa    120

aggcaaagac caagaccacc aagaagcgcc ctcagcgtgc aacatccaat gtgtttgcca    180

tgtttgacca gtcacagatt caggagttca aagaggcctt caacatgatt gatcagaaca    240

gggatggctt catcgacaag gaagatttgc atgatatgct tgcttctcta gggaagaatc    300

ccactgatgc ataccttgat gccatgatga atgaggcccc agggcccatc aatttcacca    360

tgttcctgac catgtttggt gagaagttaa atggcacaga tcctgaagat gtatcagaaa    420

cgcctttgct tgctttgatg aagaagnaca ggcaccattc aggaagatac ctaagagact    480

gttgccacca tggggggatc ggtttacana ataagaagtg gatgantgtc ctg           533
```

<210> SEQ ID NO 755
<211> LENGTH: 571
<212> TYPE: DNA
<213> ORGANISM: Homo sapiens
<220> FEATURE:
<221> NAME/KEY: misc_feature
<222> LOCATION: (1)...(571)
<223> OTHER INFORMATION: n = A,T,C or G

<400> SEQUENCE: 755

```
ggtaccttat tagaaagcga cggcaaacta tgtgccagca gccgcggtaa tacataggtc     60

gcaagcgtta tccggaatta ttgggcgtaa agcgtccgta ggttttttgc taagtctgga    120

gttaaatgct gaagctcaac ttcagtccgc tttggatact ggcaaaatag aattataaag    180

aggttagcgg aattcctagt gaagcggtgg aatgcgtaga tattaggaag aacaccaata    240

ggcgaaggca gctaactggt tatatattga cactaaggga cgaaagtgtg gggagcaaac    300

aggattagat accctggtag tccacgccgt aaacgatgat cattagttgg tggaataatt    360

tcactaacgc agctaacgcg ttaaatgatc cgcctgagta gtatgctcgc angagtgaaa    420

tttaaaggaa ttgacgggaa cccgnacaag cggtggagca tgtggtttaa tttngattct    480

acgcgtagaa ccttacccac tcttgacatc ttctgcaagc tatagagata tagtggaggt    540

tacagaatga cagatggtgc atggttgtcc g                                   571
```

<210> SEQ ID NO 756
<211> LENGTH: 570
<212> TYPE: DNA

-continued

<213> ORGANISM: Homo sapiens
<220> FEATURE:
<221> NAME/KEY: misc_feature
<222> LOCATION: (1)...(570)
<223> OTHER INFORMATION: n = A,T,C or G

<400> SEQUENCE: 756
ggtccactgg aaaggcaaca tgaccaggct gccccgcctc ctggttctgc ccaagttctc 60
cctggagact gaagtcgacc tcaggaagcc cctagagaac ctgggaatga ccgacatgtt 120
cagacagttt caggctgact tcacgagtct ttcagaccaa gagcctctcc acgtcgcgca 180
ggcgctgcag aaagtgaaga tcgaggtgaa cgagagtggc acggtggcct cctcatccac 240
agctgtcata gtctcagccc gcatggcccc cgaggagatc atcatggaca gacccttcct 300
ctttgtggtc cggcacaacc ccacaggaac agtccttttc atgggccaag tgatggaacc 360
ctgaccctgg ggaaagacgc cttcatctgg gacaaaactg gagatgcatc gggaaagaag 420
aaactccgaa gaaaagaatt ttagtgttaa tgactctttc tgaaggaaga gaaacatttg 480
cctttggtta aaagatggta aaccagatct ggcttccaag acctngcctt ttcttggagg 540
acctttaggt caaactccct agtttcacct 570

<210> SEQ ID NO 757
<211> LENGTH: 578
<212> TYPE: DNA
<213> ORGANISM: Homo sapiens
<220> FEATURE:
<221> NAME/KEY: misc_feature
<222> LOCATION: (1)...(578)
<223> OTHER INFORMATION: n = A,T,C or G

<400> SEQUENCE: 757
acaagctttt tttttttttt tttttttttt ttttttttgg gagtaagaaa aggtggggat 60
taagaanacg tttctggagg cttagggacc aaggctggtc tctttccccc ctcccaaccc 120
ccttgatccc tttctctgat caggggaaag gagctgagtg agggaggtag agttggaaag 180
ggaaggattc cacttgacag antggcacan actcctccag agtanagctt ggagggagat 240
tgaaagtgga gataatactg ctgacacctc ccttgaagct nagatgggaa atggacatac 300
ttagaaattt agtgacttta atagcctgga tttccctntn caaaactttt agaatggaaa 360
atcccatccc cttccttata tagtgacttc tacccactac cttctaccat tttctacttt 420
gggcttatga tgatggccat tatctacatg ngtttttagn accctggttt ggttctaaan 480
ggggatcttg gaacccnagn ttnttgggag atttttaaga aggaagtttt aactgaacaa 540
atggaatggg cnccagaaag aaatccaggg tnncccng 578

<210> SEQ ID NO 758
<211> LENGTH: 567
<212> TYPE: DNA
<213> ORGANISM: Homo sapiens
<220> FEATURE:
<221> NAME/KEY: misc_feature
<222> LOCATION: (1)...(567)
<223> OTHER INFORMATION: n = A,T,C or G

<400> SEQUENCE: 758
ggtacgagat tgaaaggttg agggttctac tgcaggaaga aggcacccgg aagagagaat 60
atgaaaatga gctggcaaag gtaagaaacc actataatga ggagatgagt aatttaagga 120
acaagtatga aacagagatt aacattacga agaccaccat caaggagata tccatgcaaa 180
aagaggatga ttccaaaaat cttagaaacc agcttgatag actttcaagg gaaaatcgag 240

```
atctgaagga tgaaattgtc aggctcaatg acagcatctt gcaggccact gagcagcgaa    300

ggcgagctga agaaaacgcc cttcagcaaa aggcctgtgg ctctgagata atgcagaaga    360

agcagcatct ggagatagaa ctgaagcagg tcatgcagna gcgctctgag gacaatgccc    420

ggcacaagca gtccctggag gaggctgcca agaccattca ggacaaaaat aaggagatcg    480

agagactcaa agctgagttc aggaggaggc caaccccgtt gggaatatga aaatgactga    540

taaggtagaa acattatgat gaggagg                                        567
```

<210> SEQ ID NO 759
<211> LENGTH: 266
<212> TYPE: DNA
<213> ORGANISM: Homo sapiens

<400> SEQUENCE: 759

```
ggtcaccgac ctctctcccc agctgtattt ccaaaatgtc gctttctaac aagctgacgc     60

tggacaagct ggacgttaaa gggaagcggg tcgttatgag agtcgacttc aatgttccta    120

tgaagaacaa ccagataaca aacaaccaga ggattaaggc tgctgtccca agcatcaaat    180

tctgcttgga caatggagcc aagtcggtag tccttatgag ccacctaggc cggcctgatg    240

gtgtgcccat gcctgacaag tacctg                                         266
```

<210> SEQ ID NO 760
<211> LENGTH: 381
<212> TYPE: DNA
<213> ORGANISM: Homo sapiens

<400> SEQUENCE: 760

```
ggtacactag aaagtctttt acaaaataat catcttagat caacagaaga ccaatcttca     60

atgtcgtcct gcaagatggg ttactttaac atctcctcct gttttctcca atgttctcct    120

ttagtatggc tggtaattgt tttggtgatt gccacccccct cgagatgcct tgccataagt    180

gctctgttgg ccactgtagt ctgcatatcc ctgtccatat ccatagttcc catagttata    240

cccagtataa tcatatccgc catagccact atagttttga tcaccaccat aggcactatt    300

gtaatttcca tatccttgat cataatagtt attaaatcct tggttccagt tttggccctg    360

acctcggcca cgacccctcg t                                              381
```

<210> SEQ ID NO 761
<211> LENGTH: 401
<212> TYPE: DNA
<213> ORGANISM: Homo sapiens

<400> SEQUENCE: 761

```
actcagctcc aattatctaa tattcttgaa aggatgctga tattgtttgg ttgtgtcccc     60

ccacaaatct caacttgaat tgtatctccc agaattccca cgtgttgtgg gacagaccca    120

gggggaggta attgaatcat gggggccagt ctttcccgtg ctattctcgt gacagtgaat    180

aagtctcatg agatctgatc agtttatcag gggtttctgc ttttgcttct tcctcatttt    240

ttcttgccac aatgtaagaa gtgtcttttg cctcccacca tgattctgag gcctccccag    300

ccatgtggaa ctttaagtcc aattaaacca ctttttcttc ccagtctcgg gtatgtcttt    360

atcagcagcg tgaaaacgga ctaatacagt aaattggtac c                        401
```

<210> SEQ ID NO 762
<211> LENGTH: 610
<212> TYPE: DNA

<213> ORGANISM: Homo sapiens
<220> FEATURE:
<221> NAME/KEY: misc_feature
<222> LOCATION: (1)...(610)
<223> OTHER INFORMATION: n = A,T,C or G

<400> SEQUENCE: 762

```
acgcttgttg atttcatcct catacttgtt cttgaagtct tccaccaggt cctgcatgtt     60

tcttagctct gagtccaggc ggccccgttc ccccacgatg ctgtccagct gcctcctgag    120

gttgttgatg tacagtaaaa acacatctaa catctttgaa gaccaaattt cctgctgaac    180

agtattacag atttcatgag cactggaggt ttgtgttgca gcgcttggtc ttcttggcag    240

catttgttgt gtatttggaa acagaaacac tagtgactcg agaagcagtt acagaaattc    300

ttggcattga gccagatcgg gagaaaggat ttcatctgga tgtagaagat tatctctcag    360

gagttctaat tcttgccagt gaactgtcga ggctgtctgt caacagcgtg actgctggag    420

actactcccg accccctccac atctccacct tcatcaatga gctggattcc ggttttcgcc    480

ttctcaacct gaaaaatgac tccctgagga agcgctacga cggattgaaa tatgacgtga    540

agaaagtaga aggaagtggt ctatgatctc tncatccggg ctttaataag gagacggcag    600

cagcttgtgn                                                           610
```

<210> SEQ ID NO 763
<211> LENGTH: 578
<212> TYPE: DNA
<213> ORGANISM: Homo sapiens
<220> FEATURE:
<221> NAME/KEY: misc_feature
<222> LOCATION: (1)...(578)
<223> OTHER INFORMATION: n = A,T,C or G

<400> SEQUENCE: 763

```
cgaggtaccc tgaagaactt ccctaatgcc atcgagcaca ccctgcagtg ggctcgggat     60

gagtttgaag gcctcttcaa gcagccagca gaaaatgtca accagtacgg atgctacttg    120

tccaatgatg gtaaaagggt agcttactgg ttgtcctccg attcaggtta gaatgaggag    180

gtctgcggct aggagtcaat aaagtgattg gcttagtggg cgaaatatta tgctttgttg    240

tttggatata tggaggatgg ggattattgc taggatgagg atggatagta atagggcaag    300

gacgcctcct agtttgttag ggacggatcg gagaattgtg taggcgaata ggaaatatca    360

ttcgggcttg atgtggggag gggtgtttaa ggggttggct agggtataat tgtctgggtc    420

gcctangagg tctggtgaga atagtgttaa tgtcattaag gagagaagga agaagaagta    480

agccnagggc gtctttgatt gtgtantaag ggtggaaggt gattttatcg gaatgggaag    540

tgattcctaa ggggttggtt gatcccgttc tgcaanan                            578
```

<210> SEQ ID NO 764
<211> LENGTH: 500
<212> TYPE: DNA
<213> ORGANISM: Homo sapiens

<400> SEQUENCE: 764

```
actatataac agttggcaca acccacccca caacagaaga gaacacattt ttctcaagca     60

tatgtggaat agtttccagg agaaaccatg tgttaggcca caaaacaaat cttaatgaaa    120

tgtaaaagac tgaaacacaa agtacagcat cactcggatt ctgtgtccaa tggccttagc    180

aggaagattg cttcggaatt tggcacgaac catgccactg tttccatggg cccgagttac    240

ttttccccag atgactctgg ttttgtttgg tttgccgcca ggagtgactg tgttgttctt    300
```

tgctttatat acataagcgc atctcttgcc caaatagaat tctgtttcat cttcgggccg 360
taaacacctt caattttaag aagagctgtg tgctcccttt ggttccggag accccgctta 420
tagccagcaa aaatggcctt ggaccacaag cctttcagac atagttcctt tagaagtccg 480
acttcggccg gcgaccacgc 500

<210> SEQ ID NO 765
<211> LENGTH: 578
<212> TYPE: DNA
<213> ORGANISM: Homo sapiens
<220> FEATURE:
<221> NAME/KEY: misc_feature
<222> LOCATION: (1)...(578)
<223> OTHER INFORMATION: n = A,T,C or G

<400> SEQUENCE: 765
ttccagagca tattgatgag agaaggatct gcaatgctgt ttctccagac aaggatgttg 60
atggctttca tgtaattaat gtaggacgaa tgtgtttgga tcagtattcc atgttaccgg 120
ctactccatg gggtgtgtgg gaaataatca agcgaactgg cattccaacc ctagggaaga 180
atgtggttgt ggctggaagg tcaaaaaacg ttggaatgcc cattgcaatg ttactgcaca 240
cagatggggc gcatgaacgt cccggaggtg atgccactgt tacaatatct catcgatata 300
ctcccaaaga gcagttgaag aaacatacaa ttcttgcaga tattgtaata tctgctgcag 360
gtattccaaa tctgatcaca gcagatatga tcaaggaagg agcacagtca ttgatgtggg 420
gaataaatag agttcacgat cctgtaactg tcaaacccaa gttggttgga gatgtgggat 480
tttgaaggag tcagacaaaa agctgggtat atcactccag ttcctgggan gtgtttggcc 540
ccatgacagt ggcaatgcta atgaagaata ccattntt 578

<210> SEQ ID NO 766
<211> LENGTH: 569
<212> TYPE: DNA
<213> ORGANISM: Homo sapiens
<220> FEATURE:
<221> NAME/KEY: misc_feature
<222> LOCATION: (1)...(569)
<223> OTHER INFORMATION: n = A,T,C or G

<400> SEQUENCE: 766
actgtattta tattgtttat attattttag taatgtaatg ttttgcttcc aaagattgcc 60
ttgcctttac attttgtgca aaaatagcag ctatacatta atgacataat aagtatgtct 120
agtattattt aagtgcctat tcatattttc tcatcaaagc tttttatgaa tgattataat 180
gcattttcta taaaatatta ttgctttcac tgtataccag tgattcaaac tttattgtct 240
tcaacagcaa tgacatgaaa tcactctagt tgcccatcag tggtggattg gataaagaat 300
atgtggtact atgtgactat cattgatgcc ccaggacaca gagactttat caaaaacatg 360
attacagggg acatctcaag ctgactgtgc tgtcctgatt gttgctgctg gtgttggtga 420
atttgaagct ggtatctcca agaatgggca gacccgaaag catgcccttc tggcttacac 480
ctgggtgtga aacaacctaa tggccggggt taccaaaatg ggattccact ggaccaccta 540
cagccagaag agatntgaag gaaattnnt 569

<210> SEQ ID NO 767
<211> LENGTH: 580
<212> TYPE: DNA
<213> ORGANISM: Homo sapiens
<220> FEATURE:

<221> NAME/KEY: misc_feature
<222> LOCATION: (1)...(580)
<223> OTHER INFORMATION: n = A,T,C or G

<400> SEQUENCE: 767

```
acgaagctac ccagggagat ctgaatgatg ctaaaaataa acagaaattt gttttaaagg     60
tccaaaagcc tgccaacccc tgggaattct acattgggac ccagttgatg gaaagactaa    120
agccatctat gcagcacatg tttatgaagt tctattctgc ccacttattc cagaatggca    180
gtgtattagt aggagagctc tacagctatg gaacattatt aaatgccatt aacctctata    240
aaaatacccc tgaaaaagtg atgcctcaag gtcttgtcat ctcttttgct atgagaatgc    300
tttacatgat tgagcaagtg catgactgtg aaatcattca tggagacatt aaaccagaca    360
atttcatact tggaaacgga tttttggaac aggatgatga agatgattta tctgctggct    420
tggcactgat tgacctgggt canagtatag atatgaaact tttttccaaaa ggaactatat   480
tcacagcaaa gtgtgaaaca tctgggnttt caatggtgtt gaaaatgctc ancaacaaac    540
catgggaact accagaatcg attactttgg ggttgctgca                          580
```

<210> SEQ ID NO 768
<211> LENGTH: 355
<212> TYPE: DNA
<213> ORGANISM: Homo sapiens

<400> SEQUENCE: 768

```
ggcaggtacc ctatggccta tgttgactat aagactgtgc tgcagattga tgataatgtg     60
acgtcagccg tagaaggcat caacagaatg accagagctc tcatggactc gcttgggcct    120
gagtggcgcc tgaagctgcc ctcaatcccc ttggtgcctg tttcagctca gaagaggtgg    180
aattccttgc cttcggagaa ccacaaagag atggctaaaa gcaaatccaa agaaaccaca    240
gctacaaaga acagagtgcc ttctgctggg gatgtggaga aagccagagt tctgaaggaa    300
gaaggcaatg agcttgtaaa gaagggaaac cataagaaag ctattgagaa gtacc         355
```

<210> SEQ ID NO 769
<211> LENGTH: 611
<212> TYPE: DNA
<213> ORGANISM: Homo sapiens
<220> FEATURE:
<221> NAME/KEY: misc_feature
<222> LOCATION: (1)...(611)
<223> OTHER INFORMATION: n = A,T,C or G

<400> SEQUENCE: 769

```
cgaggtacca cgatcctgat gatgaaccag tggccgatcc ttatgatcag tcctttgaaa     60
gcagggacct ccttatagat gagtggaaaa gcctgaccta tgatgaagtc atcagctttg    120
tgccaccacc ccttgaccaa gaagagatgg agtcctgagc acctggtttc tgttctgttg    180
atcccacttc actgtgaggg gaaggccttt tcacgggaac tctccaaata ttattcaagt    240
gcctcttgtt gcagagattt cctccatggt ggaagggggt gtgccgtgcg tgtgcgtgcc    300
gtgttagtgt gtgtgcatgt gtgtgtctgt ctttgtggga gggtaagaca atatgaacaa    360
actatgatca cagtgacttt acaggaggtt gtggatgctc cagggcancc ttcacccttg    420
ctcttctttc tgagaagttg gcttaaggca gaccaagatc tgctggccct tttaaggaat    480
atgttcaatg ccaaaggtaa aaaaattntg aaattggtcc ccaaatnccc gggcattgcc    540
tttcgccact ttnggcttct tcctggngan ccccaccttt gaccggtggg ggccgtanac    600
nttgacaacn n                                                         611
```

<210> SEQ ID NO 770
<211> LENGTH: 508
<212> TYPE: DNA
<213> ORGANISM: Homo sapiens
<220> FEATURE:
<221> NAME/KEY: misc_feature
<222> LOCATION: (1)...(508)
<223> OTHER INFORMATION: n = A,T,C or G

<400> SEQUENCE: 770

```
ggacaaaacc agctgaagat gaaagtgtgg agacccaggt gaatgacagc atcagtgctg      60
agacagcaga gcagatggat gtagatcagc aggagcacag tgctgaagag ggttctgttt     120
gtgatccccc acccgctacc aaagctgact ctgtggacgt tgaagtgagg gtgccagaaa     180
accatgcatc taaagttgaa ggtgataata ccaaagaaag agacttggat agagccagtg     240
agaaggtgga acctagagat gaagatttgg tggtagctca gcaaataaat gcccaaaggc     300
ccgagcccca gtcagacaat gattccagtg ccacgtgcag cgctgatgag gatgtggatg     360
gagagccaga gaggcagaga atgtttccta tggactcaaa gcctttactg ntaaacccca     420
ctggatctat actcgnctca tcttccggtn aaacccaatt cnctgggatc tggcccaant     480
tnancattna ncttgggnta ttncnncc                                        508
```

<210> SEQ ID NO 771
<211> LENGTH: 587
<212> TYPE: DNA
<213> ORGANISM: Homo sapiens
<220> FEATURE:
<221> NAME/KEY: misc_feature
<222> LOCATION: (1)...(587)
<223> OTHER INFORMATION: n = A,T,C or G

<400> SEQUENCE: 771

```
acttgttttg ggaatatatg agagaagaaa ctgctgagca ggtcagtaaa gaacagtcca      60
tttcagctgc aggacagttc tctttcccgg gacaagccta catagcctcc aagggagcca     120
aactatccct tccatgcaac aagacacctt gcatggatac tctagccatg acttgctttt     180
ggacaaaaat caactgctaa cgtttttcat ctctaatatc attaacacca tggagaaaaa     240
agaaaaaaat tcaaccctag aaaacttgac aacgagaata agaaaatcca caaggaaagg     300
tcatgctaaa actgatttga cagttgttcc atcaccgcct accacatggg cttgagactg     360
gtgacttcat ggatgcatcc cttcgatgcc ctgccaaatg tcagcttcaa gtctgtcagt     420
gaccccagtg tgatgctgcc tgccttctat tcaccaactn ctattcaaga gatccaaggg     480
ggccttgggc cgtggtaagc acanggacac ncaggtgcca agaagcccca gnaacccttt     540
tagaaaactt tgncctggga tttgggcccc ggnaaccaac cngtggn                   587
```

<210> SEQ ID NO 772
<211> LENGTH: 577
<212> TYPE: DNA
<213> ORGANISM: Homo sapiens
<220> FEATURE:
<221> NAME/KEY: misc_feature
<222> LOCATION: (1)...(577)
<223> OTHER INFORMATION: n = A,T,C or G

<400> SEQUENCE: 772

```
ggtacactgc aggagagtgc ctggcaaaaa gatcaaatgg ggctgggact tctcattggc      60
caacctgcct ttccccagaa ggagtgattt ttctatcggc acaaaagcac tatatggact     120
```

```
ggtaatggtt acaggttcag agattaccca gtgaggcctt attcctccct tccccccaaa    180

actgacacct ttgttagcca cctccccacc cacatacatt tctgccagtg ttcacaatga    240

cactcagcgg ccatgtctgg acatgagtgc ccagggaata tgcccaagct atgccttgtc    300

ctcttgtcct gtttgcattt cactgggagc ttgcactatg cagctccagt ttcctgcagt    360

gatcagggtc ctgcaagcag tggggaaggg ggccaaggta ttggaggact ccctccagct    420

ttggaagcct catccgcgtg tgtgtgtgtg tatgtgtaga caagctcttn gctctgtcac    480

ccaagctgga attgcantgg tgcaatcatg gttcacttgc agtcttgacc ttttggctca    540

agtgatcctt ccacctnacc tcctgagtac tgggacc                             577
```

```
<210> SEQ ID NO 773
<211> LENGTH: 580
<212> TYPE: DNA
<213> ORGANISM: Homo sapiens
<220> FEATURE:
<221> NAME/KEY: misc_feature
<222> LOCATION: (1)...(580)
<223> OTHER INFORMATION: n = A,T,C or G

<400> SEQUENCE: 773

ggtaccacct cctgttccta caaaaccaaa acagattaat ttgccttatt ttggacaaac     60

taatcagcca ccttcagaca ttaagccaga cggaagttct cagcagttgt caacagttgt    120

tccgtccatg ggaactaaac caaaaccagc agggcagcag ccgagagtgc tgctatctcc    180

cagcatacct tcggttggcc aagaccagac cctttctcca ggttctaagc aagaaagtcc    240

acctgctgct gccgtccggc cctttactcc ccagccttcc aaagacacct tacttccacc    300

cttcagaaaa ccccagaccg tggcagcaag ttcaatatat tccatgtata cgcaacagca    360

ggcgccagga aaaaacttca gcaggctgtg cagagcgcgt tgaccaagac tcataccaga    420

gggccacact tttcaagtgt atatggtaag cctgtaattg ctgntgncca aaatcaacag    480

cagcacccag agacatttat tcaatagcca gggcaagcct ggcagtcaga acctgaacag    540

acctgttctt tagttcagga gaaccntgaa acnaaagaat                         580
```

```
<210> SEQ ID NO 774
<211> LENGTH: 680
<212> TYPE: DNA
<213> ORGANISM: Homo sapiens
<220> FEATURE:
<221> NAME/KEY: misc_feature
<222> LOCATION: (1)...(680)
<223> OTHER INFORMATION: n = A,T,C or G

<400> SEQUENCE: 774

ggtacctggc catgggcttc cctcccacac ctgccaggac acagcctgca ggtcaggggg     60

ctaaactggg gagttttctc caaagttggg aaaggatggg aagagtaggt gggaatgggg    120

aagttacaca gctacagcag tcaggcctgt ttagtaagaa gaatcacatt taatgagttt    180

ctttcttgca gtttcagatg ctcaagtaca agtaagttat atgacaacga taacacacag    240

gaggaaagcc acggaagcac actgttgtga agttctcatg ctctacgtga agtgttatct    300

ttttttttcta agtgacagca agtttattaa gaaagtaaag gaataaaagg aatggctatt    360

tcattggcag agcaccaata aaatcatctg aaggnagatt gtgatgagtt aaangcgtat    420

atgataaacc tgaagaccaa cnagaaanta gcccacngag atntagtgga ttaagttaac    480

caagggaatt aacttgaatc attaaaaatt cttaatctgg gggaaccttt naanaanggg    540

agcttacccc ttggggcaat ttnaaaccna aagccaggtt gattgaattt aagcttacct    600
```

-continued

```
tttttcaata atccctttta aannaanggt ttnaaccttt cncttaaang gcnnnanttt    660

tcnaattgga ntttaagccg                                                680


<210> SEQ ID NO 775
<211> LENGTH: 658
<212> TYPE: DNA
<213> ORGANISM: Homo sapiens
<220> FEATURE:
<221> NAME/KEY: misc_feature
<222> LOCATION: (1)...(658)
<223> OTHER INFORMATION: n = A,T,C or G

<400> SEQUENCE: 775

ggtacctgtg ccagatgaaa ggtttgactt tctttgtcaa taccacaaac cagcaagcaa     60

aattcctgcc tttctaaatg tggtggatat tgctggcctt gtgaaaggag ctcacaatgg    120

gcagggcctg ggaatgcttt ttttatctca tattagtgcc tgtgatggca tctttcatct    180

aacacgtgct tttgaagatg atgatatcac gcacgttgaa ggaagtgtag atcctattcg    240

agatatagaa ataatacatg aagagcttca gcttaaagat gaggaaatga ttgggcccat    300

tatagataaa ctagaaaagg tggctgtgag aggaggagat aaaaaactaa aacctgaata    360

tgatataatg tgcaaagtaa aatcctgggt tatagatcaa aaagaaacct ggtcgcttct    420

atcatgattg gaatgaccaa gagattgaag tggtgaataa acccttaatt ttgactcnaa    480

anccatggnc tacttggtna acnttctgaa aaagcttcnt ttgaaggaaa ccaanggtga    540

taaaattaag aaggggtggc cagtttancc agggccttgg catcctttaa gggggcttgg    600

accttaagtt ccanaattga tcttanggna anccaagttt tggaaccacc tgncccaa      658


<210> SEQ ID NO 776
<211> LENGTH: 659
<212> TYPE: DNA
<213> ORGANISM: Homo sapiens
<220> FEATURE:
<221> NAME/KEY: misc_feature
<222> LOCATION: (1)...(659)
<223> OTHER INFORMATION: n = A,T,C or G

<400> SEQUENCE: 776

ggtactttac ggcctgatct aattgaaagt gcatcccttg ttgcaagtgg caaagctgaa     60

ctcatcaaaa cccatcacaa tgacacagag ctcatcagaa ggttgagaga ggagggaaaa    120

gtaatagaac ctctgaaaga ttttcataaa gatgaagtga gaattttggg cagagaactt    180

ggacttccag aagagttagt ttccaggcat ccatttccag gtcctggcct ggcaatcaga    240

gtaatatgtg ctgaagaacc ttatatttgt aaggactttc ctgaaaccaa caatattttg    300

aaaatagtag ctgatttttc ttgcaagtgt taaaaagcca catacccctat tcagagagtc    360

aaagcctgca caacagaaga ggatcaggag aagctgatgc caaataccag tctgcattcc    420

tgaatgcctt cttgctgcca attaaaactt naggtgtnca nggtgaactg gnngtnctac    480

cgntnccngn ngnggaatnt caggnaaaga tgaaccctgc tgggnaatcn cttattttcn    540

ggntangnnt aaaccttnga tggggccaac cttaccnggt ggttattttt tggncccccn    600

ntaaagaacc tcntnaaang tnccccnttt ttganacggg ggnttaaacc tncccgggg      659


<210> SEQ ID NO 777
<211> LENGTH: 728
<212> TYPE: DNA
<213> ORGANISM: Homo sapiens
<220> FEATURE:
```

<221> NAME/KEY: misc_feature
<222> LOCATION: (1)...(728)
<223> OTHER INFORMATION: n = A,T,C or G

<400> SEQUENCE: 777

```
acttcttgca tgttgtcaca tgttgctgtg agaatcaggt gctgcctata tggctccact     60
gggagagggc agatggaagc cgtcgcctca tctgtcgtgg aacgtgtgct gtgcacctcc    120
tccctttgct gatcttaatc tctgtccttt tactgtaata aactgtaact gtgagcctaa    180
cagctttcct gagtctagtg agtccttcta gcaaatgaaa ggagggtggt cttggagacc    240
tatgaacttg cacctgcccc cgtcgttttg agggtctggc acaggggagg gaagggctgg    300
gcctcttttg gaagggggtc ttcaatccat ttgggggtcg gggtcccaac ttcttggang    360
ggcccaacgt tccttgccca gcttccaagn ctcttcttcc cttcttaagt ccccgancct    420
tgcaaccttt gggcccctnt ggcttgtgga atcctgggaa aaaacttngt ctttttnntt    480
ancacttgaa tnngaanaac tggcccatta actnaagccc ttgcatnnct tngactnctt    540
nnatgggcaa ccttnaaggg attcccaagg gnccccctggg tttanggaaa taatgggggg    600
aaaatttttt nggaanttna anaataancc ccccccaaaa ncgggggganc cttngggccc    660
gnaacccccc ttaagggccn aaattccngn canatntggg ggggccggtn ctaaggggat    720
cccaaccc                                                             728
```

<210> SEQ ID NO 778
<211> LENGTH: 603
<212> TYPE: DNA
<213> ORGANISM: Homo sapiens
<220> FEATURE:
<221> NAME/KEY: misc_feature
<222> LOCATION: (1)...(603)
<223> OTHER INFORMATION: n = A,T,C or G

<400> SEQUENCE: 778

```
caggtacact gctgccactg ttgtgtcctc gctctgcttg ctgttgcctc acgccaggcc     60
ccgtcctgcc gtgacaccct tcatcctacc cttggaaccc caaggccaag ttggttcaaa    120
ctgttggaga acagagttgg cctgcatctg gaacacactt gtcctcagct taccatctcc    180
tcacacccca gagtggaaag gtgaacacct gcagctgagg cttggaaacg tttcttgtgt    240
tgccctgaaa aatctttgag acctcaggga ggctctgtct ctcttaaaag gtggagaaag    300
atgccattct ctccctaagg tctggtggag tctccccatc ttgcataccc ttctgcaagc    360
catctatctc tgctcactct ccaattgacc cgcctgggaa caagggatga aggaggaagt    420
tgggggcttg gggggaatcct gccagttggt gaancctgtg gcangaagga tatgtgacnt    480
agagatcctg atcttttntn ancctgctgt tggttggctt gnatatatgg atggtgactg    540
tttgnaaagn ggagtataag atgccntgct gatnggngta tgctatgctn ttangatgga    600
ctg                                                                  603
```

<210> SEQ ID NO 779
<211> LENGTH: 654
<212> TYPE: DNA
<213> ORGANISM: Homo sapiens
<220> FEATURE:
<221> NAME/KEY: misc_feature
<222> LOCATION: (1)...(654)
<223> OTHER INFORMATION: n = A,T,C or G

<400> SEQUENCE: 779

```
cgaggttttt tttttttttt tttccagtta gtgatgtcgt atttcaaaat aggtcgaaac     60
```

-continued

```
ttcagagaaa tgaaaatcgg gatatcagtg aagttattgc tctcggtgtt cctaatcctc    120

ggacttccaa tgaagttcag tatgaccaaa ggctnttcaa ccaatccaag ggtatggaca    180

gtggatttgc aggtggagaa gatgaaattt ataatgttta tgatcaagcc tggagaggtg    240

gtaaagatat ggcccagagt atttataggc ccagtaaaaa tntggacaag gacatgtatg    300

gtgatgacct agaagccaga ataaagacca acagatttgt tcccgacaag gagttttctg    360

gttcaaaccg taaacngaga ggccgagaag gaccagtgca gtttgaggaa aatccttttg    420

gtttggacaa gtttttggaa aaaacccaac ngcatggngg ctntaaaaga cccttagata    480

ccacccgcnc aaggacnnag cctgaagcca gaaaaggngg aaggattggc caggttttcc    540

aagngaatga ctttanccta acctaangag ccagnttngg ggacccttnt aaagggccgg    600

taaaaccnat ttggggccca nnccnccttn ttttttctgg gaaangggggg gtta         654
```

<210> SEQ ID NO 780
<211> LENGTH: 570
<212> TYPE: DNA
<213> ORGANISM: Homo sapiens
<220> FEATURE:
<221> NAME/KEY: misc_feature
<222> LOCATION: (1)...(570)
<223> OTHER INFORMATION: n = A,T,C or G

<400> SEQUENCE: 780

```
acagtgggca caaaacctgt gcagagtccg cagaagaggc caataaccaa gcgacccagg     60

atcagcattt caaccgactt agctacttta cacagtccca taaagcagcc accagtgaca    120

gccaacaggt tgacaatcag cattgaattg cgcctgccaa agcggttgac gaagagtccg    180

acggaaaagg agccgatcat accccngacg gaaaatatgg ccacagacaa ggaccagaga    240

gacgtgagca gcacctcaga gggtggggca tttcccttgc cgtcaaagtt ttattgataa    300

attcctttat gatcttctca ggagcattga tgaccccagt ggttgtaacc naattggaaa    360

gaaccgattg nagccactgg tgatggccaa tatcaaanct ggggtgacct tctggggccc    420

catcgctgga atctaattca agtctttaag aaagatctan gggtgatttc agaaacnagn    480

ttttnaggcc acaaaccttt aaanggcctt ttaacagcaa ggtttnttcc cgtcttagga    540

aggatncnaa nccnttggcc ggaaccncct                                     570
```

<210> SEQ ID NO 781
<211> LENGTH: 664
<212> TYPE: DNA
<213> ORGANISM: Homo sapiens
<220> FEATURE:
<221> NAME/KEY: misc_feature
<222> LOCATION: (1)...(664)
<223> OTHER INFORMATION: n = A,T,C or G

<400> SEQUENCE: 781

```
acccaaagtt ctctggggag ggccagggaa gaggctgggt gtcaaaccaa acagattttt     60

atttgcagtc gtcactgggg ccgtttcttg ctgcttattt gtctgctagc ctgctcttcc    120

agctgcatgg ccaggcgcaa ggccttgatg acatctcgca gggctgagaa atgcttggct    180

tgctgggcca gagcagattc cgctttgttc acaaaggtct ccaggtcata gtctggctgc    240

tcggtcatct cagagagctc aagccaagtc tggtccttgc tgtatgatct ccttgagctc    300

ttccatagcc ttctcctcca gcttcctgat ctgaagtcat ggctttcgtt aaaactggac    360

atctgggaaa gacagtcctt ctctttcttg gataaattgg cctggaatca ncgccccggt    420
```

-continued

```
aaaacaagct ttcatctttc tggttccant ttnattaact ggttttcact nggnccactg    480

ngggggctta ncttcttgac ctggctggna aatttaaggn ggttnaagnt tnttncccgg    540

acctattncn tggnnaaaac cngggaatna tgcnagnctt aaaattttnc ccaangaagg    600

agtccttaan accnggntaa nttggnttta cggaacnggg tggnnacctt gttttnccag    660

gncc                                                                 664
```

```
<210> SEQ ID NO 782
<211> LENGTH: 669
<212> TYPE: DNA
<213> ORGANISM: Homo sapiens
<220> FEATURE:
<221> NAME/KEY: misc_feature
<222> LOCATION: (1)...(669)
<223> OTHER INFORMATION: n = A,T,C or G

<400> SEQUENCE: 782

caggtacaag cttttttttt tttttttttt tttttggaat agaatacaac tttattttca     60

gtcatttcta tttccttggt tatgaacaaa ggtagcaaag tgcagttgta tcagcagtgc    120

caatagaaat tacagagttt ttcatatccc tttacagttt gccacaggta tcttaaaata    180

ttgnttacac tcatctctct tcagtttacc attgtttaat aggcctaccc tcgatctttt    240

tattcaatat gttaataaag aaacctatac acatagtatc accgttatca ttttaaaaat    300

attttgacac tgnatataaa tataactagc ttactttgga atcctaccta ttttaatggt    360

gnatgaaaat attattctga aattagccng gcntggnggt gcatgcctan aggcccagct    420

acttgggaag cttaaggggg aaggatccct gaacccaagg ganggccang nttcngggan    480

ctnggatgnn caatggcttc ancctnggna atngaatggg ancccttttt aaaggaaagg    540

aaanggaaat ttggattttg gnaacngann cctggnccaa aaaagggcaa aanccctgct    600

ggaanggccc tntggacctt aaatgccccn nccaaangng gnnattncca tttaannggn    660

cccncaggg                                                            669
```

```
<210> SEQ ID NO 783
<211> LENGTH: 735
<212> TYPE: DNA
<213> ORGANISM: Homo sapiens
<220> FEATURE:
<221> NAME/KEY: misc_feature
<222> LOCATION: (1)...(735)
<223> OTHER INFORMATION: n = A,T,C or G

<400> SEQUENCE: 783

acacagaagc agtgaaggac tgcacagaag ccctcaagct ggatggaaag aacgtgaagg     60

cattctacag acgggctcaa gcccacaaag cactcaagga ctataaatcc agctttgcag    120

acatcagcaa cctcctacag attgagccta ggaatggtcc tgcacagaag ttgcggcagg    180

aagtgaagca gaacctacac taaaaaccca acagggcaac tggaacccct gcctgacctt    240

acccagagaa gccatgggcc acctgctctg tgcccgctcc tgaaacccag catgccccaa    300

gtgagctctg aagccccctc ctcaatccct tgatggcctc caccctgtaa gaagctttgc    360

tttggtcaaa ttaaacttaa gtgtaatcaa accccagacc atgggtggtt gcacccagaa    420

agggncccac tnagaaccta aacgttgaag ctgnaacttt ngcccctaat tcccnaagcc    480

caagttagct tgatcccncc accggaatcc ttatttagcc aaagccnttt ngggntttgg    540

ncctggnccc aaanggggct ttgaaaaact ggaaggcttg gcccnttgga agctttnccc    600

caaaanccccc aaatttaatt ggggagntna ttttggaacn aaccttgggc tttttngggc    660
```

```
cccgggtttg gaaaggaagg ggggataaaa ccttaagggc cctggttcca aaannanccc    720

tttttnaacc ggggn                                                     735


<210> SEQ ID NO 784
<211> LENGTH: 660
<212> TYPE: DNA
<213> ORGANISM: Homo sapiens
<220> FEATURE:
<221> NAME/KEY: misc_feature
<222> LOCATION: (1)...(660)
<223> OTHER INFORMATION: n = A,T,C or G

<400> SEQUENCE: 784

cgaggtacac attgtattat atacaaacaa gcaacaacaa aaagtttcat catgtaaaca     60

aaagaatata aattatagac ataattggaa gtttcaaaca gtccttaaat cattgtgagc    120

ttctctaaaa ggcacaggtc ttggagtgtg ggcacagagc cattagtcag atgtctgggt    180

ggtctcccat aatagcaatg tatactctaa agtgggcttt ttgtgaactc tgtcagggtg    240

aatgagttag gcctcttaaa ggaatgaaat gctttcacat ttggggcaac aagtgaaaaa    300

tactgaaagg agggatacaa ctagggttag atttattggt gacagtgatt ttagaaatac    360

cactaaaaag gtggtaaaag atttctagat taaattctga ctactgnaaa tnagaaagga    420

tccttttgna nctctaccaa tggttngtga aaaattaaaa gggagaaagt gacccaggag    480

aaaccnaatt gggaagctan ggaggttcca gaaaatnccc agtcttacac gaaaaaacct    540

tganagggcc tttttaaggc caannttggg aaattacctt tgtaacttaa cttgaaaaan    600

acctgccggc ggccgttnaa aggncaattn accnctggng gccgtcttag ggnccncctc    660


<210> SEQ ID NO 785
<211> LENGTH: 254
<212> TYPE: DNA
<213> ORGANISM: Homo sapiens

<400> SEQUENCE: 785

actgctgctg gttaaggtca acctggggtg caatgctgct gtcttcatct tcggtcccga     60

agtaatgctc aataagatca aaggcctttt ggtagatctc ctggttttca tgactctgta    120

agaactcaat tttatccaga ccataagctt cttcaatcaa agcacagtaa gggttaatgc    180

cagtgccatt ccttttggct tcctgttctc caagcctcag gatattttcc aagccattta    240

gggcaacctg tacc                                                      254


<210> SEQ ID NO 786
<211> LENGTH: 688
<212> TYPE: DNA
<213> ORGANISM: Homo sapiens
<220> FEATURE:
<221> NAME/KEY: misc_feature
<222> LOCATION: (1)...(688)
<223> OTHER INFORMATION: n = A,T,C or G

<400> SEQUENCE: 786

ggtactggct gagctggaag tgccaaaaag cactcctggc tgcttctggt tccatctgat     60

gatgatgtga cacacactgc tgaaaaggcc caagcagggc aagtgggatg gctgaaggag    120

ggaaggaggg ggttcagaac ccactggcct ggatgggaga actgggtgga ggcttcccca    180

agagggaaga cagataaaca aaacaaaaca aaaactgggt aaagaggaat gaatcactca    240

gccctgatgt ttcaattcta cactgcattc ctggccagtc gcatttgttt aatgcaggca    300
```

-continued

```
tggccacagc tctcctagag aattatctca aagacccaga agggacctgg angaggccta    360

tttcttaagg ttttccagtt ggaccaaggg aangantggg ttcacttagc ttctaaaaaa    420

ggntttgaac cctaaggtta actgcctccg gaagctgctt gcttttggtt tggcttccca    480

aaaaggnttc agaatagntt tggacccctt anggaaactt ggatcaagcc cggnaancca    540

anacttnctt ggtngnaaaa tcaagggggg ctncttgggg nttanccgga agtttgggnc    600

aggntgtntt aacagggtgg ggantgacca nccnggngcc caggggcctt antaacnttg    660

ggaanccccct gnganggaan ccttnacc                                       688
```

```
<210> SEQ ID NO 787
<211> LENGTH: 708
<212> TYPE: DNA
<213> ORGANISM: Homo sapiens
<220> FEATURE:
<221> NAME/KEY: misc_feature
<222> LOCATION: (1)...(708)
<223> OTHER INFORMATION: n = A,T,C or G

<400> SEQUENCE: 787

acagtaacac aacatcaaaa gcaacacagg ctgtatacag aaacgtgggt cattcttttc     60

agccctaatg gagatgtaat taacagtatc gagcactctg gaaaatcact ctgcaggttt    120

atatggacta catggagatc atatcctgta gtgtagtgaa agctaagtcc tcaagagcca    180

tatgtataga tacacaatgt tttttaataa tctttaaaac agagatcaaa gttcatttaa    240

gtcctgtttg cattaacaaa aataaaaatg aaataaaaat gggaaccaaa tggatcatct    300

aaaaggttta aaaattccta aattgnccaa tttatccaac tggtgggaga cttaattcag    360

ggttttggaa agtccaggac tggtttcagc tgaacccaga aggcccccaa ttttgcttac    420

tggaactggc cctggggtaa gncatggaat taaaatngct tancnccttc ccctnggttt    480

tgaacttttg gccggttnga attattggtt aaaggcaggc tttaaaccaa gtttnccaac    540

ctgggctatt taacttggat cccattggga aaaattttca aanggaaatt ttttattagg    600

ggccatttca atcnaangga aaattntggg aactttggaa atnccgantc cttgntggaa    660

anaaaaaacc cnggggaaat gggnngggggg nccttnggcc cccaaccc                 708
```

```
<210> SEQ ID NO 788
<211> LENGTH: 647
<212> TYPE: DNA
<213> ORGANISM: Homo sapiens
<220> FEATURE:
<221> NAME/KEY: misc_feature
<222> LOCATION: (1)...(647)
<223> OTHER INFORMATION: n = A,T,C or G

<400> SEQUENCE: 788

ggtactctgt ctgctgaggg aatggggtat tttgactccc atagaaagca ctagcctaag     60

tcaccaaatg actgcttggt ccccactgaa gcagtgtagc tctccatagt atttttggtg    120

gttatggatt acatgtgtgg ccagctcatg ctttttcttg agcaggggct gtccatgacc    180

tgtgctcata ccatgctttc taagttctct ttggacaggg cctcagctgc tgcctcagcc    240

tgagtttcag agggtgtgta ggagtcctgg taatcttgaa gcagtttgac cacctccaaa    300

tggttgaact gcacagcatc atccagggga atggtgccca cctgtccttg gcaaaaggat    360

tcactttgca agccttgatc aggaatttaa caacttcgaa tgtgccctta nctgcagcaa    420

catgcnaanc tgggcnccaa gcataagctt tctggtccat atccatggct gacaaggcaa    480

cctttnaana ncttancatt ggcnctntnn gcngcaaata ccaggtggcc nnagcttggt    540
```

-continued

```
cccaattntg gccttacncc cggggntaan tccaaccaan gccttaggtn caaattngga    600

aattgaanan accccacttt ggcaaactgg cccctnggtt gncccat                  647
```

<210> SEQ ID NO 789
<211> LENGTH: 650
<212> TYPE: DNA
<213> ORGANISM: Homo sapiens
<220> FEATURE:
<221> NAME/KEY: misc_feature
<222> LOCATION: (1)...(650)
<223> OTHER INFORMATION: n = A,T,C or G

<400> SEQUENCE: 789

```
acctgcgcgc cctcgacgtc aatgtggcct tgcgcaaaat cgccaacttg ctgaagccag     60

acaaagagat cgtgcaggac ggtgaccata tgatcatccg cacgctgagc acttttagga    120

actacatcat ggacttccag gttgggaagg agtttgagga ggatctgaca ggcatagatg    180

accgcaagtg catgacaaca gtgagctggg acggagacaa gctccagtgt gtgcagaagg    240

gtgagaagga ggggcgtggc tggacccagt ggatcgaggg tgatgagctg cacctggaga    300

tgagagtgga aggtgtggtc tgcaagcaag tattcaagaa ggtgcagtga agcccaggca    360

gacnaccttg tcccaaagga atcagcaagg atgtgtgggc caagatcccc ctntttgccc    420

agcatgaggc aaaaatgtnc agccacccca ggctttnnta acanagctgg ctcttggttt    480

tggcactttt ccttttctta aacaaacctg ccattaagng anttggggtt caaaaaaaaa    540

aattntnnna naataaaaan tttttntctt cgcaccncct tnnggggaaa cncnantgng    600

gcggtntntt ggancnctnn tccncnttgg gnntangtat aatnttttt                650
```

<210> SEQ ID NO 790
<211> LENGTH: 646
<212> TYPE: DNA
<213> ORGANISM: Homo sapiens
<220> FEATURE:
<221> NAME/KEY: misc_feature
<222> LOCATION: (1)...(646)
<223> OTHER INFORMATION: n = A,T,C or G

<400> SEQUENCE: 790

```
gggtaattcc ggctgttgca ccatggcgtc catggggacc ctcgccttcg atgaatatgg     60

gcgccctttc ctcatcatca aggatcagga ccgcaagtcc cgtcttatgg gacttgaggc    120

cctcaagtct catataatgg cagcaaaggc tgtagcaaat acaatgagaa catcacttgg    180

accaaatggg cttgataaga tgatggtgga taaggatggg gatgtgactg taactaatga    240

tggggccacc atcttaagca tgatggatgt tgatcatcag attgccaagc tgatggtgga    300

actgnccaag tctcaggatg atgaaattgg agatggaacc acaggagtgg ttgtcctggc    360

tggtgccttg gtagaagaag cggagcaatt gctanaccca ggcattcacc caatcagaat    420

annccatngc tattaacaag ctgnttcccg ttgctattga acactggaca agaacaacga    480

taccnccctg gtgacttaan ggcaccgaac cctgattaaa ccgnaaaccc cnctnggttc    540

aagnggnaca gttgcncccc cnatngttaa atctggangc cgcctnttgc ccanttggac    600

ggaaacntta tttgctttca attaaggcaa tggccgcagn tgagan                   646
```

<210> SEQ ID NO 791
<211> LENGTH: 656
<212> TYPE: DNA
<213> ORGANISM: Homo sapiens
<220> FEATURE:

<221> NAME/KEY: misc_feature
<222> LOCATION: (1)...(656)
<223> OTHER INFORMATION: n = A,T,C or G

<400> SEQUENCE: 791

```
accatgatat ctggcagatg tataagaagg cagaggcttc cttttggacc gccgaggagg     60
tggacctctc caaggacatt cagcactggg aatccctgaa acccgaggag agatatttta    120
tatcccatgt tctggctttc tttgcagcaa gcgatggcat agtaaatgaa aacttggtgg    180
agcgatttag ccaagaagtt cagattacag aagcccgctg tttctatggc ttccaaattg    240
ccatggaaaa catacattct gaaatgtata gtcttcttat tgacacttac ataaaagatc    300
ccaaagaaag ggaatttctc ctcaatgcca ttgaaacgat gccttgtgtc aagaagaagg    360
cagactgggc ccttgcgctg gattggggac caagaggcta cctatggtga acgtgttgta    420
acctttgctg cntggaaggc atttcttttc cggtcttttg cgcgatattc tggcttaaga    480
aacgaggctg agcctggcct acantttcta angaacttat taccganatt aagggttacn    540
ctgggatttg cttgcctgaa gttnaacccc tgggacctng gccgnacccc ntangggcaa    600
ttccanccac tggngggccg tactaaggga accaacttgg gcccaacntg gggnat        656
```

<210> SEQ ID NO 792
<211> LENGTH: 640
<212> TYPE: DNA
<213> ORGANISM: Homo sapiens
<220> FEATURE:
<221> NAME/KEY: misc_feature
<222> LOCATION: (1)...(640)
<223> OTHER INFORMATION: n = A,T,C or G

<400> SEQUENCE: 792

```
ggtctgacac aatcagaaat tcgagacatc atcctgggta tggagatctc ggcaccgtca     60
cagcagcggc agcagatcgc tgagatcgag aagcagacca aggaacaatc gcagctgacg    120
gcaacacaga ctcgcactgt caacaagcat ggcgatgaga tcatcacctc caccaccagc    180
aactatgaga cccagacttt ctcatccaag actgagtgga gggtcagggc catctctgct    240
gccaacctgc acctaaggac caatcacatc tatgtttcat ctgacgacat caaggagact    300
ggctacacct acatccttcc caaagaatgt gcttaagaaa gttcatctgc atatctgacc    360
ttcgggccca aattgcagga tacctatatg gggtgagccc accagatacc cccaggtgaa    420
agagatcccc tgcattgtga tggtgcccca atggggcctt accanaacgn gcacctgctg    480
gcaantgnct aactgagacc tgcccggcgg ccgttcaang gcaattcngn nactggnggc    540
cgtctaaggg accnacttgg gccaacttgg gnaatatggc nnactggtcc tggggaatgg    600
tntccgtcca ttcccanttc anccggaanc taanggtaac                          640
```

<210> SEQ ID NO 793
<211> LENGTH: 615
<212> TYPE: DNA
<213> ORGANISM: Homo sapiens
<220> FEATURE:
<221> NAME/KEY: misc_feature
<222> LOCATION: (1)...(615)
<223> OTHER INFORMATION: n = A,T,C or G

<400> SEQUENCE: 793

```
acctacaact atatctactc cattttccaa aacagagagc tgatcccggg ctgcaacacc     60
tccaattatc agaagctccc ttaatttagg attatcaatg tatttcttaa actgcttgat    120
gttattcaaa gtttgttcag ctaactcccg ggaaggttca acaatgagag ctttcggagc    180
```

```
attggggaga aactttgttt gtgtcacctg tgcattacct gagtgctgtg atttgacaat    240

gtaaccatcc ggtgccttgg aaagagcaac aaagccatct tttggtggaa acttaaattc    300

ctcttcaccc gaagttaaat ttcagttcag cattcttcaa aacacaggca ggaaagaggg    360

cttggttttt catatgtggt ggtatttcaa atgccagacc aagancttt ccatttttgg     420

agaacttgac atgtccttat ctatatcnng tacatccatg ggatcatgcc tagngaatnc    480

tttcataata tcaaatggtg gtatggaatc ttcctgtccc caagccaatc caactggaga    540

ccttggcggc ccntanggca atcancctgn gccgctaggn ccactggcca ctggnacagg    600

cnntgtctgg aatgn                                                     615
```

<210> SEQ ID NO 794
<211> LENGTH: 709
<212> TYPE: DNA
<213> ORGANISM: Homo sapiens
<220> FEATURE:
<221> NAME/KEY: misc_feature
<222> LOCATION: (1)...(709)
<223> OTHER INFORMATION: n = A,T,C or G

<400> SEQUENCE: 794

```
acttctgaat aagttcagag ccaaccactc tcaagaaagt ggctgaggtt tggtttgcta     60

ctgctttggc taacaaggtt ttacctgtgc caggtggacc atagagaatg accccttag     120

gaggctttat acccatctct tcataatatt caggatgggc gagaggaagc tccacagatt    180

ccttaatttc ctgaatttgg ttgtccaacc ccccaatatc tgcataggtc tcctgggggg    240

ccttttctac cttcatcact gtgaccaggg gatccgtgtc atccatcagc acccctatca    300

cggnatgcac cttgtggttg agcaggaccg agcagccagg ttccagcaga tccttgctac    360

aaatgaaaga atgctgacgt antgttctga gcccacagat gtagacacga atggcatgat    420

ggcatcaatg atctctttcc aaggttccta ctgacatcgg ggtccccctc agaatcatcc    480

acttttggat ctttccttcn tcttgntttt ccttctaaag gggttcaatt tggtncccgg    540

atttcttaag ngaatctttc cttncnttga aaaaaaaaag gccnttnaaa tnctnttta     600

acctttangn aanttttaaa cccgggcctt gaattnnnaa gggggcnccc cngggggcaa    660

ttttncttgg cnnnaatttg gggcccctt  gggnttnntt ttttttttt               709
```

<210> SEQ ID NO 795
<211> LENGTH: 693
<212> TYPE: DNA
<213> ORGANISM: Homo sapiens
<220> FEATURE:
<221> NAME/KEY: misc_feature
<222> LOCATION: (1)...(693)
<223> OTHER INFORMATION: n = A,T,C or G

<400> SEQUENCE: 795

```
ggtacggcaa tcaatcttaa taatccagag agccagtcca tgcatttgga aaccagactt     60

gttcagctgg acagtgctat cagcatggaa ttgtggcagg aagcattcaa agctgtggaa    120

gatattcacg ggctattctc cttgtctaaa aaaccaccta aacctcagtt gatggcaaat    180

tactataaca aagtctcaac tgtgttttgg aaatctggaa atgctctttt tcatgcatct    240

acactccatc gtctttacca tctctctaga gaaatgagaa agaatctcac acaagacgag    300

atgcaaagaa tgtctactag agtcctttta gccactcttt ccatccctat tactcctgag    360

ccgtacatgt gcataggaac tgggatatac acaggcacag ggataggcac tggaacatat    420
```

-continued

```
tctgnctnca agtatcatct gctgaccaag aattggnctg catgtgaagg ttacagtaag    480

tacttttggc attggtaaan ggttgccaaa aaactgnttt ggnccttnan cnctttggta    540

aggggttgga aaaaggggtg gggcttaaac ctggcanttt nggttcnana agtntggaaa    600

ncctgggang ttaagggaag gtttttangg gccnttttga aatggcaatg tgggcncaat    660

ttggtggccc gtnaaaaccc cntanncaag gtn                                 693
```

<210> SEQ ID NO 796
<211> LENGTH: 452
<212> TYPE: DNA
<213> ORGANISM: Homo sapiens
<220> FEATURE:
<221> NAME/KEY: misc_feature
<222> LOCATION: (1)...(452)
<223> OTHER INFORMATION: n = A,T,C or G

<400> SEQUENCE: 796

```
ggtacattca cgtctcccgg ccgcttcacc tgaaagccat cggtctcctg ggtagtggcg     60

gtcctgtgcc attctaccag atggttgtct ggcccataca ggtctttgtc cagttcaatc    120

accaaggatt taaaaaagga agagaacttc ctcttttgtt tagtggcatc atatttggac    180

aaggctgaat cctccaggag ccgtccttct acccgaagct cccaggaagc caccgtccct    240

tccccatcct cggcatctga cttagccgga ttgaaagtgt tagaaatgaa aattcgcagc    300

ttccgttttt gcttgatggg acgtttcaag gcctcttgga tatctagccg ttcctcatga    360

tagtctggtc cagttccttt caaaagccaa gagatccata taggcctggg attctggtac    420

ctgccnggcc ggcgctcnaa nggccaattc aa                                  452
```

<210> SEQ ID NO 797
<211> LENGTH: 333
<212> TYPE: DNA
<213> ORGANISM: Homo sapiens
<220> FEATURE:
<221> NAME/KEY: misc_feature
<222> LOCATION: (1)...(333)
<223> OTHER INFORMATION: n = A,T,C or G

<400> SEQUENCE: 797

```
ggtacaagct tttttttttt tttttttttt ttttttatta ngcgcaagtg gtcaaaagtt     60

gtcaaaattg tcctcattcc tcgattgtct cttttttacc agtctcttgc ccttcaaaca    120

gaggatacct ggcctccaca tcagcccatg tgatgttgcc attggctagg tcttggacta    180

tgctgggcag ctcagagatc tctgctctta tctgccgcat tgagtcacgg tccctcagag    240

ttgcagtgtg gggggtcttg ttcactgtgt caaagtcaat ggtgacacca aaagccacgc    300

caatctcatc aagtcctggc atancgcctt ccg                                 333
```

<210> SEQ ID NO 798
<211> LENGTH: 632
<212> TYPE: DNA
<213> ORGANISM: Homo sapiens
<220> FEATURE:
<221> NAME/KEY: misc_feature
<222> LOCATION: (1)...(632)
<223> OTHER INFORMATION: n = A,T,C or G

<400> SEQUENCE: 798

```
ggtgcttttt tttttttttt tttttttttt tttttggaca cagatcactt tattggcatg     60

gctttgtttt aagaaaagga aaagtgacaa agccaagaga cagactctgc taacagatgc    120

ctgggggtgg ctggacattt ttgcctcatg ctgtgcaaag agggggatcc tggcccacac    180
```

```
atcctgctga ttccttggga caaggttgtc tgcctgggcc tcantgcacc ttcttgaata    240

cttgcttgca gaccacacct tccactctca tctccaggtg cagntcatca ccctcgatcc    300

actgggtcca gccacgcccc tccttctcac ccttctgcac acactggagc ttgnctccgc    360

cnagctcact gntgcatgca cttgcggcat ctatgcctgn caaatcctcn ttaaactctt    420

tnccaacctg gaagtncatg gatgtagtcc taaaagtgct ancgngccga tgatcatatg    480

gncaccggnc tgnaccnact tttggctggc ttancaagtt gcaattgcnn aggccattga    540

cttaggcncc agtcttcccg gcgccgtnaa ggcaatcncc attggcggnn tctagggncc    600

nntggncagt tggtnatngg caantntcng ga                                  632
```

```
<210> SEQ ID NO 799
<211> LENGTH: 462
<212> TYPE: DNA
<213> ORGANISM: Homo sapiens
<220> FEATURE:
<221> NAME/KEY: misc_feature
<222> LOCATION: (1)...(462)
<223> OTHER INFORMATION: n = A,T,C or G

<400> SEQUENCE: 799

ggtactgcgt ctgtttttgt taccccacaa ggaccagcgc cagatgttct ttgtgatcag     60

cctggatccc ccaatcaagc aaggccaaac tcgctaccac ttcctgatcc tcctcttctc    120

caaggacgag gacatttcgt tgactctgaa catgaacgag gaagaagtgg agaagcgctt    180

tgagggtcgg ctcaccaaga acatgtcagg atccctctat gagatggtca gccgggtcat    240

gaaagcactg gtaaaccgca agatcacagt gccaggcaac ttccaagggc actcaggggc    300

ccagtgcatt acctgttcct acaaggcaaa gctcaggact gctctacccg ctggagcggg    360

gcttcatcta cgtccacaaa gccacctgtg cacatncgct tcgatgagac tcctttgcaa    420

cntttgtcgt ggtacctgcc cggccggncg ttcgaaangg cc                       462
```

```
<210> SEQ ID NO 800
<211> LENGTH: 702
<212> TYPE: DNA
<213> ORGANISM: Homo sapiens
<220> FEATURE:
<221> NAME/KEY: misc_feature
<222> LOCATION: (1)...(702)
<223> OTHER INFORMATION: n = A,T,C or G

<400> SEQUENCE: 800

gaggtgtcct cccctccaag cagaccacct gtccccttct atcccagctc agagcagctg     60

acccaactca gaatctcttt cctacaggat gaagtgcctt ttgaatgtta ttttaagccg    120

agagttaatt tttctacaca acatatttcc agacatcttt tagtctttta ttgtcttaga    180

tactataaga agatgaacat gacaattttc tagaacctgg tagcgtgtgt gtgtgtggcg    240

gggggtgctg agggagggga gtgagtcaca ggagcctgtc ccccaacagg tgtgattgct    300

ctgacaacct gtggcatgct gcagggtcag gctcctgata ggaggatttc atgactatgt    360

cattgnctcc actcattttt gacccagttt ggaatgtatc tgcaattggt gtggctcaac    420

actttaggaa acaatagaat tattttatat aataattctg atggtgacca agtttngnct    480

tggagggcca caattttctt cctttgaaaa agtggacant ncctggncac ttctggnttt    540

ttaaaactta ctnggccatt ccattttggg ggtttttttg ggnnggtaaa ttgggtttgg    600

gggttaaaaa cccgtttncc agggaaaanc ccctaaaaaa nccctttggg gaattttaaa    660
```

```
anggaaaaat tctgggntaa attngggntt ttttaaaaac cc                    702


<210> SEQ ID NO 801
<211> LENGTH: 719
<212> TYPE: DNA
<213> ORGANISM: Homo sapiens
<220> FEATURE:
<221> NAME/KEY: misc_feature
<222> LOCATION: (1)...(719)
<223> OTHER INFORMATION: n = A,T,C or G

<400> SEQUENCE: 801

aggtactgcc cagagaattt tgtagacatc aagaaaactt tggaacgaga gactcgccag    60

tgccaggctc tggtgatctg gactgactgt gatagagaag gcgaaaacat cgggtttgag   120

attatccacg tgtgtaaggc tgtaaagccc aatctgcagg tgttgcgagc ccgattctct   180

gagatcacac cccatgccgt caggacagct tgtgaaaacc tgaccgagcc tgatcagagg   240

gtgagcgatg ctgtggatgt gaggcaggag ctggacctga ggattggagc tgcctttact   300

aggttccaga ccctgcggct tcagaggatt tttcctgagg tgctggcaga gcagctcatc   360

agttacggca gctgccagtt ccccacactg ggctttgtgg tggaaccggt tcaaagccat   420

tcaggctttt gnacccttgg ggccgnnaac accttaaggg ccgaatttcc agcacaactg   480

ggcgggccgt tactaagngg gantnccgaa cttngggnan cccaagcttt gggcgtnaat   540

cattngggnc ataaacttgg gttnccctgg nggngnaaaa ttgggntaat cccggtttna   600

caaatttccc cccccaactt tttccnaaac cccgggaaag ccttttaaaa ggggtnaaaa   660

acccctnggg ggnggcccct aaatggagtn ggggncttta accttcnccc ttttanant    719


<210> SEQ ID NO 802
<211> LENGTH: 646
<212> TYPE: DNA
<213> ORGANISM: Homo sapiens
<220> FEATURE:
<221> NAME/KEY: misc_feature
<222> LOCATION: (1)...(646)
<223> OTHER INFORMATION: n = A,T,C or G

<400> SEQUENCE: 802

actcatcgcc attgacctgg cctataactt gcacagtgcc tatggaaact ggttcccagg    60

cagcaagcct ctcatacaac aggccatggc caagatcatg aaggcaaacc ctgccctgta   120

tgtgttacgt gaacggatcc gcaaggggct acagctctat tcatctgaac ccactgagcc   180

ttatttgtct tctcagaact atggtgagct cttctccaac cagattatct ggtttgtgga   240

tgacaccaac gtctacagag tgactattca caagaccttt gaagggaact tgacaaccaa   300

gcccatcaac ggagccatct tcatcttcaa cccacgcaca gggcagctgt tcctcaagat   360

aatccacacg tccgtgtggg ccgggacaga agcgtttggg gcagttggct aagtggaaga   420

cagctganga ggtggccggc ctggatccga cttctggctt gtggaaggaa cagcccaagc   480

cagaatcatt ggcanccagg aanggcatgc tngacccact ngaaggngcc cttactngga   540

cttccccaaa attgggcatt aaagggntcn gggcttcnaa ttccctttc aggccnggtt    600

tnanggnggg aaaaattcgg ggaatttnat ccttaaagcc nttgnc                646


<210> SEQ ID NO 803
<211> LENGTH: 544
<212> TYPE: DNA
<213> ORGANISM: Homo sapiens
<220> FEATURE:
<221> NAME/KEY: misc_feature
```

<222> LOCATION: (1)...(544)
<223> OTHER INFORMATION: n = A,T,C or G

<400> SEQUENCE: 803
acacgtcgtc ctcccggctc aggccctcaa agaaggggat gaggtccagc agctccgtgt 60
ccgtcatgtc atcgaaccag gactgcacag gcactgcatt ctcaggatgg aagatgtatg 120
aggcagggga attgtcaaca atgatcactt tgctcagctc ccgcccaagg cgactcaggt 180
ccttcacgta gttcccacga tgaaaaacac atgattctct gaagagccgg gcccggaaca 240
caccccagcg gtctaggagg tcagccacag ggtctgcata cttggccaag ctggcagtaa 300
agagcacaca ttcaaaaagc tgcccatcct ctggaggaac tcgtccacat gtggccgctt 360
cagcacatac acctgatgta tagttccatc gattcaaccg gaacaataaa atnagcanta 420
ctaaataggc ttaaaacgaa ctgtgcacca atggttcatt ctaaatcaat ggaccaccca 480
ttcttttcca tagtcnagca ccggtacctn tggaanaang tnccttgggc gngnaccccc 540 ttan 544

<210> SEQ ID NO 804
<211> LENGTH: 642
<212> TYPE: DNA
<213> ORGANISM: Homo sapiens
<220> FEATURE:
<221> NAME/KEY: misc_feature
<222> LOCATION: (1)...(642)
<223> OTHER INFORMATION: n = A,T,C or G

<400> SEQUENCE: 804
cgaggtacat ccttgtggga gagaacctca tcaatttcca catttcttcc aagttctctt 60
gccctgagac ggattctcat cgctttggaa ggcacctgaa agaagcaatg actgacatca 120
tcactttgtt tggtctcagt tctaattcca aaaagtaatt ccactggagc tgctgggaag 180
gaaaacgagc tcttctgatg caaaccaaat gaaaaatagg cattaatcct gaccttagct 240
cgggatgaaa cactgctctt aaaaaaactc agttttcctt ccagaaaatg tgggtgtttt 300
tttttcctag aacagtatct ctcccctgtg aagcataacc ccactacttc cagacttgcc 360
ctcccttggg ggacatctga taaagtctcc cctgatgtct ccgcatcggc ttggattatt 420
aagggatgca aatcttggtg agttaatnaa ngaattanta ngggtgtggn tttacccncc 480
agtggaatgg aaatnggngt gctttntant nggcaanncg aaggcctaag ctttanggcc 540
tttaaccttt ntccangcng ggtaaacttt tggtttgntn aaaanaaaan tnnttnttaa 600
agttggggnc ccanttgagc taaccatttg ganngcctac cc 642

<210> SEQ ID NO 805
<211> LENGTH: 261
<212> TYPE: DNA
<213> ORGANISM: Homo sapiens

<400> SEQUENCE: 805
cgaggtacta cagagcccct ggacggtgtg atgttggaaa aggatgtttt ttctcaacct 60
gaaattagta atgaggctgt taatttgaca aatgttttac cagctgataa ttcatcaaca 120
ggatgctcta aatttgtcgt tatagaacct ataagtgaat tgcaggaatt tgaaaacatc 180
aagtcatcca catcattaac tcttacagtt cgaagttcac ctgctccttc agaaaatact 240
catatttctc ctttgaaatg t 261

<210> SEQ ID NO 806

<211> LENGTH: 311
<212> TYPE: DNA
<213> ORGANISM: Homo sapiens

<400> SEQUENCE: 806

```
gcggagagcg gctgatcgca gtccggaggt gaggcggaac tctgagcagg tggtccatta     60

tggctgacat gcaaaatctg gtagaaagat tggagagggc agtgggccgc ctggaggcag    120

tatctcatac ctctgacatg caccgtgggt atgcagacag tccttcaaaa gcaggagcag    180

ctccatatgt gcaggcattt gactcgctgc ttgctggtcc tgtggcagag tactccagtt    240

ctcagccaga accccgcaca ggtctttcct tatgggatac cagcccctca tacattgata    300

aattgggtac c                                                         311
```

<210> SEQ ID NO 807
<211> LENGTH: 591
<212> TYPE: DNA
<213> ORGANISM: Homo sapiens
<220> FEATURE:
<221> NAME/KEY: misc_feature
<222> LOCATION: (1)...(591)
<223> OTHER INFORMATION: n = A,T,C or G

<400> SEQUENCE: 807

```
ggtacctgtt ctttgccagt taagatacat atcttattat ctttgttttt ttcaagtcta     60

tgctcctgtt tgaagctttt cctgtaattt aggttgtctg tgaaatacct ataacatata    120

attcctatag agtatgccac atttttttc taactcattt caaatgaaat tctctcagat    180

tctagttttt gagcttgtcc actagatctg aaaataaagc atcctttcct gagtccactt    240

gaactaattg tgaatttgtt acttaattta ctggcatctt gggaaacaag ttttgctgtg    300

gcaggaaggc tgttttgaga gtgagccgtt gaagtctact ctggtttgtg gatgacattg    360

cattaggggt tatttcctgn attaccagtg ccccttgtg gcaatatact ttatgacttg    420

gaatgcaaca ccacttttaa aagcctggtt tcaagttttg aaagcattgg ttctgtgntg    480

ccataatctg aagnttctgt gaaggattat tnaagcttta aaccttncaa ggtaaaggcc    540

aaattaggcc tggaattacc tggaccttgg ncaaaaattn aaanattncn n             591
```

<210> SEQ ID NO 808
<211> LENGTH: 641
<212> TYPE: DNA
<213> ORGANISM: Homo sapiens
<220> FEATURE:
<221> NAME/KEY: misc_feature
<222> LOCATION: (1)...(641)
<223> OTHER INFORMATION: n = A,T,C or G

<400> SEQUENCE: 808

```
actaaatgga ggcacgtggg agaagggagg ggccattgag gaacaaaaat gtgttttaag     60

gaagagatgg gaaagcagag accaggtaga ggagctaggt aagctgatag gtgttgtcat    120

tggtagaaaa gaagaagata aatggatgta aggattgagg ccttggaaag tagcataggc    180

aggaaaagag gaattagaag aatacgtgaa gaagtgggaa tcatgggctg ggaagggaaa    240

ttttggaaaa ggagcacatt aaggcagaaa actcttttag agcagtggtt ttaaacttca    300

gcaatggtga tccttttata caagtatccc ttactttgga atcccaggaa gtaaaaggca    360

cattcttgtt gaagttgggg aggagcactt ggaaccctgc ttgcttaact ttttttcttt    420

tgggcccttg aagtgtagta tattttaaaa tccactggtc tanaagggag tagttaagtt    480

naagggaaan aaaggatgat tgggaaaaga tcngacccga agggactttt tggtnaccca    540
```

aaagttttng gtncccttgg aaagggaagg ggccccttt nggaattang ggaaatggaa 600
acttggaact gggnaaantt cctntnagct taaccttgan g 641

<210> SEQ ID NO 809
<211> LENGTH: 388
<212> TYPE: DNA
<213> ORGANISM: Homo sapiens
<220> FEATURE:
<221> NAME/KEY: misc_feature
<222> LOCATION: (1)...(388)
<223> OTHER INFORMATION: n = A,T,C or G

<400> SEQUENCE: 809
acaagagggt gggctgggcc aggatgcccg agggctggcc acagccaccc ccctcaaagg 60
tgttgatgag aaaagagaca ccttcttcct tgagaacatc tttcagccac aaattagggg 120
atctgttgcc tggcaataaa ggaacgaatt tataaaagag ttcaatggat ttgtgtcgac 180
attctgtctg gggcctccca caatgagcta aaagccactt gaccagatcc aataaacaca 240
atgatgcgga aggtggaaat cctcgcggca aacgtcgttt ctttgcttta tttaaagaaa 300
catgcttctt ttcaatgatg cggcataggt gatcaatggc atcacaacac tgttgaattg 360
tacctcggnc gngaccacgc taaaggcc 388

<210> SEQ ID NO 810
<211> LENGTH: 175
<212> TYPE: DNA
<213> ORGANISM: Homo sapiens

<400> SEQUENCE: 810
ggtacatcct cggccgggag tccccactgt ctctctacaa tgaggagctg gtgagcatga 60
acgtgcaggg tgattatgag ccaactgatg ccaccgggtt catcaacatc aattccctca 120
ggctgaagga atatcatcgt ctccagagca aggtcactgc caaatagacc cgtgt 175

<210> SEQ ID NO 811
<211> LENGTH: 329
<212> TYPE: DNA
<213> ORGANISM: Homo sapiens
<220> FEATURE:
<221> NAME/KEY: misc_feature
<222> LOCATION: (1)...(329)
<223> OTHER INFORMATION: n = A,T,C or G

<400> SEQUENCE: 811
ctgcgcggtt gttctctgga gcagcgttct tttatctccg tccgccttct ctcctaccta 60
agtgcgtgcc gccacccgat ggaagattcg atggacatgg acatgagccc cctgaggccc 120
cagaactatc ttttcggttg tgaactaaag gccgacaaag attatcactt taaggtggat 180
aatgatgaaa atgagcacca gttatcttta agaacggtca gtttaggggc tggtgcaaag 240
gatgagttgc acattgttga agcagangca atgaattacg aaggcagtcc aattaaagta 300
acactggcaa ctttgaaaat gtctgtacc 329

<210> SEQ ID NO 812
<211> LENGTH: 668
<212> TYPE: DNA
<213> ORGANISM: Homo sapiens
<220> FEATURE:
<221> NAME/KEY: misc_feature
<222> LOCATION: (1)...(668)
<223> OTHER INFORMATION: n = A,T,C or G

<400> SEQUENCE: 812
acggatgcta cttgtccaat gatggtaaaa gggtagctta ctggttgtcc tccgattcag 60
gttagaatga ggaggtctgc ggctaggagt caataaagtg attggcttag tgggcgaaat 120
attatgcttt gttgtttgga tatatggagg atggggatta ttgctaggat gaggatggat 180
agtaataggg caaggacgcc tcctagtttg ttagggacgg atcggagaat tgtgtangcg 240
aataggaaat atcattcggg cttgatgtgg ggaggggtgt ttaaggggtt ggctagggta 300
taattgtctg ggtcgcctag gagggctggt gagaatagtg ttaatgtcat taaggagaga 360
aggaagagaa gtnaccgaag ggcctcttta nttgtgtaat aanggttgga aggtgatttt 420
tatccgnaat tgggangtga tccctaaggg ggttggttga nccccntttc ctgccanaaa 480
tagganggtg ganttctgct tagggcttcc aataattgan gggcctnaaa tnaanttgna 540
aanggtaaat aaaacctttt naagggttgg gaccttgttt cttgngtnna nccccccttan 600 nattccattg gaacttaggc ttggncccat gtnttgggan tggcggataa ttaanttttg 660 aaattncc 668

<210> SEQ ID NO 813
<211> LENGTH: 312
<212> TYPE: DNA
<213> ORGANISM: Homo sapiens

<400> SEQUENCE: 813
ggtacaggca gggtagatct aactattgga aggaatccct aacacttttc cagggtagaa 60
ttctggctag tccaaaaagg gtccttcttt taagggtttt gagaaactag acactgcaac 120
ttattagtat cggcgacgtt tgtttggggc aaattcagct ccaggagctg cacggttgaa 180
tgcaggagga gttccaccaa ttgccccaat tccttccatt gtagcagcct gaccaaagcg 240
ttcagttgtt ggtggggtca atcccaaagt tccatccggc atcatagtgg caggtcctgg 300
aggagctggg gt 312

<210> SEQ ID NO 814
<211> LENGTH: 551
<212> TYPE: DNA
<213> ORGANISM: Homo sapiens
<220> FEATURE:
<221> NAME/KEY: misc_feature
<222> LOCATION: (1)...(551)
<223> OTHER INFORMATION: n = A,T,C or G

<400> SEQUENCE: 814
caggtactct gaagtataca caacaggtct aaacatctcc cttgtcgtaa gtagttgtgt 60
aaaattcaag ataaagattt agtctcatct tttaatgtca gtttttttcc ccatgttaaa 120
gggaatgagg aggagtcctc ttttattccc ccacaagaaa aagggagcca cattaatatg 180
tgtatattcc cataactcta atgtaagtgc ggatctccaa agcctaggga tttttccgta 240
aaagagagtg ggccgttctg gttacccttt tattagaagg gtattccacc acagagagcc 300
ggaggttttc cagatgtgtg taagagagca ggtgcgcaag gcaagcaaat gagcgcaaac 360
agtattatgg aaaacatttg agaagttagc tccatgagga ctgtgggctt cacaagagga 420
ctcgactggg tagccctggc tgacanagga cctgaaaagc ngagtattgc ttcaaacttg 480
gaaccnttca taggagccta acactgttgg aagaagtacc ttggcnggac caccttangg 540
gcaattcnag c 551

<210> SEQ ID NO 815
<211> LENGTH: 619
<212> TYPE: DNA
<213> ORGANISM: Homo sapiens
<220> FEATURE:
<221> NAME/KEY: misc_feature
<222> LOCATION: (1)...(619)
<223> OTHER INFORMATION: n = A,T,C or G

<400> SEQUENCE: 815

```
ggtactgata acttcttgct tcagttcatc tacaatgatc tttccctcta aatcccagat     60
cttgatgctg gggcctgtgg cagcacacag ccagtagcgg ttagggctga agcacagggc    120
gttgatgatg tccccaccat ctagcgtgta aaggtgtttg ccttcgttga gatcccataa    180
catggcctgg ccatccttgc ctccagaagc acagagggat ccatctggag agacagtcac    240
cgtgttcaga tagcctgtgt ggccaatgtg gttggtcttc agcttgcagt tagccaggtt    300
ccatacctttg accagcttgt cccaaccaca ggagacgatg atagggttgc tgctgttggg   360
cgagaagcgg acacaagaca cccactctga gtggctctca tcctggacag tgtattttgc    420
acacacccag ggtattccat agcttgggtg gtttacctgn ccggcggccg tcnaaanggc    480
gaattcacca tggcggccgt actagngatn caacttggnc caacttggcg gaatctggca    540
tactggttcc tngggaaatt gtttcngtcc aattccncna aattnaaccg gaagnttaaa    600
ggtaaaactt gggggccta                                                 619
```

<210> SEQ ID NO 816
<211> LENGTH: 658
<212> TYPE: DNA
<213> ORGANISM: Homo sapiens
<220> FEATURE:
<221> NAME/KEY: misc_feature
<222> LOCATION: (1)...(658)
<223> OTHER INFORMATION: n = A,T,C or G

<400> SEQUENCE: 816

```
actccagcag ccaggcatcc cagatctcct gtcctggagg gtgctggggc ccctggctcc     60
ccagagtgtg caggcagacc cccagagccc tagctcatcc atttatccat tcctcataat    120
ccagtgtcca aagagtaccc ccagcagggc agggaaggtc cctcccgggg tttacatgac    180
tgattccttc tcagaggcga ccgtggcatc ccctgcgggc ccccgatagt gtttgaggag    240
ggggtttcct tcctcaggct ctgtgcttct cgactccgta caagcttttt tttttttttt    300
tttttttttt tggaaggaga acaattttat tctaaaaata gaacttggta acaatgaaat    360
accaaaagct ggtcattata ataaaaagaa aagaanagtt taactttttt tttgtgaaaa    420
ttcnaaaatt atcactataa tatactgcca actntggtna attnganttt gaattatttc    480
ctttcatngg attatttcaa gggaaatttt taaaattngn ttttggccta aaaccttngg    540
ccgggnaccn cncttanggg gcnaaattcc aatccaantg gggggnccg taacttaagg     600
ggganccaa ccttgggnnc caancnttgg ggngtaaatc atggggcana ncntgttt       658
```

<210> SEQ ID NO 817
<211> LENGTH: 141
<212> TYPE: DNA
<213> ORGANISM: Homo sapiens

<400> SEQUENCE: 817

```
actttcttct gccataactt cttcctcagt tcctacaggt gtgacacttt tcaacttctt     60
tggaagaggc atttccactg tatcatcaga gacttggtct gatgcttcta tggtgctatc    120
```

-continued

```
ctcttcctct tcacgtgtac c                                               141


<210> SEQ ID NO 818
<211> LENGTH: 280
<212> TYPE: DNA
<213> ORGANISM: Homo sapiens

<400> SEQUENCE: 818

ggtacttaag aactcaagta tagaaataaa ctgtgggctg aagtaacatt gtaacctgct      60

cccaacatga ctgcataggt gtctaaggtt aagtgtgaag attactgtga ggtctcaagt     120

tacttgacta atcaatccca tttgaatttc aatccaagca gcatatttta cacacacctg     180

aaggaaatat cttcagtgtg ttcatgtgtg tgtctatgtg catgtatgtg taggggatag     240

gtgtaattag ggaagggctg accgaacaac attgataagt                           280


<210> SEQ ID NO 819
<211> LENGTH: 635
<212> TYPE: DNA
<213> ORGANISM: Homo sapiens
<220> FEATURE:
<221> NAME/KEY: misc_feature
<222> LOCATION: (1)...(635)
<223> OTHER INFORMATION: n = A,T,C or G

<400> SEQUENCE: 819

ggtacttgag tccttctcat gggtggggtg attgcctctt ctcatcagga gccaggagag      60

agggggacag ataggaggtg gcccatagga gcagtcccgc tgcacaatgg taggcatagg     120

ccatggcact ggactgcctc taaggactgc taaaaagaat atttttttgt ggtgtcagaa     180

ctggaaaaag cactttccct tcgggcattt ctggaaatga ttattaatcc acaaagaaga     240

actctgtaag ctttttcttg aattgtancc agtgagaaaa gcagatagac tgaagaatat     300

gaaggatagc tgagctgtnc ctncatagtg gggcatgcct aggcatatgg ctggcttgga     360

gactactgat gcttttccct gagtttgtat tggcactgan gtatggccgg cttgggccac     420

tgacttccca ntaatggaat ctgntnaaaa cttggggatt cctttagctt nntactggaa     480

gaaaantttt gtancnaaaa gatttataac cnnttagnaa taagtttncc agcancccng     540

gatttttttt nngcttgggg gttnttggcg ncctttannn aaggacnggg cnttgnnntt     600

cntctttacn aggccttgnt ntgancntgg agaan                                635


<210> SEQ ID NO 820
<211> LENGTH: 276
<212> TYPE: DNA
<213> ORGANISM: Homo sapiens

<400> SEQUENCE: 820

acatcttctt cctgagttac gcttacaaaa ttttcaaaca tagcaaccat tgatggggcg      60

gcaatcacat gacaattcac aagatcagat aaaaaacgga ccaaatacac ggcttcatta     120

taattgtttg ctttcaatga ttctttaagt tgacgaatca tggcttctac aaattctcca     180

ccaaaattgt aattcctggc attcagtagt ccaactaatg ttgtataaat tgtcagcttc     240

tcaggtaata ggcgtgcact ggattcataa atcacc                               276


<210> SEQ ID NO 821
<211> LENGTH: 728
<212> TYPE: DNA
<213> ORGANISM: Homo sapiens
<220> FEATURE:
<221> NAME/KEY: misc_feature
```

<222> LOCATION: (1)...(728)
<223> OTHER INFORMATION: n = A,T,C or G

<400> SEQUENCE: 821

```
acaatgatgc cagaagcttt ccttcaagaa gctcagataa tgaaaaaatt aagacatgat     60
aaacttgttc cactatatgc tgttgtttct gaagaaccaa tttacattgt cactgaattt    120
atgtcaaaag gaagcttatt agatttcctt aaggaaggag atggaaagta tttgaagctt    180
ccacagctgg ttgatatggc tgctcagatt gctgatggta tggcatatat tgaaagaatg    240
aactatattc accgagatct tcgggctgct aatattcttg taggagaaaa tcttgtgtgc    300
aaaatagcag actttggttt agcaaggnta attgaagaca atgaatacac agcaagacaa    360
ggtgcaaaat ttccaatcaa atggacaagc tcctgaagct gcactgnatg ggccggntta    420
caataaagtc tgaaggcctg gncattttgg aattcttgca aacccgaact tagttaccca    480
aangggnccc aatngccntt attcccaggt antnggggga aacccggnna aagtaacccn    540
ttggggcccg ggaaaccacc nccttaangg ggccnaaatt ttccaggcnn cnacttgggg    600
cggggcccgg ttancttaag gggggaatcc ccnaacnttt ggggacccca anacntttgg    660
gcgggaaaac cnatnggggn ccaaaanacc gnggntnccc ccgnggnggg naaaaaattg    720
gnnttnnc                                                             728
```

<210> SEQ ID NO 822
<211> LENGTH: 632
<212> TYPE: DNA
<213> ORGANISM: Homo sapiens
<220> FEATURE:
<221> NAME/KEY: misc_feature
<222> LOCATION: (1)...(632)
<223> OTHER INFORMATION: n = A,T,C or G

<400> SEQUENCE: 822

```
actttacggc ctgatctaat tgaaagtgca tcccttgttg caagtggcaa agctgaactc     60
atcaaaaccc atcacaatga cacagagctc atcagaaagt tgagagagga gggaaaagta    120
atagaacctc tgaaagattt tcataaagat gaagtgagaa ttttgggcag agaacttgga    180
cttccagaag agttagtttc caggcatcca tttccaggtc ctggcctggc aatcagagta    240
atatgtgctg aagaacctta tatttgtaag gactttcctg aaaccaacaa tattttgaaa    300
atagtagctg atttttctgc aagtgttaaa aagccacata ccctattaca gagagtcaaa    360
gcctgcacaa cagaagagga tcaggagaag ctgatgcaaa ttacccagtc tgcattcact    420
gaatgccttc ttgctggcca tttaaactgt aggtgtgcan ggtgactggc cgttcctcag    480
ntncttgtgg ggaatcttcc gtnaagatga acctgacttg ggancactta ttttttnggc    540
tangnttaaa ccttncatng ngnncaactt tacccangtn gnttantatt tngncccccg    600
ttaanacctt tctncnngnt cctccatttt tg                                  632
```

<210> SEQ ID NO 823
<211> LENGTH: 649
<212> TYPE: DNA
<213> ORGANISM: Homo sapiens
<220> FEATURE:
<221> NAME/KEY: misc_feature
<222> LOCATION: (1)...(649)
<223> OTHER INFORMATION: n = A,T,C or G

<400> SEQUENCE: 823

```
actgctgcaa cccatgcagc gtcaacttcg tctcatcatc cacgaagatc tccattggat     60
```

```
cttgcatgaa cttgcggcag actggacgga tctctttgct caaggtagca ctgaacatca    120

tgacctgctt ctcgtggggg gtcatgcgaa aaatttcctg gacatcccga cgcatgtcga    180

gctgttcaag catcttatca cattcatcca aaataaagtg tttaatgtgt ttgaggttga    240

ggctcttatt tcgagccagg gctaggatac ggcctggagt ccccacgacg atatgcgggc    300

agttcttctt cagcacctct tcatccttct tgatagacag accaccaaaa aaaacagcaa    360

ccttgacatt gggcatgtat ttagagaagc gctcatattc cttgctgatc tgaaaagcca    420

actcccgagt ggtgacacca tcaccagcac agacacctgc ccagtaacct ggcttccaac    480

tggttgcant gnngggccaa gaacaaacac tggtggcttt tccatgcccc natttgggct    540

tggcnccagg aaattcantt cccaaaatgg gcttgaaggg atgccnttnt gcttggactt    600

ttgacgggat gttnaaggcc ccagnttnan aatggncccg gagcaattn                649
```

```
<210> SEQ ID NO 824
<211> LENGTH: 603
<212> TYPE: DNA
<213> ORGANISM: Homo sapiens
<220> FEATURE:
<221> NAME/KEY: misc_feature
<222> LOCATION: (1)...(603)
<223> OTHER INFORMATION: n = A,T,C or G

<400> SEQUENCE: 824

acccettata aaccagcaat gtcatctgtg aggaagcaaa ttctcaagtg tctgtcattt     60

acttggttct ttttctttgt ggtcttcacc cttataccct ggaaaagtct gtaattacct    120

tagccaggaa gatagatggt catggcaagc gcacagcacc agacttactg gctcaccaag    180

atgatggaaa aaggcagatg attttttaaa aagccgtaat gactccttta gaccagccat    240

ttagcgtggt aattttgaaa ggcctagctc cattgcagac ttccaaaggg tcagctctga    300

gactgccctc caggtgggca gttgattatt tccaccagtg ttttccagag ccttaaactg    360

cctaagtgac aactacctca gttggcagga aaagagacat atagtagaaa gtgaaaaatg    420

agcagtattt gggcagatgc tatggggtac agttgaangg taaaanggac tttccttggg    480

aacccttatn ccctgngaat atgacctngg ccggacacnt taaggcnatt cacnntgngg    540

gccgtctaan ggnnccactt ggncancttg ngnaaaaggc aaactgtnct gngnaatgtn    600

ccc                                                                  603
```

```
<210> SEQ ID NO 825
<211> LENGTH: 634
<212> TYPE: DNA
<213> ORGANISM: Homo sapiens
<220> FEATURE:
<221> NAME/KEY: misc_feature
<222> LOCATION: (1)...(634)
<223> OTHER INFORMATION: n = A,T,C or G

<400> SEQUENCE: 825

tgaaaaataa actattntat ttcagtgttt gctccttgcg gttcagaagc acatctactg     60

cctggttgga acccaaggct tttataaaac cgtagagaaa tatgagctct atgtatagag    120

aaaatataca tgttgattaa ttgtgtgact ctttcctgtg caaagcagaa agttctaaat    180

gcaacagcat gattctctcc aagtccttcc ctgggatttg gggggccctg gaggctgtga    240

tctcacctcc aatagagaat ccccaattct tccagcccaa gggaggccca gncatgtaga    300

aagagcagga gataaagtca aagctgacaa ctcatgggtt ccccaagctt ctccggggca    360

ggggctatgt ttgggggcct taccctgcaa agaaggggta gctggggtgc cnaccttggt    420
```

gggtaagtgc cacactggca ctaaagctgt tgggaagtct agcattgcan ccggccaggt 480
ttatgggtna accagggtgt ccaangggtt tttttcccta aaactngggg ctnaaaggng 540
gggaccctng gcncgaaccc ccttanggcc aaatcccggc aattgggggc cntttttaan 600
gggnnccaac ttgggaccaa acttggngna atnn 634

<210> SEQ ID NO 826
<211> LENGTH: 507
<212> TYPE: DNA
<213> ORGANISM: Homo sapiens
<220> FEATURE:
<221> NAME/KEY: misc_feature
<222> LOCATION: (1)...(507)
<223> OTHER INFORMATION: n = A,T,C or G

<400> SEQUENCE: 826
ggtacctgaa gaacaaatcc cttcagggtt aagctcgaca ggacactttc cccagtccca 60
ggtttccatt tccctcattc ccaaaagggg cccctccctc tccatgcgca cacagaactt 120
ttcgctcacc caaaagtccc ttctgtctga tcttttccca tcatctttct tccctctact 180
tactactccc tctagaacag tggattttaa atatactaca cctcagggac caaaagaaaa 240
aagttaagca agcagggttc caagtgctcc tccccaactt caacaagaat gtgcctttta 300
cttcctggga ttccaaagta agggatactg tataaaagga tcaccattgc tgaagtttaa 360
aaccactgct ctaaaagagt tttctgcctt aatgtgctcc ttttccaaaa tttcccttcc 420
cagcccatga ttccacttct tcacgtattc ttctaantcc tctttttctg gctatgctac 480
ttttcnangg ctcaaaactt aaattcn 507

<210> SEQ ID NO 827
<211> LENGTH: 617
<212> TYPE: DNA
<213> ORGANISM: Homo sapiens
<220> FEATURE:
<221> NAME/KEY: misc_feature
<222> LOCATION: (1)...(617)
<223> OTHER INFORMATION: n = A,T,C or G

<400> SEQUENCE: 827
cgccagcgct gcaggagctg acatggaccc aaatcctcgg gccgccctgg agcgccaaca 60
gctccgcctt cgggagcggc aaaaattctt cgaggacatt ttacagccag agacagagtt 120
tgtctttcct ctgtcccatc cgcatctcga gtcgcagaga ccccccatag gtagtatctc 180
atccatggaa gtgaatgtgg acacactgga gcaagtagaa cttattgacc ttggggaccc 240
ggatgcagca gatgtgttct tgccttgcga agatcctcca ccaacccccc agtcgtctgg 300
gatggacaac catttggagg agctgagcct gccggtgcct acatcagaca ggaccacatc 360
taggacctct tctnctnctc ctncgactcc tncaccaacc tgcataagcc aaatccaagt 420
gatgatggag cagatacgcc cttggcacag tcngatnaga ggaggaaaag gggtnttgga 480
ngggcaaaan cttgannctg cagntagcaa tgggccctgc tanaantgnc caccttggtn 540
ttttccaatn nnacncaggc caccnaactt ttgganaaac caanttttnt tgcgnggccc 600
aaggggaagn ngnggat 617

<210> SEQ ID NO 828
<211> LENGTH: 448
<212> TYPE: DNA
<213> ORGANISM: Homo sapiens
<220> FEATURE:

<221> NAME/KEY: misc_feature
<222> LOCATION: (1)...(448)
<223> OTHER INFORMATION: n = A,T,C or G

<400> SEQUENCE: 828
actgtcacct ttttaagtgg aaagaaatat agtgtggatg atttacactc aatgggagca 60
ggggatctgc taaactctat gtttgaattt agtgagaagc taaatgccct ccaacttagt 120
gatgaagaga tgagtttgtt tacagctgtt gtcctggtat ctgcagatcg atctggaata 180
gaaaacgtca gctctgtgga ggctttgcag gaaactctca ttcgtgcact aaggacctta 240
ataatgaaaa accatccaaa tgaggcctct atttttacaa aactgcttct aaagttgcca 300
gatcttcgat ctttaaacaa catgcactct gaggagctct tggcctttaa agntcaccct 360
taaggccttn gtttatttaa ncatgaactg atggtaactg nacctcngnc gcgaccacnc 420
taaggccaat tccananact gnccggcg 448

<210> SEQ ID NO 829
<211> LENGTH: 619
<212> TYPE: DNA
<213> ORGANISM: Homo sapiens
<220> FEATURE:
<221> NAME/KEY: misc_feature
<222> LOCATION: (1)...(619)
<223> OTHER INFORMATION: n = A,T,C or G

<400> SEQUENCE: 829
cgaggtactt ttaaagcagg gagtggggaa aagtattttg aggggacatt ttcatcatca 60
gttcagcttt tttttttgg ttgttgctct tttttggggg ggttgggttt gttggtttca 120
ctgaaacatt taactacctg taaaatctaa acatggctgt tagtgtcaca ccaattcggg 180
acacaaaatg gctaacactg gaagtatgta gagagttcca gagggggact tgctcacggc 240
cagacacgga atgtaaattt gcacatcctt cgaaaagctg ccaagttgaa aatggacgag 300
taatcgcctg ctttgattca ttgaaaggcc gttgctccag ggagaactgc aaatatcttc 360
atccaccccc acatttaaaa acgcagttgg agataaatgg acgcaataac ttgattcagc 420
agaagaacat ggccatgttg gnccagcaaa tgccactagn ccatgccatg atgcctggtg 480
cccattacaa cccgngccat ngttcaattg nccaacttac cnccatgcnt aacagccgct 540 ttanncctt tggacctttt ttccancttg gcccggcaaa attttccant ggccaattgg 600
ttccgggant ccgggtcct 619

<210> SEQ ID NO 830
<211> LENGTH: 618
<212> TYPE: DNA
<213> ORGANISM: Homo sapiens
<220> FEATURE:
<221> NAME/KEY: misc_feature
<222> LOCATION: (1)...(618)
<223> OTHER INFORMATION: n = A,T,C or G

<400> SEQUENCE: 830
ggtacaccct agccaacggg acaaatccta gagggtataa aatcatctct gctcagataa 60
tcatgactta gcaagaataa gggcaaaaaa tcctgttggc ttaacgtcac tgttccacct 120
ggtgtaatat ctctcatgac agtgacacca agggaagttg actaagtcac atgtaaatta 180
ggagtgtttt aaagaatgcc atagatgttg attcttaact gctacagata acctgtaatt 240
gagcagattt aaaattcagg catacttttc catttatcca agtgctttca tttttccaga 300
tggcttcaga agtaggctcg tgggcagggc gcagacctga tctttatagg gttgacatag 360

```
aaagcagtaa gttgtggggt gaaagggcag gttgtcttca aactctgtga ggtagaatcc    420

ttnnctatac ctccatgaac attgactcgt gtgttcagag cctttggcct ctntggngga    480

gtctngctnt ttgggctcct gggcatcctt ttgaatagtc actctgtaaa actngccann    540

gctttgaaac tgggtncttt acccanggtg naagggnctt tgttggcctt tanaagggtn    600

ggncatncct ccaaaacc                                                  618
```

<210> SEQ ID NO 831
<211> LENGTH: 648
<212> TYPE: DNA
<213> ORGANISM: Homo sapiens
<220> FEATURE:
<221> NAME/KEY: misc_feature
<222> LOCATION: (1)...(648)
<223> OTHER INFORMATION: n = A,T,C or G

<400> SEQUENCE: 831

```
acatgaaaga cacgtccaca tcacagttgc ccccaaactg cctgtgctcc tcgatggtgt     60

ctctccctcc agaaaacgca tgcttattga ccttggtttt gatctgcttg gccgtgtcgg    120

tgaggaagat ggaggagttg gggtcgctgg cactcatttt ggtctgggcg ccctgcaggg    180

ctgggaagaa ggtggagtgc aacagggctg gtttaggata gccgatcctg ggggcgacgt    240

cccttgtcat tctaaagtaa ggatcctggt caatggcaca tgggataagg cactggatat    300

ccgtcctgtc tcggaagatc tgtgggaatg agttgctgaa ggagggagca gcctggatgg    360

caggaaaact gatcttccca atgcagtcgc tgtcagtgaa acncgaaaaa tgcctttcac    420

tttggtttga aggtaacatg cctttttgaa tcttcaccac attttttgta gaaaccttgg    480

nccttnatnc cccatgtagn nccaggttca naanaatntt gaaaagnctt tggtggaagg    540

tcaaaancnc caggccaant aaaggncctt tggnaatttt ttcccnggnt ataactttnt    600

nggcctgggn ccaaggtcaa nggccctttc cnaannaact ttttnggn                 648
```

<210> SEQ ID NO 832
<211> LENGTH: 689
<212> TYPE: DNA
<213> ORGANISM: Homo sapiens
<220> FEATURE:
<221> NAME/KEY: misc_feature
<222> LOCATION: (1)...(689)
<223> OTHER INFORMATION: n = A,T,C or G

<400> SEQUENCE: 832

```
gtccccacga actggcctgg ccaagcaccc cacactggag ccatctcttc ctcatatttc     60

agcagtgcag ccggggggca gggaagggca ggcagggtct gttggggtct ctttttatcc    120

ttattcctcc cccgacctaa ttgtctttgt tctgtgatta ttgggggaca cccggctccc    180

tccagacaat gccagcataa atccatccat ccaaaggcag agaaccaaag gggccatgga    240

aggttctctg tgctcctcct acccttccag tgccctaggc ctggcgactg cccctgcctt    300

ttagacccgc ctccctttta tacctgctct tgntctactg agaaaagcct ctcagcaata    360

atgntttcta gtcacttcct ccgncttcgg gacgggcgtg cctggacact tgtaccttng    420

gcccgcgaac cacgcttaag ggcgaaatt ccaagcacnc ttggccggcc ggttaccttn    480

gtngggatnc ccaaccttng gnnncccaaa ccttgggcgg taaaccatng ggnccttaac    540

ctngngttcc ctgggggngn aaaantngta atttccgggt ttacccaatt ttccncccca    600

aacnttntcc caaancccgg gaaaaccctt aaaaggnggg aaaaancccc ttgggggggg    660
```

gccctnaann nggagggtgg ngcnttanc 689

<210> SEQ ID NO 833
<211> LENGTH: 726
<212> TYPE: DNA
<213> ORGANISM: Homo sapiens
<220> FEATURE:
<221> NAME/KEY: misc_feature
<222> LOCATION: (1)...(726)
<223> OTHER INFORMATION: n = A,T,C or G

<400> SEQUENCE: 833
ggtactaatg tgaattgttc ctcagaaacg cttcttttcc atcctagtga gaagctggcc 60
ctgcaggtgg tggcagcaat ggtgttgtaa gatttcctcc cgtagttttt tctcctcatg 120
gatttgaatg aaatgccaat aacacgtcca ctttcaacgt gtagtttacg cggagcactt 180
tcgaggcctg gccgggttgg gcctacttct cacctgggcc tatcttctga actcgctagg 240
ttcttatcaa catttggggg ataactttgt atattttttt cattnggctt ttctttacca 300
gtttctgatt tttattctca atatattttt gctaaaacct atttcacaaa tnaccaccng 360
actgaaagtg tgtgnttact gatgcggccc ttgagcttcc atgggcgaaa ggagtgactt 420
ttgcagcngc cgtnaagaac ccgnaaatct ggtttnanag cnccanggaa agtngaccac 480
cnttangggg agcccccncg tangggggcg ctttgtaang cccnccnggg ggaacccccc 540
annnaccggt gggggtcctt aaaagnaana nanaccgggg gtctttaagc ttntttcctt 600
gggccacncc cccaaaannn gggnttttcc caatttntta anacnctntc ttgngggggg 660
tcctnggngg aaatggngga aaaaaangcc cnnntnnttg ttnggggngg gnaccncaan 720 gtggng 726

<210> SEQ ID NO 834
<211> LENGTH: 628
<212> TYPE: DNA
<213> ORGANISM: Homo sapiens
<220> FEATURE:
<221> NAME/KEY: misc_feature
<222> LOCATION: (1)...(628)
<223> OTHER INFORMATION: n = A,T,C or G

<400> SEQUENCE: 834
ggtacgagag tgtagccaaa gtgagaggct gagagcaaag gagacatttt tttcagtttt 60
gagtcgagta tccagacaga ggcaaatcat tttgtttaac tttttattaa agtgtaacta 120
tagaaacaca tcaatgattt ttcacaagtg gagcactgtg catacaatcg gcaccccaga 180
agccccccgt cagattccct tccagttaac tacctctcca agggaaacca ctatcctgag 240
ttctaagcgc atagattagt ttctgtctgg tttggggaga tatataaatg gaattatgca 300
ttcttcgtat ctggttnctt ttcaccaata ttatgtttgt gagatttttg gtgcatgtat 360
ttgtacagnt ttgctgattt taggtgttgc gcctcattgg gaacagtttg ctataggttg 420
aagagaaaat ttgctcttcc ggtttantgg caccanggag canaatgccc ncagtgtntg 480
gnctcngata atgggtcgaa attgggangt gggctggacn tttttnactt gntctttctg 540
atctngantc ggttncctat tcnatatttg gntntcttcg gaattnnttg ntngaacttg 600
cctgggccng gctgttctan agggnnag 628

<210> SEQ ID NO 835
<211> LENGTH: 602
<212> TYPE: DNA
<213> ORGANISM: Homo sapiens
<220> FEATURE:
<221> NAME/KEY: misc_feature
<222> LOCATION: (1)...(602)
<223> OTHER INFORMATION: n = A,T,C or G

<400> SEQUENCE: 835

```
ggtactgaaa tcacaagagc tataactgcc agagaaaaat taaatggggt cttcaagtag     60

tgactgagcc agcaaactaa gtggccaaga gggagacaag agcagctcct aaagaaggtt    120

gaagtcaagc aatctccgga acacagagga tctgaagcat ctgggcagag ccacaggcag    180

gcanggcaag gacacacagc acaccagagc agcaccgtcc ttcactgtgt gagagcaact    240

ctcaggctgc agaaccaatt gccatctcca ctgcctacag ctcaggtctc caactaccag    300

atagggagta aaaaacagtt tgattttatt cacctcaagt ctaaacacgg ngggaaaaaa    360

aactggtcta nagatggaaa ctatatttca tggggggttta ttaaacagag aaagaggaga   420

attttcacat ttcacagggc ttttcntgaa ataaagactt gatctgaaaa ggcaccctta    480

tggcangctt taacttccta agntngggna gnncccaaat tttccannaa tcttgggacc    540

ncttgcccag tngatttttt ttaaataact nagctnaatt gntnggntaa tttnataana    600

ng                                                                   602
```

<210> SEQ ID NO 836
<211> LENGTH: 355
<212> TYPE: DNA
<213> ORGANISM: Homo sapiens
<220> FEATURE:
<221> NAME/KEY: misc_feature
<222> LOCATION: (1)...(355)
<223> OTHER INFORMATION: n = A,T,C or G

<400> SEQUENCE: 836

```
acacaatgct tctgccagtc ctattcaggg ccaaggacat gtgcttataa ccatctgcca     60

aattttccaa actgtcacag taacaaccat caaattttag cagatctact ccccagtcag    120

caaaggtctg ggcatcaatg tcgtagtatc caaaactccc agggaagcct gcgcaggttt    180

tatttccaac atctgcataa atccctagct tcagtccttt gctgtgaaca taattagcta    240

gctggcgaat cccatgagga aagcgctgag ggtctgcctg aagtctgcct tctgaatctc    300

tttggggagc catccaacag tcatcaatgc agaggtacct cggncgngac cacgc         355
```

<210> SEQ ID NO 837
<211> LENGTH: 611
<212> TYPE: DNA
<213> ORGANISM: Homo sapiens
<220> FEATURE:
<221> NAME/KEY: misc_feature
<222> LOCATION: (1)...(611)
<223> OTHER INFORMATION: n = A,T,C or G

<400> SEQUENCE: 837

```
ggtttttttt ttcgtgattg tattcccata aagctttatt tgtggactct aaaatttgaa     60

ttttatgtga ttttcacata tcacaaacat tcttcttctt ttaatttttc taaccattaa    120

aattataaaa aactttctta tttttgcagg ccatacaaaa ttaggcagtg ggccaaatct    180

ggccgctagt ttagaaggtc cacggtagtc tcgctcgcag gcatggcagt tgcagctggc    240

tggggcaccc tggttctcct ccacaaggcc tttcatcctc cagaagtctg aattggcctt    300

gttcatggca ctttcagggc agcattccaa gaggtggaag ggagagtctg caaagacttc    360

tgaggctggc tccagacctc actcagtatc cccactgctc catttcagtc agagtnaagt    420
```

```
cactagtnct gcccagactc aagggatgaa gggaactgnc tntanctcat gatgaagata    480

acntgtgaaa tactgggggc tgagtttttc anttancncc agggagtaat tttcatggnt    540

taaanggcat tccccttat ttttgaagcc ntaanttcng gcntttanng ggaantaatt     600

aaccncccctt a                                                        611


<210> SEQ ID NO 838
<211> LENGTH: 650
<212> TYPE: DNA
<213> ORGANISM: Homo sapiens
<220> FEATURE:
<221> NAME/KEY: misc_feature
<222> LOCATION: (1)...(650)
<223> OTHER INFORMATION: n = A,T,C or G

<400> SEQUENCE: 838

ggtacttcca cctcgggcac attttgggaa gttgcattcc tttgtcttca aactgtgaag     60

catttacaga aacgcatcca gcaagaatat tgtccctttg agcagaaatt tatctttcaa    120

agaggtatat ttgaaaaaaa aaaaagtata tgtgaggatt tttattgatt ggggatcttg    180

gagtntttca ttgtcgctat tgatttttac ttcaatgggc tcttccaaca aggaagaagc    240

ttgctggtag cacttgctac cctgagttca tccaggccca actgtgagca aggagcacaa    300

gccacaagtc ttccagagga tgcttgattc cagtggttct gcttcaaggc tttcactgca    360

anacactaaa gatccaagaa ggccttcatg gcccncncca ngcccggatc gggtanctgg    420

ccgggcnggn cngtnnnaaa gggcnaaatt tcngcacact tggccgnccg ttactaagtn    480

ggantccnaa gcttggntan ccaagctttg gngnaattct ngggcatann nctgggtncc    540

ttgnnggnaa aatgntantc ccgtnnnaaa ttcccttcan cnnanctgan cctgaaagct    600

ttaantgggn aaacnttggg ggtccctaat tngggggacn taacntctnt              650


<210> SEQ ID NO 839
<211> LENGTH: 626
<212> TYPE: DNA
<213> ORGANISM: Homo sapiens
<220> FEATURE:
<221> NAME/KEY: misc_feature
<222> LOCATION: (1)...(626)
<223> OTHER INFORMATION: n = A,T,C or G

<400> SEQUENCE: 839

actaaacgag caggtgaagg aggctgaagg atcgtctgct gaatacaaga aagaaattga     60

ggaactaaag gaactgctac ccgaaattag agagaagata gaagatgcaa aggagtctca    120

gcgtagtggg aatgtagctg aactggctct gaaagctact ctggtggaga gttctacttc    180

aggtttcact cctggtggag gaggctcttc agtctccatg attgccagta gaaagccaac    240

agacggtgct tcctcatcaa attgtgtgac tgatatttcc caccttgtca gaaagaagcc    300

ttcacaatta tatctttaga ggaaaccaga ggaaganagt ccncggaaag atgatgcaaa    360

gaaagccaaa caagagcncg gaagtgaacg gaaggcnttt ggggatgcct gtccccaagt    420

ggaaaatgaa gtttcngaaa acantggagg aggangctga naatcaggct gaaagccngg    480

ccnccaatgg aagggaccat tgtanggctt gganctt cng gtngaaagcc nttgcttttt   540

aaaaangggg cccagncctt tcttccangg gaaaagggnt tttggaatta aangnttttt    600

tnacnttttg ganggatcct tttggt                                         626


<210> SEQ ID NO 840
<211> LENGTH: 323
```

<212> TYPE: DNA
<213> ORGANISM: Homo sapiens

<400> SEQUENCE: 840

```
ggtacagcag ccttctttgc tggaggccct tgaacttcct cctcctcctc gctgctgtcc     60

tcactgtcac tggatgaggc cttcttctta gctttcttag ccactggtcc atttgcctgt    120

aactttcgct ctgggacctt ggcagacctg ttgagccaga agctatagat gtctaagagg    180

gaagaggcat tggcatcctg ctgtgtagct cctgtcgctt tggcgaactt attggccacc    240

tctgagagtt ggttatcgcg caggaagccg agcacgaggg gatacaggtc gctgggaacc    300

acgcggcgaa tgccggcgtc cgc                                            323
```

<210> SEQ ID NO 841
<211> LENGTH: 614
<212> TYPE: DNA
<213> ORGANISM: Homo sapiens
<220> FEATURE:
<221> NAME/KEY: misc_feature
<222> LOCATION: (1)...(614)
<223> OTHER INFORMATION: n = A,T,C or G

<400> SEQUENCE: 841

```
acattgaaaa tgagggtaag atgatcatgc aggataaact ggagaaggag cggaatgatg     60

ctaagaacgc agtggaggaa tatgtgtatg aaatgagaga caagcttagt ggtgaatatg    120

agaagtttgt gagtgaagat gatcgtaaca gttttacttt gaaactggaa gatactgaaa    180

attggttgta tgaggatgga gaagaccagc caaagcaagt ttatgttgat aagttggctg    240

aattaaaaaa tctaggtcaa cctattaaga taccgtttcc aggaatctga agaacgacca    300

aaattatttg aagaactagg ggaaacagat ccaacagtat atganaataa tcagctcttt    360

caanaaacaa ggaggaccng tattgatcat ttggatgctg ctgacatgac caaggtagna    420

naaagcncaa atggaagcaa tggaattgga tgaataacca agcttaattc tgctgancaa    480

gcnatagttt gncattggnt nnagttgtta ngtccnaaga gnattgaanc ttaaanttna    540

gggctgccaa ngnctttggc cggnacncnc ntnagggcna tttcagccnc ttggcggccg    600

ttctatggnn ncnn                                                      614
```

<210> SEQ ID NO 842
<211> LENGTH: 609
<212> TYPE: DNA
<213> ORGANISM: Homo sapiens
<220> FEATURE:
<221> NAME/KEY: misc_feature
<222> LOCATION: (1)...(609)
<223> OTHER INFORMATION: n = A,T,C or G

<400> SEQUENCE: 842

```
ggtacacttg ctaaatttga atgggcangc agcaaactct gggaagactt ctaatgcttt     60

acgatacaag cgaactgcct cttcaatgtt tccctgttct cgtttgatat tggctaggtt    120

attcagagag tctgcatggg tgggacacag acggagagct gtattataac aatcttctgc    180

ttcagcaacc tgtcaaaaat gcgtgcctct ttcaagacat ttcctaaatt gatataagca    240

tccagaaagt ttgggtcaag ggtgacagcc ttttcaaagt gatgaattgc aagccaaatt    300

tccccttgtg cattgaaaac acagccaaga ttactccaag ctactgcaaa gttcggttgc    360

gtctcaattg ctttcaaata acatgccttg gcttcttcca agcgacccaa ggcttttaca    420

ggtncccagg tcactgcgaa cacagtacct gcccggcggc cgttcaaang gcgaaattca    480
```

-continued

```
gcacacttgc ggncgtanta gtggantncn agcntcggnc caacttgggn ntataatggg    540

canaactggt ccctgggggga aantggtnnc cnntaccatt tcnccacttn cgaccggaag    600

cttaaangg                                                            609
```

<210> SEQ ID NO 843
<211> LENGTH: 610
<212> TYPE: DNA
<213> ORGANISM: Homo sapiens
<220> FEATURE:
<221> NAME/KEY: misc_feature
<222> LOCATION: (1)...(610)
<223> OTHER INFORMATION: n = A,T,C or G

<400> SEQUENCE: 843

```
ggtttttttt cgcaggtatt tcctctgctt taatagacaa ttttagaaag acatgttaac     60

gggggaaaat cacacaatac taaggatctg agggccataa acatcacata tgttgagttt    120

gcttttagtt ttgtttccaa cagttcttaa ccaatgttcc tggctgtaat ctaggtgcta    180

gacgcactgc aaatcctcga aagtgtttaa gatgaaagag caatacactt aagatcttca    240

aaagtttaca ttaacagaat aagcattagc tccttttaac acacacacac aactaaatta    300

acaaatgaaa tgtgtctact tttatatatg cccataaagc agacacttaa cattgaaatt    360

tactatttta gattttcact cctttaagag ctatcaatat agacactnaa gataattcac    420

atttnaaaaa ttatctacct ggaagaatag aacttcttta agaaggaaaa agnaaaagct    480

ggtgaaacca aggattgcct ggggtnggaa ggaccgnttt naacctgggc cttaaatgnc    540

ntgagnacaa ttgattggtc nnncttgggc tntnttggta acaccggcct tcanggtttt    600

cttgacccnc                                                           610
```

<210> SEQ ID NO 844
<211> LENGTH: 675
<212> TYPE: DNA
<213> ORGANISM: Homo sapiens
<220> FEATURE:
<221> NAME/KEY: misc_feature
<222> LOCATION: (1)...(675)
<223> OTHER INFORMATION: n = A,T,C or G

<400> SEQUENCE: 844

```
ggtacacctg aattccaggc caatgaagtt cggaaagtga agaaatatga acagggattc     60

atcacagacc ctgtggtcct cagccccaag gatcgcgtgc gggatgtttt tgaggccaag    120

gcccggcatg gtttctgcgg tatcccaatc acagacacag gccggatggg gagccgcttg    180

gtgggcatca tctcctccag ggacattgat ttctcaaag aggaggaaca tgactgtttc    240

ttggaagaga taatgacaaa gagggaagac ttggtggtag cccctgcagg catcacactg    300

aaggaggcaa atgaaattct gcagcgcagc aagaagggaa agttgcccat tgtaaatgaa    360

gatgatgagc ttgtggccat cattgcccgg acagacctga agaagaatcg ggactaccca    420

ctagccttcc aaagatgccc aagaaaccag cttgcttgtg ttgggcaagc cattgggcac    480

ttcattgaag gattgaccaa ggttttangg ccttggacct ttggtttggc cccaaggctt    540

tggtgttgga attgtaaatg gggtttttgg gacttttttt ncccangggg aaaatttccc    600

ttttttttcnc nanttccaat tttgngatcc aaagtnccct tggccccggg gccgggcccg    660

tttcaaaaan gggcc                                                     675
```

<210> SEQ ID NO 845
<211> LENGTH: 620

```
<212> TYPE: DNA
<213> ORGANISM: Homo sapiens
<220> FEATURE:
<221> NAME/KEY: misc_feature
<222> LOCATION: (1)...(620)
<223> OTHER INFORMATION: n = A,T,C or G

<400> SEQUENCE: 845

acagcctaag acacaaggat ctaggcgaag tagccgccaa ataaaaaaac gaagggtcat     60

atcagattct gagagtgaca ttggtggctc tgatgtggaa tttaagccag acactaagga    120

ggaaggaagc agtgatgaaa taagcagtgg agtgggggat agtgagagtg aaggcctgaa    180

cagccctgcc aaagttgctc gaaagcggaa gagaatggtg actggaaatg gctctcttaa    240

aaggaaaagc tctaggaagg aaacgccctc agccaccaaa caagcaacta gcatttcatc    300

agaaaccaag aatactttga gagctttctc tgcccctcaa aattctgaat cccaagccca    360

cgttagtgga ggtggtgatg acagtagtcg cctactgntt ggtatcatga aactttagaa    420

tggcttaagg gaggaaaaga gaanaaatga ncncaggang aaggcctgat caccccgatt    480

ttgatgcctt tnccctntnt gggncctgga ggatttcntc aaatctttgg ancettggcc    540

nnnacccccn ttangggcgn aatccagccc ttggnggncc gttcttaggg gatcncagct    600

tgggnccaac tttggggtan                                                620

<210> SEQ ID NO 846
<211> LENGTH: 617
<212> TYPE: DNA
<213> ORGANISM: Homo sapiens
<220> FEATURE:
<221> NAME/KEY: misc_feature
<222> LOCATION: (1)...(617)
<223> OTHER INFORMATION: n = A,T,C or G

<400> SEQUENCE: 846

caggtacata aagcagattc aagggttaaa ataaaaacag aattttggag tgtggtcaaa     60

taaggtgcac agattccaga accctcagag ggcctgctgg ccctctccag acattctgtg    120

tccgtggtgc aggagctggg cccgtcccta acagctccgc actggcttag tgcagtggtg    180

ctcacagttt caggaactac taggtgaagt gtctggctca agtctgccaa gtgtcttcac    240

tccatcgtca gaagtggagc actatcccta ggttcgattc ccatgaaata ttttatgatt    300

tccatcctct ttgcccgctc ttccaaataa ggccctgtga tgccaacnaa gggggcatgg    360

ttgagggtct aaggctctca ttagggccta attctgtgtg gatatnaaca catgacagac    420

acttgctgca ncattnanga catttaaggc agaggggtca tttaangnta cttttncaaa    480

ttaatatttn gnggatnggg cagttcttac ctgnnactgg tnnttattgg ggnaattttt    540

taccangggg ctgtctattt taaatngctt nggnattacn ngtttngnac cctcnaannn    600

ctngggaaac ttnntnc                                                   617

<210> SEQ ID NO 847
<211> LENGTH: 638
<212> TYPE: DNA
<213> ORGANISM: Homo sapiens
<220> FEATURE:
<221> NAME/KEY: misc_feature
<222> LOCATION: (1)...(638)
<223> OTHER INFORMATION: n = A,T,C or G

<400> SEQUENCE: 847

ggtacaagct tttttttttt tttttttttt ttttttagc ctttccttat gagcatgcct     60
```

```
gtgttgggtt gacagtgagg gtaataatga cttgttggtt gattgtagat attgggctgt    120

taattgtcag ttcagtgttt taatctgacg caggcttatg cggaggagaa tgttttcatg    180

ttacttatac taacattagt tcttctatag ggtgatagat tggtccaatt gggtgtgagg    240

agttcagtta tatgtttggg attttttagg tagtgggtgt tgagcttgaa cgctttctta    300

attggtggct gcttttaggc ctactatggg tgttaaattt tttactctct ctacaagggt    360

ttttcctaan tggccaaaag agctggtcct tctttgggac taaccagtta aattttacca    420

ngggggaatt taanaggggt tcttgggggc caaattttaa aggtcngaac ttaagantct    480

tatcttggga caanccagnt nttcaccagg cnttggnaag ggtttngtcn gcctttaccn    540

taaaaatctt tcccnctant ttnctaccnn aaccgggggg cncttttaaa cgnnntttan    600

ggganccccc ccnggtttng gggggttnaa ctttgcnn                            638
```

<210> SEQ ID NO 848
<211> LENGTH: 347
<212> TYPE: DNA
<213> ORGANISM: Homo sapiens

<400> SEQUENCE: 848

```
ggtttttttt tttttcaaca gacaaaaaaa gtttattgaa tacaaaactc aaaggcatca     60

acagtcctgg gcccaagaga tccatggcag gaagtcaaga gttctgcttc agggtcggtc    120

tgggcagccc tggaagaagt cattgcacat gacagtgatg agtgccagga aaacagcata    180

ctcctggaag tccacctgct ggtcactgtt ctcatccagg ctgcccatca gcttcttcag    240

cccctcctca tccactttct cccccacaaa gctgggcagc tccttgtgca gaagttcctt    300

catttccccc ttactcagct tgaacttgtc gccctcttgg caggagt                  347
```

<210> SEQ ID NO 849
<211> LENGTH: 624
<212> TYPE: DNA
<213> ORGANISM: Homo sapiens
<220> FEATURE:
<221> NAME/KEY: misc_feature
<222> LOCATION: (1)...(624)
<223> OTHER INFORMATION: n = A,T,C or G

<400> SEQUENCE: 849

```
actgctggaa atacaatctt cagcaggtgc tgatgcaggc tggaatttgg ctggagcgga     60

ccctcccatt ggtttagaag ttgctttagt gggtggagca ggcttggctg gcatgctaac    120

tttggctttc tctagcatgg ccaatacctg atctttagaa gttggcttta gtttcccagt    180

agccttggcc attttttcat atcctaaatg catcatgaag aatggcaagg catcttgggc    240

cttctttcgc acatctccat ttcgatcttc taggcaggag tagagatgag gaacacaaag    300

gataaggtct gtaggggtgg aacgaagagt aggtagtttc tcaaccagcc agcccagaag    360

ctcttgcctc aagaaaggat tttcttttga gctcttcaga aagaacttct ccttcaacca    420

ttccttnatg cccantctgg ttntggccaa gcatttcaca ggtcgctang ggcaagcact    480

tcgaacattg gtcttgcttg ctccaaggac ttgggaatna angggganagc ctnaaatttt    540

ttancgggtg gcttaaaatt tggggccnan ggttattgcc aaattgtttc cagggatttn    600

aacggtttgg tggncctcgg cccg                                           624
```

<210> SEQ ID NO 850
<211> LENGTH: 636
<212> TYPE: DNA
<213> ORGANISM: Homo sapiens -continued

```
<220> FEATURE:
<221> NAME/KEY: misc_feature
<222> LOCATION: (1)...(636)
<223> OTHER INFORMATION: n = A,T,C or G

<400> SEQUENCE: 850

acaagttatc aaacttctgt ttggtaacag aatcattgac gttcatggcc ggaacacaga     60

gcttcccagc tttggagagc tgatacagcc tgtgaacacc agtcacgctc tcttccacaa    120

tgcctcggat cttcttaaac acgtttggat acttcttata aacccagtgg gttaagtctc    180

ccccatcatc caggatcatg ttggcctgcc acccatccat gttcacacag cggtcaatac    240

accaccagaa gtcatcttct gactcgccct tccaagcgaa cactgcaact ccagcctcag    300

ccagtgctgc agctacttca ttctgagttg agtagatgtt acaagcagac cagcggcact    360

gagcccccag agcacagagt gtctcaatca acacccgctg tctgggctgt gatgtgtgta    420

tcttnggccg ngaacangct taagggcgaa ttncacacaa cttggcggcc ggtacttagt    480

gggaatccan cttngntacc caagcttggg cgtaantcat ngggcatang cntggttcct    540

nggggaaant ggtatncggt tanaanttcc accaacnttc naancccgga agnnttaaan    600

gntaaaanct tngggggcct aantgagnng anntac                              636
```